(12) United States Patent
Rawlings et al.

(10) Patent No.: US 11,939,594 B2
(45) Date of Patent: Mar. 26, 2024

(54) ENGRAFTABLE CELL-BASED IMMUNOTHERAPY FOR LONG-TERM DELIVERY OF THERAPEUTIC PROTEINS

(71) Applicant: Seattle Children's Hospital, Seattle, WA (US)

(72) Inventors: David J. Rawlings, Seattle, WA (US); Richard James, Seattle, WA (US); Shaun W. Jackson, Seattle, WA (US); Iram Khan, Issaquah, WA (US); King Hung, Seattle, WA (US); Andrew M. Scharenberg, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 302 days.

(21) Appl. No.: 15/921,353

(22) Filed: Mar. 14, 2018

(65) Prior Publication Data
US 2018/0282692 A1  Oct. 4, 2018

Related U.S. Application Data

(60) Provisional application No. 62/571,918, filed on Oct. 13, 2017, provisional application No. 62/549,385, (Continued)

(51) Int. Cl.
*C12N 15/00* (2006.01)
*A61K 48/00* (2006.01)
(Continued)

(52) U.S. Cl.
CPC ........ *C12N 5/0634* (2013.01); *A61K 48/0058* (2013.01); *C07K 14/00* (2013.01); (Continued)

(58) Field of Classification Search
CPC .............................. C12N 15/00; C12N 5/0634
See application file for complete search history.

(56) References Cited

U.S. PATENT DOCUMENTS

| | | | |
|---|---|---|---|
| 2016/0289637 A1* | 10/2016 | Goldberg et al. .... | C12N 5/0635 |
| 2017/0020926 A1 | 1/2017 | Mata-Fink et al. | |
| 2019/0352614 A1* | 11/2019 | Amora et al. ......... | C12N 5/163 |

FOREIGN PATENT DOCUMENTS

| | | |
|---|---|---|
| WO | WO 11/008093 | 11/2011 |
| WO | WO 16/176191 | 11/2016 |

(Continued)

OTHER PUBLICATIONS

Jourdan et al. "An in vitro model of differentiation of memory B cells into plasmablasts and plasma cells including detailed phenotypic and molecular characterization", Blood, 2009, vol. 114, No. 25, pp. 5173-5181. (Year: 2009).*

(Continued)

*Primary Examiner* — James D Schultz
*Assistant Examiner* — James Joseph Graber
(74) *Attorney, Agent, or Firm* — Knobbe, Martens, Olson & Bear LLP

(57) ABSTRACT

The present application relates to plasma cells and plasma cell precursors that express a macromolecule, such as a protein, protein mimetic or a peptide and compositions comprising these plasma cells or plasma cell precursors. The application further relates to methods of using and making the plasma cells and plasma cell precursors that express the macromolecule. Methods of treatment comprising administering the plasma cells or plasma cell precursors are also contemplated.

15 Claims, 72 Drawing Sheets

Specification includes a Sequence Listing.

Related U.S. Application Data filed on Aug. 23, 2017, provisional application No. 62/472,493, filed on Mar. 16, 2017.

(51) Int. Cl.

| | | |
|---|---|---|
| C07K 14/00 | (2006.01) | |
| C07K 16/00 | (2006.01) | |
| C12N 5/00 | (2006.01) | |
| C12N 5/078 | (2010.01) | |
| C12N 5/0781 | (2010.01) | |
| C12N 9/22 | (2006.01) | |
| C12N 15/11 | (2006.01) | |
| C12N 15/90 | (2006.01) | |
| A61K 35/17 | (2015.01) | |
| C12N 15/113 | (2010.01) | |

(52) U.S. Cl.
CPC ............ *C07K 16/00* (2013.01); *C12N 5/0635* (2013.01); *C12N 9/22* (2013.01); *C12N 15/11* (2013.01); *C12N 15/90* (2013.01); *A61K 35/17* (2013.01); *C07K 2317/14* (2013.01); *C07K 2317/21* (2013.01); *C12N 15/113* (2013.01); *C12N 2310/20* (2017.05); *C12N 2501/056* (2013.01); *C12N 2501/2302* (2013.01); *C12N 2501/2306* (2013.01); *C12N 2501/231* (2013.01); *C12N 2501/2315* (2013.01); *C12N 2501/24* (2013.01); *C12N 2501/52* (2013.01); *C12N 2506/11* (2013.01); *C12N 2510/00* (2013.01); *C12N 2510/02* (2013.01); *C12N 2750/14143* (2013.01); *C12N 2800/80* (2013.01)

(56) References Cited

FOREIGN PATENT DOCUMENTS

| WO | WO 2018/017996 A1 | 1/2018 |
|---|---|---|
| WO | WO 18/049401 | 3/2018 |
| WO | WO 18/140573 | 8/2018 |

OTHER PUBLICATIONS

Reichlin et al. "B Cell Development Is Arrested at the Immature B Cell Stage in Mice Carrying a Mutation in the Cytoplasmic Domain of Immunoglobulin β" J. Exp. Med., vol. 193, No. 1, 2001 13-23. (Year: 2001).*

Hartley et al. "Elimination of Self-Reactive B Lymphocytes Proceeds in Two Stages: Arrested Development and Cell Death", Cell, vol. 72, 325-335, 1993. (Year: 1993).*

Jourdan et al. "IL-6 supports the generation of human long-lived plasma cells in combination with either APRIL or stromal cell-soluble factors" Leukemia (2014) 28, 1647-1656. (Year: 2014).*

Cheong et al. "Editing of mouse and human immunoglobulin genes by CRISPR-Cas9 system" Nature Communications, 7: 10934, pp. 1-10 (published: Mar. 9, 2016). (Year: 2016).*

Arakawa et al. "Requirement of the Activation-Induced Deaminase (AID) Gene for Immunoglobulin Gene Conversion", Science, 295 (5558), 1301-1306, published: 2002. (Year: 2002).*

Sather et al. "Efficient modification of CCR5 in primary human hematopoietic cells using a megaTAL nuclease and AAV donor template" Sci Transl Med, Sep. 30, 2015;7(307):307ra156. (Year: 2015).*

Rottman et al. "Cellular Localization of the Chemokine Receptor CCR5", American Journal of Pathology, vol. 151, No. 5, 1997, pp. 1341-1351. (Year: 1997).*

Wendtner et al. "Efficient gene transfer of CD40 ligand into primary B-CLL cells using recombinant adeno-associated virus (rAAV) vectors" Blood (2002) 100:1655-1661. (Year: 2002).*

Schlom et al. (2013) "The role of soluble CD40L in immunosuppression" OncoImmunology, 2:1, e22546, 3 pages. (Year: 2013).*

Richardson et al. (Jan. 20, 2016) "Enhancing homology-directed genome editing by catalytically active and inactive CRISPR-Cas9 using asymmetric donor DNA" Nature Biotechnology, vol. 34, No. 3, 339-344. (Year: 2016).*

Liao et al. (2015) "Enriching CRISPR-Cas9 targeted cells by co-targeting the HPRT gene" Nucleic acids research, 43(20), e134-e134. (Year: 2015).*

Minges Wols et al., "Plasma cell purification from murine bone marrow using a twostep isolation approach," J Immunol Methods (Jan. 1, 2008) vol. 329, Nos. 1-2, pp. 219-224.

International Search Report and Written Opinion dated Nov. 7, 2018 for International Patent Application No. PCT/US18/22469.

Adam et al., "Apelin: an antithrombotic factor that inhibits platelet function," Blood, Feb. 18, 2016; 127(7):908-20.

Amirache et al., "Mystery solved: VSV-G-LVs do not allow efficient gene transfer intounstimulated T cells, B cells, and HSCs because they lack the LDL receptor," *Blood*, Feb. 27, 2014; 123(9):1422-4.

Armitage et al., "Human B cell proliferation and Ig secretion induced by recombinant CD40 ligand are modulated by soluble cytokines," *Journal of immunology* (1993) 150: 3671-3680.

Armitage et al., "IL-15 has stimulatory activity for the induction of B cell proliferation and differentiation," *Journal of immunology*, (1995) 154: 483-490.

Aurnhammer et al., "Universal real-time PCR for the detection and quantification of adeno-associated virus serotype 2-derived inverted terminal repeat sequences," *Human gene therapy methods*, (2012) 23: 18-28.

Bell et al., "The analysis of costimulatory receptor signaling cascades in normal T lymphocytes using in vitro gene transfer and reporter gene analysis," Nat Med. Oct. 2001; 7(10):1155-8.

Boutin et al., "Prevalence of serum IgG and neutralizing factors against adeno-associated virus (AAV) types 1, 2, 5, 6, 8, and 9 in the healthy population: implications for gene therapy using AAV vectors," *Human gene therapy*, (2010) 21: 704-712.

Bovia et al., Efficient transduction of primary human B lymphocytes and nondividing myeloma B cells with HIV-1-derived lentiviral vectors, *Blood*, Mar. 1, 2003; 101(5): 1727-1733.

Calcedo et al., "Adeno-associated virus antibody profiles in newborns, children, and adolescents," *Clinical and vaccine immunology* (2011) CVI 18: 1586-1588.

Challita et al., "Multiple modifications in cis elements of the long terminal repeat ofretroviral vectors lead to increased expression and decreased DNA methylation in embryonic carcinoma cells," *Journal of virology* (1995) 69: 748-755.

Cheng et al., "Autoantibodies from long-lived 'memory' plasma cells of NZB/W mice drive immune complex nephritis," *Annals of the rheumatic diseases* (2013) 72: 2011-2017.

Cocco et al., "In Vitro Generation of Long-lived Human Plasma Cells," *J Immunol* (2012) 189(12), 5773-5785.

Cong et al., "Multiplex genome engineering using CRISPR/Cas systems," *Science* (2013) 339: 819-823.

Cotten et al., "Intracellular delivery of lipopolysaccharide during DNA transfection activates a lipid A-dependent cell death response that can be prevented by polymyxin B," *Human Gene Ther.*, Mar. 20, 1997; 8(5):555-61.

Crowl et al., "Intracellular Nucleic Acid Detection in Autoimmunity," *Annual Rev Immunol.*, Apr. 26, 2017; 35:313-336.

Ebert et al., "Lymphocyte apoptosis: induction by gene transfer techniques," *Gene Ther.*, Apr. 1997, 4(4):296-302.

Fluckiger et al., "In vitro reconstitution of human B-cell ontogeny: from CD34 (+) multipotent progenitors to Ig-secreting cells," *Blood*, Dec. 15, 1998, 92(12):4509-20.

Frecha et al., "Efficient and stable transduction of resting B lymphocytes and primary chronic lymphocyte leukemia cells using measles virus gp displaying lentiviral vectors," *Blood* (2009) 114: 3173-3180.

Hale et al., "Engineering HIV-Resistant, Anti-HIV Chimeric Antigen Receptor T Cells, Molecular therapy," *The Journal of the American Society of Gene Therapy* (2017) 25: 570-579.

(56) References Cited

OTHER PUBLICATIONS

Hellebrand et al., "Epstein-Barr virus vector-mediated gene transfer into human B cells: potential for antitumor vaccination," *Gene therapy* (2006) 13: 150-162.
Heyer et al., "Regulation of homologous recombination in eukaryotes," *Annual review of genetics* (2010) 44: 113-139.
Hirata et al., "Targeted transgene insertion into human chromosomes by adeno-associated virus vectors," *Nature biotechnology* (2002) 20: 735-738.
Janssens et al., "Efficiency of Onco-Retroviral and Lentiviral Gene Transfer into Primary Mouse and Human B-Lymphocytes Is Pseudotype Dependent," *Human Gene Therapy*, Jul. 7, 2004, vol. 14, No. 3, pp. 263-276.
Jiang et al., "TLR9 stimulation drives naive B cells to proliferate and to attain enhanced antigen presenting function," *European journal of immunology* (2007) 37: 2205-2213.
Jourdan et al., "An in vitro model of differentiation of memory B cells into plasmablasts and plasma cells including detailed phenotypic and molecular characterization," *Blood* (2009) 114: 5173-5181.
Jourdan et al., "IL-6 supports the generation of human long-lived plasma cells in combination with either APRIL or stromal cell-soluble factors," *Leukemia* (2014) 28, 1647-1656.
Khan et al., "AAV-mediated gene targeting methods for human cells," *Nature protocols* (2011) 6: 482-501.
Kim et al., "Enhanced antitumor immunotherapeutic effect of B-cell-based vaccine transduced with modified adenoviral vector containing type 35 fiber structures," *Gene therapy* (2014) 21: 106-114.
Kozmik et al., "The promoter of the CD19 gene is a target for the B-cell-specific transcription factor BSAP," *Molecular and cellular biology* (1992) 12: 2662-2672.
Lang et al., "Studies of lymphocyte reconstitution in a humanized mouse model reveal a requirement of T cells for human B cell maturation," *Journal of immunology* (2013) 190: 2090-2101.
Lei et al., "Induction of tolerance to factor VIII inhibitors by gene therapy with immunodominant A2 and C2 domains presented by B cells as Ig fusion proteins," *Blood* (2005) 105: 4865-4870.
Levy et al., "Lentiviral vectors displaying modified measles virus gp overcome pre-existing immunity in in vivo-like transduction of human T and B cells, Molecular therapy," *The Journal of the American Society of Gene Therapy* (2012) 20: 1699-1712.
Li et al., "Neutralizing antibodies against adeno-associated virus examined prospectively in pediatric patients with hemophilia," *Gene therapy* (2012) 19: 288-294.
Lin et al., "Enhanced homology-directed human genome engineering by controlled timing of CRISPR/Cas9 delivery," *eLife* (2014) 3: e04766.
Liu et al., "Homozygous defect in HIV-1 coreceptor accounts for resistance of some multiply-exposed individuals to HIV-1 infection," *Cell* (1996) 86: 367-377.
MacKay et al., "BAFF: a fundamental survival factor for B cells," *Nature reviews Immunology* (2002) 2: 465-475.
Mali et al., "RNA-guided human genome engineering via Cas9," *Science* (2013) 339: 823-826.
Melo et al., "Gene transfer of Ig-fusion proteins into B cells prevents and treats autoimmune diseases," *Journal of immunology* (2002) 168: 4788-4795.
Milone et al., Chimeric Receptors Containing CD137 Signal Transduction Domains Mediate Enhanced Survival of T Cells and Increased Antileukemic Efficacy In Vivo, Molecular Therapy, vol. 17, Issue 8, Aug. 2009, pp. 1453-1464.
Mock et al., "Efficient lentiviral transduction and transgene expression in primary human B cells," *Human gene therapy methods* (2012) 23: 408-415.
Muto et al., "The transcriptional programme of antibody class switching involves the repressor Bach2," *Nature* (2004) 429: 566-571.
Muto et al., "Bach2 represses plasma cell gene regulatory network in B cells to promote antibody class switch," *The EMBO journal* (2010) 29: 4048-4061.
Nathwani et al., "Adenovirus-associated virus vector-mediated gene transfer in hemophilia B," *The New England journal of medicine* (2011) 365: 2357-2365.
Nathwani et al., "Long-term safety and efficacy of factor IX gene therapy in hemophilia B," *The New England journal of medicine* (2014) 371: 1994-2004.
Nera et al., "Loss of Pax5 promotes plasma cell differentiation," *Immunity* (2006) 24: 283-293.
Ochiai et al., "Transcriptional regulation of germinal center B and plasma cell fates by dynamical control of IRF4," *Immunity* (2013) 38: 918-929.
Porter et al., "Chimeric Antigen Receptor-Modified T Cells in Chronic Lymphoid Leukemia," *N Eng J Med* 365;8 Aug. 25, 2011, pp. 725-723.
Radbruch et al., "Competence and competition: the challenge of becoming a long-lived plasma cell," *Nature reviews Immunology* (2006) 6: 741-750.
Ran et al., "Genome engineering using the CRISPR-Cas9 system," *Nature protocols* (2013) 8: 2281-2308.
Rawlings et al., "Long-term culture system for selective growth of human B-cell progenitors," Proc. Natl. Acad. Sci. USA vol. 92, pp. 1570-1574, Feb. 1995.
Rawlings et al., "Differentiation of human $CD34^+CD38^-$ cord blood stem cells into B cell progenitors in vitro," Experimental Hematology (1997) 25:66-72.
Rottman et al., "Cellular localization of the chemokine receptor CCR5, Correlation to cellular targets of HIV-1 infection," *The American journal of pathology* (1997) 151: 1341-1351.
Russell et al., "Human gene targeting by viral vectors," *Nature genetics* (1998) 18: 325-330.
Sather et al., "Efficient modification of CCR5 in primary human hematopoietic cells using a megaTAL nuclease and AAV donor template," *Science translational medicine* (2015) 30:7(307).
Schumann et al., "Generation of knock-in primary human T cells using Cas9 ribonucleoproteins," *Proc Natl Acad Sci U S A*, Aug. 18, 2015;112(33):10437-42.
Seiffert et al., "Efficient nucleofection of primary human B cells and B-CLL cells induces apoptosis, which depends on the microenvironment and on the structure of transfected nucleic acids," *Leukemia*, Sep. 2007, 21(9):1977-83.
Serafini et al., "Molecular evidence of inefficient transduction of proliferating human B lymphocytes by VSV-pseudotyped HIV-1-derived lentivectors," *Virology* (2004) 325: 413-424.
Shaffer et al., "Blimp-1 orchestrates plasma cell differentiation by extinguishing the mature B cell gene expression program," *Immunity* (2002) 17: 51-62.
Simioni et al., "X-linked thrombophilia with a mutant factor IX (factor IX Padua)," *The New England journal of medicine* (2009) 361: 1671-1675.
Skupsky et al., "B-cell-delivered gene therapy induces functional T regulatory cells and leads to a loss of antigen-specific effector cells, Molecular therapy," *The Journal of the American Society of Gene Therapy* (2010) 18: 1527-1535.
Slifka et al., "Humoral immunity due to long-lived plasma cells," *Immunity* (1998) 8: 363-372.
Smith et al., "Gene Transfer Properties and Structural Modeling of Human Stem Cell-derived AAV," *Mol Ther.*, Sep. 2014, 22(9): 1625-1634.
Van Tendeloo et al., "High-level transgene expression in primary human T lymphocytesand adult bone marrow CD34+ cells via electroporation-mediated gene delivery," *Gene Ther.*, Aug. 2000, 7(16):1431-7.
Villaudy et al., "Critical assessment of human antibody generation in humanized mouse models," *Journal of immunological methods* (2014) 410: 18-27.
Yu et al., "A novel humanized mouse model with significant improvement of class-switched, antigen-specific antibody production," *Blood* (2017) 129: 959-969.

(56) References Cited

OTHER PUBLICATIONS

Cheong et al., Mar. 9, 2016, Editing of mouse and human immunoglobulin genes by CRISPR-Cas9 system, Nature Communications, 7:10934, pp. 1-10.

Chu et al., Nov. 1, 2016, Efficient CRISPR-mediated mutagenesis in primary immune cells using CrispRGold and a C57BL/6 Cas9 transgenic mouse line, Proceedings of the National Academy of Sciences of the United States of America, 113(44):12514-12519.

Dever et al., Nov. 17, 2016, CRISPR/Cas9 beta-globin gene targeting in human haematopoietic stem cells, Nature, 539(7629):384-389.

Gwiazda et al., Sep. 1, 2016, High Efficiency CRISPR/Cas9-mediated Gene Editing in Primary Human T-cells Using Mutant Adenoviral E4orf6/E1b55k "Helper" Proteins, Molecular Therapy, 24(9):1570-1580.

Hubbard et al., Feb. 22, 2016, Targeted gene editing restores regulated CD40L function in X-linked hyper-IgM syndrome, Blood, 127(21):2513-2522.

Hung et al., Feb. 2018, Engineering protein-secreting plasma cells by homology-directed repair in primary human B cells, Molecular Therapy, 26(2):456-467.

Levy et al., Aug. 25, 2016, Baboon envelope pseudotyped lentiviral vectors efficiently transduce human B cells and allow active factor IX B cell secretion in vivo in NOD/SCIDgammac−/− mice, Journal of Thrombosis and Haemostasis, 14:2478-2492.

Pogson et al., Aug. 17, 2016, Immunogenomic engineering of a plug-and-(dis)play hybridoma platform, Nature Communications, 7:12535, 10 pp.

Richardson et al., Jan. 20, 2016, Enhancing homology-directed genome editing by catalytically active and inactive CRISPR-Cas9 using asymmetric donor DNA, Nature Biotechnology, 34(3):339-344.

Romano Ibarra et al., Aug. 23, 2016, Efficient Modification of the CCR5 Locus in Primary Human T Cells With megaTAL Nuclease Establishes HIV-1 Resistance, Molecular Therapy—Nucleic Acids, 5:e352, 10 pp.

Huggins, Jennifer et al., "CpG DNA activation and plasma-cell differentiation of CD27−naive human B cells" Blood, 2007, pp. 1611-1619, vol. 109.

* cited by examiner

Longevity
- Human influenza antibody titers persist for > 90 years
- Persist in non-dividing state within bode marrow survival niche without need for ongoing antigen exposure.
- Relatively resistant to immunosuppression/chemotherapy

Protein production
- Plasma cell: 2000-10,000 immunoglobulin molecules per second; ~50-340 pg protein/cell/day.
- Industrial cell-line protein production ~20-90 pg protein/cell/day

Potential for Ex vivo manipulation and generation

FIG. 2

CRISPR EDITING OF PRIMARY B CELLS

| | Plasmid Delivery (Incl. Sleeping beauty) | Lentiviral delivery | RNA (or RNP) + AAV co-delivery | RNP / ODN delivery |
|---|---|---|---|---|
| Ease | ++++ | +++ | ++ | ++++ |
| Cost | + | ++ | ++ | + |
| Efficiency | + | + | +++ | +++ |
| Specificity | + | + | ++++ | +++ |

*Note that these assessments are B cell specific

FIG. 4

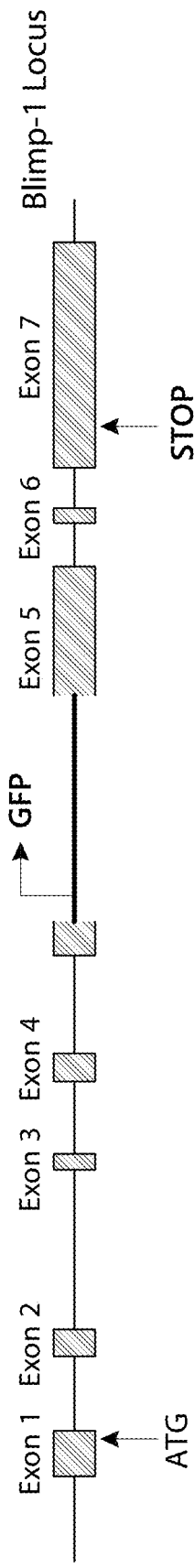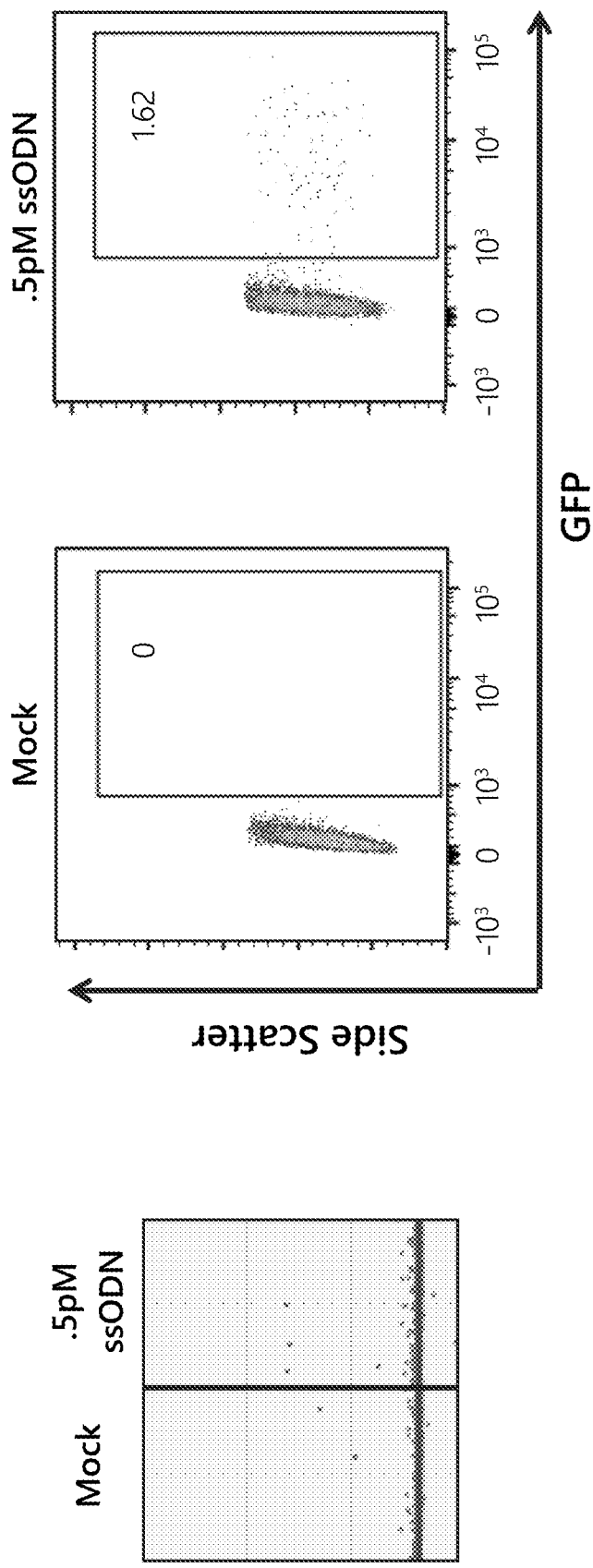
FIG. 14

Negative selection isolation of B cells from healthy donor PBMCs

FIG. 29A
10 Days Post Transplant
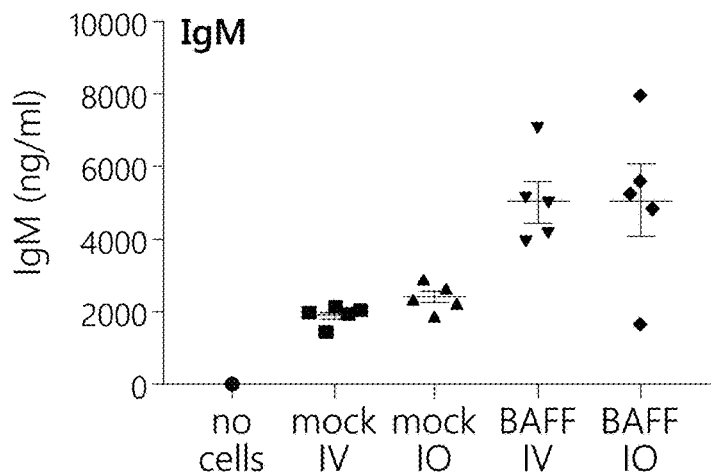
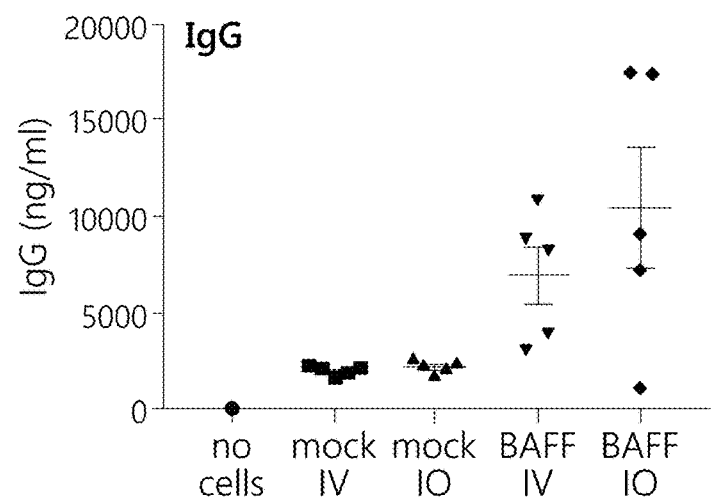
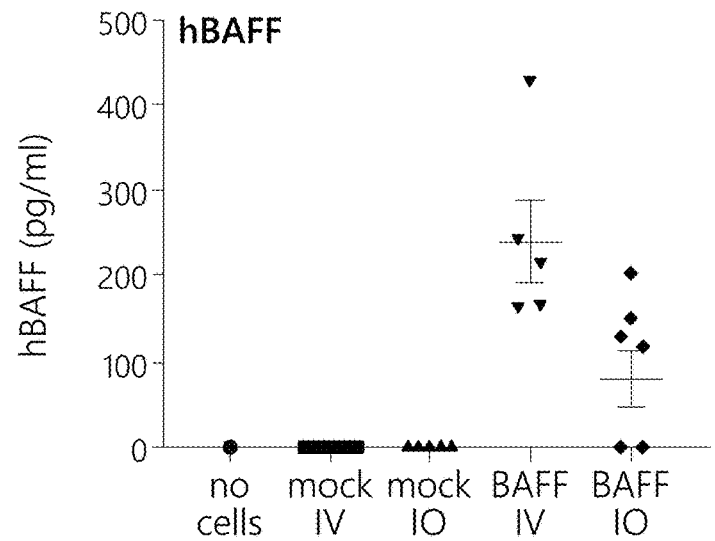

Gene disruption and protein expression

Guide to Target Candidate loci - highly expressed genes predicted to impact protein secretion

- Highly expressed in plasma cells based on RNA expression from single cell sequencing data
- Secreted proteins - extracellular or ER/Golgi
- Proteins that are not involved in vesicular transport/protein secretion

| | | |
|---|---|---|
| 001 | SLPI-2sense | Secreted protease inhibitor |
| 002 | SLPI-1sense | |
| 003 | IGKC-sense | Kappa light chain constant region |
| 004 | IGKC-antisense | |
| 005 | IGMC-sense | IgM heavy chain constant region |
| 006 | IGMC-antisense | |
| 007 | JCHAIN-1antisense | Jchain |
| 008 | JCHAIN2-sense | |
| 009 | JCHAIN-4antisense | |
| 010 | PON3-2antisense | Paraoxonase 3 - secreted protein that associates with HDL |
| 011 | PON3-3sense | |
| 012 | PRG2-3antisense | Pro eosiniphil major basic protein - secreted protein that binds HSPGs |
| 013 | PRG2-3antisense | |
| 014 | CRELD2-3sense | ER protein |
| 015 | CRELD2-4antisense | |

FIG. 35

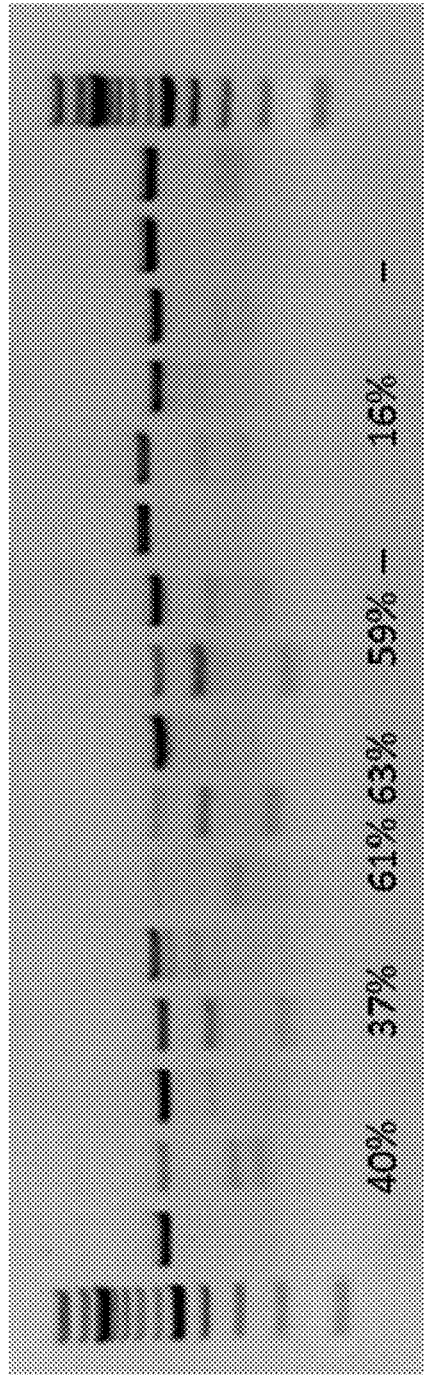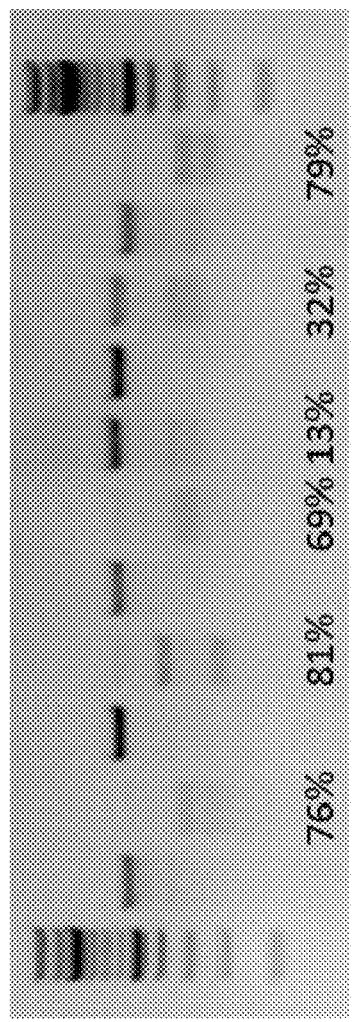
FIG. 36

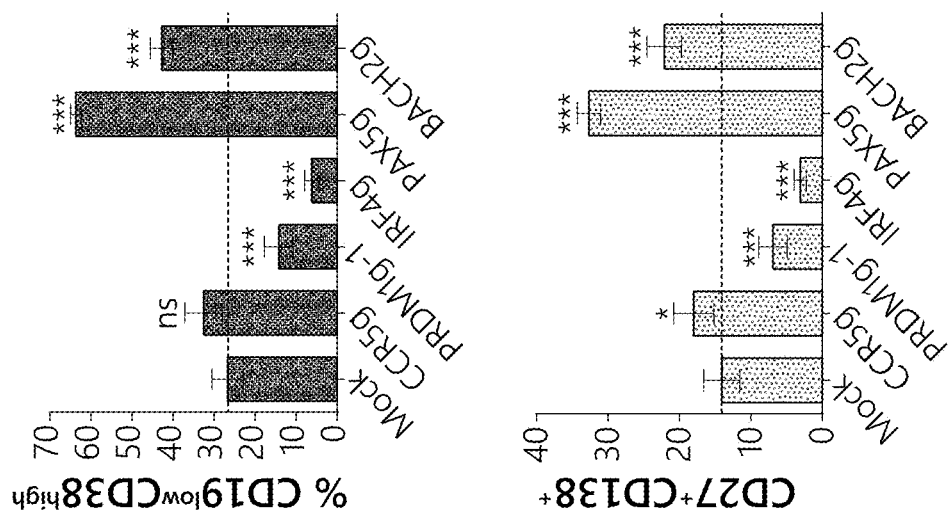
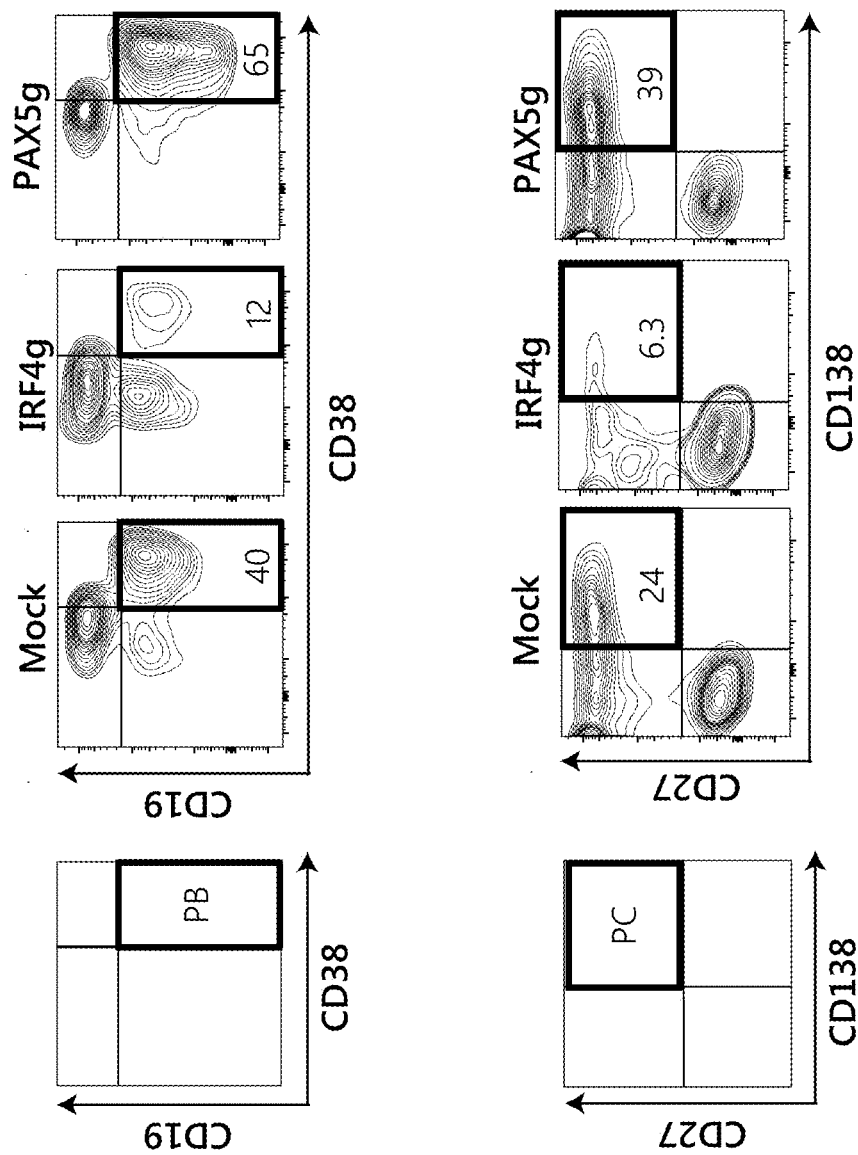
FIG. 44C

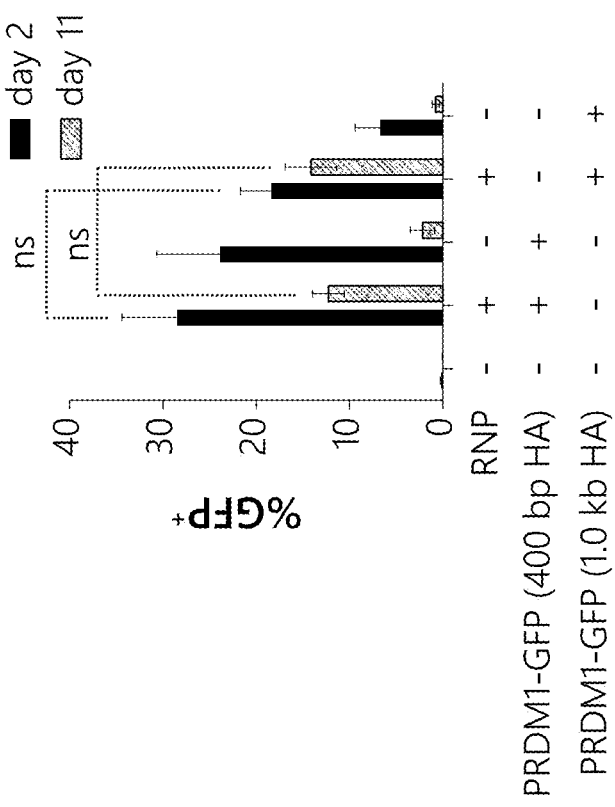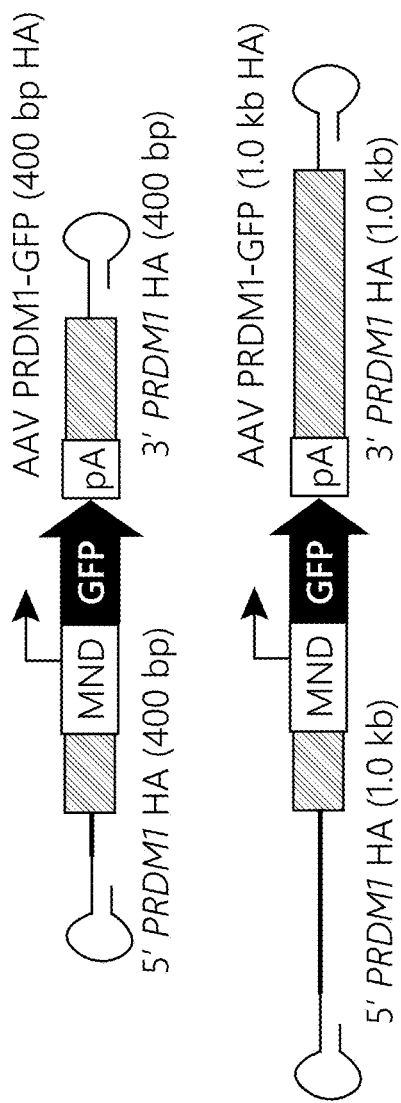
FIG. 48A
FIG. 48B

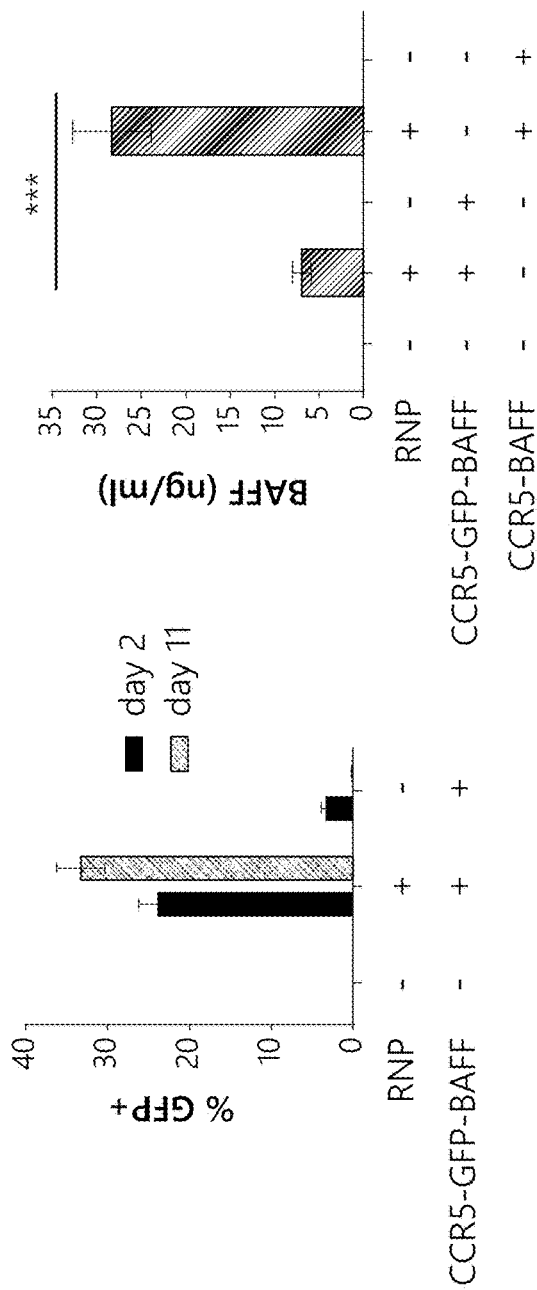
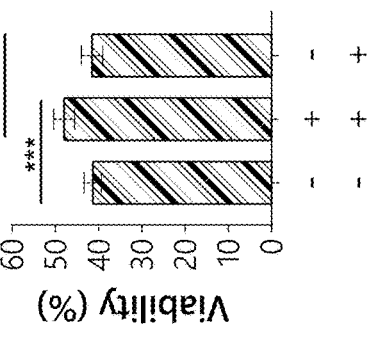
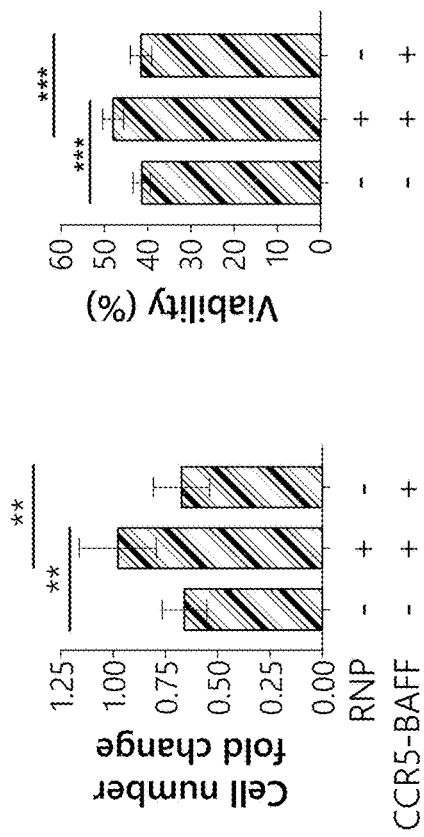
FIG. 49C
FIG. 49D

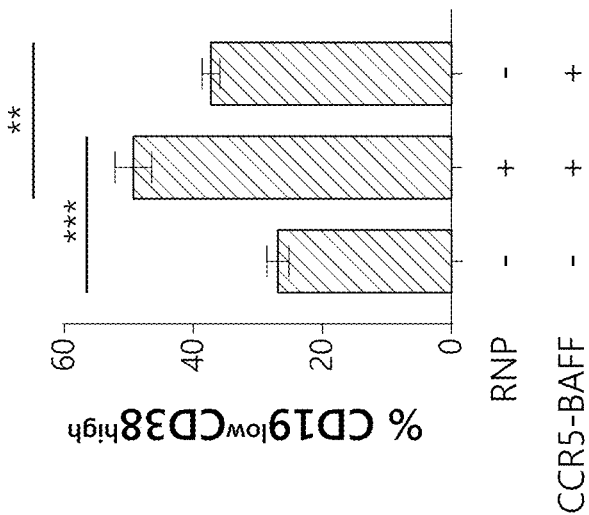
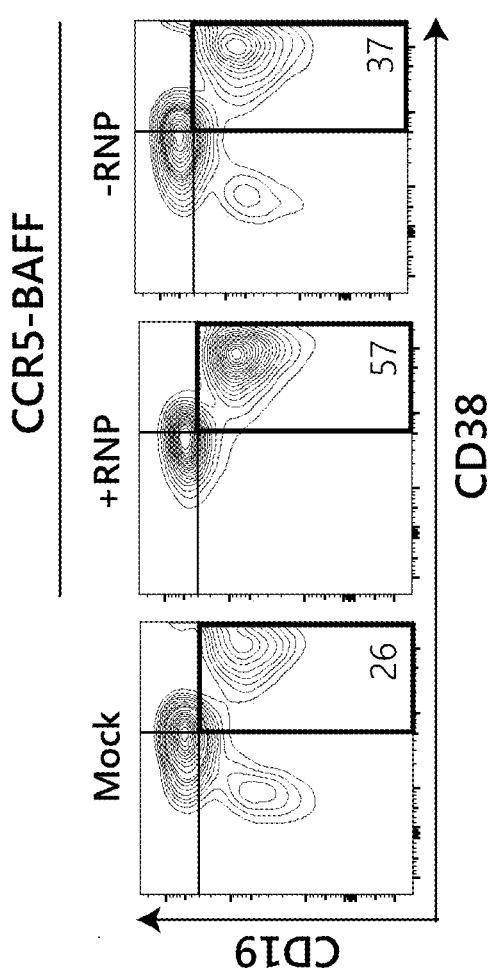
FIG. 49E

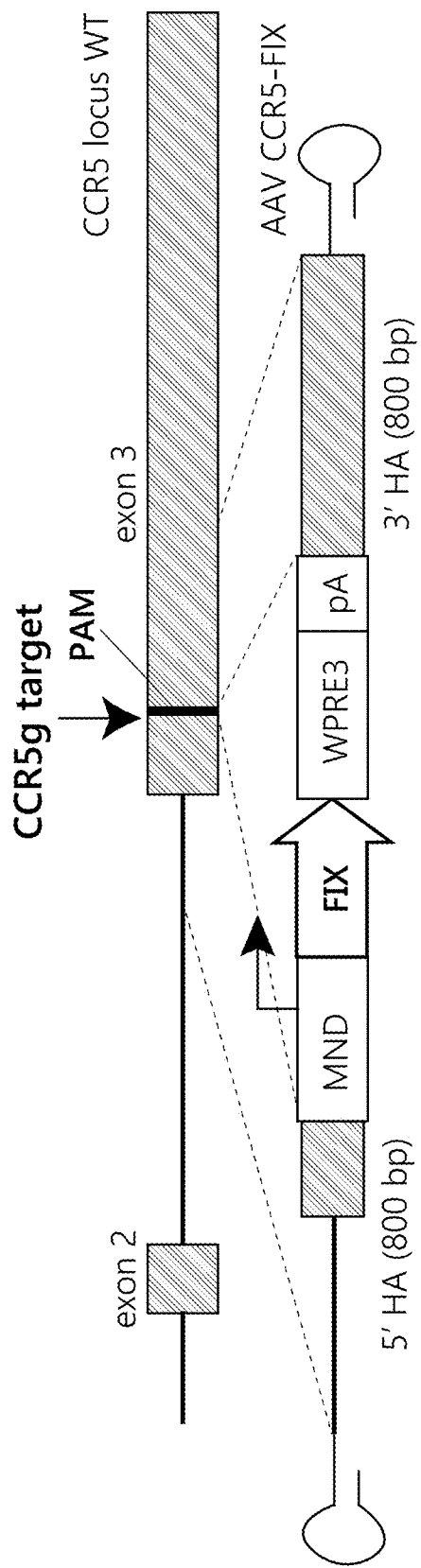
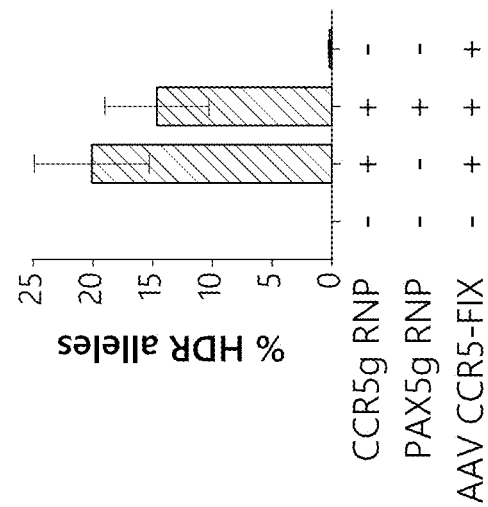
FIG. 51A
FIG. 51B

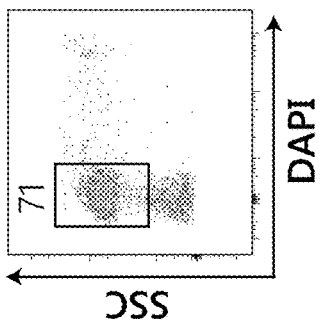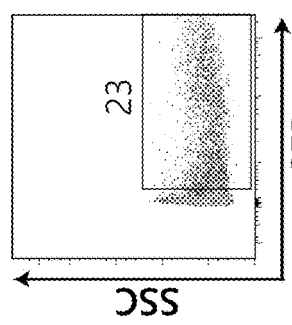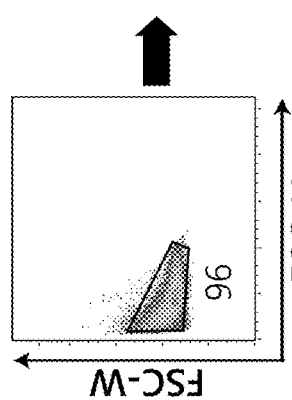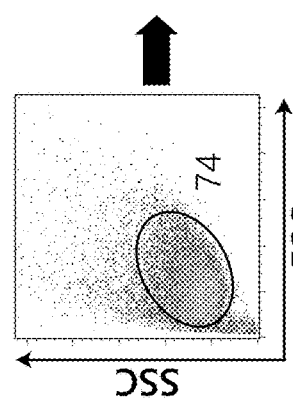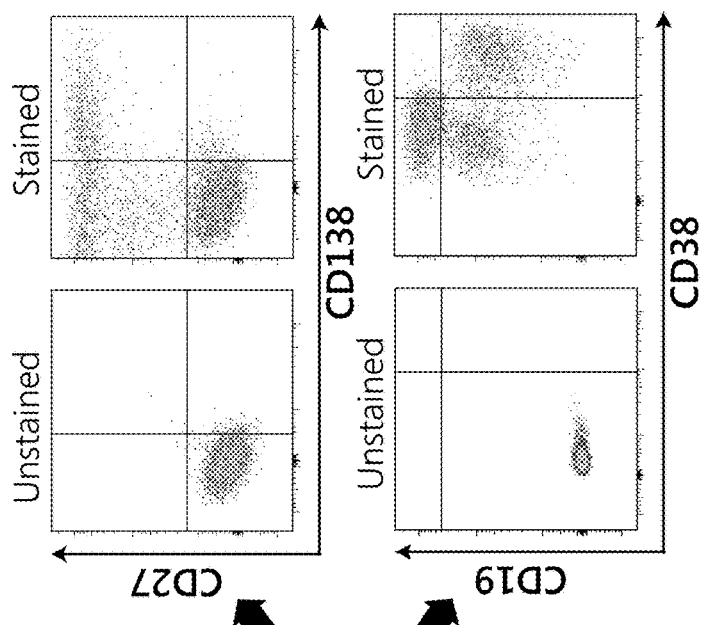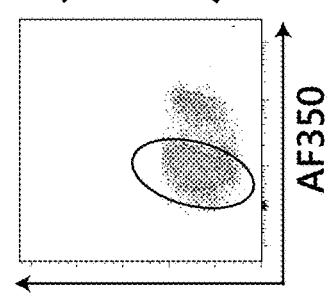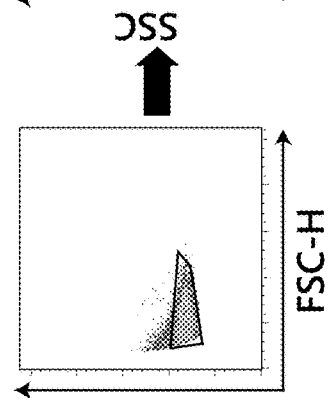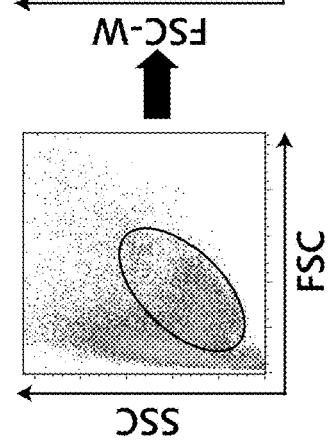
FIG. 52A
FIG. 52B
FIG. 52C

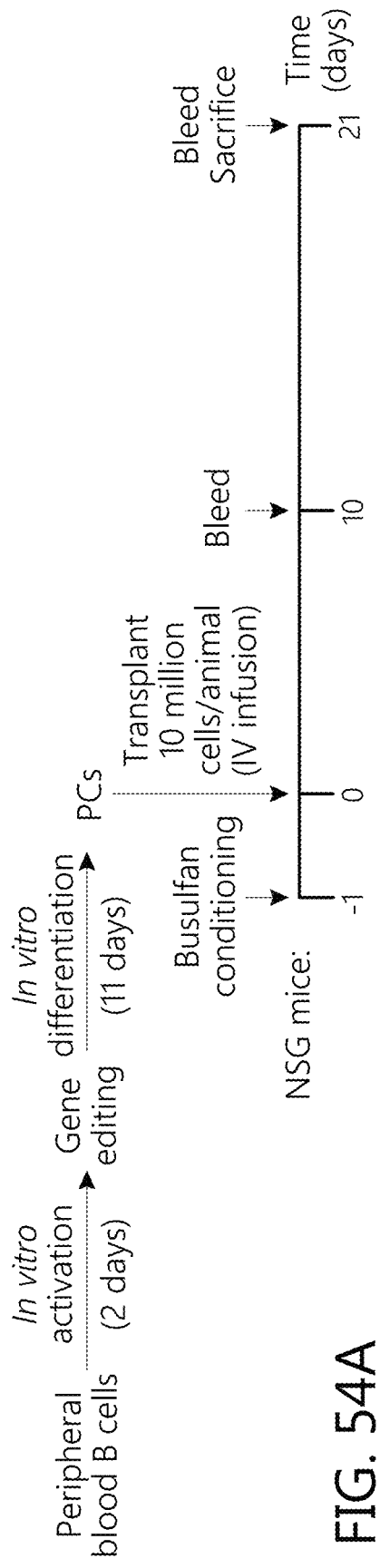
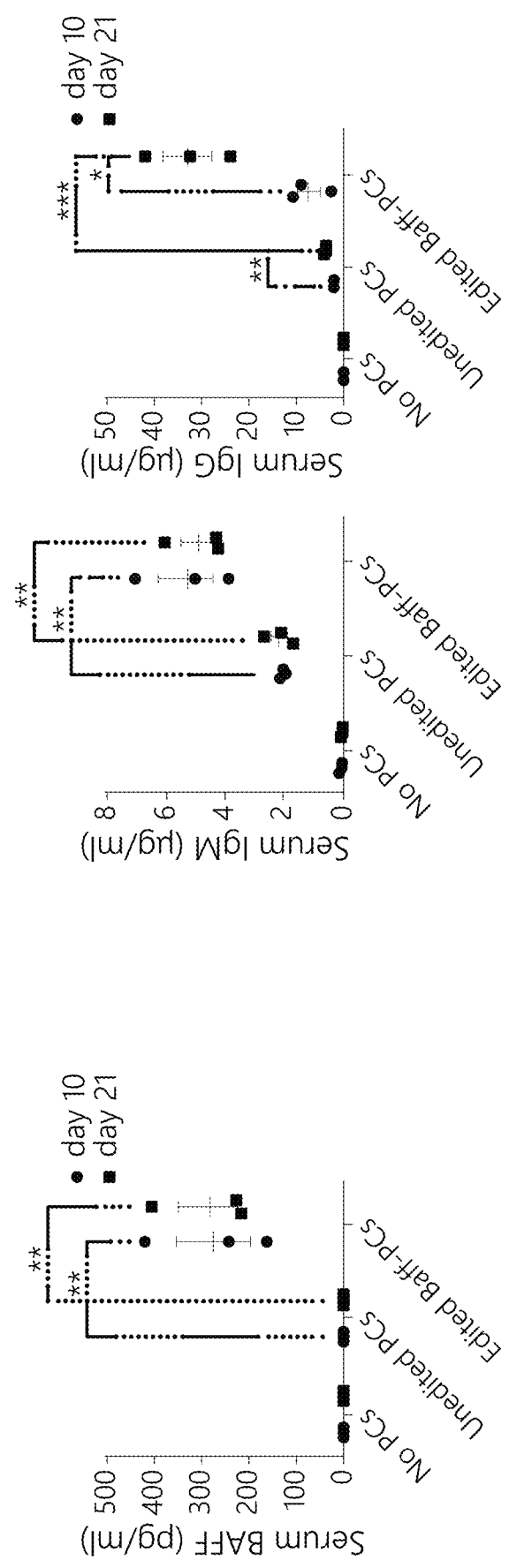
FIG. 54A
FIG. 54B
FIG. 54C

ENGRAFTABLE CELL-BASED IMMUNOTHERAPY FOR LONG-TERM DELIVERY OF THERAPEUTIC PROTEINS

CROSS REFERENCE TO RELATED APPLICATIONS

The present application claims the benefit of priority to U.S. Provisional Patent Application No. 62/472,493, filed Mar. 16, 2017, U.S. Provisional Patent Application No. 62/549,385, filed Aug. 23, 2017, and U.S. Provisional Patent Application No. 62/571,918, filed Oct. 13, 2017. The entire disclosures of the aforementioned applications are expressly incorporated by reference in their entireties.

REFERENCE TO SEQUENCE LISTING

This application incorporates by reference the Sequence Listing provided as an ASCII text file entitled SCRI133ASEQLISTING.TXT created Jun. 27, 2023, and is 182,896 bytes in size. The information in the electronic format of the Sequence Listing is incorporated herein by reference in its entirety.

FIELD OF THE INVENTION

A new approach for engineering human plasma cells or plasma cell precursors to express macromolecules such as proteins for therapeutic purposes, has been discovered. The alternatives described herein include methods requiring isolation and activation of B cells from subject-derived (autologous) or allogeneic peripheral blood mononuclear cells; genome engineering of these B cells or B cell precursors so that they express molecules, such as macromolecules, protein mimetics, proteins or peptides of interest in the absence of viral integration (with or without additional genetic modifications that modulate their eventual function and survival); expansion and differentiation of these cells into $>1e^{-6}$ long-lived plasma cells in vitro; and administration of these autologous or allogeneic engineered protein-producing plasma cells into human recipients for therapeutic application.

BACKGROUND OF THE INVENTION

To date there are limited reports of genome editing in primary B cells. These limited reports can be found, for example, in Cheong et al. 2016 and Chu et al. 2016 ("Editing of mouse and human immunoglobulin genes by CRISPR-Cas9 system." Nat Commun. 2016 Mar. 9; 7:10934. and "Efficient CRISPR-mediated mutagenesis in primary immune cells using CrispRGold and a C57BL/6 Cas9 transgenic mouse line." Proc Natl Acad Sci USA. 2016 Nov. 1; 113(44):12514-12519; both incorporated by reference in their entireties herein). These reports have used either transient transfection of plasmid DNA or lentiviral vector delivery to facilitate gene disruption. However, there are no reports available in the medical literature of using nucleases to achieve homologous recombination in primary human B cells.

One of the main problems with the use of plasmids is their low efficiency. For example, plasmid-based methods of DNA delivery to primary B cells are extremely toxic, which is likely due to innate DNA sensing and they also exhibit low efficiency (<1%). Lentiviral-based gene delivery also has low efficiency in these cells, for example, in most cases less than 5% of the cells can be transduced, and gene targeting in primary B cells has historically required use of cells from animals with transgenic expression of CAS9. In contrast, the genome engineering approach used in the alternatives described herein enables one to selectively edit the genes with introduction of gene expression cassettes by homologous recombination in more than 30% of primary human B cells and to selectively expand these cells to generate an enriched cell product expressing transgenes of interest.

Selectivity is also an issue with lentiviral and plasmid DNA. For example, lentiviral vectors integrate randomly and primarily in sites of active transcription and have the potential to be oncogenic. In contrast, nuclease targeting and homology directed repair (HDR) dependent integration of payload allow for selectivity with minimal off-target effects. The need for new approaches that allow one to achieve homologous recombination in primary human B cells is manifest.

SUMMARY OF THE INVENTION

Aspects of the alternatives described herein include, but are not limited to: (1) the use of blood-derived human B cells and/or B cell precursors as a starting material for a plasma cell molecule producing immunotherapy; (2) RNA- and protein-based transfection to facilitate delivery of candidate designer nucleases targeting a broad range of genetic loci in primary B cells that include, but are not limited to zinc finger nucleases, transcription activator-like effector nucleases (TALEN), homing endonucleases (HEs), combined TALEN-HE proteins (megaTALs) and CRISPR/Cas systems; (3) transfection of long single-stranded DNA oligonucleotides or transduction with recombinant adeno-associated virus to facilitate efficient delivery of donor DNA templates carrying therapeutic expression cassettes into primary human B cells and/or B cell precursors in order to facilitate efficient homologous recombination into a range of candidate genetic loci; (4) integrity measures that include, but are not limited to, methods to prevent somatic hypermutation of the B cell antibody locus during the engineering process including, but not limited, to disruption of the AID gene; (5) production enhancers that include, but are not limited to methods to introduce dimerizable drug-inducible activating proteins to enable selectable expansion of engineered human B cells and/or B cell precursors in vitro or in vivo; (6) safety measures that include, but are not limited to, introduction of sequences from cell surface proteins including, but not limited to, the CD20 protein into B cells and/or B cell precursors to enable targeted removal from recipients using Rituxan® or alternative therapeutic approaches; and (7) the use of a proprietary multi-step cytokine and co-culture based systems to facilitate differentiation of blood-derived B cells and/or B cell precursors into long-lived plasma cells and their survival and expansion in vitro. The human B cells as described herein, can include B cell precursors such as hematopoietic stem cells (HSCs), multi-potent progenitor (MPP) cells, lymphoid progenitor (CLP) cells, naïve B cells, GC B cell, plasmablast, early pro-B cells, late pro-B cells, large pre-B cells, small pre-B cells, immature B cells, T1 B cells, T2 B cells, marginal zone B cells, mature B cells and/or memory B cells. Without being limiting, the molecule comprises macromolecules, proteins, protein mimetics and peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, of the CRISPR/Cas system described herein, the Cas nuclease comprises Cas1, Cas2, Cas3, Cas4, Cas5, Cas6, Cas7, Cas8 or Cas9.

Multiple categories of use of a plasma cell producing a molecule, such as a macromolecule, protein or a peptide in immunotherapy are also envisioned. Exemplary alternatives are listed below:

(1) Prophylactic or therapeutic protection from infection (viral, bacterial, or parasitic) in healthy subjects or following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites;

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophasphatasia);

(3) Immune modulation via expressed cytokines, cytokine receptors, complement proteins or other inhibitory proteins including, but not limited to: Il1 receptor antagonist for treatment or amelioration of periodic fever/autoinflammatory syndromes; complement inhibitory proteins (including Factor H, Factor I) for treatment or inhibition of atypical hemolytic uremic syndrome/membranoproliferative glomerulonephritis; and/or C1 inhibitor for hereditary angioedema;

(4) Anti-fibrotic molecules including, but not limited to SCGB1A1 for the treatment of pulmonary fibrosis;

(5) Therapeutic antibodies or at least one binding portion thereof for treating or ameliorating autoimmune disorders, autoinflammatory disorders, immune dysregulation and/or cancer including but not limited to: anti-IL1 monoclonal antibodies or a binding portion thereof for the treatment or amelioration of periodic fever/autoinflammatory syndromes; anti-TNF antibodies or a binding portion thereof for the treatment or inhibition of inflammatory arthritis/inflammatory bowel disease, anti-IL33 antibodies or a binding portion thereof for the treatment or inhibition of asthma and/or anti-C5 antibodies or a binding portion thereof for the treatment or inhibition of paroxysmal nocturnal hemoglobinuria/atypical HUS;

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein);

(7) Glucose response elements upstream of insulin for the treatment or inhibition of diabetic conditions; and (8) Therapeutic monoclonal antibodies for hyper-cholesterolemia, including anti-PCSK9 inhibitory antibodies or a binding portion thereof. Preferred alternatives include the following alternatives. In some alternatives herein, the protein is a neutralizing antibody that block influenza, parainfluenza, rhinovirus, Respiratory Syncitial Virus (RSV), HIV, pathogenic bacteria, and/or parasites. In some alternatives herein, the protein is an enzyme. In some alternatives, the protein is Factor VIII, Factor IX, SERPING1 or SERPINA1. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the plasma cell expresses cytokines, cytokine receptors, complement proteins or other inhibitory proteins.

In a first aspect, a method of making plasma cells or plasma cell precursors that express a molecule is provided, the method comprising: (a)isolating B cells, (b) developing the B cells, (c) performing a first round of genome editing of the B cells for protein expression in absence of viral integration, (d) expanding the B cells and (e) differentiating the B cells, optionally, after step (c) or (d), thereby producing plasma cells or plasma cell precursors that express the molecule. In some alternatives, the molecule is a protein, protein mimetic or peptide. In some alternatives, the molecule is Factor VIII, Factor IX, SERPING1, SERPINA1, complement inhibitory protein, Factor H, Factor I, a C1 inhibitor, an anti-fibrotic molecule, SCGB1A1, a therapeutic antibody or a binding portion thereof, an anti-IL-1 monoclonal antibody, an anti-TNF antibody, an anti-IL-33 antibody, an anti-C5 antibody, an anti-thrombotic molecule, APLN, an anti-PCSK9 inhibitory antibody or binding portion thereof, a neutralizing HIV-1 antibody (bNAbs) or binding portion thereof, IFN-alpha, BAFF, APRIL, IL-10, IL-6, ADAMTS13, LIPA, GLA or ALPL. In some alternatives, the developing of the B cells is performed after the B cells are arrested at a specific phase of development or activating the B cells such that the B cells are permissive for recombination without further B cell differentiation, wherein the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration, and wherein performing the first round of genome editing of the B cells for protein expression is performed by introduction of a single stranded nucleic acid. In some alternatives, the first round of genome editing is performed by an RNA and protein based transfection and, wherein the first round of genome editing comprises delivering a nuclease, wherein the nuclease targets at least one genetic loci in the B cell and, wherein the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the first round of genome editing comprises transducing the B cell with a recombinant adeno-associated virus vector to serve as a donor template for homologous recombination into a candidate genetic loci. In some alternatives, the method further comprises preventing somatic hypermutation of an antibody locus in the B cell. In some alternatives, the method further comprises selectively increasing a proportion of gene edited B cells and, wherein the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, step (a) further comprises removing IgM positive cells. In some alternatives, the method further comprises introducing a nucleic acid, wherein the nucleic acid encodes at least one cell surface protein. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 or IL-15, wherein the plasmablast differentiation step is performed in the presence any combination of IL-2, IL-6, IL-10 or IL-15 or wherein the plasma cell differentiation step is performed in the presence any combination of IL-6, IL-15, APRIL or IFNα. In some alternatives, the plasma cells are long lived plasma cells. In some alternatives, the method further comprises purifying the plasma cells by positive selection against CD138.

In second aspect, a composition comprising a plasma cell is provided, which expresses a molecule, wherein said molecule is a heterologous protein, protein mimetic or a peptide. In some alternatives, the molecule comprises an enzyme, neutralizing antibody or binding portion thereof, cytokine, cytokine receptor, complement protein, inhibitory protein, anti-fibrotic molecule, therapeutic antibody or binding portion thereof, anti-thrombotic molecule, glucose response element, or a monoclonal antibody or binding portion thereof. In some alternatives, the composition further comprises a second B cell, wherein the second B cell secretes a molecule that induces tolerance of a peptide or that induces engraftment of the plasma cell.

In a third aspect, a method of expressing a molecule in a subject is provided comprising: administering the composition of anyone of the alternatives herein to the subject. In some alternatives, the composition comprises a plasma cell is provided, which expresses a molecule, wherein said molecule is a heterologous protein, protein mimetic or a peptide. In some alternatives, the molecule comprises an enzyme, neutralizing antibody or binding portion thereof, cytokine, cytokine receptor, complement protein, inhibitory protein, anti-fibrotic molecule, therapeutic antibody or binding portion thereof, anti-thrombotic molecule, glucose response element, or a monoclonal antibody or binding portion thereof. In some alternatives, the composition further comprises a second B cell, wherein the second B cell secretes a molecule that induces tolerance of a peptide or that induces engraftment of the plasma cell. In some alternatives, the subject has received a stem cell administration or a solid organ transplantation or is a subject identified or selected as one to receive a stem cell administration or a solid organ transplantation or, wherein the subject has an enzyme deficiency, pulmonary fibrosis, an autoimmune disorder, immune dysregulation, cancer, diabetes, HIV or hypercholesterolemia.

BRIEF DESCRIPTION OF THE DRAWINGS

FIG. 2 highlights the advantages of using engineered plasma cells for a protein delivery platform, such as longevity, protein production and its potential for ex vivo manipulation and generation.

FIG. 4 provides a table that shows different methods of CRISPR editing of the primary B cells and the benefits of the methods.

FIG. 14 shows that long template HDR is effective.

FIG. 29A and FIG. 29B shows sustained expression of human proteins in murine serum between 10 and 21 days.

FIG. 35 shows the results of the gene disruption and protein expression.

FIG. 36 shows targeting of abundant plasma cell genes using CRISPR.

FIG. 44A-44E shows Cas9-mediated disruption of PRDM1, IRF4, PAX5, or BACH2 alters B cell phenotype. (44A) Experimental workflow of the plasma cell differentiation assay. This workflow includes a three-step differentiation culture that is divided by a B cell activation phase (phase 1), a plasmablast differentiation phase (phase 2) and a plasma cell differentiation phase (phase 3) using the different cocktails of soluble factors and cytokines specified. Cells were transfected with Cas9 RNP after two days of initial activation, indels were assessed in genomic DNA on day 5, and phenotypes and IgM/IgG secretion were quantified on day 11. (44B) Schematic diagram of the roles of transcription factors PRDM1, IRF4, PAX5, and BACH2 as established by murine studies. (44C-44E) Primary B cells were activated and either mock treated, or transfected with Cas9 RNP targeting CCR5, PRDM1, IRF4, PAX5, or BACH2 and were subsequently differentiated in vitro. (44C) Top: representative flow plots showing CD19 and CD38 expression in live singlets and bar graph showing mean percentages of CD19lowCD38high plasmablasts 11 days post transfection. Bottom: representative flow plots showing CD27 and CD138 expression and bar graph showing percentage of CD27+CD138+ plasma cells 11 days post transfection (n=5, three donors). (44D) Genomic DNA was isolated five days after RNP transfection for allelic indel analysis by sequencing (n=5). (44E) Amounts of IgM (left) and IgG (right) in each culture as measured by ELISA (n=4, three donors). All bar graphs show means±SEM. n represents the number of independent experiments. Dotted lines mark mock levels. One-way ANOVA with the Sidak correction for multiple comparisons is used; *p<0.05; p<0.01; *p<0.001; ns, not significant. Statistical comparisons were made compared to mock. IFN-α, interferon α; PB, plasmablast; PC, plasma cell.

(FIG. 45A-45C) Primary B cells were activated for two days and either mock treated, or transfected with Cas9 RNP targeting CCR5, PRDM1, IRF4, PAX5, or BACH2 and were subsequently differentiated in vitro. (45A) IgG and IgM levels were quantified on day 11 by ELISA and normalized to cell numbers. IgG/IgM mass ratios were calculated and shown in bar graph (n=4). (45B) Cells were immunophenotyped on day 11 and gated on live, singlet, CD19lowCD38high plasmablasts. Left: representative CD19 histograms. Right: mean fluorescence intensities of CD19 (n=5). One-way ANOVA with the Sidak correction for multiple comparisons; *p<0.05; ***p<0.001; ns, not significant. Statistical comparisons were made compared to mock. As shown in FIG. 45 B from top.

FIG. 48A-48B shows targeted addition of GFP at the PRDM1 locus using RNP and AAV donor templates containing either 400 bp or 1.0 kb homology arms leads to stable GFP expression. (48A) Schematic of AAV PRDM1-GFP cassettes flanked by either 400 bp (top) or 1.0 kb (bottom) homology arms. The template on the top is identical to the one shown in FIG. 3. Both templates leave out the 3 bp PAM sequence. (48B) Primary B cells were activated for two days and gene-edited. Bar graph shows percentages of GFP+ cells on day 2 and day 11 after genome editing (n=3). All values are means±SEM. Unpaired two-tailed t-test; ns, not significant. HA, homology arm; ns, not significant.

FIG. 49A to 49E shows HDR-mediated integration of BAFF coding sequence at the CCR5 locus results in persistent BAFF secretion by gene-edited plasma cells and increases plasma cell differentiation and viability. (49A) Schematic of wild type CCR5 locus, CCR5g target location, an AAV construct that co-expresses GFP and BAFF via T2A linkage (AAV CCR5-GFP-BAFF) and a BAFF-expressing AAV construct (AAV CCR5-BAFF) with identical 800 bp flanking CCR5 homology arms. (49B) B cells were gene-edited after two days of in vitro activation, and were subsequently differentiated into plasma cells using the three-step culture system. Left: representative flow plots showing GFP expression on day 2 and day 11 post gene-editing in mock, CCR5-GFP-BAFF transduced cells with or without Cas9 RNP. Right: bar graph summarizing percentages of GFP+ cells on day 2 and day 11 post gene-editing (n=4, three donors). (49C) B cells were mock electroporated or transduced with AAV CCR5-GFP-BAFF or AAV CCR5-BAFF, with or without Cas9 RNP. Bar graph shows BAFF production as measured by ELISA at day 11 (n=4, three donors). (49D) Left: cells were counted at day 5 and day 11 post gene-editing. Bar graph shows fold changes in cell numbers. Right: viabilities at day 11 by flow cytometry. (n=5, four donors) (49E) Left: representative flow plots showing CD19 and CD38 expression at day 11 after genome editing using the AAV CCR5-BAFF vector. Right: bar graph summarizing percentages of CD19lowCD38high plasmablasts/plasma cells at day 11 (n=5, four donors). Both AAV CCR5-GFP-BAFF and CCR5-BAFF were added at 20,000 MOI. All bar graphs show means±SEM. N represents the number of independent experiments. One-way ANOVA was used with the Sidak correction for multiple comparisons; $p<0.01$; *$p<0.001$. PAM, protospacer adjacent motif; IL2ss, IL2 signal sequence; WT, wildtype; HA, homology arm; pA, SV40 poly-adenylation signal.

FIG. 51A-51D shows HDR-mediated integration of FIX coding sequence at the CCR5 locus leads to high levels of FIX secretion by gene-edited plasma cells ex vivo. (51A) Schematic of wild type CCR5 locus, CCR5g target location, and a FIX-expressing AAV construct with 800 bp flanking CCR5 homology arms (AAV CCR5-FIX). (51B-51D) Primary B cells were gene-edited using the AAV CCR5-FIX donor template and CCR5-targeting RNP (CCR5g RNP) with or without PAX5-targeting RNP (PAX5g RNP). B cells were subsequently differentiated in vitro. (51B) Frequency of on-target FIX integration in total alleles on day 11 after genome editing as assessed by digital droplet PCR. (51C) CD19 and CD38 expression on day 11. Left: representative flow plots; right: mean percentages of CD19lowCD38high plasmablasts (n=2). (51D) FIX production at day 11 after genome editing as measured by ELISA (n=3, two donors). AAV was added at 20,000 MOI. Bar graphs show means±SEM. n represents the number of independent experiments. One-way ANOVA with the Sidak correction for multiple comparisons were used; $p<0.01$; *$p<0.001$. PAM, protospacer adjacent motif; WPRE3, a shortened woodchuck hepatitis virus posttranscriptional regulatory element 55; WT, wildtype; HA, homology arm; pA, SV40 poly-adenylation signal.

FIG. 52A to 52C shows Outline of flow cytometry gating strategy. (52A-52B) Activated B cells were analyzed by flow cytometry. (52A) Preliminary gates for live cells (left) and singlets (middle) were used to define a viable cell population in unstained B cells before measuring fluorescence (GFP shown on right). (52B) Cells were stained with DAPI to mark dead cells. Viability levels were confirmed by quantifying percentages of DAPI-cells. (52C) Demonstration of general flow cytometry gating strategy for analyzing B cell immunophenotypes. B cells were stained with fluorochrome-conjugated anti-CD27, CD138, CD19, CD38 and live/dead stain-Alexa Fluor 350. Live singlets were defined using FSC/SSC, FSC-W/FSC-H and AF350-gates, and the resulting cell population was analyzed for expression of CD markers. Positive and negative populations were separated based on unstained controls. DAPI, 4,6-diamidino-2-phenylindole.

FIG. 54 shows Gene-edited, BAFF-expressing plasma cells stably secrete BAFF and human immunoglobulins in NSG mice. (54A) Experimental layout of NSG mouse transplant. Gene-edited B cells were generated as before after two days of in vitro B cell activation and were subsequently differentiated into plasma cells using the three-step culture system. 11 days post genome editing, cells were delivered intravenously into NSG mice (conditioned with Busulfan a day before transplant) at 10 million cells/animal. Blood samples were collected at day 10 and, finally, at day 21 when mice were sacrificed. (54B-54C) Blood serum proteins were quantified by ELISA at day 10 and day 21 (n=3). Shown are serum BAFF levels (54B) and serum human IgM and IgG levels (54C). All graphs represent means±SEM. n represents the number of mice per group. One-way ANOVA with the Sidak correction for multiple comparisons between groups was used, and paired two-tailed t-test for comparisons between two time points (day 10 vs 21); *p<0.05; p<0.01; *p<0.001. NSG, NOD/SCID/gamma-c null; PCs, plasma cells; IV, intravenous.

DEFINITIONS

Figure 1:
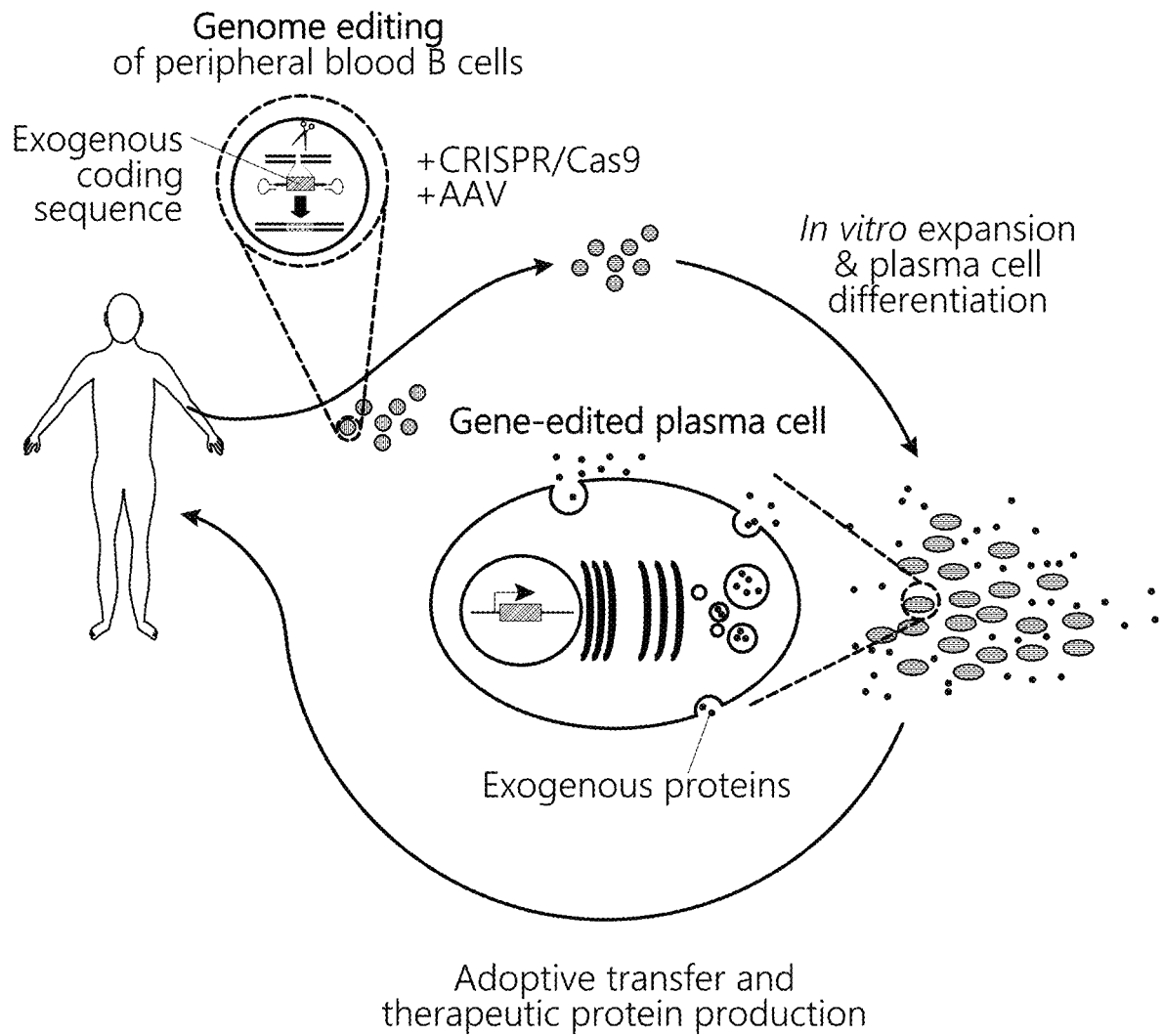
FIG. 1 shows a schematic of the potential clinical application of plasma cell therapy.

Unless defined otherwise, all technical and scientific terms used herein have the same meaning as commonly understood by one of ordinary skill in the art to which the invention pertains.

As used herein, "a" or "an" may mean one or more than one.

"About" as used herein when referring to a measurable value is meant to encompass variations of ±20% or ±10%, more preferably ±5%, even more preferably ±1%, and still more preferably ±0.1% from the specified value.

"Nucleic acid" or "nucleic acid molecule" have their plain and ordinary meaning when read in light of the specification, and may include but is not limited to, for example, polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid sequence encoding a protein is provided. In some alternatives, the nucleic acid is RNA or DNA.

"Macromolecule" has its plain and ordinary meaning when read in light of the specification, and may include but is not limited to, for example, a large molecule, such as a protein. The most common macromolecules in biochemistry can include nucleic acids, proteins, peptides, carbohydrates and macrocycles, for example. In the alternatives herein, plasma cells or plasma cell precursors are provided, wherein the plasma cells or plasma cell precursors express a macromolecule, such as a protein, protein mimetic, or a peptide. In some alternatives, the macromolecule is a prodrug.

"Prodrug" has its plain and ordinary meaning when read in light of the specification, and may include but is not limited to, for example, an inactive molecule, or macromolecule that is metabolized into a pharmacologically active drug. After administration, the prodrug is metabolized into a pharmacologically active drug. Prodrugs can be classified into two types, Type I prodrugs may be bioactivated inside the cells (intracellularly). Examples of these are anti-viral nucleoside analogs that must be phosphorylated and the lipid-lowering statins. Type II prodrugs are bioactivated outside cells (extracellularly), especially in digestive fluids or in the body's circulatory system, particularly in the blood. Examples of Type II prodrugs are salicin (described above) and certain antibody-, gene- or virus-directed enzyme prodrugs used in chemotherapy or immunotherapy.

"Proenzyme" has its plain and ordinary meaning when read in light of the specification, and may include but is not limited to, for example, a precursor of an enzyme. In some alternatives, the macromolecule is a protein, such as a proenzyme. In some alternatives, the proenzyme is Factor XI. In some alternatives, the proenzyme is from the family of the coagulation system. In some alternatives the proenzyme comprises fibrinogen.

"Protein" has its plain and ordinary meaning when read in light of the specification, and may include but is not limited to, for example, large macromolecules that comprise long chains of amino acid residues. Protein, polypeptide, and peptide can be ambiguous terms and can overlap in meaning. The term "protein" can refer to the complete biological molecule in a stable conformation, whereas "peptide" can be reserved for short amino acid oligomers that can lack a stable three-dimensional structure. The boundary between the two terms is not well defined and the number of amino acids can be close to about 20-30 residues for a peptide. The term "polypeptide" refers to a single linear chain of amino acids, usually regardless of length. Without being limiting proteins can be a serum protein, glycoprotein, lipoprotein, enzyme, nucleoprotein, structural protein, antibody, or prodrug, for example.

"B-cell activating factor" (BAFF), can also be referred to as "tumor necrosis factor ligand superfamily member 13B." BAFF has its plain and ordinary meaning when read in light of the specification, and may include but is not limited to, for example, a protein that is encoded by the TNFSF 13B gene. BAFF is a cytokine that belongs to the tumor necrosis factor (TNF) ligand family. In some alternatives herein, a B cell or plasma cell is provided, wherein the B cell or plasma cell expresses BAFF. BAFF has been shown to interact with and activate noncanonical NF-κB signaling pathways. This interaction triggers signals essential for the formation and maintenance of B cell, thus it is important for a B-cell survival. In some alternatives, the cells are manufactured to secrete BAFF to improve or enhance B-cell survival.

MHC class II molecules, have their plain and ordinary meaning when read in light of the specification, and may include but is not limited to, for example, a class of major histocompatibility complex (MHC) molecules normally found only on antigen-presenting cells such as dendritic cells, mononuclear phagocytes, some endothelial cells, thymic epithelial cells, and B cells. These cells are important in initiating immune responses.

A protein, polypeptide or peptide can also be found with a functional group or an additional moiety for functional purposes such as an enzyme co-factor, for example. Without being limiting a protein, polypeptide or peptide can comprise a hydrophobic group for membrane localization. Hydrophobic groups can be added by myristoylation, palmitoylation, isoprenylation, prenylation, farnesyltion, gerangylgeranylation or glypiation, for example.

Cofactors are another functional group, which are used for enhanced enzymatic activity. Without being limiting, cofactors can include lipolyation, Flavin moiety, heme C attachment, phophopantetheinylation, retinylidene formations.

Proteins and peptides can also comprise modified amino acids or non-natural amino acids. In some alternatives, the macromolecule comprises a protein mimetic. In some alternatives, the macromolecule is a prodrug.

In some alternatives herein, a method for of making plasma cells or plasma cell precursors that expresses a molecule, such as a protein, peptide or macromolecule is provided, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the molecule is a prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites. In some alternatives, the molecule is a macromolecule, such as a protein or an enzyme. In some alternatives, the protein or enzyme is for protein replacement, enzyme replacement and rescue of enzyme or protein deficiencies. In some alternatives, the macromolecule comprises Factor VIII, Factor IX, ADAMTS13, LIPA, SERPING1, SERPINA1, GLA, and/or ALPL. In some alternatives, the macromolecule is a prodrug.

"Cytokines" have their plain and ordinary meaning when read in light of the specification, and may include but is not limited to, for example, a group of proteins that function in cell signaling. For example cytokines can be involved in autocrine signaling, paracrine signaling and endocrine signaling as immunomodulating agents. Cytokines are important in health and disease, for example, playing a role in host responses to infection, immune responses, inflammation, trauma, sepsis, cancer, and reproduction. In some alternatives herein, a method for of making plasma cells or plasma cell precursors that expresses a molecule, such as a protein, peptide or macromolecule is provided, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the molecule is a macromolecule, such as a cytokine, cytokine receptor, complement protein or other inhibitory protein including, but not limited to: Il1 receptor antagonist for treatment or amelioration of periodic fever/autoinflammatory syndromes; complement inhibitory proteins (including Factor H, Factor I) for treatment or inhibition of atypical hemolytic uremic syndrome/membranoproliferative glomerulonephritis; and/or C1 inhibitor for hereditary angioedema.

"Anti-fibrotic molecule" has its plain and ordinary meaning when read in light of the specification, and may include but is not limited to, for example, a molecule that is used in the treatment of fibrosis, or excess fibrous connective tissue in an organ or tissue in a reparative or reactive process. Fibrosis can include pulmonary fibrosis, cystic fibrosis, Idiopathic pulmonary fibrosis, liver cirrhosis, atrial fibrosis, endomyocardial fibrosis, myocardial infarction, glial scars of the brain, arterial stiffness, Arthrofibrosis (knee, shoulder, other joints), Crohn's Disease (intestine), Dupuytren's contracture (hands, fingers), Keloid (skin), Mediastinal fibrosis (soft tissue of the mediastinum), Myelofibrosis (bone marrow), Peyronie's disease, Nephrogenic systemic fibrosis (skin), Progressive massive fibrosis (lungs), Retroperitoneal fibrosis (soft tissue of the retroperitoneum), Scleroderma/systemic sclerosis (skin, lungs) and/or some forms of adhesive capsulitis (shoulder). Without being limiting, anti-fibrotic molecules can include but is not limited to SCGB1A1 for the treatment of pulmonary fibrosis.

"Antibodies" also known as "immunoglobulins" have their plain and ordinary meaning when read in light of the specification, and may include but is not limited to, for example, large Y-shaped proteins that are secreted by plasma cells to neutralize pathogens. In some alternatives herein, a method for of making plasma cells or plasma cell precursors that expresses a molecule, such as a protein, peptide or macromolecule is provided, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the molecule is an antibody, or a portion thereof. In some alternatives herein, the plasma cell or plasma cell precursor expresses an antibody.

"Coding for" or "encoding" are used herein, has its plain and ordinary meaning when read in light of the specification, and may include but is not limited to, for example, the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

"Vector," "Expression vector" or "construct" have their plain and ordinary meaning when read in light of the specification, and may include but is not limited to, for example, a nucleic acid used to introduce heterologous nucleic acids into a cell that has regulatory elements to provide expression of the heterologous nucleic acids in the cell.

"B cells" or "B lymphocytes" have their plain and ordinary meaning when read in light of the specification, and may include but is not limited to, for example, a white blood cell type of the lymphocyte subtype. B cells are unlike lymphocytes such as T cells and natural killer cells, as B cells express B cell receptors on their cell membrane. The B cell receptors allow the B cell to bind a specific antigen, which will initiate an antibody response. B cells develop from hematopoietic stem cells. As described herein, B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof depending on the context.

B cell precursors include the cells from which the B cells are derived. Like T cells, B cells are lymphatic cells that are originated form the bone marrow, where they can reside until they are mature. The B cells, as described in the alternatives herein, include stem cells, early pro-B cells, late pro-B cells, large pre-B cells, small pre-B cells, immature B cells, T1 B cells, T2 B cells, marginal zone B cells, mature B cells, naïve B cells, plasmablasts (short-lived) cells, GC B cells, memory B cells, plasmablast cells and/or long lived plasma cells. In some alternatives of the plasma cell for expressing a molecule such as a macromolecule, protein or a peptide, the plasma cell is derived from a B cell. In some alternatives, the B cell is a memory B cell. In some alternatives, the B cell is a stem cell, early pro-B cell, late pro-B cell, large pre-B cell, small pre-B cell, immature B cell, T1 B cell, T2 B cell, marginal zone B cell, mature B cell, naïve B cell, plasmablasts (short-lived) cell, GC B cell, memory B cell, plasmablast cell or a long lived plasma cell. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the macromolecule is a prodrug.

"Memory B cells" have their plain and ordinary meaning when read in light of the specification, and may include but is not limited to, for example, the B cell sub-types that are formed within germinal centers following primary infection and are important in generating an accelerated and more robust antibody-mediated immune response in the case of re-infection. The B lymphocytes form the memory cells that can remember the same pathogen for future antibody production during future infections. In some alternatives of the plasma cell for expressing a molecule such as a macromolecule, protein or a peptide, the plasma cell is derived from a B cell. In some alternatives, the B cell is a memory B cell. In some alternatives, the macromolecule is a prodrug.

"Naïve B cell" has its plain and ordinary meaning when read in light of the specification, and may include but is not limited to, for example, a B cell that has not yet been exposed to an antigen. Once exposed to an antigen, the naïve B cell becomes a memory B cell. In some alternatives of the plasma cell for expressing a molecule such as a macromolecule, protein or a peptide, the plasma cell is derived from a B cell. In some alternatives, the B cell is a memory B cell. In some alternatives, the macromolecule is a prodrug.

"Peripheral blood mononuclear cells" (PBNC) as described herein are peripheral blood cells having a round nucleus. These cells consist of lymphocytes (T cells, B cells, NK cells) and monocytes, whereas erythrocytes and platelets have no nuclei, and neutrophils, basophils, and eosinophils have multi-lobed nuclei. In the alternatives described herein, the B cells are subject derived or are allogeneic peripheral blood mononuclear cells. In some alternatives, the B cells are blood-derived human B cells.

"Plasma cells" as described herein, are also called plasma B cells, plasmocytes, plasmacytes, or effector B cells. Plasma cells have their plain and ordinary meaning when read in light of the specification, and may include but is not limited to, for example, white blood cells that secrete antibodies and are transported by the blood plasma and the lymphatic system.

"Plasma cell precursor" can begin as an immature plasma cell. The most immature blood cell of the plasma cell lineage is called the plasmablast which can differentiate into a mature fully differentiated plasma cells. Plasmablasts can secrete more antibodies than a B cell, but less than a plasma cell. In some alternatives, a method of making a plasma cell that expresses a molecule is provided. In some alternatives, the plasma cell is a plasma cell precursor. In some alternatives, the plasma cell precursor is a plasmablast.

Cell isolation," also referred to as "isolating of cells," have their plain and ordinary meaning when read in light of the specification, and may include but is not limited to, for example, a cell separation technique. Such techniques are important in immunology and the techniques can be appreciated by those of skill in the art. Isolation or the separation of the cells can be performed, for example, by the use of antibodies against differentially expressed cell-surface molecules of targets. Without being limiting, B cells can be isolated by using a commercially available kit. Without being limiting, there are commercially available kits for B cell isolation by Miltenyi Biotec®, EasySep® Human B Cell Isolation Kit by StemCell® Technologies, and many others. In some alternatives herein, a method of making plasma cells or plasma cell precursors that express a molecule, such as macromolecule is provided, wherein the method comprises a step for isolating B cells. In some alternatives, the macromolecule is a protein, a protein mimetic or a peptide. In some alternatives, a method of making plasma cells or plasma cell precursors that express a molecule, such as a macromolecule is provided, the method comprising isolating B cells, developing the B cells, performing a first round of genome editing of the B cells for protein expression in absence of viral integration, expanding the B cells; and differentiating the B cells, optionally, after step (c) or (d), thereby producing plasma cells that express the molecule.

"Development" of a cell describes a cells differentiation to a cell type. For example, development into a B cell can occur in several stages, wherein each stage is marked by various gene expression patterns and immunoglobulin H chain and L chain gene loci arrangement. For example the B cells undergo VJ recombination as they develop. B cells develop from hematopoietic stem cells that originate from bone marrow. In some alternatives herein, a method of making plasma cells or plasma cell precursors that express a molecule such as a macromolecule is provided, wherein the method comprises a step for developing the B cells. In some alternatives, the cells are memory B cells or naïve B cells. In some alternatives, the macromolecule is a prodrug.

B cells undergo two types of selection while developing in the bone marrow to ensure proper development. For example, positive selection occurs through antigen independent signaling. Negative selection occurs through the binding of self-antigen with the B cell receptor.

"Genome editing" has its plain and ordinary meaning when read in light of the specification, and may include but is not limited to, for example, a process that include methods for genetic engineering in which DNA is inserted, deleted or replaced in the genome of a living organism. Editing a gene is also known as gene editing. In some alternatives described herein, a method of making plasma cells or plasma cell precursors that express a molecule, such as a macromolecule is provided, in which B cells or B cell precursors are subjected to at least one round of genome editing. Methods of genome editing can include, but is not limited to nucleic acid being inserted, deleted or replaced in the genome of a cell. In some alternatives, a nuclease is used to achieve this process. In some alternatives, the nuclease is engineered. In some alternatives, the methods include inducing double strand breaks that are repaired through nonhomologous end-joining (NHEJ) or homologous recombination (HR). In some alternatives, the step of genome editing is performed by introduction of a single stranded nucleic acid. In some alternatives, the at least one round of genome editing further comprises cycling the B-cells for homologous recombination of the single stranded DNA oligonucleotides or recombinant adeno-associated virus into the candidate genetic loci. In some alternatives, the genome editing of the B cells for protein expression is performed in the absence of viral integration. In some alternatives, a second round of genome editing is performed to excise a region. In some alternatives, a third round of genome editing is performed to result in expression of a drug activatable growth enhancer. In some alternatives herein, the genome editing is performed by nonpathogenic AAV mediated editing by direct homolougous recombination.

Genome editing can also employ the use of RNA and protein based transfection. For example the CRISPR/Cas system can be modified to edit genomes. This technique requires the delivery of the Cas nuclease complexed with a synthetic guide RNA (gRNA) into a cell, thus the cell's genome can be cut at a specific location and allow existing genes to be removed and/or add new ones. Thus, CRISPR/Cas and related programmable endonuclease systems are rapidly becoming significant genome editing tools of the biomedical research laboratory, with their application for gene disruption and/or gene targeting as demonstrated in a variety of cultured cell and model organism systems. In some alternatives, of the CRISPR/Cas system described herein, the Cas nuclease comprises Cas1, Cas2, Cas3, Cas4, Cas5, Cas6, Cas7, Cas8 or Cas9.

The basic components of CRISPR/Cas system comprise a target gene, a protospacer adjacent motif (PAM), a guide RNA, Cas endonuclease. An important aspect of applying CRISPR/Cas for genome editing is the need for a system to deliver the guide RNAs efficiently to a wide variety of cell types. This could, for example, involve delivery of an in vitro generated guide RNA as a nucleic acid (the guide RNA generated by in vitro transcription or chemical synthesis). In some alternatives, the nucleic acid could be rendered nuclease resistant by incorporation of modified bases.

The CRISPR-Cas system falls into two classes. The Class 1 system has a complex of multiple Cas proteins for the degradation of foreign nucleic acids. The Class 2 system has a single large Cas protein for a same purpose for the degradation of foreign nucleic acids. There are a 93 cas genes that are grouped into 35 families. 11 of the 35 families from a cas core which includes the protein families CAS1 to CAS9. As described herein, Cas comprises Cas1, Cas2, Cas3, Cas4, Cas5, Cas6, Cas7, Cas8 or Cas9.

Gene editing may also be performed by a novel non-nuclease based gene editing platform. A novel family of AAVs were previously isolated from human hematopoietic stem cells. These nonpathogenic AAVs are naturally present in healthy individuals and may possess unique gene editing and gene transfer properties. This technique is also described as AAV mediated editing by direct homolougous recombination (AmENDR™). This process is homolougous recombination by a natural biological mechanism that is used by cells to ensure highly precise DNA repair.

AAV mediated editing by direct homolougous recombination is initiated by design of homology sequence "arms" that are specific to a region of the genome and results in a permanent correction in the DNA when administered to cells. In some alternatives herein, the gene editing is performed by nonpathogenic AAV mediated editing by direct homolougous recombination. The identification of novel AAV genomes are described in Smith et al. (Mol Ther. 2014 September; 22(9): 1625-1634; incorporated by reference in its entirety herein). The novel AAVs described by Smith et al., represents a new class of genetic vector for the manipulation of HSC genomes. Furthermore, these vectors may greatly expand the ability to deliver genes to targeted tissues and cells including cells that are refractory to gene transfer which circumventing prevalent preexisting immunity to AAV2. In some alternatives, the gene editing is performed by nonpathogenic AAVs naturally present in hematopoietic cells, wherein the editing is performed by AAV mediated editing by direct homolougous recombination using the nonpathogenic AAVs as described in Smith et al.

"Engineered nucleases" have their plain and ordinary meaning when read in light of the specification, and may include but is not limited to, for example, enzymes that are engineered to be hybrid enzymes which can be used to specifically recognize a DNA sequence and efficiently edit the genome by the introduction of double-strand breaks. Without being limiting, there are four families of engineered nucleases are meganucleases, zinc finger nucleases (ZFN), transcription activator like effector-based nucleases (TALEN), and the CRISPR-Cas system.

"Meganucleases" have their plain and ordinary meaning when read in light of the specification, and may include but is not limited to, for example, endodeoxyribonucleases characterized by a large recognition site (double-stranded DNA sequences of 12 to 40 base pairs). In some alternative methods for making a plasma cell or plasma cell precursor that expresses a molecule such as a macromolecule, the method comprises: (a) isolating B cells, (b) developing the B cells, (c) performing a first round of genome editing of the B cells for protein expression in absence of viral integration, (d) expanding the B cells, and (e) differentiating the B cells, optionally, after step (c) or (d), thereby producing plasma cells that express a protein. In some alternatives, the first round of genome editing is performed by an RNA and protein based transfection. In some alternatives, the nuclease is a meganuclease.

"Zinc finger nucleases (ZFN)" have their plain and ordinary meaning when read in light of the specification, and may include but is not limited to, for example, engineered restriction enzymes that are generated by fusing a zinc finger DNA-binding domain to a DNA-cleavage domain. Zinc finger domains can be engineered to target specific desired DNA sequences and this enables zinc-finger nucleases to target unique sequences within complex genomes. In some alternative methods for making a plasma cell that expresses a molecule, such as a macromolecule, the method comprises: (a) isolating B cells, (b) developing the B cells, (c) performing a first round of genome editing of the B cells for protein expression in absence of viral integration, (d) expanding the B cells, and (e) differentiating the B cells, optionally, after step (c) or (d), thereby producing plasma cells that express a protein. In some alternatives, the first round of genome editing is performed by an RNA and protein based transfection. In some alternatives, the nuclease is a zinc finger nuclease.

"Transcription activator-like effector nucleases," (TALEN), have their plain and ordinary meaning when read in light of the specification, and may include but is not limited to, for example, restriction enzymes that can be engineered to cut specific sequences or sites in DNA. They are made by fusing a TAL effector DNA-binding domain to a DNA cleavage domain (a nuclease which cuts DNA strands). Transcription activator-like effectors (TALEs) can be engineered to bind to a desired DNA sequence, so when combined with a nuclease, the DNA can be cut at specific locations. Thus, the restriction enzymes can be introduced into cells, for use in genome editing or for genome editing in situ, a technique known as genome editing with engineered nucleases. The use of TALEN is known to those of skill in the art. In some alternatives described herein, a method of making plasma cells or plasma cell precursors that express a molecule, such as a macromolecule is provided, in which B cells or B cell precursors are subjected to at least one round of genome editing. Methods of genome editing can include, but is not limited to nucleic acid being inserted, deleted or replaced in the genome of a cell. In some alternatives, a nuclease is used to achieve this process. In some alternatives, the nuclease is engineered. In some alternatives, the methods include inducing double strand breaks that are repaired through nonhomologous end-joining (NHEJ) or homologous recombination (HR). In some alternatives, the method includes a first round of genome editing or genome editing. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary.

"Expansion" as described herein, refers to steps to increase the yield of the cells. In order for a group of cells to be useful or beneficial, the expansion of cells following isolation or extraction is necessary. The ability to expand B cell populations ex vivo is valuable for downstream applications including high throughput B cell assays and ex vivo differentiation of the cells. For example steps for increasing the number of B cells or gene edited B cells can include but are not limited to methods for introducing genetic modifications that artificially induce non-transformative expansion of gene edited B cells. Furthermore, there are also commercially available kits that comprise reagents for the growth and expansion of B cells. These methods and commercially available kits for B cell expansion can be appreciated by those of skill in the art. In some alternatives herein, the gene editing is performed by nonpathogenic AAV mediated editing by direct homoluogous recombination.

For "rapid B cell expansion," as described herein, edits to a B cell are introduced two days after activating and expanding for five additional days. It is expected that the cells will be expanded 50-fold.

"Differentiation" as described herein, refers to a cell changing from one cell type into another. Without being limiting, B cells can be differentiated based on their exposure to T cell-derived cytokines bound by B cell cytokine receptors. For example, CD40L can serve as a necessary stimulatory factor for B cell activation by binding the B cell surface receptor CD40, which can also affect differentiation. In the alternative methods described herein, the B cell is differentiated in a three step culture system comprising activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα.

"Somatic hypermutation" (or SHM) has its plain and ordinary meaning when read in light of the specification, and may include but is not limited to, for example, a cellular mechanism by which the immune system adapts to the new foreign elements that confront it (e.g. microbes), as seen during class switching. SHM diversifies B cell receptors used to recognize foreign elements (antigens) and allows the immune system to adapt its response to new threats during the lifetime of an organism. Somatic hypermutation involves a programmed process of mutation affecting the variable regions of immunoglobulin genes. Without being limiting, a cell may be stimulated to divide or proliferate after antigen recognition. During proliferation, the B cell receptor can undergo a high rate of somatic mutation that is at least $10^5$ to $10^6$ greater than the normal rate of mutation across the cellular genome. "Activation-induced cytidine deaminase," (AICDA and also known as AID), as described herein as AID, is a 24 kDa enzyme which in humans is encoded by the AICDA gene. AID creates mutations in DNA by deamination of cytosine base, which turns it into uracil (which is recognized as a thymine). Through an unknown mechanism, AID changes a C:G base pair into a U:G mismatch. The cell's DNA replication machinery recognizes the U as a T, and hence C:G is converted to a T:A base pair. During germinal center development of B lymphocytes, AID also generates other types of mutations, such as C:G to A:T. In the alternative methods described herein, the method of making plasma cells or plasma cell precursors that express a molecule, such as a macromolecule, further comprises applying methods to prevent somatic hypermutation of an antibody locus in the B cell or B cell precursor. In some alternatives, the method to prevent somatic hypermutation of an antibody locus in the B cell comprises disruption of an AID gene.

"Synthetically engineered protein" has its plain and ordinary meaning when read in light of the specification, and may include but is not limited to, for example, a protein that is made by protein or expressed from a synthetic gene that is manufactured through the method of genetic engineering. The synthetically engineered protein is usually made through rational protein design and may include unnatural amino acids as well. Furthermore the engineered protein can be transcribed and translated from a gene that is codon optimized for expression in a mammal, such as a human. In some alternatives, a method of making plasma cells or plasma cell precursors that express a molecule, such as a macromolecule is provided. In some alternatives, the macromolecule is a protein, protein mimetic or a peptide. In some alternatives, the protein is a genetically engineered protein. In some alternatives, the genetically engineered protein is encoded by a codon optimized gene. Genetically engineered proteins can also be a fusion or a chimeric protein, which are proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some alternatives, the protein is for prophylactic or therapeutic protection from infection (viral, bacterial, or parasitic) in healthy subject or following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and parasites. In some alternatives, the protein is for protein replacement, enzyme replacement or rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia). In some alternatives, the protein is for immune modulation via expressed cytokines, cytokine receptors, complement proteins or other inhibitory proteins including, but not limited to: Il1 receptor antagonist for treatment of periodic fever/autoinflammatory syndromes; complement inhibitory proteins (including Factor H, Factor I) for treatment or amelioration of atypical hemolytic uremic syndrome/membranoproliferative glomerulonephritis; and C1 inhibitor for hereditary angioedema. In some alternatives, the protein expressed is an anti-fibrotic molecule, including, but not limited to SCGB1A1 for the treatment or amelioration of pulmonary fibrosis. In some alternatives, the plasma cell or plasma cell precursor expresses a macromolecule, such as a protein, wherein the protein comprises therapeutic antibodies for autoimmune disorders, autoinflammatory disorders, immune dysregulation and cancer including but not limited to: anti-IL1 monoclonal antibodies for treatment of periodic fever/autoinflammatory syndromes; anti-TNF antibodies for inflammatory arthritis/inflammatory bowel disease, anti-IL33 antibodies for the treatment of asthma and anti-C5 antibodies for treatment of paroxysmal nocturnal hemoglobinuria/atypical HUS. In some alternatives, the plasma cell or plasma cell precursor expresses a macromolecule, such as a protein, wherein the protein is an Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein). In some alternatives, the plasma cell or plasma cell precursor expresses a macromolecule, such as a protein, wherein the protein is a glucose responses element for treatment of diabetic conditions. Synthetically engineered proteins or antibodies that are protective in viral, fungal, parasitic or bacterial infection are also contemplated. Without being limiting the synthetically engineered proteins or antibodies can be specific for HIV, viral pneumonia, or fungal infections.

"Engraftment" as described herein, refers to the expansion of cells and their cell progeny so that they can re-initiate the immune system or become incorporated into the body of the host. As such the cells may be able to grow and reproduce within the recipient. In some alternatives herein, a method of inducing engraftment of a cell that expresses a peptide for immunotherapeutic application, secreted by a B cell in a subject in need in vivo, is provided. In some alternatives, the cell expresses BAFF, APRIL, IL-10, IFN-alpha or IL-6.

A proliferation-inducing ligand (APRIL), as described herein, is also known as tumor necrosis factor ligand superfamily member 13 (TNFSF13), is a protein of the TNF superfamily recognized by the cell surface receptor TACI. In some alternatives herein, a B cell or plasma cell is provided, wherein the B cell or plasma cell expresses APRIL. In some alternatives, the plasma cell secretes IL-10 and/or IL-6. In some alternatives, the cell expresses BAFF, APRIL, IL-10, IFN-alpha or IL-6.

Those skilled in the art will appreciate that gene expression levels are dependent on many factors, such as promoter sequences and regulatory elements. Another factor for maximal protein selection is adaptation of codons of the transcript gene to the typical codon usage of a host. Many synthetic genes can be designed to increase their protein expression level. The design process of codon optimization can be to alter rare codons to codons known to increase maximum protein expression efficiency. In some alternatives, codon selection is described, wherein codon selection is performed by using algorithms that are known to those skilled in the art to create synthetic genetic transcripts optimized for higher levels of transcription and protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services. In some alternatives herein, the engineered protein is encoded by a gene, wherein the gene is codon optimized for expression in a human cell. In some alternatives, the genetically engineered protein is encoded by a codon optimized gene.

"Proprotein convertase subtilisin/kexin type 9 (PCSK9)" has its plain and ordinary meaning when read in light of the specification, and may include but is not limited to, for example, an enzyme that is expressed in many tissues and cell types. PCSK9 binds to the receptor for low-density lipoprotein particles (LDL), which typically transport 3,000 to 6,000 fat molecules (including cholesterol) per particle, within extracellular water. If PCSK9 is blocked, more LDLRs are recycled and are present on the surface of cells to remove LDL-particles from the extracellular water. Therefore, blocking PCSK9 can lower blood LDL-particle concentrations. PCSK9 orthologs are found in many species. Agents which block PCSK9 can lower LDL particle concentrations. In some alternatives, a method of making plasma cells or plasma cell precursors that express a molecule, such as a macromolecule is provided. In some alternatives, the macromolecule is a protein, protein mimetic or a peptide. In some alternatives, the protein is a genetically engineered protein. In some alternatives, the genetically engineered protein is encoded by a gene that has been codon optimized for expression in humans. In some alternatives, the genetically engineered protein is specific for PCSK9. In some alternatives, the plasma cell expressing the protein is administered to a subjects suffering from high cholesterol. In some alternatives, subject has at least 200 mg/dL of total cholesterol, wherein total cholesterol includes the levels HDL and LDL cholesterol.

In some alternatives, the plasma cell expressing the protein is administered to a subjects suffering from HIV, CMV or an autoimmune disorder. In some alternatives, the subject is suffering from multiple sclerosis. In some alternatives, the subject is suffering from Crohn's disease. In some alternatives, the protein is an antibody. In some alternatives, the protein comprises Tysabri (natalizumab) antibody or a portion thereof.

"Rituxan®" has its plain and ordinary meaning when read in light of the specification, and may include but is not limited to, for example, a medication sold under the brand name Rituxan® among others, which is a monoclonal antibody specific for CD20 and is used to treat or inhibit certain autoimmune diseases and types of cancer. It is used for non-Hodgkin's lymphoma, chronic lymphocytic leukemia, rheumatoid arthritis, idiopathic thrombocytopenic purpura, and/or pemphigus vulgaris. Rituximab is another name for this anti-CD20 monoclonal antibody. This anti-CD20 antibody is also used to treat rheumatoid arthritis. In RA, this medicine slows the inflammatory process and help reduce joint pain and swelling. This medicine is often used with other cancer or arthritis medications. The success of rituximab likely relates to a number of factors, one of which is that it is a chimeric rather than a murine antibody (Grillo-Lopez, 2000). Rituximab retains the murine CD20-binding Fab regions, but uses a human Fc portion.

"Negative selection of cells" has its plain and ordinary meaning when read in light of the specification, and may include but is not limited to, selecting out cells, for example, in which B-cells and T-cells that recognize MHC molecules bound to peptides of self-origin, or just MHC molecules with high affinity are deleted from the repertoire of immune cells. Negative selection can be performed with a commercial kit, such as a human B cell isolation kit (Miltenyi Biotec®, Auburn, CA).

"Rapamycin" also known as "sirolimus" has its plain and ordinary meaning when read in light of the specification, and may include but is not limited to, a macrolide compound that inhibits activation of T cells and B cells by reducing the production of interleukin-2 (IL-2). Rapamycin-inducible FKBP11 dimers has its plain and ordinary meaning when read in light of the specification, and may include but is not limited to, FKBP (FKBP1A) which will form a dimer in the presence of rapamycin.

The HPRT1 gene has its plain and ordinary meaning when read in light of the specification, and may include but is not limited to, a gene that provides instructions for producing an enzyme called hypoxanthine phosphoribosyltransferase 1. This enzyme allows cells to recycle purines, a type of building block of DNA and its chemical cousin RNA. Manufacturing purines uses more energy and takes more time than recycling purines, which makes recycling these molecules more efficient. Recycling purines ensures that cells have a plentiful supply of building blocks for the production of DNA and RNA. The process of recycling purines is also known as the purine salvage pathway. More than 200 mutations in the HPRT1 gene have been identified. These mutations include changes in single DNA building blocks (nucleotides) or insertions or deletions of small amounts of DNA within the gene. These changes result in either nonfunctional or very low-function hypoxanthine phosphoribosyltransferase 1. Under these conditions, uric acid, a waste product of purine breakdown, accumulates in the body and can cause gouty arthritis (arthritis caused by uric acid in the joints), kidney stones, and bladder stones. It is unclear how this enzyme deficiency causes the neurological and certain mutations in the HPRT1 gene can also cause a condition featuring gouty arthritis called HPRT-related gout, previously known as Kelley-Seegmiller syndrome. Individuals with this condition have lower than normal levels of hypoxanthine phosphoribosyltransferase 1.

"CD138" or "syndecan-1" can be used interchangeably and has its plain and ordinary meaning when read in light of the specification, and may include but is not limited to, a transmembrane (type I) heparan sulfate proteoglycan and is a member of the syndecan proteoglycan family. CD138 s a surface antigen that is expressed at high levels in plasma cells. The CD138 antigen is expressed on normal and malignant plasma cells but not mature B cells. As such, plasma cells may be purified, for example by use of CD138 positive selection and through use of CD138 antibodies attached to beads for cell purification. There are commercial kits that may be used to purify cells that are CD138 positive (e.g. The EasySep® Human CD138 Positive Selection Kit by STEMCELL®, The CD138+ Plasma Cell Isolation Kit by Miltenyl Biotech®). CD138 may be used to purify long lived plasma cells, as this population should engraft better and express more exogenous protein.

DETAILED DESCRIPTION

As described herein are the methods of making protein producing B cells, and the use of the protein producing B cells for immunotherapies. Additional alternatives can also include the protein producing B cells as well as compositions comprising the protein producing B cells. In some alternatives, the B cells express a macromolecule, such as a protein mimetic or a peptide.

Compositions and methods for inducing tolerance for a peptide secreted by a B cell or inducing engraftment is also provided herein. In some alternatives, these cells express BAFF, APRIL, IL-10, IFN-alpha or IL-6.

Methods for a reproducible system for enrichment and long-term in vitro culture of human B cell progenitors have previously been described by Rawlings et al. 1995, Rawlings et al. 1997, and Fluckinger et al 1998 ("Long-term culture system for selective growth of human B-cell progenitors." Proc. Natl. Acad. Sci. USA Vol. 92, pp. 1570-1574, February 1995, "Differentiation of human CD34+ CD38− cord blood stem cells into B cell progenitors in vitro." Exp Hematol. 1997 January; 25 (1):66-72; and "In vitro reconstitution of human B-cell ontogeny: from CD34 (+) multipotent progenitors to Ig-secreting cells." Blood. 1998 Dec. 15; 92(12):4509-20; all references incorporated by reference in their entireties). These types of systems, as previously reported, are important in the production of normal human B-lineage development and includes the production of mature Ig-secreting B cells and were used in studies of normal and abnormal early human B-lymphopoieses. In some systems, the long term in vitro culture system can be initiated with CD34+ or CD34+CD38− umbilical cord blood hematopoietic progenitors that can support normal human B-lineage development and can include the production of mature Ig-secreting B cells (Fluckiger et al. 1998). Although there are methods for isolating and developing B cells for Ig secretion, the development of plasma cells from differentiated B cells that have undergone genome engineering to express a protein has previously not been reported.

As previously reported, there has been genome editing of primary human hematopoietic cells. Co-delivery of designer nuclease mRNA and AAV donor provides a reliable approach for targeted gene modification in primary human hematopoietic cells. Such methods average in about 60% homology-directed repair (HDR) in primary T cells, multiple loci, with multiple experiments and independent donors and averages about 30-50% HDR in adult-mobilized CD34+ cells as shown in Sather et al. ("Efficient modification of CCR5 in primary human hematopoietic cells using a mega-TAL nuclease and AAV donor template." Sci Transl Med. 2015 Sep. 30; 7(307):307ra156; incorporated by reference in its entirety herein). This has also led to efficient delivery of therapeutic gene cassettes into candidate loci, such as HIV therapeutics into CCR5 locus: C46, CD19 CAR, & HIV CAR (Sather et al., Sci Transl Med. 2015 Sep. 30; 7(307); Roman-Ibarra et al., Mol Ther Nucleic Acids. 2016; 5:e352; Hale et al., Mol Ther Nucleic Acids. 2016, Hale Molec Ther Methods 2016; all incorporated by reference in their entireties herein), safe Harbor or TCRa locus-CARs and other therapeutic cassettes (Hale et al. Molec Ther Methods 2016; incorporated by reference in its entirety herein), CD40L gene in hyper-IgM syndrome to restores CD40L deficient T cell function (Hubbard et al. Blood 2016; incorporated by reference in its entirety herein), and methods to further enhance genome editing using viral helper proteins (Gwiazda et al. Mol Ther. 2016 Sep. 29; 24(9):1570-80; incorporated by reference in its entirety herein). Thus, modification of T cells (or CD34+ HSC) using this co-delivery approach is translatable to a wide range of clinical applications. However this approach was not contemplated for use in B cells.

In T cells, for example, gene targeting was used to disrupt the CCR5 gene. This was done by stable integration of gene cassette at target locus. Homology-directed repair mechanism was used using a megaTAL nuclease and rAAV donor template (Sather and Romano Ibarra et al., Sci Trans Med 2015; incorporated by reference in its entirety herein). Disruption of genes are also used to manufacture HIV protected anti-CD19CAR T cells (Milone et al, 2009 Mol Ther; Porter et al, 2011 NEJM; incorporated by reference in its entirety herein). Thus, successful techniques for genetic editing of B cells, which would also result in cells that have a long life, are much needed. As described herein, are some alternatives for B cell genetic editing, wherein the genome editing is performed by nonpathogenic AAV mediated editing by direct homolougous recombination.

As described herein, are engineered plasma cells as a macromolecule delivery platform. The macromolecule comprises proteins, protein mimetics, or peptides. The potential for the ex vivo manipulation and generation of cells include the increased longevity of the cells and protein production. For example, human influenza antibody titers can persist for over 90 years. These cells can persist in non-dividing state within bone marrow survival niche without need for ongoing antigen exposure and are relatively resistant to immunosuppression/chemotherapy. In regards to protein production, plasma cells can produce about 2000-10,000 immunoglobulin molecules per second, which can translate to about ~50-340 pg protein/cell/day. Industrial cell-line protein production can lead to about 20-90 pg protein/cell/day. The alternatives herein have the benefits of using the plasma cells, which are highlighted in FIG. 2.

There are several types of plasma cell-based therapies that are contemplated in the alternative methods described herein. This can include plasma cells that express antibodies that are specific to proteins that are expressed due to infection with a pathogen such as influenza virus, EBV, CMV, HIV, or malaria, for example. Therapeutic proteins are also contemplated. Without being limiting, therapeutic proteins can include proteins to supplement for enzyme deficiencies such as Factor VIII and Factor IX in those suffering from hemophilia, for example. In some alternatives, the therapeutic proteins can bind proteins of the lipid envelope of the influenza virus. In some alternatives, the lipid envelop proteins comprises glycoproteins hemagglutin and neuraminidase. In some alternatives, the therapeutic proteins can bind proteins of the CMV virus. In some alternatives, the proteins of the CMV virus comprises glycoprotein B.

Requirements for edited plasma cell regeneration can include, B cell activation and genome editing, B cell expansion B cell differentiation into long-lived plasma cells (LLPC). LLPC make up about 0.1-1% of all bone-marrow cells in healthy individuals. In mice there are about ~$10^6$ plasma cells, and in humans there are about ~$10^9$ plasma cells. There are also antigen specific LLPCs as described in Radbruch et al. ("Competence and competition: the challenge of becoming a long-lived plasma cell." Nat Rev Immunol. 2006 October; 6(10):741-50; incorporated by reference in its entirety herein). Exposure to tetanus toxoid led to tetanus-specific IgG concentrations of 10-20 μg/mL, which also implies a number of $0.8-1.6 \times 10^6$ tetanus-specific LLPCs. However there is a competition for the LLPC to reside in the bone marrow or spleen survival niche. Plasma cell longevity in the bone marrow was shown to be more than 90 days of survival without turnover. It was shown in Radbruch et al., and Slifka et al, adoptive transfer of $1.5 \times 10^4$ virus-specific plasma cells in absence of conditioning resulted in readily detectable anti-viral antibody ("Competence and competition: the challenge of becoming a long-lived plasma cell." Nat Rev Immunol. 2006 October; 6(10): 741-50; and "Humoral Immunity Due to Long-Lived Plasma Cells." Immunity, Vol. 8, 363-372, March, 1998; incorporated by reference in their entireties herein). Thus, for clinical efficacy, the number of engrafted engineered plasma cells should be at least $1\text{-}10\times10^6$ of edited long-lived plasma cells, and may be sufficient for many applications described herein. In some alternatives of the methods of treating, inhibiting or ameliorating a disease, such as cancer, in a subject in need or expressing a protein in a subject in need, the subject is administered at least $1\text{-}10\times10^6$ of edited long-lived plasma cells that express a protein, or a composition which is used to deliver at least $1\text{-}10\times10^6$ of edited long-lived plasma cells that express a protein. In some alternatives, the subject receives $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$ or $9\times10^9$ edited long-lived plasma cells that express a protein or any number of cells in between a range defined by any two aforementioned values. In some alternatives herein, the genome editing is performed by nonpathogenic AAV mediated editing by direct homolougous recombination.

The generation of gene-edited long-lived plasma cells also requires specific steps in the editing of the primary B cells as well as optimization of B cell differentiation. To date, there is existing literature in murine as well as human B cell editing. In murine studies, sgRNA was delivered into CAS9 transgenic murine B cells which led to gene disruption of candidate genetic loci including application to sgRNA screens. It was also shown that retroviral delivery of sgRNA (plus antibiotic drug selection) in primary B cells leads to up 80% gene disruption. However, was HR not tested in the B cells, furthermore, it is not clinically feasible to used transgenic CAS9 and integrating viral vector for sgRNA delivery into B cells ("Efficient CRISPR-mediated mutagenesis in primary immune cells using CrispRGold and a C57BL/6 Cas9 transgenic mouse line." Proc Natl Acad Sci USA. 2016 Nov. 1; 113(44):12514-12519; incorporated by reference in its entirety herein). Retroviral and LV-based, CRISPR/CAS9 delivery in murine B cells and hybridomas was also performed by Cheong et al. ("Editing of mouse and human immunoglobulin genes by CRISPR-Cas9 system." Nat Commun. 2016 Mar. 9; 7:10934; incorporated by reference in its entirety herein). Editing was performed of the Ig locus to mediate Ig class-switch. However, the technique had very low efficiency and again, HR was not tested by Cheong et al. Additionally, the techniques provided were not clinically feasible for use in B cells because of the long-term CAS9 expression from an integrated viral vector (Cheong et al.).

Figure 3:
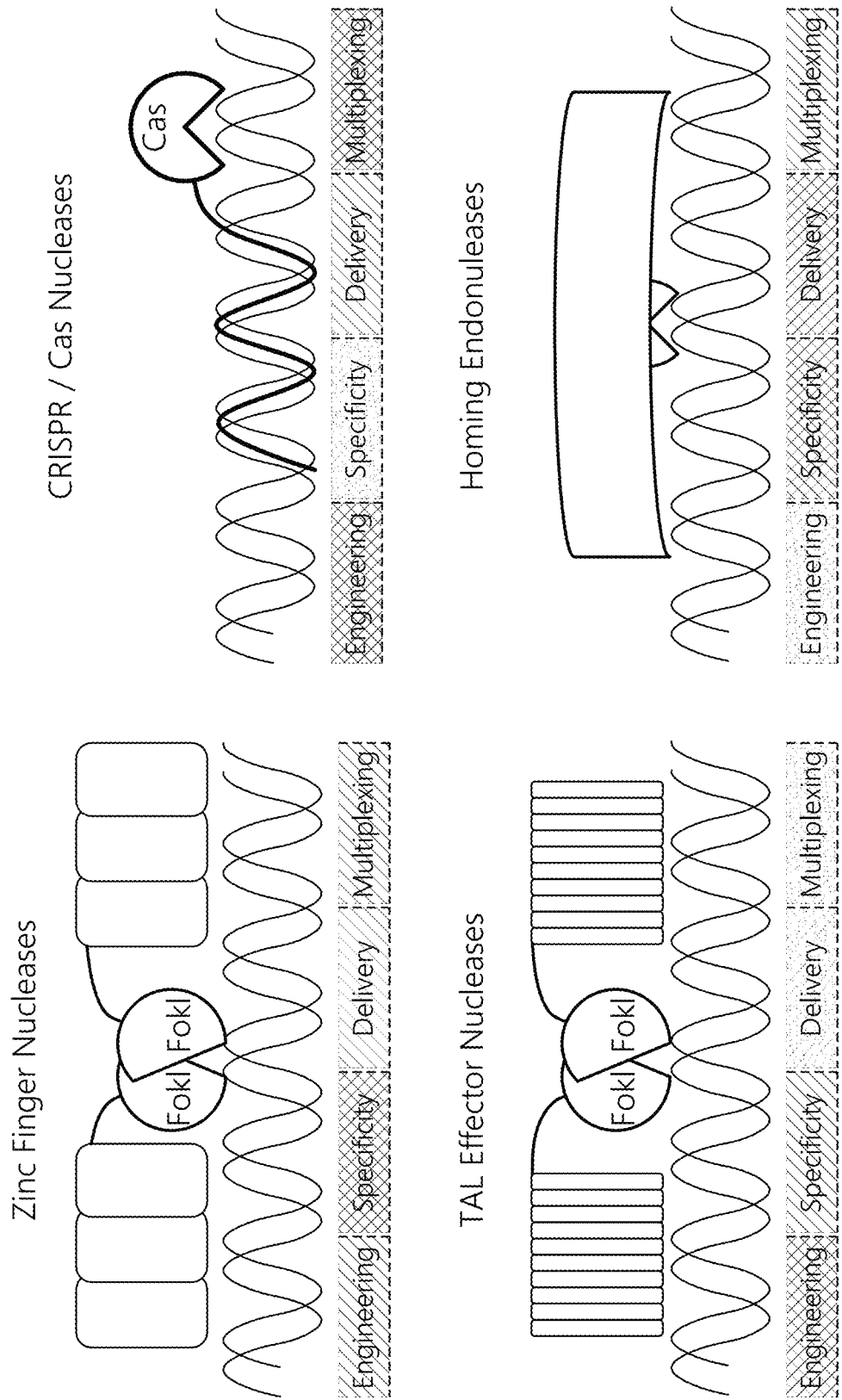
FIG. 3 shows candidate nuclease platforms that can be used in the alternatives described herein, such as, for example, zinc finger nucleases, CRISPR/Cas Nuclease systems, TAL effector nucleases and homing endonucleases.

For the preferred alternatives described herein, the candidate nuclease platform used for the methods of making the plasma cell from the B cell includes genetically engineered nucleases, zinc finger nucleases, CRISPR/Cas Nucleases, TAL Effector Nucleases, and Homing Endonucleases (FIG. 3). Options for genetic modification of B cells in the alternatives described herein are RNA (or RNP) plus AAV co-delivery as well as RNP/ODN (oligodeoxynucleotides) delivery. As shown in the tables of FIG. 4, this table shows qualitative comparisons of the approaches described herein, where 4 plus indicates a positive result and the 1 plus sign describes negative outcome. These tables show that RNP+ AAV or RNP+ODN are both specific, cost-effective and efficient.

Figure 5:
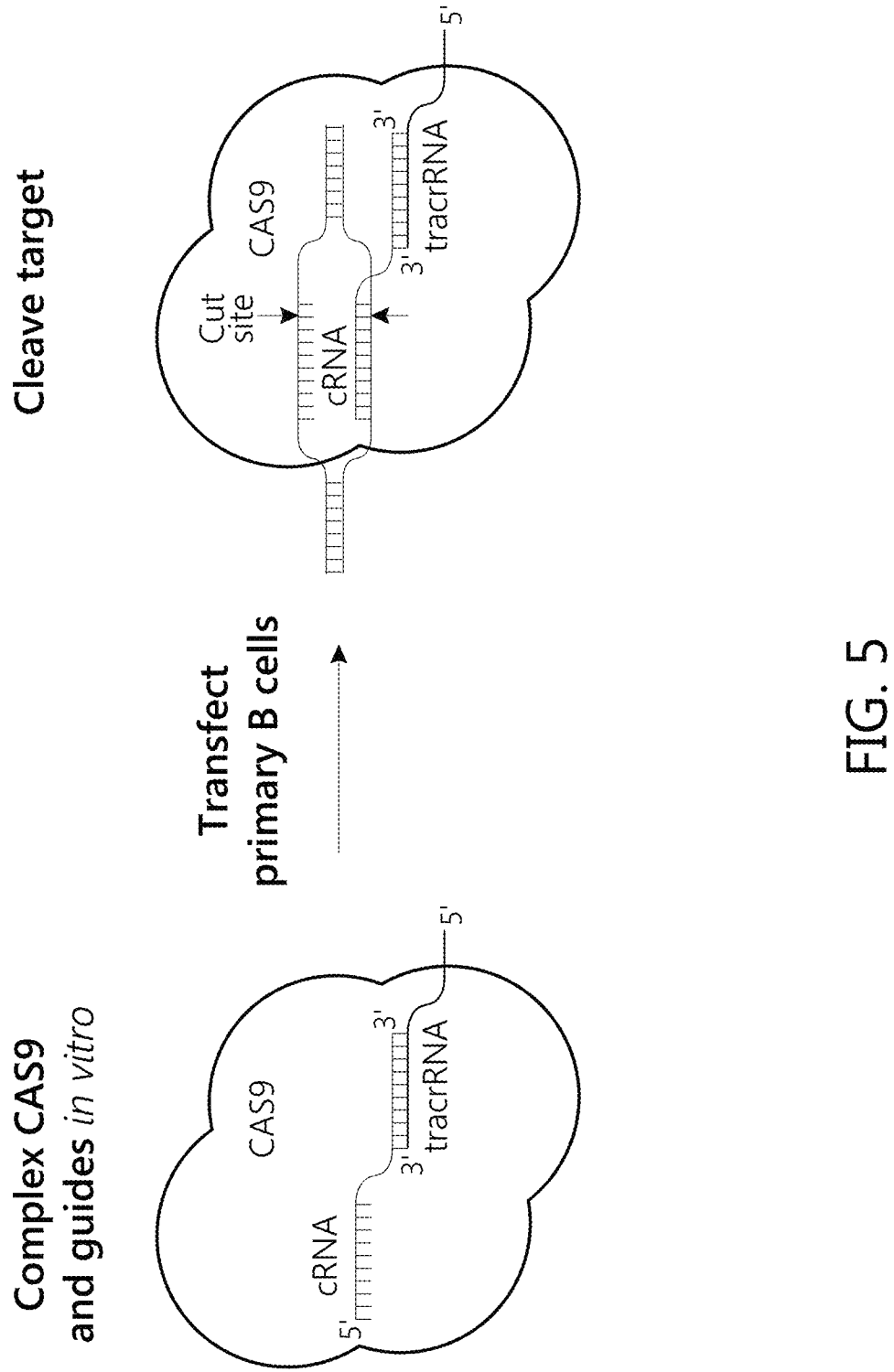
FIG. 5 shows the ribonucleoprotein strategy for the editing of B cells.

Also contemplated are ribonucleoprotein strategies for editing B cells. As shown in FIG. 5, complex CAS nuclease and RNA guides are prepared in vitro. The CAS nuclease and guides are then used to transfect the isolated primary B cells to cleave the desired target in the B cell genome. In some alternatives, the guide sequence comprises a sequence set forth in any one of SEQ ID NO: 63-112.

Genome Modification Rates, NHEJ and Site-Specific Homology Directed Repair (HDR) Genome Editing in Primary Human B Cells.

Genome modification rates of human B cell lines as described in the alternatives herein, are 10-fold greater than previous methods for genome editing reported; and provide the first demonstration of NHEJ and, most importantly, of site-specific homology directed repair (HDR) genome editing in primary human B cells. In fact, the literature show methods that do not provide a clinically translatable methodology for use in primary human B cells. In one study, CAS9 transgenic mice were generated and utilized. In this setting, CAS9 expression was achieved using a ubiquitous transgenic expression vector and guide RNAs were subsequently introduced via lentiviral vectors into CAS9 transgenic murine B cells, as described by Chu et al. ("Efficient CRISPR-mediated mutagenesis in primary immune cells using CrispRGold and a C57BL/6 Cas9 transgenic mouse line," Proc. Natl. Sci., 2016, Nov. 1; 113(44); 12514-12519; incorporated by reference in its entirety herein). Chu et al. did not show evidence of homology directed repair (HDR) and did not perform any work using primary human B cells. In a second report, retroviral delivery of CAS9 and guide RNAs to initiate gene disruption (NHEJ) in murine primary B cells and in human B cell lines was used by Cheong et al. ("Editing of mouse and human immunoglobulin genes by CRISPR-Cas9 system," Nature Commun, 2016 Mar. 9; 7:10934; incorporated by reference in its entirety herein). This disruption strategy was used to initiate class switch recombination and drive switching to specific antibody constant regions. In this case, disruption percentage (NHEJ) rates were low (5-10%) and there was no demonstration of HDR. In addition, no work was performed in primary human B cells. More recently, homology directed repair (HDR) was used by Pogson et al. in B cell lines to alter the antibody specificity of a hybridoma cell line ("Immunogenomic engineering of a plug-and-(dis)-play hybridoma platform; Nat. Commun. 2016 Aug. 17; 7: 12535; incorporated by reference in its entirety herein). In this case, the repair rates were modest (5%) and the authors utilized plasmid-based DNA delivery of the repair template and the CRISPR nuclease reagents. Again, no work was performed using primary human B cells. As described herein, none of these delivery systems are likely to result in the high efficiency genome editing that have been observed in the primary B cells (rates of 80% NHEJ or rates of ~40% HDR) of the alternatives herein. In fact, the editing rates of the alternatives described herein are surprising, because they significantly outpace the efforts of others in the literature regarding sustained gene expression following either transgene integration with lentiviral vectors or any existing genome editing approach utilized in B cells.

In some alternatives herein, the genome editing is performed by nonpathogenic AAV mediated editing by direct homolougous recombination.

The Yield of DNA Delivery is Greater than the Published Rates of DNA Delivery to Primary Human B Cells and has a Sustained Gene Expression.

The alternatives as described herein, have increased the yield of DNA delivery>1 log over published rates to primary human B cells. This advance is achieved in greatly facilitating HDR rates by either transfecting with single-stranded DNA oligonucleotides or transduction with capsid-specific AAV. Previous studies by Kim et al. using recombinant adenovirus have shown that vectors utilizing the serotype Ad-K35 can transduce primary human B cells at a rate of ~75% ("Enhanced antitumor immunotherapeutic effect of B-cell-based vaccine transduced with modified adenoviral vector containing type 35 fiber structures." Gene Ther. 2014, January; 21(1): 106-114). This vector serotype was designed for delivery of B cell vaccines, but in contrast to the sustained gene expression that is observed in the alternatives described herein, the HDR gene-edited loci in primary B cells, adenovirus delivery does not lead to long-term gene expression in B cells. In addition, adenoviral infected B cells are likely to be subject to immune responses in vivo that would make delivery of ex vivo adenoviral infected B cells highly problematic. In previous studies, recombinant Epstein-Barr virus (EBV) vector systems have also been developed for episomal-based gene delivery. Modified EBV vectors are capable of transducing of >80% of primary human B cells or CLL tumor cells as shown in Hellebrand et al. ("Epstein-Barr virus vector-mediated gene transfer into human B cells: potential for antitumor vaccination." Gene Ther. 2006, January; 13(2): 150-162). However, this vector class is associated with loss in episomal DNA over time leading to absence of long-term expression; further, recombinant EBV infected B cells express EBV viral proteins and therefore remain capable of triggering T cell mediated immune responses in EBV exposed individuals (the vast majority of the human subjects). In contrast to the relative efficiency of transient gene delivery using adenovirus or EBV, integrating gamma-retroviral or lentiviral (LV) vectors are extremely inefficient for transducing human B cells as shown by Serafini et al., Bovia et al. and Janssens et al. ("Molecular evidence of inefficient transduction of proliferating human B lymphocytes by VSV-pseudotyped HIV-1-derived lentivectors." Virology. 2004 Au 1; 325(2); 413-424, "Efficient transduction of primary human B lymphocytes and nondividing myeloma B cells with HIV-1-derived lentiviral vectors." Blood. 2003 Mar. 1; 101(5): 1727-1733, "Efficient and stable transduction of resting B lymphocytes and primary chronic lymphocyte leukemia cells using measles virus gp displaying lentiviral vectors." Blood. 2009 Oct. 8; 114(15): 3173-3180, "Efficiency of onco-retroviral and lentiviral gene transfer into primary mouse and human B-lymphocytes is pseudotype dependent." Hum Gene Ther. 2003 Feb. 10; 14(3):263-76; all incorporated by reference in their entireties herein). Several studies by Amirache et al. have shown that the VSV-G envelope typically used for LV vectors is ineffective in B cells (<5% transduction) because primary B cells lack the LDL receptor used by the VSV-G coat protein ("Mystery solved: VSV-G-LVs do not allow efficient gene transfer into unstimulated T cells, B cells, and HSCs because they lack the LDL receptor." Blood. 2014 Feb. 27; 123(9):1422-4; incorporated by reference in its entirety herein). In addition to lacking LV receptors, B cells likely express uncharacterized factors downstream of the receptor that limit LV transduction as described by Serafini et al. ("Molecular evidence of inefficient transduction of proliferating human B lymphocytes by VSV-pseudotyped HIV-1-derived lentivectors." Virology. 2004 Aug. 1; 325(2): 413-24; incorporated by reference in its entirety herein). As reported by Bovia et al., higher levels of transduction with VSV-G LV in primary human B cells (~25%) in the setting of sustained 4-5 day co-cultures with a mouse T cell tumor line (EL-4) or following co-infection with Epstein Barr virus. However, transduction using a clinically translatable system (e.g., without tumor cell lines and using only cytokine and CD40L-based stimulation) remained very low at 2% as shown by Bovia et al. ("Efficient transduction of primary human B lymphocytes and nondividing myeloma B cells with HIV-1-derived lentiviral vectors." Blood. 2003 Mar. 1; 101(5):1727-33, incorporated by reference in its entirety herein). Newer LV vectors employing alternative envelopes including either baboon retrovirus envelope protein (BaEV), measles virus envelope (MV) or gibbon-ape leukemia virus envelope (GALV) have demonstrated increased transduction efficiency of up to 50% with baboon endogenous retrovirus (BaEV), measles virus (MV) and Gibbon ape leukemia virus (GALV) as shown by Levy et al., ("Baboon envelope pseudotyped lentiviral vectors efficiently transduce human B cells and allow active factor IX B cell secretion in vivo in NOD/SCIDγc−/− mice." J Thromb Haemost. 2016 December; 14(12):2478-2492; "Baboon envelope pseudotyped lentiviral vectors efficiently transduce human B cells and allow active factor IX B cell secretion in vivo in NOD/SCIDγc−/− mice." J Thromb Haemost. 2016 December; 14(12):2478-2492; "Lentiviral vectors displaying modified measles virus gp overcome pre-existing immunity in in vivo-like transduction of human T and B cells," Mol Ther. 2012 September; 20(9):1699-712; "Efficient transduction of healthy and malignant plasma cells by lentiviral vectors pseudotyped with measles virus glycoproteins." Leukemia. 2012 July; 26(7):1663-70; "Measles virus glycoprotein-pseudotyped lentiviral vector-mediated gene transfer into quiescent lymphocytes requires binding to both SLAM and CD46 entry receptors." J Virol. 2011 June; 85(12):5975-85; "Efficient and stable transduction of resting B lymphocytes and primary chronic lymphocyte leukemia cells using measles virus gp displaying lentiviral vectors." Blood. 2009 Oct. 8; 114(15):3173-80; and "Efficient lentiviral transduction and transgene expression in primary human B cells." Hum Gene Ther Methods. 2012 December; 23(6):408-15; all references incorporated in their entireties herein), but at the cost of drastically lower viral titers. Because the titers of BaEV, GALV and MV LV vectors are much lower (>10-20-fold lower for BaEV, GALV and 100-fold lower for MV) than LV vectors using VSV-G coats, the practicality of transducing large numbers of primary B cells is limited, because high efficiency integration requires viral quantities that result in unacceptable toxicity. In summary, the demonstration of 40% stable expression of reporter genes following HDR into target loci in primary B cells with concomitant high-levels of cell viability greatly exceeds the frequency of sustained gene expression reported for either integrating or non-integrating viral vectors, which is shown by the results of the alternative methods described herein.

Several Steps are Used to Limit the Deleterious Impact of Innate Immune Signaling that is Trigged by Foreign DNA in Primary B Cells.

As described herein, there are several steps to limit the deleterious impact of innate immune signaling triggered by foreign DNA in primary B cells. In essentially all cell types, cytosolic self- or foreign-DNA (viral, bacterial, plasmid or oligonucleotide) binds to and activates the DNA sensor cGAS, leading to synthesis of the second messenger 2'3'-cGAMP which, in turn, triggers STING-dependent downstream signaling leading to type-I interferon production and additional transcriptional changes which is described in Crowl et al. ("Intracellular Nucleic Acid Detection in Autoimmunity." Annu Rev Immunol. 2017 Jan. 30; "cGAS-cGAMP-STING: The three musketeers of cytosolic DNA sensing and signaling." IUBMB Life. 2016 November; 68(11):858-870). In addition to cytosolic DNA sensing, many cell types (including human B cells) express endosomal toll-like receptors (TLRs) that recognize and respond to endosomal-delivered double-stranded DNA (dsDNA) ligands, triggering MyD88 dependent signals that promote type-I interferon and pro-inflammatory gene expression. The outcome of exogenous DNA-triggered innate signals is dependent upon the route of DNA delivery, the quantity of DNA delivered, DNA structure and cell lineage. In primary B, and T lymphocytes, transfection of dsDNA oligonucleotides promotes rapid cell death via apoptosis as described by Seiffert et al., Bell et al., Van Tendeloo et al., Cotten et al., and Ebert et al. ("Efficient nucleofection of primary human B cells and B-CLL cells induces apoptosis, which depends on the microenvironment and on the structure of transfected nucleic acids." Leukemia. 2007 September; 21(9):1977-83); "The analysis of costimulatory receptor signaling cascades in normal T lymphocytes using in vitro gene transfer and reporter gene analysis." Nat Med. 2001 October; 7(10):1155-8; "High-level transgene expression in primary human T lymphocytes and adult bone marrow CD34+ cells via electroporation-mediated gene delivery." Gene Ther. 2000 August; 7(16):1431-7; "Intracellular delivery of lipopolysaccharide during DNA transfection activates a lipid A-dependent cell death response that can be prevented by polymyxin B." Hum Gene Ther. 1997 Mar. 20; 8(5):555-61; and "Lymphocyte apoptosis: induction by gene transfer techniques." Gene Ther. 1997 April; 4(4):296-302; all incorporated by reference in their entireties herein). Introduction of plasmid DNA by transfection in primary T lymphocytes has been tested by multiple investigators as a means to achieve transgene expression. The effectiveness of this approach has been limited by low efficiency and high toxicity. Previous studies demonstrate expression ranging from 15-75% with progressively poorer viability (<30%) as expression increases ("The analysis of costimulatory receptor signaling cascades in normal T lymphocytes using in vitro gene transfer and reporter gene analysis." Nat Med. 2001 October; 7(10):1155-8; "High-level transgene expression in primary human T lymphocytes and adult bone marrow CD34+ cells via electroporation-mediated gene delivery." Gene Ther. 2000 August; 7(16):1431-7; "Gene transfection and expression in resting and activated murine CD4 T cell subsets." J Immunol Methods. 2003 November; 282(1-2):93-102; all incorporated by reference in their entireties herein). Low cell viability correlates with transfection triggered cell apoptosis ("Lymphocyte apoptosis: induction by gene transfer techniques." Gene Ther. 1997 April; 4(4):296-302; incorporated by reference in its entirety herein). While higher viably is observed using plasmid "Nucleofection" (perhaps due to reduced cytosolic DNA content), expression using this approach was also shown to be low ("High-efficiency transfection of primary human and mouse T lymphocytes using RNA electroporation." Mol Ther. 2006 January; 13(1):151-9; incorporated by reference in its entirety herein). While limited published data exist for B cells, the results from the experiments of the alternatives described herein suggest even poorer DNA transfection efficiencies with higher toxicity in primary B cells. These observations have lead most groups to abandoning plasmid DNA transfection for gene delivery. While not directly tested, cytosolic or endosomal DNA sensing likely explains this observed toxicity and strongly imply that this approach would not work for DNA template delivery for B cell genome editing. Consistent with this idea, in primary B cells plasmid DNA transfection also triggers TLR9-dependent type-I interferon and pro-inflammatory gene expression ("Oligonucleotide delivery by nucleofection does not rescue the reduced proliferation phenotype of gene-edited cells." Nucleic Acid Ther. 2012 December; 22(6):405-13; incorporated by reference in its entirety herein); and this plasmid driven type-I interferon production is independent of CpG motifs. The alternatives described herein, avoids the toxicity problem associated with transducing primary B cells, which have not been previously reported.

Thus, triggering of these pathways is likely highly problematic for efficient B cell editing and HDR. Taking these observations into consideration, the alternative methods described herein utilize single-stranded DNA (ssDNA) delivery to limit these deleterious responses to foreign DNA. The rationale for choosing ssDNA donor templates is that the binding constant of cGAS for ssDNA (1.5 µM) is dramatically higher than that for dsDNA (87 nM), leading to the hypothesis that ssDNA is likely to elicit lower innate immune signaling in response to transfection than dsDNA ("Structure of human cGAS reveals a conserved family of second-messenger enzymes in innate immunity." Cell Rep. 2013 May 30; 3(5):1362-8; incorporated by reference in its entirety herein). Further, ssDNA are poorly recognized by TLR9 and hence not expected to trigger TLR9 innate signaling—an additional challenge not encountered in T cell editing. Therefore two exemplary alternatives for delivery ssDNA are described: a) modified ssDNA donor oligonucleotides via transfection ("Chemically modified guide RNAs enhance CRISPR-Cas genome editing in human primary cells." Nat Biotechnol. 2015 September; 33(9):985-9; and "Enhancing homology-directed genome editing by catalytically active and inactive CRISPR-Cas9 using asymmetric donor DNA." Nat Biotechnol. 2016 March; 34(3):339-44; both references incorporated by reference in their entireties herein); or b) ssDNA as recombinant AAV genomes.

B Cells have a High Capacity for Site-Specific HDR Editing

The alternatives described herein have unexpectedly demonstrated that B cells have a high capacity for site-specific HDR editing. Site-specific genome editing (HDR) in ~100% of primary B cells have been observed in which one can detect transduction or transfection with templates for homology-directed-repair by using the alternative methods of editing as described herein. While others have described methods for high rates of HDR-genome editing in primary T cells, even in the most optimized settings, HDR rates (~20-50%) remain below the levels of AAV or oligonucleotide gene delivery (80-100%)("Highly efficient homology-driven genome editing in human T cells by combining zinc-finger nuclease mRNA and AAV6 donor delivery." Nucleic Acids Res. 2016 Feb. 18; 44(3):e30; Sather et al., Sci Transl Med. 2015 Sep. 30; 7(307); and "Generation of knock-in primary human T cells using Cas9 ribonucleoproteins." Proc Natl Acad Sci USA. 2015 Aug. 18; 112(33): 10437-42; both references incorporated by reference in their entireties herein). Importantly, despite advances in modulating AAV turnover using co-delivery of other viral proteins leading to marked increase in AAV genomes and/or reduced AAV turnover in T cells, HDR rates are only modestly increased ("High Efficiency CRISPR/Cas9-mediated Gene Editing in Primary Human T-cells Using Mutant Adenoviral E4orf6/E1b55k "Helper" Proteins." Mol Ther. 2016 Sep. 29; 24(9):1570-80; incorporated by reference in its entirety herein). Thus, relative to other primary cell types commonly used for site-specific genome editing applications, a remarkable efficiency for HDR in primary human B cells have uncovered, which has not been demonstrated or previously reported. It is hypothesized that these unexpected findings showing surprisingly efficient HDR in human B cells reflects an unusual aspect of primary B cell biology and is perhaps related to an increased permissiveness to DNA breaks and resolution by HDR that has evolved to facilitate safe genomic modification during germinal center B cell activation and class-switch recombination.

Optimal B Cell Culturing Conditions to Enable High Rates of Site-Specific Genome Editing and Subsequence Expansion and Differentiation of Gene-Edited Cells.

As described herein, the alternative methods have determined optimal B cell culturing conditions to enable high rates of site-specific genome editing and subsequent expansion and differentiation of gene edited cells. In several other primary cell types, several researchers have found that persistence in the G2 phase of cell cycle or high degrees of cell cycling promotes HDR during site-specific genome editing ("High Efficiency CRISPR/Cas9-mediated Gene Editing in Primary Human T-cells Using Mutant Adenoviral E4orf6/E1b55k "Helper" Proteins." Mol Ther. 2016 Sep. 29; 24(9):1570-80; incorporated by reference in its entirety herein). In this exemplary alternative, the cell culture conditions were optimized to enable rapid cycling of undifferentiated B cells, and thus increased the time the cells spend in G2 ("Regulation of homologous recombination in eukaryotes." Annu Rev Genet. 2010; 44:113-39. "Enhanced homology-directed human genome engineering by controlled timing of CRISPR/Cas9 delivery." Elife. 2014 Dec. 15; 3:e04766; "High Efficiency CRISPR/Cas9-mediated Gene Editing in Primary Human T-cells Using Mutant Adenoviral E4orf6/E1b55k "Helper" Proteins." Mol Ther. 2016 Sep. 29; 24(9):1570-80; incorporated by reference in its entirety herein). In some alternatives, reagents are delivered for site-specific genome editing during this cycling phase, leading to efficient HDR-gene editing. In some alternatives, the culture conditions were further optimized, wherein the edited cell populations are expanded to high numbers and to subsequently enable the terminal differentiation of these edited and expanded B cells into long-lived plasma B cells during secondary and tertiary culture phases, respectively. This experimental design has not been previously considered for genome engineering of primary B human cells. In some alternatives herein, the gene editing is performed by nonpathogenic AAV mediated editing by direct homolougous recombination.

Several alternatives are described herein, included among these are: (a) designing editing strategies for target loci that were found in several alternatives to be highly expressed in antibody secreting B cells (JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1, and others) and that are not subject to aberrant somatic hypermutation or required for differentiation into antibody secreting cells; (b) inserting genetic modifications that artificially induce triggerable, non-transformative expansion of edited cells including, but not limited to, disruption of HPRT locus and selection of gene edited cells using 6-TG; (c) development of a targeted sequencing method to ensure the integrity of the B cell product at loci that are known to confer susceptibility to non-Hodgkin's lymphoma or multiple myeloma; (d) designing protein producing products for clinical situations where stable delivery of the protein by a B cell provides clinical benefit by avoiding organ toxicity or immune responses observed in some AAV delivery studies (for example, Factor IX), by enabling delivery of multiple different protein simultaneously (delivery of multiple neutralizing antibodies for HIV or other pathogens), or promoting stable, steady-state levels of protein delivery over time. These would not be subject to aberrant somatic hypermutation, as previously described ("Two levels of protection for the B cell genome during somatic hypermutation." Nature. 2008 Feb. 14; 451(7180): 841-5; "DNA damage defines sites of recurrent chromosomal translocations in B lymphocytes." Nature. 2012 Feb. 7; 484(7392):69-74; "Translocation-capture sequencing reveals the extent and nature of chromosomal rearrangements in B lymphocytes." Cell. 2011 Sep. 30; 147(1):95-106; all incorporated by reference in their entireties herein).

In some alternatives herein, the gene editing is performed by nonpathogenic AAV mediated editing by direct homolougous recombination.

Development of In Vivo Pre-Clinical Models

Additional alternatives contemplated herein are in vivo pre-clinical models that can be used to assess the efficacy of the B cells. Murine models exist that could be used for this purpose.

CRISPR/Cas9, crRNA, tracrRNA

In the alternatives herein, CRISPR guide targets at the BLIMP1, IRF4, BCL6, PAX5, MITF, BACH2, IRF8 loci were designed for several alternative methods described herein, using the online MIT CRISPR design tool and the Broad Institute sgRNA design tool. A tracrRNA recognition sequence (GUUUUAGAGCUAUGCU; SEQ ID NO: 1) was added to the 3' end of each selected guide target to form the complete synthetic crRNA sequence. The crRNA guides were synthesized by IDT® with additional modifications—phosphorothioate linkages between the four nucleotides on the 5' end and the 3' end, as well as 2'O-methyl groups on the three nucleotides on the 5' end and the 3' end). The tracrRNA with proprietary chemical modifications, as well as the recombinant Cas9 nuclease were also purchased from IDT®.

Prior to delivery of the nuclease into cells (method shown in FIG. 5), the crRNA and tracrRNA were mixed at a 1:1 molar ratio. The mixture was heat-shocked at 95° C. for 5 minutes and then incubated at room temperature for 30-60 minutes to allow crRNA: tracrRNA hybrids to form. Next, the crRNA:tracrRNA hybrids were mixed with the Cas9 nuclease at a 1.2:1 molar ratio and incubated at room temperature for 10-20 minutes to allow Cas9:crRNA: tracrRNA complexes to form. The Cas9 ribonucleoprotein (RNP) complexes were then delivered into cells by electroporation.

Single-Stranded ODNs

All single-stranded ODNs (ssODNs) were commercially synthesized by IDT® (Ultramer® DNA Oligonucleotides) with phosphorothioate linkages between the three nucleotides on the 5' end as well as the 3' end.

Production of Recombinant AAV

AAV stocks were produced as previously described in Khan et al. (Khan I F, Hirata R K, Russell D W. AAV-mediated gene targeting methods for human cells. Nature Protocols (2011) 6, 482-501; incorporated by reference in its entirety herein). The AAV vector, serotype 6 helper plasmid (pRepCap6) and HgT1-adeno helper plasmid were transfected into HEK293T cells. Cells were harvested 48 hours later, lysed by 3 freeze-thaw cycles, treated with benzonase, and the cell lysate was purified using an iodixanol density column.

Primary Human CD19+ B Cell Genome Editing

Peripheral blood mononuclear cells (PBMCs) collected from CD34+ negative selection flow-through from whole blood of healthy male donors post hematopoietic stem cell mobilization were purchased from Fred Hutchinson Cancer Research Center. Alternatively, PBMC were collected from healthy donors using an IRB approved protocol. CD19$^+$ B cells were isolated from PBMCs by negative selection using a human B cell isolation kit (Miltenyi Biotec®, Auburn, CA) and cultured in Iscove's modified Dulbecco's medium (IMDM, Thermo Fisher Scientific®) supplemented with 10% fetal bovine serum and 55 µM beta-mercaptoethanol at 1-1.5×10⁶ cells/mi. B cells were activated with 100 ng/ml of recombinant human MEGACD40L® (Enzo Life Sciences®), 1 µg/ml of CpG oligodeoxynucleotide 2006 (Invitrogen®), 50 ng/ml of IL-2 (Peprotech®), 50 ng/ml of IL-10 (Peprotech®) and 10 ng/ml of IL-15 (Peprotech®) for 48 hours. Cells were then electroporated with Cas9 RNP complexes using the Neon Transfection System (ThermoFisher Scientific®) as follows. Cells were washed with PBS and resuspended in Neon Buffer T. 30.5 pmol Cas9 RNP per 3×10⁵ cells was added to the resuspension so that the final cell density was 3×10⁷ cells/ml. Cells were then electroporated (1700V, 20 ms, 1 pulse) in 10-µl Neon tips, and then transferred into pre-warmed B cell culture medium with MEGACD40L®, CpG, IL-2, IL-10 and IL-15 and cultured at 1.5×10⁶ cells/ml. For samples transfected with an ssODN donor template, ssODN was added concurrently with Cas9 RNP at 30 pmol per 3×10⁵ cells, unless otherwise specified. For samples transduced with AAV, AAV was added to the culture immediately after electroporation. The added AAV volume was 20% of the cell culture volume, unless otherwise specified. Culture volume was doubled 24 hours after electroporation, and medium was replenished every two to three days thereafter to maintain a cell density of 1×10⁶ cells/ml.

Flow Cytometry

Flow cytometric analysis was done on an LSR II flow cytometer (BD Biosciences®) and data were analyzed using FlowJo software (TreeStar). To assess B cell surface marker expressions, cells were stained with fluorophore-conjugated antibodies: CD19-PECy7 (clone HIB19, eBioscience®), CD27-APC (clone 0323, Life Technologies®), CD20-PE (clone L27, BD Biosciences®), CD38-PerCPCy5.5 (clone HIT2, BD Biosciences®), CD138-Alexa Fluor 700 (clone MI15, BioLegend®), HLA-DR-FITC (clone L243, BD Biosciences®); CD19-PECy7 (clone HIB19, eBioscience®), CD27-APC (clone 0323, Life Technologies®), CD20-FITC (clone L27, BD Biosciences®), CD38-PerCPCy5.5 (clone HIT2, BD Biosciences®), CD138-Alexa Fluor 700 (clone MI15, BioLegend®), IgD-PE (clone IA6-2, BD Biosciences®), IgM-Pacific Blue (clone MHM-88, BioLegend®). Dead cells were excluded using Fixable Live/Dead stain-Alexa Fluor 350 (LifeTechnologies®).

Plasma Cell Differentiation Assays

In the alternatives herein, plasma cells were differentiated in vitro using a three-step culture system as previously characterized in Jourdan et al. (Jourdan M, Caraux A, De Vos J, Fiol G, Larroque M, Cognot C, Bret C, Duperray C, Hose D, Klein B. An in vitro model of differentiation of memory B cells into plasmablasts and plasma cells including detailed phenotypic and molecular characterization. Blood (2009) 114(25), 5173-5181; incorporated by reference in its entirety herein). CD19⁺ B cells isolated from PBMCs were activated for 2 days with MEGACD40L® (100 ng/ml), CpG (1 µg/ml), IL-2 (50 ng/ml), IL-10 (50 ng/ml) and IL-15 (10 ng/ml) and edited as outlined. Cells were then expanded for another 5 days in the same cocktail. Next, cells were washed and seeded in medium with IL-2 (50 ng/ml), IL-6 (50 ng/ml), IL-10 (50 ng/ml) and IL-15 (10 ng/ml) for 3 days. At day 10, cells were washed and seeded in medium with IL-6 (50 ng/ml), IL-15 (10 ng/ml) and human interferon-α 2B (100 U/ml, Sigma-Aldrich®) for 3 days to stimulate plasma cell differentiation. At day 13, cell phenotypes were analyzed by immunofluorescence. To obtain a purified population of plasma cells, a BD® FACSAria II cell sorter (BD Biosciences®) was used to sort cells stained with CD27-APC (clone 0323, Life Technologies®) and CD138-Alexa Fluor 700 (clone MI15, BioLegend®).

In the alternatives herein, experiments were performed to optimize the long-term maintenance of in vitro generated plasma cells in the culture. In order to do this, plasma cell viability were compared using the following culture systems or combinations thereof: i) plasma cell culture on M2-10B4 stromal cells as described in Cocco et al. (Cocco M, Stephenson S, Care M A, Newton D, Barnes N A, Davison A, Rawstron A, Westhead D R, Doody G M, Tooze R M. In Vitro Generation of Long-lived Human Plasma Cells. J Immunol (2012) 189(12), 5773-5785; incorporated by reference in its entirety herein); ii) culture without stromal cells in media supplemented with combinations of IL-6 (10-50 mg/mL), APRIL (200 ng/mL), BAFF (200 ng/mL), IGF1 (10 ng/mL) and/or SDF-1 (200 ng/mL) as described in Jourdan et al. (Jourdan M, Cren M, Robert N, Bolloré K, Fest T, Duperray C, Guilloton F, Hose D, Tarte K, Klein B. IL-6 supports the generation of human long-lived plasma cells in combination with either APRIL or stromal cell-soluble factors. Leukemia (2014) 28, 1647-1656; incorporated by reference in its entirety herein). It is anticipated that these culture conditions will allow long-term maintenance of in vitro generated plasma cells for >3 months.

Molecular Analyses—PCR, T7, Sequences

Figure 6:
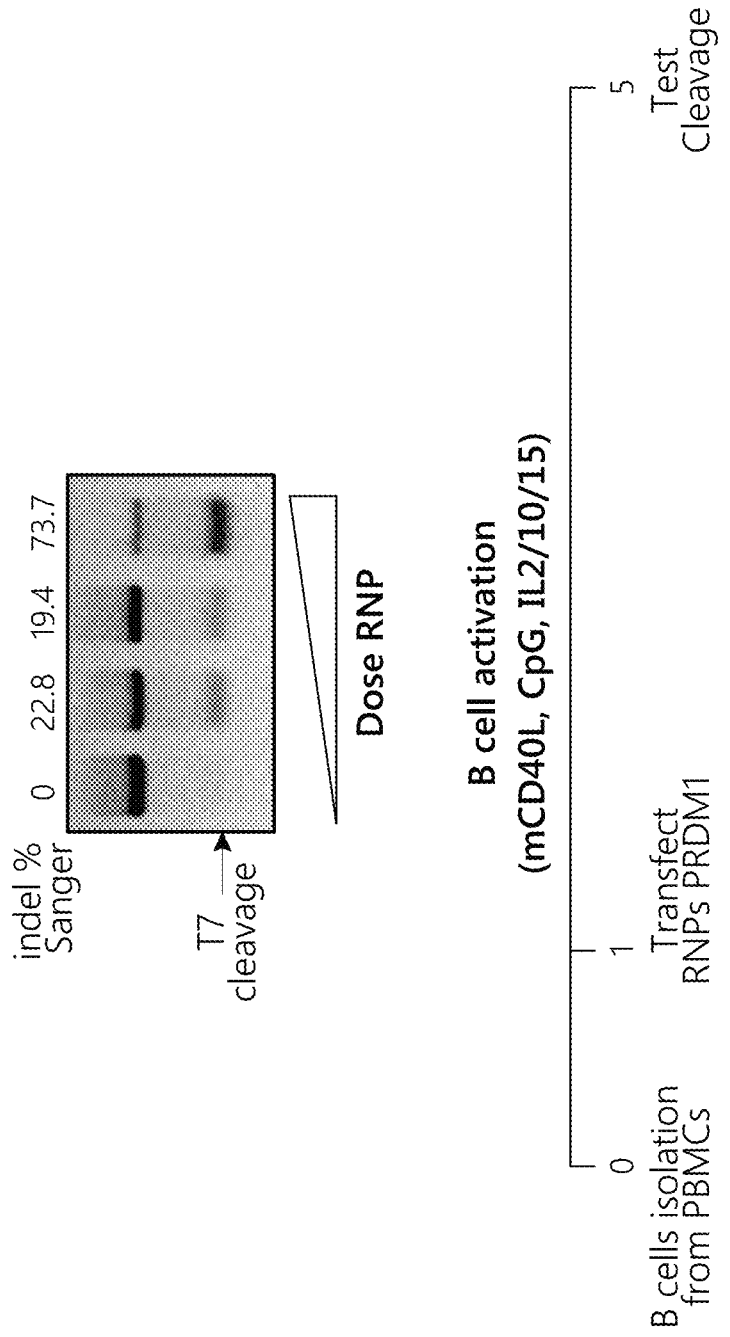
FIG. 6 shows the indel in a Sanger sequencing gel. As shown, increasing the concentration of ribonuclease increased the T7 cleavage during a 5 day DNA cleavage protocol. For the experiment, B cells were isolated from peripheral blood mononuclear cells at day zero and transfected with ribonucleoproteins and a PR domain zinc finger protein at day 1. The cells were then activated with mCD40L, CpG and IL2, IL10, and IL15. At day 5, the DNA was extracted from the cell to test for DNA cleavage.
Figure 7:
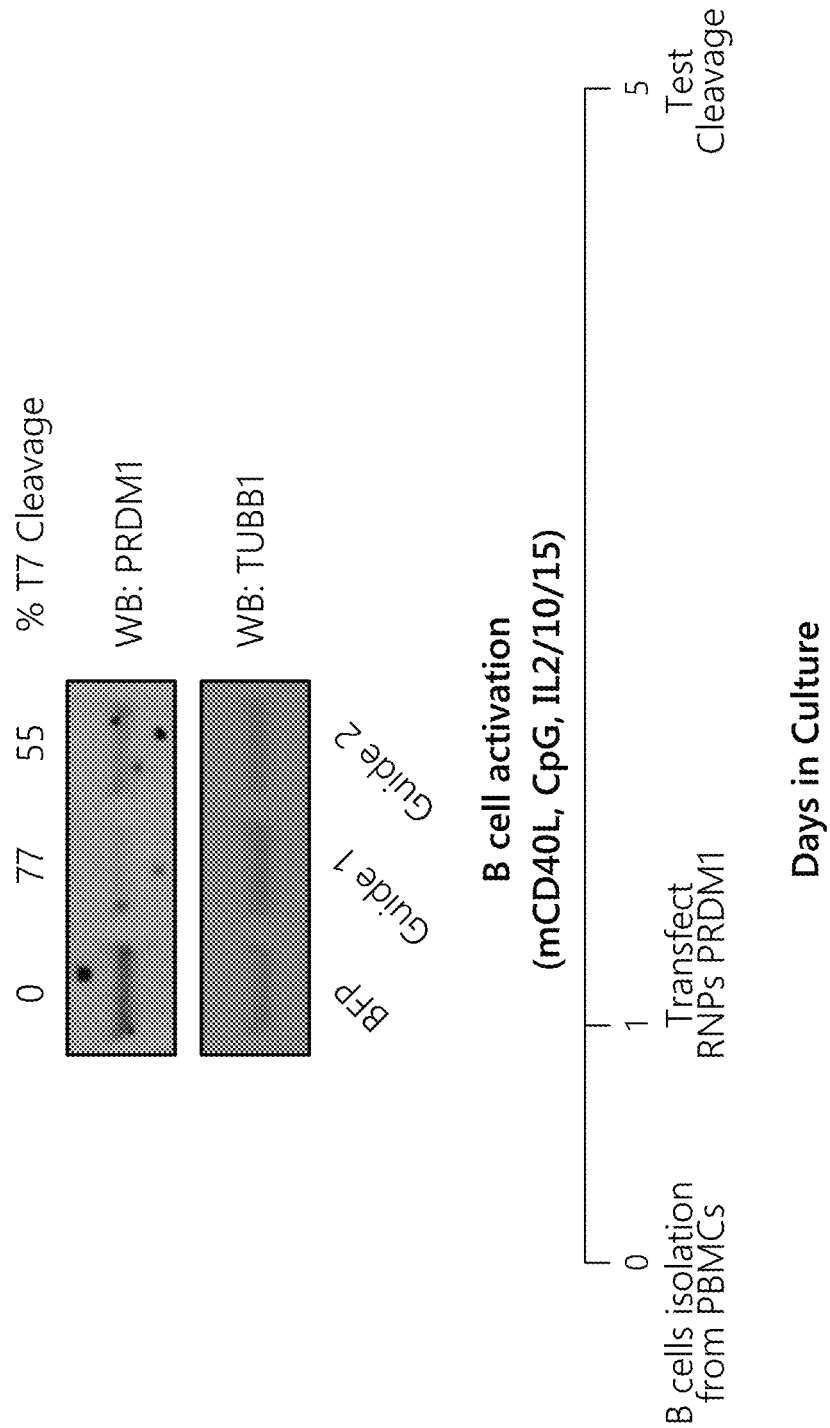
FIG. 7 shows a Western blot, which illustrates results from a T7 cleavage. The antibodies were directed to PRDM1 and TUBB1.

To assess the efficacy of guide RNA-CAS9 transfection for gene disruption applications in primary B cells, following transfection of PRDM1-targeting guide complexes, a variety of molecular analyses were used including a T7 endonuclease cleavage assay, Sanger sequencing and western blot. To sequence individual alleles, the DNA flanking the cleavage site was amplified via polymerase chain reaction (PCR) using locus-specific primers. Individual DNA molecules from this PCR reaction were cloned into bacterial plasmids, which were subsequently transformed to yield colonies, each expressing unique sequences. These were individually sequenced to assess the percentage of insertions or deletions initiated by the PRDM1 guides (FIG. 6). As shown in the gel, an increase in the dose of RNP led to increased cleavage. In parallel, T7 endonuclease cleavage was used of the same locus-specific PCR products as described above. To do, so the PCR products were melted by heating to 90 degrees Celsius and allowed to reanneal by lowering the temperature. Treatment of these re-annealed products with T7 endonuclease, which cleaves mis-matched DNA, initiates the formation of higher mobility DNA that enabled visualization and quantification of insertion and deletion frequency (FIG. 6). Finally, western blots using antibodies that specifically bind PRDM1 demonstrate that disruption of the gene with PRDM1 guides also blocks protein expression from that locus (FIG. 7).

Target Guide RNA Sequences

Target guide sequences used herein are as follows in the below table:

TABLE 1

Guide RNA sequences
Methods for inducing tolerance of a peptide for immunotherapeutic application, secreted by a B cell in a subject in need in vivo and/or increasing engraftment of the B cell in a subject in need.

| Gene | Sequence | SEQ ID NO: |
|---|---|---|
| PAX5 | UGU GAA UGG ACG GCC ACU CC | 2 |
| PAX5 | UGU AGU CCG CCA GAG GAU AG | 3 |
| IRF8 | AUU GAC AGU AGC AUG UAU CC | 4 |
| IRF8 | CGG AAA UGU CCA GUU GGG AC | 5 |

TABLE 1-continued

Guide RNA sequences
Methods for inducing tolerance of a peptide for
immunotherapeutic application, secreted by a B
cell in a subject in need in vivo and/or
increasing engraftment of the B cell in a subject
in need.

| Gene | Sequence | SEQ ID NO: |
|---|---|---|
| BACH2 | GUU CCU GCG CAU GCA CAA CC | 6 |
| BACH2 | CUG UGA CGU GAC UUU GAU CG | 7 |
| CCR5 | CAA UGU GUC AAC UCU UGA CA | 8 |
| CCR5 | GCU GUG UUU GCG UCU CUC CC | 9 |
| CARD11 | CAAUGACCUUACACUGACGC | 10 |
| PRDM1 | UGAUGGCGGUACUUCGGUUC | 11 |
| PRDM1 | AGGAUGCGGAUAUGACUCUG | 12 |
| PRDM1 | GGGGAGCGAGUGAUGUACGU | 13 |

In some alternatives, a method of making B cells, plasma cells or plasma cell precursors that expresses a macromolecule is provided. The B cell or plasma cell can be administered in some alternative methods described herein, with a second cell that expresses a macromolecule that promotes tolerance of a protein or a peptide and/or promotes engraftment of the B cell or plasma cell. Thus, the two cells can be administered in parallel in order to provide a subject with a therapeutic protein as well as a second protein that allows sustained protein replacement in a subject in need.

The method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the macromolecule. In some alternatives, the macromolecule is a protein, protein mimetic or peptide.

In some alternatives, the protein, protein mimetic, or peptide comprises natural amino acids and/or unnatural amino acids.

In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. Mixtures of different types of B cells can also be utilized. As described herein, B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof.

In some alternatives, the B cells in step (a) comprise memory B cells and/or naïve B cells.

In some alternatives, the developing of the B cells is performed after the B cells are arrested at a specific phase of development and/or activating the B cells such that the B cells are permissive for recombination without further B cell differentiation.

In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell.

In some alternatives, performing the first round of genome editing of the B cells for protein expression is performed in the absence of viral integration.

In some alternatives, performing the first round of genome editing of the B cells for protein expression is performed by introduction of a single stranded nucleic acid.

In some alternatives, the B cells are subject derived or are allogeneic peripheral blood mononuclear cells.

In some alternatives, the B cells are blood-derived human B cells.

In some alternatives, the first round of genome editing is performed by an RNA and protein based transfection.

In some alternatives, the first round of genome editing comprises delivering a nuclease, wherein the nuclease targets at least one genetic loci in the B cell.

In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1.

In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease.

In some alternatives, the Cas nuclease comprises Cas1, Cas2, Cas3, Cas4, Cas5, Cas6, Cas7, Cas8 or Cas9.

In some alternatives, the nuclease or synthetic guide RNAs targeting clustered regularly interspersed short palindromic repeat DNA (CRISPR) coupled to the CAS nuclease are delivered via translatable RNA or recombinant protein. In some alternatives, the guide sequence comprises a sequence set forth in any one of SEQ ID NO: 2-13 or 63-112.

In some alternatives, the first round of genome editing comprises transfecting with single stranded DNA oligonucleotides for homologous recombination into a candidate genetic loci. In some alternatives, the single stranded DNA oligonucleotides are unmodified. In other alternatives, the single stranded DNA oligonucleotides are modified with 5' or 3' phosphorothioate linkages as repair templates.

In some alternatives, the first round of genome editing comprises transducing the B cell with a recombinant adeno-associated virus vector to serve as a donor template for homologous recombination into a candidate genetic loci.

In some alternatives, the recombinant adeno-associated virus vector is single-stranded, double stranded or self-complementary.

In some alternatives, the method further comprises applying methods to prevent somatic hypermutation of an antibody locus in the B cell.

In some alternatives, the method to prevent somatic hypermutation of an antibody locus in the B cell comprises disruption of an AID gene.

In some alternatives, the method further comprises selectively increasing a proportion of gene edited B cells.

In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cell short lived drug activatable growth enhancers; and (d) inserting genetic modifications that artificially induce non-transformative expansion of gene edited B cells. In some alternatives, the first round of genome editing further comprises techniques for homology-directed repair.

In some alternatives, the second round of genome editing results in the excision of the IgM constant region.

In some alternatives, the second round of genome editing results in the B cells mimicking a class-switch to IgG1 positive cells.

In some alternatives, step (a) of the step increasing the proportion of gene edited B cells further comprises removing IgM positive cells.

In some alternatives, method further comprises activating the IgG1 positive cells and expanding the IgG1 positive cells, wherein the expanding is performed by exogenous antigens that specifically bind the inserted surface-expressed IgG1.

In some alternatives, the IgM positive cells are removed by negative selection.

In some alternatives, the expanding the IgG1 positive cells is performed by exogenous antigens that specifically bind the inserted surface-expressed IgG1.

In some alternatives, the drug activatable growth enhancers expressed after the third round of genome editing are rapamycin-inducible FKBP11 dimers.

In some alternatives, the activatable growth enhancers that are RNA transfected into the B cells of step (c) are rapamycin-inducible FKBP11 dimers.

In some alternatives, the inserting genetic modifications that artificially induce triggerable, non-transformative expansion of edited cells results in disruption of a HPRT locus and negative selection of non-edited cells.

In some alternatives, the negative selecting of non-edited cells is performed by 6-thioguanine.

In some alternatives, the method further comprising introducing nucleic acid, wherein the nucleic acid encodes at least one cell surface protein.

In some alternatives, the at least one cell surface protein is CD20.

In some alternatives, the first round of genome editing further comprises cycling the B-cells for homologous recombination of the single stranded DNA oligonucleotides or recombinant adeno-associated virus into the candidate genetic loci.

In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned lengths.

In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof.

In some alternatives, the isolating is performed by isolation of naïve or memory B cells.

In some alternatives, the isolating is performed from isolation from healthy donor PBMCs or cell apheresis collections.

In some alternatives, the differentiating step is performed in a three-step culture system comprising an activation and proliferation step, a plasmablast differentiation step, and a plasma cell differentiation step.

In some alternatives, the activation and proliferation step is performed in the presence of any combination of MCD40L (CD40 trimer), CpG, IL-2, IL-10 and/or IL-15.

In some alternatives, the plasmablast differentiation step is performed in the presence any combination of IL-2, IL-6, IL-10 and/or IL-15.

In some alternatives, the plasma cell differentiation step is performed in the presence any combination of IL-6, IL-15, APRIL and/or IFNα.

In some alternatives, the single stranded DNA oligonucleotides or the recombinant adenovirus comprises a sequence encoding the protein.

In some alternatives, the protein comprises an enzyme, monoclonal antibody or a binding portion thereof, neutralizing antibodies or a binding portions thereof, therapeutic antibodies or binding portions thereof, cytokine, cytokine receptor, complement protein, inhibitory protein, anti-fibrotic molecule, anti-thrombotic molecule, coagulation factor, glucose response element or a synthetic engineered protein.

In some alternatives, the protein is Factor VIII, Factor IX, SERPING1 or SERPINA1, wherein the protein is Factor VIII, Factor IX, SERPING1 or SERPINA1.

In some alternatives, the enzyme is ADAMTS13, LIPA, GLA, or ALPL.

In some alternatives, the protein is a receptor antagonist for treatment of periodic fever/autoinflammatory syndromes or complement inhibitory proteins.

In some alternatives, the compliment inhibitory protein is Factor H, Factor I or a C1 inhibitor.

In some alternatives, the protein is an anti-fibrotic molecule, wherein the anti-fibrotic molecule is SCGB1A1.

In some alternatives, the therapeutic antibody or a binding portion thereof is specific for a protein or other molecule expressed in autoimmune disorders, autoinflammatory disorders, immune dysregulation and/or cancer.

In some alternatives, the antibody is an anti-IL1 monoclonal antibody, anti-TNF antibody, anti-IL33 antibody or anti-C5 antibody or a binding portion of any one or more of these antibodies.

In some alternatives, the protein is an anti-thrombotic molecule, wherein the anti-thrombotic molecule is APLN.

In some alternatives, the protein comprises an anti-PCSK9 inhibitory antibody or a binding portion thereof.

In some alternatives, the protein comprises broadly neutralizing HIV-1 antibodies (bNAbs), or a binding portion thereof.

In some alternatives, the protein is an engineered protein, wherein the engineered protein is protective in viral, fungal, parasitic or bacterial infection.

In some alternatives, the engineered protein comprises an antibody or a binding portion thereof, wherein the antibody or a binding portion thereof is specific for an antigen that is expressed by a virus, fungus, parasite or bacteria.

In some alternatives, the protein comprises an antibody or a binding portion thereof, wherein the antibody or a binding portion thereof is specific for an antigen that is expressed in a viral, fungal, parasitic or bacterial infection.

In some alternatives, the B cell or plasma cell manufactured by any one of the alternatives described herein is provided. In some alternatives, the B cell or plasma cell that expresses the macromolecule is provided to subject in need. In some alternatives, the subject has a disease. In some alternatives, the subject is in need of engraftment of the B cell or plasma cell. In some alternatives, a method of inducing tolerance of a peptide for immunotherapeutic application, secreted by a B cell in a subject in need in vivo and/or increasing engraftment or survival of the B cell in a subject in need.

In some alternatives, the method comprises administering the plasma cell or B cell manufactured by any one of the alternatives described herein, wherein the plasma cell or B cell expresses a macromolecule for therapy or a peptide for immunotherapy and administration of a second B cell. In some alternatives, the second B cell expresses a second macromolecule, wherein the second macromolecule promotes tolerance of a peptide or protein for therapeutic application and/or engraftment. In some alternatives, the second macromolecule comprises IFN-alpha, BAFF, APRIL, IL-10 or IL-6.

Gene editing can be performed to manufacture an active B cell line that also co-expresses inhibitory cytokines such as IL-10.

In some alternatives, of the methods for inducing tolerance, about 700K cells/mL for a subject in need of treatment or therapy, may be therapeutic. That equates to ~700 million cells per liter in a person. These cells will likely dissipate within a month, but could provide therapeutic benefit for much longer periods. For inflammatory disease, these treatments would likely have to be repeated. For graft tolerization, it may be at least a one-time therapy.

Alternative 1: Editing of Primary B Cells

As shown in FIG. 7, primary B cells were edited. Peripheral blood mononuclear cells (PBMCs) collected from CD34+ negative selection flow-through from whole blood of healthy male donors post hematopoietic stem cell mobilization were purchased from Fred Hutchinson Cancer Research Center. Alternatively, PBMC were collected from healthy donors using an IRB approved protocol. CD19+ B cells were isolated from PBMCs by negative selection using a human B cell isolation kit (Miltenyi Biotec®, Auburn, CA) and cultured in Iscove's modified Dulbecco's medium (IMDM, Thermo Fisher Scientific®) supplemented with 10% fetal bovine serum and 55 µM beta-mercaptoethanol at $1-1.5\times10^6$ cells/ml. B cells were activated with 100 ng/ml of recombinant human MEGACD40L® (Enzo Life Sciences®), 1 µg/ml of CpG oligodeoxynucleotide 2006 (Invitrogen®), 50 ng/ml of IL-2 (Peprotech®), 50 ng/ml of IL-10 (Peprotech®) and 10 ng/ml of IL-15 (Peprotech®) for 48 hours. Cells were then electroporated with Cas9 RNP complexes using the Neon Transfection System (ThermoFisher Scientific®) as follows. Cells were washed with PBS and resuspended in Neon Buffer T. 30.5 pmol Cas9 RNP per $3\times10^5$ cells was added to the resuspension so that the final cell density was $3\times10^7$ cells/ml. Cells were then electroporated (1700V, 20 ms, 1 pulse) in 10-µl Neon tips, and then transferred into pre-warmed B cell culture medium with MEGACD40L®, CpG, IL-2, IL-10 and IL-15 and cultured at $1.5\times10^6$ cells/ml. For samples transfected with an ssODN donor template, ssODN was added concurrently with Cas9 RNP at 30 pmol per $3\times10^5$ cells, unless otherwise specified. For samples transduced with AAV, AAV was added to the culture immediately after electroporation. The added AAV volume was 20% of the cell culture volume, unless otherwise specified. Culture volume was doubled 24 hours after electroporation, and medium was replenished every two to three days thereafter to maintain a cell density of $1\times10^6$ cells/ml.

Alternative 2: PRDM1 Disruption Limits Plasmablast Generation

Figure 8:
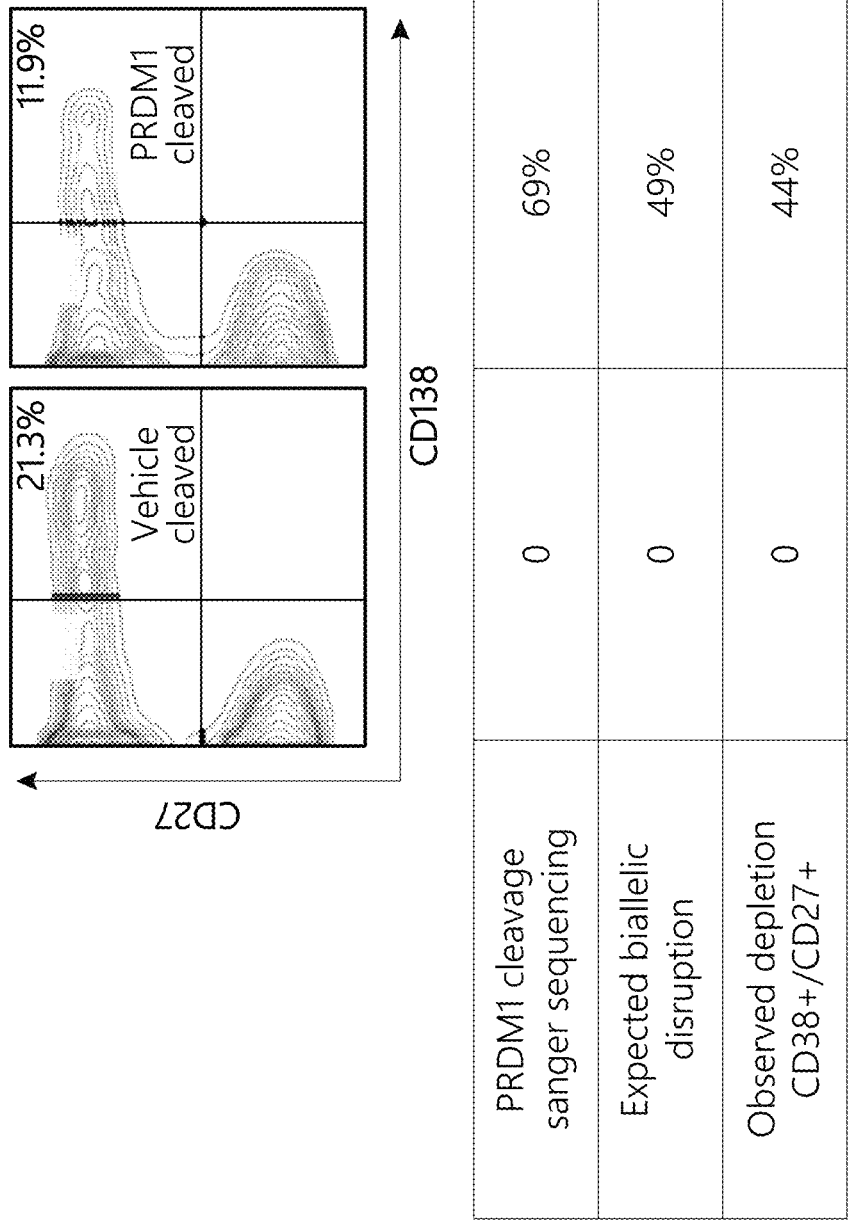
FIG. 8 shows that PRDM1 disruption limits plasmablast generation.
Figure 9:
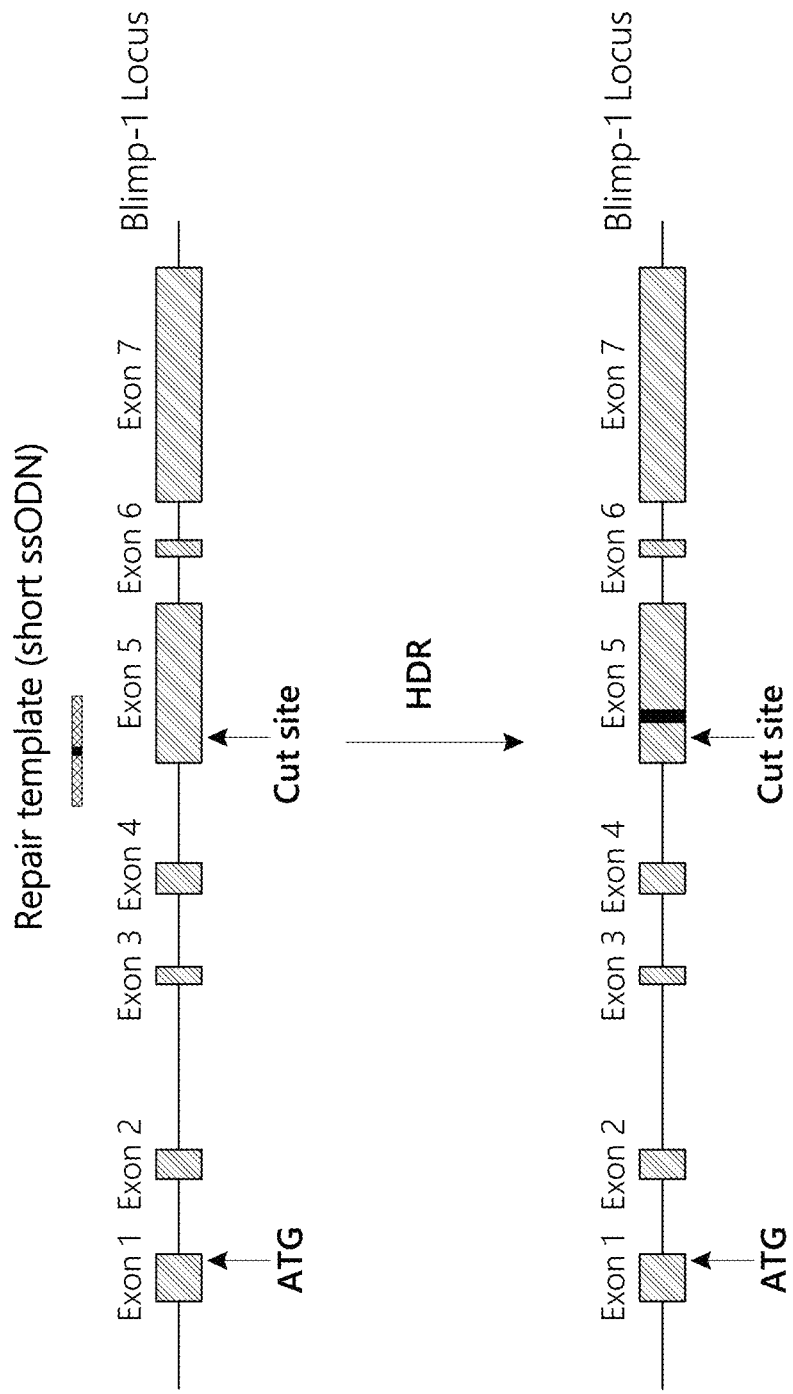
FIG. 9 shows homologous-directed repair (HDR) using single-stranded DNA templates.
Figure 10:
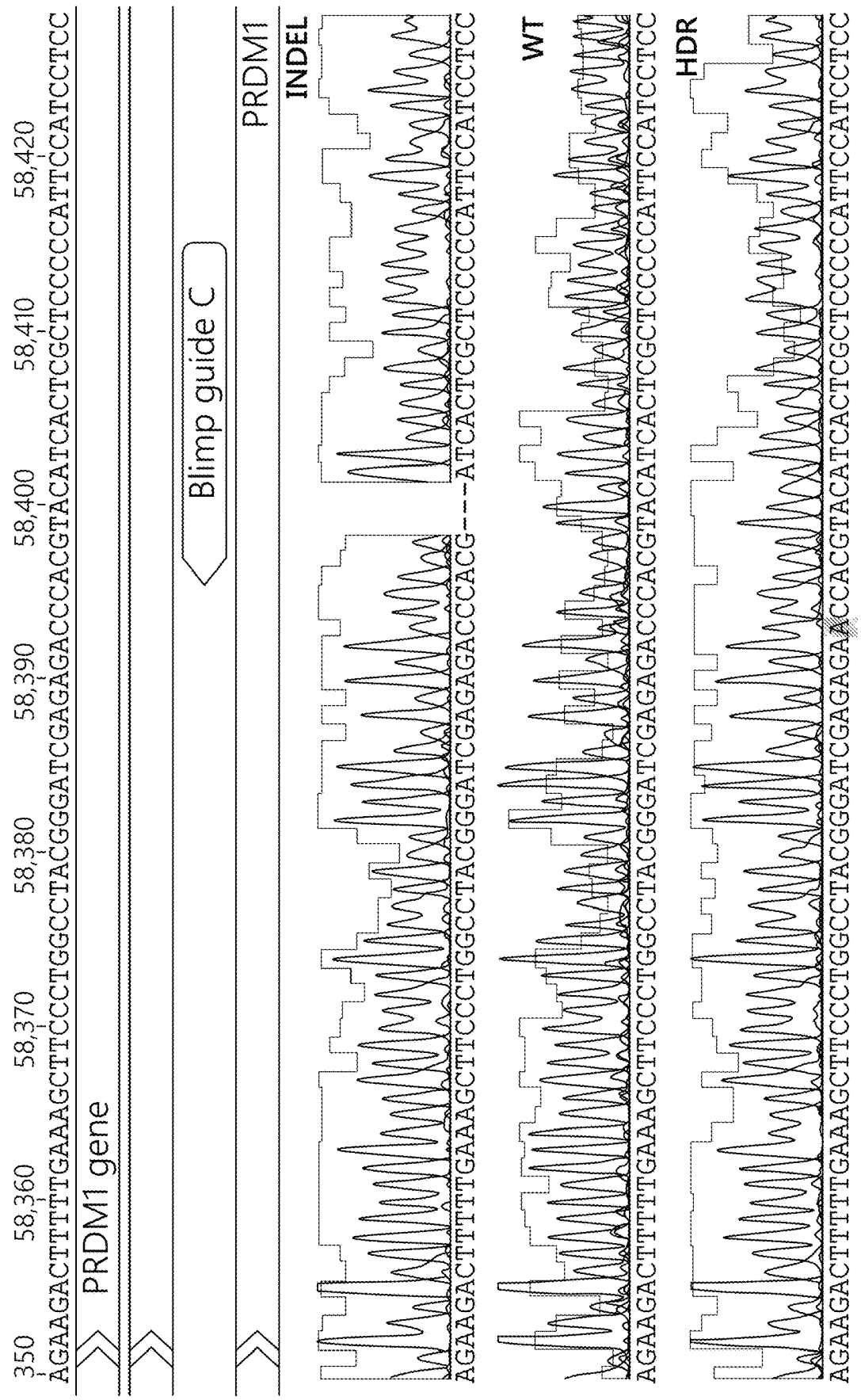
FIG. 10 shows homologous-directed repair (HDR) using single-stranded DNA templates.
Figure 10:
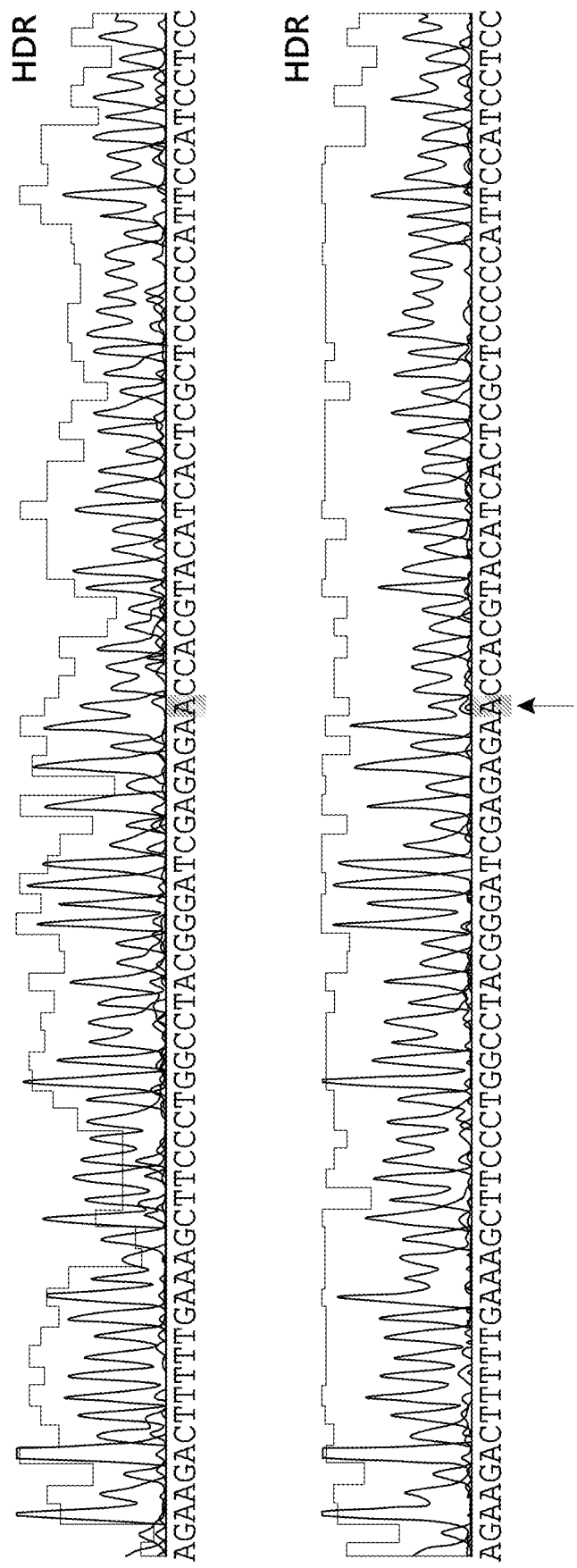
Figure 10:
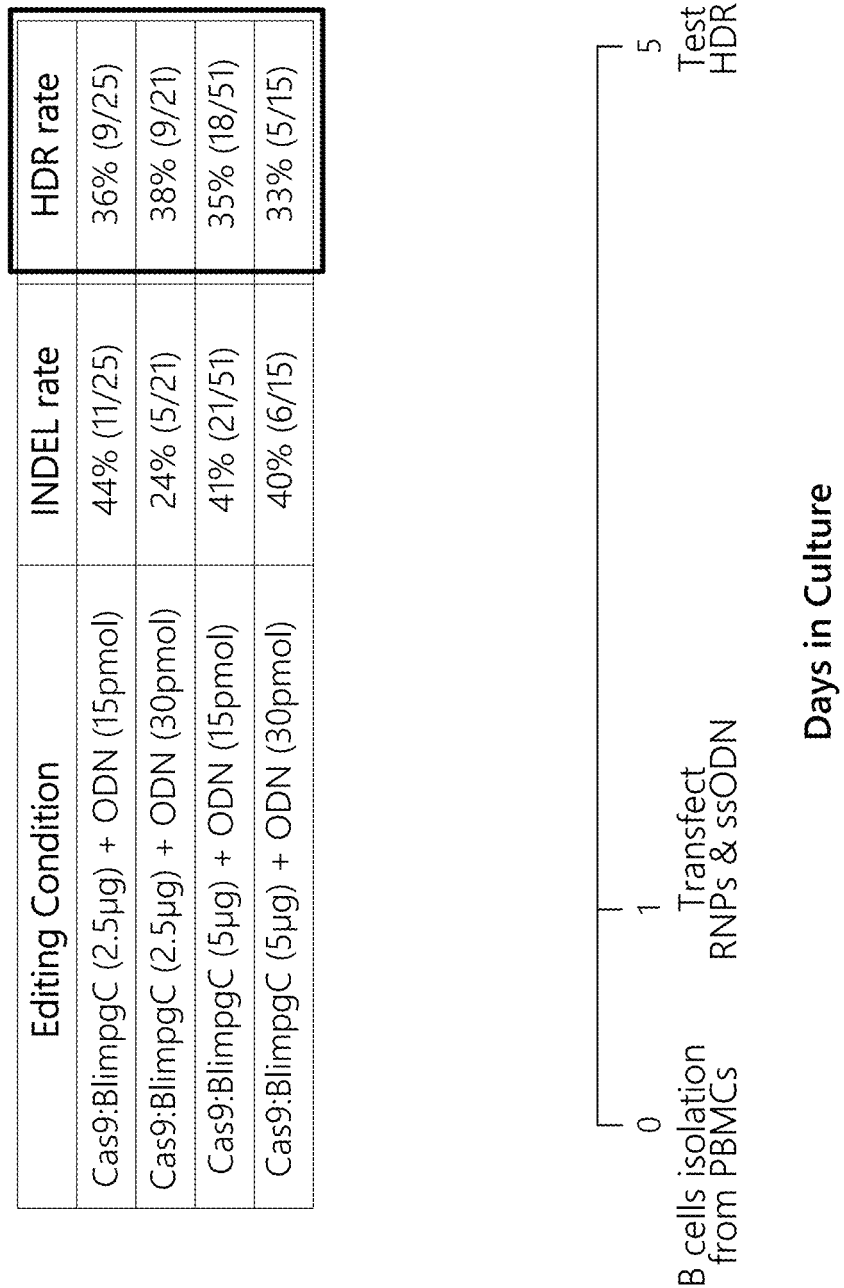

Plasma cell differentiation was performed as described in the section entitled "Plasma cell differentiation assays" of this paper. Sanger sequencing was used to calculate the total allelic disruption frequencies of PRDM1 in this experiment (69%). Based on these numbers, the expected biallelic disruption frequency was 49%. Because biallelic disruption or PRDM1 blocks plasmablast differentiation, it is expected that the number of plasmablasts to decrease ~49%. To quantify plasmablasts, flow cytometry was used. Flow cytometric analysis was done on an LSR II flow cytometer (BD Biosciences®) and data were analyzed using FlowJo software (TreeStar). To assess B cell surface marker expressions, cells were stained with fluorophore-conjugated antibodies: CD19-PECy7 (clone HIB19, eBioscience®), CD27-APC (clone 0323, Life Technologies®), CD20-PE (clone L27, BD Biosciences®), CD38-PerCPCy5.5 (clone HIT2, BD Biosciences®), CD138-Alexa Fluor 700 (clone MI15, BioLegend®), HLA-DR-FITC (clone L243, BD Biosciences®); CD19-PECy7 (clone HIB19, eBioscience®), CD27-APC (clone 0323, Life Technologies®), CD20-FITC (clone L27, BD Biosciences®), CD38-PerCPCy5.5 (clone HIT2, BD Biosciences®), CD138-Alexa Fluor 700 (clone MI15, BioLegend®), IgD-PE (clone IA6-2, BD Biosciences®), IgM-Pacific Blue (clone MHM-88, BioLegend®). Dead cells were excluded using Fixable Live/Dead stain-Alexa Fluor 350 (LifeTechnologies®). Consistent with the hypothesis, the observed depletion of plasmablasts (CD38+/CD27+) was at 44%, which closely mimics the observed bi-allelic disruption frequency (FIG. 8).

Alternative 3: Homologous-Directed Repair (HDR) Using Single-Stranded DNA Templates Homologous directed repair was performed using single stranded ODNs. The ssODNs were commercially synthesized by IDT® (Ultramer® DNA Oligonucleotides) with phosphorothioate linkages between the three nucleotides on the 5' end as well as the 3' end. For samples transfected with an ssODN donor template, ssODN was added concurrently with Cas9 RNP at 30 pmol per $3\times10^5$ cells, unless otherwise specified.

Figure 11:
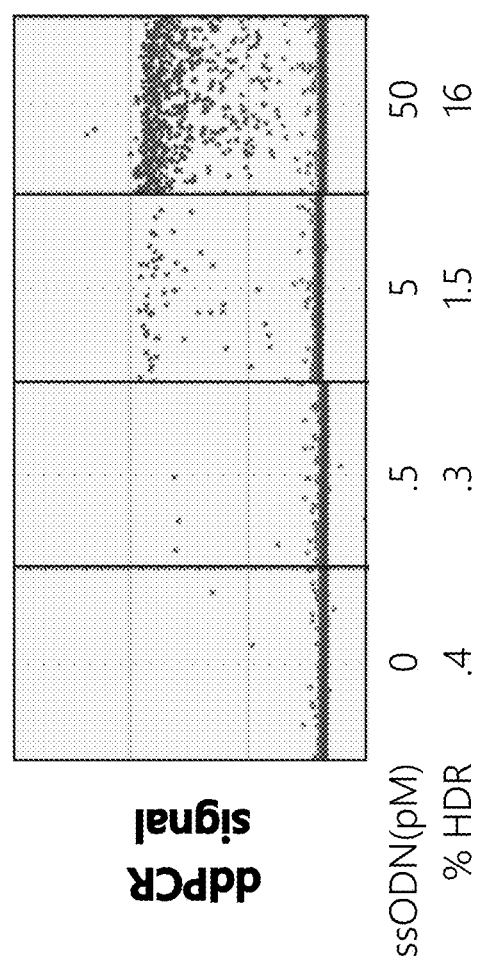
FIG. 11 shows dose response of short oligonucleotide HDR.
Figure 12:
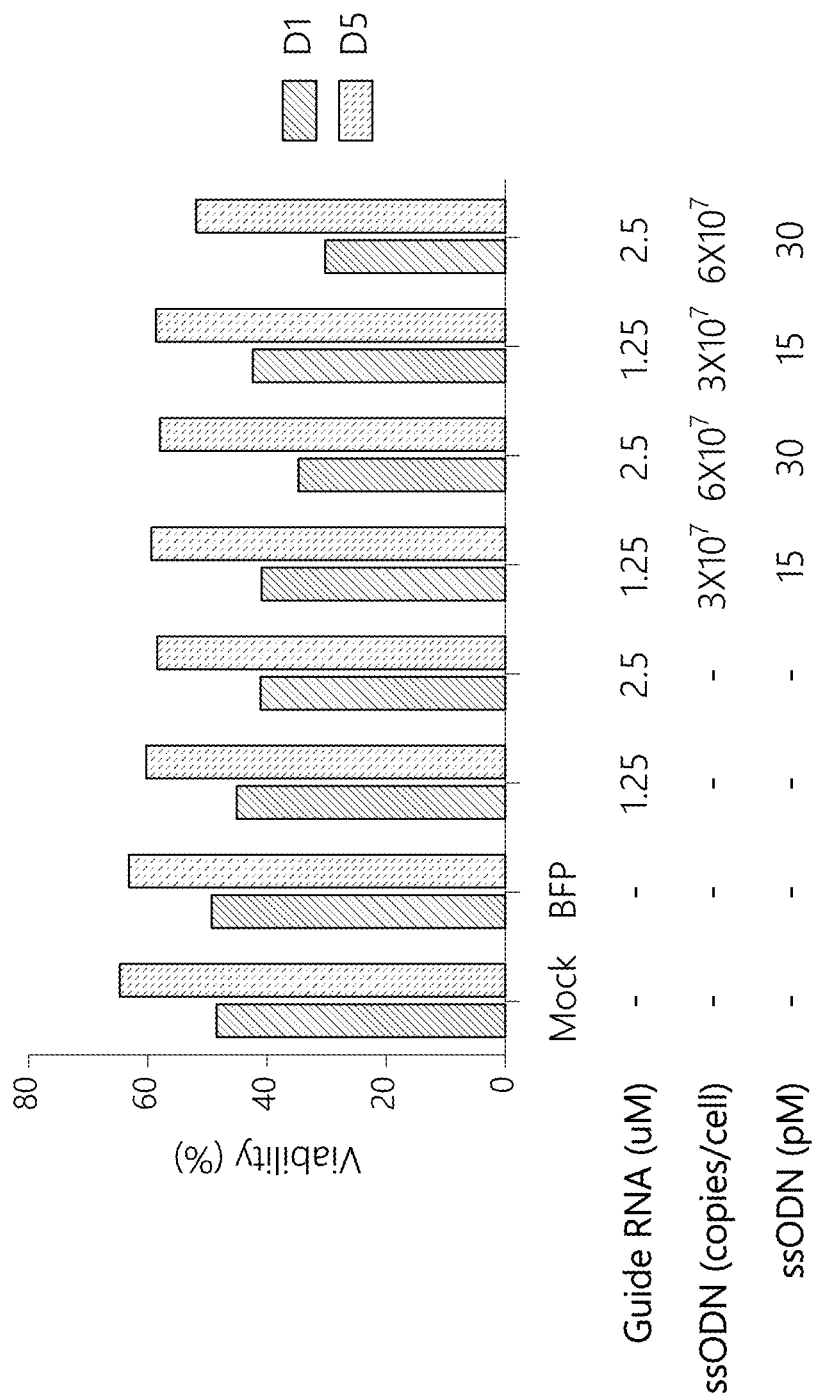
FIG. 12 shows low toxicity in setting of high-efficiency HDR.
Figure 13:
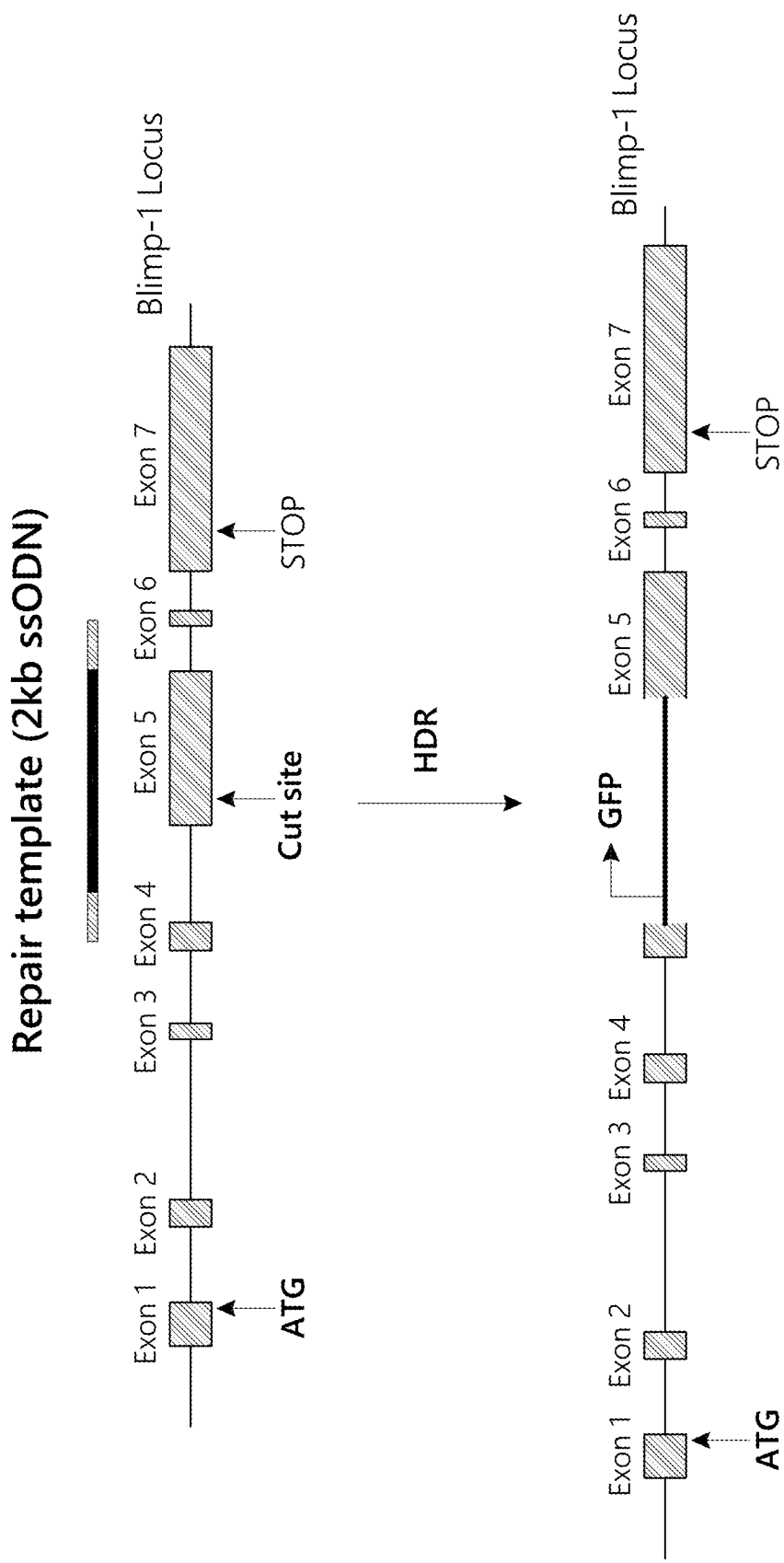
FIG. 13 shows long oligonucleotide templates for HDR.

The expression of the Blimp-1 protein (PR domain zinc finger protein 1) in B lymphocytes can lead to an immune response through proliferation and differentiation of antibody secreting plasma cells. As schematized in FIG. 9, the initial strategy for testing HDR in B cells was to use single-stranded oligonucleotides (ssODNs) to insert sequence into the PRDM1 locus at Exon 5 (FIG. 9-14). This site is shown in the light grey in Exon 5 of FIG. 9. Varying amounts of Cas9:PRDM1-C with the single stranded ODNs were tested to see how they both can affect HDR rate. These were initially analyzed by PCR cloning combined with colony sequencing (Please see section entitled Molecular Analyses-PCT, T7, sequences). The sequencing traces showed the single base-change which were used to assess HDR, which was quantified (FIG. 10, bold dark box under the table headed HDR rate). Next, allele-specific digital PCR was used to quantify HDR rates over a wider range of repair template concentration and found that 50 pM ssODN resulted in the highest rates of HDR (FIG. 11). In the same experiment, B cell viability was quantified by flow cytometry (See section entitled PRDM1 disruption limits plasmablast generation for methods of flow cytometry), demonstrating that although 30 pM ssODN combined with 2.5 uM guide RNA results in a decrease of viability at day 1, the cells recover by day 5 (FIG. 12). As shown in FIG. 12, the days are consecutively D1 followed by D5 on the bar graphs. Next, the ssODN approach was expanded to include larger oligonucleotides (schematized in FIG. 13). As shown in FIG. 13, the repair template is inserted within exon 5 at the cutsite. As shown in FIG. 14, long template HDR is also effective in the editing of B cells, which has not been previously reported. In summary, there was surprisingly low toxicity as well as high-efficiency HDR as compared to using high titer AAV repair templates, which were shown to cause toxicity at $3\times10^5$ copies/cell.

The AAV repair template sequences are shown below as follows:

1079_pscAAV-MND.GFP (SEQ ID NO: 14)

```
   1 AAGCTTCCCG GGGGGATCTG GGCCACTCCC TCTCTGCGCG CTCGCTCGCT CACTGAGGCC
  61 GGGCGACCAA AGGTCGCCCG ACGCCCGGGC TTTGCCCGGG CGGCCTCAGT GAGCGAGCGA
 121 GCGCGCAGAG AGGGAGTGGC CAACTCCATC ACTAGGGGTT CCTGGAGGGG TGGAGTCGTG
 181 ACCTAGGGAA CAGAGAAACA GGAGAATATG GGCCAAACAG GATATCTGTG GTAAGCAGTT
 241 CCTGCCCCGG CTCAGGGCCA AGAACAGTTG AACAGCAGA ATATGGGCCA AACAGGATAT
 301 CTGTGGTAAG CAGTTCCTGC CCCGGCTCAG GCCAAGAAC AGATGGTCCC CAGATGCGGT
 361 CCCGCCCTCA GCAGTTTCTA GAGAACCATC AGATGTTTCC AGGGTGCCCC AAGGACCTGA
 421 AATGACCCTG TGCCTTATTT GAACTAACCA ATCAGTTCGC TTCTCGCTTC TGTTCGCGCG
 481 CTTCTGCTCC CCGAGCTCTA TATAAGCAGA GCTCGTTTAG TGAACCGTCA GATCGCCTGG
 541 AGACGCCATC CACGCTGTTT TGACTTCCAT AGAAGGATCC TCGAGGCCAC CATGGTGAGC
 601 AAGGGCGAGG AGCTGTTCAC CGGGGTGGTG CCCATCCTGG TCGAGCTGGA CGGCGACGTA
 661 AACGGCCACA AGTTCAGCGT GTCCGGCGAG GGCGAGGGCG ATGCCACCTA CGGCAAGCTG
 721 ACCCTGAAGT TCATCTGCAC CACCGGCAAG CTGCCCGTGC CCTGGCCCAC CCTCGTGACC
 781 ACCCTGACCT ACGGCGTGCA GTGCTTCAGC CGCTACCCCG ACCACATGAA GCAGCACGAC
 841 TTCTTCAAGT CCGCCATGCC CGAAGGCTAC GTCCAGGAGC GCACCATCTT CTTCAAGGAC
 901 GACGGCAACT ACAAGACCCG CGCCGAGGTG AAGTTCGAGG GCGACACCCT GGTGAACCGC
 961 ATCGAGCTGA AGGGCATCGA CTTCAAGGAG GACGGCAACA TCCTGGGGCA CAAGCTGGAG
1021 TACAACTACA ACAGCCACAA CGTCTATATC ATGGCCGACA AGCAGAAGAA CGGCATCAAG
1081 GTGAACTTCA AGATCCGCCA CAACATCGAG GACGGCAGCG TGCAGCTCGC CGACCACTAC
1141 CAGCAGAACA CCCCCATCGG CGACGGCCCC GTGCTGCTGC CCGACAACCA CTACCTGAGC
1201 ACCCAGTCCG CCCTGAGCAA AGACCCCAAC GAGAAGCGCG ATCACATGGT CCTGCTGGAG
1261 TTCGTGACCG CCGCCGGGAT CACTCTCGGC ATGGACGAGC TGTACAAGTA AGCGGCCGCA
1321 ATTCACCCCA CCAGTGCAGG CTGCCTATCA GAAAGTGGTG GCTGGTGTGG CTAATGCCCT
1381 GGCCCACAAG TATCACTAAG CTCGCTTTCT TGCTGTCCAA TTTCTATTAA AGGTTCCTTT
1441 GTTCCCTAAG TCCAACTACT AAACTGGGGG ATATTATGAA GGGCCTTGAG CATCTGGATT
1501 CTGCCTAATA AAAAACATTT ATTTTCATTG CAATGATGTA TTTAAATTAT TTCTGAATAT
1561 TTTACTAAAA AGGGAATGTG GGAGGTCAGT GCATTTAAAA CATAAAGAAA TGAAGAGCTA
1621 GTTCAAACCT TGGGAAAATA CACTATATCT TAAACTCCAT GAAAGAAGGT GAGGCTGCAA
1681 ACAGCTAATG CACATTGGCA ACAGCCCCTG ATGCCTATGC CTTATTCATC CCTCAGAAAA
1741 GGATTCAAGT AGAGGCTTGA TTTGGAGGTT AAAGTTTTGC TATGCTGTAT TTTACATTAC
1801 TTATTGTTTT AGCTGTCCTC ATGAATGTCT TTTCACTACC CATTTGCTTA TCCTGCATCT
1861 CTCAGCCTTG ACTCCACTCA GTTCTCTTGC TTAGAGATAC CACCTTTCCC CTGAAGTGTT
1921 CCTTCCATGT TTTACGGCGA GATGGTTTCT CCTCGCCTGG CCACTCAGCC TTAGTTGTCT
1981 CTGTTGTCTT ATAGAGGTCT ACTTGAAGAA GGAAAAACAG GGGCATGGT TTGACTGTCC
2041 TGTGAGCCCT TCTTCCCTGC CTCCCCCACT CACAGTGACA CTAGTCCACT CCCTCTCTGC
2101 GCGCTCGCTC GCTCACTGAG GCCGGGCGAC CAAAGGTCGC CCGACGCCCG GCTTTGCCC
2161 GGGCGGCCTC AGTGAGCGAG CGAGCGCGCA GAGAGGGACA GATCCGGGCC CGCATGCGTC
2221 GACAATTCAC TGGCCGTCGT TTTACAACGT CGTGACTGGG AAAACCCTGG CGTTACCCAA
```

-continued

```
2281 CTTAATCGCC TTGCAGCACA TCCCCCTTTC GCCAGCTGGC GTAATAGCGA AGAGGCCCGC

2341 ACCGATCGCC CTTCCCAACA GTTGCGCAGC CTGAATGGCG AATGGCGCCT GATGCGGTAT

2401 TTTCTCCTTA CGCATCTGTG CGGTATTTCA CACCGCATAT GGTGCACTCT CAGTACAATC

2461 TGCTCTGATG CCGCATAGTT AAGCCAGCCC CGACACCCGC CAACACCCGC TGACGCGCCC

2521 TGACGGGCTT GTCTGCTCCC GGCATCCGCT TACAGACAAG CTGTGACCGT CTCCGGGAGC

2581 TGCATGTGTC AGAGGTTTTC ACCGTCATCA CCGAAACGCG CGAGACGAAA GGGCCTCGTG

2641 ATACGCCTAT TTTTATAGGT TAATGTCATG ATAATAATGG TTTCTTAGAC GTCAGGTGGC

2701 ACTTTTCGGG GAAATGTGCG CGGAACCCCT ATTTGTTTAT TTTTCTAAAT ACATTCAAAT

2761 ATGTATCCGC TCATGAGACA ATAACCCTGA TAAATGCTTC AATAATATTG AAAAAGGAAG

2821 AGTATGAGTA TTCAACATTT CCGTGTCGCC CTTATTCCCT TTTTTGCGGC ATTTTGCCTT

2881 CCTGTTTTTG CTCACCCAGA AACGCTGGTG AAAGTAAAAG ATGCTGAAGA TCAGTTGGGT

2941 GCACGAGTGG GTTACATCGA ACTGGATCTC AACAGCGGTA AGATCCTTGA GAGTTTTCGC

3001 CCCGAAGAAC GTTTTCCAAT GATGAGCACT TTTAAAGTTC TGCTATGTGG CGCGGTATTA

3061 TCCCGTATTG ACGCCGGGCA AGAGCAACTC GGTCGCCGCA TACACTATTC TCAGAATGAC

3121 TTGGTTGAGT ACTCACCAGT CACAGAAAAG CATCTTACGG ATGGCATGAC AGTAAGAGAA

3181 TTATGCAGTG CTGCCATAAC CATGAGTGAT AACACTGCGG CCAACTTACT TCTGACAACG

3241 ATCGGAGGAC CGAAGGAGCT AACCGCTTTT TTGCACAACA TGGGGGATCA TGTAACTCGC

3301 CTTGATCGTT GGGAACCGGA GCTGAATGAA GCCATACCAA ACGACGAGCG TGACACCACG

3361 ATGCCTGTAG CAATGGCAAC AACGTTGCGC AAACTATTAA CTGGCGAACT ACTTACTCTA

3421 GCTTCCCGGC AACAATTAAT AGACTGGATG GAGGCGGATA AAGTTGCAGG ACCACTTCTG

3481 CGCTCGGCCC TTCCGGCTGG CTGGTTTATT GCTGATAAAT CTGGAGCCGG TGAGCGTGGG

3541 TCTCGCGGTA TCATTGCAGC ACTGGGGCCA GATGGTAAGC CCTCCCGTAT CGTAGTTATC

3601 TACACGACGG GGAGTCAGGC AACTATGGAT GAACGAAATA GACAGATCGC TGAGATAGGT

3661 GCCTCACTGA TTAAGCATTG GTAACTGTCA GACCAAGTTT ACTCATATAT ACTTTAGATT

3721 GATTTAAAAC TTCATTTTTA ATTTAAAAGG ATCTAGGTGA AGATCCTTTT TGATAATCTC

3781 ATGACCAAAA TCCCTTAACG TGAGTTTTCG TTCCACTGAG CGTCAGACCC CGTAGAAAAG

3841 ATCAAAGGAT CTTCTTGAGA TCCTTTTTTT CTGCGCGTAA TCTGCTGCTT GCAAACAAAA

3901 AAACCACCGC TACCAGCGGT GGTTTGTTTG CCGGATCAAG AGCTACCAAC TCTTTTTCCG

3961 AAGGTAACTG GCTTCAGCAG AGCGCAGATA CCAAATACTG TTCTTCTAGT GTAGCCGTAG

4021 TTAGGCCACC ACTTCAAGAA CTCTGTAGCA CCGCCTACAT ACCTCGCTCT GCTAATCCTG

4081 TTACCAGTGG CTGCTGCCAG TGGCGATAAG TCGTGTCTTA CCGGGTTGGA CTCAAGACGA

4141 TAGTTACCGG ATAAGGCGCA GCGGTCGGGC TGAACGGGGG GTTCGTGCAC ACAGCCCAGC

4201 TTGGAGCGAA CGACCTACAC CGAACTGAGA TACCTACAGC GTGAGCTATG AGAAAGCGCC

4261 ACGCTTCCCG AAGGGAGAAA GGCGGACAGG TATCCGGTAA GCGGCAGGGT CGGAACAGGA

4321 GAGCGCACGA GGGAGCTTCC AGGGGGAAAC GCCTGGTATC TTTATAGTCC TGTCGGGTTT

4381 CGCCACCTCT GACTTGAGCG TCGATTTTTG TGATGCTCGT CAGGGGGGCG GAGCCTATGG

4441 AAAAACGCCA GCAACGCGGC CTTTTTACGG TTCCTGGCCT TTTGCTGGCC TTTTGCTCAC

4501 ATGTTCTTTC CTGCGTTATC CCCTGATTCT GTGGATAACC GTATTACCGC CTTTGAGTGA

4561 GCTGATACCG CTCGCCGCAG CCGAACGACC GAGCGCAGCG AGTCAGTGAG CGAGGAAGCG

4621 GAAGAGCGCC CAATACGCAA ACCGCCTCTC CCCGCGCGTT GGCCGATTCA TTAATGCAGC

4681 TGGCACGACA GGTTTCCCGA CTGGAAAGCG GGCAGTGAGC GCAACGCAAT TAATGTGAGT
```

```
4741 TAGCTCACTC ATTAGGCACC CCAGGCTTTA CACTTTATGC TTCCGGCTCG TATGTTGTGT

4801 GGAATTGTGA GCGGATAACA ATTTCACACA GGAAACAGCT ATGACCATGA TTACGCCAAG

4861 CTCTCGAGAT CTAGA
```

1347_pscAAV.Blimp.0.4 kb.MND.GFP (SEQ ID NO: 15)
```
   1 AAGCTTCCCG GGGGGATCTG GGCCACTCCC TCTCTGCGCG CTCGCTCGCT CACTGAGGCC

61 GGGCGACCAA AGGTCGCCCG ACGCCCGGGC TTTGCCCGGG CGGCCTCAGT GAGCGAGCGA

121 GCGCGCAGAG AGGGAGTGGC CAACTCCATC ACTAGGGGTT CCTGGAGGGG TGGAGTCGTG

181 ACCTAGGACG CGTGCCAGCT GTTACTCAGG TTTTCTCAAG AAGGAGGAGC AACTTTGGCA

241 GTTTTGCTTC AGTTCTCTCT AGCCCTCTGT GTAATCGCCC CTTTTTCTTT ATTTCAGCAC

301 AAACACAGAG CAGTCTAAAG CAACCGAGCA CTGAGAAAAA TGAACTCTGC CCAAAGAATG

361 TCCCAAAGAG AGAGTACAGC GTGAAAGAAA TCCTAAAATT GGACTCCAAC CCCTCCAAAG

421 GAAAGGACCT CTACCGTTCT AACATTTCAC CCCTCACATC AGAAAAGGAC CTCGATGACT

481 TTAGAAGACG TGGGAGCCCC GAAATGCCCT TCTACCCTCG GGTCGTTTAC CCCATCCGGG

541 CCCCTCTGCC AGAAGACTTT TTGAAAGCTT CCCTGGCCTA CGGGATCGAG AGAGAACAGA

601 GAAACAGGAG AATATGGGCC AAACAGGATA TCTGTGGTAA GCAGTTCCTG CCCCGGCTCA

661 GGGCCAAGAA CAGTTGGAAC AGCAGAATAT GGGCCAAACA GGATATCTGT GGTAAGCAGT

721 TCCTGCCCCG GCTCAGGGCC AAGAACAGAT GGTCCCCAGA TGCGGTCCCG CCCTCAGCAG

781 TTTCTAGAGA ACCATCAGAT GTTTCCAGGG TGCCCCAAGG ACCTGAAATG ACCCTGTGCC

841 TTATTTGAAC TAACCAATCA GTTCGCTTCT CGCTTCTGTT CGCGCGCTTC TGCTCCCCGA

901 GCTCTATATA AGCAGAGCTC GTTTAGTGAA CCGTCAGATC GCCTGGAGAC GCCATCCACG

961 CTGTTTTGAC TTCCATAGAA GGATCTCGAG GCCACCATGG TGAGCAAGGG CGAGGAGCTG

1021 TTCACCGGGG TGGTGCCCAT CCTGGTCGAG CTGGACGGCG ACGTAAACGG CCACAAGTTC

1081 AGCGTGTCCG GCGAGGGCGA GGGCGATGCC ACCTACGGCA AGCTGACCCT GAAGTTCATC

1141 TGCACCACCG GCAAGCTGCC CGTGCCCTGG CCCACCCTCG TGACCACCCT GACCTACGGC

1201 GTGCAGTGCT TCAGCCGCTA CCCCGACCAC ATGAAGCAGC ACGACTTCTT CAAGTCCGCC

1261 ATGCCCGAAG GCTACGTCCA GGAGCGCACC ATCTTCTTCA AGGACGACGG CAACTACAAG

1321 ACCCGCGCCG AGGTGAAGTT CGAGGGCGAC ACCCTGGTGA ACCGCATCGA GCTGAAGGGC

1381 ATCGACTTCA AGGAGGACGG CAACATCCTG GGGCACAAGC TGGAGTACAA CTACAACAGC

1441 CACAACGTCT ATATCATGGC CGACAAGCAG AAGAACGGCA TCAAGGTGAA CTTCAAGATC

1501 CGCCACAACA TCGAGGACGG CAGCGTGCAG CTCGCCGACC ACTACCAGCA GAACACCCCC

1561 ATCGGCGACG GCCCCGTGCT GCTGCCCGAC AACCACTACC TGAGCACCCA GTCCGCCCTG

1621 AGCAAAGACC CCAACGAGAA GCGCGATCAC ATGGTCCTGC TGGAGTTCGT GACCGCCGCC

1681 GGGATCACTC TCGGCATGGA CGAGCTGTAC AAGTAAACTA GTGTCGACTG CTTTATTTGT

1741 GAAATTTGTG ATGCTATTGC TTTATTTGTA ACCATTATAA GCTGCAATAA ACAAGTTAAC

1801 AACAACAATT GCATTCATTT TATGTTTCAG GTTCAGGGGG AGGTGTGGGA GGTTTTTTAA

1861 AACGTACATC ACTCGCTCCC CCATTCCATC CTCCACCACT CCAAGCCCCT CTGCAAGAAG

1921 CAGCCCCGAC CAAAGCCTCA AGAGCTCCAG CCCTCACAGC AGCCCTGGGA ATACGGTGTC

1981 CCCTGTGGGC CCCGGCTCTC AAGAGCACCG GGACTCCTAC GCTTACTTGA ACGCGTCCTA

2041 CGGCACGGAA GGTTTGGGCT CCTACCCTGG CTACGCACCC CTGCCCCACC TCCCGCCAGC

2101 TTTCATCCCC TCGTACAACG CTCACTACCC CAAGTTCCTC TTGCCCCCCT ACGGCATGAA
```

-continued

```
2161 TTGTAATGGC CTGAGCGCTG TGAGCAGCAT GAATGGCATC AACAACTTTG GCCTCTTCCC

2221 GAGGCTGTGC CCTGTCTACA GCAATCTCCT CGGTGGGGGC ACTAGTCCAC TCCCTCTCTG

2281 CGCGCTCGCT CGCTCACTGA GGCCGGGCGA CCAAAGGTCG CCCGACGCCC GGGCTTTGCC

2341 CGGGCGGCCT CAGTGAGCGA GCGAGCGCGC AGAGAGGGAC AGATCCGGGC CCGCATGCGT

2401 CGACAATTCA CTGGCCGTCG TTTTACAACG TCGTGACTGG GAAAACCCTG GCGTTACCCA

2461 ACTTAATCGC CTTGCAGCAC ATCCCCCTTT CGCCAGCTGG CGTAATAGCG AAGAGGCCCG

2521 CACCGATCGC CCTTCCCAAC AGTTGCGCAG CCTGAATGGC GAATGGCGCC TGATGCGGTA

2581 TTTTCTCCTT ACGCATCTGT GCGGTATTTC ACACCGCATA TGGTGCACTC TCAGTACAAT

2641 CTGCTCTGAT GCCGCATAGT TAAGCCAGCC CCGACACCCG CCAACACCCG CTGACGCGCC

2701 CTGACGGGCT TGTCTGCTCC CGGCATCCGC TTACAGACAA GCTGTGACCG TCTCCGGGAG

2761 CTGCATGTGT CAGAGGTTTT CACCGTCATC ACCGAAACGC GCGAGACGAA AGGGCCTCGT

2821 GATACGCCTA TTTTTATAGG TTAATGTCAT GATAATAATG GTTTCTTAGA CGTCAGGTGG

2881 CACTTTTCGG GGAAATGTGC GCGGAACCCC TATTTGTTTA TTTTTCTAAA TACATTCAAA

2941 TATGTATCCG CTCATGAGAC AATAACCCTG ATAAATGCTT CAATAATATT GAAAAAGGAA

3001 GAGTATGAGT ATTCAACATT TCCGTGTCGC CCTTATTCCC TTTTTTGCGG CATTTTGCCT

3061 TCCTGTTTTT GCTCACCCAG AAACGCTGGT GAAAGTAAAA GATGCTGAAG ATCAGTTGGG

3121 TGCACGAGTG GGTTACATCG AACTGGATCT CAACAGCGGT AAGATCCTTG AGAGTTTTCG

3181 CCCCGAAGAA CGTTTTCCAA TGATGAGCAC TTTTAAAGTT CTGCTATGTG GCGCGGTATT

3241 ATCCCGTATT GACGCCGGGC AAGAGCAACT CGGTCGCCGC ATACACTATT CTCAGAATGA

3301 CTTGGTTGAG TACTCACCAG TCACAGAAAA GCATCTTACG GATGGCATGA CAGTAAGAGA

3361 ATTATGCAGT GCTGCCATAA CCATGAGTGA TAACACTGCG GCCAACTTAC TTCTGACAAC

3421 GATCGGAGGA CCGAAGGAGC TAACCGCTTT TTTGCACAAC ATGGGGGATC ATGTAACTCG

3481 CCTTGATCGT TGGGAACCGG AGCTGAATGA AGCCATACCA AACGACGAGC GTGACACCAC

3541 GATGCCTGTA GCAATGGCAA CAACGTTGCG CAAACTATTA ACTGGCGAAC TACTTACTCT

3601 AGCTTCCCGG CAACAATTAA TAGACTGGAT GGAGGCGGAT AAAGTTGCAG GACCACTTCT

3661 GCGCTCGGCC CTTCCGGCTG GCTGGTTTAT TGCTGATAAA TCTGGAGCCG GTGAGCGTGG

3721 GTCTCGCGGT ATCATTGCAG CACTGGGGCC AGATGGTAAG CCCTCCCGTA TCGTAGTTAT

3781 CTACACGACG GGGAGTCAGG CAACTATGGA TGAACGAAAT AGACAGATCG CTGAGATAGG

3841 TGCCTCACTG ATTAAGCATT GGTAACTGTC AGACCAAGTT TACTCATATA TACTTTAGAT

3901 TGATTTAAAA CTTCATTTTT AATTTAAAAG GATCTAGGTG AAGATCCTTT TTGATAATCT

3961 CATGACCAAA ATCCCTTAAC GTGAGTTTTC GTTCCACTGA GCGTCAGACC CCGTAGAAAA

4021 GATCAAAGGA TCTTCTTGAG ATCCTTTTTT TCTGCGCGTA ATCTGCTGCT TGCAAACAAA

4081 AAAACCACCG CTACCAGCGG TGGTTTGTTT GCCGGATCAA GAGCTACCAA CTCTTTTTCC

4141 GAAGGTAACT GGCTTCAGCA GAGCGCAGAT ACCAAATACT GTTCTTCTAG TGTAGCCGTA

4201 GTTAGGCCAC CACTTCAAGA ACTCTGTAGC ACCGCCTACA TACCTCGCTC TGCTAATCCT

4261 GTTACCAGTG GCTGCTGCCA GTGGCGATAA GTCGTGTCTT ACCGGGTTGG ACTCAAGACG

4321 ATAGTTACCG GATAAGGCGC AGCGGTCGGG CTGAACGGGG GGTTCGTGCA CACAGCCCAG

4381 CTTGGAGCGA ACGACCTACA CCGAACTGAG ATACCTACAG CGTGAGCTAT GAGAAAGCGC

4441 CACGCTTCCC GAAGGGAGAA AGGCGGACAG GTATCCGGTA AGCGGCAGGG TCGGAACAGG

4501 AGAGCGCACG AGGGAGCTTC CAGGGGGAAA CGCCTGGTAT CTTTATAGTC CTGTCGGGTT

4561 TCGCCACCTC TGACTTGAGC GTCGATTTTT GTGATGCTCG TCAGGGGGGC GGAGCCTATG
```

```
4621 GAAAAACGCC AGCAACGCGG CCTTTTTACG GTTCCTGGCC TTTTGCTGGC CTTTTGCTCA
4681 CATGTTCTTT CCTGCGTTAT CCCCTGATTC TGTGGATAAC CGTATTACCG CCTTTGAGTG
4741 AGCTGATACC GCTCGCCGCA GCCGAACGAC CGAGCGCAGC GAGTCAGTGA GCGAGGAAGC
4801 GGAAGAGCGC CCAATACGCA AACCGCCTCT CCCCGCGCGT TGGCCGATTC ATTAATGCAG
4861 CTGGCACGAC AGGTTTCCCG ACTGGAAAGC GGGCAGTGAG CGCAACGCAA TTAATGTGAG
4921 TTAGCTCACT CATTAGGCAC CCCAGGCTTT ACACTTTATG CTTCCGGCTC GTATGTTGTG
4981 TGGAATTGTG AGCGGATAAC AATTTCACAC AGGAAACAGC TATGACCATG ATTACGCCAA
5041 GCTCTCGAGA TCTAGA
```

1348_pAAV.Blimp.0.4 kb.MND.GFP.pA (SEQ ID NO: 16)
```
   1 CAGCTGCGCG CTCGCTCGCT CACTGAGGCC GCCCGGGCAA AGCCCGGGCG TCGGGCGACC
  61 TTTGGTCGCC CGGCCTCAGT GAGCGAGCGA GCGCGCAGAG AGGGAGTGGC CAACTCCATC
 121 ACTAGGGGTT CCTTGTAGTT AATGATTAAC CCGCCATGCT ACTTATCTAC ACGCGTGCCA
 181 GCTGTTACTC AGGTTTTCTC AAGAAGGAGG AGCAACTTTG GCAGTTTTGC TTCAGTTCTC
 241 TCTAGCCCTC TGTGTAATCG CCCCTTTTTC TTTATTTCAG CACAAACACA GAGCAGTCTA
 301 AAGCAACCGA GCACTGAGAA AAATGAACTC TGCCCAAAGA ATGTCCCAAA GAGAGAGTAC
 361 AGCGTGAAAG AAATCCTAAA ATTGGACTCC AACCCCTCCA AAGGAAAGGA CCTCTACCGT
 421 TCTAACATTT CACCCCTCAC ATCAGAAAAG GACCTCGATG ACTTTAGAAG ACGTGGGAGC
 481 CCCGAAATGC CCTTCTACCC TCGGGTCGTT TACCCCATCC GGGCCCCTCT GCCAGAAGAC
 541 TTTTTGAAAG CTTCCCTGGC CTACGGGATC GAGAGAGAAC AGAGAAACAG GAGAATATGG
 601 GCCAAACAGG ATATCTGTGG TAAGCAGTTC CTGCCCCGGC TCAGGGCCAA GAACAGTTGG
 661 AACAGCAGAA TATGGGCCAA ACAGGATATC TGTGGTAAGC AGTTCCTGCC CCGGCTCAGG
 721 GCCAAGAACA GATGGTCCCC AGATGCGGTC CCGCCCTCAG CAGTTTCTAG AAACCATCA
 781 GATGTTTCCA GGGTGCCCCA AGGACCTGAA ATGACCCTGT GCCTTATTTG AACTAACCAA
 841 TCAGTTCGCT TCTCGCTTCT GTTCGCGCGC TTCTGCTCCC CGAGCTCTAT ATAAGCAGAG
 901 CTCGTTTAGT GAACCGTCAG ATCGCCTGGA GACGCCATCC ACGCTGTTTT GACTTCCATA
 961 GAAGGATCTC GAGGCCACCA TGGTGAGCAA GGGCGAGGAG CTGTTCACCG GGGTGGTGCC
1021 CATCCTGGTC GAGCTGGACG GCGACGTAAA CGGCCACAAG TTCAGCGTGT CCGGCGAGGG
1081 CGAGGGCGAT GCCACCTACG GCAAGCTGAC CCTGAAGTTC ATCTGCACCA CCGGCAAGCT
1141 GCCCGTGCCC TGGCCCACCC TCGTGACCAC CCTGACCTAC GGCGTGCAGT GCTTCAGCCG
1201 CTACCCCGAC CACATGAAGC AGCACGACTT CTTCAAGTCC GCCATGCCCG AAGGCTACGT
1261 CCAGGAGCGC ACCATCTTCT TCAAGGACGA CGGCAACTAC AAGACCCGCG CCGAGGTGAA
1321 GTTCGAGGGC GACACCCTGG TGAACCGCAT CGAGCTGAAG GGCATCGACT TCAAGGAGGA
1381 CGGCAACATC CTGGGGCACA AGCTGGAGTA CAACTACAAC AGCCACAACG TCTATATCAT
1441 GGCCGACAAG CAGAAGAACG GCATCAAGGT GAACTTCAAG ATCCGCCACA ACATCGAGGA
1501 CGGCAGCGTG CAGCTCGCCG ACCACTACCA GCAGAACACC CCCATCGGCG ACGGCCCCGT
1561 GCTGCTGCCC GACAACCACT ACCTGAGCAC CCAGTCCGCC CTGAGCAAAG ACCCCAACGA
1621 GAAGCGCGAT CACATGGTCC TGCTGGAGTT CGTGACCGCC GCCGGGATCA CTCTCGGCAT
1681 GGACGAGCTG TACAAGTAAA CTAGTGTCGA CTGCTTTATT TGTGAAATTT GTGATGCTAT
1741 TGCTTTATTT GTAACCATTA TAAGCTGCAA TAAACAAGTT AACAACAACA ATTGCATTCA
1801 TTTTATGTTT CAGGTTCAGG GGGAGGTGTG GGAGGTTTTT TAAAACGTAC ATCACTCGCT
```

-continued

```
1861 CCCCCATTCC ATCCTCCACC ACTCCAAGCC CCTCTGCAAG AAGCAGCCCC GACCAAAGCC

1921 TCAAGAGCTC CAGCCCTCAC AGCAGCCCTG GGAATACGGT GTCCCCTGTG GGCCCCGGCT

1981 CTCAAGAGCA CCGGGACTCC TACGCTTACT TGAACGCGTC CTACGGCACG GAAGGTTTGG

2041 GCTCCTACCC TGGCTACGCA CCCCTGCCCC ACCTCCCGCC AGCTTTCATC CCCTCGTACA

2101 ACGCTCACTA CCCCAAGTTC CTCTTGCCCC CCTACGGCAT GAATTGTAAT GGCCTGAGCG

2161 CTGTGAGCAG CATGAATGGC ATCAACAACT TTGGCCTCTT CCCGAGGCTG TGCCCTGTCT

2221 ACAGCAATCT CCTCGGTGGG GGCATCTAGA GTAGATAAGT AGCATGGCGG GTTAATCATT

2281 AACTACAAGG AACCCCTAGT GATGGAGTTG GCCACTCCCT CTCTGCGCGC TCGCTCGCTC

2341 ACTGAGGCCG GGCGACCAAA GGTCGCCCGA CGCCCGGGCT TTGCCCGGGC GGCCTCAGTG

2401 AGCGAGCGAG CGCGCCAGCT GGCGTAATAG CGAAGAGGCC CGCACCGATC GCCCTTCCCA

2461 ACAGTTGCGC AGCCTGAATG GCGAATGGCG ATTCCGTTGC AATGGCTGGC GGTAATATTG

2521 TTCTGGATAT TACCAGCAAG GCCGATAGTT TGAGTTCTTC TACTCAGGCA AGTGATGTTA

2581 TTACTAATCA AGAAGTATT GCGACAACGG TTAATTTGCG TGATGGACAG ACTCTTTTAC

2641 TCGGTGGCCT CACTGATTAT AAAAACACTT CTCAGGATTC TGGCGTACCG TTCCTGTCTA

2701 AAATCCCTTT AATCGGCCTC CTGTTTAGCT CCCGCTCTGA TTCTAACGAG GAAAGCACGT

2761 TATACGTGCT CGTCAAAGCA ACCATAGTAC GCGCCCTGTA GCGGCGCATT AAGCGCGGCG

2821 GGTGTGGTGG TTACGCGCAG CGTGACCGCT ACACTTGCCA GCGCCCTAGC GCCCGCTCCT

2881 TTCGCTTTCT TCCCTTCCTT TCTCGCCACG TTCGCCGGCT TTCCCCGTCA AGCTCTAAAT

2941 CGGGGGCTCC CTTTAGGGTT CCGATTTAGT GCTTTACGGC ACCTCGACCC CAAAAAACTT

3001 GATTAGGGTG ATGGTTCACG TAGTGGGCCA TCGCCCTGAT AGACGGTTTT TCGCCCTTTG

3061 ACGTTGGAGT CCACGTTCTT TAATAGTGGA CTCTTGTTCC AAACTGGAAC AACACTCAAC

3121 CCTATCTCGG TCTATTCTTT TGATTTATAA GGGATTTTGC CGATTTCGGC CTATTGGTTA

3181 AAAAATGAGC TGATTTAACA AAAATTTAAC GCGAATTTTA ACAAAATATT AACGTTTACA

3241 ATTTAAATAT TTGCTTATAC AATCTTCCTG TTTTTGGGGC TTTTCTGATT ATCAACCGGG

3301 GTACATATGA TTGACATGCT AGTTTTACGA TTACCGTTCA TCGATTCTCT TGTTTGCTCC

3361 AGACTCTCAG GCAATGACCT GATAGCCTTT GTAGAGACCT CTCAAAAATA GCTACCCTCT

3421 CCGGCATGAA TTTATCAGCT AGAACGGTTG AATATCATAT TGATGGTGAT TTGACTGTCT

3481 CCGGCCTTTC TCACCCGTTT GAATCTTTAC CTACACATTA CTCAGGCATT GCATTTAAAA

3541 TATATGAGGG TTCTAAAAAT TTTTATCCTT GCGTTGAAAT AAAGGCTTCT CCCGCAAAAG

3601 TATTACAGGG TCATAATGTT TTTGGTACAA CCGATTTAGC TTTATGCTCT GAGGCTTTAT

3661 TGCTTAATTT TGCTAATTCT TTGCCTTGCC TGTATGATTT ATTGGATGTT GGAATCGCCT

3721 GATGCGGTAT TTTCTCCTTA CGCATCTGTG CGGTATTTCA CACCGCATAT GGTGCACTCT

3781 CAGTACAATC TGCTCTGATG CCGCATAGTT AAGCCAGCCC CGACACCCGC CAACACCCGC

3841 TGACGCGCCC TGACGGGCTT GTCTGCTCCC GGCATCCGCT TACAGACAAG CTGTGACCGT

3901 CTCCGGGAGC TGCATGTGTC AGAGGTTTTC ACCGTCATCA CCGAAACGCG CGAGACGAAA

3961 GGGCCTCGTG ATACGCCTAT TTTTATAGGT TAATGTCATG ATAATAATGG TTTCTTAGAC

4021 GTCAGGTGGC ACTTTTCGGG GAAATGTGCG CGGAACCCCT ATTTGTTTAT TTTTCTAAAT

4081 ACATTCAAAT ATGTATCCGC TCATGAGACA ATAACCCTGA TAAATGCTTC AATAATATTG

4141 AAAAAGGAAG AGTATGAGTA TTCAACATTT CCGTGTCGCC CTTATTCCCT TTTTTGCGGC

4201 ATTTTGCCTT CCTGTTTTTG CTCACCCAGA AACGCTGGTG AAAGTAAAAG ATGCTGAAGA

4261 TCAGTTGGGT GCACGAGTGG GTTACATCGA ACTGGATCTC AACAGCGGTA AGATCCTTGA
```

-continued

```
4321 GAGTTTTCGC CCCGAAGAAC GTTTTCCAAT GATGAGCACT TTTAAAGTTC TGCTATGTGG

4381 CGCGGTATTA TCCCGTATTG ACGCCGGGCA AGAGCAACTC GGTCGCCGCA TACACTATTC

4441 TCAGAATGAC TTGGTTGAGT ACTCACCAGT CACAGAAAAG CATCTTACGG ATGGCATGAC

4501 AGTAAGAGAA TTATGCAGTG CTGCCATAAC CATGAGTGAT AACACTGCGG CCAACTTACT

4561 TCTGACAACG ATCGGAGGAC CGAAGGAGCT AACCGCTTTT TTGCACAACA TGGGGGATCA

4621 TGTAACTCGC CTTGATCGTT GGGAACCGGA GCTGAATGAA GCCATACCAA ACGACGAGCG

4681 TGACACCACG ATGCCTGTAG CAATGGCAAC AACGTTGCGC AAACTATTAA CTGGCGAACT

4741 ACTTACTCTA GCTTCCCGGC AACAATTAAT AGACTGGATG GAGGCGGATA AAGTTGCAGG

4801 ACCACTTCTG CGCTCGGCCC TTCCGGCTGG CTGGTTTATT GCTGATAAAT CTGGAGCCGG

4861 TGAGCGTGGG TCTCGCGGTA TCATTGCAGC ACTGGGGCCA GATGGTAAGC CCTCCCGTAT

4921 CGTAGTTATC TACACGACGG GGAGTCAGGC AACTATGGAT GAACGAAATA GACAGATCGC

4981 TGAGATAGGT GCCTCACTGA TTAAGCATTG GTAACTGTCA GACCAAGTTT ACTCATATAT

5041 ACTTTAGATT GATTTAAAAC TTCATTTTTA ATTTAAAAGG ATCTAGGTGA AGATCCTTTT

5101 TGATAATCTC ATGACCAAAA TCCCTTAACG TGAGTTTTCG TTCCACTGAG CGTCAGACCC

5161 CGTAGAAAAG ATCAAAGGAT CTTCTTGAGA TCCTTTTTTT CTGCGCGTAA TCTGCTGCTT

5221 GCAAACAAAA AAACCACCGC TACCAGCGGT GGTTTGTTTG CCGGATCAAG AGCTACCAAC

5281 TCTTTTTCCG AAGGTAACTG GCTTCAGCAG AGCGCAGATA CCAAATACTG TCCTTCTAGT

5341 GTAGCCGTAG TTAGGCCACC ACTTCAAGAA CTCTGTAGCA CCGCCTACAT ACCTCGCTCT

5401 GCTAATCCTG TTACCAGTGG CTGCTGCCAG TGGCGATAAG TCGTGTCTTA CCGGGTTGGA

5461 CTCAAGACGA TAGTTACCGG ATAAGGCGCA GCGGTCGGGC TGAACGGGGG GTTCGTGCAC

5521 ACAGCCCAGC TTGGAGCGAA CGACCTACAC CGAACTGAGA TACCTACAGC GTGAGCTATG

5581 AGAAAGCGCC ACGCTTCCCG AAGGGAGAAA GGCGGACAGG TATCCGGTAA GCGGCAGGGT

5641 CGGAACAGGA GAGCGCACGA GGGAGCTTCC AGGGGGAAAC GCCTGGTATC TTTATAGTCC

5701 TGTCGGGTTT CGCCACCTCT GACTTGAGCG TCGATTTTTG TGATGCTCGT CAGGGGGGCG

5761 GAGCCTATGG AAAAACGCCA GCAACGCGGC CTTTTTACGG TTCCTGGCCT TTTGCTGGCC

5821 TTTTGCTCAC ATGTTCTTTC CTGCGTTATC CCCTGATTCT GTGGATAACC GTATTACCGC

5881 CTTTGAGTGA GCTGATACCG CTCGCCGCAG CCGAACGACC GAGCGCAGCG AGTCAGTGAG

5941 CGAGGAAGCG GAAGAGCGCC CAATACGCAA ACCGCCTCTC CCCGCGCGTT GGCCGATTCA

6001 TTAATG

1361_pAAV.Blimp1.1.0 kb.MND.GFP.pA
                                                          (SEQ ID NO: 17)
   1 CAGCTGCGCG CTCGCTCGCT CACTGAGGCC GCCCGGGCAA AGCCCGGGCG TCGGGCGACC

61 TTTGGTCGCC CGGCCTCAGT GAGCGAGCGA GCGCGCAGAG AGGGAGTGGC CAACTCCATC

121 ACTAGGGGTT CCTTGTAGTT AATGATTAAC CCGCCATGCT ACTTATCTAC ACGCGTGGTA

181 AACCATGAAC ATCAGAAAGA CTTTTATTAA CCTATGACAG GGTCCCCACC CCAGTATTTT

241 TCCACTCCAT TAAAATGGAA GTTTTTTTTT TTTTTTCTT TTTTGAGACA GAGTTTTGCT

301 CTTGTTGCCC AGTCTGGAGT GCAATGGCAC AATCTCGGCT CACCACAACC TCCACCTCCC

361 AGATTCAAGC GATTCTTCTG CCTCAGCCTC CCAAGTAGCT GGGATTACAG GTGTGCGCCA

421 CCACGCCCAG CTAATTTTGT ATTTTTAGTA GAGATGGGGT TTCTCCATGT TGGTCAGGCT

481 GGTCTCGAAC TTCCGACCTC AGGTGATCCG CCCACCTCGG CCTCCCAAAG TGCTGGGATT

541 ACAGGCAAGA GCCACTGCAT CCAGCTTAGG CTATCTTACT CCAGCCTAAA CAGCAATTTT
```

-continued

```
 601 CTATCATAAG GTCTGTACTA ATGAAAACAG AATCACCCAA GGCTGCTGTT TGTTCTGTCT

661 GTGCTGCCAT TGTCCGCATT TTGCTGAGGA GGAAACGGAA CTGCACTTTT GAGTGAGTGG

721 CCCAGAGCCT TCTAGAATGA GAGTGCGTTG GAAGCCAGAT ATGTGGCGAT TGTGTCGCCA

781 GCTGTTACTC AGGTTTTCTC AAGAAGGAGG AGCAACTTTG GCAGTTTTGC TTCAGTTCTC

841 TCTAGCCCTC TGTGTAATCG CCCCTTTTTC TTTATTTCAG CACAAACACA GAGCAGTCTA

901 AAGCAACCGA GCACTGAGAA AAATGAACTC TGCCCAAAGA ATGTCCCAAA GAGAGAGTAC

961 AGCGTGAAAG AAATCCTAAA ATTGGACTCC AACCCCTCCA AAGGAAAGGA CCTCTACCGT

1021 TCTAACATTT CACCCCTCAC ATCAGAAAAG GACCTCGATG ACTTTAGAAG ACGTGGGAGC

1081 CCCGAAATGC CCTTCTACCC TCGGGTCGTT TACCCCATCC GGGCCCCTCT GCCAGAAGAC

1141 TTTTTGAAAG CTTCCCTGGC CTACGGGATC GAGAGAGAAC AGAGAAACAG GAGAATATGG

1201 GCCAAACAGG ATATCTGTGG TAAGCAGTTC CTGCCCCGGC TCAGGGCCAA GAACAGTTGG

1261 AACAGCAGAA TATGGGCCAA ACAGGATATC TGTGGTAAGC AGTTCCTGCC CCGGCTCAGG

1321 GCCAAGAACA GATGGTCCCC AGATGCGGTC CCGCCCTCAG CAGTTTCTAG AACCATCA

1381 GATGTTTCCA GGGTGCCCCA AGGACCTGAA ATGACCCTGT GCCTTATTTG AACTAACCAA

1441 TCAGTTCGCT TCTCGCTTCT GTTCGCGCGC TTCTGCTCCC CGAGCTCTAT ATAAGCAGAG

1501 CTCGTTTAGT GAACCGTCAG ATCGCCTGGA GACGCCATCC ACGCTGTTTT GACTTCCATA

1561 GAAGGATCTC GAGGCCACCA TGGTGAGCAA GGGCGAGGAG CTGTTCACCG GGGTGGTGCC

1621 CATCCTGGTC GAGCTGGACG GCGACGTAAA CGGCCACAAG TTCAGCGTGT CCGGCGAGGG

1681 CGAGGGCGAT GCCACCTACG GCAAGCTGAC CCTGAAGTTC ATCTGCACCA CCGGCAAGCT

1741 GCCCGTGCCC TGGCCCACCC TCGTGACCAC CCTGACCTAC GGCGTGCAGT GCTTCAGCCG

1801 CTACCCCGAC CACATGAAGC AGCACGACTT CTTCAAGTCC GCCATGCCCG AAGGCTACGT

1861 CCAGGAGCGC ACCATCTTCT TCAAGGACGA CGGCAACTAC AAGACCCGCG CCGAGGTGAA

1921 GTTCGAGGGC GACACCCTGG TGAACCGCAT CGAGCTGAAG GGCATCGACT TCAAGGAGGA

1981 CGGCAACATC CTGGGGCACA AGCTGGAGTA CAACTACAAC AGCCACAACG TCTATATCAT

2041 GGCCGACAAG CAGAAGAACG GCATCAAGGT GAACTTCAAG ATCCGCCACA ACATCGAGGA

2101 CGGCAGCGTG CAGCTCGCCG ACCACTACCA GCAGAACACC CCCATCGGCG ACGGCCCCGT

2161 GCTGCTGCCC GACAACCACT ACCTGAGCAC CCAGTCCGCC CTGAGCAAAG ACCCCAACGA

2221 GAAGCGCGAT CACATGGTCC TGCTGGAGTT CGTGACCGCC GCCGGGATCA CTCTCGGCAT

2281 GGACGAGCTG TACAAGTAAA CTAGTGTCGA CTGCTTTATT TGTGAAATTT GTGATGCTAT

2341 TGCTTTATTT GTAACCATTA TAAGCTGCAA TAAACAAGTT AACAACAACA ATTGCATTCA

2401 TTTTATGTTT CAGGTTCAGG GGGAGGTGTG GGAGGTTTTT TAAAACGTAC ATCACTCGCT

2461 CCCCCATTCC ATCCTCCACC ACTCCAAGCC CCTCTGCAAG AAGCAGCCCC GACCAAAGCC

2521 TCAAGAGCTC CAGCCCTCAC AGCAGCCCTG GGAATACGGT GTCCCCTGTG GCCCCGGCT

2581 CTCAAGAGCA CCGGGACTCC TACGCTTACT TGAACGCGTC CTACGGCACG GAAGGTTTGG

2641 GCTCCTACCC TGGCTACGCA CCCCTGCCCC ACCTCCCGCC AGCTTTCATC CCCTCGTACA

2701 ACGCTCACTA CCCCAAGTTC CTCTTGCCCC CCTACGGCAT GAATTGTAAT GGCCTGAGCG

2761 CTGTGAGCAG CATGAATGGC ATCAACAACT TTGGCCTCTT CCCGAGGCTG TGCCCTGTCT

2821 ACAGCAATCT CCTCGGTGGG GGCAGCCTGC CCCACCCCAT GCTCAACCCC ACTTCTCTCC

2881 CGAGCTCGCT GCCCTCAGAT GGAGCCCGGA GGTTGCTCCA GCCGGAGCAT CCCAGGGAGG

2941 TGCTTGTCCC GGCGCCCCAC AGTGCCTTCT CCTTTACCGG GGCCGCCGCC AGCATGAAGG

3001 ACAAGGCCTG TAGCCCCACA AGCGGGTCTC CCACGGCGGG AACAGCCGCC ACGGCAGAAC
```

```
3061 ATGTGGTGCA GCCCAAAGCT ACCTCAGCAG CGATGGCAGC CCCCAGCAGC GACGAAGCCA
3121 TGAATCTCAT TAAAAACAAA AGAAACATGA CCGGCTACAA GACCCTTCCC TACCCGCTGA
3181 AGAAGCAGAA CGGCAAGATC AAGTACGAAT GCAACGTTTG CGCCAAGACT TTCGGCCAGC
3241 TCTCCAATCT GAAGGTAGGC CTTGAGAGAG AGCAGTCCAA GGGGCTGTGA GTGCATGCTT
3301 GTGTTTGTAT TTAGCTTGCT TTCCATGGGG TATCGATTGC ATTTGCAGTA GTATGAGCCC
3361 CCGGTTGGGG ATAGTGGGTA TGGATTCCGC CTGGCTTTTG CCACTTCTAG CTCTTTGACT
3421 TTGGACAAGT GACTTCCCTT CTCCTCTAGA GTAGATAAGT AGCATGGCGG GTTAATCATT
3481 AACTACAAGG AACCCCTAGT GATGGAGTTG GCCACTCCCT CTCTGCGCGC TCGCTCGCTC
3541 ACTGAGGCCG GGCGACCAAA GGTCGCCCGA CGCCCGGGCT TTGCCCGGGC GGCCTCAGTG
3601 AGCGAGCGAG CGCGCCAGCT GGCGTAATAG CGAAGAGGCC CGCACCGATC GCCCTTCCCA
3661 ACAGTTGCGC AGCCTGAATG GCGAATGGCG ATTCCGTTGC AATGGCTGGC GGTAATATTG
3721 TTCTGGATAT TACCAGCAAG GCCGATAGTT TGAGTTCTTC TACTCAGGCA AGTGATGTTA
3781 TTACTAATCA AGAAGTATT GCGACAACGG TTAATTTGCG TGATGGACAG ACTCTTTTAC
3841 TCGGTGGCCT CACTGATTAT AAAAACACTT CTCAGGATTC TGGCGTACCG TTCCTGTCTA
3901 AAATCCCTTT AATCGGCCTC CTGTTTAGCT CCCGCTCTGA TTCTAACGAG GAAAGCACGT
3961 TATACGTGCT CGTCAAAGCA ACCATAGTAC GCGCCCTGTA GCGGCGCATT AAGCGCGGCG
4021 GGTGTGGTGG TTACGCGCAG CGTGACCGCT ACACTTGCCA GCGCCCTAGC GCCCGCTCCT
4081 TTCGCTTTCT TCCCTTCCTT TCTCGCCACG TTCGCCGGCT TTCCCCGTCA AGCTCTAAAT
4141 CGGGGGCTCC CTTTAGGGTT CCGATTTAGT GCTTTACGGC ACCTCGACCC CAAAAAACTT
4201 GATTAGGGTG ATGGTTCACG TAGTGGGCCA TCGCCCTGAT AGACGGTTTT TCGCCCTTTG
4261 ACGTTGGAGT CCACGTTCTT TAATAGTGGA CTCTTGTTCC AAACTGGAAC AACACTCAAC
4321 CCTATCTCGG TCTATTCTTT TGATTTATAA GGGATTTTGC CGATTTCGGC CTATTGGTTA
4381 AAAAATGAGC TGATTTAACA AAAATTTAAC GCGAATTTTA ACAAAATATT AACGTTTACA
4441 ATTTAAATAT TTGCTTATAC AATCTTCCTG TTTTTGGGGC TTTTCTGATT ATCAACCGGG
4501 GTACATATGA TTGACATGCT AGTTTTACGA TTACCGTTCA TCGATTCTCT TGTTTGCTCC
4561 AGACTCTCAG GCAATGACCT GATAGCCTTT GTAGAGACCT CTCAAAAATA GCTACCCTCT
4621 CCGGCATGAA TTTATCAGCT AGAACGGTTG AATATCATAT TGATGGTGAT TTGACTGTCT
4681 CCGGCCTTTC TCACCCGTTT GAATCTTTAC CTACACATTA CTCAGGCATT GCATTTAAAA
4741 TATATGAGGG TTCTAAAAAT TTTTATCCTT GCGTTGAAAT AAAGGCTTCT CCCGCAAAAG
4801 TATTACAGGG TCATAATGTT TTTGGTACAA CCGATTTAGC TTTATGCTCT GAGGCTTTAT
4861 TGCTTAATTT TGCTAATTCT TTGCCTTGCC TGTATGATTT ATTGGATGTT GGAATCGCCT
4921 GATGCGGTAT TTTCTCCTTA CGCATCTGTG CGGTATTTCA CACCGCATAT GGTGCACTCT
4981 CAGTACAATC TGCTCTGATG CCGCATAGTT AAGCCAGCCC CGACACCCGC CAACACCCGC
5041 TGACGCGCCC TGACGGGCTT GTCTGCTCCC GGCATCCGCT TACAGACAAG CTGTGACCGT
5101 CTCCGGGAGC TGCATGTGTC AGAGGTTTTC ACCGTCATCA CCGAAACGCG CGAGACGAAA
5161 GGGCCTCGTG ATACGCCTAT TTTTATAGGT TAATGTCATG ATAATAATGG TTTCTTAGAC
5221 GTCAGGTGGC ACTTTTCGGG GAAATGTGCG CGGAACCCCT ATTTGTTTAT TTTTCTAAAT
5281 ACATTCAAAT ATGTATCCGC TCATGAGACA ATAACCCTGA TAAATGCTTC AATAATATTG
5341 AAAAAGGAAG AGTATGAGTA TTCAACATTT CCGTGTCGCC CTTATTCCCT TTTTTGCGGC
5401 ATTTTGCCTT CCTGTTTTTG CTCACCCAGA AACGCTGGTG AAAGTAAAAG ATGCTGAAGA
```

-continued

```
5461 TCAGTTGGGT GCACGAGTGG GTTACATCGA ACTGGATCTC AACAGCGGTA AGATCCTTGA

5521 GAGTTTTCGC CCCGAAGAAC GTTTTCCAAT GATGAGCACT TTTAAAGTTC TGCTATGTGG

5581 CGCGGTATTA TCCCGTATTG ACGCCGGGCA AGAGCAACTC GGTCGCCGCA TACACTATTC

5641 TCAGAATGAC TTGGTTGAGT ACTCACCAGT CACAGAAAAG CATCTTACGG ATGGCATGAC

5701 AGTAAGAGAA TTATGCAGTG CTGCCATAAC CATGAGTGAT AACACTGCGG CCAACTTACT

5761 TCTGACAACG ATCGGAGGAC CGAAGGAGCT AACCGCTTTT TTGCACAACA TGGGGGATCA

5821 TGTAACTCGC CTTGATCGTT GGGAACCGGA GCTGAATGAA GCCATACCAA ACGACGAGCG

5881 TGACACCACG ATGCCTGTAG CAATGGCAAC AACGTTGCGC AAACTATTAA CTGGCGAACT

5941 ACTTACTCTA GCTTCCCGGC AACAATTAAT AGACTGGATG GAGGCGGATA AAGTTGCAGG

6001 ACCACTTCTG CGCTCGGCCC TTCCGGCTGG CTGGTTTATT GCTGATAAAT CTGGAGCCGG

6061 TGAGCGTGGG TCTCGCGGTA TCATTGCAGC ACTGGGGCCA GATGGTAAGC CCTCCCGTAT

6121 CGTAGTTATC TACACGACGG GGAGTCAGGC AACTATGGAT GAACGAAATA GACAGATCGC

6181 TGAGATAGGT GCCTCACTGA TTAAGCATTG GTAACTGTCA GACCAAGTTT ACTCATATAT

6241 ACTTTAGATT GATTTAAAAC TTCATTTTTA ATTTAAAAGG ATCTAGGTGA AGATCCTTTT

6301 TGATAATCTC ATGACCAAAA TCCCTTAACG TGAGTTTTCG TTCCACTGAG CGTCAGACCC

6361 CGTAGAAAAG ATCAAAGGAT CTTCTTGAGA TCCTTTTTTT CTGCGCGTAA TCTGCTGCTT

6421 GCAAACAAAA AAACCACCGC TACCAGCGGT GGTTTGTTTG CCGGATCAAG AGCTACCAAC

6481 TCTTTTTCCG AAGGTAACTG GCTTCAGCAG AGCGCAGATA CCAAATACTG TCCTTCTAGT

6541 GTAGCCGTAG TTAGGCCACC ACTTCAAGAA CTCTGTAGCA CCGCCTACAT ACCTCGCTCT

6601 GCTAATCCTG TTACCAGTGG CTGCTGCCAG TGGCGATAAG TCGTGTCTTA CCGGGTTGGA

6661 CTCAAGACGA TAGTTACCGG ATAAGGCGCA GCGGTCGGGC TGAACGGGGG GTTCGTGCAC

6721 ACAGCCCAGC TTGGAGCGAA CGACCTACAC CGAACTGAGA TACCTACAGC GTGAGCTATG

6781 AGAAAGCGCC ACGCTTCCCG AAGGGAGAAA GGCGGACAGG TATCCGGTAA GCGGCAGGGT

6841 CGGAACAGGA GAGCGCACGA GGGAGCTTCC AGGGGGAAAC GCCTGGTATC TTTATAGTCC

6901 TGTCGGGTTT CGCCACCTCT GACTTGAGCG TCGATTTTTG TGATGCTCGT CAGGGGGGCG

6961 GAGCCTATGG AAAAACGCCA GCAACGCGGC CTTTTTACGG TTCCTGGCCT TTTGCTGGCC

7021 TTTTGCTCAC ATGTTCTTTC CTGCGTTATC CCCTGATTCT GTGGATAACC GTATTACCGC

7081 CTTTGAGTGA GCTGATACCG CTCGCCGCAG CCGAACGACC GAGCGCAGCG AGTCAGTGAG

7141 CGAGGAAGCG GAAGAGCGCC CAATACGCAA ACCGCCTCTC CCCGCGCGTT GGCCGATTCA

7201 TTAATG
```

1366_CCR5.MND.BAFF_CRISPR.HR (SEQ ID NO: 18)

```
  1 CAGCTGCGCG CTCGCTCGCT CACTGAGGCC GCCCGGGCAA AGCCCGGGCG TCGGGCGACC

61 TTTGGTCGCC CGGCCTCAGT GAGCGAGCGA GCGCGCAGAG AGGGAGTGGC CAACTCCATC

121 ACTAGGGGTT CCTTGTAGTT AATGATTAAC CCGCCATGCT ACTTATCTAC GTAGCCATGC

181 TCTAGCGGCC TCGGCTCTG CATAAATAAA AAAATTAGT CAGCCATGAG CTTGGACGCG

241 TTTGGTGTGG TGGCGCCTGT AGTCCCCAGC CACTTGGAGG GGTGAGGTGA GAGGATTGCT

301 TGAGCCCGGG ATGGTCCAGG CTGCAGTGAG CCATGATCGT GCCACTGCAC TCCAGCCTGG

361 GCGACAGAGT GAGACCCTGT CTCACAACAA CAACAACAAC AACAAAAAGG CTGAGCTGCA

421 CCATGCTTGA CCCAGTTTCT TAAAATTGTT GTCAAAGCTT CATTCACTCC ATGGTGCTAT

481 AGAGCACAAG ATTTTATTTG GTGAGATGGT GCTTTCATGA ATTCCCCCAA CAGAGCCAAG

541 CTCTCCATCT AGTGGACAGG GAAGCTAGCA GCAAACCTTC CCTTCACTAC AAAACTTCAT
```

```
 601 TGCTTGGCCA AAAAGAGAGT TAATTCAATG TAGACATCTA TGTAGGCAAT TAAAAACCTA
 661 TTGATGTATA AAACAGTTTG CATTCATGGA GGGCAACTAA ATACATTCTA GGACTTTATA
 721 AAAGATCACT TTTTATTTAT GCACAGGGTG GAACAAGATG GATTATCAAG TGTCAAGTCC
 781 AATCTATGAC ATCAATTATT ATACATCGGA GCCCTGCCAA AAAATCAATG TGAAGCAAAT
 841 CGCAGCCCGC CTCCTGCCTC CGCTCTACTC ACTGGTGTTC ATCTTTGGTT TTGTGGGCAA
 901 CATGCTGGTC ATCCTCATCC TGATAAACTG CAAAAGGCTG AAGAGCATGA CTGACATCTA
 961 CCTGCTCAAC CTGGCCATCT CTGACCTGTT TTTCCTTCTT ACTGTCCCCT TCTGGGCTCA
1021 CTATGCTGCC GCCCAGTGGG ACTTTGGAAA TACAATGTGT CAACGAACAG AGAAACAGGA
1081 GAATATGGGC CAAACAGGAT ATCTGTGGTA AGCAGTTCCT GCCCCGGCTC AGGGCCAAGA
1141 ACAGTTGGAA CAGCAGAATA TGGGCCAAAC AGGATATCTG TGGTAAGCAG TTCCTGCCCC
1201 GGCTCAGGGC CAAGAACAGA TGGTCCCCAG ATGCGGTCCC GCCCTCAGCA GTTTCTAGAG
1261 AACCATCAGA TGTTTCCAGG GTGCCCCAAG GACCTGAAAT GACCCTGTGC CTTATTTGAA
1321 CTAACCAATC AGTTCGCTTC TCGCTTCTGT TCGCGCGCTT CTGCTCCCCG AGCTCTATAT
1381 AAGCAGAGCT CGTTTAGTGA ACCGTCAGAT CGCCTGGAGA CGCCATCCAC GCTGTTTTGA
1441 CTTCCATAGA AGGATCTCGA GGCCACCATG TACCGGATGC AGCTGCTGAG CTGCATCGCA
1501 CTGAGCCTGG CACTGGTGAC CAACAGCGCA GTGCAGGGAC CAGAGGAGAC CGTGACCCAG
1561 GACTGCCTGC AGCTGATCGC AGACAGCGAG ACCCCCACCA TCCAGAAGGG CAGCTACACC
1621 TTCGTGCCCT GGCTGCTGAG CTTCAAGCGG GGCAGCGCCC TGGAGGAGAA GGAGAACAAG
1681 ATTCTGGTGA AGGAGACCGG CTACTTCTTC ATCTACGGCC AGGTGCTGTA CACCGATAAG
1741 ACCTACGCCA TGGGCCACCT GATCCAGCGG AAGAAGGTGC ACGTGTTCGG CGACGAGCTG
1801 AGCCTGGTGA CCCTGTTCCG GTGCATCCAG AACATGCCCG AGACCCTGCC CAACAACAGC
1861 TGCTACAGCG CAGGAATCGC AAAGCTGGAG GAGGGCGACG AGCTGCAGCT GGCAATCCCC
1921 CGGGAGAACG CACAGATCAG CCTGGACGGC GACGTGACCT TCTTCGGCGC CCTGAAGCTC
1981 CTGTGAGTCG ACTGCTTTAT TTGTGAAATT TGTGATGCTA TTGCTTTATT TGTAACCATT
2041 ATAAGCTGCA ATAAACAAGT TAACAACAAC AATTGCATTC ATTTTATGTT TCAGGTTCAG
2101 GGGGAGGTGT GGGAGGTTTT TTAAACTCTA TTTTATAGGC TTCTTCTCTG GAATCTTCTT
2161 CATCATCCTC CTGACAATCG ATAGGTACCT GGCTGTCGTC CATGCTGTGT TTGCTTTAAA
2221 AGCCAGGACG GTCACCTTTG GGGTGGTGAC AAGTGTGATC ACTTGGGTGG TGGCTGTGTT
2281 TGCGTCTCTC CCAGGAATCA TCTTTACCAG ATCTCAAAAA GAAGGTCTTC ATTACACCTG
2341 CAGCTCTCAT TTTCCATACA GTCAGTATCA ATTCTGGAAG AATTTCCAGA CATTAAAGAT
2401 AGTCATCTTG GGGCTGGTCC TGCCGCTGCT TGTCATGGTC ATCTGCTACT CGGGAATCCT
2461 AAAAACTCTG CTTCGGTGTC GAAATGAGAA GAAGAGGCAC AGGGCTGTGA GGCTTATCTT
2521 CACCATCATG ATTGTTTATT TTCTCTTCTG GGCTCCCTAC AACATTGTCC TTCTCCTGAA
2581 CACCTTCCAG GAATTCTTTG GCCTGAATAA TTGCAGTAGC TCTAACAGGT TGGACCAAGC
2641 TATGCAGGTG ACAGAGACTC TTGGGATGAC GCACTGCTGC ATCAACCCCA TCATCTATGC
2701 CTTTGTCGGG GAGAAGTTCA GAAACTACCT CTTAGTCTTC TTCCAAAAGC ACATTGCCAA
2761 ACGCTTCTGC AAATGCTGTT CTATTTTCCA GCAAGAGGCT CCCGAGCGAG CAAGCTCAGT
2821 TTACACCCGA TCCACTGGGG AGCAGGAAAT ATCTGTGGGC TTGTGACACG GACTCAAGTG
2881 GGCTGGTGAC CCAGTCAGAG TTGTGCACAT GGCTTAGTTT TCATACACAC CGCGGTCTAG
2941 AGCATGGCTA CGTAGATAAG TAGCATGGCG GGTTAATCAT TAACTACAAG GAACCCCTAG
```

-continued

```
3001 TGATGGAGTT GGCCACTCCC TCTCTGCGCG CTCGCTCGCT CACTGAGGCC GGGCGACCAA

3061 AGGTCGCCCG ACGCCCGGGC TTTGCCCGGG CGGCCTCAGT GAGCGAGCGA GCGCGCCAGC

3121 TGGCGTAATA GCGAAGAGGC CCGCACCGAT CGCCCTTCCC AACAGTTGCG CAGCCTGAAT

3181 GGCGAATGGC GATTCCGTTG CAATGGCTGG CGGTAATATT GTTCTGGATA TTACCAGCAA

3241 GGCCGATAGT TTGAGTTCTT CTACTCAGGC AAGTGATGTT ATTACTAATC AAAGAAGTAT

3301 TGCGACAACG GTTAATTTGC GTGATGGACA GACTCTTTTA CTCGGTGGCC TCACTGATTA

3361 TAAAAACACT TCTCAGGATT CTGGCGTACC GTTCCTGTCT AAAATCCCTT AATCGGCCT

3421 CCTGTTTAGC TCCCGCTCTG ATTCTAACGA GGAAAGCACG TTATACGTGC TCGTCAAAGC

3481 AACCATAGTA CGCGCCCTGT AGCGGCGCAT TAAGCGCGGC GGGTGTGGTG GTTACGCGCA

3541 GCGTGACCGC TACACTTGCC AGCGCCCTAG CGCCCGCTCC TTTCGCTTTC TTCCCTTCCT

3601 TTCTCGCCAC GTTCGCCGGC TTTCCCCGTC AAGCTCTAAA TCGGGGGCTC CCTTTAGGGT

3661 TCCGATTTAG TGCTTTACGG CACCTCGACC CCAAAAAACT TGATTAGGGT GATGGTTCAC

3721 GTAGTGGGCC ATCGCCCTGA TAGACGGTTT TTCGCCCTTT GACGTTGGAG TCCACGTTCT

3781 TTAATAGTGG ACTCTTGTTC CAAACTGGAA CAACACTCAA CCCTATCTCG GTCTATTCTT

3841 TTGATTTATA AGGGATTTTG CCGATTTCGG CCTATTGGTT AAAAAATGAG CTGATTTAAC

3901 AAAAATTTAA CGCGAATTTT AACAAAATAT TAACGTTTAC AATTTAAATA TTTGCTTATA

3961 CAATCTTCCT GTTTTGGGG CTTTTCTGAT TATCAACCGG GGTACATATG ATTGACATGC

4021 TAGTTTTACG ATTACCGTTC ATCGATTCTC TTGTTTGCTC CAGACTCTCA GGCAATGACC

4081 TGATAGCCTT TGTAGAGACC TCTCAAAAAT AGCTACCCTC TCCGGCATGA ATTTATCAGC

4141 TAGAACGGTT GAATATCATA TTGATGGTGA TTTGACTGTC TCCGGCCTTT CTCACCCGTT

4201 TGAATCTTTA CCTACACATT ACTCAGGCAT TGCATTTAAA ATATATGAGG GTTCTAAAAA

4261 TTTTTATCCT TGCGTTGAAA TAAAGGCTTC TCCCGCAAAA GTATTACAGG GTCATAATGT

4321 TTTTGGTACA ACCGATTTAG CTTTATGCTC TGAGGCTTTA TTGCTTAATT TTGCTAATTC

4381 TTTGCCTTGC CTGTATGATT TATTGGATGT TGGAATCGCC TGATGCGGTA TTTTCTCCTT

4441 ACGCATCTGT GCGGTATTTC ACACCGCATA TGGTGCACTC TCAGTACAAT CTGCTCTGAT

4501 GCCGCATAGT TAAGCCAGCC CCGACACCCG CCAACACCCG CTGACGCGCC CTGACGGGCT

4561 TGTCTGCTCC CGGCATCCGC TTACAGACAA GCTGTGACCG TCTCCGGGAG CTGCATGTGT

4621 CAGAGGTTTT CACCGTCATC ACCGAAACGC GCGAGACGAA AGGGCCTCGT GATACGCCTA

4681 TTTTTATAGG TTAATGTCAT GATAATAATG GTTTCTTAGA CGTCAGGTGG CACTTTTCGG

4741 GGAAATGTGC GCGGAACCCC TATTTGTTTA TTTTTCTAAA TACATTCAAA TATGTATCCG

4801 CTCATGAGAC AATAACCCTG ATAAATGCTT CAATAATATT GAAAAAGGAA GAGTATGAGT

4861 ATTCAACATT TCCGTGTCGC CCTTATTCCC TTTTTTGCGG CATTTTGCCT TCCTGTTTTT

4921 GCTCACCCAG AAACGCTGGT GAAAGTAAAA GATGCTGAAG ATCAGTTGGG TGCACGAGTG

4981 GGTTACATCG AACTGGATCT CAACAGCGGT AAGATCCTTG AGAGTTTTCG CCCCGAAGAA

5041 CGTTTTCCAA TGATGAGCAC TTTTAAAGTT CTGCTATGTG GCGCGGTATT ATCCCGTATT

5101 GACGCCGGGC AAGAGCAACT CGGTCGCCGC ATACACTATT CTCAGAATGA CTTGGTTGAG

5161 TACTCACCAG TCACAGAAAA GCATCTTACG GATGGCATGA CAGTAAGAGA ATTATGCAGT

5221 GCTGCCATAA CCATGAGTGA TAACACTGCG GCCAACTTAC TTCTGACAAC GATCGGAGGA

5281 CCGAAGGAGC TAACCGCTTT TTTGCACAAC ATGGGGGATC ATGTAACTCG CCTTGATCGT

5341 TGGGAACCGG AGCTGAATGA AGCCATACCA AACGACGAGC GTGACACCAC GATGCCTGTA

5401 GCAATGGCAA CAACGTTGCG CAAACTATTA ACTGGCGAAC TACTTACTCT AGCTTCCCGG
```

-continued

```
5461 CAACAATTAA TAGACTGGAT GGAGGCGGAT AAAGTTGCAG GACCACTTCT GCGCTCGGCC

5521 CTTCCGGCTG GCTGGTTTAT TGCTGATAAA TCTGGAGCCG GTGAGCGTGG GTCTCGCGGT

5581 ATCATTGCAG CACTGGGGCC AGATGGTAAG CCCTCCCGTA TCGTAGTTAT CTACACGACG

5641 GGGAGTCAGG CAACTATGGA TGAACGAAAT AGACAGATCG CTGAGATAGG TGCCTCACTG

5701 ATTAAGCATT GGTAACTGTC AGACCAAGTT TACTCATATA TACTTTAGAT TGATTTAAAA

5761 CTTCATTTTT AATTTAAAAG GATCTAGGTG AAGATCCTTT TTGATAATCT CATGACCAAA

5821 ATCCCTTAAC GTGAGTTTTC GTTCCACTGA GCGTCAGACC CCGTAGAAAA GATCAAAGGA

5881 TCTTCTTGAG ATCCTTTTTT TCTGCGCGTA ATCTGCTGCT TGCAAACAAA AAACCACCG

5941 CTACCAGCGG TGGTTTGTTT GCCGGATCAA GAGCTACCAA CTCTTTTTCC GAAGGTAACT

6001 GGCTTCAGCA GAGCGCAGAT ACCAAATACT GTCCTTCTAG TGTAGCCGTA GTTAGGCCAC

6061 CACTTCAAGA ACTCTGTAGC ACCGCCTACA TACCTCGCTC TGCTAATCCT GTTACCAGTG

6121 GCTGCTGCCA GTGGCGATAA GTCGTGTCTT ACCGGGTTGG ACTCAAGACG ATAGTTACCG

6181 GATAAGGCGC AGCGGTCGGG CTGAACGGGG GGTTCGTGCA CACAGCCCAG CTTGGAGCGA

6241 ACGACCTACA CCGAACTGAG ATACCTACAG CGTGAGCTAT GAGAAAGCGC CACGCTTCCC

6301 GAAGGGAGAA AGGCGGACAG GTATCCGGTA AGCGGCAGGG TCGGAACAGG AGAGCGCACG

6361 AGGGAGCTTC CAGGGGGAAA CGCCTGGTAT CTTTATAGTC CTGTCGGGTT TCGCCACCTC

6421 TGACTTGAGC GTCGATTTTT GTGATGCTCG TCAGGGGGGC GGAGCCTATG GAAAAACGCC

6481 AGCAACGCGG CCTTTTTACG GTTCCTGGCC TTTTGCTGGC CTTTTGCTCA CATGTTCTTT

6541 CCTGCGTTAT CCCCTGATTC TGTGGATAAC CGTATTACCG CCTTTGAGTG AGCTGATACC

6601 GCTCGCCGCA GCCGAACGAC CGAGCGCAGC GAGTCAGTGA GCGAGGAAGC GGAAGAGCGC

6661 CCAATACGCA AACCGCCTCT CCCCGCGCGT TGGCCGATTC ATTAATG
```

1367_CCR5.MND.BAFF.2A.GFP (SEQ ID NO: 19)

```
   1 CAGCTGCGCG CTCGCTCGCT CACTGAGGCC GCCCGGGCAA AGCCCGGGCG TCGGGCGACC

61 TTTGGTCGCC CGGCCTCAGT GAGCGAGCGA GCGCGCAGAG AGGGAGTGGC CAACTCCATC

121 ACTAGGGGTT CCTTGTAGTT AATGATTAAC CCGCCATGCT ACTTATCTAC GTAGCCATGC

181 TCTAGCGGCC TCGGCCTCTG CATAAATAAA AAAAATTAGT CAGCCATGAG CTTGGACGCG

241 TTTGGTGTGG TGGCGCCTGT AGTCCCCAGC CACTTGGAGG GGTGAGGTGA GAGGATTGCT

301 TGAGCCCGGG ATGGTCCAGG CTGCAGTGAG CCATGATCGT GCCACTGCAC TCCAGCCTGG

361 GCGACAGAGT GAGACCCTGT CTCACAACAA CAACAACAAC AACAAAAAGG CTGAGCTGCA

421 CCATGCTTGA CCCAGTTTCT TAAAATTGTT GTCAAAGCTT CATTCACTCC ATGGTGCTAT

481 AGAGCACAAG ATTTTATTTG GTGAGATGGT GCTTTCATGA ATTCCCCCAA CAGAGCCAAG

541 CTCTCCATCT AGTGGACAGG GAAGCTAGCA GCAAACCTTC CCTTCACTAC AAAACTTCAT

601 TGCTTGGCCA AAAAGAGAGT TAATTCAATG TAGACATCTA TGTAGGCAAT TAAAAACCTA

661 TTGATGTATA AAACAGTTTG CATTCATGGA GGGCAACTAA ATACATTCTA GGACTTTATA

721 AAAGATCACT TTTATTTAT GCACAGGGTG GAACAAGATG GATTATCAAG TGTCAAGTCC

781 AATCTATGAC ATCAATTATT ATACATCGGA GCCCTGCCAA AAAATCAATG TGAAGCAAAT

841 CGCAGCCCGC CTCCTGCCTC CGCTCTACTC ACTGGTGTTC ATCTTTGGTT TTGTGGGCAA

901 CATGCTGGTC ATCCTCATCC TGATAAACTG CAAAAGGCTG AAGAGCATGA CTGACATCTA

961 CCTGCTCAAC CTGGCCATCT CTGACCTGTT TTTCCTTCTT ACTGTCCCCT TCTGGGCTCA

1021 CTATGCTGCC GCCCAGTGGG ACTTTGGAAA TACAATGTGT CAACGAACAG AGAAACAGGA
```

-continued

```
1081 GAATATGGGC CAAACAGGAT ATCTGTGGTA AGCAGTTCCT GCCCCGGCTC AGGGCCAAGA

1141 ACAGTTGGAA CAGCAGAATA TGGGCCAAAC AGGATATCTG TGGTAAGCAG TTCCTGCCCC

1201 GGCTCAGGGC CAAGAACAGA TGGTCCCCAG ATGCGGTCCC GCCCTCAGCA GTTTCTAGAG

1261 AACCATCAGA TGTTTCCAGG GTGCCCCAAG GACCTGAAAT GACCCTGTGC CTTATTTGAA

1321 CTAACCAATC AGTTCGCTTC TCGCTTCTGT TCGCGCGCTT CTGCTCCCCG AGCTCTATAT

1381 AAGCAGAGCT CGTTTAGTGA ACCGTCAGAT CGCCTGGAGA CGCCATCCAC GCTGTTTTGA

1441 CTTCCATAGA AGGATCTCGA GGCCACCATG TACCGGATGC AGCTGCTGAG CTGCATCGCA

1501 CTGAGCCTGG CACTGGTGAC CAACAGCGCA GTGCAGGGAC CAGAGGAGAC CGTGACCCAG

1561 GACTGCCTGC AGCTGATCGC AGACAGCGAG ACCCCCACCA TCCAGAAGGG CAGCTACACC

1621 TTCGTGCCCT GGCTGCTGAG CTTCAAGCGG GGCAGCGCCC TGGAGGAGAA GGAGAACAAG

1681 ATTCTGGTGA AGGAGACCGG CTACTTCTTC ATCTACGGCC AGGTGCTGTA CACCGATAAG

1741 ACCTACGCCA TGGGCCACCT GATCCAGCGG AAGAAGGTGC ACGTGTTCGG CGACGAGCTG

1801 AGCCTGGTGA CCCTGTTCCG GTGCATCCAG AACATGCCCG AGACCCTGCC CAACAACAGC

1861 TGCTACAGCG CAGGAATCGC AAAGCTGGAG GAGGGCGACG AGCTGCAGCT GGCAATCCCC

1921 CGGGAGAACG CACAGATCAG CCTGGACGGC GACGTGACCT TCTTCGGCGC CCTGAAGCTC

1981 CTGGGATCCG GTGAGGGCAG AGGAAGTCTT CTAACATGCG GTGACGTGGA GGAGAATCCG

2041 GGCCCCATGG TGAGCAAGGG CGAGGAGCTG TTCACCGGGG TGGTGCCCAT CCTGGTCGAG

2101 CTGGACGGCG ACGTAAACGG CCACAAGTTC AGCGTGTCCG GCGAGGGCGA GGGCGATGCC

2161 ACCTACGGCA AGCTGACCCT GAAGTTCATC TGCACCACCG GCAAGCTGCC CGTGCCCTGG

2221 CCCACCCTCG TGACCACCCT GACCTACGGC GTGCAGTGCT TCAGCCGCTA CCCCGACCAC

2281 ATGAAGCAGC ACGACTTCTT CAAGTCCGCC ATGCCCGAAG GCTACGTCCA GGAGCGCACC

2341 ATCTTCTTCA AGGACGACGG CAACTACAAG ACCCGCGCCG AGGTGAAGTT CGAGGGCGAC

2401 ACCCTGGTGA ACCGCATCGA GCTGAAGGGC ATCGACTTCA AGGAGGACGG CAACATCCTG

2461 GGGCACAAGC TGGAGTACAA CTACAACAGC CACAACGTCT ATATCATGGC CGACAAGCAG

2521 AAGAACGGCA TCAAGGTGAA CTTCAAGATC CGCCACAACA TCGAGGACGG CAGCGTGCAG

2581 CTCGCCGACC ACTACCAGCA GAACACCCCC ATCGGCGACG GCCCCGTGCT GCTGCCCGAC

2641 AACCACTACC TGAGCACCCA GTCCGCCCTG AGCAAAGACC CCAACGAGAA GCGCGATCAC

2701 ATGGTCCTGC TGGAGTTCGT GACCGCCGCC GGGATCACTC TCGGCATGGA CGAGCTGTAC

2761 AAGTGAATCT AGAGTCGACT GCTTTATTTG TGAAATTTGT GATGCTATTG CTTTATTTGT

2821 AACCATTATA AGCTGCAATA AACAAGTTAA CAACAACAAT TGCATTCATT TTATGTTTCA

2881 GGTTCAGGGG GAGGTGTGGG AGGTTTTTTA AACTCTATTT TATAGGCTTC TTCTCTGGAA

2941 TCTTCTTCAT CATCCTCCTG ACAATCGATA GGTACCTGGC TGTCGTCCAT GCTGTGTTTG

3001 CTTTAAAAGC CAGGACGGTC ACCTTTGGGG TGGTGACAAG TGTGATCACT TGGGTGGTGG

3061 CTGTGTTTGC GTCTCTCCCA GGAATCATCT TTACCAGATC TCAAAAGAA GGTCTTCATT

3121 ACACCTGCAG CTCTCATTTT CCATACAGTC AGTATCAATT CTGGAAGAAT TTCCAGACAT

3181 TAAAGATAGT CATCTTGGGG CTGGTCCTGC CGCTGCTTGT CATGGTCATC TGCTACTCGG

3241 GAATCCTAAA AACTCTGCTT CGGTGTCGAA ATGAGAAGAA GAGGCACAGG GCTGTGAGGC

3301 TTATCTTCAC CATCATGATT GTTTATTTTC TCTTCTGGGC TCCCTACAAC ATTGTCCTTC

3361 TCCTGAACAC CTTCCAGGAA TTCTTTGGCC TGAATAATTG CAGTAGCTCT AACAGGTTGG

3421 ACCAAGCTAT GCAGGTGACA GAGACTCTTG GGATGACGCA CTGCTGCATC AACCCCATCA

3481 TCTATGCCTT TGTCGGGGAG AAGTTCAGAA ACTACCTCTT AGTCTTCTTC CAAAAGCACA
```

-continued

```
3541 TTGCCAAACG CTTCTGCAAA TGCTGTTCTA TTTTCCAGCA AGAGGCTCCC GAGCGAGCAA
3601 GCTCAGTTTA CACCCGATCC ACTGGGGAGC AGGAAATATC TGTGGGCTTG TGACACGGAC
3661 TCAAGTGGGC TGGTGACCCA GTCAGAGTTG TGCACATGGC TTAGTTTTCA TACACACCGC
3721 GGTCTAGAGC ATGGCTACGT AGATAAGTAG CATGGCGGGT TAATCATTAA CTACAAGGAA
3781 CCCCTAGTGA TGGAGTTGGC CACTCCCTCT CTGCGCGCTC GCTCGCTCAC TGAGGCCGGG
3841 CGACCAAAGG TCGCCCGACG CCCGGGCTTT GCCCGGGCGG CCTCAGTGAG CGAGCGAGCG
3901 CGCCAGCTGG CGTAATAGCG AAGAGGCCCG CACCGATCGC CCTTCCCAAC AGTTGCGCAG
3961 CCTGAATGGC GAATGGCGAT TCCGTTGCAA TGGCTGGCGG TAATATTGTT CTGGATATTA
4021 CCAGCAAGGC CGATAGTTTG AGTTCTTCTA CTCAGGCAAG TGATGTTATT ACTAATCAAA
4081 GAAGTATTGC GACAACGGTT AATTTGCGTG ATGGACAGAC TCTTTTACTC GGTGGCCTCA
4141 CTGATTATAA AAACACTTCT CAGGATTCTG GCGTACCGTT CCTGTCTAAA ATCCCTTTAA
4201 TCGGCCTCCT GTTTAGCTCC CGCTCTGATT CTAACGAGGA AGCACGTTA TACGTGCTCG
4261 TCAAAGCAAC CATAGTACGC GCCCTGTAGC GGCGCATTAA GCGCGGCGGG TGTGGTGGTT
4321 ACGCGCAGCG TGACCGCTAC ACTTGCCAGC GCCCTAGCGC CCGCTCCTTT CGCTTTCTTC
4381 CCTTCCTTTC TCGCCACGTT CGCCGGCTTT CCCCGTCAAG CTCTAAATCG GGGGCTCCCT
4441 TTAGGGTTCC GATTTAGTGC TTTACGGCAC CTCGACCCCA AAAAACTTGA TTAGGGTGAT
4501 GGTTCACGTA GTGGGCCATC GCCCTGATAG ACGGTTTTTC GCCCTTTGAC GTTGGAGTCC
4561 ACGTTCTTTA ATAGTGGACT CTTGTTCCAA ACTGGAACAA CACTCAACCC TATCTCGGTC
4621 TATTCTTTTG ATTTATAAGG GATTTTGCCG ATTTCGGCCT ATTGGTTAAA AAATGAGCTG
4681 ATTTAACAAA AATTTAACGC GAATTTTAAC AAAATATTAA CGTTTACAAT TTAAATATTT
4741 GCTTATACAA TCTTCCTGTT TTTGGGGCTT TTCTGATTAT CAACCGGGGT ACATATGATT
4801 GACATGCTAG TTTTACGATT ACCGTTCATC GATTCTCTTG TTTGCTCCAG ACTCTCAGGC
4861 AATGACCTGA TAGCCTTTGT AGAGACCTCT CAAAAATAGC TACCCTCTCC GGCATGAATT
4921 TATCAGCTAG AACGGTTGAA TATCATATTG ATGGTGATTT GACTGTCTCC GGCCTTTCTC
4981 ACCCGTTTGA ATCTTTACCT ACACATTACT CAGGCATTGC ATTTAAAATA TATGAGGGTT
5041 CTAAAAATTT TTATCCTTGC GTTGAAATAA AGGCTTCTCC CGCAAAAGTA TTACAGGGTC
5101 ATAATGTTTT TGGTACAACC GATTTAGCTT TATGCTCTGA GGCTTTATTG CTTAATTTTG
5161 CTAATTCTTT GCCTTGCCTG TATGATTTAT TGGATGTTGG AATCGCCTGA TGCGGTATTT
5221 TCTCCTTACG CATCTGTGCG GTATTTCACA CCGCATATGG TGCACTCTCA GTACAATCTG
5281 CTCTGATGCC GCATAGTTAA GCCAGCCCCG ACACCCGCCA ACACCCGCTG ACGCGCCCTG
5341 ACGGGCTTGT CTGCTCCCGG CATCCGCTTA CAGACAAGCT GTGACCGTCT CCGGGAGCTG
5401 CATGTGTCAG AGGTTTTCAC CGTCATCACC GAAACGCGCG AGACGAAAGG GCCTCGTGAT
5461 ACGCCTATTT TTATAGGTTA ATGTCATGAT AATAATGGTT TCTTAGACGT CAGGTGGCAC
5521 TTTTCGGGGA AATGTGCGCG GAACCCCTAT TTGTTTATTT TTCTAAATAC ATTCAAATAT
5581 GTATCCGCTC ATGAGACAAT AACCCTGATA AATGCTTCAA TAATATTGAA AAAGGAAGAG
5641 TATGAGTATT CAACATTTCC GTGTCGCCCT TATTCCCTTT TTTGCGGCAT TTTGCCTTCC
5701 TGTTTTTGCT CACCCAGAAA CGCTGGTGAA AGTAAAAGAT GCTGAAGATC AGTTGGGTGC
5761 ACGAGTGGGT TACATCGAAC TGGATCTCAA CAGCGGTAAG ATCCTTGAGA GTTTTCGCCC
5821 CGAAGAACGT TTTCCAATGA TGAGCACTTT TAAAGTTCTG CTATGTGGCG CGGTATTATC
5881 CCGTATTGAC GCCGGGCAAG AGCAACTCGG TCGCCGCATA CACTATTCTC AGAATGACTT
```

-continued

```
5941 GGTTGAGTAC TCACCAGTCA CAGAAAAGCA TCTTACGGAT GGCATGACAG TAAGAGAATT

6001 ATGCAGTGCT GCCATAACCA TGAGTGATAA CACTGCGGCC AACTTACTTC TGACAACGAT

6061 CGGAGGACCG AAGGAGCTAA CCGCTTTTTT GCACAACATG GGGGATCATG TAACTCGCCT

6121 TGATCGTTGG GAACCGGAGC TGAATGAAGC CATACCAAAC GACGAGCGTG ACACCACGAT

6181 GCCTGTAGCA ATGGCAACAA CGTTGCGCAA ACTATTAACT GGCGAACTAC TTACTCTAGC

6241 TTCCCGGCAA CAATTAATAG ACTGGATGGA GGCGGATAAA GTTGCAGGAC CACTTCTGCG

6301 CTCGGCCCTT CCGGCTGGCT GGTTTATTGC TGATAAATCT GGAGCCGGTG AGCGTGGGTC

6361 TCGCGGTATC ATTGCAGCAC TGGGGCCAGA TGGTAAGCCC TCCCGTATCG TAGTTATCTA

6421 CACGACGGGG AGTCAGGCAA CTATGGATGA ACGAAATAGA CAGATCGCTG AGATAGGTGC

6481 CTCACTGATT AAGCATTGGT AACTGTCAGA CCAAGTTTAC TCATATATAC TTTAGATTGA

6541 TTTAAAACTT CATTTTTAAT TTAAAAGGAT CTAGGTGAAG ATCCTTTTTG ATAATCTCAT

6601 GACCAAAATC CCTTAACGTG AGTTTTCGTT CCACTGAGCG TCAGACCCCG TAGAAAAGAT

6661 CAAAGGATCT TCTTGAGATC CTTTTTTTCT GCGCGTAATC TGCTGCTTGC AAACAAAAAA

6721 ACCACCGCTA CCAGCGGTGG TTTGTTTGCC GGATCAAGAG CTACCAACTC TTTTTCCGAA

6781 GGTAACTGGC TTCAGCAGAG CGCAGATACC AAATACTGTC CTTCTAGTGT AGCCGTAGTT

6841 AGGCCACCAC TTCAAGAACT CTGTAGCACC GCCTACATAC CTCGCTCTGC TAATCCTGTT

6901 ACCAGTGGCT GCTGCCAGTG GCGATAAGTC GTGTCTTACC GGGTTGGACT CAAGACGATA

6961 GTTACCGGAT AAGGCGCAGC GGTCGGGCTG AACGGGGGGT TCGTGCACAC AGCCCAGCTT

7021 GGAGCGAACG ACCTACACCG AACTGAGATA CCTACAGCGT GAGCTATGAG AAAGCGCCAC

7081 GCTTCCCGAA GGGAGAAAGG CGGACAGGTA TCCGGTAAGC GGCAGGGTCG GAACAGGAGA

7141 GCGCACGAGG GAGCTTCCAG GGGGAAACGC CTGGTATCTT TATAGTCCTG TCGGGTTTCG

7201 CCACCTCTGA CTTGAGCGTC GATTTTTGTG ATGCTCGTCA GGGGGGCGGA GCCTATGGAA

7261 AAACGCCAGC AACGCGGCCT TTTTACGGTT CCTGGCCTTT TGCTGGCCTT TTGCTCACAT

7321 GTTCTTTCCT GCGTTATCCC CTGATTCTGT GGATAACCGT ATTACCGCCT TTGAGTGAGC

7381 TGATACCGCT CGCCGCAGCC GAACGACCGA GCGCAGCGAG TCAGTGAGCG AGGAAGCGGA

7441 AGAGCGCCCA ATACGCAAAC CGCCTCTCCC CGCGCGTTGG CCGATTCATT AATG
```

SEQ ID NO: 51
1079_pscAAV-MND.GFP
1079_pscAAV-MND.GFP (SEQ ID NO: 51)

ORIGIN

```
    1 aagcttcccg gggggatctg ggccactccc tctctgcgcg ctcgctcgct cactgaggcc 61 gggcgaccaa aggtcgcccg acgcccgggc tttgcccggg cggcctcagt gagcgagcga 121 gcgcgcagag agggagtggc caactccatc actaggggtt cctggagggg tggagtcgtg 181 acctagggaa cagagaaaca ggagaatatg gccaaacag gatatctgtg gtaagcagtt 241 cctgccccgg ctcagggcca agaacagttg gaacagcaga atatgggcca acaggatat 301 ctgtggtaag cagttcctgc cccggctcag ggccaagaac agatggtccc cagatgcggt 361 cccgccctca gcagtttcta gagaaccatc agatgtttcc agggtgcccc aaggacctga 421 aatgaccctg tgccttattt gaactaacca atcagttcgc ttctcgcttc tgttcgcgcg 481 cttctgctcc ccgagctcta tataagcaga gctcgtttag tgaaccgtca gatcgcctgg 541 agacgccatc cacgctgttt tgacttccat agaaggatcc tcgagccac catggtgagc 601 aagggcgagg agctgttcac cggggtggtg cccatcctgg tcgagctgga cggcgacgta 661 aacggccaca agttcagcgt gtccggcgag ggcgagggcg atgccaccta cggcaagctg
```

-continued

```
 721 accctgaagt tcatctgcac caccggcaag ctgcccgtgc cctggcccac cctcgtgacc 781 accctgacct acggcgtgca gtgcttcagc cgctacoccg accacatgaa gcagcacgac 841 ttcttcaagt ccgccatgcc cgaaggctac gtccaggagc gcaccatctt cttcaaggac 901 gacggcaact acaagacccg cgccgaggtg aagttcgagg gcgacaccct ggtgaaccgc 961 atcgagctga agggcatcga cttcaaggag gacggcaaca tcctggggca caagctggag 1021 tacaactaca acagccacaa cgtctatatc atggccgaca gcagaagaa cggcatcaag 1081 gtgaacttca agatccgcca caacatcgag gacggcagcg tgcagctcgc cgaccactac 1141 cagcagaaca cccccatcgg cgacggcccc gtgctgctgc ccgacaacca ctacctgagc 1201 acccagtccg ccctgagcaa agaccccaac gagaagcgcg atcacatggt cctgctggag 1261 ttcgtgaccg ccgccgggat cactctcggc atggacgagc tgtacaagta agcggccgca 1321 attcaccca ccagtgcagg ctgcctatca gaaagtggtg gctggtgtgg ctaatgccct 1381 ggcccacaag tatcactaag ctcgctttct tgctgtccaa tttctattaa ggttcctttt 1441 gttccctaag tccaactact aaactggggg atattatgaa gggccttgag catctggatt 1501 ctgcctaata aaaaacattt attttcattg caatgatgta tttaaattat ttctgaatat 1561 tttactaaaa agggaatgtg ggaggtcagt gcatttaaaa cataaagaaa tgaagagcta 1621 gttcaaacct tgggaaaata cactatatct taaactccat gaaagaaggt gaggctgcaa 1681 acagctaatg cacattggca acagccctg atgcctatgc cttattcatc cctcagaaaa 1741 ggattcaagt agaggcttga tttggaggtt aaagttttgc tatgctgtat tttacattac 1801 ttattgtttt agctgtcctc atgaatgtct tttcactacc catttgctta tcctgcatct 1861 ctcagccttg actccactca gttctcttgc ttagagatac ccacctttcc ctgaagtgtt 1921 ccttccatgt tttacggcga gatggtttct cctcgcctgg ccactcagcc ttagttgtct 1981 ctgttgtctt atagaggtct acttgaagaa ggaaaaacag ggggcatggt tgactgtcc 2041 tgtgagccct tcttccctgc ctcccccact cacagtgaca ctagtccact ccctctctgc 2101 gcgctcgctc gctcactgag gccgggcgac caaaggtcgc ccgacgcccg ggctttgccc 2161 gggcggcctc agtgagcgag cgagcgcgca gagagggaca gatccgggcc cgcatgcgtc 2221 gacaattcac tggccgtcgt tttacaacgt cgtgactggg aaaaccctgg cgttacccaa 2281 cttaatcgcc ttgcagcaca tcccccttc gccagctggc gtaatagcga agaggcccgc 2341 accgatcgcc cttcccaaca gttgcgcagc ctgaatggcg aatggcgcct gatgcggtat 2401 tttctcctta cgcatctgtg cggtatttca caccgcatat ggtgcactct cagtacaatc 2461 tgctctgatg ccgcatagtt aagccagccc cgacacccgc caacacccgc tgacgcgccc 2521 tgacgggctt gtctgctccc ggcatccgct tacagacaag ctgtgaccgt ctccgggagc 2581 tgcatgtgtc agaggttttc accgtcatca ccgaaacgcg cgagacgaaa gggcctcgtg 2641 atacgcctat ttttataggt taatgtcatg ataataatgg tttcttagac gtcaggtggc 2701 acttttcggg gaaatgtgcg cggaaccct atttgtttat ttttctaaat acattcaaat 2761 atgtatccgc tcatgagaca ataaccctga taaatgcttc aataatattg aaaaaggaag 2821 agtatgagta ttcaacattt ccgtgtcgcc cttattccct tttttgcggc attttgcctt 2881 cctgtttttg ctcacccaga aacgctggtg aaagtaaaag atgctgaaga tcagttgggt 2941 gcacgagtgg gttacatcga actggatctc aacagcggta agatccttga gttttcgc 3001 cccgaagaac gttttccaat gatgagcact tttaaagttc tgctatgtgg cgcggtatta 3061 tcccgtattg acgccgggca agagcaactc ggtcgccgca tacactattc tcagaatgac 3121 ttggttgagt actcaccagt cacagaaaag catcttacgg atggcatgac agtaagagaa
```

-continued

```
3181 ttatgcagtg ctgccataac catgagtgat aacactgcgg ccaacttact tctgacaacg
3241 atcggaggac cgaaggagct aaccgctttt ttgcacaaca tgggggatca tgtaactcgc
3301 cttgatcgtt gggaaccgga gctgaatgaa gccataccaa acgacgagcg tgacaccacg
3361 atgcctgtag caatggcaac aacgttgcgc aaactattaa ctggcgaact acttactcta
3421 gcttcccggc aacaattaat agactggatg gaggcggata agttgcagg accacttctg
3481 cgctcggccc ttccggctgg ctggtttatt gctgataaat ctggagccgg tgagcgtggg
3541 tctcgcggta tcattgcagc actggggcca gatggtaagc cctcccgtat cgtagttatc
3601 tacacgacgg ggagtcaggc aactatggat gaacgaaata gacagatcgc tgagataggt
3661 gcctcactga ttaagcattg gtaactgtca gaccaagttt actcatatat actttagatt
3721 gatttaaaac ttcattttta atttaaaagg atctaggtga agatcctttt tgataatctc
3781 atgaccaaaa tcccttaacg tgagttttcg ttccactgag cgtcagaccc cgtagaaaag
3841 atcaaaggat cttcttgaga tccttttttt ctgcgcgtaa tctgctgctt gcaaacaaaa
3901 aaaccaccgc taccagcggt ggtttgtttg ccggatcaag agctaccaac tcttttttccg
3961 aaggtaactg gcttcagcag agcgcagata ccaaatactg ttcttctagt gtagccgtag
4021 ttaggccacc acttcaagaa ctctgtagca ccgcctacat acctcgctct gctaatcctg
4081 ttaccagtgg ctgctgccag tggcgataag tcgtgtctta ccgggttgga ctcaagacga
4141 tagttaccgg ataaggcgca gcggtcgggc tgaacggggg gttcgtgcac acagcccagc
4201 ttggagcgaa cgacctacac cgaactgaga tacctacagc gtgagctatg agaaagcgcc
4261 acgcttcccg aagggagaaa ggcggacagg tatccggtaa gcggcagggt cggaacagga
4321 gagcgcacga gggagcttcc agggggaaac gcctggtatc tttatagtcc tgtcgggttt
4381 cgccacctct gacttgagcg tcgatttttg tgatgctcgt caggggggcg gagcctatgg
4441 aaaaacgcca gcaacgcggc ctttttacgg ttcctggcct tttgctggcc ttttgctcac
4501 atgttctttc ctgcgttatc ccctgattct gtggataacc gtattaccgc ctttgagtga
4561 gctgataccg ctcgccgcag ccgaacgacc gagcgcagcg agtcagtgag cgaggaagcg
4621 gaagagcgcc caatacgcaa accgcctctc cccgcgcgtt ggccgattca ttaatgcagc
4681 tggcacgaca ggtttcccga ctggaaagcg ggcagtgagc gcaacgcaat taatgtgagt
4741 tagctcactc attaggcacc ccaggcttta cactttatgc ttccggctcg tatgttgtgt
4801 ggaattgtga gcggataaca atttcacaca ggaaacagct atgaccatga ttacgccaag
4861 ctctcgagat ctaga
```

1347_pscAAV.Blimp.0.4 kb.MND.GFP
(SEQ ID NO: 52)
```
  1 aagcttcccg gggggatctg gccactccc tctctgcgcg ctcgctcgct cactgaggcc
 61 gggcgaccaa aggtcgcccg acgcccgggc tttgcccggg cggcctcagt gagcgagcga
121 gcgcgcagag agggagtggc caactccatc actaggggtt cctggagggg tggagtcgtg
181 acctaggacg cgtgccagct gttactcagg ttttctcaag aaggaggagc aactttggca
241 gttttgcttc agttctctct agccctctgt gtaatcgccc cttttctttt atttcagcac
301 aaacacagag cagtctaaag caaccgagca ctgagaaaaa tgaactctgc ccaaagaatg
361 tcccaaagag agagtacagc gtgaaagaaa tcctaaaatt ggactccaac ccctccaaag
421 gaaaggacct ctaccgttct aacatttcac ccctcacatc agaaaggac ctcgatgact
481 ttagaagacg tgggagcccc gaatgccct tctaccctcg gtcgtttac cccatccggg
541 cccctctgcc agaagacttt ttgaaagctt ccctggccta cgggatcgag agagaacaga
```

-continued

```
 601 gaaacaggag aatatgggcc aaacaggata tctgtggtaa gcagttcctg ccccggctca
 661 gggccaagaa cagttggaac agcagaatat gggccaaaca ggatatctgt ggtaagcagt
 721 tcctgccccg gctcagggcc aagaacagat ggtccccaga tgcggtcccg ccctcagcag
 781 tttctagaga accatcagat gtttccaggg tgcccaagg acctgaaatg accctgtgcc
 841 ttatttgaac taaccaatca gttcgcttct cgcttctgtt cgcgcgcttc tgctccccga
 901 gctctatata agcagagctc gtttagtgaa ccgtcagatc gcctggagac gccatccacg
 961 ctgttttgac ttccatagaa ggatctcgag gccaccatgg tgagcaaggg cgaggagctg
1021 ttcaccgggg tggtgcccat cctggtcgag ctggacggcg acgtaaacgg ccacaagttc
1081 agcgtgtccg gcgagggcga gggcgatgcc acctacggca agctgaccct gaagttcatc
1141 tgcaccaccg gcaagctgcc cgtgccctgg cccaccctcg tgaccaccct gacctacggc
1201 gtgcagtgct tcagccgcta ccccgaccac atgaagcagc acgacttctt caagtccgcc
1261 atgcccgaag gctacgtcca ggagcgcacc atcttcttca aggacgacgg caactacaag
1321 acccgcgccg aggtgaagtt cgagggcgac accctggtga accgcatcga gctgaagggc
1381 atcgacttca aggaggacgg caacatcctg ggcacaagc tggagtacaa ctacaacagc
1441 cacaacgtct atatcatggc cgacaagcag aagaacggca tcaaggtgaa cttcaagatc
1501 cgccacaaca tcgaggacgg cagcgtgcag ctcgccgacc actaccagca gaacaccccc
1561 atcggcgacg gccccgtgct gctgcccgac aaccactacc tgagcaccca gtccgccctg
1621 agcaaagacc ccaacgagaa gcgcgatcac atggtcctgc tggagttcgt gaccgccgcc
1681 gggatcactc tcggcatgga cgagctgtac aagtaaacta gtgtcgactg ctttatttgt
1741 gaaatttgtg atgctattgc tttatttgta accattataa gctgcaataa acaagttaac
1801 aacaacaatt gcattcattt tatgtttcag gttcaggggg aggtgtggga ggttttttaa
1861 aacgtacatc actcgctccc ccattccatc ctccaccact ccaagcccct ctgcaagaag
1921 cagccccgac caaagcctca agagctccag ccctcacagc agccctggga atacggtgtc
1981 ccctgtgggc cccggctctc aagagcaccg ggactcctac gcttacttga acgcgtccta
2041 cggcacggaa ggtttgggct cctaccctgg ctacgcaccc ctgccccacc tcccgccagc
2101 tttcatcccc tcgtacaacg ctcactaccc caagttcctc ttgccccct acggcatgaa
2161 ttgtaatggc ctgagcgctg tgagcagcat gaatggcatc aacaactttg gcctcttccc
2221 gaggctgtgc cctgtctaca gcaatctcct cggtggggc actagtccac tccctctctg
2281 cgcgctcgct cgctcactga ggccgggcga ccaaaggtcg cccgacgccc gggctttgcc
2341 cgggcggcct cagtgagcga gcgagcgcgc agagagggac agatccgggc cgcatgcgt
2401 cgacaattca ctggccgtcg ttttacaacg tcgtgactgg gaaaaccctg gcgttaccca
2461 acttaatcgc cttgcagcac atccccctt cgccagctgg cgtaatagcg aagaggcccg
2521 caccgatcgc ccttcccaac agttgcgcag cctgaatggc gaatggcgcc tgatgcggta
2581 ttttctcctt acgcatctgt gcggtatttc acaccgcata tggtgcactc tcagtacaat
2641 ctgctctgat gccgcatagt taagccagcc ccgacacccg ccaacacccg ctgacgcgcc
2701 ctgacgggct tgtctgctcc cggcatccgc ttacagacaa gctgtgaccg tctccgggag
2761 ctgcatgtgt cagaggtttt caccgtcatc accgaaacgc gcgagacgaa agggcctcgt
2821 gatacgccta ttttttatagg ttaatgtcat gataataatg gtttcttaga cgtcaggtgg
2881 cactttttcgg ggaaatgtgc gcggaacccc tatttgttta ttttttctaaa tacattcaaa
2941 tatgtatccg ctcatgagac aataaccctg ataaatgctt caataatatt gaaaaaggaa
3001 gagtatgagt attcaacatt tccgtgtcgc ccttattccc ttttttgcgg cattttgcct
```

-continued

```
3061 tcctgttttt gctcacccag aaacgctggt gaaagtaaaa gatgctgaag atcagttggg
3121 tgcacgagtg ggttacatcg aactggatct caacagcggt aagatccttg agagttttcg
3181 ccccgaagaa cgttttccaa tgatgagcac ttttaaagtt ctgctatgtg gcgcggtatt
3241 atcccgtatt gacgccgggc aagagcaact cggtcgccgc atacactatt ctcagaatga
3301 cttggttgag tactcaccag tcacagaaaa gcatcttacg gatggcatga cagtaagaga
3361 attatgcagt gctgccataa ccatgagtga taacactgcg ccaacttac ttctgacaac
3421 gatcggagga ccgaaggagc taaccgcttt tttgcacaac atgggggatc atgtaactcg
3481 ccttgatcgt tgggaaccgg agctgaatga agccatacca aacgacgagc gtgacaccac
3541 gatgcctgta gcaatggcaa caacgttgcg caaactatta actggcgaac tacttactct
3601 agcttcccgg caacaattaa tagactggat ggaggcggat aaagttgcag gaccacttct
3661 gcgctcggcc cttccggctg gctggtttat tgctgataaa tctggagccg gtgagcgtgg
3721 gtctcgcggt atcattgcag cactggggcc agatggtaag ccctcccgta tcgtagttat
3781 ctacacgacg gggagtcagg caactatgga tgaacgaaat agacagatcg ctgagatagg
3841 tgcctcactg attaagcatt ggtaactgtc agaccaagtt tactcatata ctttagat
3901 tgatttaaaa cttcatttt aatttaaaag gatctaggtg aagatccttt tgataatct
3961 catgaccaaa atcccttaac gtgagttttc gttccactga gcgtcagacc ccgtagaaaa
4021 gatcaaagga tcttcttgag atccttttt tctgcgcgta atctgctgct tgcaaacaaa
4081 aaaaccaccg ctaccagcgg tggtttgttt gccggatcaa gagctaccaa ctctttttcc
4141 gaaggtaact ggcttcagca gagcgcagat accaaatact gttcttctag tgtagccgta
4201 gttaggccac cacttcaaga actctgtagc accgcctaca tacctcgctc tgctaatcct
4261 gttaccagtg gctgctgcca gtggcgataa gtcgtgtctt accgggttgg actcaagacg
4321 atagttaccg gataaggcgc agcggtcggg ctgaacgggg ggttcgtgca cacagcccag
4381 cttggagcga acgacctaca ccgaactgag atacctacag cgtgagctat gagaaagcgc
4441 cacgcttccc gaagggagaa aggcggacag gtatccggta agcggcaggg tcggaacagg
4501 agagcgcacg agggagcttc cagggggaaa cgcctggtat ctttatagtc ctgtcgggtt
4561 tcgccacctc tgacttgagc gtcgattttt gtgatgctcg tcaggggggc ggagcctatg
4621 gaaaaacgcc agcaacgcgg cctttttacg gttcctggcc ttttgctggc cttttgctca
4681 catgttcttt cctgcgttat cccctgattc tgtggataac cgtattaccg cctttgagtg
4741 agctgatacc gctcgccgca gccgaacgac cgagcgcagc gagtcagtga gcgaggaagc
4801 ggaagagcgc ccaatacgca aaccgcctct ccccgcgcgt tggccgattc attaatgcag
4861 ctggcacgac aggtttcccg actggaaagc gggcagtgag cgcaacgcaa ttaatgtgag
4921 ttagctcact cattaggcac cccaggcttt acactttatg cttccggctc gtatgttgtg
4981 tggaattgtg agcggataac aatttcacac aggaaacagc tatgaccatg attacgccaa
5041 gctctcgaga tctaga
```

1348_pAAV.Blimp.0.4 kb.MND.GFP.pA (SEQ ID NO: 53)

```
  1 cagctgcgcg ctcgctcgct cactgaggcc gcccgggcaa agcccgggcg tcgggcgacc
 61 tttggtcgcc cggcctcagt gagcgagcga gcgcgcagag agggagtggc caactccatc
121 actaggggtt ccttgtagtt aatgattaac ccgccatgct acttatctac acgcgtgcca
181 gctgttactc aggttttctc aagaaggagg agcaactttg gcagttttgc ttcagttctc
241 tctagccctc tgtgtaatcg ccccttttc tttatttcag cacaaacaca gagcagtcta
```

-continued

```
 301 aagcaaccga gcactgagaa aaatgaactc tgcccaaaga atgtcccaaa gagagagtac 361 agcgtgaaag aaatcctaaa attggactcc aacccctcca aaggaaagga cctctaccgt 421 tctaacattt caccccctcac atcagaaaag gacctcgatg actttagaag acgtgggagc 481 cccgaaatgc ccttctaccc tcgggtcgtt taccccatcc gggcccctct gccagaagac 541 tttttgaaag cttccctggc ctacgggatc gagagagaac agagaaacag gagaatatgg 601 gccaaacagg atatctgtgg taagcagttc ctgccccggc tcagggccaa gaacagttgg 661 aacagcagaa tatgggccaa acaggatatc tgtggtaagc agttcctgcc ccggctcagg 721 gccaagaaca gatggtcccc agatgcggtc ccgccctcag cagtttctag agaaccatca 781 gatgtttcca gggtgcccca aggacctgaa atgaccctgt gccttatttg aactaaccaa 841 tcagttcgct tctcgcttct gttcgcgcgc ttctgctccc cgagctctat ataagcagag 901 ctcgtttagt gaaccgtcag atcgcctgga gacgccatcc acgctgtttt gacttccata 961 gaaggatctc gaggccacca tggtgagcaa gggcgaggag ctgttcaccg ggtggtgcc 1021 catcctggtc gagctggacg gcgacgtaaa cggccacaag ttcagcgtgt ccggcgaggg 1081 cgagggcgat gccacctacg gcaagctgac cctgaagttc atctgcacca ccggcaagct 1141 gcccgtgccc tggcccaccc tcgtgaccac cctgacctac ggcgtgcagt gcttcagccg 1201 ctacccgac cacatgaagc agcacgactt cttcaagtcc gccatgcccg aaggctacgt 1261 ccaggagcgc accatcttct tcaaggacga cggcaactac aagacccgcg ccgaggtgaa 1321 gttcgagggc gacacccctgg tgaaccgcat cgagctgaag ggcatcgact tcaaggagga 1381 cggcaacatc ctggggcaca gctggagta caactacaac agccacaacg tctatatcat 1441 ggccgacaag cagaagaacg gcatcaaggt gaacttcaag atccgccaca acatcgagga 1501 cggcagcgtg cagctcgccg accactacca gcagaacacc cccatcggcg acggccccgt 1561 gctgctgccc gacaaccact acctgagcac ccagtccgcc ctgagcaaag accccaacga 1621 gaagcgcgat cacatggtcc tgctggagtt cgtgaccgcc gccgggatca ctctcggcat 1681 ggacgagctg tacaagtaaa ctagtgtcga ctgctttatt tgtgaaattt gtgatgctat 1741 tgctttattt gtaaccatta taagctgcaa taaacaagtt aacaacaaca attgcattca 1801 ttttatgttt caggttcagg gggaggtgtg ggaggttttt taaaacgtac atcactcgct 1861 cccccattcc atcctccacc actccaagcc cctctgcaag aagcagcccc gaccaaagcc 1921 tcaagagctc cagccctcac agcagccctg ggaatacggt gtccctgtg ggccccggct 1981 ctcaagagca ccgggactcc tacgcttact tgaacgcgtc ctacggcacg gaaggtttgg 2041 gctcctaccc tggctacgca cccctgcccc acctcccgcc agctttcatc ccctcgtaca 2101 acgctcacta ccccaagttc ctcttgcccc cctacggcat gaattgtaat ggcctgagcg 2161 ctgtgagcag catgaatggc atcaacaact ttggcctctt cccgaggctg tgccctgtct 2221 acagcaatct cctcggtggg ggcatctaga gtagataagt agcatggcgg gttaatcatt 2281 aactacaagg aaccccctagt gatggagttg gccactccct ctctgcgcgc tcgctcgctc 2341 actgaggccg gcgaccaaa ggtcgcccga cgcccgggct tgccggccgg ggcctcagtg 2401 agcgagcgag cgcgccagct ggcgtaatag cgaagaggcc cgcaccgatc gcccttccca 2461 acagttgcgc agcctgaatg gcgaatggcg attccgttgc aatggctggc ggtaatattg 2521 ttctggatat taccagcaag gccgatagtt tgagttcttc tactcaggca agtgatgtta 2581 ttactaatca agaagtatt gcgacaacgg ttaatttgcg tgatggacag actcttttac 2641 tcggtggcct cactgattat aaaaacactt ctcaggattc tggcgtaccg ttcctgtcta 2701 aaatcccttt aatcggcctc ctgtttagct cccgctctga ttctaacgag gaaagcacgt
```

-continued

```
2761 tatacgtgct cgtcaaagca accatagtac gcgccctgta gcggcgcatt aagcgcggcg
2821 ggtgtggtgg ttacgcgcag cgtgaccgct acacttgcca gcgccctagc gcccgctcct
2881 ttcgctttct tcccttcctt tctcgccacg ttcgccggct ttccccgtca agctctaaat
2941 cgggggctcc ctttagggtt ccgatttagt gctttacggc acctcgaccc caaaaaactt
3001 gattagggtg atggttcacg tagtgggcca tcgccctgat agacggtttt tcgccctttg
3061 acgttggagt ccacgttctt taatagtgga ctcttgttcc aaactggaac aacactcaac
3121 cctatctcgg tctattcttt tgatttataa gggattttgc cgatttcggc ctattggtta
3181 aaaaatgagc tgatttaaca aaaatttaac gcgaattttta acaaaatatt aacgtttaca
3241 atttaaatat ttgcttatac aatcttcctg tttttgggc ttttctgatt atcaaccggg
3301 gtacatatga ttgacatgct agttttacga ttaccgttca tcgattctct tgtttgctcc
3361 agactctcag gcaatgacct gatagccttt gtagagacct ctcaaaaata gctaccctct
3421 ccggcatgaa tttatcagct agaacggttg aatatcatat tgatggtgat ttgactgtct
3481 ccggcctttc tcacccgttt gaatctttac ctacacatta ctcaggcatt gcatttaaaa
3541 tatatgaggg ttctaaaaat ttttatcctt gcgttgaaat aaaggcttct cccgcaaaag
3601 tattacaggg tcataatgtt tttggtacaa ccgatttagc tttatgctct gaggctttat
3661 tgcttaattt tgctaattct ttgccttgcc tgtatgattt attggatgtt ggaatcgcct
3721 gatgcggtat tttctcctta cgcatctgtg cggtatttca caccgcatat ggtgcactct
3781 cagtacaatc tgctctgatg ccgcatagtt aagccagccc cgacacccgc caacacccgc
3841 tgacgcgccc tgacgggctt gtctgctccc ggcatccgct tacagacaag ctgtgaccgt
3901 ctccggagc tgcatgtgtc agaggttttc accgtcatca ccgaaacgcg cgagacgaaa
3961 gggcctcgtg atacgcctat ttttataggt taatgtcatg ataataatgg tttcttagac
4021 gtcaggtggc acttttcggg gaaatgtgcg cggaacccct atttgtttat ttttctaaat
4081 acattcaaat atgtatccgc tcatgagaca ataaccctga taaatgcttc aataatattg
4141 aaaaaggaag agtatgagta ttcaacattt ccgtgtcgcc cttattccct tttttgcggc
4201 attttgcctt cctgtttttg ctcacccaga aacgctggtg aaagtaaaag atgctgaaga
4261 tcagttgggt gcacgagtgg gttacatcga actggatctc aacagcggta agatccttga
4321 gagttttcgc cccgaagaac gttttccaat gatgagcact tttaaagttc tgctatgtgg
4381 cgcggtatta tcccgtattg acgccgggca agagcaactc ggtcgccgca tacactattc
4441 tcagaatgac ttggttgagt actcaccagt cacagaaaag catcttacgg atggcatgac
4501 agtaagagaa ttatgcagtg ctgccataac catgagtgat aacactgcgg ccaacttact
4561 tctgacaacg atcggaggac cgaaggagct aaccgctttt ttgcacaaca tgggggatca
4621 tgtaactcgc cttgatcgtt gggaaccgga gctgaatgaa gccataccaa acgacgagcg
4681 tgacaccacg atgcctgtag caatggcaac aacgttgcgc aaactattaa ctggcgaact
4741 acttactcta gcttcccggc aacaattaat agactggatg gaggcggata agttgcagg
4801 accacttctg cgctcggccc ttccggctgg ctggtttatt gctgataaat ctggagccgg
4861 tgagcgtggg tctcgcggta tcattgcagc actggggcca gatggtaagc cctcccgtat
4921 cgtagttatc tacacgacgg ggagtcaggc aactatggat gaacgaaata cagagatcgc
4981 tgagataggt gcctcactga ttaagcattg gtaactgtca gaccaagttt actcatatat
5041 actttagatt gatttaaaac ttcattttta atttaaaagg atctaggtga agatcctttt
5101 tgataatctc atgaccaaaa tcccttaacg tgagttttcg ttccactgag cgtcagaccc
```

-continued

```
5161 cgtagaaaag atcaaaggat cttcttgaga tcctttttt ctgcgcgtaa tctgctgctt
5221 gcaaacaaaa aaaccaccgc taccagcggt ggtttgtttg ccggatcaag agctaccaac
5281 tcttttttccg aaggtaactg gcttcagcag agcgcagata ccaaatactg tccttctagt
5341 gtagccgtag ttaggccacc acttcaagaa ctctgtagca ccgcctacat acctcgctct
5401 gctaatcctg ttaccagtgg ctgctgccag tggcgataag tcgtgtctta ccgggttgga
5461 ctcaagacga tagttaccgg ataaggcgca gcggtcgggc tgaacggggg gttcgtgcac
5521 acagcccagc ttggagcgaa cgacctacac cgaactgaga tacctacagc gtgagctatg
5581 agaaagcgcc acgcttcccg aagggagaaa ggcggacagg tatccggtaa gcggcagggt
5641 cggaacagga gagcgcacga gggagcttcc agggggaaac gcctggtatc tttatagtcc
5701 tgtcgggttt cgccacctct gacttgagcg tcgatttttg tgatgctcgt caggggggcg
5761 gagcctatgg aaaaacgcca gcaacgcggc cttttttacgg ttcctggcct tttgctggcc
5821 ttttgctcac atgttctttc ctgcgttatc ccctgattct gtggataacc gtattaccgc
5881 ctttgagtga gctgataccg ctcgccgcag ccgaacgacc gagcgcagcg agtcagtgag
5941 cgaggaagcg gaagagcgcc caatacgcaa accgcctctc cccgcgcgtt ggccgattca
6001 ttaatg
//
```

1361_pAAV.Blimp1.1.0 kb.MND.GFP.pA (SEQ ID NO: 54)

```
  1 cagctgcgcg ctcgctcgct cactgaggcc gcccgggcaa agcccgggcg tcgggcgacc
 61 tttggtcgcc cggcctcagt gagcgagcga gcgcgcagag agggagtggc caactccatc
121 actaggggtt ccttgtagtt aatgattaac ccgccatgct acttatctac acgcgtggta
181 aaccatgaac atcagaaaga cttttattaa cctatgacag ggtccccacc ccagtatttt
241 tccactccat taaaatggaa gttttttttt tttttttctt ttttgagaca gagttttgct
301 cttgttgccc agtctggagt gcaatggcac aatctcggct caccacaacc tccacctccc
361 agattcaagc gattcttctg cctcagcctc ccaagtagct gggattacag gtgtgcgcca
421 ccacgcccag ctaattttgt attttttagta gagatggggt ttctccatgt tggtcaggct
481 ggtctcgaac ttccgacctc aggtgatccg cccacctcgg cctcccaaag tgctgggatt
541 acaggcaaga gccactgcat ccagcttagg ctatcttact ccagcctaaa cagcaatttt
601 ctatcataag gtctgtacta atgaaaacag aatcacccaa ggctgctgtt tgttctgtct
661 gtgctgccat tgtccgcatt tgctgagga ggaaacggaa ctgcacttt gagtgagtgg
721 cccagagcct tctagaatga gagtgcgttg gaagccagat atgtggcgat tgtgtcgcca
781 gctgttactc aggttttctc aagaaggagg agcaactttg gcagttttgc ttcagttctc
841 tctagccctc tgtgtaatcg cccctttttc tttatttcag cacaaacaca gagcagtcta
901 aagcaaccga gcactgagaa aaatgaactc tgcccaaaga atgtcccaaa gagagagtac
961 agcgtgaaag aaatcctaaa attggactcc aaccctcca aggaaagga cctctaccgt
1021 tctaacattt caccctcac atcagaaaag gacctcgatg actttagaag acgtgggagc
1081 cccgaaatgc ccttctaccc tcgggtcgtt taccccatcc gggcccctct gccagaagac
1141 ttttttgaaag cttccctggc ctacgggatc gagagagaac agagaaacag gagaatatgg
1201 gccaaacagg atatctgtgg taagcagttc ctgccccgc tcagggccaa gaacagttgg
1261 aacagcagaa tatgggccaa acaggatatc tgtggtaagc agttcctgcc ccggctcagg
1321 gccaagaaca gatggtcccc agatgcggtc ccgccctcag cagtttctag agaaccatca
1381 gatgtttcca gggtgcccca aggacctgaa atgaccctgt gccttatttg aactaaccaa
```

-continued

```
1441 tcagttcgct tctcgcttct gttcgcgcgc ttctgctccc cgagctctat ataagcagag 1501 ctcgtttagt gaaccgtcag atcgcctgga gacgccatcc acgctgtttt gacttccata 1561 gaaggatctc gaggccacca tggtgagcaa gggcgaggag ctgttcaccg gggtggtgcc 1621 catcctggtc gagctggacg gcgacgtaaa cggccacaag ttcagcgtgt ccggcgaggg 1681 cgagggcgat gccacctacg gcaagctgac cctgaagttc atctgcacca ccggcaagct 1741 gcccgtgccc tggcccaccc tcgtgaccac cctgacctac ggcgtgcagt gcttcagccg 1801 ctaccccgac cacatgaagc agcacgactt cttcaagtcc gccatgcccg aaggctacgt 1861 ccaggagcgc accatcttct tcaaggacga cggcaactac aagacccgcg ccgaggtgaa 1921 gttcgagggc gacaccctgg tgaaccgcat cgagctgaag ggcatcgact tcaaggagga 1981 cggcaacatc ctggggcaca agctggagta caactacaac agccacaacg tctatatcat 2041 ggccgacaag cagaagaacg gcatcaaggt gaacttcaag atccgccaca acatcgagga 2101 cggcagcgtg cagctcgccg accactacca gcagaacacc cccatcggcg acggccccgt 2161 gctgctgccc gacaaccact acctgagcac ccagtccgcc ctgagcaaag accccaacga 2221 gaagcgcgat cacatggtcc tgctggagtt cgtgaccgcc gccgggatca ctctcggcat 2281 ggacgagctg tacaagtaaa ctagtgtcga ctgctttatt tgtgaaattt gtgatgctat 2341 tgctttattt gtaaccatta taagctgcaa taaacaagtt aacaacaaca attgcattca 2401 ttttatgttt caggttcagg gggaggtgtg ggaggttttt taaaacgtac atcactcgct 2461 cccccattcc atcctccacc actccaagcc cctctgcaag aagcagcccc gaccaaagcc 2521 tcaagagctc cagccctcac agcagccctg gaatacggt gtccctgtg ggccccggct 2581 ctcaagagca ccgggactcc tacgcttact tgaacgcgtc ctacggcacg gaaggtttgg 2641 gctcctaccc tggctacgca cccctgcccc acctcccgcc agctttcatc ccctcgtaca 2701 acgctcacta ccccaagttc ctcttgcccc cctacggcat gaattgtaat ggcctgagcg 2761 ctgtgagcag catgaatggc atcaacaact ttggcctctt cccgaggctg tgccctgtct 2821 acagcaatct cctcggtggg ggcagcctgc cccacccat gctcaacccc acttctctcc 2881 cgagctcgct gccctcagat ggagcccgga ggttgctcca gccggagcat cccagggagg 2941 tgcttgtccc ggcgccccac agtgccttct cctttaccgg ggccgccgcc agcatgaagg 3001 acaaggcctg tagccccaca agcgggtctc ccacggcggg aacagccgcc acggcagaac 3061 atgtggtgca gcccaaagct acctcagcag cgatggcagc cccagcagc gacgaagcca 3121 tgaatctcat taaaaacaaa agaaacatga ccggctacaa gacccttccc tacccgctga 3181 agaagcagaa cggcaagatc aagtacgaat gcaacgtttg cgccaagact tcggccagc 3241 tctccaatct gaaggtaggc cttgagagag agcagtccaa ggggctgtga gtgcatgctt 3301 gtgtttgtat ttagcttgct ttccatgggg tatcgattgc atttgcagta gtatgagccc 3361 ccggttgggg atagtgggta tggattccgc ctggcttttg ccacttctag ctctttgact 3421 ttggacaagt gacttccctt ctcctctaga gtagataagt agcatggcgg gttaatcatt 3481 aactacaagg aaccctagt gatggagttg gccactccct ctctgcgcgc tcgctcgctc 3541 actgaggccg ggcgaccaaa ggtcgcccga cgcccgggct tgcccgggc ggcctcagtg 3601 agcgagcgag cgcgccagct ggcgtaatag cgaagaggcc cgcaccgatc gcccttccca 3661 acagttgcgc agcctgaatg gcgaatgcg attccgttgc aatggctggc ggtaatattg 3721 ttctggatat taccagcaag gccgatagtt tgagttcttc tactcaggca agtgatgtta 3781 ttactaatca aagaagtatt gcgacaacg ttaatttgcg tgatggacag actcttttac 3841 tcggtggcct cactgattat aaaaacactt ctcaggattc tggcgtaccg ttcctgtcta
```

-continued

```
3901 aaatcccttt aatcggcctc ctgtttagct cccgctctga ttctaacgag gaaagcacgt
3961 tatacgtgct cgtcaaagca accatagtac gcgccctgta gcggcgcatt aagcgcggcg
4021 ggtgtggtgg ttacgcgcag cgtgaccgct acacttgcca gcgccctagc gcccgctcct
4081 ttcgctttct tcccttcctt tctcgccacg ttcgccggct ttccccgtca agctctaaat
4141 cggggctcc ctttagggtt ccgatttagt gctttacggc acctcgaccc caaaaaactt
4201 gattagggtg atggttcacg tagtgggcca tcgccctgat agacggtttt cgcccttg
4261 acgttggagt ccacgttctt taatagtgga ctcttgttcc aaactggaac aacactcaac
4321 cctatctcgg tctattcttt tgatttataa gggattttgc cgatttcggc ctattggtta
4381 aaaaatgagc tgatttaaca aaaatttaac gcgaatttta acaaaatatt aacgtttaca
4441 atttaaatat ttgcttatac aatcttcctg tttttgggc ttttctgatt atcaaccggg
4501 gtacatatga ttgacatgct agttttacga ttaccgttca tcgattctct tgtttgctcc
4561 agactctcag gcaatgacct gatagccttt gtagagacct ctcaaaaata gctaccctct
4621 ccggcatgaa tttatcagct agaacggttg aatatcatat tgatggtgat ttgactgtct
4681 ccggcctttc tcaccgttt gaatcttac ctacacatta ctcaggcatt gcatttaaaa
4741 tatatgaggg ttctaaaaat ttttatcctt gcgttgaaat aaaggcttct cccgcaaaag
4801 tattacaggg tcataatgtt tttggtacaa ccgatttagc tttatgctct gaggctttat
4861 tgcttaattt tgctaattct ttgccttgcc tgtatgattt attggatgtt ggaatcgcct
4921 gatgcggtat tttctcctta cgcatctgtg cggtatttca caccgcatat ggtgcactct
4981 cagtacaatc tgctctgatg ccgcatagtt aagccagccc cgacaccgc caacacccgc
5041 tgacgcgccc tgacgggctt gtctgctccc ggcatccgct tacagacaag ctgtgaccgt
5101 ctccgggagc tgcatgtgtc agaggttttc accgtcatca ccgaaacgcg cgagacgaaa
5161 gggcctcgtg atacgcctat ttttataggt taatgtcatg ataataatgg tttcttagac
5221 gtcaggtggc acttttcggg gaaatgtgcg cggaaccct atttgtttat ttttctaaat
5281 acattcaaat atgtatccgc tcatgagaca ataaccctga taaatgcttc aataatattg
5341 aaaaaggaag agtatgagta ttcaacattt ccgtgtcgcc cttattccct tttttgcggc
5401 attttgcctt cctgtttttg ctcacccaga aacgctggtg aaagtaaaag atgctgaaga
5461 tcagttgggt gcacgagtgg gttacatcga actggatctc aacagcggta agatccttga
5521 gagttttcgc cccgaagaac gttttccaat gatgagcact tttaaagttc tgctatgtgg
5581 cgcggtatta tcccgtattg acgccgggca agagcaactc ggtcgccgca tacactattc
5641 tcagaatgac ttggttgagt actcaccagt cacagaaaag catcttacgg atggcatgac
5701 agtaagagaa ttatgcagtg ctgccataac catgagtgat aacactgcgg ccaacttact
5761 tctgacaacg atcggaggac cgaaggagct aaccgctttt ttgcacaaca tgggggatca
5821 tgtaactcgc cttgatcgtt gggaaccgga gctgaatgaa gccataccaa acgacgagcg
5881 tgacaccacg atgcctgtag caatggcaac aacgttgcgc aaactattaa ctggcgaact
5941 acttactcta gcttcccggc aacaattaat agactggatg gaggcggata agttgcagg
6001 accacttctg cgctcggccc ttccggctgg ctggtttatt gctgataaat ctggagccgg
6061 tgagcgtggg tctcgcggta tcattgcagc actggggcca gatggtaagc cctcccgtat
6121 cgtagttatc tacacgacgg ggagtcaggc aactatggat gaacgaaata gacagatcgc
6181 tgagataggt gcctcactga ttaagcattg gtaactgtca gaccaagttt actcatatat
6241 actttagatt gatttaaaac ttcatttta atttaaaagg atctaggtga agatccttt
```

-continued

```
6301 tgataatctc atgaccaaaa tcccttaacg tgagttttcg ttccactgag cgtcagaccc 6361 cgtagaaaag atcaaaggat cttcttgaga tcctttttt ctgcgcgtaa tctgctgctt 6421 gcaaacaaaa aaaccaccgc taccagcggt ggtttgtttg ccggatcaag agctaccaac 6481 tcttttttccg aaggtaactg gcttcagcag agcgcagata ccaaatactg tccttctagt 6541 gtagccgtag ttaggccacc acttcaagaa ctctgtagca ccgcctacat acctcgctct 6601 gctaatcctg ttaccagtgg ctgctgccag tggcgataag tcgtgtctta ccgggttgga 6661 ctcaagacga tagttaccgg ataaggcgca gcggtcgggc tgaacggggg gttcgtgcac 6721 acagcccagc ttggagcgaa cgacctacac cgaactgaga tacctacagc gtgagctatg 6781 agaaagcgcc acgcttcccg aagggagaaa ggcggacagg tatccggtaa gcggcagggt 6841 cggaacagga gagcgcacga gggagcttcc agggggaaac gcctggtatc tttatagtcc 6901 tgtcgggttt cgccacctct gacttgagcg tcgatttttg tgatgctcgt caggggggcg 6961 gagcctatgg aaaaacgcca gcaacgcggc cttttacgg ttcctggcct tttgctggcc 7021 ttttgctcac atgttctttc ctgcgttatc ccctgattct gtggataacc gtattaccgc 7081 ctttgagtga gctgataccg ctcgccgcag ccgaacgacc gagcgcagcg agtcagtgag 7141 cgaggaagcg gaagagcgcc caatacgcaa accgcctctc cccgcgcgtt ggccgattca 7201 ttaatg
//
```

1366_CCR5.MND.BAFF_CRISPR.HR
(SEQ ID NO: 55)
LOCUS #1366\CCR5.MND.B 6707 bp DNA circular SYN 10-MAR.-2017
ORIGIN

```
   1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag atttatttg gtgagatggt gctttcatga attcccccaa cagagccaag 541 ctctccatct agtggacagg gaagctagca gcaaaccttc ccttcactac aaaacttcat 601 tgcttggcca aaaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacaggtgt gaacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct ctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtcccag atgcggtccc gccctcagca gtttctagag 1261 aaccatcaga tgtttccagg gtgccccaag gacctgaaat gaccctgtgc cttatttgaa
```

-continued

```
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga ggccaccatg taccggatgc agctgctgag ctgcatcgca
1501 ctgagcctgg cactggtgac caacagcgca gtgcagggac cagaggagac cgtgacccag
1561 gactgcctgc agctgatcgc agacagcgag accccccacca tccagaaggg cagctacacc
1621 ttcgtgccct ggctgctgag cttcaagcgg ggcagcgccc tggaggagaa ggagaacaag
1681 attctggtga aggagaccgg ctacttcttc atctacggcc aggtgctgta caccgataag
1741 acctacgcca tgggccacct gatccagcgg aagaaggtgc acgtgttcgg cgacgagctg
1801 agcctggtga ccctgttccg gtgcatccag aacatgcccg agaccctgcc caacaacagc
1861 tgctacagcg caggaatcgc aaagctggag gagggcgacg agctgcagct ggcaatcccc
1921 cgggagaacg cacagatcag cctggacggc gacgtgacct tcttcggcgc cctgaagctc
1981 ctgtgagtcg actgctttat ttgtgaaatt tgtgatgcta ttgctttatt tgtaaccatt
2041 ataagctgca ataaacaagt taacaacaac aattgcattc attttatgtt tcaggttcag
2101 ggggaggtgt gggaggtttt ttaaactcta ttttataggc ttcttctctg gaatcttctt
2161 catcatcctc ctgacaatcg ataggtacct ggctgtcgtc catgctgtgt ttgctttaaa
2221 agccaggacg gtcacctttg gggtggtgac aagtgtgatc acttgggtgg tggctgtgtt
2281 tgcgtctctc ccaggaatca tctttaccag atctcaaaaa gaaggtcttc attacacctg
2341 cagctctcat tttccataca gtcagtatca attctggaag aatttccaga cattaaagat
2401 agtcatcttg gggctggtcc tgccgctgct tgtcatggtc atctgctact cgggaatcct
2461 aaaaactctg cttcggtgtc gaaatgagaa gaagaggcac agggctgtga ggcttatctt
2521 caccatcatg attgtttatt ttctcttctg ggctccctac aacattgtcc ttctcctgaa
2581 caccttccag gaattctttg gcctgaataa ttgcagtagc tctaacaggt tggaccaagc
2641 tatgcaggtg acagagactc ttgggatgac gcactgctgc atcaaccccca tcatctatgc
2701 ctttgtcggg gagaagttca gaaactacct cttagtcttc ttccaaaagc acattgccaa
2761 acgcttctgc aaatgctgtt ctatttccca gcaagaggct cccgagcgag caagctcagt
2821 ttacacccga tccactgggg agcaggaaat atctgtgggc ttgtgacacg gactcaagtg
2881 ggctggtgac ccagtcagag ttgtgcacat ggcttagttt tcatacacac cgcggtctag
2941 agcatggcta cgtagataag tagcatggcg ggttaatcat taactacaag gaacccctag
3001 tgatggagtt ggccactccc tctctgcgcg ctcgctcgct cactgaggcc gggcgaccaa
3061 aggtcgcccg acgcccgggc tttgcccggg cggcctcagt gagcgagcga gcgcgccagc
3121 tggcgtaata gcgaagaggc ccgcaccgat cgcccttccc aacagttgcg cagcctgaat
3181 ggcgaatggc gattccgttg caatggctgg cggtaatatt gttctggata ttaccagcaa
3241 ggccgatagt ttgagttctt ctactcaggc aagtgatgtt attactaatc aaagaagtat
3301 tgcgacaacg gttaatttgc gtgatggaca gactctttta ctcggtggcc tcactgatta
3361 taaaaacact tctcaggatt ctggcgtacc gttcctgtct aaaatcccctt taatcggcct
3421 cctgtttagc tcccgctctg attctaacga ggaaagcacg ttatacgtgc tcgtcaaagc
3481 aaccatagta cgcgccctgt agcggcgcat taagcgcggc gggtgtggtg gttacgcgca
3541 gcgtgaccgc tacacttgcc agcgccctag cgcccgctcc tttcgctttc ttcccttcct
3601 ttctcgccac gttcgccggc tttccccgtc aagctctaaa tcggggggctc cctttagggt
3661 tccgatttag tgctttacgg cacctcgacc ccaaaaaact tgattagggt gatggttcac
3721 gtagtgggcc atcgccctga tagacggttt ttcgcccttt gacgttggag tccacgttct
```

-continued

```
3781 ttaatagtgg actcttgttc caaactggaa caacactcaa ccctatctcg gtctattctt
3841 ttgatttata agggattttg ccgatttcgg cctattggtt aaaaaatgag ctgatttaac
3901 aaaaatttaa cgcgaatttt aacaaaatat taacgtttac aatttaaata tttgcttata
3961 caatcttcct gttttgggg cttttctgat tatcaaccgg ggtacatatg attgacatgc
4021 tagttttacg attaccgttc atcgattctc ttgtttgctc cagactctca ggcaatgacc
4081 tgatagcctt tgtagagacc tctcaaaaat agctaccctc tccggcatga atttatcagc
4141 tagaacggtt gaatatcata ttgatggtga tttgactgtc tccggccttt ctcacccgtt
4201 tgaatcttta cctacacatt actcaggcat tgcatttaaa atatatgagg gttctaaaaa
4261 ttttatcct tgcgttgaaa taaaggcttc tcccgcaaaa gtattacagg gtcataatgt
4321 ttttggtaca accgatttag ctttatgctc tgaggcttta ttgcttaatt ttgctaattc
4381 tttgccttgc ctgtatgatt tattggatgt tggaatcgcc tgatgcggta ttttctcctt
4441 acgcatctgt gcggtatttc acaccgcata tggtgcactc tcagtacaat ctgctctgat
4501 gccgcatagt taagccagcc ccgacacccg ccaacacccg ctgacgcgcc ctgacgggct
4561 tgtctgctcc cggcatccgc ttacagacaa gctgtgaccg tctccgggag ctgcatgtgt
4621 cagaggtttt caccgtcatc accgaaacgc gcgagacgaa agggcctcgt gatacgccta
4681 tttttatagg ttaatgtcat gataataatg gtttcttaga cgtcaggtgg cacttttcgg
4741 ggaaatgtgc gcggaacccc tatttgttta ttttctaaaa tacattcaaa tatgtatccg
4801 ctcatgagac aataaccctg ataaatgctt caataatatt gaaaaggaa gagtatgagt
4861 attcaacatt tccgtgtcgc ccttattccc ttttttgcgg cattttgcct tcctgttttt
4921 gctcacccag aaacgctggt gaaagtaaaa gatgctgaag atcagttggg tgcacgagtg
4981 ggttacatcg aactggatct caacagcggt aagatccttg agagttttcg ccccgaagaa
5041 cgttttccaa tgatgagcac ttttaaagtt ctgctatgtg gcgcggtatt atcccgtatt
5101 gacgccgggc aagagcaact cggtcgccgc atacactatt ctcagaatga cttggttgag
5161 tactcaccag tcacagaaaa gcatcttacg gatggcatga cagtaagaga attatgcagt
5221 gctgccataa ccatgagtga taacactgcg gccaacttac ttctgacaac gatcggagga
5281 ccgaaggagc taaccgcttt tttgcacaac atgggggatc atgtaactcg ccttgatcgt
5341 tgggaaccgg agctgaatga agccatacca aacgacgagc gtgacaccac gatgcctgta
5401 gcaatggcaa caacgttgcg caaactatta actggcgaac tacttactct agcttcccgg
5461 caacaattaa tagactggat ggaggcggat aaagttgcag gaccacttct gcgctcggcc
5521 cttccggctg gctggtttat tgctgataaa tctggagccg gtgagcgtgg gtctcgcggt
5581 atcattgcag cactggggcc agatggtaag ccctcccgta tcgtagttat ctacacgacg
5641 gggagtcagg caactatgga tgaacgaaat agacagatcg ctgagatagg tgcctcactg
5701 attaagcatt ggtaactgtc agaccaagtt tactcatata tactttagat tgatttaaaa
5761 cttcattttt aatttaaaag gatctaggtg aagatccttt ttgataatct catgaccaaa
5821 atcccttaac gtgagttttc gttccactga gcgtcagacc ccgtagaaaa gatcaaagga
5881 tcttcttgag atcctttttt tctgcgcgta atctgctgct tgcaaacaaa aaaaccaccg
5941 ctaccagcgg tggtttgttt gccggatcaa gagctaccaa ctctttttcc gaaggtaact
6001 ggcttcagca gagcgcagat accaaatact gtccttctag tgtagccgta gttaggccac
6061 cacttcaaga actctgtagc accgcctaca tacctcgctc tgctaatcct gttaccagtg
6121 gctgctgcca gtggcgataa gtcgtgtctt accgggttgg actcaagacg atagttaccg
```

-continued

```
6181 gataaggcgc agcggtcggg ctgaacgggg ggttcgtgca cacagcccag cttggagcga 6241 acgacctaca ccgaactgag atacctacag cgtgagctat gagaaagcgc cacgcttccc 6301 gaagggagaa aggcggacag gtatccggta agcggcaggg tcggaacagg agagcgcacg 6361 agggagcttc caggggggaaa cgcctggtat ctttatagtc ctgtcgggtt tcgccacctc 6421 tgacttgagc gtcgattttt gtgatgctcg tcagggggc ggagcctatg gaaaaacgcc 6481 agcaacgcgg ccttttttacg gttcctggcc ttttgctggc cttttgctca catgttcttt 6541 cctgcgttat cccctgattc tgtggataac cgtattaccg cctttgagtg agctgatacc 6601 gctcgccgca gccgaacgac cgagcgcagc gagtcagtga gcgaggaagc ggaagagcgc 6661 ccaatacgca aaccgcctct ccccgcgcgt tggccgattc attaatg
//
```

1367_CCR5.MND.BAFF.2A.GFP (SEQ ID NO: 56)

LOCUS #1367\CCR5.MND.B 7494 bp DNA circular SYN 10-MAR.-2017
ORIGIN

```
   1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag attttatttg gtgagatggt gctttcatga attcccccaa cagagccaag 541 ctctccatct agtggacagg gaagctagca gcaaaccttc ccttcactac aaaacttcat 601 tgcttggcca aaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacagggtg gaacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct ctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtccccag atgcggtccc gccctcagca gtttctagag 1261 aaccatcaga tgtttccagg gtgccccaag gacctgaaat gaccctgtgc cttatttgaa 1321 ctaaccaatc agttcgcttc tcgcttctgt tcgcgcgctt ctgctccccg agctctatat 1381 aagcagagct cgtttagtga accgtcgat cgcctggaga cgccatccac gctgttttga 1441 cttccataga aggatctcga ggccaccatg taccggatgc agctgctgag ctgcatcgca 1501 ctgagcctgg cactggtgac caacagcgca gtgcagggac cagaggagac cgtgacccag 1561 gactgcctgc agctgatcgc agacagcgag acccccacca tccagaaggg cagctacacc 1621 ttcgtgccct ggctgctgag cttcaagcgg ggcagcgccc tggaggagaa ggagaacaag 1681 attctggtga aggagaccgg ctacttcttc atctacggcc aggtgctgta caccgataag
```

-continued

```
1741 acctacgcca tgggccacct gatccagcgg aagaaggtgc acgtgttcgg cgacgagctg 1801 agcctggtga ccctgttccg gtgcatccag aacatgcccg agaccctgcc caacaacagc 1861 tgctacagcg caggaatcgc aaagctggag gagggcgacg agctgcagct ggcaatcccc 1921 cgggagaacg cacagatcag cctggacggc gacgtgacct cttcggcgc cctgaagctc 1981 ctgggatccg gtgagggcag aggaagtctt ctaacatgcg gtgacgtgga ggagaatccg 2041 ggccccatgg tgagcaaggg cgaggagctg ttcaccgggg tggtgcccat cctggtcgag 2101 ctggacggcg acgtaaacgg ccacaagttc agcgtgtccg gcgagggcga gggcgatgcc 2161 acctacggca agctgaccct gaagttcatc tgcaccaccg gcaagctgcc cgtgccctgg 2221 cccaccctcg tgaccaccct gacctacggc gtgcagtgct tcagccgcta ccccgaccac 2281 atgaagcagc acgacttctt caagtccgcc atgcccgaag gctacgtcca ggagcgcacc 2341 atcttcttca aggacgacgg caactacaag acccgcgccg aggtgaagtt cgagggcgac 2401 accctggtga accgcatcga gctgaagggc atcgacttca aggaggacgg caacatcctg 2461 gggcacaagc tggagtacaa ctacaacagc cacaacgtct atatcatggc cgacaagcag 2521 aagaacggca tcaaggtgaa cttcaagatc cgccacaaca tcgaggacgg cagcgtgcag 2581 ctcgccgacc actaccagca gaacaccccc atcggcgacg gccccgtgct gctgcccgac 2641 aaccactacc tgagcaccca gtccgccctg agcaaagacc ccaacgagaa gcgcgatcac 2701 atggtcctgc tggagttcgt gaccgccgcc gggatcactc tcggcatgga cgagctgtac 2761 aagtgaatct agagtcgact gctttatttg tgaaatttgt gatgctattg ctttatttgt 2821 aaccattata agctgcaata acaagttaa caacaacaat tgcattcatt ttatgtttca 2881 ggttcagggg gaggtgtggg aggttttta aactctattt tataggcttc ttctctggaa 2941 tcttcttcat catcctcctg acaatcgata ggtacctggc tgtcgtccat gctgtgtttg 3001 ctttaaaagc caggacggtc acctttgggg tggtgacaag tgtgatcact tgggtggtgg 3061 ctgtgtttgc gtctctccca ggaatcatct ttaccagatc tcaaaaagaa ggtcttcatt 3121 acacctgcag ctctcatttt ccatacagtc agtatcaatt ctggaagaat ttccagacat 3181 taaagatagt catcttgggg ctggtcctgc cgctgcttgt catggtcatc tgctactcgg 3241 gaatcctaaa aactctgctt cggtgtcgaa atgagaagaa gaggcacagg gctgtgaggc 3301 ttatcttcac catcatgatt gtttattttc tcttctgggc tccctacaac attgtccttc 3361 tcctgaacac cttccaggaa ttctttggcc tgaataattg cagtagctct aacaggttgg 3421 accaagctat gcaggtgaca gagactcttg ggatgacgca ctgctgcatc aaccccatca 3481 tctatgcctt tgtcggggag aagttcagaa actacctctt agtcttcttc caaaagcaca 3541 ttgccaaacg cttctgcaaa tgctgttcta ttttccagca agaggctccc gagcgagcaa 3601 gctcagttta caccccgatcc actggggagc aggaaatatc tgtgggcttg tgacacggac 3661 tcaagtgggc tggtgaccca gtcagagttg tgcacatggc ttagttttca tacacaccgc 3721 ggtctagagc atggctacgt agataagtag catggcgggt taatcattaa ctacaaggaa 3781 cccctagtga tggagttggc cactccctct ctgcgcgctc gctcgctcac tgaggccggg 3841 cgaccaaagg tcgcccgacg cccgggcttt gcccgggcgg cctcagtgag cgagcgagcg 3901 cgccagctgg cgtaatagcg aagaggcccg caccgatcgc ccttcccaac agttgcgcag 3961 cctgaatggc gaatggcgat ccgttgcaa tggctggcgg taatattgtt ctggatatta 4021 ccagcaaggc cgatagtttg agttcttcta ctcaggcaag tgatgttatt actaatcaaa 4081 gaagtattgc gacaacggtt aatttgcgtg atggacagac tctttactc ggtggcctca 4141 ctgattataa aaacacttct caggattctg gcgtaccgtt cctgtctaaa atccctttaa
```

```
4201 tcggcctcct gtttagctcc cgctctgatt ctaacgagga aagcacgtta tacgtgctcg
4261 tcaaagcaac catagtacgc gccctgtagc ggcgcattaa gcgcggcggg tgtggtggtt
4321 acgcgcagcg tgaccgctac acttgccagc gccctagcgc ccgctccttt cgctttcttc
4381 ccttcctttc tcgccacgtt cgccggcttt ccccgtcaag ctctaaatcg ggggctccct
4441 ttagggttcc gatttagtgc tttacggcac ctcgacccca aaaaacttga ttagggtgat
4501 ggttcacgta gtgggccatc gccctgatag acggttttc gcccttttgac gttggagtcc
4561 acgttcttta atagtggact cttgttccaa actggaacaa cactcaaccc tatctcggtc
4621 tattcttttg atttataagg gattttgccg atttcggcct attggttaaa aaatgagctg
4681 atttaacaaa aatttaacgc gaattttaac aaaatattaa cgtttacaat ttaaatattt
4741 gcttatacaa tcttcctgtt tttggggctt ttctgattat caaccggggt acatatgatt
4801 gacatgctag ttttacgatt accgttcatc gattctcttg tttgctccag actctcaggc
4861 aatgacctga tagcctttgt agagacctct caaaaatagc taccctctcc ggcatgaatt
4921 tatcagctag aacggttgaa tatcatattg atggtgattt gactgtctcc ggcctttctc
4981 acccgtttga atctttacct acacattact caggcattgc atttaaaata tatgagggtt
5041 ctaaaaattt ttatccttgc gttgaaataa aggcttctcc cgcaaaagta ttacagggtc
5101 ataatgtttt tggtacaacc gatttagctt tatgctctga ggctttattg cttaattttg
5161 ctaattcttt gccttgcctg tatgatttat tggatgttgg aatcgcctga tgcggtattt
5221 tctccttacg catctgtgcg gtatttcaca ccgcatatgg tgcactctca gtacaatctg
5281 ctctgatgcc gcatagttaa gccagccccg acacccgcca cacccgctg acgcgccctg
5341 acgggcttgt ctgctcccgg catccgctta cagacaagct gtgaccgtct ccgggagctg
5401 catgtgtcag aggttttcac cgtcatcacc gaaacgcgcg agacgaaagg gcctcgtgat
5461 acgcctattt ttataggtta atgtcatgat aataatggtt tcttagacgt caggtggcac
5521 ttttcgggga aatgtgcgcg gaaccccctat ttgtttattt ttctaaatac attcaaatat
5581 gtatccgctc atgagacaat aaccctgata aatgcttcaa taatattgaa aaaggaagag
5641 tatgagtatt caacatttcc gtgtcgccct tattcccttt tttgcggcat tttgccttcc
5701 tgttttgct cacccagaaa cgctggtgaa agtaaaagat gctgaagatc agttgggtgc
5761 acgagtgggt tacatcgaac tggatctcaa cagcggtaag atccttgaga gttttcgccc
5821 cgaagaacgt tttccaatga tgagcacttt taaagttctg ctatgtggcg cggtattatc
5881 ccgtattgac gccgggcaag agcaactcgg tcgccgcata cactattctc agaatgactt
5941 ggttgagtac tcaccagtca cagaaaagca tcttacggat ggcatgacag taagagaatt
6001 atgcagtgct gccataacca tgagtgataa cactgcggcc aacttacttc tgacaacgat
6061 cggaggaccg aaggagctaa ccgcttttt gcacaacatg gggatcatg taactcgcct
6121 tgatcgttgg gaaccggagc tgaatgaagc cataccaaac gacgagcgtg acaccacgat
6181 gcctgtagca atggcaacaa cgttgcgcaa actattaact ggcgaactac ttactctagc
6241 ttcccggcaa caattaatag actggatgga ggcggataaa gttgcaggac cacttctgcg
6301 ctcggccctt ccggctggct ggtttattgc tgataaatct ggagccggtg agcgtgggtc
6361 tcgcggtatc attgcagcac tggggccaga tggtaagccc tcccgtatcg tagttatcta
6421 cacgacgggg agtcaggcaa ctatggatga acgaaataga cagatcgctg agataggtgc
6481 ctcactgatt aagcattggt aactgtcaga ccaagtttac tcatatatac tttagattga
6541 tttaaaactt cattttaat ttaaaaggat ctaggtgaag atcctttttg ataatctcat
```

```
6601 gaccaaaatc ccttaacgtg agttttcgtt ccactgagcg tcagaccccg tagaaaagat 6661 caaaggatct tcttgagatc ctttttttct gcgcgtaatc tgctgcttgc aaacaaaaaa 6721 accaccgcta ccagcggtgg tttgtttgcc ggatcaagag ctaccaactc tttttccgaa 6781 ggtaactggc ttcagcagag cgcagatacc aaatactgtc cttctagtgt agccgtagtt 6841 aggccaccac ttcaagaact ctgtagcacc gcctacatac ctcgctctgc taatcctgtt 6901 accagtggct gctgccagtg gcgataagtc gtgtcttacc gggttggact caagacgata 6961 gttaccggat aaggcgcagc ggtcgggctg aacggggggt tcgtgcacac agcccagctt 7021 ggagcgaacg acctacaccg aactgagata cctacagcgt gagctatgag aaagcgccac 7081 gcttcccgaa gggagaaagg cggacaggta tccggtaagc ggcagggtcg aacaggaga 7141 gcgcacgagg gagcttccag ggggaaacgc ctggtatctt tatagtcctg tcgggtttcg 7201 ccacctctga cttgagcgtc gatttttgtg atgctcgtca gggggcgga gcctatggaa 7261 aaacgccagc aacgcggcct ttttacggtt cctggccttt tgctggcctt ttgctcacat 7321 gttctttcct gcgttatccc ctgattctgt ggataaccgt attaccgcct ttgagtgagc 7381 tgataccgct cgccgcagcc gaacgaccga gcgcagcgag tcagtgagcg aggaagcgga 7441 agagcgccca atacgcaaac cgcctctccc cgcgcgttgg ccgattcatt aatg
//

1378_CCR5.MND.mCherry.2A.coFIXpadua.WPRE.pa
                                                        (SEQ ID NO: 57)
LOCUS #1378 8330 bp DNA circular UNA 09-AUG.-2017
DEFINITION Gibson Assembly of mCherry T2A - coFIXpadua into 1367 XhoI +
SalI (6.2 kb).
ORIGIN
    1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag attttatttg gtgagatggt gctttcatga attcccccaa cagagccaag 541 ctctccatct agtggacagg gaagctagca gcaaaccttc ccttcactac aaaacttcat 601 tgcttggcca aaaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacagggtg gaacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct ctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtcccag atgcggtccc gccctcagca gtttctagag 1261 aaccatcaga tgtttccagg gtgccccaag gacctgaaat gaccctgtgc cttatttgaa
```

-continued

```
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga ggccaccatg gtgagcaagg gcgaggagga taacatggcc
1501 atcatcaagg agttcatgcg cttcaaggtg cacatggagg ctccgtgaa cggccacgag
1561 ttcgagatcg agggcgaggg cgagggccgc ccctacgagg cacccagac cgccaagctg
1621 aaggtgacca agggtggccc cctgcccttc gctgggaca tcctgtcccc tcagttcatg
1681 tacggctcca aggcctacgt gaagcacccc gccgacatcc ccgactactt gaagctgtcc
1741 ttccccgagg gcttcaagtg ggagcgcgtg atgaacttcg aggacggcgg cgtggtgacc
1801 gtgacccagg actcctctct gcaggacggc gagttcatct acaaggtgaa gctgcgcggc
1861 accaacttcc cctccgacgg ccccgtaatg cagaagaaga ccatgggctg ggaggcctcc
1921 tccgagcgga tgtaccccga ggacggcgcc ctgaagggcg agatcaagca gaggctgaag
1981 ctgaaggacg gcggccacta cgacgctgag gtcaagacca cctacaaggc caagaagccc
2041 gtgcagctgc ccgcgcccta caacgtcaac atcaagttgg acatcacctc ccacaacgag
2101 gactacacca tcgtggaaca gtacgaacgc gccgagggcc gccactccac cggcggcatg
2161 gacgagctgt acaagggatc cggtgagggc agaggaagtc ttctaacatg cggtgacgtg
2221 gaggagaatc cgggcccat gatcatggcc gagagccctg gcctgatcac catctgcctg
2281 ctgggctacc tgctgagcgc cgagtgcacc gtgttcctgg accacgagaa cgccaacaag
2341 atcctgaacc ggcccaagag atacaacagc ggcaagctgg aggagttcgt gcagggcaac
2401 ctggagaggg agtgcatgga ggagaagtgc agcttcgagg aggccaggga agtgttcgag
2461 aacaccgagc ggaccaccga gttctggaag cagtacgtgg acggcgacca gtgcgagagc
2521 aacccttgcc tgaacggcgg cagctgcaag gacgacatca cagctacga gtgctggtgc
2581 cctttcggct tcgagggcaa gaactgcgag ctggacgtga cctgcaacat caagaacggc
2641 cgctgcgagc agttctgcaa gaacagcgcc gacaacaaag tggtgtgtag ctgcaccgag
2701 ggctacagac tggccgagaa ccagaagagc tgcgagcccg ccgtgccctt ccctgcggc
2761 agagtgagcg tgtcccagac cagcaagctg accagagccg agaccgtgtt ccccgacgtg
2821 gactacgtga atagcaccga ggccgagacc atcctggaca acatcaccca gagcacccag
2881 tccttcaacg acttcaccag agttgtgggc ggcgaggacg ccaagcccgg ccagttcccc
2941 tggcaggtgg tgctgaacgg caaagtggat gccttctgcg gcggcagcat cgtgaacgag
3001 aagtggatcg tgacagccgc ccactgcgtg gagaccggcg tgaagatcac cgtggtggcc
3061 ggcgaacaca atatcgagga gaccgagcac accgagcaga gcggaacgt catccggatt
3121 atccccacc acaactacaa cgccgccatc aacaagtaca accacgacat cgccctgctg
3181 gagctggacg agcctctggt gctgaatagc tacgtgaccc ccatctgcat cgccgacaag
3241 gagtacacca acatcttcct gaagttcggc agcggctacg tgtccggctg gggcagagtg
3301 ttccacaagg gcagaagcgc cctggtgctg cagtacctga gagtgccct ggtggacaga
3361 gccacctgcc tgttgagcac caagttcacc atctacaaca acatgttctg cgccggcttc
3421 cacgagggcg gcagagacag ctgccagggc gacagcggcg accccacgt gaccgaagtg
3481 gagggcacca gcttcctgac cggcatcatc agctggggcg aggagtgcgc catgaagggc
3541 aagtacggca tctacaccaa agtgagccgg tacgtgaact ggatcaagga gaaaaccaag
3601 ctgacctgag tcgactgctt tatttgtgaa atttgtgatg ctattgcttt atttgtaacc
3661 attataagct gcaataaaca agttaacaac aacaattgca ttcattttat gtttcaggtt
3721 cagggggagg tgtgggaggt tttttaaact ctatttata ggcttcttct ctggaatctt
```

-continued

```
3781 cttcatcatc ctcctgacaa tcgataggta cctggctgtc gtccatgctg tgtttgcttt
3841 aaaagccagg acggtcacct ttggggtggt gacaagtgtg atcacttggg tggtggctgt
3901 gtttgcgtct ctcccaggaa tcatctttac cagatctcaa aaagaaggtc ttcattacac
3961 ctgcagctct cattttccat acagtcagta tcaattctgg aagaatttcc agacattaaa
4021 gatagtcatc ttggggctgg tcctgccgct gcttgtcatg gtcatctgct actcgggaat
4081 cctaaaaact ctgcttcggt gtcgaaatga gaagaagagg cacagggctg tgaggcttat
4141 cttcaccatc atgattgttt attttctctt ctgggctccc tacaacattg tccttctcct
4201 gaacaccttc caggaattct ttggcctgaa taattgcagt agctctaaca ggttggacca
4261 agctatgcag gtgacagaga ctcttgggat gacgcactgc tgcatcaacc ccatcatcta
4321 tgcctttgtc ggggagaagt tcagaaacta cctcttagtc ttcttccaaa agcacattgc
4381 caaacgcttc tgcaaatgct gttctatttt ccagcaagag gctcccgagc gagcaagctc
4441 agtttacacc cgatccactg gggagcagga aatatctgtg ggcttgtgac acggactcaa
4501 gtgggctggt gacccagtca gagttgtgca catggcttag ttttcataca caccgcggtc
4561 tagagcatgg ctacgtagat aagtagcatg gcgggttaat cattaactac aaggaacccc
4621 tagtgatgga gttggccact ccctctctgc gcgctcgctc gctcactgag gccgggcgac
4681 caaaggtcgc ccgacgcccg ggctttgccc gggcggcctc agtgagcgag cgagcgcgcc
4741 agctggcgta atagcgaaga ggcccgcacc gatcgccctt cccaacagtt gcgcagcctg
4801 aatggcgaat ggcgattccg ttgcaatggc tggcggtaat attgttctgg atattaccag
4861 caaggccgat agtttgagtt cttctactca ggcaagtgat gttattacta atcaaagaag
4921 tattgcgaca acggttaatt tgcgtgatgg acagactctt ttactcggtg gcctcactga
4981 ttataaaaac acttctcagg attctggcgt accgttcctg tctaaaatcc ctttaatcgg
5041 cctcctgttt agctcccgct ctgattctaa cgaggaaagc acgttatacg tgctcgtcaa
5101 agcaaccata gtacgcgccc tgtagcggcg cattaagcgc ggcgggtgtg gtggttacgc
5161 gcagcgtgac cgctacactt gccagcgccc tagcgcccgc tcctttcgct ttcttccctt
5221 cctttctcgc cacgttcgcc ggctttcccc gtcaagctct aaatcggggg ctccctttag
5281 ggttccgatt tagtgcttta cggcacctcg accccaaaaa acttgattag ggtgatggtt
5341 cacgtagtgg gccatcgccc tgatagacgg ttttcgccc tttgacgttg gagtccacgt
5401 tctttaatag tggactcttg ttccaaactg gaacaacact caaccctatc tcggtctatt
5461 cttttgattt ataagggatt tgccgatttc ggcctattg gttaaaaaat gagctgattt
5521 aacaaaaatt taacgcgaat tttaacaaaa tattaacgtt tacaatttaa atatttgctt
5581 atacaatctt cctgttttg gggcttttct gattatcaac cggggtacat atgattgaca
5641 tgctagtttt acgattaccg ttcatcgatt ctcttgtttg ctccagactc tcaggcaatg
5701 acctgatagc ctttgtagag acctctcaaa aatagctacc ctctccggca tgaatttatc
5761 agctagaacg gttgaatatc atattgatgg tgatttgact gtctccggcc tttctcaccc
5821 gtttgaatct ttacctacac attactcagg cattgcattt aaaatatatg agggttctaa
5881 aaattttat ccttgcgttg aaataaaggc ttctcccgca aaagtattac agggtcataa
5941 tgttttggt acaaccgatt tagctttatg ctctgaggct ttattgctta attttgctaa
6001 ttctttgcct tgcctgtatg atttattgga tgttggaatc gcctgatgcg gtattttctc
6061 cttacgcatc tgtgcggtat ttcacaccgc atatggtgca ctctcagtac aatctgctct
6121 gatgccgcat agttaagcca gccccgacac ccgccaacac ccgctgacgc gccctgacgg
```

-continued

```
6181 gcttgtctgc tcccggcatc cgcttacaga caagctgtga ccgtctccgg gagctgcatg 6241 tgtcagaggt tttcaccgtc atcaccgaaa cgcgcgagac gaaagggcct cgtgatacgc 6301 ctattttat aggttaatgt catgataata atggtttctt agacgtcagg tggcactttt 6361 cggggaaatg tgcgcggaac ccctatttgt ttatttttct aaatacattc aaatatgtat 6421 ccgctcatga acaataacc ctgataaatg cttcaataat attgaaaaag gaagagtatg 6481 agtattcaac atttccgtgt cgcccttatt cccttttttg cggcattttg ccttcctgtt 6541 tttgctcacc cagaaacgct ggtgaaagta aaagatgctg aagatcagtt gggtgcacga 6601 gtgggttaca tcgaactgga tctcaacagc ggtaagatcc ttgagagttt tcgccccgaa 6661 gaacgttttc caatgatgag cacttttaaa gttctgctat gtggcgcggt attatcccgt 6721 attgacgccg ggcaagagca actcggtcgc cgcatacact attctcagaa tgacttggtt 6781 gagtactcac cagtcacaga aaagcatctt acggatggca tgacagtaag agaattatgc 6841 agtgctgcca taaccatgag tgataacact gcggccaact tacttctgac aacgatcgga 6901 ggaccgaagg agctaaccgc ttttttgcac aacatggggg atcatgtaac tcgccttgat 6961 cgttgggaac cggagctgaa tgaagccata ccaaacgacg agcgtgacac cacgatgcct 7021 gtagcaatgg caacaacgtt gcgcaaacta ttaactggcg aactacttac tctagcttcc 7081 cggcaacaat taatagactg gatggaggcg gataaagttg caggaccact tctgcgctcg 7141 gcccttccgg ctggctggtt tattgctgat aaatctggag ccggtgagcg tgggtctcgc 7201 ggtatcattg cagcactggg gccagatggt aagccctccc gtatcgtagt tatctacacg 7261 acggggagtc aggcaactat ggatgaacga atagacaga tcgctgagat aggtgcctca 7321 ctgattaagc attggtaact gtcagaccaa gtttactcat atatacttta gattgattta 7381 aaacttcatt tttaatttaa aaggatctag gtgaagatcc tttttgataa tctcatgacc 7441 aaaatccctt aacgtgagtt ttcgttccac tgagcgtcag accccgtaga aaagatcaaa 7501 ggatcttctt gagatccttt ttttctgcgc gtaatctgct gcttgcaaac aaaaaaacca 7561 ccgctaccag cggtggtttg tttgccggat caagagctac caactctttt tccgaaggta 7621 actggcttca gcagagcgca gataccaaat actgtccttc tagtgtagcc gtagttaggc 7681 caccacttca agaactctgt agcaccgcct acatacctcg ctctgctaat cctgttacca 7741 gtggctgctg ccagtggcga taagtcgtgt cttaccgggt tggactcaag acgatagtta 7801 ccggataagg cgcagcggtc gggctgaacg gggggttcgt gcacacagcc cagcttggag 7861 cgaacgacct acaccgaact gagatacta cagcgtgagc tatgagaaag cgccacgctt 7921 cccgaaggga gaaaggcgga caggtatccg gtaagcggca gggtcggaac aggagagcgc 7981 acgagggagc ttccagggg aaacgcctgg tatctttata gtcctgtcgg gtttcgccac 8041 ctctgacttg agcgtcgatt tttgtgatgc tcgtcagggg gcggagcct atggaaaaac 8101 gccagcaacg cggcctttt acggttcctg gccttttgct ggccttttgc tcacatgttc 8161 tttcctgcgt tatcccctga ttctgtggat aaccgtatta ccgcctttga gtgagctgat 8221 accgctcgcc gcagccgaac gaccgagcgc agcgagtcag tgagcgagga agcggaagag 8281 cgcccaatac gcaaaccgcc tctccccgcg cgttggccga ttcattaatg
//
```

1376_CCR5.MND.FiX.coFIXpadua.WPRE.pA (SEQ ID NO: 58)
LOCUS (#1376)\CCR5.MND 7806 bp DNA circular SYN 09-AUG.-2017
ORIGIN

```
  1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc
```

-continued

```
 121 actaggggtt ccttgtagtt aatgattaac ccgccatgct acttatctac gtagccatgc
 181 tctagcggcc tcggcctctg cataaataaa aaaaattagt cagccatgag cttggacgcg
 241 tttggtgtgg tggcgcctgt agtccccagc cacttggagg ggtgaggtga gaggattgct
 301 tgagcccggg atggtccagg ctgcagtgag ccatgatcgt gccactgcac tccagcctgg
 361 gcgacagagt gagaccctgt ctcacaacaa caacaacaac aacaaaaagg ctgagctgca
 421 ccatgcttga cccagtttct taaaattgtt gtcaaagctt cattcactcc atggtgctat
 481 agagcacaag attttatttg gtgagatggt gctttcatga attcccccaa cagagccaag
 541 ctctccatct agtggacagg gaagctagca gcaaaccttc ccttcactac aaaacttcat
 601 tgcttggcca aaagagagt taattcaatg tagacatcta tgtaggcaat taaaaaccta
 661 ttgatgtata aaacagtttg cattcatgga gggcaactaa atacattcta ggactttata
 721 aaagatcact ttttatttat gcacagggtg gaacaagatg gattatcaag tgtcaagtcc
 781 aatctatgac atcaattatt atacatcgga gccctgccaa aaaatcaatg tgaagcaaat
 841 cgcagcccgc ctcctgcctc cgctctactc actggtgttc atctttggtt ttgtgggcaa
 901 catgctggtc atcctcatcc tgataaactg caaaaggctg aagagcatga ctgacatcta
 961 cctgctcaac ctggccatct ctgacctgtt tttccttctt actgtcccct ctgggctca
1021 ctatgctgcc gcccagtggg actttggaaa tacaatgtgt caacgaacag agaaacagga
1081 gaatatgggc caaacaggat atctgtggta agcagttcct gccccggctc agggccaaga
1141 acagttggaa cagcagaata tgggccaaac aggatatctg tggtaagcag ttcctgcccc
1201 ggctcagggc caagaacaga tggtcccag atgcggtccc gccctcagca gtttctagag
1261 aaccatcaga tgtttccagg gtgccccaag acctgaaat gaccctgtgc cttatttgaa
1321 ctaaccaatc agttcgcttc tcgcttctgt tcgcgcgctt ctgctcccg agctctatat
1381 aagcagagct cgtttagtga accgtcagat cgcctggaga cgccatccac gctgttttga
1441 cttccataga aggatctcga gatgatcatg gccgagagcc ctggcctgat caccatctgc
1501 ctgctgggct acctgctgag cgccgagtgc accgtgttcc tggaccacga aacgccaac
1561 aagatcctga accggcccaa gagatacaac agcggcaagc tggaggagtt cgtgcagggc
1621 aacctggaga gggagtgcat ggaggagaag tgcagcttcg aggaggccag ggaagtgttc
1681 gagaacaccg agcggaccac cgagttctgg aagcagtacg tggacggcga ccagtgcgag
1741 agcaacccct tgcctgaacg gcggcagctg caaggacgaca tcaacagcta cgagtgctgg
1801 tgcccttcg gcttcgaggg caagaactgc gagctggacg tgacctgcaa catcaagaac
1861 ggccgctgcg agcagttctg caagaacagc gccgacaaca aagtggtgtg tagctgcacc
1921 gagggctaca cactggccga aaccagaag agctgcgagc ccgccgtgcc cttcccctgc
1981 ggcagagtga gcgtgtccca gaccagcaag ctgaccagag ccgagaccgt gttccccgac
2041 gtggactacg tgaatagcac cgaggccgag accatcctgg acaacatcac ccagagcacc
2101 cagtccttca acgacttcac cagagttgtg ggcggcgagg acgccaagcc cggccagttc
2161 ccctggcagg tggtgctgaa cggcaaagtg gatgccttct cggcggcag catcgtgaac
2221 gagaagtgga tcgtgacagc cgcccactgc gtggagaccg gcgtgaagat caccgtggtg
2281 gccggcgaac acaatatcga ggagaccgag cacaccgagc agaagcggaa cgtcatccgg
2341 attatccccc accacaacta caacgccgcc atcaacaagt acaaccacga catcgccctg
2401 ctggagctgg acgagcctct ggtgctgaat agctacgtga cccccatctg catcgccgac
2461 aaggagtaca ccaacatctt cctgaagttc ggcagcggct acgtgtccgg ctggggcaga
2521 gtgttccaca agggcagaag cgccctggtg ctgcagtacc tgagagtgcc cctggtggac
```

```
2581 agagccacct gcctgttgag caccaagttc accatctaca acaacatgtt ctgcgccggc
2641 ttccacgagg gcggcagaga cagctgccag ggcgacagcg gcggaccccca cgtgaccgaa
2701 gtggagggca ccagcttcct gaccggcatc atcagctggg gcgaggagtg cgccatgaag
2761 ggcaagtacg gcatctacac caaagtgagc cggtacgtga actggatcaa ggagaaaacc
2821 aagctgacct gagtcgacga taatcaacct ctggattaca aaatttgtga agattgact
2881 ggtattctta actatgttgc tccttttacg ctatgtggat acgctgcttt aatgcctttg
2941 tatcatgcta ttgcttcccg tatggctttc attttctcct ccttgtataa atcctggtta
3001 gttcttgcca cggcggaact catcgccgcc tgccttgccc gctgctggac aggggctcgg
3061 ctgttgggca ctgacaattc cgtgggtcga ctgctttatt tgtgaaattt gtgatgctat
3121 tgctttattt gtaaccatta taagctgcaa taaacaagtt aacaacaaca attgcattca
3181 ttttatgttt caggttcagg gggaggtgtg ggaggttttt taaactctat tttataggct
3241 tcttctctgg aatcttcttc atcatcctcc tgacaatcga taggtacctg gctgtcgtcc
3301 atgctgtgtt tgctttaaaa gccaggacgg tcacctttgg ggtggtgaca agtgtgatca
3361 cttgggtggt ggctgtgttt gcgtctctcc caggaatcat ctttaccaga tctcaaaaag
3421 aaggtcttca ttacacctgc agctctcatt ttccatacag tcagtatcaa ttctggaaga
3481 atttccagac attaaagata gtcatcttgg ggctggtcct gccgctgctt gtcatggtca
3541 tctgctactc gggaatccta aaaactctgc ttcggtgtcg aaatgagaag aagaggcaca
3601 gggctgtgag gcttatcttc accatcatga ttgtttattt tctcttctgg gctccctaca
3661 acattgtcct tctcctgaac accttccagg aattctttgg cctgaataat tgcagtagct
3721 ctaacaggtt ggaccaagct atgcaggtga cagagactct tgggatgacg cactgctgca
3781 tcaaccccat catctatgcc tttgtcgggg agaagttcag aaactacctc ttagtcttct
3841 tccaaaagca cattgccaaa cgcttctgca atgctgttc tattttccag caagaggctc
3901 ccgagcgagc aagctcagtt tacacccgat ccactgggga gcaggaaata tctgtgggct
3961 tgtgacacgg actcaagtgg gctggtgacc cagtcagagt tgtgcacatg gcttagtttt
4021 catacacacc gcggtctaga gcatggctac gtagataagt agcatggcgg gttaatcatt
4081 aactacaagg aaccctagt gatggagttg gccactccct ctctgcgcgc tcgctcgctc
4141 actgaggccg ggcgaccaaa ggtcgcccga cgcccgggct ttgcccgggc ggcctcagtg
4201 agcgagcgag cgcgccagct ggcgtaatag cgaagaggcc cgcaccgatc gcccttccca
4261 acagttgcgc agcctgaatg gcgaatggcg attccgttgc aatggctggc ggtaatattg
4321 ttctggatat taccagcaag gccgatagtt tgagttcttc tactcaggca agtgatgtta
4381 ttactaatca aagaagtatt gcgacaacgg ttaatttgcg tgatggacag actcttttac
4441 tcggtggcct cactgattat aaaaacactt ctcaggattc tggcgtaccg ttcctgtcta
4501 aaatcccttt aatcggcctc ctgtttagct cccgctctga ttctaacgag gaaagcacgt
4561 tatacgtgct cgtcaaagca accatagtac gcgccctgta gcggcgcatt aagcgcggcg
4621 ggtgtggtgg ttacgcgcag cgtgaccgct acacttgcca gcgccctagc gcccgctcct
4681 ttcgctttct tcccttcctt tctcgccacg ttcgccggct ttccccgtca gctctaaat
4741 cgggggctcc ctttagggtt ccgatttagt gctttacggc acctcgaccc caaaaaactt
4801 gattagggtg atggttcacg tagtgggcca tcgccctgat agacggtttt tcgccctttg
4861 acgttggagt ccacgttctt taatagtgga ctcttgttcc aaactggaac aacactcaac
4921 cctatctcgg tctattcttt tgatttataa gggattttgc cgatttcggc ctattggtta
```

-continued

```
4981 aaaaatgagc tgatttaaca aaaatttaac gcgaattttta acaaaatatt aacgtttaca
5041 atttaaatat ttgcttatac aatcttcctg tttttggggc ttttctgatt atcaaccggg
5101 gtacatatga ttgacatgct agttttacga ttaccgttca tcgattctct tgtttgctcc
5161 agactctcag gcaatgacct gatagccttt gtagagacct ctcaaaaata gctaccctct
5221 ccggcatgaa tttatcagct agaacggttg aatatcatat tgatggtgat ttgactgtct
5281 ccggcctttc tcacccgttt gaatctttac ctacacatta ctcaggcatt gcatttaaaa
5341 tatatgaggg ttctaaaaat ttttatcctt gcgttgaaat aaaggcttct cccgcaaaag
5401 tattacaggg tcataatgtt tttggtacaa ccgatttagc tttatgctct gaggctttat
5461 tgcttaattt tgctaattct ttgccttgcc tgtatgattt attggatgtt ggaatcgcct
5521 gatgcggtat tttctcctta cgcatctgtg cggtatttca caccgcatat ggtgcactct
5581 cagtacaatc tgctctgatg ccgcatagtt aagccagccc cgacacccgc caacacccgc
5641 tgacgcgccc tgacgggctt gtctgctccc ggcatccgct tacagacaag ctgtgaccgt
5701 ctccgggagc tgcatgtgtc agaggttttc accgtcatca ccgaaacgcg cgagacgaaa
5761 gggcctcgtg atacgcctat ttttataggt taatgtcatg ataataatgg tttcttagac
5821 gtcaggtggc acttttcggg gaaatgtgcg cggaacccct atttgtttat ttttctaaat
5881 acattcaaat atgtatccgc tcatgagaca ataaccctga taaatgcttc aataatattg
5941 aaaaaggaag agtatgagta ttcaacattt ccgtgtcgcc cttattccct tttttgcggc
6001 attttgcctt cctgtttttg ctcacccaga aacgctggtg aaagtaaaag atgctgaaga
6061 tcagttgggt gcacgagtgg gttacatcga actggatctc aacagcggta agatccttga
6121 gagttttcgc cccgaagaac gttttccaat gatgagcact tttaaagttc tgctatgtgg
6181 cgcggtatta tcccgtattg acgccgggca agagcaactc ggtcgccgca tacactattc
6241 tcagaatgac ttggttgagt actcaccagt cacagaaaag catcttacgg atggcatgac
6301 agtaagagaa ttatgcagtg ctgccataac catgagtgat aacactgcgg ccaacttact
6361 tctgacaacg atcggaggac cgaaggagct aaccgctttt ttgcacaaca tgggggatca
6421 tgtaactcgc cttgatcgtt gggaaccgga gctgaatgaa gccataccaa acgacgagcg
6481 tgacaccacg atgcctgtag caatggcaac aacgttgcgc aaactattaa ctggcgaact
6541 acttactcta gcttcccggc aacaattaat agactggatg gaggcggata agttgcagg
6601 accacttctg cgctcggccc ttccggctgg ctggtttatt gctgataaat ctggagccgg
6661 tgagcgtggg tctcgcggta tcattgcagc actggggcca gatggtaagc cctcccgtat
6721 cgtagttatc tacacgacgg ggagtcaggc aactatggat gaacgaaata gacagatcgc
6781 tgagataggt gcctcactga ttaagcattg gtaactgtca gaccaagttt actcatatat
6841 actttagatt gatttaaaac ttcattttta atttaaaagg atctaggtga agatccttt
6901 tgataatctc atgaccaaaa tcccttaacg tgagttttcg ttccactgag cgtcagaccc
6961 cgtagaaaag atcaaaggat cttcttgaga tccttttttt ctgcgcgtaa tctgctgctt
7021 gcaaacaaaa aaaccaccgc taccagcggt ggtttgtttg ccggatcaag agctaccaac
7081 tcttttccg aaggtaactg gcttcagcag agcgcagata ccaaatactg tccttctagt
7141 gtagccgtag ttaggccacc acttcaagaa ctctgtagca ccgcctacat acctcgctct
7201 gctaatcctg ttaccagtgg ctgctgccag tggcgataag tcgtgtctta ccgggttgga
7261 ctcaagacga tagttaccgg ataaggcgca gcggtcgggc tgaacggggg gttcgtgcac
7321 acagcccagc ttggagcgaa cgacctacac cgaactgaga tacctacagc gtgagctatg
7381 agaaagcgcc acgcttcccg aagggagaaa ggcggacagg tatccggtaa gcggcagggt
```

-continued

```
7441 cggaacagga gagcgcacga gggagcttcc aggggggaaac gcctggtatc tttatagtcc
7501 tgtcgggttt cgccacctct gacttgagcg tcgattttg tgatgctcgt cagggggcg
7561 gagcctatgg aaaaacgcca gcaacgcggc cttttacgg ttcctggcct tttgctggcc
7621 ttttgctcac atgttctttc ctgcgttatc ccctgattct gtggataacc gtattaccgc
7681 ctttgagtga gctgataccg ctcgccgcag ccgaacgacc gagcgcagcg agtcagtgag
7741 cgaggaagcg gaagagcgcc caatacgcaa accgcctctc ccgcgcgtt ggccgattca
7801 ttaatg
```

SEQ ID NO: 59
Description: pAAV_CCR5.MND.II2ss.ADP.mAPRIL

```
   1 cagctgcgcg ctcgctcgct cactgaggcc gcccgggcaa agcccgggcg tcgggcgacc
  61 tttggtcgcc cggcctcagt gagcgagcga gcgcgcagag agggagtggc caactccatc
 121 actaggggtt ccttgtagtt aatgattaac ccgccatgct acttatctac gtagccatgc
 181 tctagcggcc tcggcctctg cataaataaa aaaaattagt cagccatgag cttggacgcg
 241 tttggtgtgg tggcgcctgt agtccccagc cacttggagg ggtgaggtga gaggattgct
 301 tgagcccggg atggtccagg ctgcagtgag ccatgatcgt gccactgcac tccagcctgg
 361 gcgacagagt gagaccctgt ctcacaacaa caacaacaac aacaaaaagg ctgagctgca
 421 ccatgcttga cccagtttct taaaattgtt gtcaaagctt cattcactcc atggtgctat
 481 agagcacaag attttatttg gtgagatggt gctttcatga attccccaa cagagccaag
 541 ctctccatct agtggacagg gaagctagca gcaaaccttc ccttcactac aaaacttcat
 601 tgcttggcca aaaagagagt taattcaatg tagacatcta tgtaggcaat taaaaaccta
 661 ttgatgtata aaacagtttg cattcatgga gggcaactaa atacattcta ggactttata
 721 aaagatcact ttttatttat gcacagggtg gaacaagatg gattatcaag tgtcaagtcc
 781 aatctatgac atcaattatt atacatcgga gccctgccaa aaaatcaatg tgaagcaaat
 841 cgcagcccgc ctcctgcctc cgctctactc actggtgttc atctttggtt ttgtgggcaa
 901 catgctggtc atcctcatcc tgataaactg caaaaggctg aagagcatga ctgacatcta
 961 cctgctcaac ctggccatct ctgacctgtt tttccttctt actgtcccct ctgggctca
1021 ctatgctgcc gcccagtggg actttggaaa tacaatgtgt caacgaacag agaaacagga
1081 gaatatgggc caaacaggat atctgtggta gcagttcct gccccggctc agggccaaga
1141 acagttggaa cagcagaata tgggccaaac aggatatctg tggtaagcag ttcctgcccc
1201 ggctcagggc caagaacaga tggtcccag atgcggtccc gccctcagca gtttctagag
1261 aaccatcaga tgtttccagg gtgccccaag gacctgaaat gaccctgtgc cttatttgaa
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga gatgtatcgg atgcagctct tgagctgtat cgctctgtca
1501 ctggcacttg ttaccaactc agaggatgac gttaccacca cggaagaact tgcgcccgct
1561 ttggtaccgc ctccgaaagg aacctgtgcc ggttggatgg ctggaatacc aggacatccc
1621 ggacacaatg gaacgccagg acgggatgga cgcgacggca cgcccggaga aaaggggag
1681 aaagggatg caggcttgct cgggccaaag gcgaaaccg cgacgttgg aatgacaggc
1741 gctgaaggac ctcggggttt ccgggaacc ccgggccgca agggcgaacc tggcgaggcc
1801 gccgcagtat tgcacagaa acagaaaaag caacattccg tccttcatct ggtccccatc
1861 aacgcaacct ccaaggatga tagtgatgtg accgaggtaa tgtggcaacc cgcgcttagg
```

-continued

```
1921 cgaggaagag gtctgcaggc gcagggatac ggggtgcgaa tccaagatgc tggggtgtac
1981 ctgctgtact cacaggtttt gtttcaggac gtaacattta cgatgggca ggtcgtgtcc
2041 cgagaaggac aagggagaca ggaaacactc ttccggtgta ttagaagtat gccttcacat
2101 cctgatcgcg cttacaactc ttgttattcc gctggcgtct ttcacttgca tcagggcgac
2161 atcctttcag tgataattcc gagagcgcgg gctaagttga atcttagccc ccacggcaca
2221 tttctcggat tcgtgaagct ttgatgagtc gactgcttta tttgtgaaat ttgtgatgct
2281 attgctttat ttgtaaccat tataagctgc aataaacaag ttaacaacaa caattgcatt
2341 cattttatgt ttcaggttca gggggaggtg tgggaggttt tttaaactct attttatagg
2401 cttcttctct ggaatcttct tcatcatcct cctgacaatc gataggtacc tggctgtcgt
2461 ccatgctgtg tttgctttaa aagccaggac ggtcacctt ggggtggtga caagtgtgat
2521 cacttgggtg gtggctgtgt ttgcgtctct cccaggaatc atctttacca gatctcaaaa
2581 agaaggtctt cattacacct gcagctctca ttttccatac agtcagtatc aattctggaa
2641 gaatttccag acattaaaga tagtcatctt ggggctggtc ctgccgctgc ttgtcatggt
2701 catctgctac tcgggaatcc taaaaactct gcttcggtgt cgaaatgaga agaagaggca
2761 cagggctgtg aggcttatct tcaccatcat gattgtttat tttctcttct gggctcccta
2821 caacattgtc cttctcctga acaccttcca ggaattcttt ggcctgaata attgcagtag
2881 ctctaacagg ttgaccaag ctatgcaggt gacagagact cttgggatga cgcactgctg
2941 catcaacccc atcatctatg cctttgtcgg ggagaagttc agaaactacc tcttagtctt
3001 cttccaaaag cacattgcca aacgcttctg caaatgctgt tctatttttcc agcaagaggc
3061 tcccgagcga gcaagctcag tttacacccg atccactggg gagcaggaaa tatctgtggg
3121 cttgtgacac ggactcaagt gggctggtga cccagtcaga gttgtgcaca tggcttagtt
3181 ttcatacaca ccgcggtcta gagcatggct acgtagataa gtagcatggc gggttaatca
3241 ttaactacaa ggaacccta gtgatggagt tggccactcc ctctctgcgc gctcgctcgc
3301 tcactgaggc cgggcgacca aaggtcgccc gacgcccggg ctttgcccgg cggcctcag
3361 tgagcgagcg agcgcgccag ctggcgtaat agcgaagagg cccgcaccga tcgcccttcc
3421 caacagttgc gcagcctgaa tggcgaatgg cgattccgtt gcaatggctg gcggtaatat
3481 tgttctggat attaccagca aggccgatag tttgagttct tctactcagg caagtgatgt
3541 tattactaat caaagaagta ttgcgacaac ggttaatttg cgtgatggac agactctttt
3601 actcggtggc ctcactgatt ataaaaacac ttctcaggat tctggcgtac cgttcctgtc
3661 taaaatccct ttaatcggcc tcctgtttag ctcccgctct gattctaacg aggaaagcac
3721 gttatacgtg ctcgtcaaag caaccatagt acgcgccctg tagcggcgca ttaagcgcgg
3781 cgggtgtggt ggttacgcgc agcgtgaccg ctacacttgc cagcgcccta gcgcccgctc
3841 ctttcgcttt cttcccttcc tttctcgcca cgttcgccgg ctttccccgt caagctctaa
3901 atcgggggct ccctttaggg ttccgattta gtgctttacg gcacctcgac cccaaaaaac
3961 ttgattaggg tgatggttca cgtagtgggc catcgccctg atagacggtt tttcgccctt
4021 tgacgttgga gtccacgttc tttaatagtg gactcttgtt ccaaactgga acaacactca
4081 accctatctc ggtctattct tttgatttat aagggatttt gccgatttcg gcctattggt
4141 taaaaaatga gctgatttaa caaaaattta acgcgaattt taacaaaata ttaacgttta
4201 caatttaaat atttgcttat acaatcttcc tgttttttggg cttttctga ttatcaaccg
4261 gggtacatat gattgacatg ctagttttac gattaccgtt catcgattct cttgtttgct
4321 ccagactctc aggcaatgac ctgatagcct ttgtagagac ctctcaaaaa tagctaccct
```

```
4381 ctccggcatg aatttatcag ctagaacggt tgaatatcat attgatggtg atttgactgt
4441 ctccggcctt tctcacccgt ttgaatcttt acctacacat tactcaggca ttgcatttaa
4501 aatatatgag ggttctaaaa attttttatcc ttgcgttgaa ataaaggctt ctcccgcaaa
4561 agtattacag ggtcataatg ttttttggtac aaccgattta gctttatgct ctgaggcttt
4621 attgcttaat tttgctaatt ctttgccttg cctgtatgat ttattggatg ttggaatcgc
4681 ctgatgcggt attttctcct tacgcatctg tgcggtattt cacaccgcat atggtgcact
4741 ctcagtacaa tctgctctga tgccgcatag ttaagccagc cccgacaccc gccaacaccc
4801 gctgacgcgc cctgacgggc ttgtctgctc ccggcatccg cttacagaca gctgtgacc
4861 gtctccggga gctgcatgtg tcagaggttt tcaccgtcat caccgaaacg cgcgagacga
4921 aagggcctcg tgatacgcct attttttatag gttaatgtca tgataataat ggtttcttag
4981 acgtcaggtg gcacttttcg gggaaatgtg cgcggaaccc ctatttgttt attttttctaa
5041 atacattcaa atatgtatcc gctcatgaga caataaccct gataaatgct tcaataatat
5101 tgaaaaagga gagtatgag tattcaacat ttccgtgtcg cccttattcc cttttttgcg
5161 gcattttgcc ttcctgtttt tgctcaccca gaaacgctgg tgaaagtaaa agatgctgaa
5221 gatcagttgg gtgcacgagt gggttacatc gaactggatc tcaacagcgg taagatcctt
5281 gagagttttc gccccgaaga acgttttcca atgatgagca cttttaaagt tctgctatgt
5341 ggcgcggtat tatcccgtat tgacgccggg caagagcaac tcggtcgccg catacactat
5401 tctcagaatg acttggttga gtactcacca gtcacagaaa agcatcttac ggatggcatg
5461 acagtaagag aattatgcag tgctgccata accatgagtg ataacactgc ggccaactta
5521 cttctgacaa cgatcggagg accgaaggag ctaaccgctt ttttgcacaa catgggggat
5581 catgtaactc gccttgatcg ttgggaaccg gagctgaatg aagccatacc aaacgacgag
5641 cgtgacacca cgatgcctgt agcaatggca acaacgttgc gcaaactatt aactggcgaa
5701 ctacttactc tagcttcccg gcaacaatta atagactgga tggaggcgga taaagttgca
5761 ggaccacttc tgcgctcggc ccttccggct ggctggttta ttgctgataa atctggagcc
5821 ggtgagcgtg ggtctcgcgg tatcattgca gcactggggc cagatggtaa gccctcccgt
5881 atcgtagtta tctacacgac ggggagtcag gcaactatgg atgaacgaaa tagacagatc
5941 gctgagatag gtgcctcact gattaagcat tggtaactgt cagaccaagt ttactcatat
6001 atactttaga ttgatttaaa acttcatttt taatttaaaa ggatctaggt gaagatcctt
6061 tttgataatc tcatgaccaa aatcccttaa cgtgagtttt cgttccactg agcgtcagac
6121 cccgtagaaa agatcaaagg atcttcttga gatccttttt ttctgcgcgt aatctgctgc
6181 ttgcaaacaa aaaaaccacc gctaccagcg gtggtttgtt tgccggatca agagctacca
6241 actctttttc cgaaggtaac tggcttcagc agagcgcaga taccaaatac tgtccttcta
6301 gtgtagccgt agttaggcca ccacttcaag aactctgtag caccgcctac atacctcgct
6361 ctgctaatcc tgttaccagt ggctgctgcc agtggcgata agtcgtgtct taccgggttg
6421 gactcaagac gatagttacc ggataaggcg cagcggtcgg gctgaacggg gggttcgtgc
6481 acacagccca gcttggagcg aacgacctac accgaactga gatacctaca gcgtgagcta
6541 tgagaaagcg ccacgcttcc cgaagggaga aaggcggaca ggtatccggt aagcggcagg
6601 gtcggaacag gagagcgcac gagggagctt ccaggggaa acgcctggta tctttatagt
6661 cctgtcgggt ttcgccacct ctgacttgag cgtcgatttt tgtgatgctc gtcaggggg
6721 cggagcctat ggaaaaacgc cagcaacgcg gcctttttac ggttcctggc cttttgctgg
```

-continued

```
6781 cctttgctc acatgttctt tcctgcgtta tcccctgatt ctgtggataa ccgtattacc
6841 gcctttgagt gagctgatac cgctcgccgc agccgaacga ccgagcgcag cgagtcagtg
6901 agcgaggaag cggaagagcg cccaatacgc aaaccgcctc tccccgcgcg ttggccgatt
6961 cattaatg
```

SEQ ID NO: 60
Description: pAAV.CCR5.MND.IL6.Frun.T2A.GFP

```
   1 cagctgcgcg ctcgctcgct cactgaggcc gcccgggcaa agcccgggcg tcgggcgacc
  61 tttggtcgcc cggcctcagt gagcgagcga gcgcgcagag agggagtggc caactccatc
 121 actaggggtt ccttgtagtt aatgattaac ccgccatgct acttatctac gtagccatgc
 181 tctagcggcc tcggcctctg cataaataaa aaaaattagt cagccatgag cttgacgcg
 241 tttggtgtgg tggcgcctgt agtccccagc cacttggagg ggtgaggtga gaggattgct
 301 tgagcccggg atggtccagg ctgcagtgag ccatgatcgt gccactgcac tccagcctgg
 361 gcgacagagt gagaccctgt ctcacaacaa caacaacaac aacaaaaagg ctgagctgca
 421 ccatgcttga cccagtttct taaaattgtt gtcaaagctt cattcactcc atggtgctat
 481 agagcacaag atttatttg gtgagatggt gctttcatga attcccccaa cagagccaag
 541 ctctccatct agtggacagg gaagctagca gcaaaccttc ccttcactac aaaacttcat
 601 tgcttggcca aaaagagagt taattcaatg tagacatcta tgtaggcaat taaaaaccta
 661 ttgatgtata aaacagtttg cattcatgga gggcaactaa atacattcta ggactttata
 721 aaagatcact ttttattat gcacagggtg gaacaagatg gattatcaag tgtcaagtcc
 781 aatctatgac atcaattatt atacatcgga gccctgccaa aaaatcaatg tgaagcaaat
 841 cgcagcccgc ctcctgcctc cgctctactc actggtgttc atctttggtt ttgtgggcaa
 901 catgctggtc atcctcatcc tgataaactg caaaaggctg aagagcatga ctgacatcta
 961 cctgctcaac ctggccatct ctgacctgtt tttccttctt actgtcccct ctgggctca
1021 ctatgctgcc gcccagtggg actttggaaa tacaatgtgt caacgaacag agaaacagga
1081 gaatatgggc caaacaggat atctgtggta agcagttcct gccccggctc agggccaaga
1141 acagttggaa cagcagaata tgggccaaac aggatatctg tggtaagcag ttcctgcccc
1201 ggctcagggc caagaacaga tggtccccag atgcggtccc gccctcagca gtttctagag
1261 aaccatcaga tgtttccagg gtgccccaag gacctgaaat gaccctgtgc cttatttgaa
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga gatgaacagt ttttctactt ctgccttcgg accgtcgcc
1501 tttagcctgg gcctgctgct ggtgctgcct gccgcattcc ccgctcctgt gccccctgga
1561 gaagactcca aggatgtcgc cgctcctcac agacagccac tgactagctc cgagaggatc
1621 gacaaacaga tccgctacat tctggatggc attagcgccc tgcgcaagga aacctgcaac
1681 aaatccaata tgtgtgagtc tagtaaggaa gcactggccg agaacaatct gaacctgccc
1741 aagatggctg agaaagacgg ctgcttccag tctgggttta tgaggaaac ctgtctggtg
1801 aaaatcatta cagggctgct ggagttcgaa gtctacctgg aatatctgca gaaccgattt
1861 gagtcaagcg aggaacaggc tcgggcagtg cagatgagca caaaggtcct gatccagttc
1921 ctgcagaaga aagccaaaaa tctggacgct attaccacac agatcccac taccaacgct
1981 tctctgctga ccaagctgca ggcacagaat cagtggctgc aggatatgac aactcacctg
2041 atcctgagga gtttcaaaga atttctgcag tcctctctgc gggcactgag acagatgcgc
2101 gctaagcgag gatccggtga gggcagagga agtcttctaa catgcggtga cgtggaggag
```

-continued

```
2161 aatccgggcc ccatggtgag caagggcgag gagctgttca ccggggtggt gcccatcctg
2221 gtcgagctgg acggcgacgt aaacggccac aagttcagcg tgtccggcga gggcgagggc
2281 gatgccacct acggcaagct gaccctgaag ttcatctgca ccaccggcaa gctgcccgtg
2341 ccctggccca ccctcgtgac caccctgacc tacggcgtgc agtgcttcag ccgctacccc
2401 gaccacatga agcagcacga cttcttcaag tccgccatgc ccgaaggcta cgtccaggag
2461 cgcaccatct tcttcaagga cgacggcaac tacaagaccc gcgccgaggt gaagttcgag
2521 ggcgacaccc tggtgaaccg catcgagctg aagggcatcg acttcaagga ggacggcaac
2581 atcctggggc acaagctgga gtacaactac aacagccaca acgtctatat catggccgac
2641 aagcagaaga acggcatcaa ggtgaacttc aagatccgcc acaacatcga ggacggcagc
2701 gtgcagctcg ccgaccacta ccagcagaac acccccatcg gcgacggccc cgtgctgctg
2761 cccgacaacc actacctgag cacccagtcc gccctgagca agacccccaa cgagaagcgc
2821 gatcacatgg tcctgctgga gttcgtgacc gccgccggga tcactctcgg catggacgag
2881 ctgtacaagt gaatctagag tcgactgctt tatttgtgaa atttgtgatg ctattgcttt
2941 atttgtaacc attataagct gcaataaaca agttaacaac aacaattgca ttcattttat
3001 gtttcaggtt caggggagg tgtgggaggt tttttaaact ctattttata ggcttcttct
3061 ctggaatctt cttcatcatc ctcctgacaa tcgataggta cctggctgtc gtccatgctg
3121 tgtttgcttt aaaagccagg acggtcacct ttggggtggt gacaagtgtg atcacttggg
3181 tggtggctgt gtttgcgtct ctcccaggaa tcatctttac cagatctcaa aaagaaggtc
3241 ttcattacac ctgcagctct cattttccat acagtcagta tcaattctgg aagaatttcc
3301 agacattaaa gatagtcatc ttggggctgg tcctgccgct gcttgtcatg gtcatctgct
3361 actcgggaat cctaaaaact ctgcttcggt gtcgaaatga aagaagagg cacagggctg
3421 tgaggcttat cttcaccatc atgattgttt attttctctt ctgggctccc tacaacattg
3481 tccttctcct gaacaccttc caggaattct ttggcctgaa taattgcagt agctctaaca
3541 ggttggacca agctatgcag gtgacagaga ctcttgggat gacgcactgc tgcatcaacc
3601 ccatcatcta tgcctttgtc ggggagaagt tcagaaacta cctcttagtc ttcttccaaa
3661 agcacattgc caaacgcttc tgcaaatgct gttctatttt ccagcaagag gctcccgagc
3721 gagcaagctc agtttacacc cgatccactg gggagcagga aatatctgtg ggcttgtgac
3781 acggactcaa gtgggctggt gacccagtca gagttgtgca catggcttag ttttcataca
3841 caccgcggtc tagagcatgg ctacgtagat aagtagcatg gcgggttaat cattaactac
3901 aaggaacccc tagtgatgga gttggccact ccctctctgc gcgctcgctc gctcactgag
3961 gccgggcgac caaaggtcgc ccgacgcccg ggctttgccc gggcggcctc agtgagcgag
4021 cgagcgcgcc agctggcgta atagcgaaga ggcccgcacc gatcgccctt cccaacagtt
4081 gcgcagcctg aatggcgaat ggcgattccg ttgcaatggc tggcggtaat attgttctgg
4141 atattaccag caaggccgat agtttgagtt cttctactca ggcaagtgat gttattacta
4201 atcaaagaag tattgcgaca acggttaatt tgcgtgatgg acagactctt ttactcggtg
4261 gcctcactga ttataaaaac acttctcagg attctggcgt accgttcctg tctaaaatcc
4321 ctttaatcgg cctcctgttt agctcccgct ctgattctaa cgaggaaagc acgttatacg
4381 tgctcgtcaa agcaaccata gtacgcgccc tgtagcggcg cattaagcgc ggcgggtgtg
4441 gtggttacgc gcagcgtgac cgctacactt gccagcgccc tagcgcccgc tcctttcgct
4501 ttcttccctt cctttctcgc cacgttcgcc ggctttcccc gtcaagctct aaatcggggg
```

-continued

```
4561 ctcccttag ggttccgatt tagtgcttta cggcacctcg accccaaaaa acttgattag 4621 ggtgatggtt cacgtagtgg gccatcgccc tgatagacgg tttttcgccc tttgacgttg 4681 gagtccacgt tctttaatag tggactcttg ttccaaactg gaacaacact caacccctatc 4741 tcggtctatt cttttgattt ataagggatt ttgccgattt cggcctattg gttaaaaaat 4801 gagctgattt aacaaaaatt taacgcgaat tttaacaaaa tattaacgtt tacaatttaa 4861 atatttgctt atacaatctt cctgttttg gggcttttct gattatcaac cggggtacat 4921 atgattgaca tgctagtttt acgattaccg ttcatcgatt ctcttgtttg ctccagactc 4981 tcaggcaatg acctgatagc ctttgtagag acctctcaaa aatagctacc ctctccggca 5041 tgaatttatc agctagaacg gttgaatatc atattgatgg tgatttgact gtctccggcc 5101 tttctcaccc gtttgaatct ttacctacac attactcagg cattgcattt aaaatatatg 5161 agggttctaa aaattttat ccttgcgttg aaataaaggc ttctcccgca aaagtattac 5221 agggtcataa tgtttttggt acaaccgatt tagctttatg ctctgaggct ttattgctta 5281 attttgctaa ttctttgcct tgcctgtatg atttattgga tgttggaatc gcctgatgcg 5341 gtattttctc cttacgcatc tgtgcggtat ttcacaccgc atatggtgca ctctcagtac 5401 aatctgctct gatgccgcat agttaagcca gccccgacac ccgccaacac ccgctgacgc 5461 gccctgacgg gcttgtctgc tcccggcatc cgcttacaga caagctgtga ccgtctccgg 5521 gagctgcatg tgtcagaggt tttcaccgtc atcaccgaaa cgcgcgagac gaaagggcct 5581 cgtgatacgc ctatttttat aggttaatgt catgataata atggtttctt agacgtcagg 5641 tggcacttt cggggaaatg tgcgcggaac ccctatttgt ttattttct aaatacattc 5701 aaatatgtat ccgctcatga caataaccc ctgataaatg cttcaataat attgaaaaag 5761 gaagagtatg agtattcaac atttccgtgt cgcccttatt ccctttttg cggcattttg 5821 ccttcctgtt tttgctcacc cagaaacgct ggtgaaagta aaagatgctg aagatcagtt 5881 gggtgcacga gtgggttaca tcgaactgga tctcaacagc ggtaagatcc ttgagagttt 5941 tcgccccgaa gaacgttttc caatgatgag cactttttaaa gttctgctat gtggcgcggt 6001 attatcccgt attgacgccg ggcaagagca actcggtcgc cgcatacact attctcagaa 6061 tgacttggtt gagtactcac cagtcacaga aaagcatctt acggatggca tgacagtaag 6121 agaattatgc agtgctgcca taaccatgag tgataacact gcggccaact tacttctgac 6181 aacgatcgga ggaccgaagg agctaaccgc ttttttgcac aacatggggg atcatgtaac 6241 tcgccttgat cgttgggaac cggagctgaa tgaagccata ccaaacgacg agcgtgacac 6301 cacgatgcct gtagcaatgg caacaacgtt gcgcaaacta ttaactggcg aactacttac 6361 tctagcttcc cggcaacaat taatagactg gatggaggcg gataaagttg caggaccact 6421 tctgcgctcg gcccttccgg ctggctggtt tattgctgat aaatctggag ccggtgagcg 6481 tgggtctcgc ggtatcattg cagcactggg gccagatggt aagccctccc gtatcgtagt 6541 tatctacacg acggggagtc aggcaactat ggatgaacga aatagacaga tcgctgagat 6601 aggtgcctca ctgattaagc attggtaact gtcagaccaa gtttactcat atatacttta 6661 gattgattta aaacttcatt tttaatttaa aaggatctag gtgaagatcc ttttttgataa 6721 tctcatgacc aaaatccctt aacgtgagtt ttcgttccac tgagcgtcag accccgtaga 6781 aaagatcaaa ggatcttctt gagatccttt ttttctgcgc gtaatctgct gcttgcaaac 6841 aaaaaaacca ccgctaccag cggtggtttg tttgccggat caagagctac caactctttt 6901 tccgaaggta actggcttca gcagagcgca gataccaaat actgtccttc tagtgtagcc 6961 gtagttaggc caccacttca agaactctgt agcaccgcct acatacctcg ctctgctaat
```

-continued

```
7021 cctgttacca gtggctgctg ccagtggcga taagtcgtgt cttaccgggt tggactcaag
7081 acgatagtta ccggataagg cgcagcggtc gggctgaacg gggggttcgt gcacacagcc
7141 cagcttggag cgaacgacct acaccgaact gagataccta cagcgtgagc tatgagaaag
7201 cgccacgctt cccgaaggga gaaaggcgga caggtatccg gtaagcggca gggtcggaac
7261 aggagagcgc acgagggagc ttccaggggg aaacgcctgg tatctttata gtcctgtcgg
7321 gtttcgccac ctctgacttg agcgtcgatt tttgtgatgc tcgtcagggg gcggagcct
7381 atggaaaaac gccagcaacg cggccttttt acggttcctg ccttttgct ggccttttgc
7441 tcacatgttc tttcctgcgt tatccctga ttctgtggat aaccgtatta ccgcctttga
7501 gtgagctgat accgctcgcc gcagccgaac gaccgagcgc agcgagtcag tgagcgagga
7561 agcggaagag cgcccaatac gcaaaccgcc tctccccgcg cgttggccga ttcattaatg
```

SEQ ID NO: 61
Description: pAAV CCR5.MND.II2ss-ADP.mAPRIL.Furin.T2A.GFP

```
   1 cagctgcgcg ctcgctcgct cactgaggcc gcccgggcaa agcccgggcg tcgggcgacc
  61 tttggtcgcc cggcctcagt gagcgagcga gcgcgcagag agggagtggc caactccatc
 121 actaggggtt ccttgtagtt aatgattaac ccgccatgct acttatctac gtagccatgc
 181 tctagcggcc tcggcctctg cataaataaa aaaaattagt cagccatgag cttgacgcg
 241 tttggtgtgg tggcgcctgt agtccccagc cacttggagg ggtgaggtga gaggattgct
 301 tgagcccggg atggtccagg ctgcagtgag ccatgatcgt gccactgcac tccagcctgg
 361 gcgacagagt gagaccctgt ctcacaacaa caacaacaac aacaaaaagg ctgagctgca
 421 ccatgcttga cccagtttct taaaattgtt gtcaaagctt cattcactcc atggtgctat
 481 agagcacaag atttatttg gtgagatggt gctttcatga attcccccaa cagagccaag
 541 ctctccatct agtggacagg gaagctagca gcaaaccttc ccttcactac aaaacttcat
 601 tgcttggcca aaagagagt taattcaatg tagacatcta tgtaggcaat taaaaaccta
 661 ttgatgtata aaacagtttg cattcatgga gggcaactaa atacattcta ggactttata
 721 aaagatcact ttttatttat gcacagggtg gaacaagatg gattatcaag tgtcaagtcc
 781 aatctatgac atcaattatt atacatcgga gccctgccaa aaaatcaatg tgaagcaaat
 841 cgcagcccgc ctcctgcctc cgctctactc actggtgttc atctttggtt ttgtgggcaa
 901 catgctggtc atcctcatcc tgataaactg caaaaggctg aagagcatga ctgacatcta
 961 cctgctcaac ctggccatct ctgacctgtt tttccttctt actgtcccct ctgggctca
1021 ctatgctgcc gcccagtggg actttggaaa tacaatgtgt caacgaacag agaaacagga
1081 gaatatgggc caaacaggat atctgtggta agcagttcct gccccggctc agggccaaga
1141 acagttggaa cagcagaata tgggccaaac aggatatctg tggtaagcag ttcctgcccc
1201 ggctcagggc caagaacaga tggtccccag atgcggtccc gccctcagca gtttctagag
1261 aaccatcaga tgtttccagg gtgccccaag gacctgaaat gaccctgtgc cttatttgaa
1321 ctaaccaatc agttcgcttc tcgcttctgt tcgcgcgctt ctgctccccg agctctatat
1381 aagcagagct cgtttagtga accgtcgat cgcctggaga cgccatccac gctgttttga
1441 cttccataga aggatctcga gatgtatcgg atgcagctct tgagctgtat cgctctgtca
1501 ctggcacttg ttaccaactc agaggatgac gttaccacca cggaagaact tgcgcccgct
1561 ttggtaccgc ctccgaaagg aacctgtgcc ggttggatgg ctggaatacc aggacatccc
1621 ggacacaatg gaacgccagg acgggatgga cgcgacggca cgcccggaga aaaaggggag
1681 aaaggggatg caggcttgct cgggccaaag ggcgaaaccg cgcgacgttgg aatgacaggc
```

-continued

```
1741 gctgaaggac ctcggggttt tccgggaacc ccgggccgca agggcgaacc tggcgaggcc
1801 gccgcagtat tgacacagaa acagaaaaag caacattccg tccttcatct ggtccccatc
1861 aacgcaacct ccaaggatga tagtgatgtg accgaggtaa tgtggcaacc cgcgcttagg
1921 cgaggaagag gtctgcaggc gcagggatac ggggtgcgaa tccaagatgc tggggtgtac
1981 ctgctgtact cacaggtttt gtttcaggac gtaacattta cgatggggca ggtcgtgtcc
2041 cgagaaggac aagggagaca ggaaacactc ttccggtgta ttagaagtat gccttcacat
2101 cctgatcgcg cttacaactc ttgttattcc gctggcgtct ttcacttgca tcagggcgac
2161 atcctttcag tgataattcc gagagcgcgg gctaagttga atcttagccc ccacggcaca
2221 tttctcggat tcgtgaagct tcgcgctaag cgaggatccg gtgagggcag aggaagtctt
2281 ctaacatgcg gtgacgtgga ggagaatccg ggccccatgg tgagcaaggg cgaggagctg
2341 ttcaccgggg tggtgcccat cctggtcgag ctggacggcg acgtaaacgg ccacaagttc
2401 agcgtgtccg gcgagggcga gggcgatgcc acctacggca agctgaccct gaagttcatc
2461 tgcaccaccg gcaagctgcc cgtgccctgg cccaccctcg tgaccaccct gacctacggc
2521 gtgcagtgct tcagccgcta ccccgaccac atgaagcagc acgacttctt caagtccgcc
2581 atgcccgaag gctacgtcca ggagcgcacc atcttcttca aggacgacgg caactacaag
2641 acccgcgccg aggtgaagtt cgagggcgac accctggtga accgcatcga gctgaagggc
2701 atcgacttca aggaggacgg caacatcctg ggcacaagc tggagtacaa ctacaacagc
2761 cacaacgtct atatcatggc cgacaagcag aagaacggca tcaaggtgaa cttcaagatc
2821 cgccacaaca tcgaggacgg cagcgtgcag ctcgccgacc actaccagca gaacaccccc
2881 atcggcgacg gccccgtgct gctgcccgac aaccactacc tgagcaccca gtccgccctg
2941 agcaaagacc ccaacgagaa gcgcgatcac atggtcctgc tggagttcgt gaccgccgcc
3001 gggatcactc tcggcatgga cgagctgtac aagtgaatct agagtcgact gctttatttg
3061 tgaaatttgt gatgctattg ctttatttgt aaccattata agctgcaata acaagttaa
3121 caacaacaat tgcattcatt ttatgtttca ggttcagggg gaggtgtggg aggttttta
3181 aactctattt tataggcttc ttctctggaa tcttcttcat catcctcctg acaatcgata
3241 ggtacctggc tgtcgtccat gctgtgtttg ctttaaaagc caggacggtc acctttgggg
3301 tggtgacaag tgtgatcact tgggtggtgg ctgtgtttgc gtctctccca ggaatcatct
3361 ttaccagatc tcaaaaagaa ggtcttcatt acacctgcag ctctcatttt ccatacagtc
3421 agtatcaatt ctggaagaat ttccagacat taaagatagt catcttgggg ctggtcctgc
3481 cgctgcttgt catggtcatc tgctactcgg gaatcctaaa aactctgctt cggtgtcgaa
3541 atgagaagaa gaggcacagg gctgtgaggc ttatcttcac catcatgatt gtttattttc
3601 tcttctgggc tccctacaac attgtccttc tcctgaacac cttccaggaa ttctttggcc
3661 tgaataattg cagtagctct aacaggttgg accaagctat gcaggtgaca gagactcttg
3721 ggatgacgca ctgctgcatc aacccccatca tctatgcctt tgtcggggag aagttcagaa
3781 actacctctt agtcttcttc caaaagcaca ttgccaaacg cttctgcaaa tgctgttcta
3841 ttttccagca agaggctccc gagcgagcaa gctcagttta cacccgatcc actggggagc
3901 aggaaatatc tgtgggcttg tgacacggac tcaagtgggc tggtgaccca gtcagagttg
3961 tgcacatggc ttagttttca tacacaccgc ggtctagagc atggctacgt agataagtag
4021 catggcgggt taatcattaa ctacaaggaa ccctagtga tggagttggc cactccctct
4081 ctgcgcgctc gctcgctcac tgaggccggg cgaccaaagg tcgcccgacg cccgggcttt
4141 gcccggcgg cctcagtgag cgagcgagcg cgccagctgg cgtaatagcg aagaggcccg
```

-continued

```
4201 caccgatcgc ccttcccaac agttgcgcag cctgaatggc gaatggcgat tccgttgcaa
4261 tggctggcgg taatattgtt ctggatatta ccagcaaggc cgatagtttg agttcttcta
4321 ctcaggcaag tgatgttatt actaatcaaa gaagtattgc gacaacggtt aatttgcgtg
4381 atggacagac tcttttactc ggtggcctca ctgattataa aaacacttct caggattctg
4441 gcgtaccgtt cctgtctaaa atccctttaa tcggcctcct gtttagctcc cgctctgatt
4501 ctaacgagga aagcacgtta tacgtgctcg tcaaagcaac catagtacgc gccctgtagc
4561 ggcgcattaa gcgcggcggg tgtggtggtt acgcgcagcg tgaccgctac acttgccagc
4621 gccctagcgc ccgctccttt cgctttcttc ccttcctttc tcgccacgtt cgccggcttt
4681 ccccgtcaag ctctaaatcg gggctccctt tagggttcc gatttagtgc tttacggcac
4741 ctcgacccca aaaaacttga ttagggtgat ggttcacgta gtgggccatc gccctgatag
4801 acggttttc gcccttgac gttggagtcc acgttcttta atagtggact cttgttccaa
4861 actggaacaa cactcaaccc tatctcggtc tattcttttg atttataagg gattttgccg
4921 atttcggcct attggttaaa aaatgagctg atttaacaaa aatttaacgc gaattttaac
4981 aaaatattaa cgtttacaat ttaaatattt gcttatacaa tcttcctgtt tttggggctt
5041 ttctgattat caaccggggt acatatgatt gacatgctag ttttacgatt accgttcatc
5101 gattctcttg tttgctccag actctcaggc aatgacctga tagcctttgt agagacctct
5161 caaaaatagc taccctctcc ggcatgaatt tatcagctag aacggttgaa tatcatattg
5221 atggtgattt gactgtctcc ggcctttctc acccgtttga atctttacct acacattact
5281 caggcattgc atttaaaata tatgagggtt ctaaaaattt ttatccttgc gttgaaataa
5341 aggcttctcc cgcaaaagta ttacagggtc ataatgtttt tggtacaacc gatttagctt
5401 tatgctctga ggctttattg cttaattttg ctaattcttt gccttgcctg tatgatttat
5461 tggatgttgg aatcgcctga tgcggtattt tctccttacg catctgtgcg gtatttcaca
5521 ccgcatatgg tgcactctca gtacaatctg ctctgatgcc gcatagttaa gccagccccg
5581 acacccgcca acaccgctg acgcgccctg acgggcttgt ctgctcccgg catccgctta
5641 cagacaagct gtgaccgtct ccgggagctg catgtgtcag aggttttcac cgtcatcacc
5701 gaaacgcgcg agacgaaagg gcctcgtgat acgcctattt ttataggtta atgtcatgat
5761 aataatggtt tcttagacgt caggtggcac ttttcgggga atgtgcgcg aaccccctat
5821 ttgtttattt ttctaaatac attcaaatat gtatccgctc atgagacaat aaccctgata
5881 aatgcttcaa taatattgaa aaaggaagag tatgagtatt caacatttcc gtgtcgccct
5941 tattcccttt tttgcggcat tttgccttcc tgttttgct cacccagaaa cgctggtgaa
6001 agtaaaagat gctgaagatc agttgggtgc acgagtgggt tacatcgaac tggatctcaa
6061 cagcggtaag atccttgaga gttttcgccc cgaagaacgt tttccaatga tgagcacttt
6121 taaagttctg ctatgtggcg cggtattatc ccgtattgac gccgggcaag agcaactcgg
6181 tcgccgcata cactattctc agaatgactt ggttgagtac tcaccagtca cagaaaagca
6241 tcttacggat ggcatgacag taagagaatt atgcagtgct gccataacca tgagtgataa
6301 cactgcggcc aacttacttc tgacaacgat cggaggaccg aaggagctaa ccgcttttt
6361 gcacaacatg ggggatcatg taactcgcct tgatcgttgg gaaccggagc tgaatgaagc
6421 cataccaaac gacgagcgtg acaccacgat gcctgtagca atggcaacaa cgttgcgcaa
6481 actattaact ggcgaactac ttactctagc ttcccggcaa caattaatag actggatgga
6541 ggcggataaa gttgcaggac cacttctgcg ctcggccctt ccggctggct ggtttattgc
```

```
6601 tgataaatct ggagccggtg agcgtgggtc tcgcggtatc attgcagcac tggggccaga 6661 tggtaagccc tcccgtatcg tagttatcta cacgacgggg agtcaggcaa ctatggatga 6721 acgaaataga cagatcgctg agataggtgc ctcactgatt aagcattggt aactgtcaga 6781 ccaagtttac tcatatatac tttagattga tttaaaactt cattttaat ttaaaaggat 6841 ctaggtgaag atccttttg ataatctcat gaccaaaatc ccttaacgtg agttttcgtt 6901 ccactgagcg tcagaccccg tagaaaagat caaaggatct tcttgagatc ctttttttct 6961 gcgcgtaatc tgctgcttgc aaacaaaaaa accaccgcta ccagcggtgg tttgtttgcc 7021 ggatcaagag ctaccaactc tttttccgaa ggtaactggc ttcagcagag cgcagatacc 7081 aaatactgtc cttctagtgt agccgtagtt aggccaccac ttcaagaact ctgtagcacc 7141 gcctacatac ctcgctctgc taatcctgtt accagtggct gctgccagtg gcgataagtc 7201 gtgtcttacc gggttggact caagacgata gttaccggat aaggcgcagc ggtcgggctg 7261 aacggggggt tcgtgcacac agcccagctt ggagcgaacg acctacaccg aactgagata 7321 cctacagcgt gagctatgag aaagcgccac gcttcccgaa gggagaaagg cggacaggta 7381 tccggtaagc ggcagggtcg gaacaggaga gcgcacgagg gagcttccag ggggaaacgc 7441 ctggtatctt tatagtcctg tcgggtttcg ccacctctga cttgagcgtc gatttttgtg 7501 atgctcgtca gggggggcgga gcctatggaa aaacgccagc aacgcggcct ttttacggtt 7561 cctggccttt tgctggcctt ttgctcacat gttctttcct gcgttatccc ctgattctgt 7621 ggataaccgt attaccgcct ttgagtgagc tgataccgct cgccgcagcc gaacgaccga 7681 gcgcagcgag tcagtgagcg aggaagcgga agagcgccca atacgcaaac cgcctctccc 7741 cgcgcgttgg ccgattcatt aatg
```

SEQ ID NO: 62
Description: pAAV CCR5 MND IL6

```
   1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag attttatttg gtgagatggt gctttcatga attccccaa cagagccaag 541 ctctccatct agtggacagg gaagctagca gcaaaccttc ccttcactac aaaacttcat 601 tgcttggcca aaaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacagggtg gaacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct ctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc
```

-continued

```
1201 ggctcagggc caagaacaga tggtcccag atgcggtccc gccctcagca gtttctagag 1261 aaccatcaga tgtttccagg gtgccccaag gacctgaaat gaccctgtgc cttatttgaa 1321 ctaaccaatc agttcgcttc tcgcttctgt tcgcgcgctt ctgctccccg agctctatat 1381 aagcagagct cgtttagtga accgtcagat cgcctggaga cgccatccac gctgttttga 1441 cttccataga aggatctcga gatgaacagt ttttctactt ctgccttcgg acccgtcgcc 1501 tttagcctgg gcctgctgct ggtgctgcct gccgcattcc ccgctcctgt gccccctgga 1561 gaagactcca aggatgtcgc cgctcctcac agacagccac tgactagctc cgagaggatc 1621 gacaaacaga tccgctacat tctggatggc attagcgccc tgcgcaagga aacctgcaac 1681 aaatccaata tgtgtgagtc tagtaaggaa gcactggccg agaacaatct gaacctgccc 1741 aagatggctg agaaagacgg ctgcttccag tctgggttta atgaggaaac ctgtctggtg 1801 aaaatcatta cagggctgct ggagttcgaa gtctacctgg aatatctgca gaaccgattt 1861 gagtcaagcg aggaacaggc tcgggcagtg cagatgagca caaaggtcct gatccagttc 1921 ctgcagaaga aagccaaaaa tctggacgct attaccacac cagatcccac taccaacgct 1981 tctctgctga ccaagctgca ggcacagaat cagtggctgc aggatatgac aactcacctg 2041 atcctgagga gtttcaaaga atttctgcag tcctctctgc gggcactgag acagatgtga 2101 gtcgactgct ttatttgtga aatttgtgat gctattgctt tatttgtaac cattataagc 2161 tgcaataaac aagttaacaa caacaattgc attcatttta tgtttcaggt tcaggggag 2221 gtgtgggagg ttttttaaac tctattttat aggcttcttc tctggaatct tcttcatcat 2281 cctcctgaca atcgataggt acctggctgt cgtccatgct gtgtttgctt taaaagccag 2341 gacggtcacc tttggggtgg tgacaagtgt gatcacttgg gtggtggctg tgtttgcgtc 2401 tctcccagga atcatcttta ccagatctca aaaagaaggt cttcattaca cctgcagctc 2461 tcattttcca tacagtcagt atcaattctg gaagaatttc cagacattaa agatagtcat 2521 cttgggctg gtcctgccgc tgcttgtcat ggtcatctgc tactcgggaa tcctaaaaac 2581 tctgcttcgg tgtcgaaatg agaagaagag gcacagggct gtgaggctta tcttcaccat 2641 catgattgtt tattttctct tctgggctcc ctacaacatt gtccttctcc tgaacacctt 2701 ccaggaattc tttggcctga ataattgcag tagctctaac aggttggacc aagctatgca 2761 ggtgacagag actcttggga tgacgcactg ctgcatcaac cccatcatct atgcctttgt 2821 cggggagaag ttcagaaact acctcttagt cttcttccaa aagcacattg ccaaacgctt 2881 ctgcaaatgc tgttctattt tccagcaaga ggctcccgag cgagcaagct cagtttacac 2941 ccgatccact ggggagcagg aaatatctgt gggcttgtga cacggactca agtgggctgg 3001 tgacccagtc agagttgtgc acatggctta gttttcatac acaccgcggt ctagagcatg 3061 gctacgtaga taagtagcat ggcgggttaa tcattaacta caaggaaccc ctagtgatgg 3121 agttggccac tccctctctg cgcgctcgct cgctcactga ggccgggcga ccaaaggtcg 3181 cccgacgccc gggctttgcc cggcggcct cagtgagcga gcgagcgcgc cagctggcgt 3241 aatagcgaag aggcccgcac cgatcgccct tcccaacagt tgcgcagcct gaatggcgaa 3301 tggcgattcc gttgcaatgg ctggcggtaa tattgttctg gatattacca gcaaggccga 3361 tagtttgagt tcttctactc aggcaagtga tgttattact aatcaaagaa gtattgcgac 3421 aacggttaat ttgcgtgatg gacagactct tttactcggt ggcctcactg attataaaaa 3481 cacttctcag gattctggcg taccgttcct gtctaaaatc cctttaatcg gcctcctgtt 3541 tagctcccgc tctgattcta acgaggaaag cacgttatac gtgctcgtca aagcaaccat
```

```
3601 agtacgcgcc ctgtagcggc gcattaagcg cggcgggtgt ggtggttacg cgcagcgtga
3661 ccgctacact tgccagcgcc ctagcgcccg ctcctttcgc tttcttccct tcctttctcg
3721 ccacgttcgc cggctttccc cgtcaagctc taaatcgggg gctcccttta gggttccgat
3781 ttagtgcttt acggcacctc gaccccaaaa aacttgatta gggtgatggt tcacgtagtg
3841 ggccatcgcc ctgatagacg gttttttcgcc ctttgacgtt ggagtccacg ttctttaata
3901 gtggactctt gttccaaact ggaacaaac tcaaccctat ctcggtctat tcttttgatt
3961 tataagggat tttgccgatt tcggcctatt ggttaaaaaa tgagctgatt taacaaaaat
4021 ttaacgcgaa ttttaacaaa atattaacgt ttacaattta aatatttgct tatacaatct
4081 tcctgttttt ggggcttttc tgattatcaa ccggggtaca tatgattgac atgctagttt
4141 tacgattacc gttcatcgat tctcttgttt gctccagact ctcaggcaat gacctgatag
4201 cctttgtaga gacctctcaa aaatagctac cctctccggc atgaatttat cagctagaac
4261 ggttgaatat catattgatg gtgatttgac tgtctccggc ctttctcacc cgtttgaatc
4321 tttacctaca cattactcag gcattgcatt taaaatatat gagggttcta aaaattttta
4381 tccttgcgtt gaaataaagg cttctcccgc aaaagtatta cagggtcata atgttttttgg
4441 tacaaccgat ttagctttat gctctgaggc tttattgctt aattttgcta attctttgcc
4501 ttgcctgtat gatttattgg atgttggaat cgcctgatgc ggtattttct ccttacgcat
4561 ctgtgcggta tttcacaccg catatggtgc actctcagta caatctgctc tgatgccgca
4621 tagttaagcc agccccgaca cccgccaaca cccgctgacg cgccctgacg ggcttgtctg
4681 ctcccggcat ccgcttacag acaagctgtg accgtctccg ggagctgcat gtgtcagagg
4741 ttttcaccgt catcaccgaa acgcgcgaga cgaaagggcc tcgtgatacg cctatttttta
4801 taggttaatg tcatgataat aatggtttct tagacgtcag gtggcacttt tcggggaaat
4861 gtgcgcggaa cccctatttg tttatttttc taaatacatt caaatatgta tccgctcatg
4921 agacaataac cctgataaat gcttcaataa tattgaaaaa ggaagagtat gagtattcaa
4981 catttccgtg tcgcccttat tcccttttt gcggcatttt gccttcctgt ttttgctcac
5041 ccagaaacgc tggtgaaagt aaaagatgct gaagatcagt tgggtgcacg agtgggttac
5101 atcgaactgg atctcaacag cggtaagatc cttgagagtt ttcgccccga gaacgtttt
5161 ccaatgatga gcacttttaa agttctgcta tgtggcgcgg tattatcccg tattgacgcc
5221 gggcaagagc aactcggtcg ccgcatacac tattctcaga atgacttggt tgagtactca
5281 ccagtcacag aaaagcatct tacgatggc atgacagtaa gagaattatg cagtgctgcc
5341 ataaccatga gtgataacac tgcggccaac ttacttctga caacgatcgg aggaccgaag
5401 gagctaaccg cttttttgca caacatgggg gatcatgtaa ctcgccttga tcgttgggaa
5461 ccggagctga atgaagccat accaaacgac gagcgtgaca ccacgatgcc tgtagcaatg
5521 gcaacaacgt tgcgcaaact attaactggc gaactactta ctctagcttc ccggcaacaa
5581 ttaatagact ggatggaggc ggataaagtt gcaggaccac ttctgcgctc ggcccttccg
5641 gctggctggt ttattgctga taaatctgga gccggtgagc gtgggtctcg cggtatcatt
5701 gcagcactgg ggccagatgg taagccctcc cgtatcgtag ttatctacac gacggggagt
5761 caggcaacta tggatgaacg aaatagacag atcgctgaga taggtgcctc actgattaag
5821 cattggtaac tgtcagacca agtttactca tatatacttt agattgattt aaaacttcat
5881 ttttaattta aaaggatcta ggtgaagatc ctttttgata atctcatgac caaaatccct
5941 taacgtgagt tttcgttcca ctgagcgtca gaccccgtag aaaagatcaa aggatcttct
6001 tgagatcctt ttttttctgcg cgtaatctgc tgcttgcaaa caaaaaaacc accgctacca
```

```
-continued
6061 gcggtggttt gtttgccgga tcaagagcta ccaactcttt ttccgaaggt aactggcttc 6121 agcagagcgc agataccaaa tactgtcctt ctagtgtagc cgtagttagg ccaccacttc 6181 aagaactctg tagcaccgcc tacatacctc gctctgctaa tcctgttacc agtggctgct 6241 gccagtggcg ataagtcgtg tcttaccggg ttggactcaa gacgatagtt accggataag 6301 gcgcagcggt cgggctgaac ggggggttcg tgcacacagc ccagcttgga gcgaacgacc 6361 tacaccgaac tgagatacct acagcgtgag ctatgagaaa gcgccacgct tcccgaaggg 6421 agaaaggcgg acaggtatcc ggtaagcggc agggtcggaa caggagagcg cacgagggag 6481 cttccagggg gaaacgcctg gtatctttat agtcctgtcg ggtttcgcca cctctgactt 6541 gagcgtcgat ttttgtgatg ctcgtcaggg gggcggagcc tatggaaaaa cgccagcaac 6601 gcggcctttt tacggttcct ggccttttgc tggccttttg ctcacatgtt ctttcctgcg 6661 ttatcccctg attctgtgga taaccgtatt accgcctttg agtgagctga taccgctcgc 6721 cgcagccgaa cgaccgagcg cagcgagtca gtgagcgagg aagcggaaga gcgcccaata 6781 cgcaaaccgc ctctccccgc gcgttggccg attcattaat g
```

Alternative 4: Testing Primary B Cell Transduction with AAV

Figure 15:
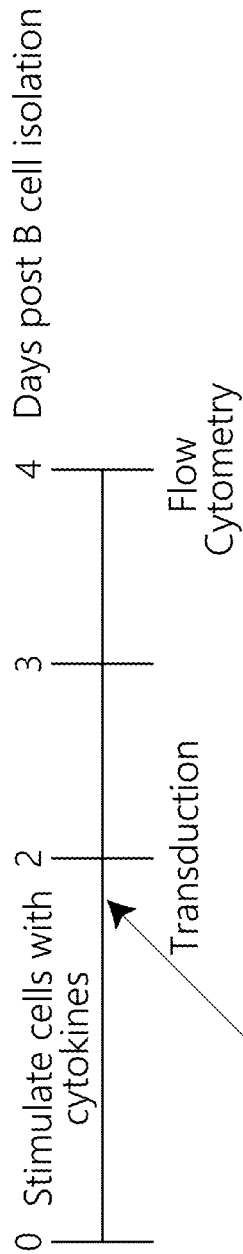
FIG. 15 shows results from the testing of primary B cell transduction with AAV vectors. Provided in the right panel is the percent GFP expression with different AAV serotypes. From left to right are AAV serotypes by culture volume from 2%, 5% and 10%. The bottom panel shows the percent viability of the cells after 48 hours post transduction. From left to right consecutively in the graph are the AAV amount by culture volume of 2%, 5% and 10%.
Figure 15:
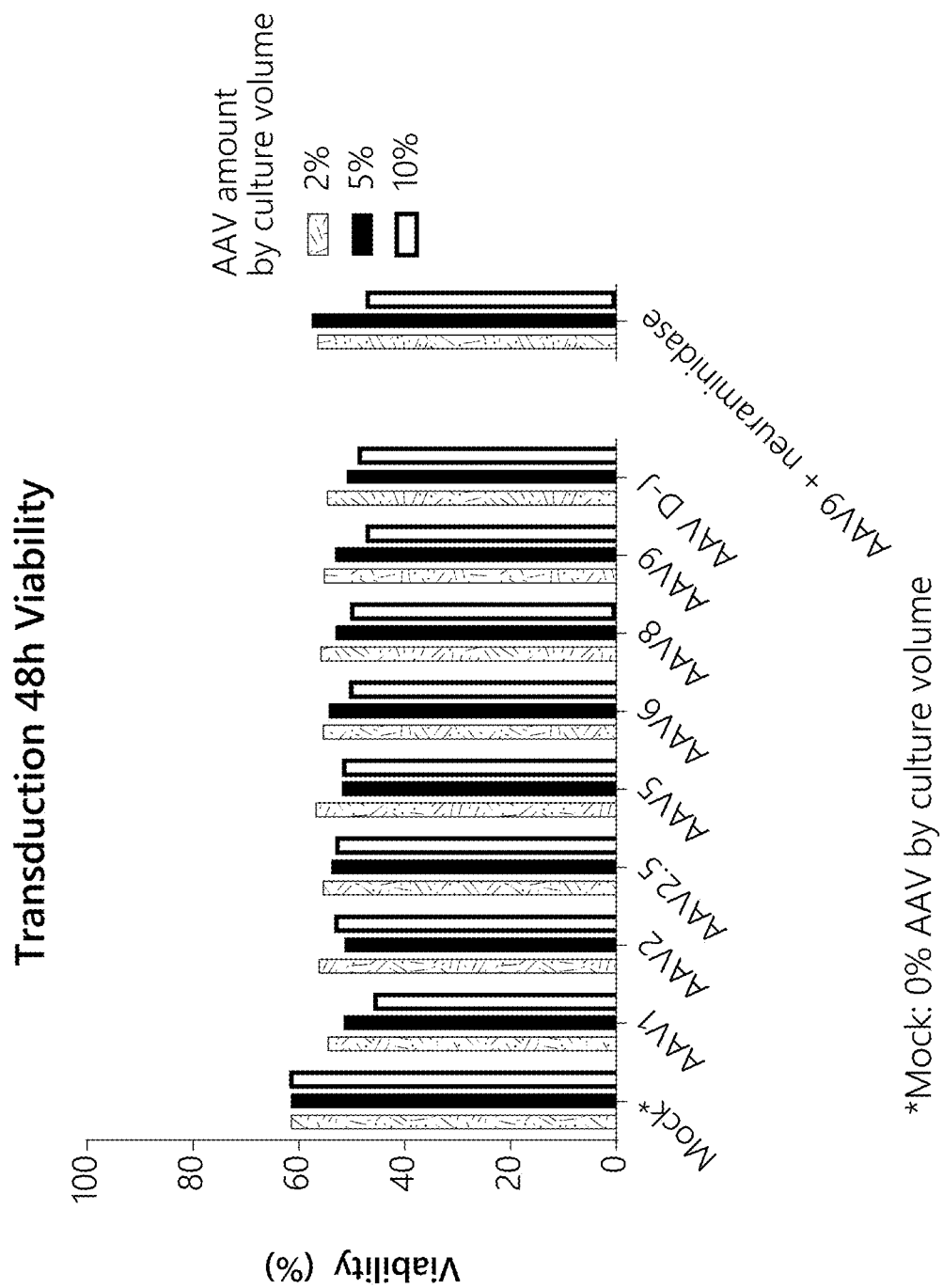
Figure 15:
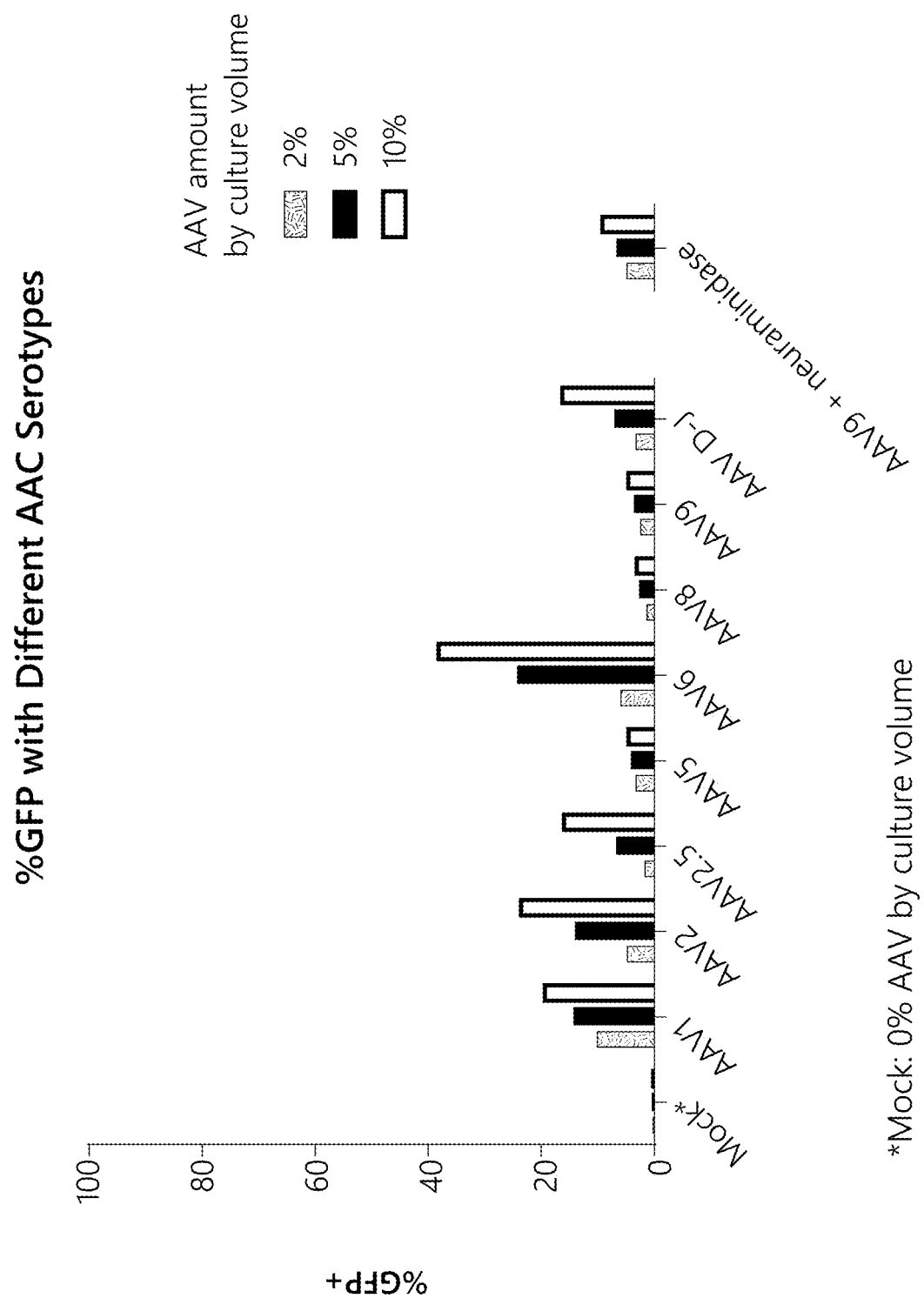
Figure 16:
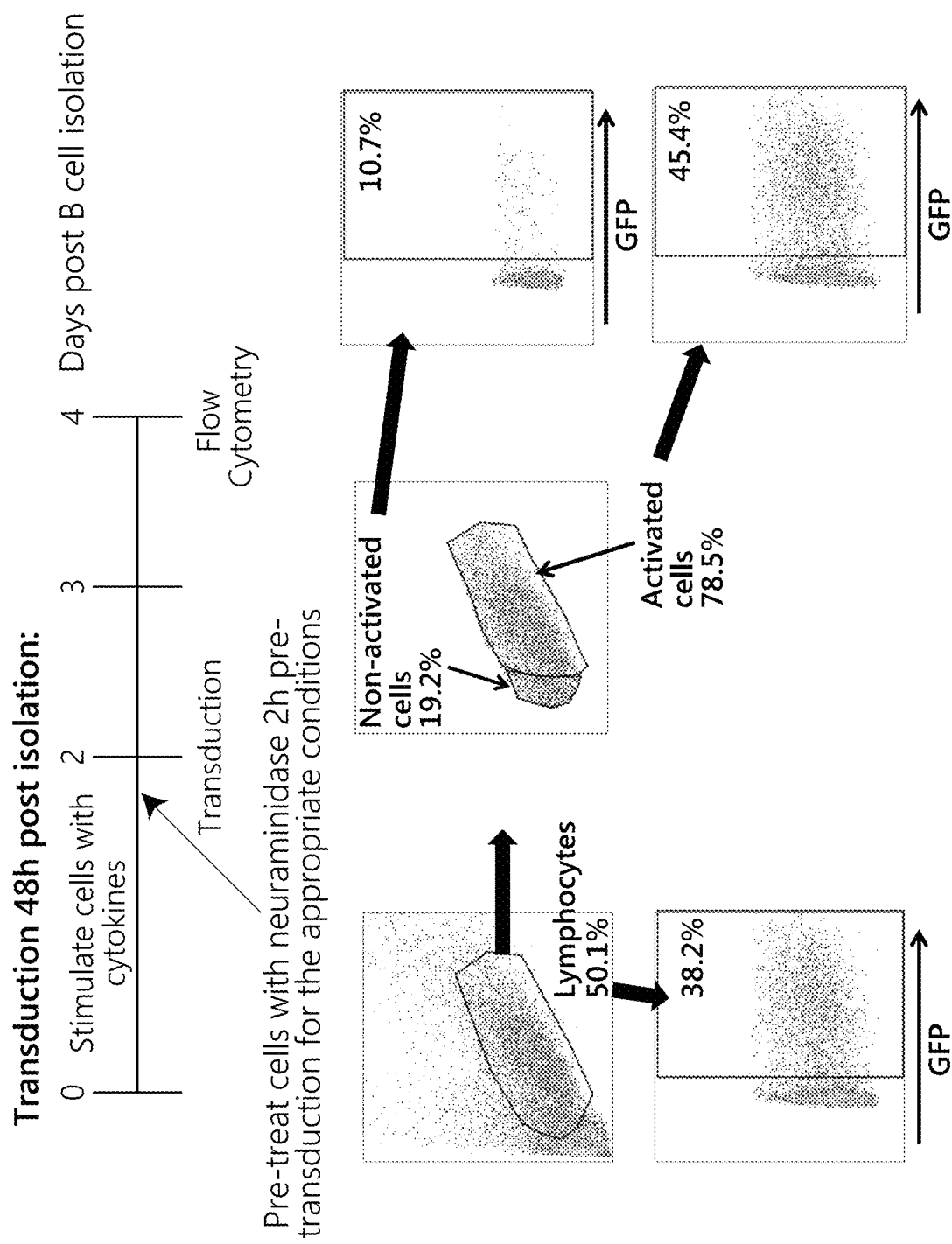
FIG. 16 shows results from the testing of primary B cell transduction with AAV vectors.
Figure 17:
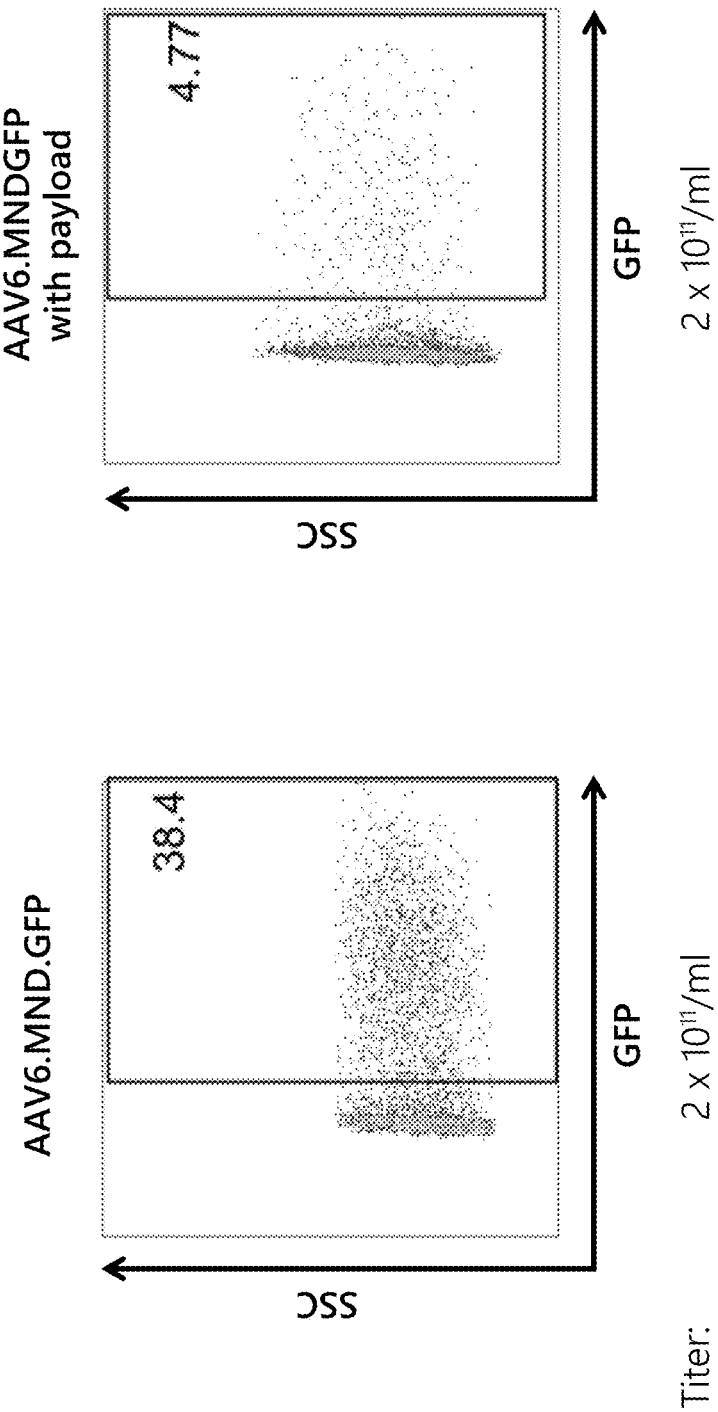
FIG. 17 shows results from transduction of B cells using AAV6.

Collection of cells and transduction of the B cells with AAV are described in the section entitled "Primary human CD19+ cell gene editing" of this paper. Cells were also pretreated with neuraminidase at least two hours prior to transduction for the appropriate conditions. As shown in FIG. 15, the AAV amount transduced into the cells varied by culture volume. As shown in the bar graphs the AAV is in order on the x axis as the AAV amount by culture volume at 2%, 5% and 10% consecutively. As shown, the percent GFP expressed with different AAV serotypes was increased using serotype AAV6. As shown in FIG. 16, AAV6 transduction in primary B cells is more effective in activated B cells. As expected, larger AAV6 vectors (AAV6.MNDGFP with payload) exhibit lower transduction rates than smaller AAV6 vectors (FIG. 17).

Figure 18:
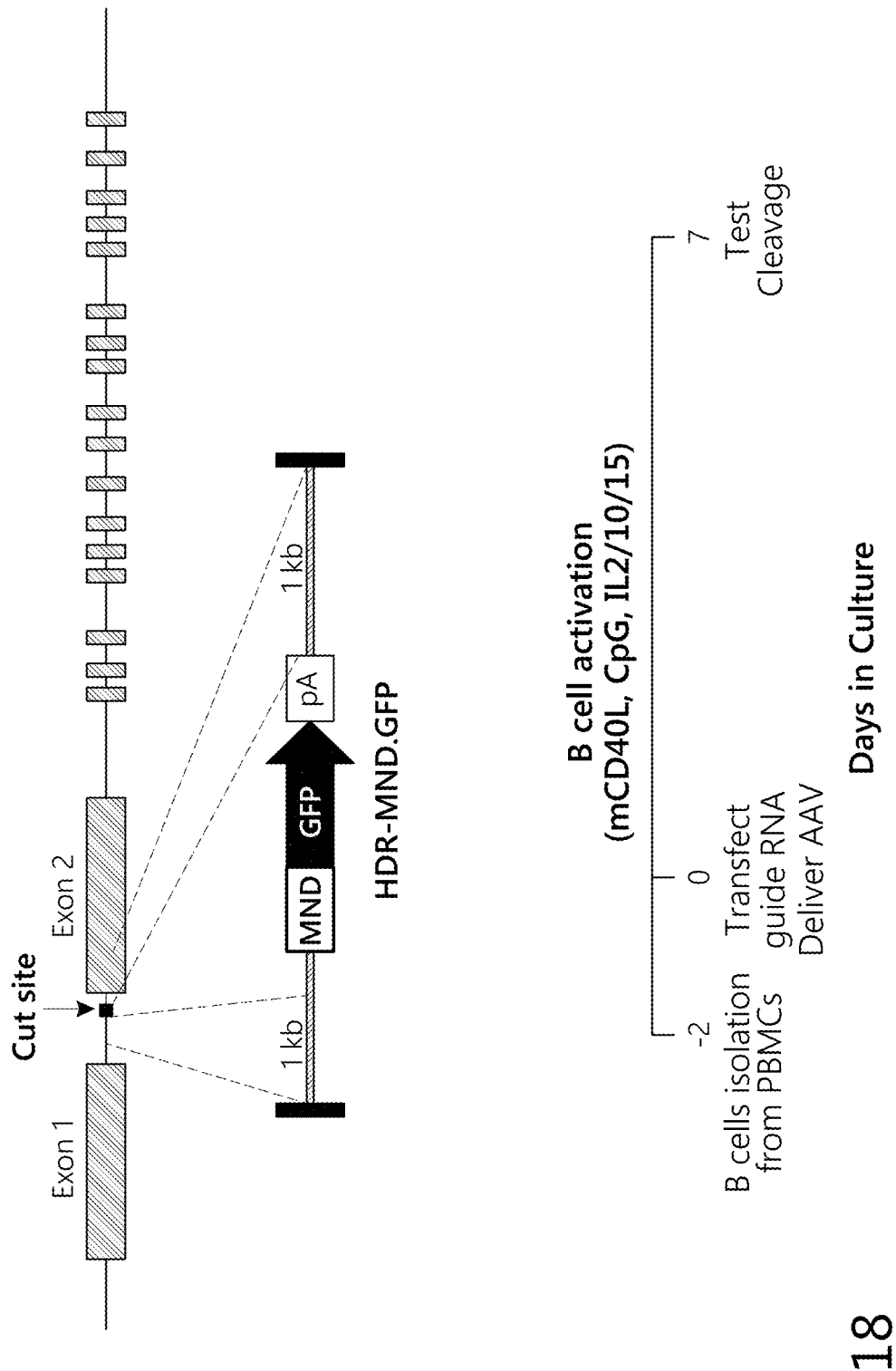
FIG. 18 shows the strategy of homologous-directed repair (HDR) using AAV repair templates.
Figure 20:
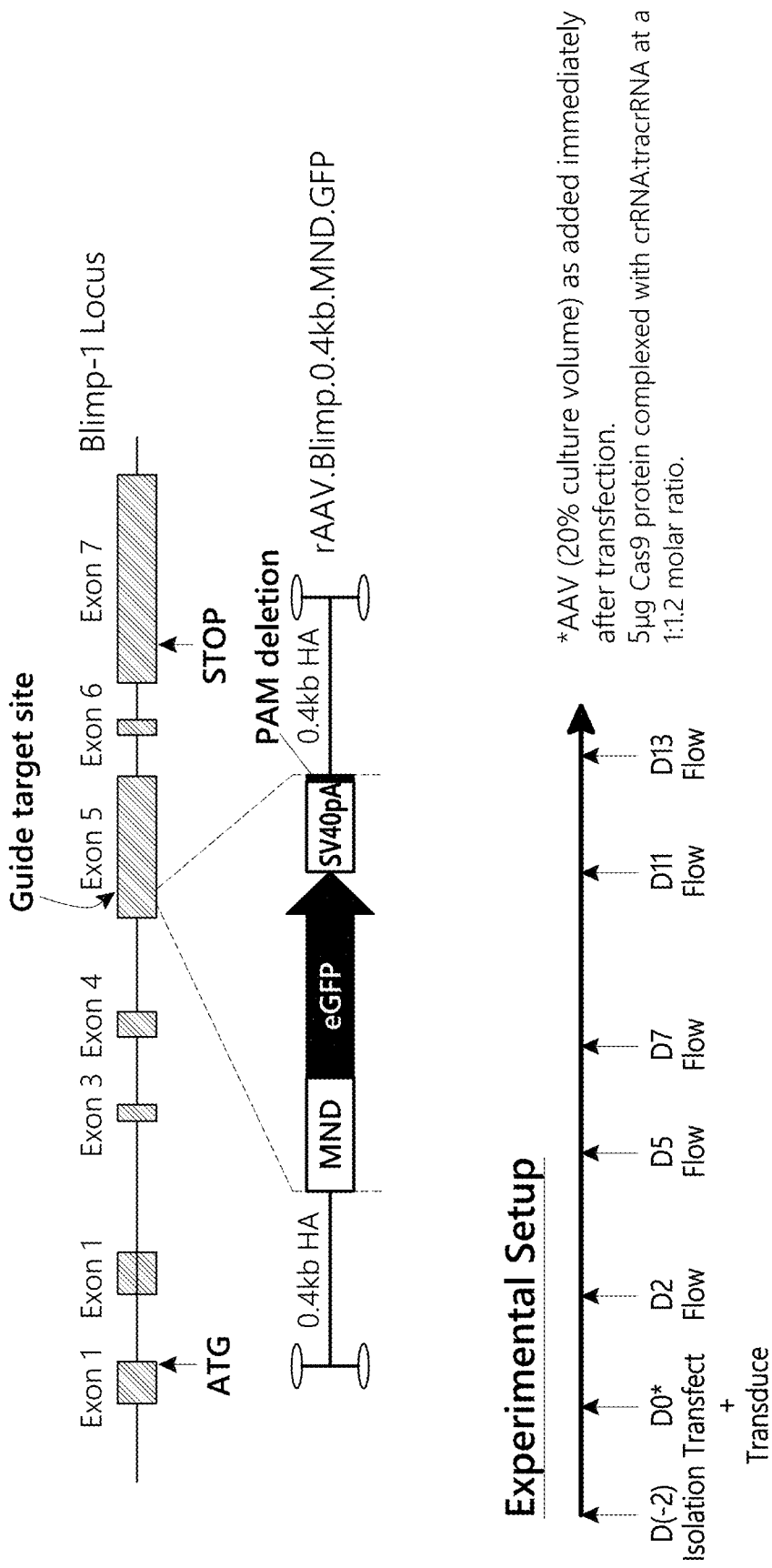
FIG. 20 shows the strategy of Homologous-directed repair (HDR) using AAV repair templates.
Figure 22:
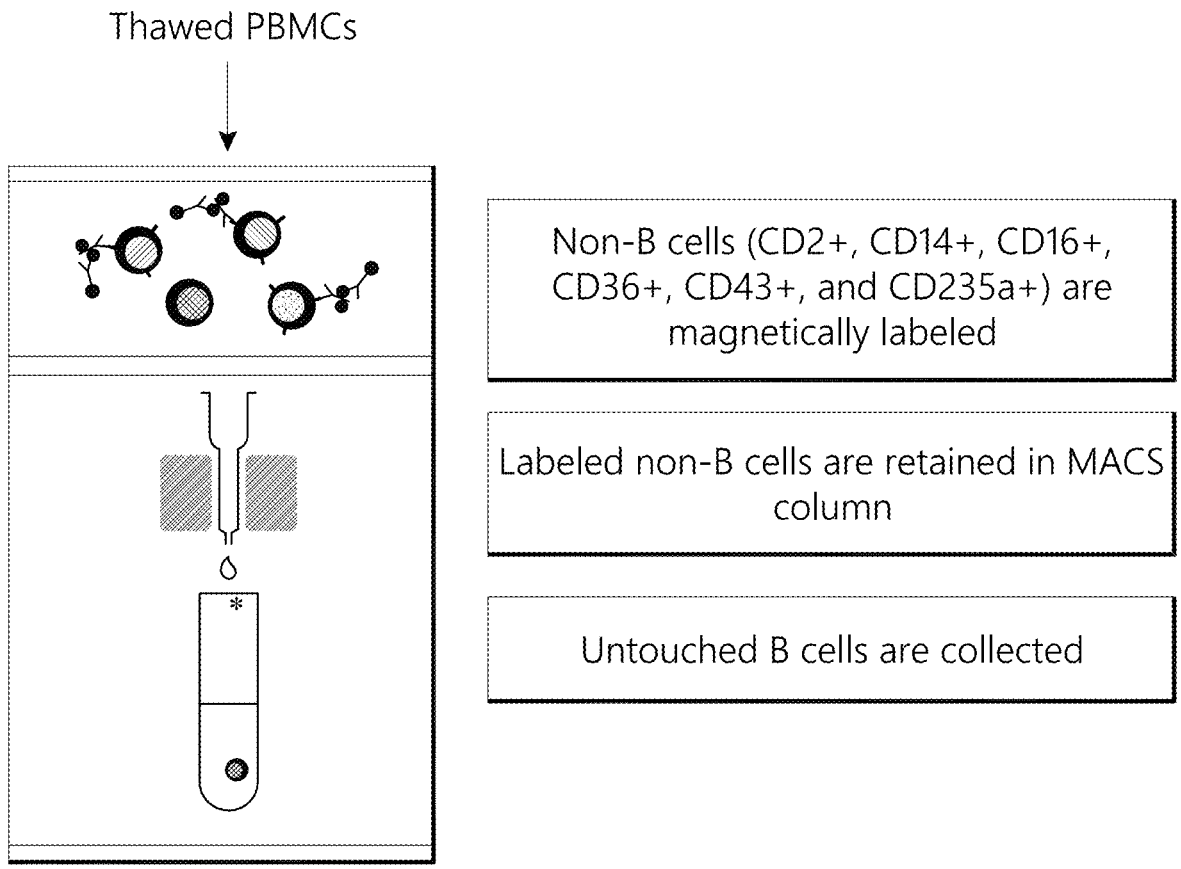
FIG. 22 shows the culturing and genome editing strategy using negative selection isolation of B cells from healthy donor PBMCs.

The strategy for homologous directed repair using AAV repair templates are shown in FIGS. 18 and 20. Briefly, peripheral blood mononuclear cells (PBMCs) collected from CD34+ negative selection flow-through from whole blood of healthy male donors post hematopoietic stem cell mobilization were purchased (FIG. 22). CD19+ B cells were isolated from PBMCs by negative selection using a human B cell isolation kit (Miltenyi Biotec®, Auburn, CA) and cultured in Iscove's modified Dulbecco's medium (IMDM, Thermo Fisher Scientific®) supplemented with 10% fetal bovine serum and 55 µM beta-mercaptoethanol at 1-1.5×10$^6$ cells/ml. B cells were activated with 100 ng/ml of recombinant human MEGACD40L® (Enzo Life Sciences®), 1 µg/ml of CpG oligodeoxynucleotide 2006 (Invitrogen®), 50 ng/ml of IL-2 (Peprotech®), 50 ng/ml of IL-10 (Peprotech®) and 10 ng/ml of IL-15 (Peprotech®) for 48 hours. Cells were then electroporated with Cas9 RNP complexes using the Neon Transfection System (ThermoFisher Scientific®) as follows. Cells were washed with PBS and resuspended in Neon Buffer T. 30.5 µmol Cas9 RNP per 3×10$^5$ cells was added to the resuspension so that the final cell density was 3×10$^7$ cells/ml. Cells were then electroporated (1700V, 20 ms, 1 pulse) in 10-µl Neon tips, and then transferred into prewarmed B cell culture medium with MEGACD40L®, CpG, IL-2, IL-10 and IL-15 and cultured at 1.5×10$^6$ cells/ml. For samples transfected with an ssODN donor template, ssODN was added concurrently with Cas9 RNP at 30 pmol per 3×10$^5$ cells, unless otherwise specified. For samples transduced with AAV, AAV was added to the culture immediately after electroporation. The added AAV volume was 20% of the cell culture volume, unless otherwise specified. Culture volume was doubled 24 hours after electroporation, and medium was replenished every two to three days thereafter to maintain a cell density of 1×10$^6$ cells/ml.

Figure 19:
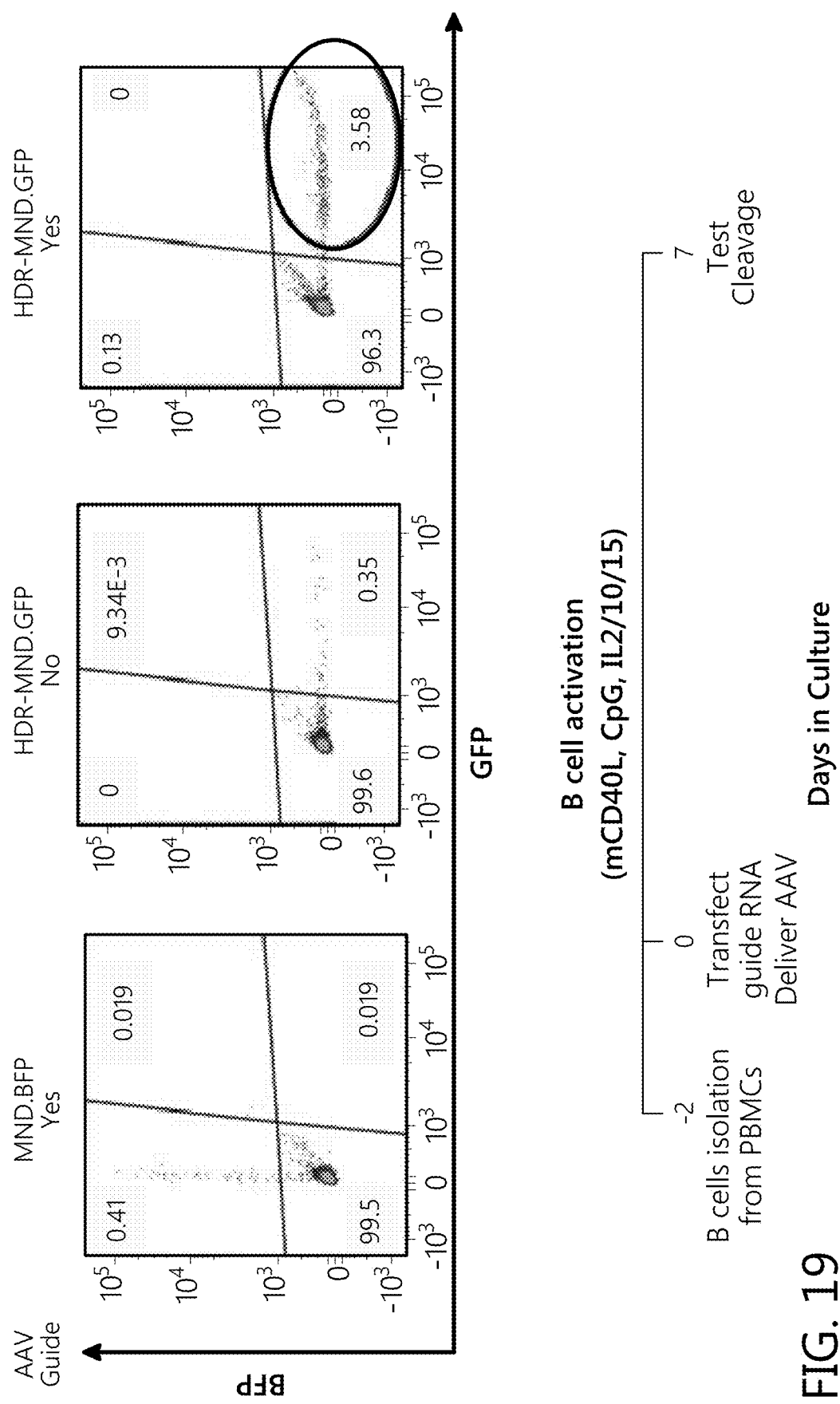
FIG. 19 shows that CRISPR and AAV repair template co-delivery mediates HDR in primary B cells.
Figure 21:
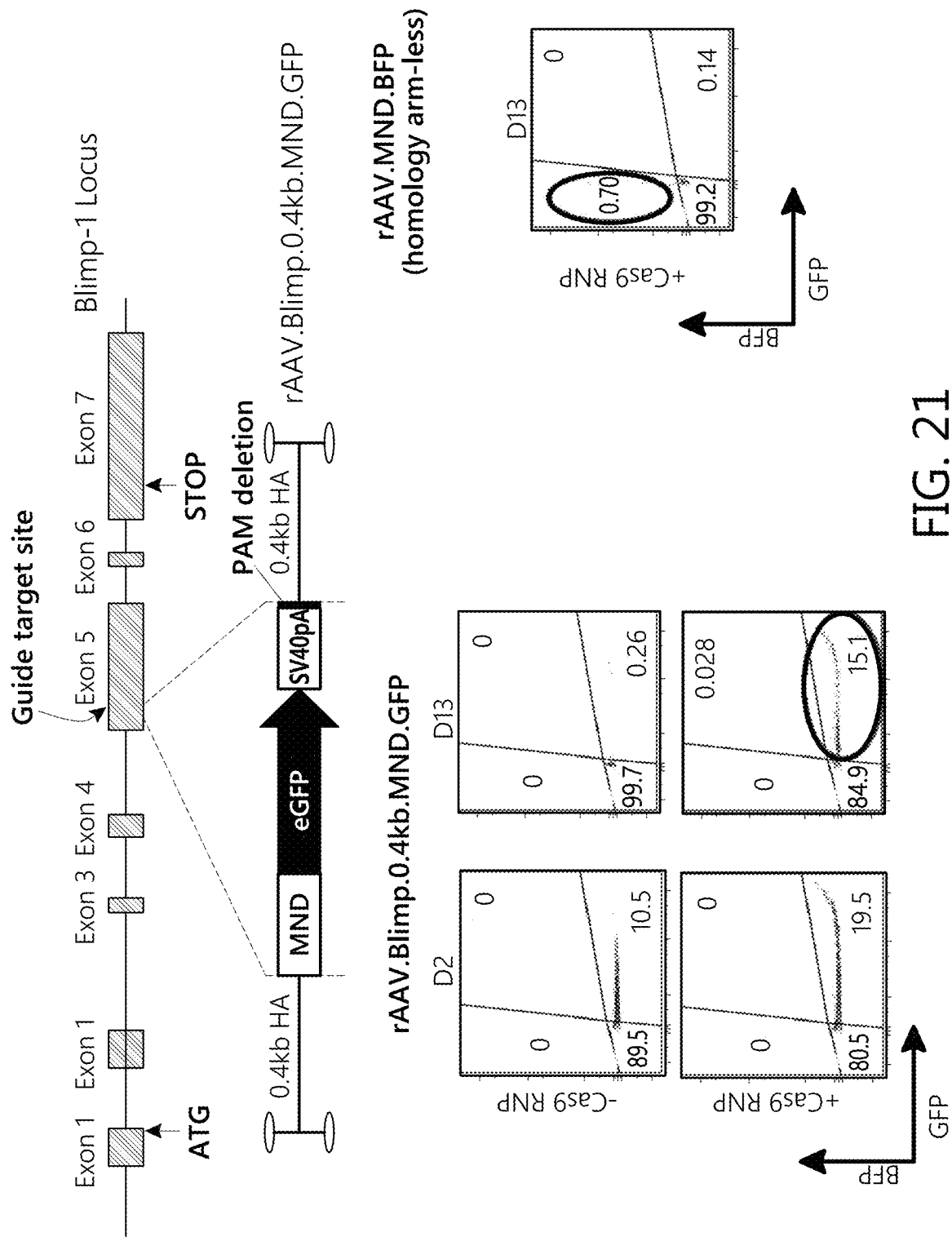
FIG. 21 shows CRISPR and AAV repair template co-delivery mediates HDR in primary B cells.

To test HDR using the RNP-AAV approach, B cells were transduced under 3 conditions: (1) PRDM1 RNPs and AAV vector lacking PRDM1 homology arms (MND.BFP), (2) no RNP and AAV vector with PRDM1 homology arms (HDR-MND.GFP) and (3) PRDM1 RNPs and AAV vector with PRDM1 homology arms (HDR-MND.GFP). Shortly after transfection and transduction and following plasmablast differentiation, the degree of BFP and GFP were quantified in B cells using flow cytometry to determine the HDR frequency. As expected, AAV6-driven expression is evident at day 2 in all conditions, but stable GFP expression is only detectable in the condition that had matching RNPs and repair templates. As shown in FIGS. 19 and 21, this initial experiment shows that CRISPR and AAV repair template co-delivery mediates high-efficiency HDR in primary B cells.

Alternative 5: Optimization of Plasma Cell Differentiation.

Another required step for edited plasma cell generation includes B cell expansion. Experimental set up is shown in FIG. 20. As shown in FIG. 22, B cells are negatively selected from healthy donor PBMCs. B cells were obtained using the B Cell Isolation Kit II from Miltenyi Biotec®. The Non-B cells (CD2+, CD14+, CD16+, CD36+, CD43+, and CD235a+) are magnetically labeled and labeled non-B cells are retained in MACS column. The untouched B cells are then collected.

The culture and editing protocol comprises culturing isolated B cells in Mega-CD40L® CpG+ IL-2+ IL-10+ IL-15 at 1.5×10$^6$ cells/ml for 48 h. This is then followed by editing, transfecting and transducing the cells, which are then reseeded at 1.0×10$^6$-1.5×10$^6$ cells/ml on day 2. The cells are then split on day 3, then every 2-3 days thereafter. The stimulation conditions are optimized for B cell activation, proliferation and RNA/protein delivery by electroporation with a naïve/memory B cell phenotype.

Figure 23:
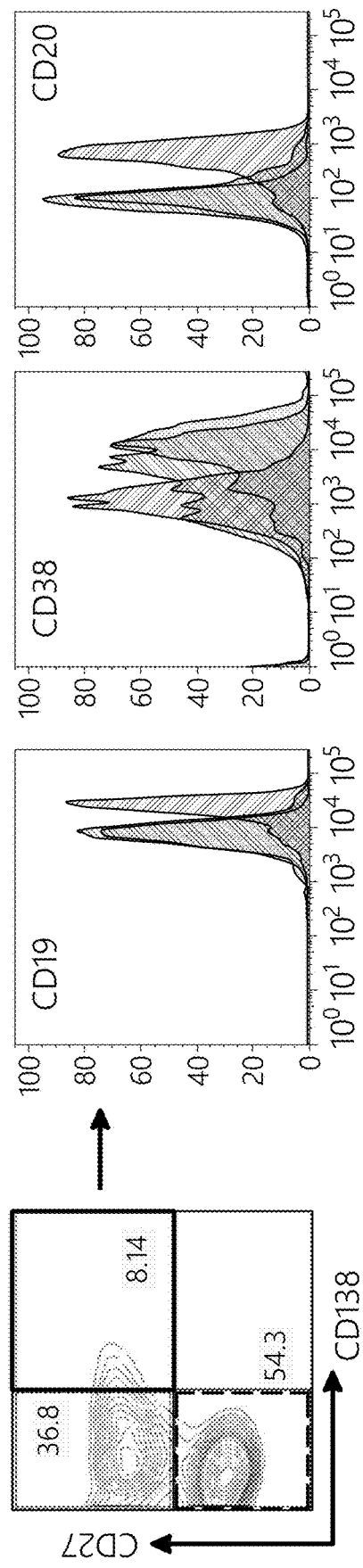
FIG. 23 shows B cell phenotype at end of expansion phase.
Figure 24:
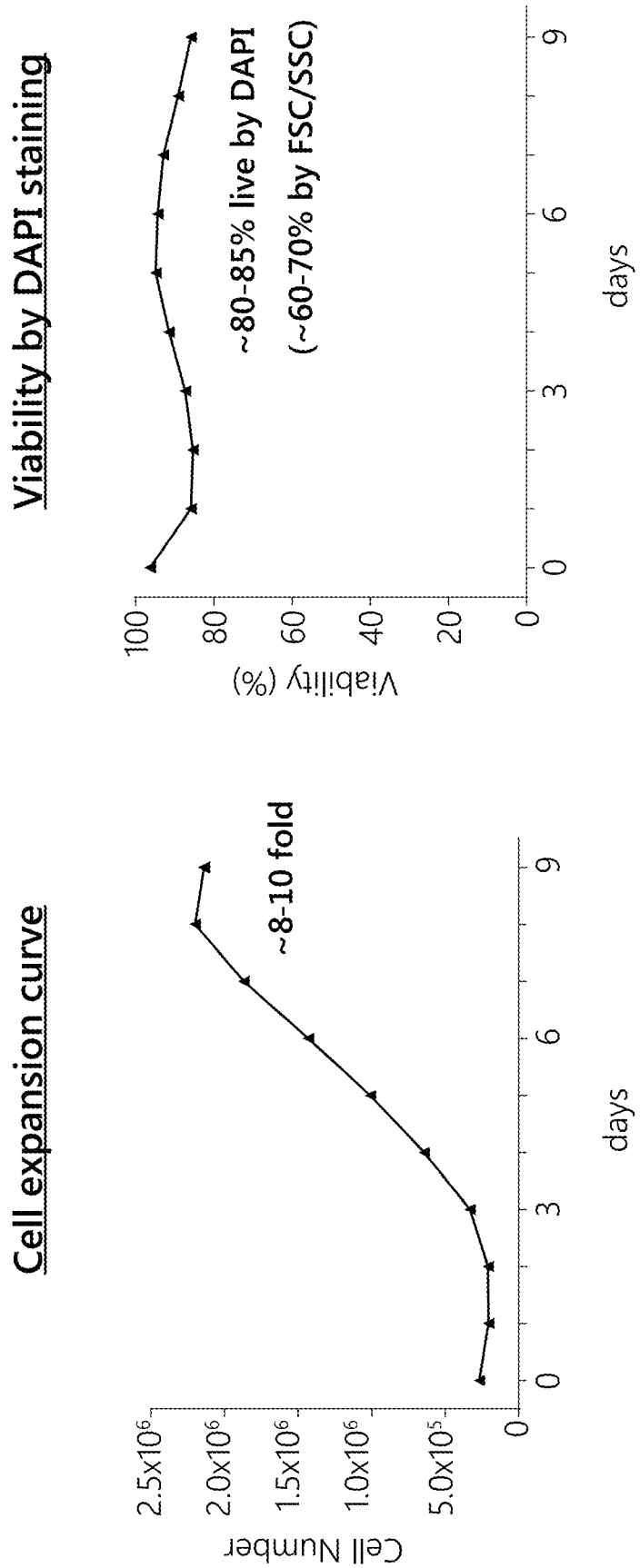
FIG. 24 shows B cell expansion results. The left panel shows the cell expansion curve and the right panel shows the viability by DAPI staining.

The cells were then phenotyped at the end of the expansion phase at day 9 during the culture. Shown in FIG. 23 is a flow cytometry analysis, which was gated for CD27 and CD138. Most of the cells remained CD138-CD27− after 9 days in culture, and this population was primarily CD19$^{high}$CD38$^{low}$CD20$^{+-}$, which is equivalent to naïve and activated B cells. The number of B cells were also shown to be at 8-10 fold greater at day 9 and were shown to have a viability of about 80-85% (FIG. 24).

B Cell Differentiation into Long-Lived Plasma Cells

Figure 25:
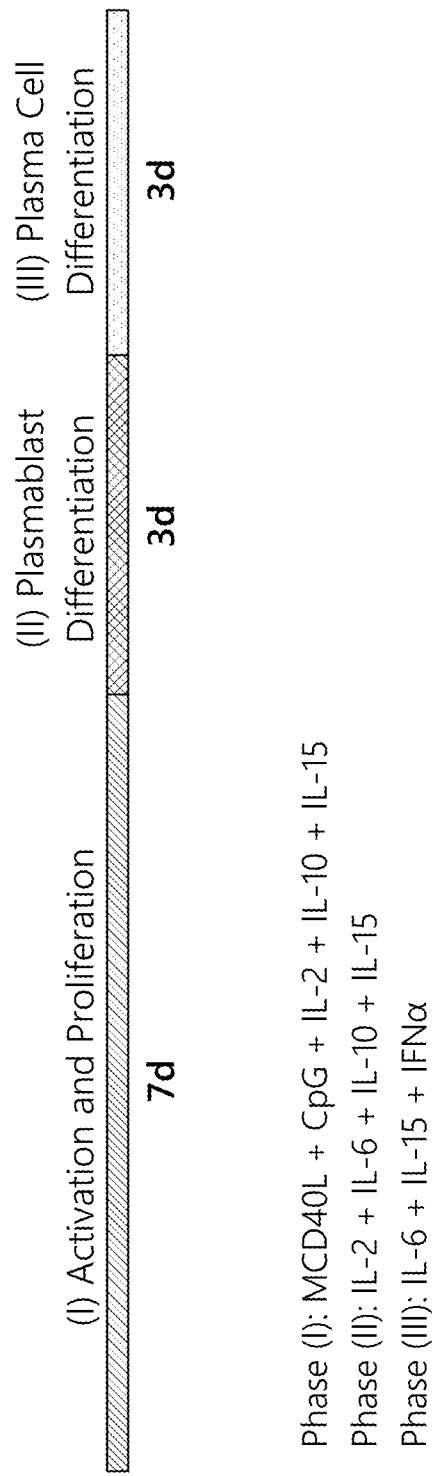
FIG. 25 shows Plasma cell differentiation using the 3-step culture system.

Cells were differentiated using a three step culture system as shown in FIG. 25. Activation and proliferation steps included addition of MCD40L+CpG+IL-2+IL-10+IL-15 to the culture for the first 7 days. Afterwards, at phase II, IL-2+IL-6+IL-10+IL-15 was added to the culture for plasmablast differentiation for the next three days. The final step, phase III, included addition of IL-6+IL-15+IFNα to allow for plasma cell differentiation. The cells were obtained and washed between the phases before addition of the culture additives.

Figure 26:
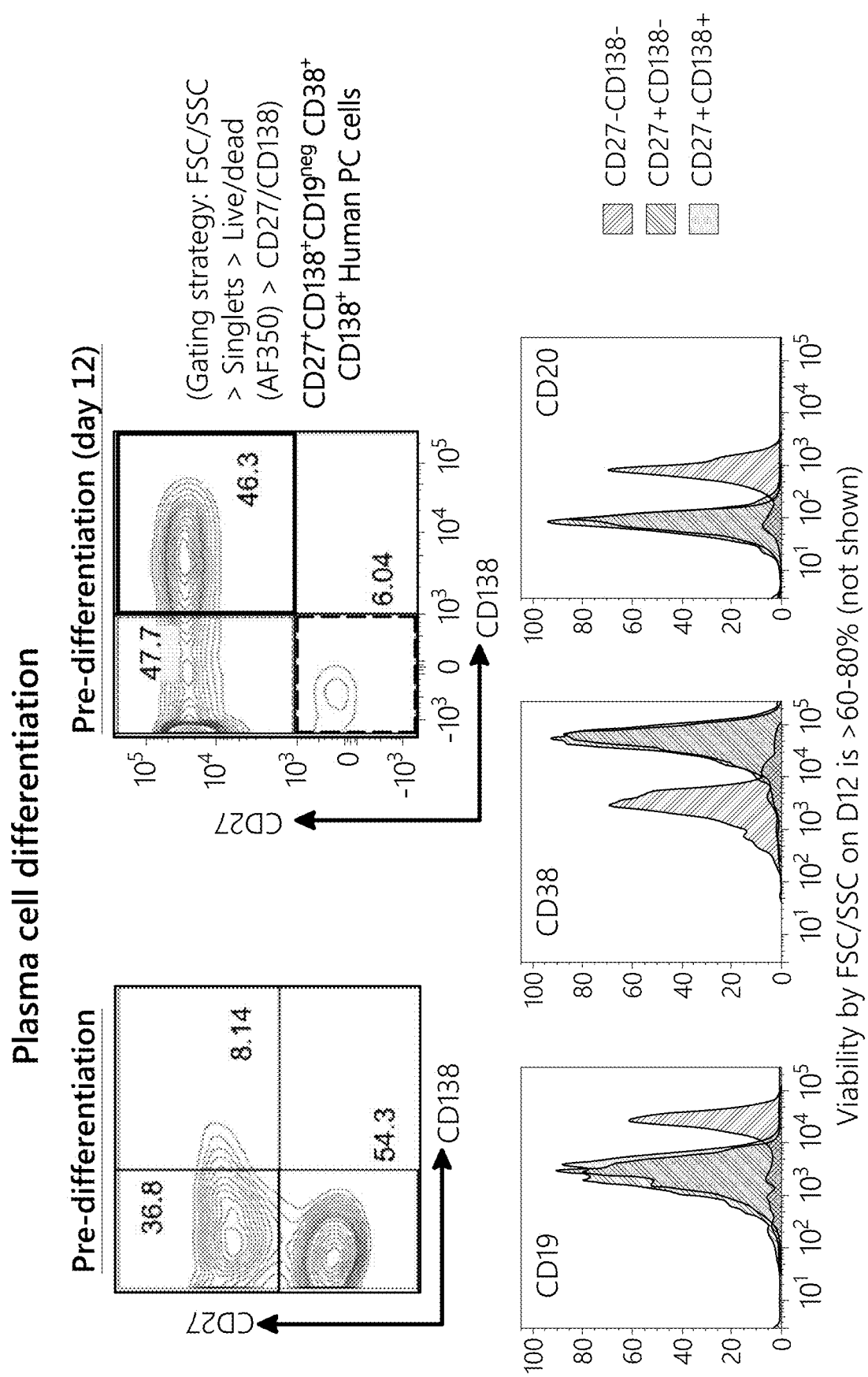
FIG. 26 shows results of plasma cell differentiation at pre-differentiation and at post-differentiation (day 12).

The cells were tested before and after the B cell differentiation steps. Cells were subjected to FACs analysis gated for CD27 and CD138. In comparison of the pre differentiated and the post differentiated cells, at day 12, there is an increase of CD27+CD138+CD19neg CD38+ CD138+ Human PC cells (FIG. 26). There is also an increase of viability of the cells by FSC/SSC on day 12 which was greater than 60-80%.

In summary, the alternatives provided herein established methods for efficient/non-toxic genome editing in primary human B cells using RNPs, and methods for efficient HDR (>30% using RNP and short ODN). There is also initial demonstration of HDR-mediated introduction of larger 2-4 Kb expression cassettes (using RNP with long ODN or AAV) which has not previously been seen before for B cells. Furthermore, the alternatives have established sequential culture systems to generate and maintain human plasma cells.

Figure 27:
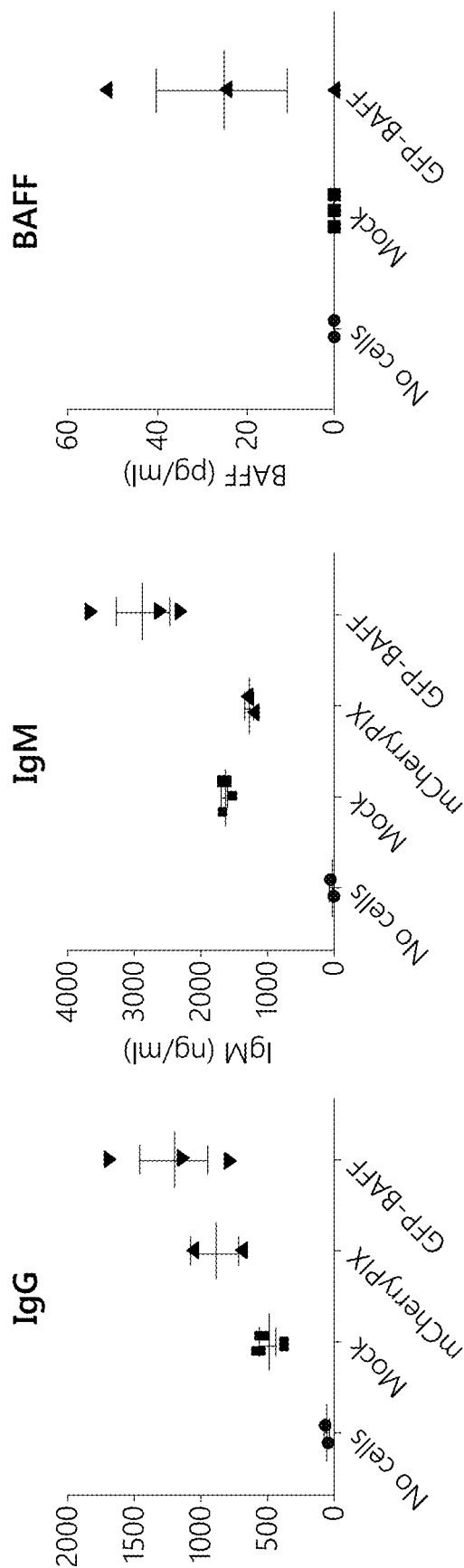
FIG. 27 shows the demonstration of quantifiable secretion of an exogenous protein in an animal model.

Alternative 6: Demonstration of Quantifiable Secretion of an Exogenous Protein in an Animal Model Naïve human B cells were isolated from PBMCs, and expanded in B cell activation cocktail (mCD40, CpG, IL2/10/15) for 2 days. At this point, 1 million cells were mock transfected or transfected with CCR5-targeting RNPs and transduced with homology-directed repair templates sufficient to deliver mCherry-Factor IX or eGFP-BAFF to the B cells. Following 5 additional days of activation, the cells were differentiated into plasmablasts for 3 days via incubation with IL2/6/15 and subsequently into plasma cells by incubation with IL6/15 and IFNalpha. 3 million of this population of plasma cells from each condition was implanted into NSG mice (NOD, Cg-Prkcd$^{SCID}$, Il2rg$^{tm1Wjl}$/SzJ) using retroorbital injection. Following 7 days, a blood draw was taken from each mouse and the quantity of human IgG, human IgM and human BAFF was determined by ELISA. As observed in the left two panels, plasma cells expressing BAFF produce more IgM and IgG than unedited cells. Furthermore, human BAFF is quantifiable in these animals implanted with BAFF-edited plasma cells. (FIG. 27)

Data Showing Sustained In Vivo Engraftment of Gene-Edited Human Plasma B Cells and Increased Engraftment of Edited B Cells that Express BAFF (Introduced by HDR Based Gene Editing).

Figure 28:
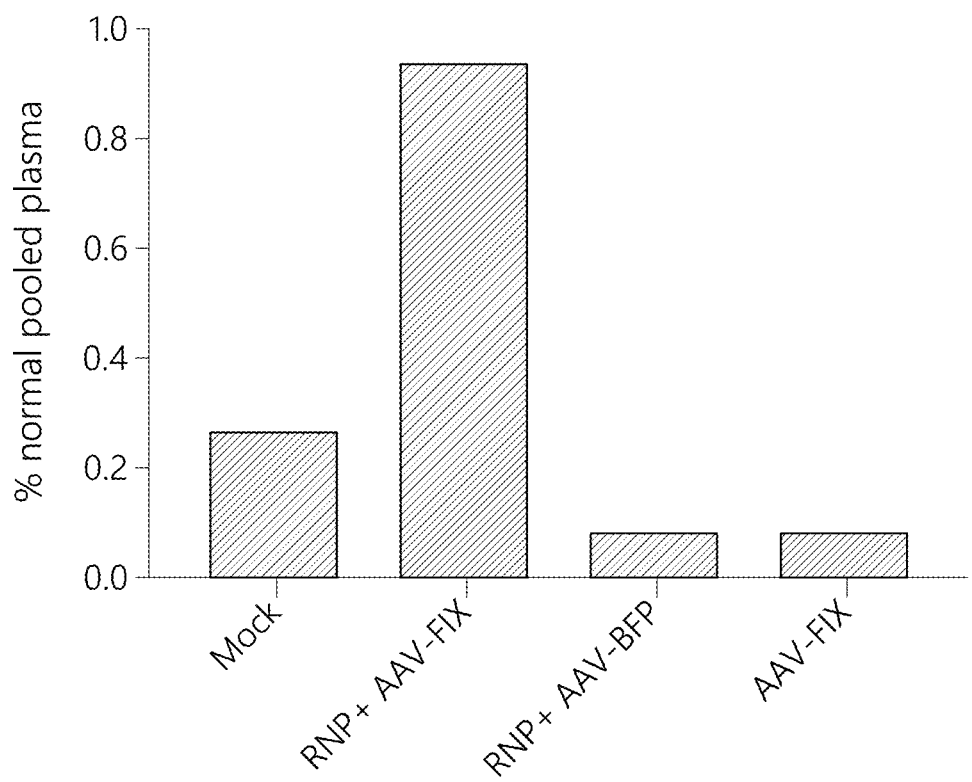
FIG. 28 shows the demonstration of the ability of B cells to produce functionally active Factor IX.
Figure 29B:
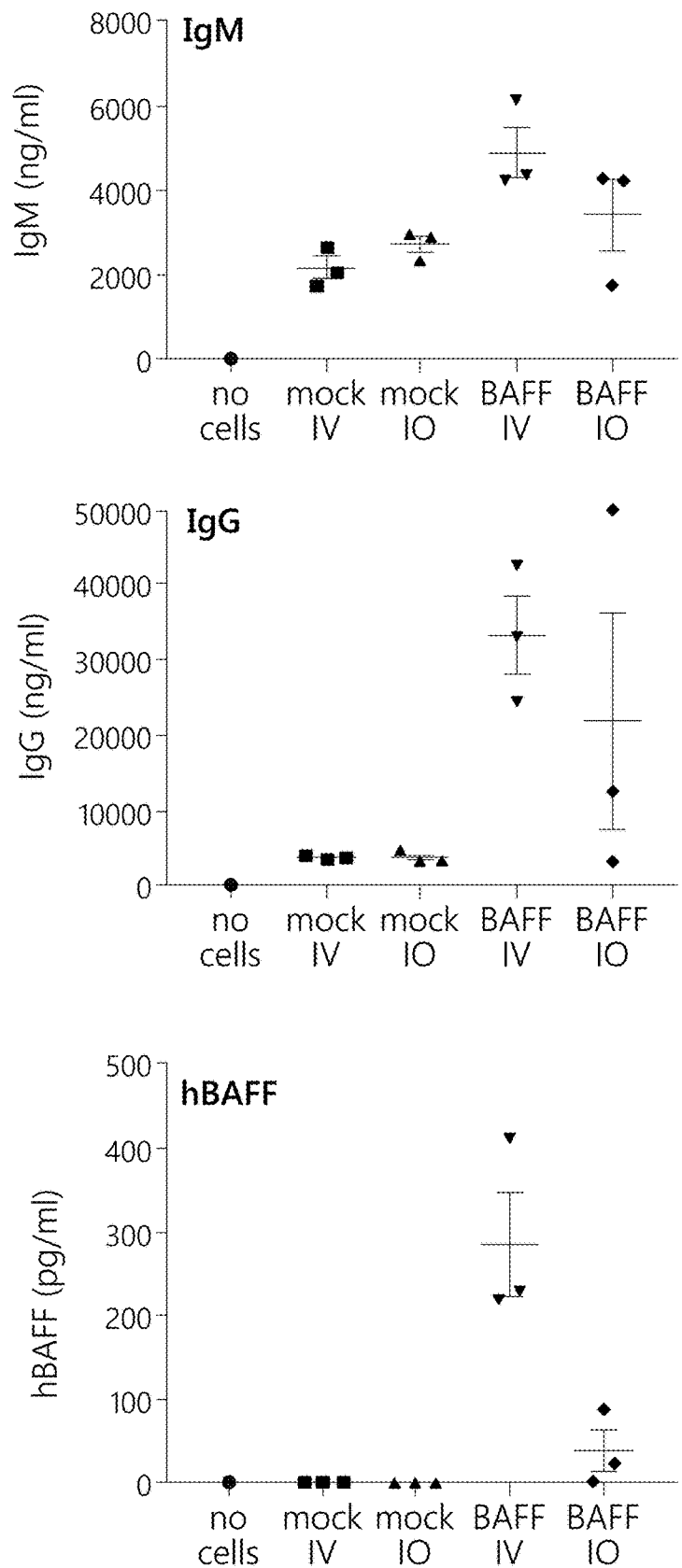

Naïve human B cells from peripheral blood mononuclear cells were expanded in B cell activation cocktail (mCD40, CpG, IL2/10/15) for 2 days. At this point, 1 million cells were mock transfected or transfected with CCR5-targeting RNPs and transduced with homology-directed repair templates sufficient to deliver eGFP-BAFF to the B cells. Following 5 additional days of activation, the cells were differentiated into plasmablasts for 3 days via incubation with IL2/6/15 and subsequently into plasma cells by incubation with IL6/15 and IFNalpha. 10 million cells from this population from each condition was adoptively transferred into NSG mice (NOD, Cg-Prkcd$^{SCID}$, Il2rg$^{tm1Wjl}$/SzJ) via either retroorbital or intraosseous injection. At Day 10 (FIG. 29A) and 21 (FIG. 29B) following transplantation, serum abundance of human IgM, human IgG and hBAFF was measured by ELISA. Comparison of FIG. 29A and FIG. 29B show sustained expression of human proteins in murine serum between 10 and 21 days, indicating that edited human plasma cells are stably engraftable in mice. Further, these data show that secretion of hBAFF by gene-edited plasma cells enhances PC engraftment. (FIG. 28).

Alternative 7: Demonstration of the Ability of B Cells to Produce Functionally Active Factor IX Naïve human B cells were isolated from PBMCs, and expanded in B cell activation cocktail (mCD40, CpG, IL2/10/15) for 2 days. At this point, 1 million cells were mock transfected, RNP transfected, AAV transduced or transfected with CCR5-targeting RNPs and transduced with homology-directed repair templates sufficient to deliver Factor IX to the B cells. Following 5 additional days of activation, the cells were differentiated into plasmablasts for 3 days via incubation with IL2/6/15 and subsequently into plasma cells by incubation with IL6/15 and IFNalpha. 6 days prior to the termination of the study, 1 million cells per mL from each condition were incubated with Vitamin K1 (5 ug/mL). The supernatants from all conditions were subjected to a chromogenic assay of Factor IX activity. Using this assay, it was found that plasma cells edited to integrate exogenous Factor IX produce enzymatically active protein.

Alternative 8: Assessing the Impact of Disruption and Survival

Figure 30:
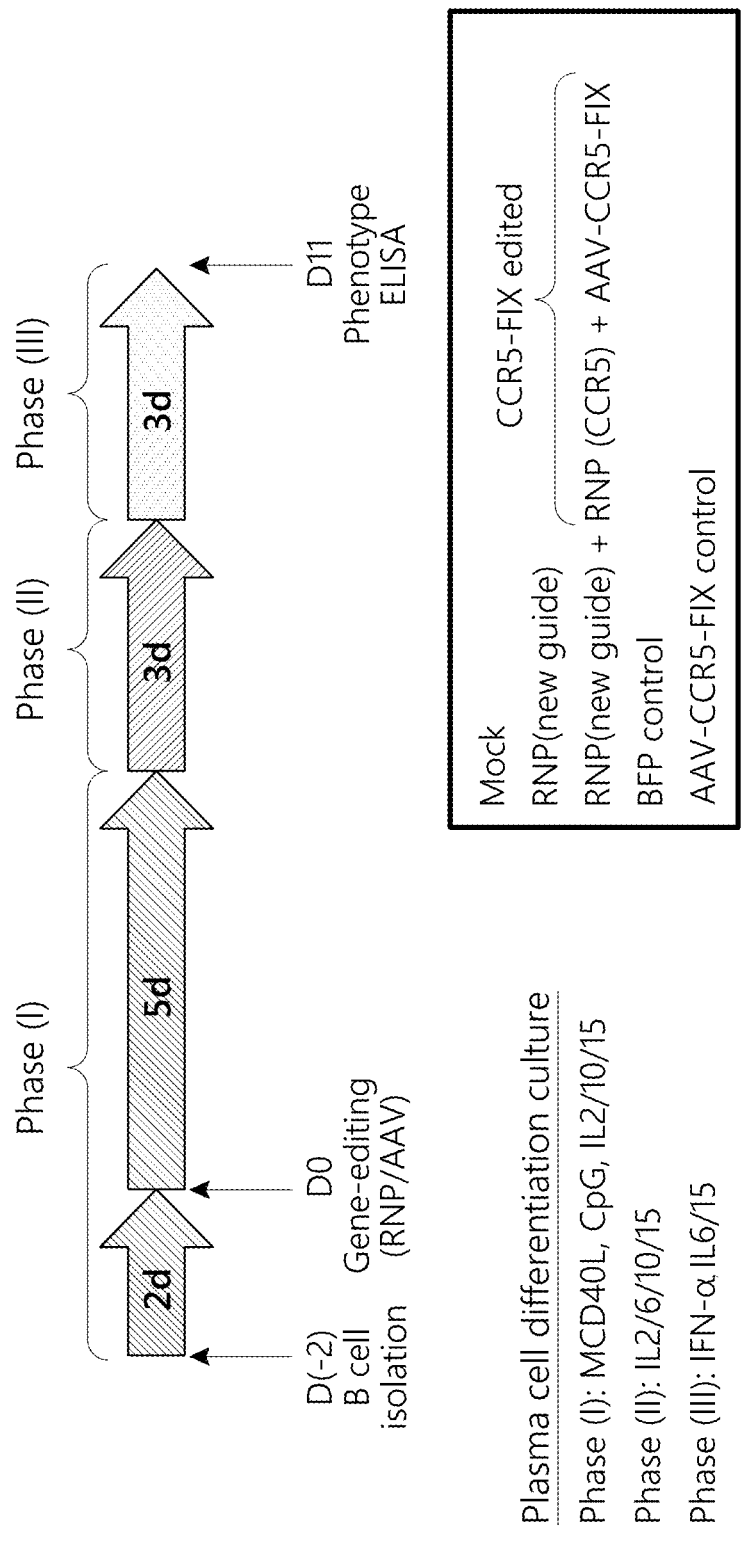
FIG. 30 shows the experimental design for gene disruption and protein expression.

The objective of the further experimentation was to determine the impart of gene disruption on the survival and differentiation of the cells. Also performed, was a combinatorial gene disruption with HDR at CCR5 (FIX) (FIG. 30).

For the first phase at −2 days, B cells were isolated. At day 0, the cells were edited with a RNP/AAV vector (phase 1). In the first phase, the plasma cell differentiation culture comprised MCD40L, CpG, and a mixture comprising IL2/IL10/IL15. The first phase of plasma cell differentiation was carried out for 5 days. At phase 2 (3 days), the plasma cell differentiation culture comprised IL2/IL6/I115. At phase 3 (3 days), the plasma cell differentiation culture comprised IFN-α, IL6 and IL15.

Alternative 9: Long Lived Human Antibody Production in Mice

Primary B cells were expanded in culture and edited as described. Following differentiation into plasma cells, 10 million were injected into NSG mice using either retroorbital (RO) or intra-osseous (IO) injection. The mice were bled at the indicated time points. Human IgG (IgM not shown) was quantified using ELISA. Each dot represents data from an individual recipient mouse at the indicated time point. These data show that gene edited human plasma cells can live for long periods in this murine model despite the absence of human cytokines. These data also show that autocrine production of human BAFF can further promote sustained survival of gene edited PCs.

Several groups of mice were under four editing conditions: group 1) mock unedited cells; group 2) cells edited with the CCR5-RPN+AAV-GFP-BAFF; group 3) Mock unedited cells and group 4) CCR5-RNP+AAV-GFP-BAFF. Groups 1 and 2 were administered the cells by retro-orbital injection (10E+06 cells/animal) and groups 3 and 4 were administered the cells by intra-osseous injection (10E+06 cells/animal). Each group had 5 mice. As shown, the sets of cells from left to right under the "no cells" area are the week one, week 3, week 5, week 5, week 7, week 9, week 11, week 13, week 15, week 17 and week 19 cells cells, this order is kept throughout the x-axis for mock IO, BAFF IO, Mock R O and BAFF RO. The mock unedited cells (Group 1) have minimal expression of the IgG. However, cells of group 2 have an increase of IgG expression that peaks at week 3 and 5. The cells of Group 3 (mock unedited) also show minimal expression of IgG, whereas the cells of Group 4 have an increase of IgG that peaks at week 3 and 5. As shown, cells administered with the CCR5-RNP with the AAV-GFP-BAFF with either tero-orbital injection or intra-osseous injection show long-lived human antibody production in mice.

Figure 31:
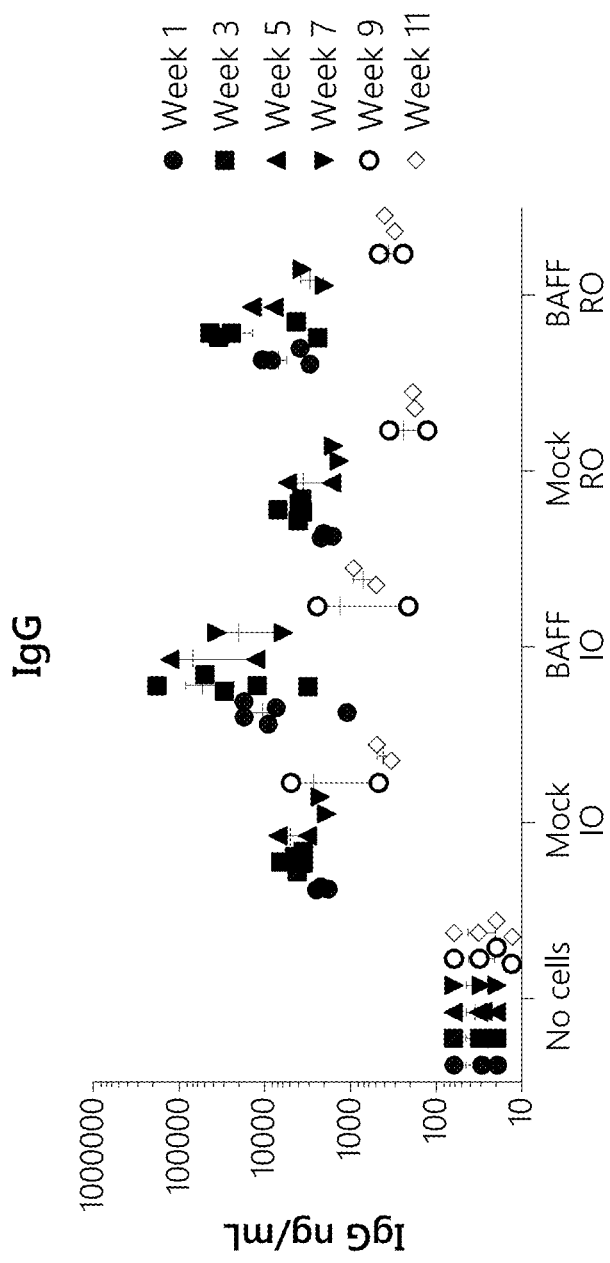
FIG. 31 shows the long lived human antibody production in mice.

Primary B cells were expanded in culture and edited as described. Following differentiation into plasma cells, 10 million were injected into NSG mice using either retro-orbital (RO) or intra-osseous (IO) injection. The mice were bled at the indicated time points. Human IgG (IgM not shown) was quantified using ELISA. Each dot represents data from an individual recipient mouse at the indicated time point. These data show that gene edited human plasma cells can live for long periods in this murine model despite the absence of human cytokines. These data also show that autocrine production of human BAFF can further promote sustained survival of gene edited PCs. (FIG. 31).

Alternative 10: Expression of Human IL6 in Mice Confers a Growth Advantage for Transplanted Ex Vivo Differentiated Human Plasma Cells.

Figure 32:
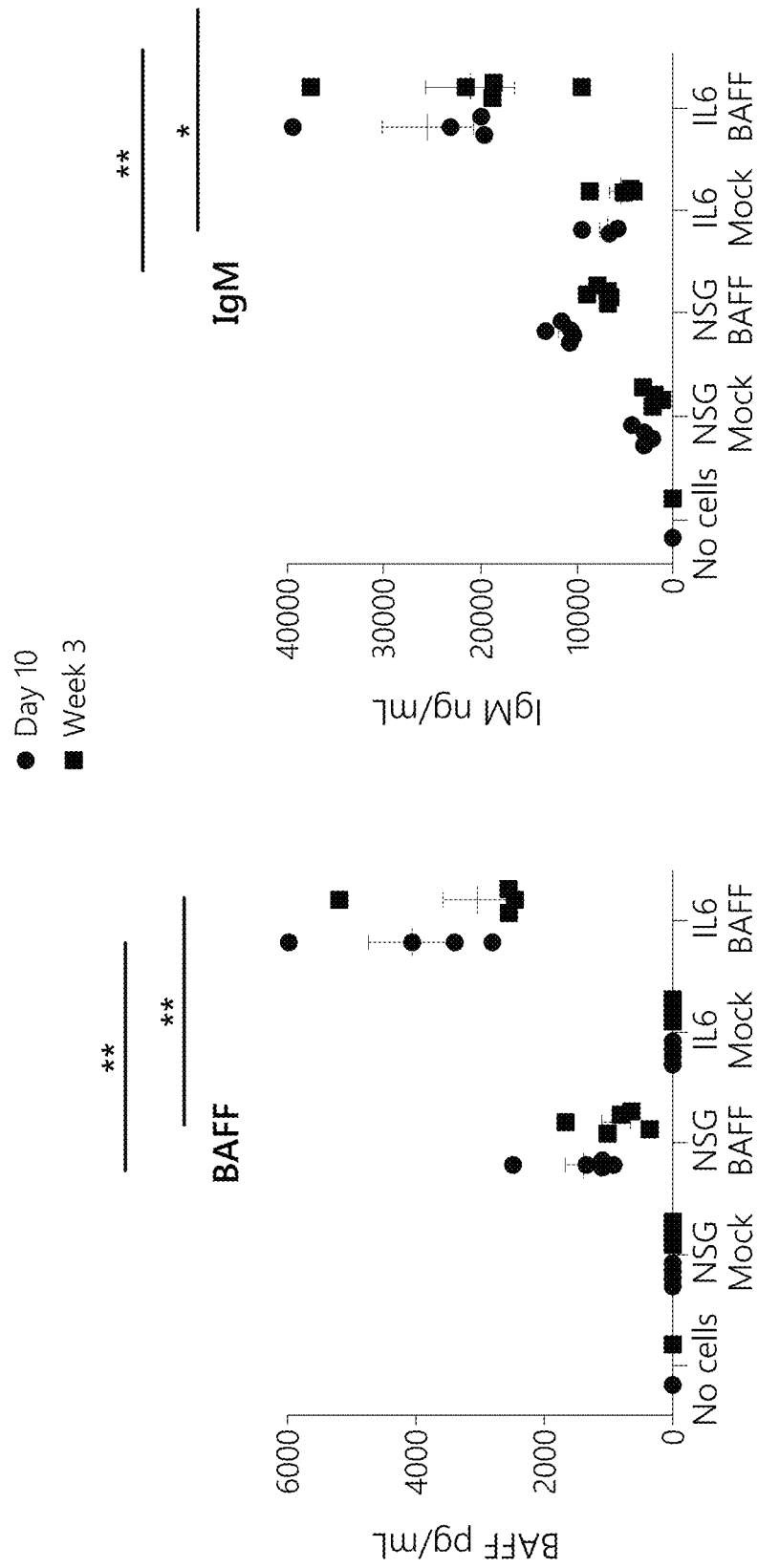
FIG. 32 shows expression of human IL6 in mice confers a growth advantage for transplanted ex vivo differentiated human plasma cells.

Neonatal NSG mice were injected with lentiviral vectors expressing human IL6 and used for adoptive cell transfer at approximately 8-12 wk of age. Primary human B cells were expanded in culture and edited as described (mock or BAFF delivered to the CCR5 locus). Following differentiation into plasma cells, 10 million were injected into NSG mice using retro-orbital (RO) injection. The mice were bled at the indicated time points. Human BAFF or IgM was quantified using ELISA. Each dot represents data from an individual recipient mouse at the indicated time point. These data show that human IL6 secretion can confer an in vivo survival advantage to transplanted human plasma cells and that this can synergize with autocrine expression of human BAFF in gene edited cells (FIG. 32).

Alternative 11: High IL6 Expression Correlates with High Plasma Cell Secretion.

Figure 33:
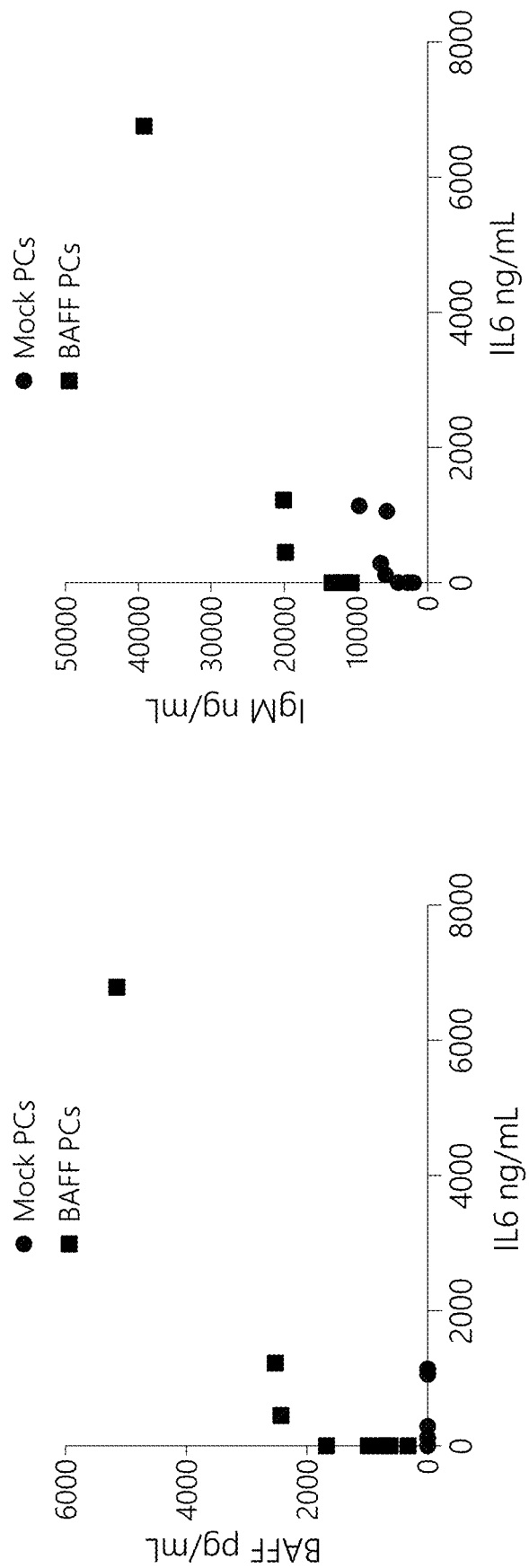
FIG. 33 shows high IL6 expression correlates with high plasma cell secretion.

Neonatal NSG mice were injected with lentiviral vectors expressing human IL6 and used for adoptive transfer of human cells at 8-12 wks of age. Primary human B cells were expanded in culture and edited as described (mock or BAFF delivered to the CCR5 locus). Following differentiation into plasma cells, 10 million were injected into NSG mice using either retroorbital (RO) injection. The mice were bled at the indicated time points. Human IL6, BAFF or IgM was quantified using ELISA. Each dot represents data from an individual recipient mouse at the indicated time point. These data demonstrate that the levels of human IL6 directly correlated with the levels of human protein production by the gene-edited transplanted cells, and likely the number of surviving long-lived plasma cells (FIG. 33).

Alternative 12: In Vitro Human APRIL Treatment Correlates with Increased Plasma Cell Antibody Secretion In Vivo.

Figure 34:
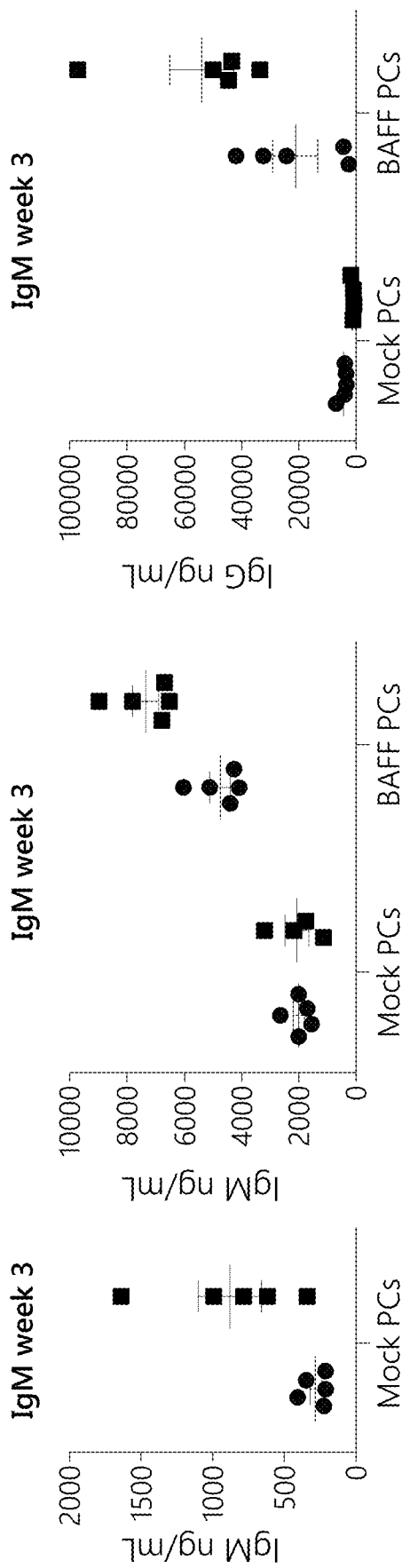
FIG. 34 shows in vitro human APRIL treatment correlates with increased plasma cell antibody secretion in vivo.

Primary B cells were expanded in culture and edited so that BAFF or mock is delivered to the CCR5 locus. During differentiation into plasma cells, the cells were cultured in the presence of trimeric APRIL (Mega-April™) or mock. After 12 days in culture, IgM and IgG secretion was quantified by ELISA. Each dot is from an experiment from an individual donor. These data show that April promotes antibody production in in vitro derived gene-edited human plasma cells. (FIG. 34). Shown in FIG. 35, are the results of the gene disruption and protein expression.

Alternative 13: Targeting of Abundant Plasma Cell Genes Using CRISPR.

Primary human B cells were expanded in culture and edited to disrupt the indicated loci. 5 days following transfection, genomic DNA was harvested for amplification and quantification of insertions and deletions using a T7 endonuclease I cleavage assay. As demonstrated and quantified, multiple guides successfully disrupt the target loci. (FIG. 36).

Alternative 14: Multiplexed Genome Editing to Introduce FIX and Increase Protein Secretion in Human Plasma Cells.

Figure 37:
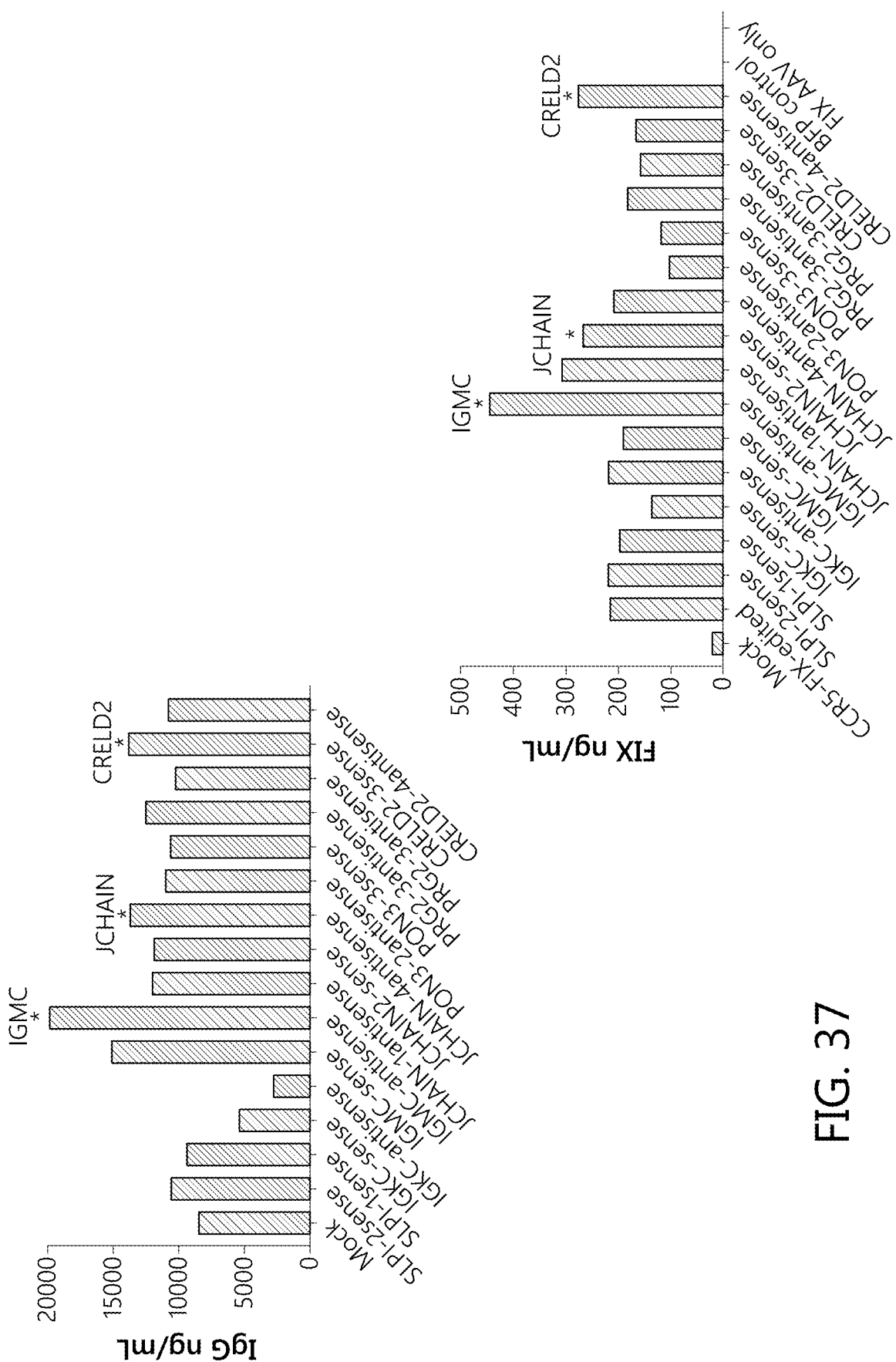
FIG. 37 shows multiplexed genome editing to introduce FIX and increase protein secretion in human plasma cells.

Primary human B cells were expanded in culture and edited to disrupt the indicated loci. Using multiplexed editing, FIX was also introduced into the CCR5 locus by homology-directed repair. After three-step differentiation into plasma cells, IgG and FIX were quantified by ELISA. These data show that knocking out a subset of highly expressed genes, including the heavy chain (IGMC), JCHAIN and CRELD2, production of IgG and FIX in gene edited plasma cells can be increased. (FIG. 37).

Alternative 15: Knock-Out of BANK1 Promotes Plasma Cell Differentiation and Antibody Production.

Figure 38:
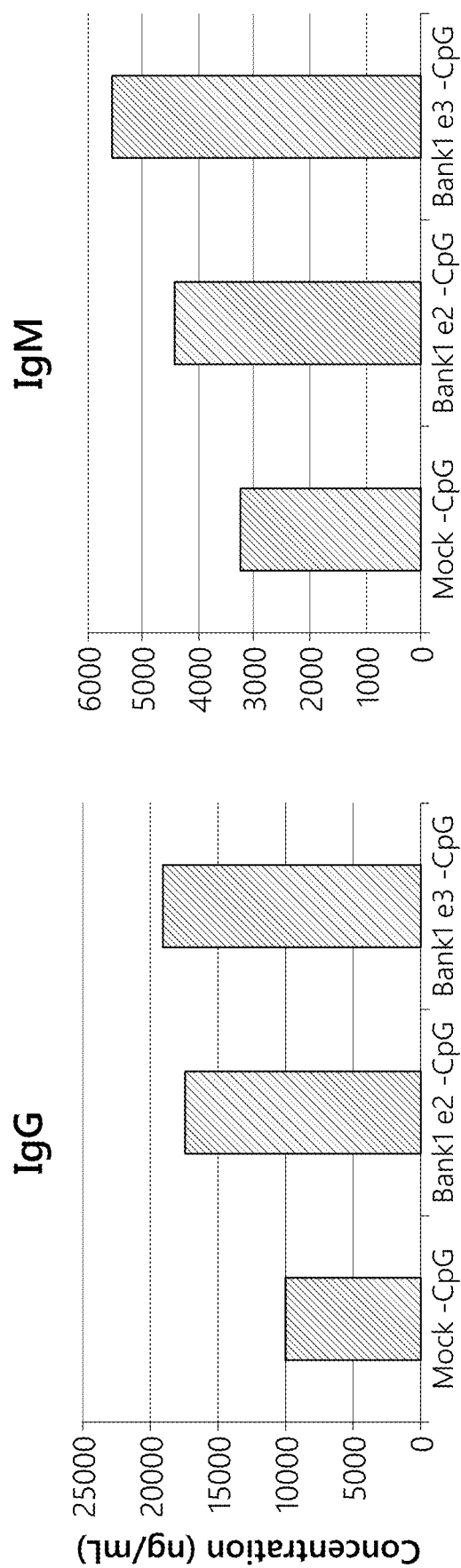
FIG. 38 shows knock-out of BANK1 promotes plasma cell differentiation and antibody production.

Primary human B cells were expanded in culture and edited to disrupt BANK1. After three-step differentiation into plasma cells, IgG and IgM were quantified by ELISA. These data show that knocking out the B cell developmental regulator BANK1, IgG and IgM can lead to increased production of in gene edited plasma cells. (FIG. 38). Consistent with these data disruption of BANK1 also promotes PC differentiation.

Alternative 16: Long-Lived Plasma Cells Secrete More Immunoglobulin on a Per Cell Basis.

Figure 39:
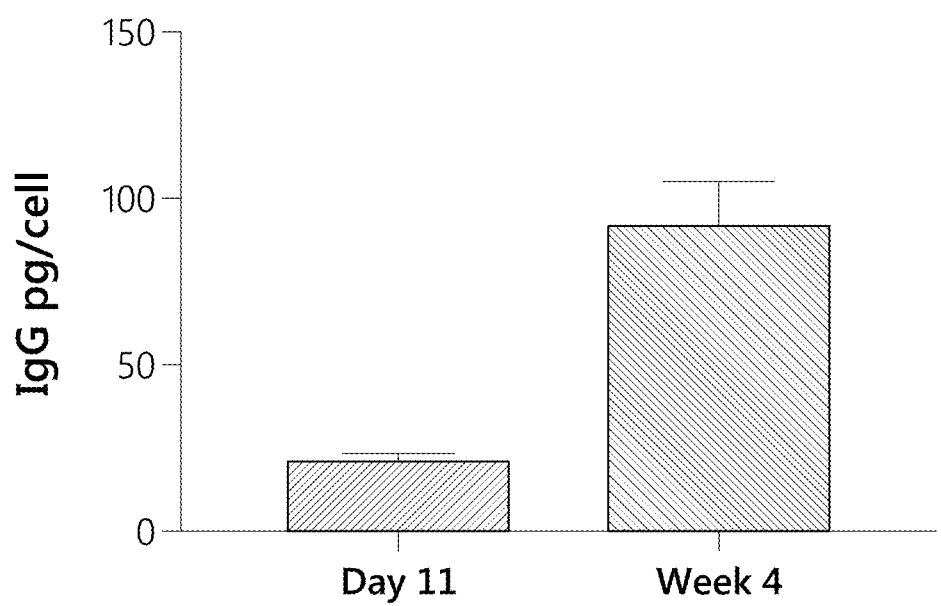
FIG. 39 shows long-lived plasma cells secrete more immunoglobulin on a per cell basis.

Primary human B cells were expanded in culture. After three-step differentiation into plasma cells, plasma cells (CD138 enriched cells) were cultured for an additional 3 weeks in the presence of IFN-beta, IL6, IL15 and trimeric APRIL. Three days following a media change, IgG was quantified by ELISA at day 11 and at 4 weeks. These data show that long-lived plasma cells produce substantially more IgG on a per cell basis (n=2 donors). (FIG. 39).

Alternative 17. In Vivo Delivery of Human APRIL or IL6 Enables Increased Long-Term Secretion by Edited Long-Lived Plasma Cells Neonatal NSG mice were injected with lentiviral vectors expressing human IL6 and/or APRIL and used for adoptive cell transfer at approximately 8-12 wk of age. Primary human B cells were expanded in culture and edited as described (mock or BAFF delivered to the CCR5 locus). Following differentiation into plasma cells, 10 million were injected into NSG mice using retro-orbital (RO) injection. The mice were bled at the indicated time points. Human BAFF was quantified using ELISA. Each dot represents data from an individual recipient mouse at the indicated time point. These data show that human IL6 and APRIL secretion can confer increase the long-term production of an exogenously delivered protein (BAFF) by edited human plasma cells. (Figure Alternative 18: Engineering Protein-Secreting Plasma Cells by Homology-Directed Repair in Primary Human B Cells A method is presented for high-efficiency, homology-directed genome editing in primary human B cells for the purposes of producing therapeutic proteins.

B cells differentiate into long-lived plasma cells that provide humoral immunity by secreting large quantities of antibodies. The ability to engineer primary human B cells to secrete a de novo protein may allow the creation of novel plasma cell therapies for protein deficiency diseases and other clinical applications. To achieve this goal, methods for efficient genome editing of primary B cells isolated from peripheral blood were developed, followed by ex vivo differentiation into plasma cells. By delivering CRISPR/Cas9 ribonucleoprotein (RNP) complexes under conditions of rapid B cell expansion, site-specific gene disruption at multiple loci in primary human B cells was achieved (with editing rates up to 94%). This method was first used to modulate plasma cell differentiation by disrupting key developmental regulatory genes. Next, RNPs were co-delivered with either single-stranded DNA oligonucleotide or adeno-associated viruses containing a homologous repair template. Using either delivery method, targeted sequence integration at high efficiency (up to 40%) via homology-directed repair was achieved. This method enabled engineering of plasma cells to secrete B-cell activating factor (BAFF) or factor IX (FIX) at high levels. These results highlight the utility of genome editing in studying human B cell biology and demonstrate a novel strategy for modifying human plasma cells to secrete therapeutic proteins.

Long-lived plasma cells stably reside in the bone marrow for decades and secrete large quantities of antibodies. Consequently, plasma cells engineered to produce de novo proteins have the potential to be curative therapies for protein deficiency diseases, prophylaxis for infectious diseases and many other applications. However, the development of plasma cell therapeutics has been limited by technical challenges in the in vitro modification, culture, expansion and differentiation of primary human B cells. B cells can be transduced at high rates by recombinant adenovirus or Epstein-Barr virus (EBV) vectors, which deliver transgenes as episomes. However, episomal DNA expression is lost over time, limiting use of these vectors in applications that require long-term transgene expression. Unlike non-integrating vectors, gamma retrovirus (yRV) and lentivirus (LV) randomly integrate into the host genome and can be used to introduce stably expressing transgenes. However, these vectors are inefficient at transducing primary human B cells. LV that employ alternative envelopes, including that of baboon retrovirus, measles virus, or gibbon-ape leukemia virus exhibit higher B cell transduction rates (up to ~50%), but have low viral titers that make large-scale production challenging. Because yRV and LV vectors do not efficiently transduce B cells while transduction by non-integrating vectors results in only transient transgene expression, neither platform is currently effective for delivering long-term expression of exogenous genes to B cells on a therapeutic scale.

An alternative method for introducing stable protein expression is genome editing via homology-directed repair (HDR). Following cleavage by an engineered site-specific nuclease, DNA double-strand breaks were resolved through non-homologous end joining (NHEJ), an error-prone DNA repair pathway that typically leads to variable insertions or deletions (indels), or HDR, which repairs DNA by copying a homologous donor template. Delivery of exogenous DNA flanked by DNA homologous to the genomic sequence around the break site can lead to incorporation of the exogenous sequence in a site-specific manner. HDR-mediated genome editing in B cells may have several advantages over viral vector transduction for therapeutic applications, including decreased risk of insertional mutagenesis and sustained transgene expression. Many have recently achieved high-efficiency HDR delivery of therapeutic transgenes to hematopoietic cells including primary human T cells and hematopoietic stem cells, but similar approaches are yet to be applied in modification of primary human B cells.

The clustered regularly interspaced short palindromic repeats (CRISPR)/CRISPR-associated protein 9 (Cas9) system is an RNA-guided nuclease platform that is easily engineered to efficiently target specific sites in the genome for cleavage, generating double-strand DNA breaks. The use of site-specific nucleases for gene disruption or HDR in B cells is currently limited to transformed or lymphoma-derived cell lines and murine models and has required plasmid- or LV-based CRISPR/Cas9 delivery. Described herein is a method of high-efficiency genome editing in human peripheral blood B cells (75-90% gene disruption or 10-40% HDR) by delivering CRISPR/Cas9 ribonucleoprotein (RNP) complexes alone or in combination with single-stranded DNA oligonucleotide (ssODN) or adeno-associated virus (AAV) repair templates, respectively. In the alternatives herein it is shown that edited primary B cells can subsequently be differentiated in culture into plasma cells that produce physiological doses of therapeutic proteins including human Factor IX (FIX).

Conditions for Expansion of Primary Naïve Human B Cells

Figure 40B:
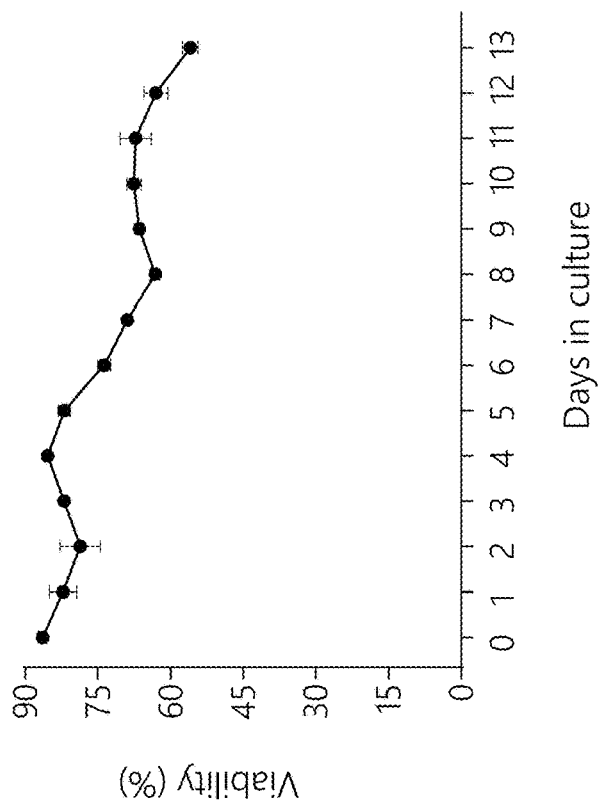
FIG. 40A shows B cell activation cocktail leads to expansion of naïve B cells in vitro. (40A-40C) Primary human CD19+ B cells were isolated from PBMCs and cultured with MEGACD40L®, CpG, IL2, IL10 and IL15 for 13 days. Fresh medium with the soluble factors was replenished every one or two days to maintain a cell density of ~1×10$^6$ cells/ml. Cells were counted every day (a) and viabilities were measured using 4',6-diamidino-2-phenylindole (DAPI) staining (b) (n=2). Line graphs show means±SEM. (c) Cell samples were stained using anti-CD27, CD138, CD19, CD38, IgD and IgM antibodies after 0, 2, 8, and 13 days of culture. Immunophenotypes were analyzed by flow cytometry.
Figure 40A:
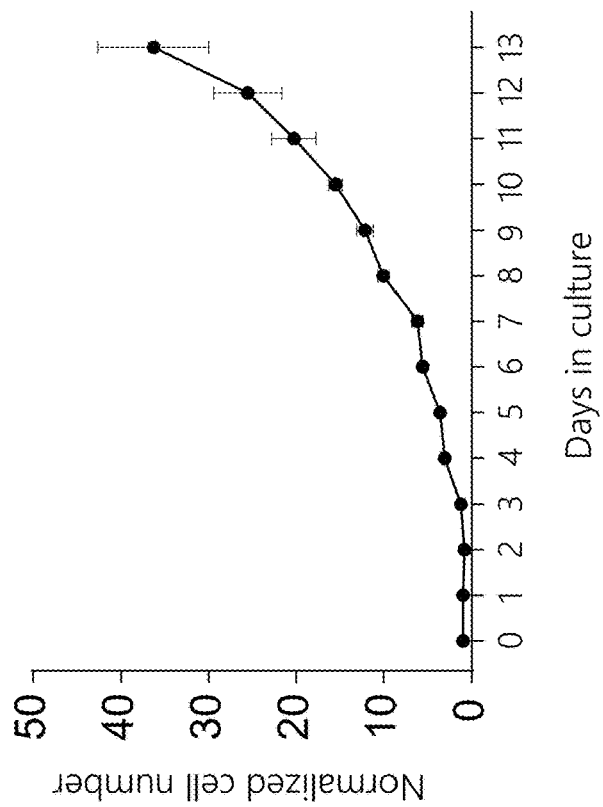
Figure 40C:
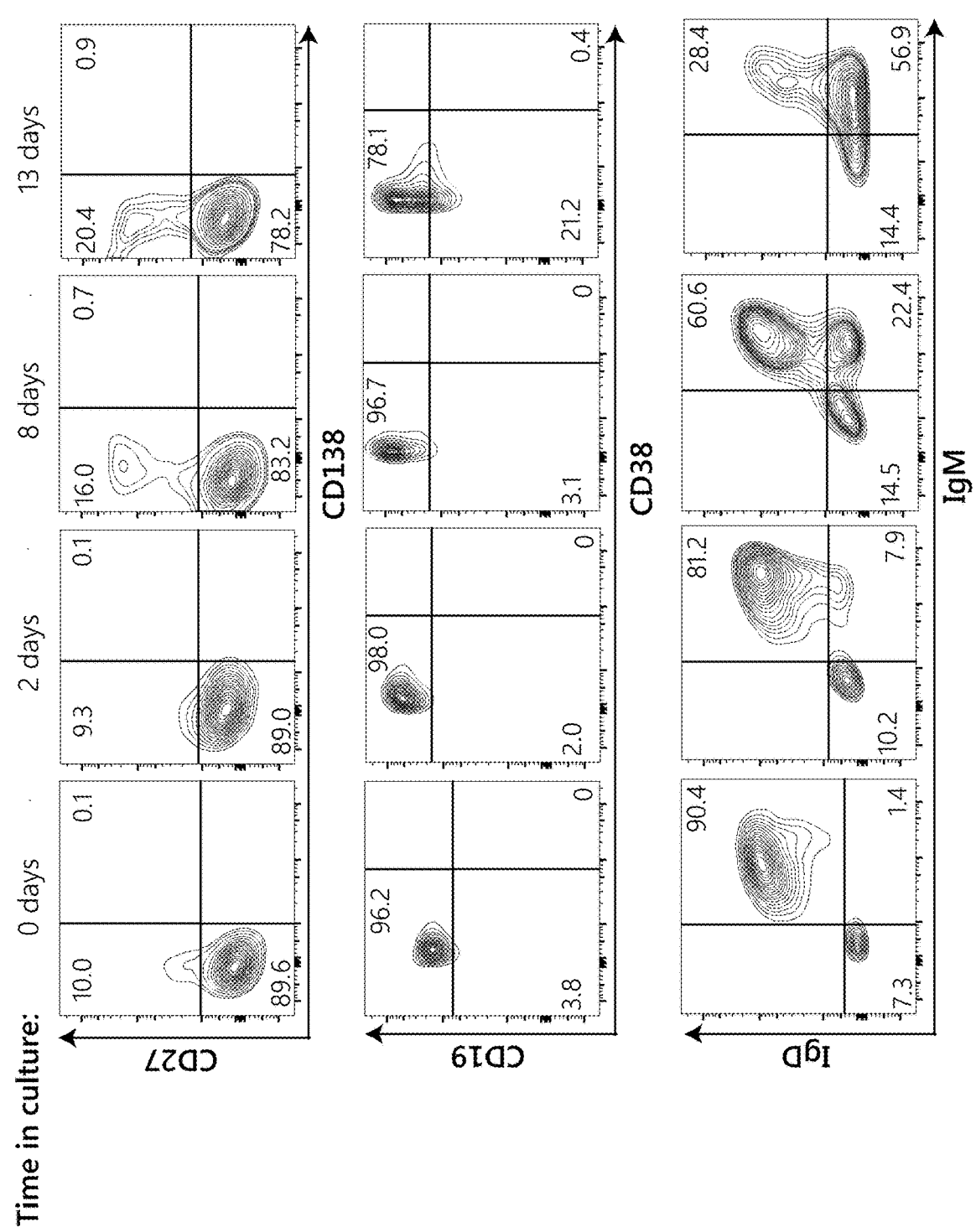

Rapid cell cycling and/or persistence in the S/G2 phases of the cell cycle promote HDR in both cell lines and primary hematopoietic cells. Based on previous reports demonstrating rapid expansion of primary human B cells ex vivo, a combination of stimulants (hereafter called "B cell activation cocktail") was initially used that included artificially oligomerized CD40 ligand (MEGACD40L®; two linked CD40L trimers) in association with CpG, IL2, IL10, and IL15. Primary human CD19$^+$ B cells from peripheral blood mononuclear cells (PBMCs) were isolated and cultured them for 13 days with this B cell activation cocktail. This approach resulted in a ~36-fold expansion of B cells (FIG. 40A), while preserving viability at >60% (FIG. 40B). Despite having proliferated over 13 days, most cells maintained a naïve B cell phenotype (CD27$^-$CD138$^-$CD38$^{low/-}$CD19$^{high}$IgM$^+$ IgD$^+$; FIG. 40C), demonstrating that the B cell activation cocktail facilitates rapid cycling and ex vivo maintenance of naïve primary human B cells.

Cas9-Mediated Disruption of CCR5 and PRDM1 in Primary Human B Cells

Figure 41:
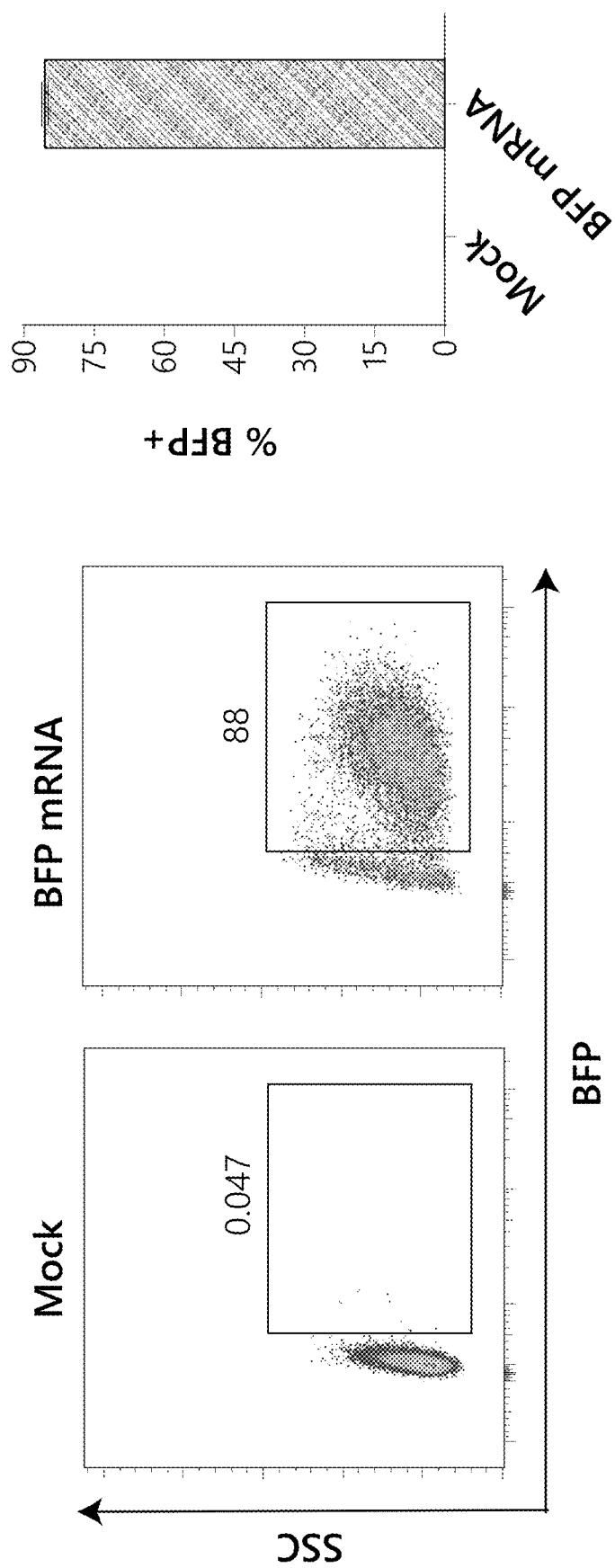
FIG. 41 shows primary B cells are effectively electroporated with mRNA encoding blue fluorescent protein (BFP). B cells were activated for two days in culture and transfected with BFP mRNA using the optimal electroporation settings. Percentages of BFP+ cells were measured 24 hours after transfection by flow cytometry. Left: representative flow plots showing BFP expression of mock and BFP mRNA electroporated B cells. Right: bar graph showing percentages of BFP+ cells (n=5). All values are means±SEM.
Figure 42A:
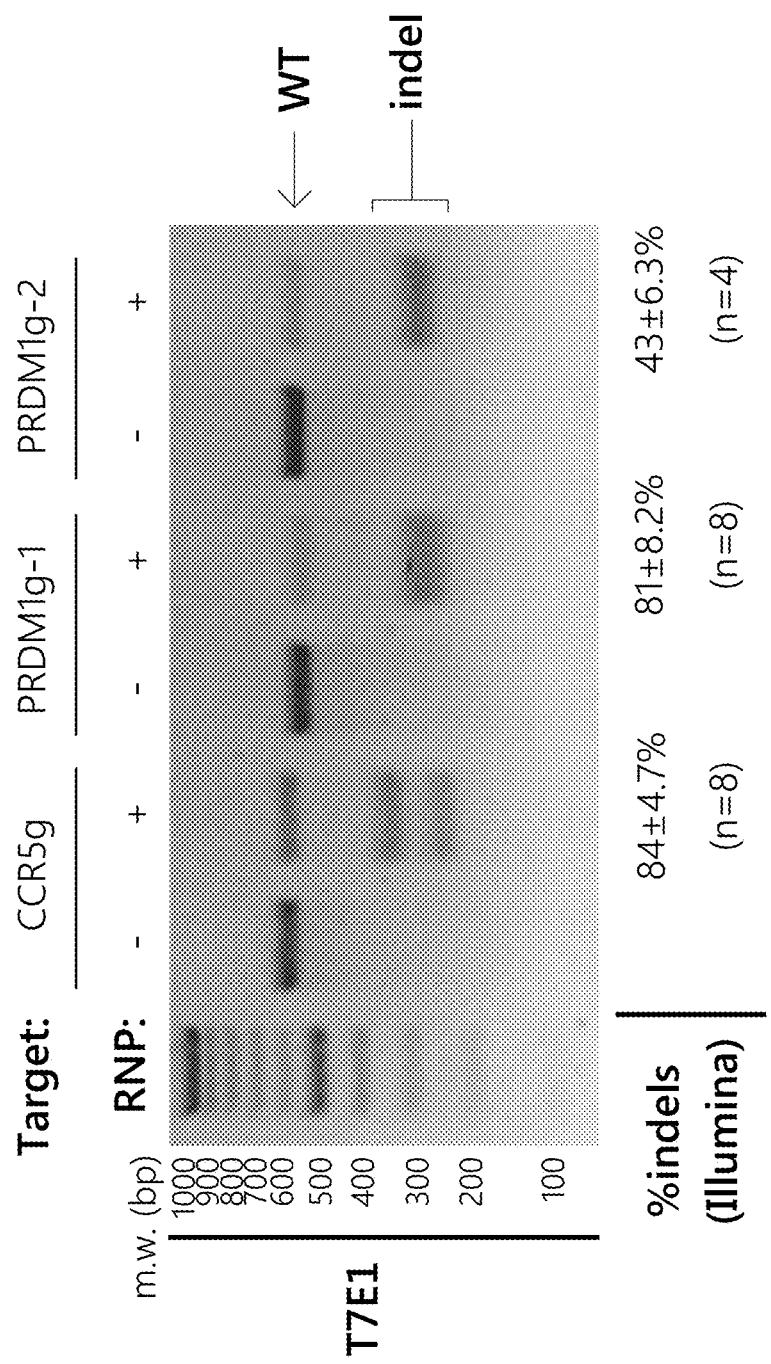
FIG. 42 shows Cas9 RNP induces site-specific indels or a precise single-nucleotide change in the presence of an ssODN in primary human B cells. (42A) CD19+ B cells were isolated and activated in vitro for two days, mock treated or transfected with Cas9 RNPs targeting CCR5 or PRDM1 (CCR5g, PRDM1g-1 or PRDM1g-2) and cultured for five additional days. Total genomic DNA was isolated on day 5, target regions were PCR amplified and analyzed using the T7 endonuclease 1 (T7E1) assay (one representative experiment shown) or sequencing for percentages of on-target indels (112,000 reads per experimental condition). (42B) Diagram of wild type PRDM1 locus, PRDM1g-2 target location and the ssODN donor template containing a single-nucleotide change. (42C, D) B cells were activated for two days and mock treated, electroporated with Cas9 RNP-PRDM1g-2 alone, or with the ssODN donor template at serially increasing doses from 7.5 pmol to 120 pmol. (42C) Viabilities of B cells 2 days and 5 days after genome editing (n=3, three donors). No significant difference in viability was observed between mock and up to 30 pmol ssODN plus RNP either on day 2 or day 5. The bar graph shows means±SEM. (42D) Percentage of HDR, indel and wildtype (WT) alleles in total genomic DNA extracted 5 days after genome editing as assessed by sequencing (greater than 1 million reads per experimental condition). N represents the number of independent experiments. One-way ANOVA with the Sidak correction for multiple comparisons is used; ***p<0.001; ns, not significant. WT, wild-type. As shown in 42D of the bar graphs, the top black portions of the bar are wild type, light grey is HDR and the bottom grey is indel.
Figure 42B:
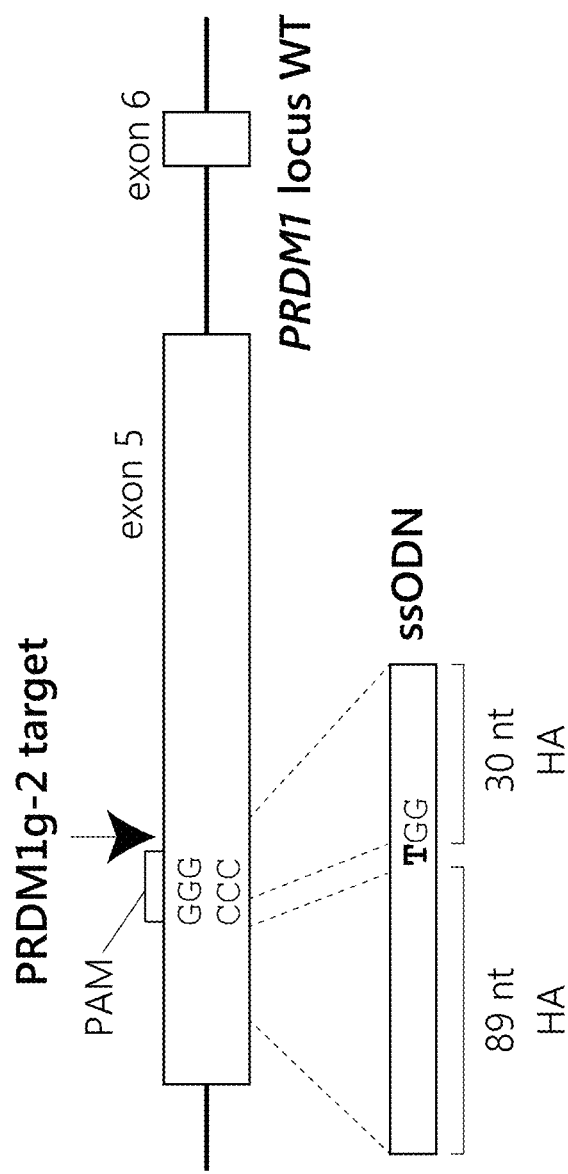
Figure 42D:
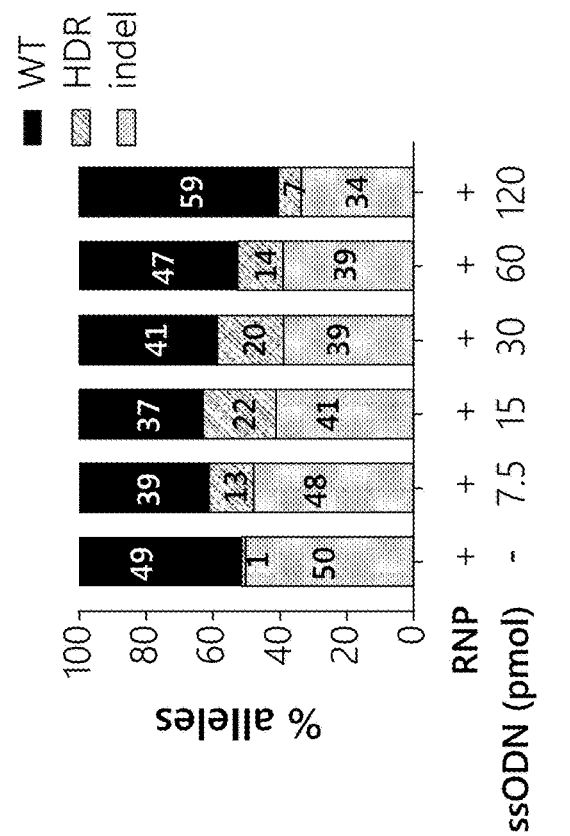
Figure 42C:
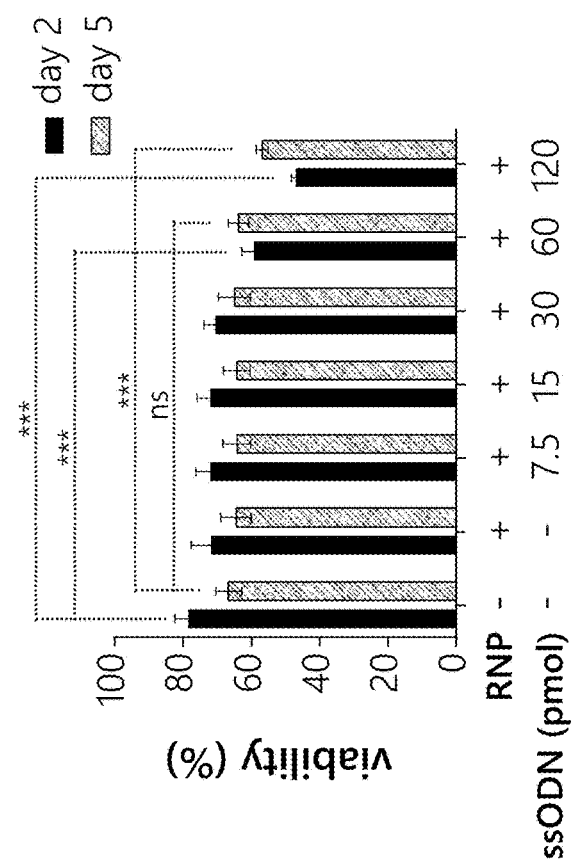

To assess the efficiency of Cas9-induced indels in B cells, CRISPR guide RNAs (gRNAs) were designed that target CCR5 (which is not expressed in human B cells and has no known significance in plasma cell development) or PRDM1 (encoding BLIMP1, a protein required for B cell differentiation into plasma cells). After optimizing electroporation based upon mRNA (FIG. 41), 30 pmol Cas9-guide ribonucleoprotein (RNP) complexes were transfected into B cells, cultured for five additional days under activating conditions and extracted total genomic DNA to assess nuclease-induced indels using the T7 endonuclease 1 assay (FIG. 42). Sequencing confirmed on-target indels and revealed that the RNPs induced high indel frequencies at each guide target site (43-84%; FIG. 42A). Western blot also verified concomitant PRDM1 protein reduction in the PRDM1-expressing TMD8 lymphoma cell line (FIG. 43A).

Figure 43B:
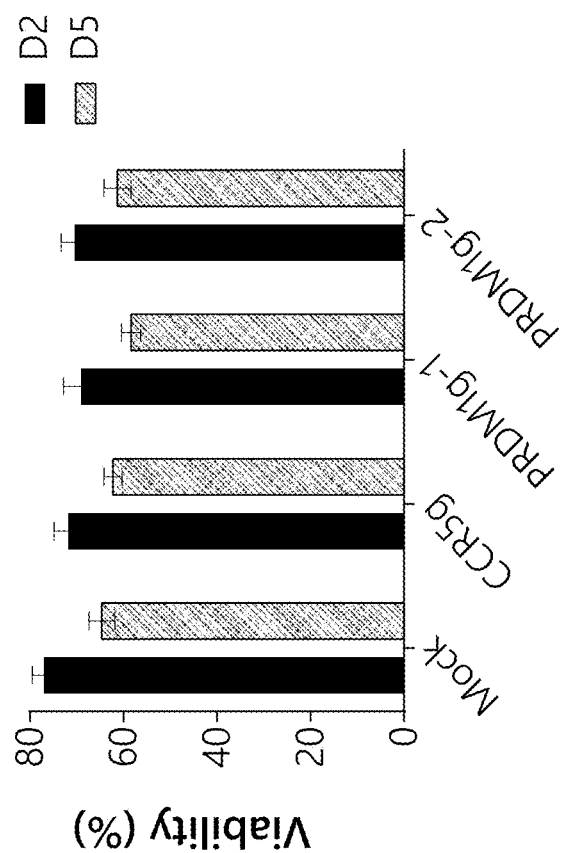
FIGS. 43A and 43B shows Cas9-mediated gene disruption is associated with protein reduction and high cell viabilities. (43A) TMD8 cells were mock treated or transfected with either of the two PRDM1-targeting RNPs and protein levels were analyzed five days later by western blot. (43B) Viabilities of primary human B cells two days or five days after genome editing.
Figure 43A:
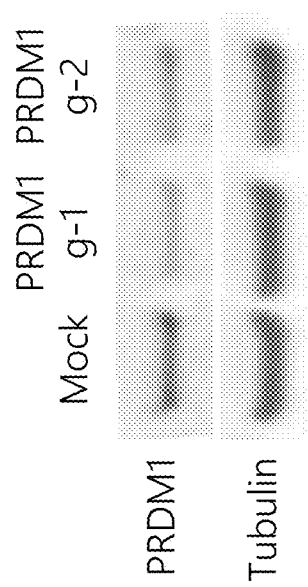

Finally, it was found that B cells remained viable despite these genome modifications (FIG. 43B). These data show that high-efficiency Cas9-mediated gene disruption is achievable in primary human B cells.

HDR-Mediated Single-Nucleotide Substitution at the PRDM1 Locus Using an ssODN Donor Template Cas9-induced DNA lesions can be seamlessly repaired via the HDR pathway in the presence of a donor template with homology sequences flanking the lesion. An ssODN was initially tested an as a donor template based on promising results in other cell types. A 120-base ssODN was designed containing asymmetric homology arms (89 bases 5' and 30 bases 3') that flank the PRDM1g-2 target site, with a single-nucleotide change at the $90^{th}$ position that mutates the last nucleotide of the protospacer adjacent motif (PAM; GGG to GGT; FIG. 42B). This single nucleotide change was designed to both prevent Cas9-mediated cleavage of the repaired sequence and to serve as a molecular marker for HDR. In this experiment, primary human B cells were activated for two days and then transfected with Cas9 RNP in conjunction with various doses of the ssODN. Two and five days following transfection, cells transfected with ≤30 pmol ssODN had comparable viabilities to Cas9 RNP transfected control cells (FIG. 42C). In cells receiving 15 or 30 pmol ssODN, sequencing of the PRDM1 target region on day 5 post-transfection revealed 20-22% of alleles had undergone HDR while another 37-41% had indels (FIG. 42D), an overall editing rate marginally higher than that observed in the Cas9 RNP control (FIG. 42D). Thus, ssODN donor templates can be used to achieve high rates of HDR in primary human B cells with low cytotoxicity.

Cas9-Mediated Disruption of Genes that Regulate Plasma Cell Development

Figures 44A, 44B:
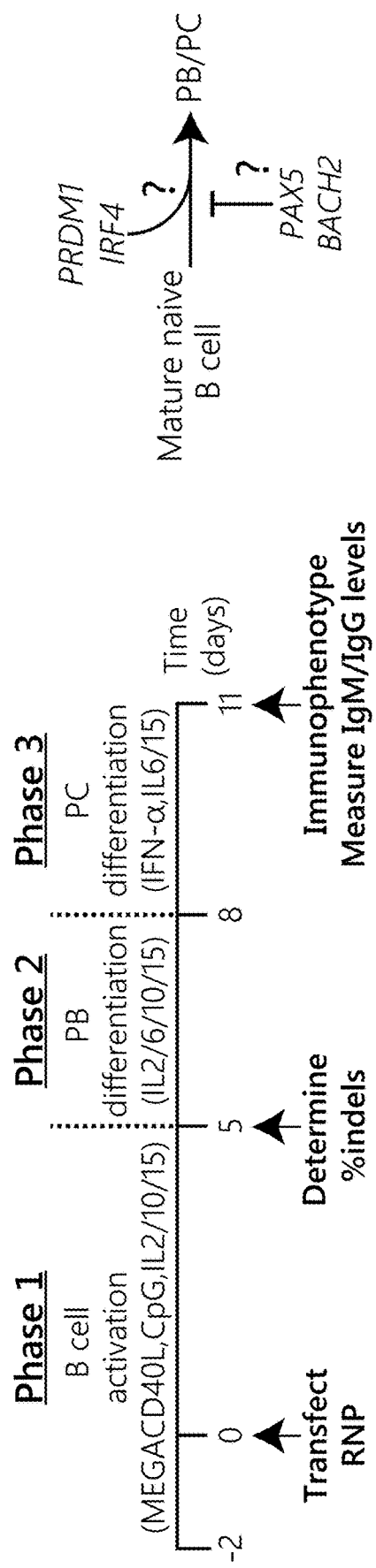
Figure 44D:
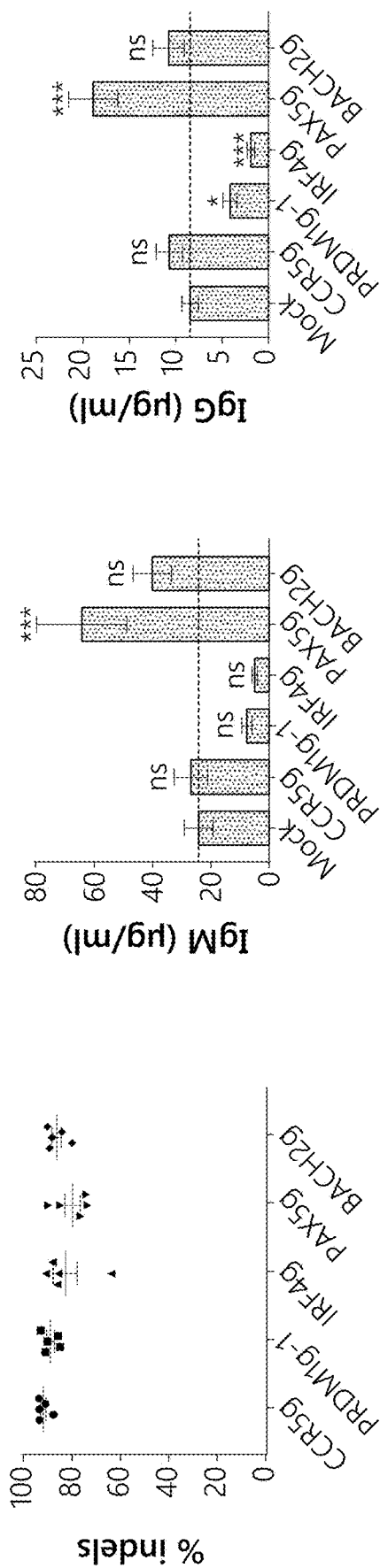
Figure 45A:
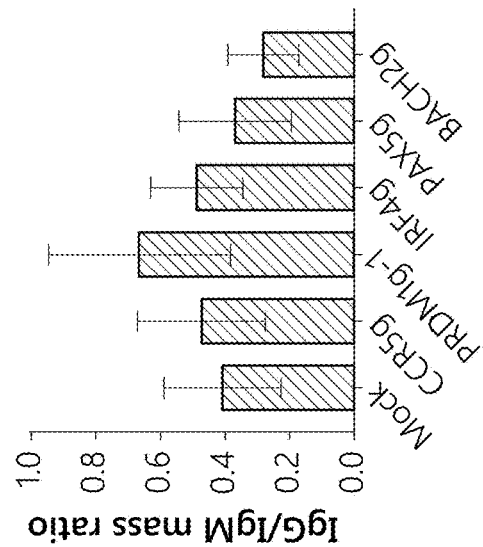
FIG. 45A-45C shows Cas9 RNPs targeting CCR5, PRDM1, IRF4, PAX5, and BACH2 lead to high levels of gene disruption in primary human B cells.
Figure 45B:
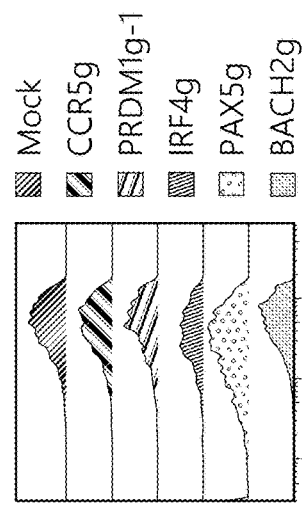
Figure 45C:
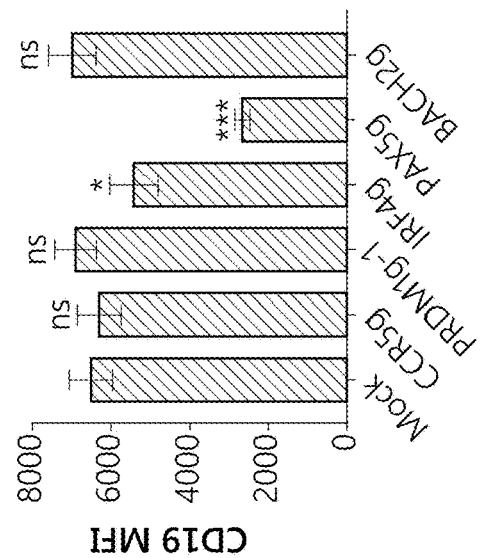

It was next investigated whether Cas9-induced gene disruption can be used to study gene roles in human plasma cell development and antibody production. To do so, an experimental workflow was developed that includes inducing NHEJ-mediated gene disruption in activated naïve human B cells using Cas9 RNPs and subsequently differentiating naïve B cells into plasma cells ($CD19^{low}CD38^{high}CD27^+$ $CD138^+$) using a three-step plasma cell culture system (see FIG. 44A). As a proof of concept, four genes were studied encoding transcription factors previously reported to regulate plasma cell development in murine studies: IRF4 and PRDM1/BLIMP1 are required for plasma cell differentiation (FIG. 44B), while PAX5 and BACH2 antagonize plasma cell differentiation in mice (FIG. 44B). CRISPR guides were designed targeting each of these four genes, and were transfected into primary B cells with Cas9 RNP targeting each gene independently and subsequently induced in vitro plasma cell differentiation (FIG. 44A). As a control, cells were also transfected with Cas9 RNPs targeting CCR5. Following differentiation, significantly lower percentages of $CD19^{low}$ $CD38^{high}$ and $CD27^+CD138^+$ plasma cells were detected in cultures transfected with PRDM1- or IRF4-targeting RNPs compared to cells transfected with CCR5-targeting RNP or mock transfected cells (mean indel percentages=89%, 83% and 92% at the PRDM1, IRF4 and CCR5 target sites, respectively; FIG. 44C, 44D). As antibody secretion is a major function of plasma cells, IgM and IgG levels were measured in cell culture supernatants by enzyme-linked immunosorbent assay (ELISA) and found IgG to be significantly decreased in the PRDM1- and IRF4-targeted B cell cultures (FIG. 44E). Together, as predicted, these data imply that both PRDM1 and IRF4 are required for human plasma cell differentiation and antibody production. Conversely, significant increases in the percentages of plasma cells in cultures transfected with either PAX5 or BACH2-targeting RNPs were observed (mean indel percentages=80% and 86% at the PAX5 and BACH2 target sites, respectively; FIG. 44C, 44D). Concomitant increases in IgM and IgG secretion in PAX5-targeted and an increase in IgM secretion in BACH2-targeted cultures were also observed (FIG. 44E). Again, as predicted, these data indicate that Cas9-mediated disruption of PAX5 or BACH2 enhances human plasma cell differentiation. Further, the IgG/IgM ratio in BACH2-targeted B cell cultures was markedly lower than mock or CCR5-targeted cultures (FIG. 44E, FIG. 45A) and plasmablasts in PAX5-targeted cultures exhibited decreased surface CD19 expression (FIG. 45B), both consistent with previous studies in mice. Taken together, these results demonstrate that CRISPR/Cas9-induced gene disruption in primary B cells is useful for interrogating gene products that may modulate human plasma cell development and function.

Figure 46B:
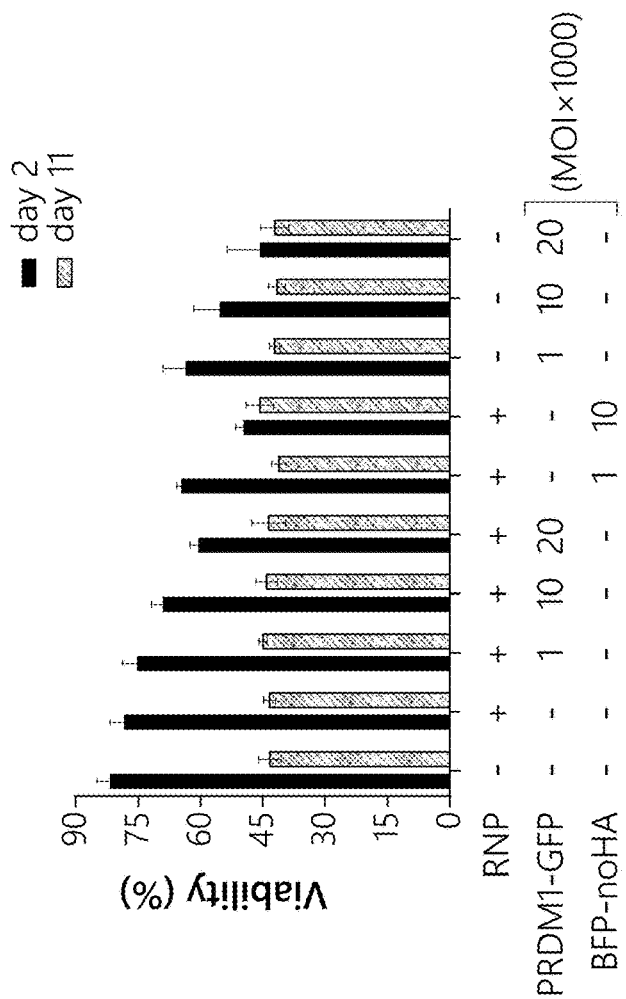
FIG. 46A-46B shows AAV-transduced B cells are marked by rapid recovery and comparable viabilities to mock at experimental endpoint. (46A) Primary B cells were activated for two days in culture and transduced with scAAV GFP of various serotypes at 25,000 MOI. Bar graph shows viabilities two days after transduction (n=3). (46B) Primary B cells were activated for two days and gene-edited using PRDM1-targeting RNP and AAV PRDM1-GFP at different MOIs. Bar graph shows cell viabilities on day 2 and 11 in mock, BFP-no-HA control or PRDM1-GFP edited B cell cultures (n=4). All values are means SEM. As shown in 46B in the bar graphs are Day 2 and Day 11 consecutively.
Figure 46A:
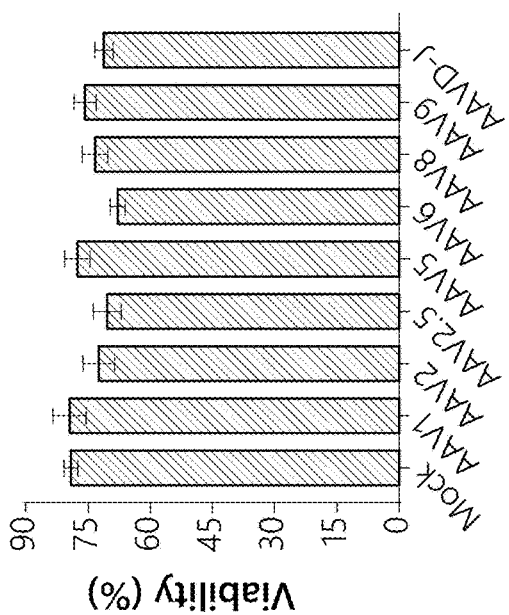
Figure 47A:
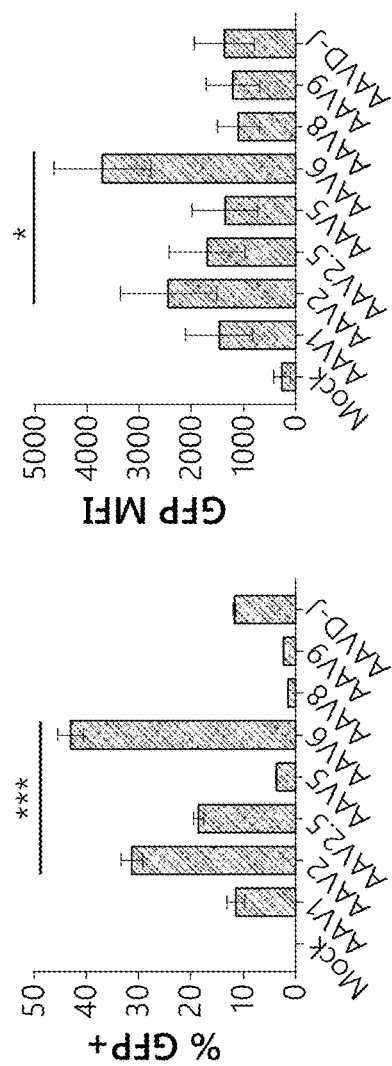
FIG. 47A-47D shows HDR-mediated GFP addition at the PRDM1 locus using Cas9 RNP and an AAV6 donor template leads to progressively increased GFP expression in a dose-dependent manner. (47A) B cells were activated for two days and were either mock treated or transduced with the GFP-expressing scAAV packaged using a comprehensive panel of AAV serotypes (1, 2, 2.5, 5, 6, 8, 9 or D-J) at a multiplicity of infection (MOI) of 25,000. Shown are the percentages of GFP+ cells (left) and mean fluorescence intensities (right) (n=3, three donors). (47B) Schematic of wild type PRDM1 locus, PRDM1g-2 target location and an AAV GFP expression cassette with 400 bp flanking PRDM1 homology arms (AAV PRDM1-GFP). The 3-base PAM sequence is deleted from the AAV template homology sequence. (47C, 47D) B cells were activated for two days and were either mock treated or transfected with Cas9 RNP-PRDM1g-2 with or without AAV transduction. Cells were subsequently cultured under the same activating condition for 11 days. (47C) Top: representative flow plots showing BFP and GFP expressions on day 2 and day 11 after genome editing. The boxed area of the bottom row second panel highlights the GFP+ population in the gene-edited B cells. Bottom: bar graph showing percentages of GFP+ cells on day 2 and day 11 after gene-editing (n=4, four donors). All bar graphs show means±SEM. n represents the number of independent experiments. One-way ANOVA with the Sidak correction for multiple comparisons is used; *$p<0.05$; ***$p<0.001$; ns, not significant. MFI, mean fluorescence intensity. PAM, protospacer adjacent motif; WT, wildtype; HA, homology arm; pA, SV40 poly-adenylation signal.

Site-Specific HDR at the PRDM1 Locus Using Co-Delivery of RNP and AAV Donor Template HDR using ssODN donor templates is not suitable for delivering payloads larger than ~400 bases due to current limitations of the fidelity of ssODN synthesis. In contrast, adeno-associated virus (AAV) can package up to ~4.7 kilobases (kb) of ssDNA donor template. Many have used AAV to deliver candidate HDR templates leading to high levels of HDR in multiple cell types and at a variety of loci. Of note, there is no published data regarding the capacity of AAV to transduce primary human B cells. To investigate AAV transduction efficiency in human B cells, a self-complementary AAV (scAAV) was designed with a green fluorescent protein (GFP) coding sequence driven by MND, a robust retroviral-derived ubiquitous promoter. Activated B cells was transduced with this vector packaged using various serotypes and quantified GFP expression two days post transduction by flow cytometry. Regardless of serotype, it was observed minimal loss of cell viability following viral exposure (FIG. 46A). It was observed the highest percentage of $GFP^+$ cells (mean=43%) and highest mean fluorescence intensity in B cells transduced with AAV serotype 6 (FIG. 47A).

Figure 47B:
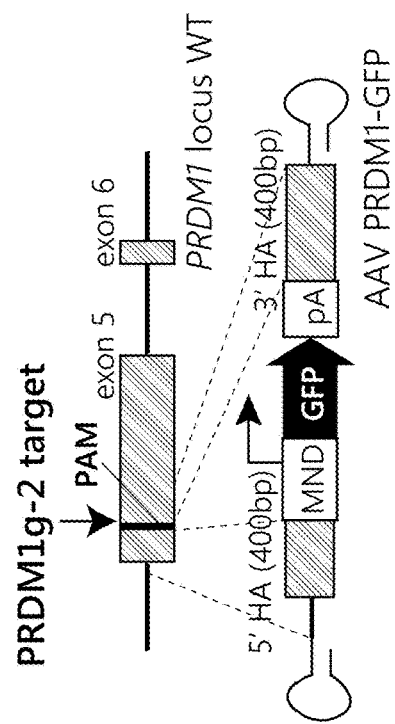
Figure 47C:
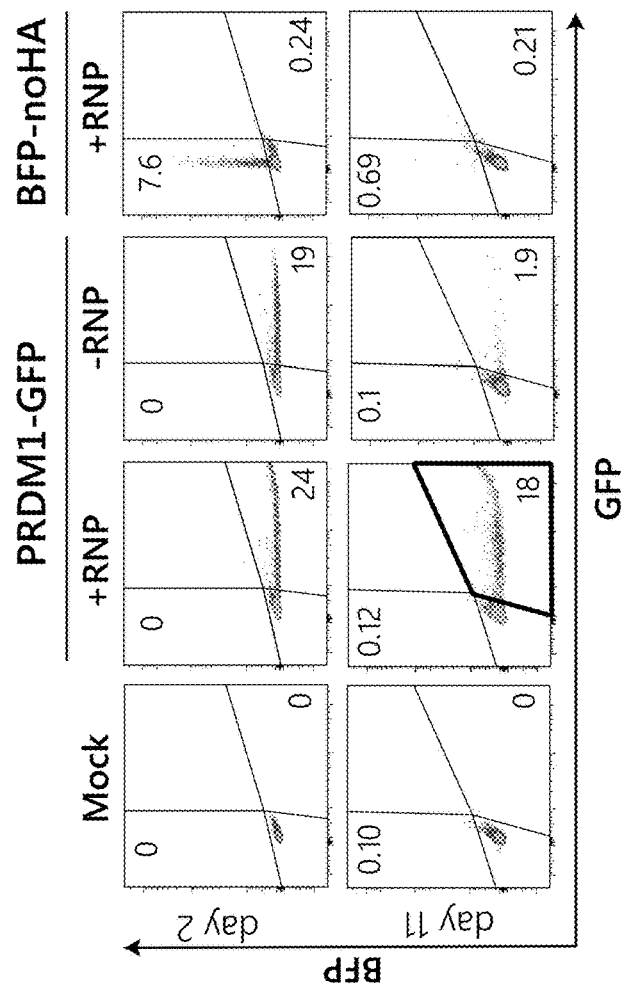
Figure 47D:
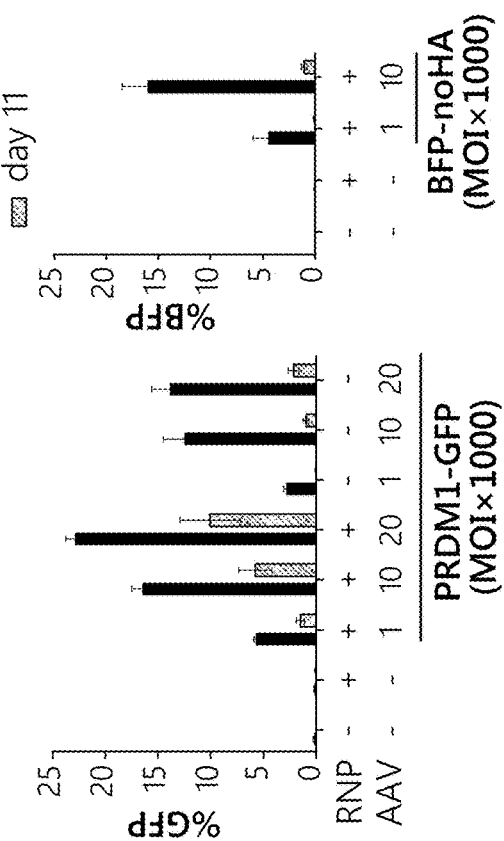

Because the packaging size of single-stranded AAV (ssAAV) is greater than scAAV, the efficacy of HDR-mediated integration of larger payloads was next assessed by delivering ssAAV into B cells. Initially, an AAV6 donor template containing an MND-driven GFP cassette flanked by 400 bp homology arms at the PRDM1g-2 target site was designed (PRDM1-GFP; FIG. 47B). The PAM was not included in the repair template, thereby rendering the repaired sequence non-cleavable by Cas9 (FIG. 47B). After activation and electroporation with or without Cas9 RNP, B cells were transduced with AAV6 PRDM1-GFP at various MOI and cultured for 11 additional days with the same activating factors. Although it was initially observed a 30% viability loss at the highest AAV dose, these cultures eventually recovered and exhibited comparable viabilities by day 11 (FIG. 46B). At the highest AAV MOI, it was observed that there was persistent GFP expression in ~10% of cells that received both the PRDM1-targeting RNP and AAV repair template, while 2% of cells that were treated with the AAV alone had persistent GFP expression (FIG. 47C). In addition, cells were co-treated with the PRDM1-targeting RNP and a non-targeting AAV BFP control (MND-BFP without homology arms; BFP-noHA) and observed ~1% BFP expression at the endpoint (FIG. 47C), indicating that the majority of GFP expression resulting from co-delivery of PRDM1-targeting RNP and PRDM1-GFP was likely driven by HDR-mediated integration. It was also found that higher AAV doses correlated with increased percentages of GFP+ cells. Finally, it was found that increasing homology arm lengths from 400 bp to 1.0 kb did not lead to higher levels of HDR (measured as persistent GFP expression; FIG. 48A-48B). Together, these data support the conclusion that co-delivery of Cas9 RNP and AAV can lead to efficient, targeted genomic integration of transgene, likely via the HDR pathway.

Figure 49A:
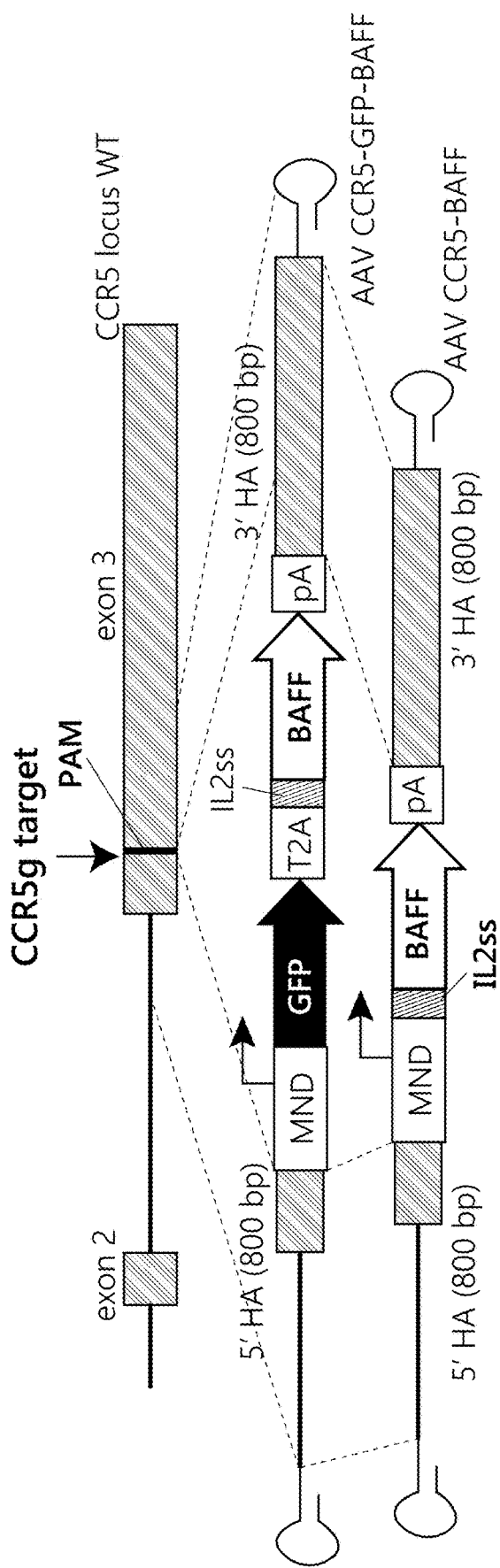
Figure 49B:
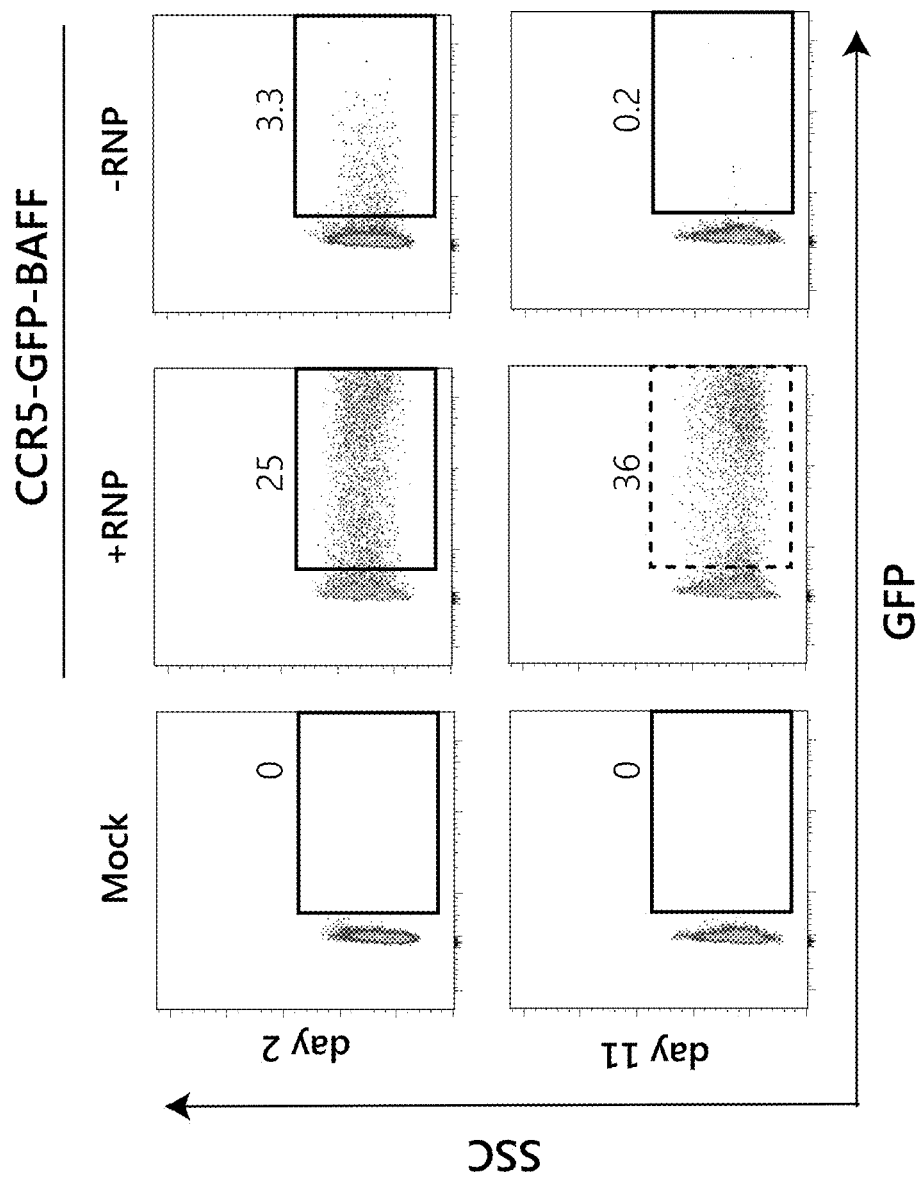
Figure 50:
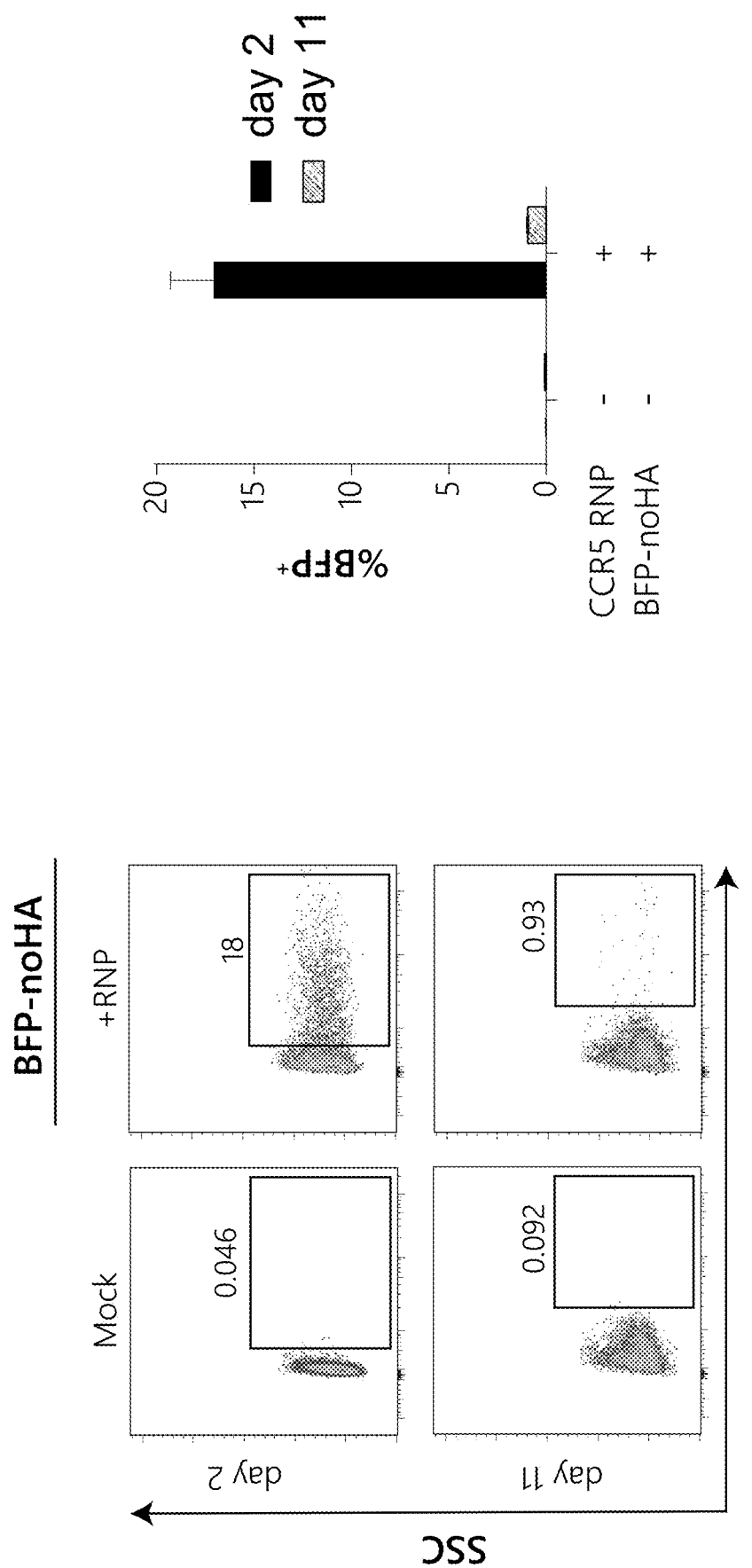
FIG. 50 shows that using AAV without CCR5 homology leads to minimal fluorochrome expression. B cells were either mock electroporated or co-treated with CCR5-targeting RNP and an AAV BFP-noHA control after two days of in vitro activation, and were subsequently differentiated into plasma cells using the three-step culture system. Representative flow plots on day 2 and day 11 (left) and bar graph showing mean percentages of BFP+ cells±SEM (n=4).

Introduction of a BAFF Expression Cassette into CCR5 Leads to Secretion of Functionally Active BAFF It was next assessed whether primary B cells could be engineered to secrete active proteins with predicted functionality. As a first test of this approach, HDR-mediated knock-in strategy to engineer de novo expression of the B-cell activating factor (BAFF) was used. Of note, the HDR studies targeting the PRDM1 locus (described above) were anticipated to underrepresent HDR efficiencies due to the negative impact of PRDM1 disruption on plasma B cell differentiation and the relative inefficiency of the guide used in the studies (PRDM1g-2; FIG. 42A). Therefore, the CCR5 locus was targeted as a "safe harbor" because: (a) it is not transcriptionally active in human B cells; (b) it is not required for plasma cell differentiation (FIG. 44A-44D); and (c) heterozygous and homozygous null mutations in CCR5 are innocuous to human carriers. Two AAV6 repair templates were designed: one contained MND-driven GFP and BAFF linked with a T2A self-cleaving peptide (CCR5-GFP-BAFF) and the other contained only an MND-BAFF expression cassette (CCR5-BAFF). Both donor constructs contained 800 bp homology arms around the CCR5 guide target site (FIG. 49A). Following RNP transfection and/or AAV transduction, cells were cultured using the three-step plasma cell culture system (FIG. 44A). As in earlier PRDM1-targeting experiments, persistent GFP expression was observed (mean=33% GFP$^+$) only in the condition containing both CCR5-targeting RNP and AAV (FIG. 49B, FIG. 50). While use of both donor templates led to BAFF secretion, B cells targeted by CCR5-BAFF (repair template solely containing BAFF) exhibited much higher levels of BAFF secretion (4.1 fold increase) relative to those targeted by CCR5-GFP-BAFF (template containing BAFF downstream of the T2A linkage) (FIG. 49C) To determine if this exogenous BAFF is functional, cell expansion and plasmablast formation was assessed following genome editing and in vitro differentiation. In the CCR5-BAFF edited culture that contained the highest concentration of exogenous BAFF, increases in cell number was observed, viability and percentage of CD19$^{low}$ CD38high plasmablasts relative to controls that lacked Cas9 RNP (FIG. 49D-49E). This is consistent with previous studies showing that BAFF promotes both human and murine B cell survival and differentiation. Taken together, these results show that Cas9 RNP- and AAV-mediated genome editing of primary human B cells can be used to generate functional, protein-secreting human plasma cells.

Figure 51C:
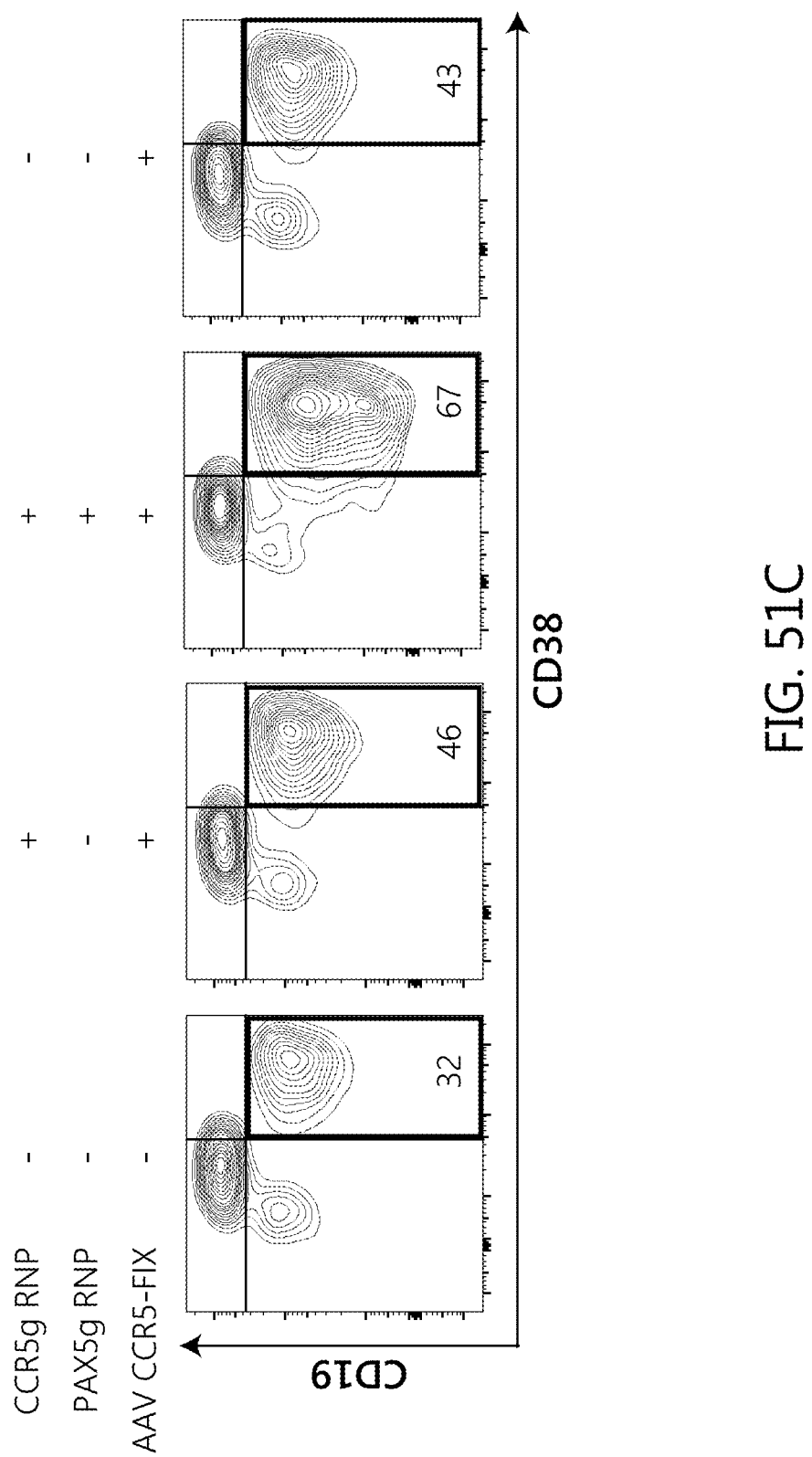
Figure 51D:
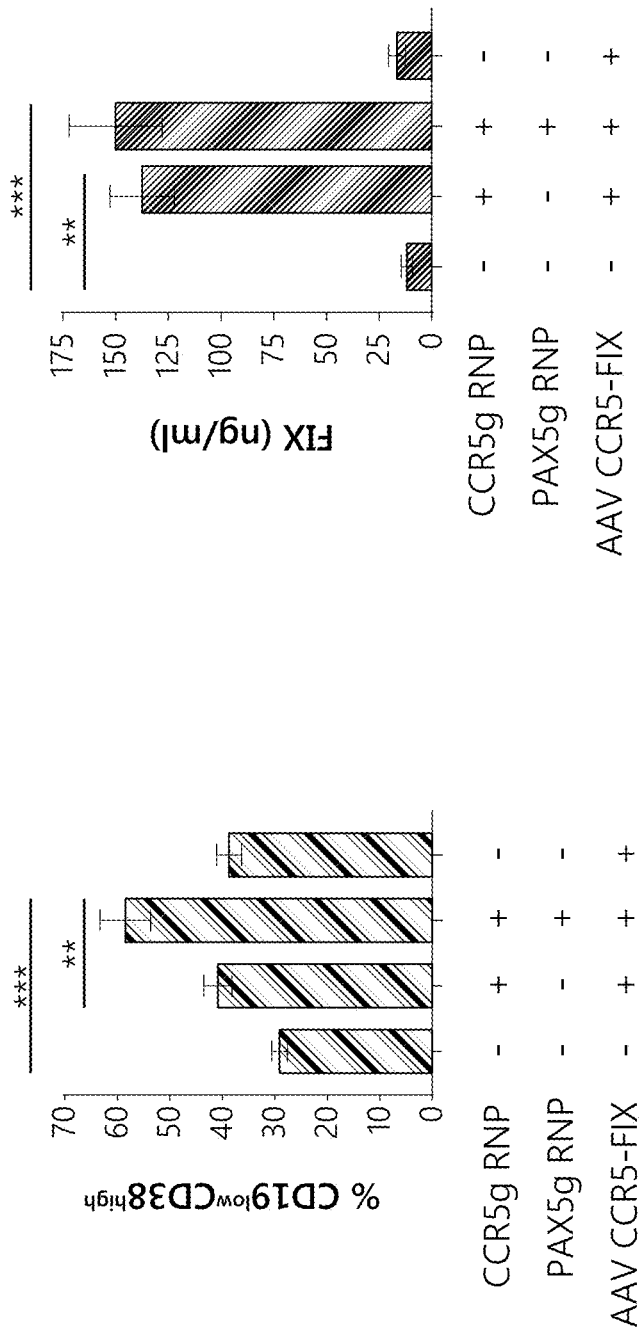
Figure 53A:
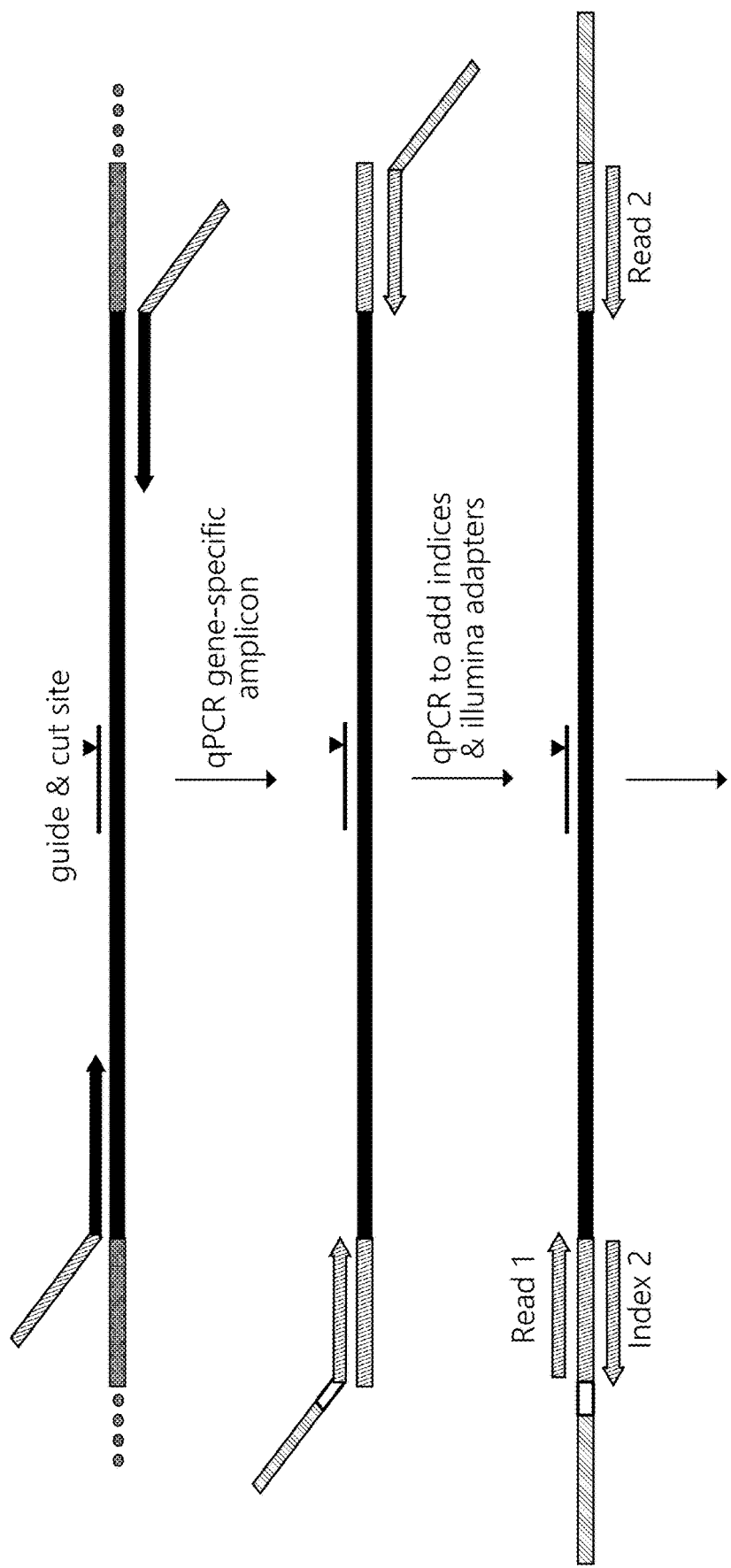
FIG. 53A-53D shows a description of library preparation and molecular analysis of gene disruption and ssODN editing studies. (53A) Genomic DNA flanking the cut site was initially amplified using sequence specific primers to introduce molecular adapters (orange bars). After bead-based purification to remove primers and enzyme, these sequences were amplified with primers containing molecular indices unique to each experiment (red bar) and cluster-generating sequences (purple bars). The samples were purified, pooled and analyzed using a NextSeq® 500 Mid-kit. Finally, the data were de-multiplexed, indel and HDR frequencies were quantified using the CRISPResso software package. (53B) An example from one replicate showing indel frequency and read-depth for the IRF4 guide. (53C) A histogram showing the percent insertion, deletion and substitutions plotted relative to the guide cut site (dotted line) in the 150 bp read sequence. (53D) The number of sequences corresponding to each indel size quantified in this experiment (negative and positive numbers represent deletions and insertions, respectively).
Figures 53B, 53C, 53D:
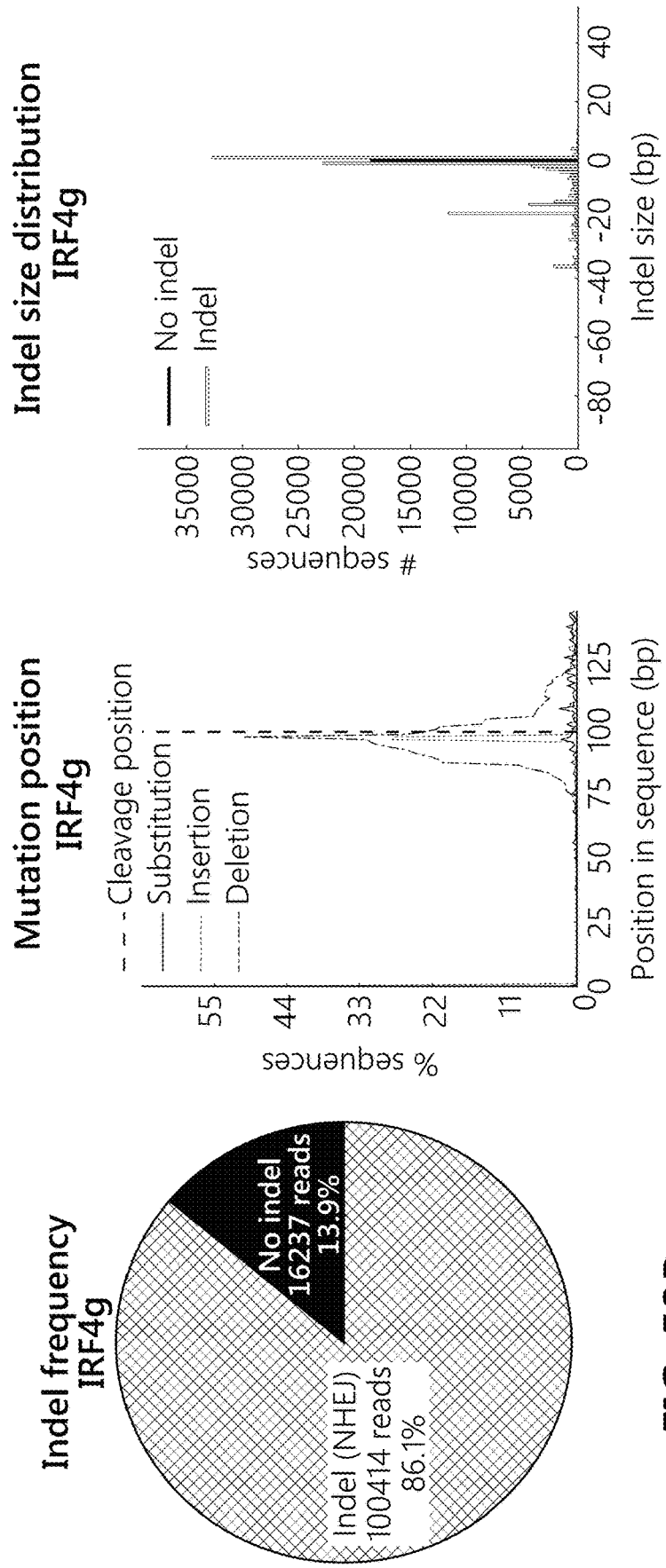
Figure 55:
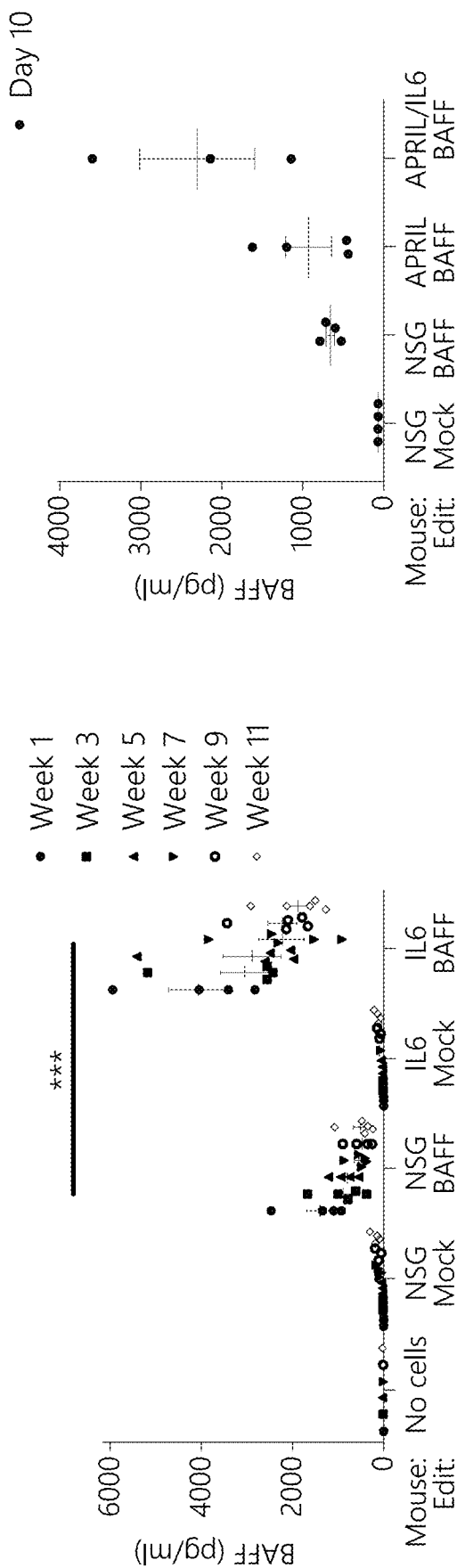
FIG. 55 shows data that demonstrates that in vivo delivery of human APRIL or IL6 enables increased long-term secretion by edited long-lived plasma cells. Primary human B cells were expanded in culture and edited as described in the alternatives herein. Following differentiation into plasma cells, 10 million were injected into NSG mice. Human BAFF was quantified using ELISA. Each dot represents data from an individual recipient mouse at the indicated time point.

Generation of FIX-Secreting Human Plasma Cells Via HDR-Mediated Integration at the CCR5 Locus Engineering exogenous protein production in plasma cells may have therapeutic applications in protein deficiency diseases such as hemophilia B, which is caused by a deficiency of FIX. To generate plasma B cells capable of secreting exogenous human FIX, an AAV vector containing an MND-driven FIX (codon-optimized FIX-R338L Padua variant) expression cassette was co-delivered, with the same flanking CCR5 homology arms as described above (CCR5-FIX), into primary human B cells with or without CCR5-targeting RNP (FIG. 51A). To also boost plasma cell differentiation in these cultures, PAX5-targeting RNPs were also co-delivered in a subset of CCR5-targeted cells. Although similar rates of HDR at the CCR5 locus across conditions were observed (FIG. 51B), following plasma cell differentiation increases in CD19$^{low}$ CD38$^{high}$ plasmablast percentages in the cultures that received CCR5- and PAX5-targeting RNPs were observed (FIG. 51C With or without delivery of PAX5-targeting RNPs, high levels of de novo FIX secretion in the cultures were detected (FIG. 51D). In addition, HDR cultures co-treated with both CCR5- and PAX5-targeting RNPs exhibited similar FIX production in dually-edited cell populations (FIG. 51D). These data demonstrate FIX production via targeted HDR in gene-modified human B cells and the use of multi-locus modifications to simultaneously drive plasma cell differentiation and de novo protein secretion.

BAFF-Secreting Human Plasma Cells Exhibited High Secretory Capabilities in NSG Mice It was then tested whether autocrine BAFF secretion can promote plasma cell survival in humanized mice. Gene-edited B cells were first generated using the CCR5-targeting RNP and the CCR5-GFP-BAFF AAV donor template. These cells were differentiated into plasma cells in vitro using the three-step culture system as before and subsequently transplanted into immuno-deficient NOD/SCID/gamma-c null (NSG) mice via intravenous infusion (FIG. 54A). Equal numbers of unedited plasma cells were also transplanted into parallel recipient mice as controls. Blood samples were collected at days 10 and 21 and serum human proteins were quantified by ELISA (FIG. 54A). As expected, human BAFF was detected in mice that received BAFF-expressing plasma cells, but not in mice that received unedited plasma cells (FIG. 54B). Also was predicted, human IgM and IgG were detected only in mice that received plasma cells but not in the untreated mice (FIG. 54C). It was also found that serum BAFF and IgM levels remained stable from day 10 to day 21, while IgG levels significantly increased in this period (FIGS. 54B, 54C). Most strikingly, significantly higher levels of serum IgM and IgG were observed in mice that received BAFF-expressing plasma cells compared to mice that received unedited plasma cells (FIG. 54C; difference in IgG levels at day 10 was not significant). These findings demonstrate that gene-modified plasma cells maintain stable secretory capacities in an immune-compromised murine setting for at least 3 weeks and support the hypothesis that expression of a survival factor such as BAFF via genome editing promotes plasma cell secretory function and/or survival in vivo.

As described, high rates of gene disruption in primary human B cells at multiple loci using CRISPR/Cas9 RNPs were accomplished. This method is applied to modeling the impact of genetic changes on human plasma B cell differentiation. It also demonstrates the use of Cas9 RNP in combination with ssODN or AAV6 repair templates to achieve high-efficiency HDR in B cells and to engineer secretion of functional and therapeutically relevant proteins. Importantly, gene-modified cells obtained a plasma cell phenotype and remained viable for several weeks in culture, providing evidence of utility for adoptive cell therapies using engineered human plasma cells.

Cas9-mediated disruption of PRDM1, IRF4, PAX5, or BACH2, which either promote (PRDM1, IRF4) or inhibit (PAX5, BACH2) plasma cell differentiation in mice, led to human B cell phenotypes consistent with these regulatory roles. The ability to easily disrupt genes or induce single-base changes using Cas9 RNP with or without ssODN-mediated HDR will facilitate further study of the impact of genetic changes on human B cell development. When combined with differentiation in vitro, this system is useful as a high-throughput model for studying genetic mutations that alter human B cell development, including somatic and/or germ-line mutations associated with a range of human B cell disorders (in B cell lymphoma and in autoimmune disorders including systemic lupus erythematosus); as well as a range of mechanistic studies designed to assess candidate genes identified by genome-wide association studies.

The results of the alternative methods described herein show that Cas9 RNP and ssODN or AAV co-delivery into B cells leads to high levels of HDR with minimal toxicity. Compared to double-stranded DNA transfection, which promotes apoptosis in primary B and T cells, single-stranded DNA delivery, either as ssODN or recombinant AAV, is relatively non-toxic to primary B cells. It is hypothesized that both approaches may be protected from cyclic GMP-AMP synthase (cGAS)-dependent type I interferon responses prevalent in primary B cells. Consistent with this, compared with dsDNA, ssDNA exhibits significantly lower binding affinity for the cytosolic DNA sensor cGAS.

The development of an alternative method for the efficient, site-specific introduction of transgenes via HDR opens the possibility of engineering plasma cells to act as autologous "cell factories," capable of delivering sustained, high doses of therapeutic proteins to subjects. As a proof of concept, plasma cells were engineered to secrete FIX. Deficiency of FIX is the cause of hemophilia B, a genetic disease characterized by blood clotting defects. Current treatment for hemophilia B is limited to protein replacement therapy, which is costly and non-curative. Recent gene therapy trials reported long-term FIX expression in patients after intravenous injection of a liver-tropic AAV8-FIX vector; however, pre-existing AAV neutralizing antibodies to all known AAV serotypes are prevalent in humans and greatly limit in vivo AAV transduction, making a significant group of patients with anti-AAV antibodies ineligible for treatment. In addition, systemic AAV delivery induces humoral immunity against AAV that prevents subsequent delivery, thus limiting AAV therapy to a single dose and/or necessitating use of alternative serotypes. Delivery of ex vivo gene-edited plasma cells producing FIX would remove the requirement for systemic AAV delivery and likely avoid limitations posed by AAV neutralizing antibodies.

In addition, immune responses to therapeutic proteins comprise a key unaddressed challenge. Based on evidence that B cell delivery can induce tolerance, an additional application of B cell editing technology is to deliver smaller numbers of short-lived B cells producing FIX, or other therapeutic proteins, with the goal of inducing tolerance to the secreted product.

The experiments above demonstrate high rates of locus-specific genome editing in primary human B cells. These engineered B cells retain the ability to differentiate into plasma cells ex vivo and secrete physiological doses of therapeutic proteins such as FIX. The ability to efficiently target specific loci enables us to drive B cell differentiation and secretory programs. Thus, creative multiplexing of gene disruption and HDR will provide ever more powerful tools to coordinately optimize protein secretion, cellular phenotype and long-term survival.

CRISPR/Cas9 Reagents and ssODNs

CRISPR guide targets at the CCR5, PRDM1, IRF4, PAX5, BACH2 loci were identified using an online MIT CRISPR design tool and the Broad Institute sgRNA design tool. A tracrRNA recognition sequence (5' GUUUUA-GAGCUAUGCU 3' (SEQ ID NO: 1)) was added to the 3' end of each selected guide target to form the complete synthetic crRNA sequence. As shown in Table 2 below are guide sequences used in the alternative herein:

TABLE 2

Guide RNA sequences for CCR5, PRDM1, IRF4, PAX5, and BACH2. Each synthesized crRNA comprises a protospacer immediately followed by a tracrRNA binding sequence.

| Guide designation | Protospacer | tracrRNA binding sequence |
|---|---|---|
| CCR5g | CAAUGUGUCAACUCUUGACAGUUUUAGAGCUAUGCU | |
| PRDM1g-1 | AGGATGCGGATATGACTCTG | |
| PRDM1g-2 | GGGGAGCGAGTGATGTACGT | |
| IRF4g | CAAGCAGGACTACAACCGCG | |
| PAX5g | UGUGAAUGGACGGCCACUCC | |
| βACH2g | GUUCCUGCGCAUGCACAACC | |

As shown in the Table 2 above are the sequences for CCR5G (SEQ ID NO: 20), PRDM1g-1 (SEQ ID NO: 21), PRDM1g-2 (SEQ ID NO: 22), IRF4g (SEQ ID NO: 23), PAX5G (SEQ ID NO: 24), BACH2g (SEQ ID NO: 25) and the tracrRNA binding sequence (SEQ ID NO: 26). The crRNA guides were synthesized by IDT® with additional modifications: phosphorothioate linkages between the four nucleotides on each end, as well as 2'O-methyl groups on the three nucleotides on each end. The tracrRNA with proprietary chemical modifications, as well as the recombinant Cas9 nuclease were also purchased from IDT®. In some alternatives, the guide sequence comprises a sequence set forth in any one of SEQ ID NO: 2-13, 20-25 or 63-112.

Prior to delivery of the nuclease into cells, the crRNA and tracrRNA were mixed at an equimolar ratio. The mixture was heat-shocked at 95° C. for 5 minutes and then incubated at room temperature for 30-60 minutes to allow crRNA:tracrRNA hybrids to form. Next, the crRNA:tracrRNA hybrids were mixed with the Cas9 nuclease at a 1.2:1 molar ratio and incubated at room temperature for 10-20 minutes to allow Cas9:crRNA:tracrRNA complexes to form. The Cas9 ribonucleoprotein (RNP) complexes were then delivered into cells by electroporation.

Single-stranded oligonucleotides (ssODNs) were commercially synthesized by IDT® (Ultramer® DNA Oligonucleotides) with phosphorothioate linkages between the three nucleotides on each end.

Production of Recombinant AAV Vectors

The self-complementary AAV GFP (scAAV GFP) construct contains an MND promoter, enhanced green fluorescence protein (eGFP) and an α globin polyadenylation (pA) signal in an scAAV plasmid backbone. In contrast, all AAV donor templates designed for HDR experiments were cloned into single-stranded AAV plasmid backbones. PRDM1-GFP (400 bp homology arms) contains an MND promoter followed by eGFP and an SV40 pA signal. This MND-eGFP-SV40 pA cassette is flanked by two 400 bp sequences homologous to PRDM1, with the 5' arm spanning from 106,104,721 to 106,105,120 and the 3' arm spanning from 106,105,124 to 106,105,523 on chromosome 6, with reference to the UCSC December 2013 human genome assembly (GRCh38/hg38). PRDM1-GFP (1 kb homology arms) contains an identical MND-eGFP-SV40 pA cassette that is flanked by two 1 kb sequences homologous to PRDM1, with the 5' arm spanning from 106,104,121 to 106,105,120 and the 3' arm spanning from 106,105,124 to 106,106,123 on chromosome 6 (GRCh38/hg38). BFP-noHA contains MND promoter-driven blue fluorescent protein (mTagBFP; Evrogen) and an SV40 pA tail without genomic homology. CCR5-GFP-BAFF comprises an MND promoter-driven eGFP and T2A cleavage peptide linking a BAFF coding sequence, which is preceded by an IL2 signal sequence (IL2ss), and an SV40 pA tail. This cassette is flanked by a 823 bp 5' CCR5 homology arm, spanning from 46,372,387 to 46,373,209, and a 804 bp 3' CCR5 homology arm, spanning from 46,373,221 to 46,374,024 on chromosome 3 (GRCh38/hg38). CCR5-BAFF comprises identical CCR5 homology arms flanking a similar cassette, to the exclusion of eGFP and the T2A peptide (i.e. BAFF directly under the MND promoter). Finally, CCR5-FIX substitutes a FIX coding sequence and a succeeding modified woodchuck hepatitis virus posttranscriptional regulatory element (WPRE3) for the IL2ss and BAFF coding sequence in CCR5-BAFF.

AAV stocks were produced as known in the art. The AAV vector, serotype helper and HgT1-adeno helper plasmids were transfected into HEK293T cells. Cells were harvested 48 hours later, lysed by 3 freeze-thaw cycles, and the cell lysate was treated with benzonase. Virions with recombinant AAV genomes were purified using an iodixanol density gradient.

All multiplicity of infection (MOI) calculations were based on qPCR-based titers of AAV genomes using ITR specific primers and probe.

Primary Human CD19+ B Cell Genome Editing

Peripheral blood mononuclear cells (PBMCs) were collected from whole blood of consented donors and cryopreserved. After thaw, PBMCs were treated with 1×ACK buffer; CD19+ B cells were subsequently isolated from PBMCs by negative selection using a human B cell isolation kit (Miltenyi Biotec®, Auburn, CA) and cultured in Iscove's modified Dulbecco's medium (IMDM; Thermo Fisher Scientific®) supplemented with 10% fetal bovine serum and 55 µM beta-mercaptoethanol at 1-1.5×10$^6$ cells/ml. B cells were activated with 100 ng/ml of recombinant human MEGACD40L® (Enzo Life Sciences®), 1 µg/ml of CpG oligodeoxynucleotide 2006 (Invitrogen®), 50 ng/ml of IL2 (Peprotech®), 50 ng/ml of IL10 (Peprotech®) and 10 ng/ml of IL15 (Peprotech®) for two days. Cells were then electroporated with Cas9 RNP complexes using the Neon Transfection System (ThermoFisher Scientific®) as follows. Cells were washed with PBS and resuspended in Neon Buffer T. 30 pmol Cas9 RNP per 3×10$^5$ cells was added to the resuspension so that the final cell density was 3×10$^7$ cells/ml. Cells were electroporated (1700 V, 20 ms, 1 pulse) in 10-µl Neon tips, and then transferred into pre-warmed B cell culture medium with MEGACD40L®, CpG, IL2, IL10 and IL15 and cultured at 1.5×10$^6$ cells/ml. For samples transfected with an ssODN donor template, ssODN was transfected concurrently with Cas9 RNP at the specified amount. For samples transduced with AAV, AAV was added to the culture immediately after electroporation at MOIs ranging from 10,000 to 100,000. Culture volume was doubled 24 hours after electroporation, and medium was replenished every two to three days thereafter to maintain a cell density of 1×10$^6$ cells/ml. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days.

Flow Cytometry

Flow cytometric analysis was done on an LSR II flow cytometer (BD Biosciences®) and data were analyzed using FlowJo software (TreeStar). To assess fluorochrome expression in B cells, flow gates were drawn on FSC/SSC populations corresponding to live cell sizes and singlets were defined using FSC-W/FSC-H gates; BFP$^+$ or GFP$^+$ gates were then used to define fluorescent cells (FIG. 52A). Viabilities of these cells were also confirmed by staining them separately with 4,6-Diamidino-2-phenylindole (DAPI) and subsequently quantifying percentages of DAPI-live cells by flow cytometry (FIG. 52B). To assess B cell surface marker expressions, cells were stained with fluorophore-conjugated antibodies: CD19-PECy7 (clone HIB19, eBioscience®), CD27-APC (clone 0323, Life Technologies®), CD38-PerCPCy5.5 (clone HIT2, BD Biosciences®) or CD38-FITC (clone T16, Beckman Coulter®), CD138-Alexa Fluor 700 (clone MI15, BioLegend®), IgD-PE (clone IA6-2, BD Biosciences®), IgM-Pacific Blue (clone MHM-88, BioLegend®). Dead cells were excluded using Fixable Live/Dead stain-Alexa Fluor 350 (LifeTechnologies®) (FIG. 52C for the general gating strategy used for analyzing B cell immunophenotypes).

Plasma Cell Differentiation Culture

Plasma cells were differentiated in vitro using a three-step culture system as known in the art. CD19+ B cells isolated from PBMCs were activated for 2 days with MEGACD40L® (100 ng/ml), CpG (1 µg/ml), IL2 (50 ng/ml), IL10 (50 ng/ml) and IL15 (10 ng/ml) and gene-edited as outlined above. Cells were then expanded for another 5 days in the same cocktail. Next, cells were washed with 1×PBS and seeded in medium with IL2 (50 ng/ml), IL6 (50 ng/ml), IL10 (50 ng/ml) and IL15 (10 ng/ml) for 3 days. At day 8 after gene-editing, cells were washed with 1×PBS and seeded in medium with IL6 (50 ng/ml), IL15 (10 ng/ml) and human interferon-α 2B (100 U/ml, Sigma-Aldrich®) for 3 days to stimulate plasma cell differentiation. At day 11 after gene-editing, cell phenotypes were analyzed by immunofluorescence.

In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days.

Molecular Analyses of Gene Disruption and Single-Nucleotide HDR

Total genomic DNA was isolated from 0.2-1.0×10$^6$ cells using a DNeasy Blood & Tissue Kit (Qiagen). To assess gene disruption using the T7 endonuclease 1 assay, guide target genomic regions were first amplified using either AccuPrime™ Pfx DNA Polymerase (ThermoFisher Scientific®) or PrimeSTAR® GXL DNA Polymerase (Takara Bio) with primers about 250-350 bp away from the guide target site (See table 3 below).

TABLE 3

Primers used for molecular analysis of gene-edited B cells.

| Assay | Genomic target | Forward primer | Reverse primer | Probe |
|---|---|---|---|---|
| T7E1 assay | CCR5g | ATGTGAAGCAAATCGCAGCC | TCCCGAGTAGCAGATGACCA | |
| | PRDM1g-1 | TAGCATTTAAAAACCTTGCTTCTTTTCAAG | TACAGATTCTCAGAGGTTTTCAGAGA | |
| | PRDM1g-2 | CAGTCTAAAGCAACCGAGCAC | CTTGGGGTAGTGAGCGTTGTA | |
| Illumina sequencing | CCR5g | GGCAACATGCTGGTCATCCT | GGTGACCGTCCTGGCTTTTA | |
| | PRDM1g-1 | CTCTCAGAAGGAGCCACAGG | TTGGTGGCATACTTGAAAAGC | |
| | PRDM1g-2 | CCCCTCACATCAGAAAAGGA | CTGGAGCTCTTGAGGCTTTG | |
| | IRF4g | AGATCGACAGCGGCAAGTA | GAGGCCTCCTTTCCTCCTC | |
| | PAX5g | CACAGCGGTGCTTCTCCTAT | GCCTCGAGCTACTGCCTTTA | |
| | BACH2g | TGAGGGATTCGGGACAATAG | AGTTCTCGCAGTCCTCGTGT | |
| In-out ddPCR | CCR5 (HDR) | GGTATGATGCTTAGAACAGTGAT | CCATATTCTGCTGTTCCAACG | CCTGGGCAACATAGTGTGATC |
| | ActB | ACTCTGCAGGTTCTATTTGC | AATGATCTGAGGAGGGAAGG | ATCAAGGTGGGTGTCTTTCC |

As shown in Table 3 above, the forward primers for CCR5g, PRDM1g-1, and PRDM1g-2 for the T7E1 assay are SEQ ID NO: 27, 28 and 29, respectively. The reverse primers for CCR5g, PRDM1g-1, and PRDM1g-2 for the T7E assay are SEQ ID NO: 30, 31 and 32 respectively. As shown in table 3, the forward primers for CCR5g, PRDM1g-1, PRDM1g-2, IRF4g, PAX5g, and BACH2g are SEQ ID NO: 33, 34, 35, 36, 37 and 38 respectively, for the sequencing in the Illumina sequencing. The reverse primers for CCR5g, PRDM1g-1, PRDM1g-2, IRF4g, PAX5g, and BACH2g are SEQ ID NO: 39, 40, 41, 42, 43 and 44, respectively, for in the Illumina sequencing. The forward primers for CCR5 (HDR) and ActB are SEQ ID NO: 45 and 46, respectively, for the in-out ddPCR. The reverse primers for CCR5 (HDR) and ActB are SEQ ID NO: 47 and 48, respectively, for the in-out ddPCR. The probe for CCR5 comprises SEQ ID NO: 49 and the probe for ActC comprises SEQ ID NO: 50.

PCR products were then purified using NucleoSpin Gel and PCR Clean-up kit (Macherey-Nagel®). 200 ng purified PCR product were denatured and re-annealed in 1×NEB Buffer 2 (New England Biolabs®, Ipswich, MA) in 19 µl total volume, after which 10 U of T7 endonuclease I (New England Biolabs®) was added to the re-annealed PCR product and the samples were incubated for 1 hour at 37° C. The reactions were immediately run on an agarose gel for imaging.

To quantify frequencies of on-target indels or nucleotide substitutions, allelic modifications by sequencing was assessed (FIG. 53A-53D). Locus-specific primers were first designed (Table 3) within 150 bp from each guide target site, each primer also containing an adaptor sequence on the 5' end. To prepare samples for sequencing, amplification was performed each using qPCR starting with 250 ng of genomic DNA using PrimeSTAR® GXL Polymerase with SYBR Green I Nucleic Acid Gel Stain until reaction reached the exponential phase. The samples were purified with Agencourt® AMPure® XP and amplified using qPCR for another 6 cycles with primers that contain unique index sequences for each experimental condition, as well as the p5 and p7 cluster generating sequences. The primers were removed using Agencourt® Ampure® XP and purity of the amplicon was confirmed using a 4-12% Novex® TBE PAGE Gel. Next, amplicons from each locus and experiment were pooled at equimolar concentrations and sequenced on a NextSeq® 500 in paired-end run mode with a NextSeq® 500/550 Mid Output Kit v2. Reads were filtered for quality and grouped by sample index. Next, 112,000 reads per condition and experiment were aligned to the wild type sequences of each amplicon using the CRISPResso[57] aligner and analysis suite (the aligner runs a variant of the Needleman-Wunsch algorithm). The minimum average read quality score (phred33) was set to 30 and indels/substitutions were specifically quantified within a 30 bp window around each guide target.

To calculate editing rates at the CCR5 locus, "in-out" ddPCR was performed with forward oligo binding the CCR5 locus outside the homology region and reverse within the AAV insert. A similar size amplicon (1.3 kb) was generated for ActB gene to serve as a control. Probes for both amplicons were labeled with FAM and reactions for each were performed in different wells. The oligo and probe sequences are included in Table 3. The PCR reactions were partitioned into droplets using droplet-generating oil for probes on a QX200 Droplet Generator. Amplification was performed using ddPCR Supermix for Probes without UTP (Bio-Rad®), 900 nM of primers and 250 nM of Probe. 50 ng of genomic DNA was used in a 25 µl amplification reaction containing 1% DMSO and run according to manufacturer's directions. The droplets were scanned using the QX200 Droplet Digital PCR System (Bio-Rad®) and analyzed using QuantaSoft software. The editing rates were calculated as a ratio of the copies/l from CCR5/ActB positive droplets.

ELISA 3 days prior to measuring culture protein levels, cells were collected, washed with PBS and then resuspended in new culture medium at 1×10$^6$ cells/ml. After 3 days, the culture supernatant was collected and Ig or recombinant protein secretion levels were determined by enzyme-linked immunosorbent assay (ELISA). IgG and IgM concentrations were measured using Human IgG total ELISA Ready-SET-Go® and Human IgM total ELISA Ready-SET-Go® kits (eBioscience®, San Diego, CA). BAFF concentrations were measured using a Human BAFF/BLyS/Quantikine ELISA Kit (R&D Systems®, Minneapolis, MN), and FIX concentrations were measured using a FIX Human ELISA Kit (Abcam®, Cambridge, MA).

Western Blot

TMD8 cells were mock treated or transfected with 30 pmol of either of the PRDM1-targeting RNPs. After five additional days of culture, cells were lysed in RIPA and the lysate was run on a NuPAGE® 4-12% Bis-Tris protein gel. Cell Signaling Blimp-1/PRDI-BF1 Rabbit mAb #9115 was used as the primary antibody for the PRDM1 locus and Licor IRDye® 800CW Goat anti-Rabbit IgG (H+L) was used as the secondary antibody.

Statistical Analysis

Statistical analyses were performed using Graphpad Prism® 7 (GraphPad®, San Diego, CA). p-values between two groups were calculated using the unpaired two-tailed t-test, while p values in multiple comparisons were calculated using one-way ANOVA with the Sidak correction as specified. Values from independent experiments are shown as means±SEM.

Data Availability

Accession codes: all sequencing data are accessible at the NCBI Sequence Read Archive through the following study accession number: SRP113557.

More Alternatives

The ability to engineer primary human B cells to differentiate into long-lived plasma cells and secrete a de novo protein may allow the creation of novel plasma cell therapies for protein deficiency diseases and other clinical applications. Methods for efficient genome editing of primary B cells isolated from peripheral blood were initially developed as described in the alternatives herein. By delivering CRISPR/Cas9 ribonucleoprotein (RNP) complexes under conditions of rapid B cell expansion, site-specific gene disruption at multiple loci in primary human B cells was achieved (with editing rates up to 94%). This method was used to alter ex vivo plasma cell differentiation by disrupting developmental regulatory genes. Next, RNPs were co-delivered with either single-stranded DNA oligonucleotide or adeno-associated viruses containing homologous repair template. Using either delivery method, targeted sequence integration at high efficiency (up to 40%) via homology-directed repair was achieved. This method enabled engineering of plasma cells to secrete factor IX (FIX) or B-cell activating factor (BAFF) at high levels. Finally, as shown in the alternatives herein, introduction of BAFF into plasma cells promotes their engraftment into humanized mice. The results as shown in the alternatives herein, highlight the utility of genome editing in studying human B cell biology and demonstrate a novel strategy for modifying human plasma cells to secrete therapeutic proteins.

Long-lived plasma cells stably reside in the bone marrow for decades and secrete large quantities of antibodies. Consequently, plasma cells engineered to produce de novo proteins have the potential to be curative therapies for protein deficiency diseases, prophylaxis for infectious diseases and many other applications. However, the development of plasma cell therapeutics has been limited by technical challenges in the in vitro modification, culture, expansion and differentiation of primary human B cells. B cells can be transduced at high rates by recombinant adenovirus or Epstein-Barr virus (EBV) vectors, which deliver transgenes as episomes. However, episomal DNA expression is lost over time, limiting use of these vectors in applications that require long-term transgene expression. Unlike non-integrating vectors, gamma retrovirus (γRV) and lentivirus (LV) randomly integrate into the host genome and can be used to introduce stably expressing transgenes. However, these vectors are inefficient at transducing primary human B cells. LV that employ alternative envelopes, including that of baboon retrovirus, measles virus, or gibbon-ape leukemia virus exhibit higher B cell transduction rates (up to ~50%), but have low viral titers that make large-scale production challenging. Because γRV and LV vectors do not efficiently transduce B cells while transduction by non-integrating vectors results in only transient transgene expression, neither platform is currently effective for delivering long-term expression of exogenous genes to B cells on a therapeutic scale.

An alternative method for introducing stable protein expression is genome editing via homology-directed repair (HDR). As described herein, in several alternatives, genome editing may be performed by HDR. Following cleavage by an engineered site-specific nuclease, DNA double-strand breaks are resolved through non-homologous end joining (NHEJ), an error-prone DNA repair pathway that typically leads to variable insertions or deletions (indels), or HDR, which repairs DNA by copying a homologous donor template. Delivery of exogenous DNA flanked by DNA homologous to the genomic sequence around the break site can lead to incorporation of the exogenous sequence in a site-specific manner. HDR-mediated genome editing in B cells may have several advantages over viral vector transduction for therapeutic applications, including decreased risk of insertional mutagenesis and sustained transgene expression. As described herein, high-efficiency HDR delivery of therapeutic transgenes to hematopoietic cells including primary human T cells and hematopoietic stem cells may be achieved, which was also a technique that is performed by others, but similar approaches are yet to be applied in modification of primary human B cells.

The clustered regularly interspaced short palindromic repeats (CRISPR)/CRISPR-associated protein 9 (Cas9) system is an RNA-guided nuclease platform that is easily engineered to efficiently target specific sites in the genome for cleavage, generating double-strand DNA breaks. The use of site-specific nucleases for gene disruption or HDR in B cells is currently limited to transformed or lymphoma-derived cell lines and murine models and has required plasmid- or LV-based CRISPR/Cas9 delivery. Here, as described in the alternatives herein, is high-efficiency genome editing in human peripheral blood B cells (75-90% gene disruption or 10-40% HDR) by delivering CRISPR/Cas9 ribonucleoprotein (RNP) complexes alone or in combination with single-stranded DNA oligonucleotide (ssODN) or adeno-associated virus (AAV) repair templates, respectively. As shown in the alternatives herein, edited primary B cells can subsequently be differentiated in culture into plasma cells that produce physiological doses of therapeutic proteins including human factor IX (FIX).

Conditions for Expansion of Primary Naïve Human B Cells

Rapid cell cycling and/or persistence in the S/G2 phases of the cell cycle promote HDR in both cell lines and primary hematopoietic cells. Based on previous reports demonstrating rapid expansion of primary human B cells ex vivo, a combination of stimulants were initially used (hereafter called "B cell activation cocktail") that included artificially oligomerized CD40 ligand (MEGACD40L®; two linked CD40L trimers) in association with CpG, IL-2, IL-10, and IL-15. Primary human CD19$^+$ B cells from peripheral blood mononuclear cells (PBMCs) were isolated and cultured them for 13 days with this B cell activation cocktail. This treatment resulted in a ~36-fold expansion of B cells (FIG. 40), while preserving viability at >60% (FIG. 41). Most cells maintained a naïve B cell phenotype (CD27$^-$CD138$^-$CD38$^{low/-}$CD19$^{high}$IgM$^+$IgD$^+$; FIG. 40C) over the 13-day culture; however, IgD expression was gradually downregulated (FIG. 40C), demonstrating some ex vivo skewing due to stimulation. Together, these data demonstrate that the B cell activation cocktail facilitates rapid cycling of naïve and activated primary human B cells.

Cas9-Mediated Disruption of CCR5 and PRDM1 in Primary Human B Cells

To assess the efficiency of Cas9-induced indels in B cells, CRISPR guide RNAs (gRNAs) were designed that target CCR5 (which is not expressed in human B cells and has no known significance in plasma cell development) or PRDM1 (encoding BLIMP1, a protein required for B cell differentiation into plasma cells). After optimizing electroporation using mRNA (FIG. 41), 30 pmol Cas9-guide ribonucleoprotein (RNP) complexes were transfected into B cells, cultured them for five additional days under activating conditions and extracted total genomic DNA to assess nuclease-induced indels using the T7 endonuclease 1 assay (FIG. 42A). Sequencing confirmed on-target indels and revealed that the RNPs induced high indel frequencies at each guide target site (43-84%; FIG. 42A). Western blot also verified concomitant PRDM1 protein reduction in the PRDM1-expressing TMD8 lymphoma cell line (FIG. 47A; ~65% knockdown). Finally, it was discovered that B cells remained viable despite these genome modifications (FIG. 47B). These data show that high-efficiency Cas9-mediated gene disruption is achievable in primary human B cells.

HDR-Mediated Single-Nucleotide Substitution at the PRDM1 Locus Using an ssODN Donor Template Cas9-induced DNA lesions can be seamlessly repaired via the HDR pathway in the presence of a donor template with homology sequences flanking the lesion. An ssODN was initially tested as a donor template based on promising results in other cell types. A 120-base ssODN containing asymmetric homology arms (89 bases 5' and 30 bases 3') was designed that flank the PRDM1g-2 target site, with a single-nucleotide change at the $90^{th}$ position that mutates the last nucleotide of the protospacer adjacent motif (PAM; GGG to GGT; FIG. 42B). This single nucleotide change was designed to both prevent Cas9-mediated cleavage of the repaired sequence and to serve as a molecular marker for HDR. In this experiment, primary human B cells were activated for two days and then transfected with Cas9 RNP in conjunction with various doses of the ssODN. Two and five days following transfection, cells transfected with ≤30 pmol ssODN had comparable viabilities to Cas9 RNP transfected control cells (FIG. 42C). In cells receiving 15 or 30 pmol ssODN, sequencing of the PRDM1 target region on day 5 post-transfection revealed 20-22% of alleles had undergone HDR while another 37-41% had indels (FIG. 42D), an overall editing rate marginally higher than that observed in the Cas9 RNP control (FIG. 42D). Thus, ssODN donor templates can be used to achieve high rates of HDR in primary human B cells with low cytotoxicity.

Cas9-Mediated Disruption of Genes that Regulate Plasma Cell Development

It was then investigated whether Cas9-induced gene disruption can be used to study gene roles in human plasma cell development and antibody production. An experimental workflow was developed that includes inducing NHEJ-mediated gene disruption in activated naïve human B cells using Cas9 RNPs and subsequently differentiating naïve B cells into plasma cells (CD19$^{low}$CD38$^{high}$CD27$^+$ CD138$^+$) using a three-step plasma cell culture system (see FIG. 44A). As a proof of concept, four genes encoding transcription factors previously reported to regulate plasma cell development in murine studies were studied: IRF4 and PRDM1/BLIMP1 are required for plasma cell differentiation (FIG. 44B), while PAX5 and BACH2 antagonize plasma cell differentiation in mice (FIG. 44B). CRISPR guides targeting each of these four genes were designed, transfected primary B cells with Cas9 RNP targeting each gene independently and subsequently induced in vitro plasma cell differentiation (FIG. 44A). As a control, cells were also transfected with Cas9 RNPs targeting CCR5. Following differentiation, significantly lower percentages of CD19$^{low}$CD38$^{high}$ and CD27$^+$CD138$^+$ plasma cells in cultures transfected with PRDM1- or IRF4-targeting RNPs compared to cells transfected with CCR5-targeting RNP or mock transfected cells were detected (mean indel percentages=89%, 83% and 92% at the PRDM1, IRF4 and CCR5 target sites, respectively; FIG. 44C, 44D). As antibody secretion is a major function of plasma cells, IgM and IgG levels were measured in cell culture supernatants by enzyme-linked immunosorbent assay (ELISA) and found IgG to be significantly decreased in the PRDM1- and IRF4-targeted B cell cultures (FIG. 44E). Together, as predicted, these data imply that both PRDM1 and IRF4 are required for human plasma cell differentiation and antibody production. Conversely, it was observed that there was significant increases in the percentages of plasma cells in cultures transfected with either PAX5 or BACH2-targeting RNPs (mean indel percentages=80% and 86% at the PAX5 and BACH2 target sites, respectively; FIG. 44C, 44D). Concomitant increases in IgM and IgG secretion in PAX5-targeted cultures were also observed (FIG. 44E). Again, as predicted, these data indicate that Cas9-mediated disruption of PAX5 or BACH2 enhances human plasma cell differentiation. Further, the IgG/IgM ratio in BACH2-targeted B cell cultures was markedly lower than mock or CCR5-targeted cultures (FIG. 44E, FIG. 45A) and plasmablasts in PAX5-targeted cultures exhibited decreased surface CD19 expression (FIG. 45B), both consistent with previous studies in mice. Taken together, these results demonstrate that CRISPR/Cas9-induced gene disruption in primary B cells is useful for interrogating gene products that may modulate human plasma cell development and function.

Site-Specific HDR at the PRDM1 Locus Using Co-Delivery of RNP and AAV Donor Template HDR using ssODN donor templates is not suitable for delivering payloads larger than ~400 bases due to current limitations of the fidelity of ssODN synthesis. In contrast, adeno-associated virus (AAV) can package up to ~4.7 kilobases (kb) of ssDNA donor template. Many have used AAV to deliver candidate HDR templates leading to high levels of HDR in multiple cell types and at a variety of loci. Of note, there is no published data regarding the capacity of AAV to transduce primary human B cells. To investigate AAV transduction efficiency in human B cells, a self-complementary AAV (scAAV) with a green fluorescent protein (GFP) coding sequence driven by MND, a robust retroviral-derived ubiquitous promoter was designed. Activated B cells were transduced with this vector packaged using various serotypes and quantified GFP expression two days post transduction by flow cytometry. Regardless of serotype, it was observed that there was minimal loss of cell viability following viral exposure (FIG. 51A). It was observed that the highest percentage of GFP$^+$ cells (mean=43%) and highest mean fluorescence intensity in B cells were transduced with AAV serotype 6 (FIG. 47A).

Because the packaging size of single-stranded AAV (ssAAV) is greater than scAAV, the efficacy of HDR-mediated integration of larger payloads by delivering ssAAV into B cells was next assessed. Initially, an AAV6 donor template containing an MND-driven GFP cassette flanked by 400 bp homology arms at the PRDM1g-2 target site (PRDM1-GFP was designed; FIG. 47B). The PAM was not included in the repair template, thereby rendering the repaired sequence non-cleavable by Cas9 (FIG. 47B). After activation and electroporation with or without Cas9 RNP, B cells were transduced with AAV6 PRDM1-GFP at various MOI and cultured for 11 additional days with the same activating factors. Although it was initially observed that a 30% viability loss at the highest AAV dose, these cultures eventually recovered and exhibited comparable viabilities by day 11 (FIG. 46B). At the highest AAV MOI, it was observed that there was persistent GFP expression in ~10% of cells that received both the PRDM1-targeting RNP and AAV repair template, while 2% of cells that were treated with the AAV alone had persistent GFP expression (FIG. 47C). In addition, cells were co-treated with the PRDM1-targeting RNP and a non-targeting AAV BFP control (MND-BFP without homology arms; BFP-noHA) and observed ~1% BFP expression at the endpoint (FIG. 47C), indicating that the majority of GFP expression resulting from co-delivery of PRDM1-targeting RNP and PRDM1-GFP was likely driven by HDR-mediated integration. It was also found that higher AAV doses correlated with increased percentages of GFP+ cells. Finally, it was found that increasing homology arm lengths from 400 bp to 1.0 kb did not lead to higher levels of HDR (measured as persistent GFP expression; FIG. 48A, 48B). Together, these data support the conclusion that co-delivery of Cas9 RNP and AAV can lead to efficient, targeted genomic integration of transgene, likely via the HDR pathway.

Generation of Active FIX-Secreting Human Plasma Cells Via HDR-Mediated Integration at the CCR5 Locus Engineering exogenous protein production in plasma cells may have therapeutic applications in protein deficiency diseases such as hemophilia B, which is caused by a deficiency of FIX. To assess whether primary B cells could be engineered to secrete active proteins with predicted functionality, HDR-mediated knock-in strategy was used to engineer de novo expression of FIX. Of note, our HDR studies targeting the PRDM1 locus (described above) were anticipated to underrepresent HDR efficiencies due to the negative impact of PRDM1 disruption on plasma B cell differentiation and the relative inefficiency of the guide used in the studies (PRDM1g-2; FIG. 42A). Therefore, the CCR5 locus as a "safe harbor" was targeted because: (a) it is not transcriptionally active in human B cells; (b) it is not required for plasma cell differentiation (FIG. 44A-D); and (c) heterozygous and homozygous null mutations in CCR5 are innocuous to human carriers. To generate plasma B cells capable of secreting exogenous human FIX, an AAV vector containing an MND-driven FIX (human codon-optimized FIX-R338L Padua variant) expression cassette was co-delivered, with the same flanking CCR5 homology arms as described above (CCR5-FIX), into primary human B cells with or without CCR5-targeting RNP (FIG. 49A). To also boost plasma cell differentiation in these cultures, PAX5-targeting RNPs were also co-delivered in a subset of CCR5-targeted cells. Although it was observed that similar HDR rates of ~15-20% at the CCR5 locus across conditions (FIG. 49B), following plasma cell differentiation it was observed that increases in CD19$^{low}$ CD38high plasmablast percentages in the cultures that received both CCR5- and PAX5-targeting RNPs (FIG. 49C). With or without delivery of PAX5-targeting RNPs, high levels of de novo FIX secretion were detected in the cultures (FIG. 49D). In addition, dual-edited HDR cultures co-treated with both CCR5- and PAX5-targeting RNPs exhibited similar levels of FIX production (FIG. 49D).

To assess whether the FIX produced by gene-edited plasma cells is active, cultures were supplemented with vitamin K1 to enable vitamin K-dependent post-translational carboxylation of FIX and subsequently measured FIX activity levels using a chromogenic assay. It was found that FIX activity was significantly higher in the vitamin K1-supplemented, gene-edited plasma cell cultures (FIG. 49E). Despite low levels of activity in the BFP-noHA negative controls, this background was absent when FBS was completely removed from cultures, suggesting that this is likely non-specific assay background originating from murine FIX present in FBS. More importantly, FIX produced by gene-edited plasma cells exhibited high specific activity (~63 IU/mg protein) in a vitamin K-dependent manner (FIG. 49F). These data demonstrate production of highly functional FIX via targeted HDR in gene-edited human B cells using Cas9 RNP and AAV and illustrate the possibility of multi-locus modifications to simultaneously drive plasma cell differentiation and de novo protein secretion.

Engineered BAFF Secretion Via HDR Improves Plasma Cell Survival In Vitro

In order to use gene edited plasma cells in a therapeutic setting, their long-term survival will be required. One strategy to improve plasma cell survival is to engineer cells that secrete survival factors in an autocrine manner. As a first test of this approach, HDR-mediated knock-in strategy of the alternatives herein was used to engineer de novo expression of the B-cell activating factor (BAFF). Two AAV6 repair templates were designed: one contained MND-driven GFP and BAFF linked with a T2A self-cleaving peptide (CCR5-GFP-BAFF) and the other contained only an MND-BAFF expression cassette (CCR5-BAFF). Both donor constructs contained 800 bp homology arms around the CCR5 guide target site (FIG. 51A). Following RNP transfection and/or AAV transduction, cells were cultured using the three-step plasma cell culture system (FIG. 44A). As in earlier PRDM1-targeting experiments, it was observed that persistent GFP expression (mean=33% GFP$^+$) only in the condition containing both CCR5-targeting RNP and AAV (FIG. 51B, FIG. 50). Regardless of the template used, it was observed that there was similar rates of HDR as quantified by digital PCR (~28-31% HDR; FIG. 51C). While use of both donor templates led to BAFF secretion, B cells targeted by CCR5-BAFF (repair template solely containing BAFF) exhibited much higher levels of BAFF secretion (4.1 fold increase) relative to those targeted by CCR5-GFP-BAFF (template containing BAFF downstream of the T2A linkage) (FIG. 51D). To determine if this exogenous BAFF is functional, cell expansion and plasmablast formation was assessed following genome editing and in vitro differentiation. In the CCR5-BAFF edited culture that contained the highest concentration of exogenous BAFF, increases in cell number was observed, viability and percentage of CD19$^{low}$ CD38$^{high}$ plasmablasts relative to controls that lacked Cas9 RNP (FIG. 51E, 51F). This is consistent with previous studies showing that BAFF promotes both human and murine B cell survival and differentiation. Taken together, these results show that Cas9 RNP- and AAV-mediated genome editing can be used to generate functional, BAFF-secreting human plasma cells with improved in vitro survival.

Described herein are high rates of gene disruption in primary human B cells at multiple loci using CRISPR/Cas9 RNPs. This method is applied to modeling the impact of genetic changes on human plasma B cell differentiation. It is also demonstrated that the use of Cas9 RNP in combination with ssODN or AAV6 repair templates achieves high-efficiency HDR in B cells and to engineer secretion of functional and therapeutically relevant proteins. Importantly, gene-modified cells obtained a plasma cell phenotype following 13 days of culture (including 2 days pre-editing) in vitro and are detectable in humanized mice for an additional 3 weeks, providing evidence of the utility of this approach for adoptive cell therapies using engineered human plasma cells.

Cas9-mediated disruption of PRDM1, IRF4, PAX5, or BACH2, which either promote (PRDM1, IRF4) or inhibit (PAX5, BACH2) plasma cell differentiation in mice, led to human B cell phenotypes consistent with these regulatory roles. The ability to easily disrupt genes or induce single-base changes using Cas9 RNP with or without ssODN-mediated HDR will facilitate further study of the impact of genetic changes on human B cell development. When combined with differentiation in vitro, this system could be used as a high-throughput model for studying genetic mutations that alter human B cell development, including somatic and/or germ-line mutations associated with a range of human B cell disorders (in B cell lymphoma and in autoimmune disorders including systemic lupus erythematosus); as well as a range of mechanistic studies designed to assess candidate genes identified by genome-wide association studies.

The development of a method for the efficient, site-specific introduction of transgenes via HDR opens the possibility of engineering plasma cells to act as autologous "cell factories," capable of delivering sustained, high doses of therapeutic proteins to patients. As a proof of concept, plasma cells were engineered to secrete FIX. Deficiency of FIX is the cause of hemophilia B, a genetic disease characterized by blood clotting defects. Current treatment for hemophilia B is limited to protein replacement therapy, which is costly and non-curative. Recent gene therapy trials reported long-term FIX expression in patients after intravenous injection of a liver-tropic AAV8-FIX vector; however, pre-existing AAV neutralizing antibodies to all known AAV serotypes are prevalent in humans and greatly limit in vivo AAV transduction, making a significant group of patients with anti-AAV antibodies ineligible for treatment. In addition, systemic AAV delivery induces humoral immunity against AAV that prevents subsequent delivery, thus limiting AAV therapy to a single dose and/or necessitating use of alternative serotypes. Delivery of ex vivo gene-edited plasma cells producing FIX would remove the requirement for systemic AAV delivery and likely avoid limitations posed by AAV neutralizing antibodies.

In addition, immune responses to therapeutic proteins comprise a key unaddressed challenge. Based on evidence that B cell delivery can induce tolerance, an additional application of B cell editing technology would be to deliver smaller numbers of short-lived B cells producing FIX, or other immunogenic proteins, with the goal of inducing tolerance to the secreted product.

The engraftment studies contrast with the majority of those previously reported using human cells. In most other successful studies, human stem cells have been engrafted into neonatal humanized murine models, including co-engraftment with human liver and thymus (pelanta review). In these cases, CD34$^+$ stem cells can differentiate into B cells and even mature B cells. However, the majority of the engrafted cells remain in the transitional and/or immature developmental stages. Further, the demonstration that engineering mature B cells to express human BAFF confers a significant engraftment advantage parallels studies showing that access to human cytokines, including IL6, SIRPα, or T cell factors promote B cell maturation and the ability to respond to immunization in mice.

In summary, the alternatives herein, demonstrate high rates of locus-specific genome editing in primary human B cells. These engineered B cells retain the ability to differentiate into plasma cells ex vivo and secrete physiological doses of therapeutic proteins such as FIX. The ability to efficiently target specific loci enables us to drive B cell differentiation and secretory programs. Thus, creative multiplexing of gene disruption and HDR will provide ever more powerful tools to coordinately optimize protein secretion, cellular phenotype and long-term survival.

CRISPR/Cas9 Reagents and ssODNs crRNAs targeting the CCR5, PRDM1, IRF4, PAX5, BACH2 loci were identified using the MIT CRISPR design tool and the Broad Institute sgRNA design tool and synthesized (IDT®) containing phosphorothioate linkages and 2'O-methyl modifications. Single-stranded oligonucleotides (ssODNs) were commercially synthesized by IDT® (Ultramer® DNA Oligonucleotides) with phosphorothioate linkages. crRNA and tracrRNA (IDT®) hybrids were mixed with Cas9 nuclease (IDT®) at a 1.2:1 ratio and delivered with or without ssODNs to cells by Neon electroporation (ThermoFisher Scientific®).

Production of Recombinant AAV Vectors

The AAV vector, serotype helper and HgT1-adeno helper plasmids were transfected into HEK293T cells. Cells were harvested 48 hours later, lysed by 3 freeze-thaw cycles, and the cell lysate was treated with benzonase. Virions with recombinant AAV genomes were purified using an iodixanol density gradient. All multiplicity of infection (MOI) calculations were based on qPCR-based titers of AAV genomes using ITR specific primers and probe.

Samples and Primary Human B Cell Genome Editing

Peripheral blood mononuclear cells (PBMCs) were collected from whole blood of consented donors and cryopreserved. CD19$^+$ B cells were subsequently isolated by negative selection (Pan-B cell kit, Miltenyi Biotec®) and cultured in Iscove's modified Dulbecco's medium (IMDM; Thermo Fisher Scientific®) supplemented with 10% fetal bovine serum (FBS) and 55 µM beta-mercaptoethanol at 1-1.5×10$^6$ cells/ml. B cells were activated with 100 ng/ml of recombinant human MEGACD40L® (Enzo Life Sciences®), 1 µg/ml of CpG oligodeoxynucleotide 2006 (Invitrogen®), 50 ng/ml of IL2 (Peprotech®), 50 ng/ml of IL-10 (Peprotech®) and 10 ng/ml of IL15 (Peprotech®) for two days. Cells were then electroporated with Cas9 RNP complexes. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days.

Flow Cytometry

Flow cytometric analysis was done on an LSR II flow cytometer (BD Biosciences) and data were analyzed using FlowJo software (TreeStar). Flow cytometry gating for fluorescent proteins (FIG. 52A), viability (FIG. 52B) and immunophenotyping (FIG. 52C) are described.

Plasma Cell Differentiation Culture

Plasma cells were differentiated in vitro using a three-step culture system as previously described. CD19' B cells were activated and gene-edited as outlined above and expanded for five days in the same cocktail. Following washing with 1×PBS, the cells were seeded in medium with IL-2 (50 ng/ml), IL-6 (50 ng/ml), IL-10 (50 ng/ml) and IL-15 (10 ng/ml) for three days. Next, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation

ELISA 3 days prior to measuring culture protein levels, cells were collected, washed with PBS and then resuspended in new culture medium at $1 \times 10^6$ cells/ml. After 3 days, the culture supernatant was collected and protein secretion levels were determined by enzyme-linked immunosorbent assay (ELISA) for IgG and IgM (Ready-SET-GO®, eBioscience®, San Diego, CA), BAFF (BAFF/BLyS/Quantikine ELISA Kit, R&D Systems®, Minneapolis, MN) and FIX (FIX Human ELISA Kit, Abcam®, Cambridge, MA).

FIX Chromogenic Assay

Activity of recombinant FIX expressed by gene-edited B cells was assessed using a chromogenic assay (Rox Factor IX, 900020). The procedure was performed following the manufacturer's instructions. Absorbance values were measured using a VICTOR3™ plate reader (PerkinElmer®). A human normal pooled plasma standard was used to establish the calibration curve.

To assess FIX activity in edited plasma cell cultures, B cells were edited and differentiated in vitro. At day 8 post genome editing, FBS content was reduced from 10% to 2% of culture to reduce assay background. Insulin, transferrin, sodium selenite were added to cultures to maintain cell survival in the reduced FBS environment. Finally, in specified cultures that were supplemented with vitamin K1 5 µg/ml of vitamin K1 was added to the medium for generating active FIX via vitamin K-dependent carboxylation. 0.005% was used to increase solubility of vitamin K1.

NSG Mouse Transplant

NOD/SCID/gamma-c null (NSG) mice were purchased from Jackson Laboratories and maintained in a designated pathogen-free facility at the Seattle Children's Research Institute (SCRI). All animal studies were performed according to the Association for Assessment and Accreditation of Laboratory Animal Care (AAALAC) standards, and were approved by the SCRI Institutional Animal Care and Use Committee (IACUC).

In the NSG transplant experiment, NSG mice were conditioned with 25 mg/kg of Busulfan (Selleckchem®) via intraperitoneal injection. 24 hours after conditioning, $10 \times 10^6$ in vitro differentiated plasma B cells, either mock or edited BAFF-expressing, were delivered into each 6- to 8-week-old NSG recipient via retro-orbital infusion. Mice were bled at day 10 and sacrificed at day 21 post infusion. All peripheral blood samples were collected in serum separator tubes for serum collection.

Statistical Analysis and Data Availability

Statistical analyses were performed using Graphpad Prism® 7 (GraphPad®, San Diego, CA). Because there wasn't obvious skewing in any of the conditions and there was minimal variation within conditions, it is assumed all data followed a normal distribution. p values in multiple comparisons were calculated using one-way ANOVA with the Sidak correction; p values in comparisons between two groups were calculated using paired two-tailed t-test. Values from independent experiments are shown as means±SEM. All sequencing data are accessible at the NCBI Sequence Read Archive through the following accession number: SRP113557.

Methods for Making Plasma Cells or Plasma Cell Precursors that Express a Macromolecule, Such as a Protein, Protein Mimetic or a Peptide, and Making a Long Lived Plasma Cell.

Described herein are methods for making long lived plasma cells. In some alternatives, these plasma cells can also express a desired macromolecule, such as a protein, an antibody, enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. These cells can then be used for treatment, amelioration, or inhibition of a disease such as cancer by e.g., utilizing immunotherapy.

The method of making a plasma cell or plasma cell precursor that expresses a molecule, such as a macromolecule is provided in several alternatives herein. The method comprises isolating B cells, developing the B cells, performing a first round of genome editing of the B cells for protein expression in absence of viral integration, expanding the B cells; and differentiating the B cells, optionally, after step (c) or (d), thereby producing plasma cells or plasma cell precursors that express the molecule. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells in step (a) comprise memory B cells and/or naïve B cells. In some alternatives, the developing of the B cells is performed after the B cells are arrested at a specific phase of development and/or activating the B cells such that the B cells are permissive for recombination without further B cell differentiation. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cell. In some alternatives, the method to prevent somatic hypermutation of an antibody locus in the B cell comprises disruption of an AID gene. In some alternatives, the method further comprises selectively increasing a proportion of gene edited B cells. In some alternatives, the step of increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment, amelioration, or inhibition of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding fragment thereof is specific for a protein or other molecule expressed in autoimmune disorders, autoinflammatory disorders, immune dysregulation and cancer. In some alternatives, the antibody or binding fragment thereof is an anti-IL-1 monoclonal antibody, anti-TNF antibody, anti-IL-33 antibody or anti-C5 antibody or a binding fragment of one or more of these antibodies. In some alternatives, the protein is an anti-thrombotic molecule, wherein the anti-thrombotic molecule is APLN. In some alternatives, the protein comprises an anti-PCSK9 inhibitory antibody or a binding fragment thereof. In some alternatives, the protein comprises broadly neutralizing HIV-1 antibodies (bNAbs) or a binding portion thereof. In some alternatives, the protein comprises a prodrug or a proenzyme. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or binding portion thereof is specific for an antigen that is expressed in a virus, fungus, parasite or bacteria. In some alternatives, the protein comprises an antibody or portion thereof, wherein the antibody or portion thereof is specific for an antigen that is express in a viral, fungal, parasitic or bacterial infection. In some alternatives herein, the genome editing is performed by nonpathogenic AAV mediated editing by direct homolougous recombination. In some alternatives herein, the protein comprises an enzyme, monoclonal antibody or a binding portion thereof, neutralizing antibodies or a binding portions thereof, therapeutic antibodies or binding portions thereof, cytokine, cytokine receptor, complement protein, inhibitory protein, anti-fibrotic molecule, anti-thrombotic molecule, coagulation factor, glucose response element or a synthetic engineered protein. In some alternatives herein, the protein is Factor VIII, Factor IX, SERPING1 or SERPINA1. In some alternatives herein, the enzyme is ADAMTS13, LIPA, GLA, or ALPL. In some alternatives herein, the protein is a receptor antagonist for treatment of periodic fever/autoinflammatory syndromes or complement inhibitory proteins. In some alternatives herein, the compliment inhibitory protein is Factor H, Factor I or a C1 inhibitor. In some alternatives herein, the protein is an anti-fibrotic molecule, wherein the anti-fibrotic molecule is SCGB1A1. In some alternatives herein, the therapeutic antibody or a binding portion thereof is specific for a protein or other molecule expressed in autoimmune disorders, autoinflammatory disorders, immune dysregulation and/or cancer. In some alternatives herein, the antibody is an anti-IL-1 monoclonal antibody, anti-TNF antibody, anti-IL-33 antibody or anti-C5 antibody or a binding portion of any one or more of these antibodies. In some alternatives herein, the protein is an anti-thrombotic molecule, wherein the anti-thrombotic molecule is APLN. In some alternatives herein, the protein comprises an anti-PCSK9 inhibitory antibody or a binding portion thereof. In some alternatives herein, the protein comprises broadly neutralizing HIV-1 antibodies (bNAbs), or a binding portion thereof. In some alternatives herein, the protein is an engineered protein, wherein the engineered protein is protective in viral, fungal, parasitic or bacterial infection. In some alternatives herein, the engineered protein comprises an antibody or a binding portion thereof, wherein the antibody or a binding portion thereof is specific for an antigen that is expressed by a virus, fungus, parasite or bacteria. In some alternatives herein, the protein comprises an antibody or a binding portion thereof, wherein the antibody or a binding portion thereof is specific for an antigen that is expressed on a viral, fungal, parasitic or bacterial infection. In some alternatives herein, the method further comprises purifying the plasma cells or plasma cell precursors after step e) by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection. Novel aspects of the alternatives described herein can include, but are not limited to: (1) the use of blood-derived human B cells as a starting material for a plasma cell protein producing immunotherapy; (2) RNA- and protein-based transfection to facilitate delivery of candidate designer nucleases targeting a broad range of genetic loci in primary B cells that include, but are not limited to zinc finger nucleases, transcription activator-like effector nucleases (TALEN), homing endonucleases (HEs), combined TALEN-HE proteins (megaTALs) and clustered regularly interspersed short palindromic repeat DNA (CRISPR) coupled to the CAS nuclease; (3) transfection of long single-stranded DNA oligonucleotides or transduction with recombinant adeno-associated virus to facilitate efficient delivery of donor DNA templates carrying therapeutic expression cassettes into primary human B cells in order to facilitate efficient homologous recombination into a range of candidate genetic loci; (4) integrity measures that include, but are not limited to, methods to prevent somatic hypermutation of the B cell antibody locus during the engineering process including, but not limited, to disruption of the AID gene; (5) production enhancers that include, but are not limited to methods to introduce dimerizable drug-inducible activating proteins to enable selectable expansion of engineered human B cells in vitro or in vivo; (6) safety measures that include, but are not limited to, introduction of sequences from cell surface proteins including, but not limited to, the CD20 protein into B cells to enable targeted removal from recipients using Rituxan® or alternative therapeutic approaches; and (7) the use of a proprietary multi-step cytokine and co-culture based systems to facilitate differentiation of blood-derived B cells into long-lived plasma cells and their survival and expansion in vitro.

In some alternatives, the plasma cell or plasma cell precursor expresses a macromolecule, such as a protein, wherein the protein is used in a protocol such as immunotherapy, as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for the treatment or inhibition of periodic fever/autoinflammatory syndromes; complement inhibitory proteins (including Factor H, Factor I) for the treatment or inhibition of atypical hemolytic uremic syndrome/membranoproliferative glomerulonephritis; and/or C1 inhibitor for hereditary angioedema.

Anti-fibrotic molecules including, but not limited to SCGB1A1 for the treatment or inhibition of pulmonary fibrosis.

Therapeutic antibodies or a binding portion thereof for autoimmune disorders, autoinflammatory disorders, immune dysregulation and/or cancer including but not limited to: anti-IL-1 monoclonal antibodies or a binding portion thereof for treatment or inhibition of periodic fever/autoinflammatory syndromes; anti-TNF antibodies or a binding portion thereof for inflammatory arthritis/inflammatory bowel disease, anti-IL-33 antibodies or a binding portion thereof for the treatment or inhibition of asthma and anti-C5 antibodies or a binding portion thereof for treatment or inhibition of paroxysmal nocturnal hemoglobinuria/atypical HUS.

Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

Methods for Making a Long Lived Plasma Cell.

Methods for making a long lived plasma cell are also provided. Long lived plasma cells that express protein can survive in a subject in a need for a treatment or inhibition of a disease such as cancer and such approaches eliminate the need to provide administering of cells within a short time frame.

The method of making a long lived plasma cell, comprises: isolating B cells; activating the B cells; a first round of genome editing of the B cells for molecule expression in the absence of viral integration; expanding the B cells; and differentiating the B cells. In some alternatives, the B cells in the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, first round of genome editing comprises transducing the B cell with a recombinant adeno-associated virus vector for homologous recombination into a candidate genetic loci. In some alternatives, method further comprises applying methods to prevent somatic hypermutation of an antibody locus and other target loci in the B cell. In some alternatives, the method to prevent somatic hypermutation of an antibody locus in the B cell comprises disruption of an AID gene. In some alternatives, the method further comprises introducing production enhancers into the B cell or disruption of candidate loci within the B cell to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment, amelioration, or inhibition of periodic fever/autoinflammatory syndromes, complement inhibitory proteins (including Factor H, Factor I) for treatment, amelioration, or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a macromolecule, such as a protein, protein mimetic or peptide is used in a therapeutic protocol such as immunotherapy as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for the treatment or inhibition of periodic fever/autoinflammatory syndromes; complement inhibitory proteins (including Factor H, Factor I) for the treatment or inhibition of atypical hemolytic uremic syndrome/membranoproliferative glomerulonephritis; and/or C1 inhibitor for hereditary angioedema.

(4) Anti-fibrotic molecules including, but not limited to SCGB1A1 for the treatment or inhibition of pulmonary fibrosis.

(5) Therapeutic antibodies or a binding portion thereof for autoimmune disorders, autoinflammatory disorders, immune dysregulation and/or cancer including but not limited to: anti-IL1 monoclonal antibodies or a binding portion thereof for treatment or inhibition of periodic fever or autoinflammatory syndromes; anti-TNF antibodies or a binding portion thereof for inflammatory arthritis/inflammatory bowel disease, anti-IL-33 antibodies or a binding portion thereof for the treatment or inhibition of asthma and/or anti-C5 antibodies or a binding portion thereof for the treatment or inhibition of paroxysmal nocturnal hemoglobinuria/atypical HUS.

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for the treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

Plasma Cells that Express Protein

Plasma cells plasma cell precursors that express macromolecules such as protein, protein mimetics or peptides are provided by the alternatives herein. Plasma cells are provided wherein the plasma cells are also manufactured by the alternative methods described herein. The plasma cell that expresses the macromolecule is long-lived and can be expected to survive within either the bone marrow or within the spleen. In some alternatives, the macromolecule is a protein, protein mimetic or a peptide. The plasma cells created as described herein can persist in non-dividing state within bone marrow survival niche without need for ongoing antigen exposure. They are also relatively resistant to immunosuppression/chemotherapy. Additionally, the plasma cells can be used in conjunction with CAR T cell therapy, which can be used in subjects in need that are suffering from a disease such as cancer, a bacterial or a viral infection so as to treat, ameliorate, or inhibit the disease, cancer or bacterial or viral infection. In some alternatives, the plasma cell expresses CD20.

In some alternatives, a plasma cell that expresses a molecule such as a macromolecule, is provided. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the cell is derived from a B cell. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever/autoinflammatory syndromes, complement inhibitory proteins (including Factor H, Factor I) for treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell expresses CD20 for removal from a subject.

The plasma cell or plasma cell precursor can be manufactured by any one of the alternative methods provided herein. The method of making a plasma cell or plasma cell precursor that expresses a molecule, such as a macromolecule is provided in several alternatives herein. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. The method comprises isolating B cells, developing the B cells, performing a first round of genome editing of the B cells for protein expression in absence of viral integration, expanding the B cells; and differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the B cell in the isolating step comprises B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the guide sequence comprises a sequence set forth in any one of SEQ ID NO: 2-13, 20-25 or 63-112. In some alternatives, the Cas nuclease comprises Cas1, Cas2, Cas3, Cas4, Cas5, Cas6, Cas7, Cas8 or Cas9. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cell. In some alternatives, the method to prevent somatic hypermutation of an antibody locus in the B cell comprises disruption of an AID gene. In some alternatives, the method further comprises selectively increasing a proportion of gene edited B cells. In some alternatives, the step of increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed in a virus, fungus, parasite or bacteria. In some alternatives, the protein comprises an antibody or a binding portion thereof, wherein the antibody or a binding portion thereof is specific for an antigen that is expressed in a viral, fungal, parasitic or bacterial infection. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a macromolecule is a long lived plasma cell. The macromolecule can be a protein, protein mimetic or a peptide. The plasma cell or plasma cell precursor can be manufactured by any one of the alternative methods for making a long lived plasma cell. The method of making a long lived plasma cell, comprises: isolating B cells; activating the B cells; a first round of genome editing of the B cells for protein expression in the absence of viral integration; expanding the B cells; and differentiating the B cells. In some alternatives, the B cells in the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, first round of genome editing comprises transducing the B cell with a recombinant adeno-associated virus vector for homologous recombination into a candidate genetic loci. In some alternatives, method further comprises applying methods to prevent somatic hypermutation of an antibody locus and other target loci in the B cell. In some alternatives, the method to prevent somatic hypermutation of an antibody locus in the B cell comprises disruption of an AID gene. In some alternatives, the method further comprises introducing production enhancers into the B cell or disruption of candidate loci within the B cell to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL, and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives herein, the genome editing is performed by nonpathogenic AAV mediated editing by direct homolougous recombination. In some alternatives, the plasma cell expresses CD20. In some alternatives, the plasma cell is purified by positive selection against CD138.

In some alternatives of the plasma cell or plasma cell precursor, the plasma cell or plasma cell precursor is derived from a B cell or B cell precursor. In some alternatives the plasma cell or plasma cell precursor expresses a macromolecule such as a protein, protein mimetic or a peptide. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever or autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell expressing the protein is a long lived plasma cell. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a molecule, such as protein mimetic, protein or peptide is used in a therapeutic protocol such as an immunotherapy as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for treatment or inhibition of periodic fever/autoinflammatory syndromes; complement inhibitory proteins (including Factor H, Factor I) for treatment or inhibition of atypical hemolytic uremic syndrome/membranoproliferative glomerulonephritis; and/or C1 inhibitor for hereditary angioedema.

(4) Anti-fibrotic molecules including, but not limited to SCGB1A1 for the treatment or inhibition of pulmonary fibrosis.

(5) Therapeutic antibodies or a binding portion thereof for autoimmune disorders, autoinflammatory disorders, immune dysregulation and/or cancer including but not limited to: anti-IL-1 monoclonal antibodies or a binding portion thereof for treatment or inhibition of periodic fever/autoinflammatory syndromes; anti-TNF antibodies or a binding portion thereof for inflammatory arthritis/inflammatory bowel disease, anti-IL-33 antibodies or a binding portion thereof for the treatment or inhibition of asthma and/or anti-C5 antibodies or a binding portion thereof for the treatment or inhibition of paroxysmal nocturnal hemoglobinuria/atypical HUS.

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for the treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

Compositions

Compositions are provided herein, wherein the composition comprises the plasma cell manufactured by any one of the alternative methods provided herein or the cell of any one of the alternative cells provided herein. The composition can comprise a plasma cell or plasma cell precursor that expresses a molecule, such as a macromolecule or a plasma cell that is also a long lived plasma cell. In some alternatives, the composition comprises the plasma cell manufactured by any one of the alternatives herein and a second B cell, wherein the second B cell secretes a macromolecule for inducing tolerance of a peptide for immunotherapeutic application or for inducing engraftment of the plasma cell manufactured by any one of anyone of the alternatives herein. In some alternatives, the macromolecule expressed by the second B cell comprises IFN-alpha, BAFF, APRIL, IL-10 or IL-6. In some alternatives, the composition comprises the plasma cell manufactured by any one of anyone of the alternatives herein or comprising the cell of anyone of the alternatives herein.

The plasma cell or plasma cell precursor can be manufactured by any one of the alternative methods provided herein. The method of making a plasma cell or plasma cell precursor that expresses a molecule, such as a macromolecule is provided in several alternatives herein. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. The method comprises isolating B cells, developing the B cells, performing a first round of genome editing of the B cells for protein expression in absence of viral integration, expanding the B cells; and differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the guide sequence comprises a sequence set forth in any one of SEQ ID NO: 2-13, 20-25 or 63-112. In some alternatives, the Cas nuclease comprises Cas1, Cas2, Cas3, Cas4, Cas5, Cas6, Cas7, Cas8 or Cas9. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the step of increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, antifibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody or a binding portion thereof is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or portion thereof is specific for an antigen that is express by a viral, fungal, parasitic or bacterial infection. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a macromolecule is a long lived plasma cell. The macromolecule can comprise protein, a protein mimetic or a peptide. The plasma cell or plasma cell precursor can be manufactured by any one of the alternative methods for making a long lived plasma cell. The method of making a long lived plasma cell, comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, first round of genome editing comprises transducing the B cell with a recombinant adeno-associated virus vector for homologous recombination into a candidate genetic loci. In some alternatives, method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with IX PBS and seeded in medium with IL-6 (50 ng/ml), IL-15 (10 ng/ml) and human interferon-α 2B (100 U/ml, Sigma-Aldrich®) for three days to stimulate plasma cell differentiation In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL, and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, IL-6, Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a macromolecule, such as a protein, protein mimetic or peptide, in the composition is used in a therapeutic application such as immunotherapy as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for the treatment or inhibition of periodic fever/autoinflammatory syndromes; complement inhibitory proteins (including Factor H, Factor I) for the treatment or inhibition of atypical hemolytic uremic syndrome/membranoproliferative glomerulonephritis; and/or C1 inhibitor for hereditary angioedema.

(4) Anti-fibrotic molecules including, but not limited to SCGB1A1 for the treatment or inhibition of pulmonary fibrosis.

(5) Therapeutic antibodies or a binding portion thereof for the treatment or inhibition of autoimmune disorders, autoinflammatory disorders, immune dysregulation and/or cancer including but not limited to: anti-IL-1 monoclonal antibodies or a binding portion thereof for treatment of periodic fever/autoinflammatory syndromes; anti-TNF antibodies or a binding portion thereof for inflammatory arthritis/inflammatory bowel disease, anti-IL-33 antibodies or a binding portion thereof for the treatment or inhibition of asthma and/or anti-C5 antibodies or a binding portion thereof for the treatment or inhibition of paroxysmal nocturnal hemoglobinuria/atypical HUS.

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for the treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

In some alternatives of the composition, the composition comprises a cell. In some alternatives of the plasma cell, the plasma cell is derived from a B cell. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the cell expresses a macromolecule such as a protein, protein mimetic or a peptide. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell expressing the protein is a long lived plasma cell. In some alternatives herein, the genome editing is performed by nonpathogenic AAV mediated editing by direct homolougous recombination.

Expression of a Macromolecule, Such as a Protein, Protein Mimetic or Peptide in a Subject in Need.

Described herein, are therapeutic methods for providing a desired macromolecule to a subject in need. In some alternatives, the macromolecule is a protein, protein mimetic or a peptide. The subject in need can be suffering from an enzyme deficiency, cancer, bacterial disease, viral disease or a parasitic infection. In some alternatives, the subject in need suffers from cancer or a subject having cancer is selected or identified to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof before, after or simultaneous to introducing, providing, or administering any one or more of the cells of any of the alternatives described herein. In some alternatives, the cellular therapy is CAR T-cell therapy.

The method of expressing a molecule, such as a macromolecule in a subject in need can comprise: administering a plasma cell manufactured by any one of the alternative methods herein, the plasma cell that expresses the macromolecule of any one of the alternative methods herein, or the composition of any one of the alternative methods herein into the subject in need. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity.

The methods for manufacturing the cell include the alternative methods for making a long lived plasma cell, and alternative methods for making a plasma cell or plasma cell precursor that expresses a molecule, such as a macromolecule. Compositions comprising the plasma cell of the alternatives herein can also be used.

The composition comprises the plasma cell manufactured by any one of the alternative methods provided herein or the cell of any one of the alternative cells provided herein. The composition can comprise a plasma cell or plasma cell precursor that expresses a molecule, such as a macromolecule or a plasma cell that is also a long lived plasma cell.

The plasma cell can be manufactured by any one of the alternative methods provided herein. The method of making a plasma cell or plasma cell precursor that expresses a molecule, such as a macromolecule is provided in several alternatives herein. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. The method comprises isolating B cells, developing the B cells, performing a first round of genome editing of the B cells for protein expression in absence of viral integration, expanding the B cells; and differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cells. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the guide sequence comprises a sequence set forth in any one of SEQ ID NO: 2-13, 20-25 or 63-112. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the step of increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 μg/ml of CpG oligodeoxynucleotide 2006, 50 ng/ml of IL2, 50 ng/ml of IL10 and 10 ng/ml of IL15 for two days. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1.

In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL-1 monoclonal antibody, anti-TNF antibody, anti-IL-33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed in a virus, fungus, parasite or bacteria. In some alternatives, the protein comprises an antibody or a binding portion thereof, wherein the antibody or a binding portion thereof is specific for an antigen that is expressed in a viral, fungal, parasitic or bacterial infection. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives, the plasma cell or plasma cell precursor that expresses a macromolecule is a long lived plasma cell. In some alternatives, the macromolecule is a protein, protein mimetic or a peptide. The plasma cell can be manufactured by any one of the alternative methods for making a long lived plasma cell. The method of making a long lived plasma cell, comprises: isolating B cells; activating the B cells; a first round of genome editing of the B cells for protein expression in the absence of viral integration; expanding the B cells; and differentiating the B cells. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cells. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, first round of genome editing comprises transducing the B cell with a recombinant adeno-associated virus vector for homologous recombination into a candidate genetic loci. In some alternatives, method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were seeded in medium with IL-2 (50 ng/ml), IL-6 (50 ng/ml), IL-10 (50 ng/ml) and IL-15 (10 ng/ml) for three days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL, and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes, complement inhibitory proteins (including Factor H, Factor I) for the treatment or inhibition of atypical hemolytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives of the composition, the composition comprises a cell. In some alternatives of the plasma cell, the plasma cell is derived from a B cell. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the cell expresses a macromolecule such as a protein, protein mimetic or a peptide. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell expressing the protein is a long lived plasma cell. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives of the method of expressing a macromolecule in a subject in need, the administering is performed by adoptive transfer. In some alternatives, the macromolecule is a protein, protein mimetic or a peptide. In some alternatives of the method of expressing protein in a subject in need, the subject has received a stem cell administration or solid organ transplantation. In some alternatives of the method of expressing the macromolecule in a subject in need, the subject suffers from influenza, parainfluenza, rhinovirus, respiratory syncytial virus, HIV, or other pathogenic bacteria, virus, fungus or parasite. In some alternatives of the method of expressing the macromolecule in a subject in need, the subject suffers from an enzyme deficiency. In some alternatives of the method of expressing the macromolecule in a subject in need, the subject suffers from pulmonary fibrosis. In some alternatives of the method of expressing the macromolecule in a subject in need, the subject suffers from an autoimmune disorder, immune dysregulation or cancer. In some alternatives of the method of expressing the macromolecule in a subject in need, the subject suffers from diabetes. In some alternatives of the method of expressing protein in a subject in need, the subject suffers from hypercholesterolemia. In some alternatives of the method of expressing the macromolecule in a subject in need, the subject is also receiving CAR T-cell therapy. In some alternatives, the plasma cell expresses CD20. In some alternatives, the method further comprises monitoring of patient the subject following plasma cell transplantation administration. In some alternatives, the subject is determined to no longer need treatment and the method further comprises administering Rituxan® or an anti-CD20 antibody for targeted removal of the plasma cells.

In some alternatives, the plasma cell that expresses the macromolecule is used in a therapeutic application such as immunotherapy as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for the treatment or inhibition of periodic fever/autoinflammatory syndromes; complement inhibitory proteins (including Factor H, Factor I) for the treatment or inhibition of atypical hemolytic uremic syndrome/membranoproliferative glomerulonephritis; and/or C1 inhibitor for hereditary angioedema.

(4) Anti-fibrotic molecules including, but not limited to SCGB1A1 for the treatment or inhibition of pulmonary fibrosis.

(5) Therapeutic antibodies or a binding portion thereof for the treatment or inhibition of autoimmune disorders, autoinflammatory disorders, immune dysregulation and/or cancer including but not limited to: anti-IL-1 monoclonal antibodies or a binding portion thereof for the treatment or inhibition of periodic fever/autoinflammatory syndromes; anti-TNF antibodies or a binding portion thereof for the treatment of or inhibition of inflammatory arthritis/inflammatory bowel disease, anti-IL-33 antibodies or a binding portion thereof for the treatment or inhibition of asthma and/or anti-C5 antibodies or a binding portion thereof for the treatment or inhibition of paroxysmal nocturnal hemoglobinuria/atypical HUS.

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for the treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

In some alternatives of the methods of treating a subject in need or expressing a macromolecule in a subject in need, the subject is administered at least $1-10\times10^6$ of edited long-lived plasma cells that express a macromolecule, or a composition, which is used to deliver at least $1-10\times10^6$ of edited long-lived plasma cells that express the macromolecule. In some alternatives, the macromolecule is a protein, protein mimetic or a peptide. In some alternatives, the subject receives $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$ or $9\times10^9$ edited long-lived plasma cells that express a protein or any number of cells in between a range defined by any two aforementioned values. In some alternatives, the plasma cell expresses CD20. In some alternatives, the method further comprises monitoring of patient the subject following plasma cell transplantation administration. In some alternatives, the subject is determined to no longer need treatment and the method further comprises administering Rituxan® or an anti-CD20 antibody for targeted removal of the plasma cells.

Methods of Ameliorating a Disease in a Subject

A method of ameliorating a disease such as cancer in a subject is also contemplated. The method comprises administering a plasma cell or plasma cell precursor manufactured by any one of the alternative methods provided herein or the plasma cell that expresses a macromolecule manufactured by any one of the alternative methods provided herein, or the composition of any one of the alternative compositions provided herein into the subject in need. In some alternatives, the macromolecule is a protein, protein mimetic or a peptide. In some alternatives, the subject in need suffers from cancer or a subject having cancer is selected or identified to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof before, after or simultaneous to introducing, providing, or administering any one or more of the cells of any of the alternatives described herein. In some alternatives, the cellular therapy is CAR T-cell therapy. In some alternatives, the plasma cell expresses CD20. In some alternatives, the method further comprises monitoring of patient the subject following plasma cell transplantation administration. In some alternatives, the subject is determined to no longer need treatment and the method further comprises administering Rituxan® or an anti-CD20 antibody for targeted removal of the plasma cells.

The composition comprises the plasma cell manufactured by any one of the alternative methods provided herein or the cell of any one of the alternative cells provided herein. The composition can comprise a plasma cell or plasma cell precursor that expresses a molecule, such as a macromolecule or a plasma cell that is also a long lived plasma cell.

The plasma cell can be manufactured by any one of the alternative methods provided herein. The method of making a plasma cell or plasma cell precursor that expresses a molecule, such as a macromolecule is provided in several alternatives herein. In some alternatives, the macromolecule is a protein, protein mimetic or a peptide. The method comprises isolating B cells, developing the B cells, performing a first round of genome editing of the B cells for protein expression in absence of viral integration, expanding the B cells; and differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the guide sequence comprises a sequence set forth in any one of SEQ ID NO: 2-13, 20-25 or 63-112. In some alternatives, the Cas nuclease comprises Cas1, Cas2, Cas3, Cas4, Cas5, Cas6, Cas7, Cas8 or Cas9. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the step of increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned lengths. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed in a virus, fungus, parasite or bacteria. In some alternatives, the protein comprises an antibody or a binding portion thereof, wherein the antibody or a binding portion thereof is specific for an antigen that is expressed in a viral, fungal, parasitic or bacterial infection. In some alternatives herein, the genome editing is performed by nonpathogenic AAV mediated editing by direct homolougous recombination. In some alternatives herein, the method further comprises purifying the plasma cells of step d), wherein the purifying is performed after the expanding step. In some alternatives herein, the purifying comprises positive selecting of cells against CD138. In some alternatives herein, the selecting the plasma cells is performed by an anti-CD138 antibody for targeted removal of the plasma cells.

In some alternatives, the plasma cell or plasma cell precursor that expresses a macromolecule is a long lived plasma cell. In some alternatives, the macromolecule is a protein, protein mimetic or a peptide. The plasma cell can be manufactured by any one of the alternative methods for making a long lived plasma cell. The method of making a long lived plasma cell, comprises: isolating B cells; activating the B cells; a first round of genome editing of the B cells for protein expression in the absence of viral integration; expanding the B cells; and differentiating the B cells. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, first round of genome editing comprises transducing the B cell with a recombinant adeno-associated virus vector for homologous recombination into a candidate genetic loci. In some alternatives, method further comprises applying methods to prevent somatic hypermutation of an antibody locus and other target loci in the B cells. In some alternatives, the method to prevent somatic hypermutation of an antibody locus in the B cell comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any of the two aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were washed with IX PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL, and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives herein, the genome editing is performed by nonpathogenic AAV mediated editing by direct homolougous recombination. In some alternatives herein, the method further comprises purifying the plasma cells of step d), wherein the purifying is performed after the expanding step. In some alternatives herein, the purifying comprises positive selecting of cells against CD138. In some alternatives herein, the selecting the plasma cells is performed by an anti-CD138 antibody for targeted removal of the plasma cells.

In some alternatives of the composition, the composition comprises a plasma cell or plasma cell precursor. In some alternatives of the plasma cell, the plasma cell is derived from a B cell. In some alternatives, the B cell comprises B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the plasma cell or plasma cell precursor expresses a macromolecule such as a protein, protein mimetic or a peptide. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell expressing the protein is a long lived plasma cell. In some alternatives herein, the genome editing is performed by nonpathogenic AAV mediated editing by direct homolougous recombination. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection.

In some alternatives of the method of treating or ameliorating a disease in a subject in need, the administering is performed by adoptive transfer. In some alternatives of the method of ameliorating a disease in a subject in need, the subject has received a stem cell administration or solid organ transplantation. In some alternatives of the method of treating or ameliorating a disease in a subject in need, the subject suffers from influenza, parainfluenza, rhinovirus, respiratory syncytial virus, HIV, or other pathogenic bacteria, virus, fungus or parasite. In some alternatives of the method of treating or ameliorating a disease in a subject in need, the subject suffers from an enzyme deficiency. In some alternatives of the method of treating or ameliorating a disease in a subject in need, the subject suffers from pulmonary fibrosis. In some alternatives of the method of treating or ameliorating a disease in a subject in need, the subject suffers from an autoimmune disorder, immune dysregulation or cancer. In some alternatives of the method of treating or ameliorating a disease in a subject in need, the subject suffers from diabetes. In some alternatives of the method of treating or ameliorating a disease in a subject in need, the subject suffers from hypercholesterolemia. In some alternatives of the method of treating or ameliorating a disease in a subject in need, the subject is receiving therapy. In some alternatives of the method of treating or ameliorating a disease in a subject in need, the subject is selected to receive cancer therapy, diabetes therapy, HIV treatment, or viral therapy. In some alternatives of the method of treating or ameliorating a disease in a subject in need, the subject is also receiving CAR T-cell therapy. In some alternatives of the method, the method further comprises monitoring of patient the subject following plasma cell transplantation. In some alternatives, the subject is determined to no longer need treatment and the method further comprises administering Rituxan® or an anti-CD20 antibody for targeted removal of the plasma cells.

In some alternatives, the plasma cell or plasma cell precursor that expresses a macromolecule such as a protein, protein mimetic or a peptide is used in a therapeutic application such as immunotherapy as envisioned below:

(1) Prophylactic or therapeutic protection from infection (viral, bacterial, or parasitic) following stem cell administration or solid-organ transplantation in pediatric and adult subjects including, but not limited to neutralizing antibodies that block influenza, parainfluenza, rhinovirus, Respiratory Syncitial Virus (RSV), HIV, pathogenic bacteria, and/or parasites.

(2) Protein replacement, enzyme replacement and rescue of enzyme deficiencies including, but not limited to Factor VIII (Hemophilia A), Factor IX (Hemophilia B), ADAMTS13 (Hereditary TTP), LIPA (lysosomal acid deficiency), SERPING1 (hereditary angioedema), SERPINA1 (alpha1 anti-trypsin deficiency), GLA (Fabry disease), and/or ALPL (Hypophosphatasia).

(3) Immune modulation via expressed cytokines, cytokine receptors, complement proteins or other inhibitory proteins including, but not limited to: Il1 receptor antagonist for the treatment or inhibition of periodic fever/autoinflammatory syndromes; complement inhibitory proteins (including Factor H, Factor I) for the treatment or inhibition of atypical hemolytic uremic syndrome/membranoproliferative glomerulonephritis; and/or C1 inhibitor for hereditary angioedema.

(4) Anti-fibrotic molecules including, but not limited to SCGB1A1 for the treatment or inhibition of pulmonary fibrosis.

(5) Therapeutic antibodies or a binding portion thereof for the treatment or inhibition of autoimmune disorders, autoinflammatory disorders, immune dysregulation and/or cancer including but not limited to: anti-IL-1 monoclonal antibodies or a binding portion thereof for the treatment or inhibition of periodic fever/autoinflammatory syndromes; anti-TNF antibodies or a binding portion thereof for the treatment or inhibition of inflammatory arthritis/inflammatory bowel disease, anti-IL-33 antibodies or a binding portion thereof for the treatment or inhibition of asthma and/or anti-C5 antibodies for the treatment or inhibition of paroxysmal nocturnal hemoglobinuria/atypical HUS.

(6) Anti-thrombotic molecules including, but not limited to APLN to block platelet function. Antithrombotic molecules are further described by Adam et al. ("Apelin: an antithrombotic factor that inhibits platelet function." Blood. 2016 Feb. 18; 127(7):908-20; incorporated by reference in its entirety herein).

(7) Glucose responses elements upstream of insulin for the treatment or inhibition of diabetic conditions.

(8) Therapeutic monoclonal antibodies or a binding portion thereof for the treatment or inhibition of hyper-cholesterolemia, including anti-PCSK9 inhibitory antibodies or a binding portion thereof.

In some alternatives of the methods of treating or ameliorating a disease such as cancer in a subject in need or expressing a protein in a subject in need, the subject is administered at least $1\text{-}10\times10^6$ of edited long-lived plasma cells that express a macromolecule such as a protein, protein mimetic or a peptide, or a composition which is used to deliver at least $1\text{-}10\times10^6$ of edited long-lived plasma cells that express the macromolecule. In some alternatives, the subject receives $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $1\times10^7$, $2\times10^7$, $3\times10^7$, $4\times10^7$, $5\times10^7$, $6\times107$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$ or $9\times10^9$ edited long-lived plasma cells that express the macromolecule or any number of cells in between a range defined by any two aforementioned values. In some alternatives of the method, the method further comprises monitoring of patient the subject following plasma cell transplantation. In some alternatives, the subject is determined to no longer need treatment and the method further comprises administering Rituxan®.

Methods of Expressing a Protein in a Subject

Methods of expressing a macromolecule, such as a protein, protein mimetic or peptide in a subject in need is provided, wherein the subject is receiving their own gene edited cells as a therapeutic. The method comprises (a) isolating B cells; (b) developing the B cells; (c) performing a first round of genome editing of the B cells for protein expression in absence of viral integration; (d) expanding the B cells; differentiating the B cells, optionally, after step (c) or (d), thereby producing plasma cells that express a protein; and (e) administering the B cells into the subject in need. In some alternatives, the molecule is a macromolecule, such as a protein, protein mimetic or peptide. In some alternatives, the macromolecule is a prodrug. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the guide sequence comprises a sequence set forth in any one of SEQ ID NO: 2-13, 20-25 or 63-112. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) performing a second round of genome editing on the B cells to excise a region, further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 g/ml of CpG oligodeoxynucleotide 2006, 50 ng/ml of IL2, 50 ng/ml of IL10 and 10 ng/ml of IL15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/auto-inflammatory syndromes or complement inhibitory proteins. In some alternatives, the complement inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is express in a viral, fungal, parasitic or bacterial infection. In some alternatives, the protein comprises an antibody or a binding portion thereof, wherein the antibody or a binding portion thereof is specific for an antigen that is expressed on a virus, fungus, parasite or bacteria. In some alternatives, the administering is performed by adoptive transfer. In some alternatives, the subject has received a stem cell administration or solid organ transplantation. In some alternatives, the subject suffers from influenza, parainfluenza, rhinovirus, respiratory syncytial virus, HIV, or other pathogenic bacteria, virus, fungus or parasite. In some alternatives, the subject suffers from an enzyme deficiency. In some alternatives, the subject suffers from pulmonary fibrosis. In some alternatives, the subject suffers from an autoimmune disorder, immune dysregulation or cancer. In some alternatives, the subject suffers from diabetes. In some alternatives, the subject suffers from hypercholesterolemia. In some alternatives, the subject is receiving therapy. In some alternatives, the subject is selected or identified to receive a cancer therapy, diabetes therapy, HIV treatment, or viral therapy. In some alternatives, the subject is also receiving CAR T-cell therapy. In some alternatives, the subject in need suffers from cancer or a subject having cancer is selected or identified to receive an anti-cancer therapy. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the method further comprises administering a cellular therapy to the subject in need thereof before, after or simultaneous to introducing, providing, or administering any one or more of the cells of any of the alternatives described herein. In some alternatives, the cellular therapy is CAR T-cell therapy. In some alternatives herein, the genome editing is performed by nonpathogenic AAV mediated editing by direct homologous recombination. In some alternatives, the method further comprises purifying the plasma cells. In some alternatives, the purifying comprises positive selecting of cells against CD138. In some alternatives, the selecting the plasma cells is performed by an anti-CD138 antibody for targeted removal of the plasma cells. In some alternatives, the purifying comprises using anti-CD138 beads for plasma cell selection.

In some alternatives of the methods of treating a subject in need for a disease such as cancer or expressing a macromolecule, such as a protein, protein mimetic or a peptide in a subject in need, the subject is administered at least $1$-$10 \times 10^6$ of edited long-lived plasma cells that express the macromolecule, or a composition which is used to deliver at least $1$-$10 \times 10^6$ of edited long-lived plasma cells that express a protein. In some alternatives, the subject receives $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $\mathbf{7 \times 10^9}$, $8 \times 10^9$ or $9 \times 10^9$ edited long-lived plasma cells that express a protein or any number of cells in between a range defined by any two aforementioned values. In some alternatives, the method further comprise monitoring of patient the subject following plasma cell transplantation. In some alternatives, the subject is determined to no longer need treatment and the method further comprises administering Rituxan® or an anti-CD20 antibody for targeted removal of the plasma cells.

Targeting and Sequencing Methods to Ensure the Integrity of the Terminal B Cell Product Methods are further contemplated to further assess the B cell product that is manufactured by the alternative methods herein. These methods are used prior to adding the cells to the composition or delivery of the cells to a subject in need.

Samples of the product cells, such as a long lived plasma cells or plasma cells that are expressing protein are used for DNA extraction to assay for disruption at their targeted sequences. Additionally, the cells are further tested for expression of specific proteins.

Developing a deep and targeted sequencing method to ensure the integrity of the terminal B cell product at a loci known to be modified by AID and/or confer susceptibility to non-Hodgkin's lymphoma or multiple myeloma is also proposed. To do this microarrays coupled to DNA oligos will be developed and used to enrich for exonic and genomic DNA flanking genes known to have mutations associated with non-Hodgkin's lymphoma or myeloma (~500 genes). To assess the integrity of the product, genomic DNA from the product will be captured and use high-throughput sequencing with detailed coverage (>1000×) to determine if mutations are present. Additional sequences can be used for the described alternatives:

| Guide RNA sequences | |
|---|---|
| Gene | Sequence |
| PAX5 | UGU GAA UGG ACG GCC ACU CC (SEQ ID NO: 2) |
| PAX5 | UGU AGU CCG CCA GAG GAU AG (SEQ ID NO: 3) |
| IRF8 | AUU GAC AGU AGC AUG UAU CC (SEQ ID NO: 4) |
| IRF8 | CGG AAA UGU CCA GUU GGG AC (SEQ ID NO: 5) |
| BACH2 | GUU CCU GCG CAU GCA CAA CC (SEQ ID NO: 6) |
| BACH2 | CUG UGA CGU GAC UUU GAU CG (SEQ ID NO: 7) |
| CCR5 | CAA UGU GUC AAC UCU UGA CA (SEQ ID NO: 8) |
| CCR5 | GCU GUG UUU GCG UCU CUC CC (SEQ ID NO: 9) |
| CARD11 | CAAUGACCUUACACUGACGC (SEQ ID NO: 10) |
| PRDM1 | UGAUGGCGGUACUUCGGUUC (SEQ ID NO: 11) |
| PRDM1 | AGGAUGCGGAUAUGACUCUG (SEQ ID NO: 12) |
| PRDM1 | GGGGAGCGAGUGAUGUACGU (SEQ ID NO: 13) |

| AAV repair template sequence list (sequences below) |
|---|
| Construct Name |
| 1079_pscAAV-MND.GFP |
| 1347_pscAAV.Blimp.0.4kb.MND.GFP |
| 1348_pAAV.Blimp.0.4kb.MND.GFP.pA |
| 1361_pAAV.Blimp1.1.0kb.MND.GFP.pA |
| 1366_CCR5.MND.BAFF_CRISPR.HR |
| 1367_CCR5.MND.BAFF.2A.GFP |
| 1378_CCR5.MND.mCherry.2A.coFIXpadua.WPRE.pa |
| 1376_CCR5.MND.FiX.coFIXpadua.WPRE.pA |

1079_pscAAV.GFP (SEQ ID NO: 51)

ORIGIN
```
   1 aagcttcccg gggggatctg ggccactccc tctctgcgcg ctcgctcgct cactgaggcc
  61 gggcgaccaa aggtcgcccg acgcccgggc tttgcccggg cggcctcagt gagcgagcga
 121 gcgcgcagag agggagtggc caactccatc actaggggtt cctggagggg tggagtcgtg
 181 acctagggaa cagagaaaca ggagaatatg gccaaacag gatatctgtg gtaagcagtt
 241 cctgccccgg ctcagggcca agaacagttg gaacagcaga atatgggcca acaggatat
 301 ctgtggtaag cagttcctgc cccggctcag ggccaagaac agatggtccc cagatgcggt
 361 cccgccctca gcagtttcta gagaaccatc agatgtttcc agggtgcccc aaggacctga
 421 aatgaccctg tgccttattt gaactaacca atcagttcgc ttctcgcttc tgttcgcgcg
 481 cttctgctcc ccgagctcta tataagcaga gctgtttag tgaaccgtca gatcgcctgg
 541 agacgccatc cacgctgttt tgacttccat agaaggatcc tcgaggccac catggtgagc
 601 aagggcgagg agctgttcac cggggtggtg cccatcctgg tcgagctgga cggcgacgta
 661 aacggccaca gttcagcgt gtccggcgag ggcgagggcg atgccaccta cggcaagctg
 721 accctgaagt tcatctgcac caccggcaag ctgcccgtgc cctggcccac cctcgtgacc
 781 accctgacct acggcgtgca gtgcttcagc cgctaccccg accacatgaa gcagcacgac
 841 ttcttcaagt ccgccatgcc cgaaggctac gtccaggagc gcaccatctt cttcaaggac
 901 gacggcaact acaagacccg cgccgaggtg aagttcgagg gcgacaccct ggtgaaccgc
 961 atcgagctga agggcatcga cttcaaggag gacggcaaca tcctggggca aagctggag
1021 tacaactaca acagccacaa cgtctatatc atggccgaca gcagaagaa cggcatcaag
1081 gtgaacttca gatccgcca acatcgag gacggcagcg tgcagctcgc cgaccactac
1141 cagcagaaca ccccatcgg cgacggcccc gtgctgctgc ccgacaacca ctacctgagc
1201 acccagtccg ccctgagcaa agacccaac gagaagcgcg atcacatggt cctgctggag
1261 ttcgtgaccg ccgccgggat cactctcggc atggacgagc tgtacaagta agcggccgca
1321 attcacccca ccagtgcagg ctgcctatca gaaagtggtg gctggtgtgg ctaatgccct
1381 ggcccacaag tatcactaag ctcgctttct tgctgtccaa tttctattaa aggttccttt
```

-continued

```
1441 gttccctaag tccaactact aaactggggg atattatgaa gggccttgag catctggatt 1501 ctgcctaata aaaacatttt attttcattg caatgatgta tttaaattat ttctgaatat 1561 tttactaaaa agggaatgtg ggaggtcagt gcatttaaaa cataaagaaa tgaagagcta 1621 gttcaaacct tgggaaaata cactatatct taaactccat gaaagaaggt gaggctgcaa 1681 acagctaatg cacattggca acagccctg atgcctatgc cttattcatc cctcagaaaa 1741 ggattcaagt agaggcttga tttggaggtt aaagttttgc tatgctgtat tttacattac 1801 ttattgtttt agctgtcctc atgaatgtct tttcactacc catttgctta tcctgcatct 1861 ctcagccttg actccactca gttctcttgc ttagagatac cacctttccc ctgaagtgtt 1921 ccttccatgt tttacggcga gatggtttct cctcgcctgg ccactcagcc ttagttgtct 1981 ctgttgtctt atagaggtct acttgaagaa ggaaaaacag ggggcatggt ttgactgtcc 2041 tgtgagccct tcttccctgc ctcccccact cacagtgaca ctagtccact ccctctctgc 2101 gcgctcgctc gctcactgag gccgggcgac caaaggtcgc ccgacgcccg ggctttgccc 2161 gggcggcctc agtgagcgag cgagcgcgca gagagggaca gatccgggcc cgcatgcgtc 2221 gacaattcac tggccgtcgt tttacaacgt cgtgactggg aaaaccctgg cgttacccaa 2281 cttaatcgcc ttgcagcaca tccccctttc gccagctggc gtaatagcga gaggcccgc 2341 accgatcgcc cttcccaaca gttgcgcagc ctgaatggcg aatggcgcct gatgcggtat 2401 tttctcctta cgcatctgtg cggtatttca caccgcatat ggtgcactct cagtacaatc 2461 tgctctgatg ccgcatagtt aagccagccc cgacacccgc caacacccgc tgacgcgccc 2521 tgacgggctt gtctgctccc ggcatccgct tacagacaag ctgtgaccgt ctccgggagc 2581 tgcatgtgtc agaggttttc accgtcatca ccgaaacgcg cgagacgaaa gggcctcgtg 2641 atacgcctat ttttataggt taatgtcatg ataataatgg tttcttagac gtcaggtggc 2701 acttttcggg gaaatgtgcg cggaaccccct atttgtttat ttttctaaat acattcaaat 2761 atgtatccgc tcatgagaca ataaccctga taaatgcttc aataatattg aaaaaggaag 2821 agtatgagta ttcaacattt ccgtgtcgcc cttattccct ttttttgcggc attttgcctt 2881 cctgttttttg ctcacccaga aacgctggtg aaagtaaaag atgctgaaga tcagttgggt 2941 gcacgagtgg gttacatcga actggatctc aacagcggta agatccttga gagttttcgc 3001 cccgaagaac gttttccaat gatgagcact tttaaagttc tgctatgtgg cgcggtatta 3061 tcccgtattg acgccgggca agagcaactc ggtcgccgca tacactattc tcagaatgac 3121 ttggttgagt actcaccagt cacagaaaag catcttacgg atggcatgac agtaagagaa 3181 ttatgcagtg ctgccataac catgagtgat aacactgcgg ccaacttact tctgacaacg 3241 atcggaggac cgaaggagct aaccgctttt ttgcacaaca tgggggatca tgtaactcgc 3301 cttgatcgtt gggaaccgga gctgaatgaa gccataccaa acgacgagcg tgacaccacg 3361 atgcctgtag caatggcaac aacgttgcgc aaactattaa ctggcgaact acttactcta 3421 gcttcccggc aacaattaat agactggatg gaggcggata agttgcagg accacttctg 3481 cgctcggccc ttccggctgg ctggtttatt gctgataaat ctggagccgg tgagcgtggg 3541 tctcgcggta tcattgcagc actggggcca gatggtaagc cctcccgtat cgtagttatc 3601 tacacgacgg ggagtcaggc aactatggat gaacgaaata gacagatcgc tgagataggt 3661 gcctcactga ttaagcattg gtaactgtca gaccaagttt actcatatat actttagatt 3721 gatttaaaac ttcatttta atttaaaagg atctaggtga agatccttttt tgataatctc 3781 atgaccaaaa tcccttaacg tgagttttcg ttccactgag cgtcagaccc cgtagaaaag 3841 atcaaaggat cttcttgaga tccttttttt ctgcgcgtaa tctgctgctt gcaaacaaaa
```

-continued

```
3901 aaaccaccgc taccagcggt ggtttgtttg ccggatcaag agctaccaac tcttttccg
3961 aaggtaactg gcttcagcag agcgcagata ccaaatactg ttcttctagt gtagccgtag
4021 ttaggccacc acttcaagaa ctctgtagca ccgcctacat acctcgctct gctaatcctg
4081 ttaccagtgg ctgctgccag tggcgataag tcgtgtctta ccgggttgga ctcaagacga
4141 tagttaccgg ataaggcgca gcggtcgggc tgaacggggg gttcgtgcac acagcccagc
4201 ttggagcgaa cgacctacac cgaactgaga tacctacagc gtgagctatg agaaagcgcc
4261 acgcttcccg aagggagaaa ggcggacagg tatccggtaa gcggcagggt cggaacagga
4321 gagcgcacga gggagcttcc aggggggaaac gcctggtatc tttatagtcc tgtcgggttt
4381 cgccacctct gacttgagcg tcgatttttg tgatgctcgt caggggggcg gagcctatgg
4441 aaaaacgcca gcaacgcggc cttttttacgg ttcctggcct tttgctggcc ttttgctcac
4501 atgttctttc ctgcgttatc ccctgattct gtggataacc gtattaccgc ctttgagtga
4561 gctgataccg ctcgccgcag ccgaacgacc gagcgcagcg agtcagtgag cgaggaagcg
4621 gaagagcgcc caatacgcaa accgcctctc cccgcgcgtt ggccgattca ttaatgcagc
4681 tggcacgaca ggtttcccga ctggaaagcg ggcagtgagc gcaacgcaat taatgtgagt
4741 tagctcactc attaggcacc ccaggcttta cactttatgc ttccggctcg tatgttgtgt
4801 ggaattgtga gcggataaca atttcacaca ggaaacagct atgaccatga ttacgccaag
4861 ctctcgagat ctaga
```

1347_pscAAV.Blimp.0.4 kb.MND.GFP (SEQ ID NO: 52)

LOCUS (#1347)\pscAAV.B 5056 bp DNA circular 10-MAR.-2017
DEFINITION File from St. Jude Vector Lab.
ACCESSION urn.local . . . 2c-6onxobo
ORIGIN

```
   1 aagcttcccg gggggatctg gccactccc tctctgcgcg ctcgctcgct cactgaggcc
  61 gggcgaccaa aggtcgcccg acgcccgggc tttgcccggg cggcctcagt gagcgagcga
 121 gcgcgcagag agggagtggc caactccatc actagggggtt cctggagggg tggagtcgtg
 181 acctaggacg cgtgccagct gttactcagg ttttctcaag aaggaggagc aactttggca
 241 gttttgcttc agttctctct agccctctgt gtaatcgccc ctttttcttt atttcagcac
 301 aaacacagag cagtctaaag caaccgagca ctgagaaaaa tgaactctgc ccaaagaatg
 361 tcccaaagag agagtacagc gtgaaagaaa tcctaaaatt ggactccaac ccctccaaag
 421 gaaaggacct ctaccgttct aacatttcac ccctcacatc agaaaaggac ctcgatgact
 481 ttagaagacg tgggagcccc gaaatgccct tctacccctcg ggtcgtttac cccatccggg
 541 cccctctgcc agaagacttt ttgaaagctt ccctggccta cgggatcgag agagaacaga
 601 gaaacaggag aatatgggcc aaacaggata tctgtggtaa gcagttcctg ccccggctca
 661 gggccaagaa cagttggaac agcagaatat gggccaaaca ggatatctgt ggtaagcagt
 721 tcctgccccg gctcagggcc aagaacagat ggtccccaga tgcggtcccg ccctcagcag
 781 tttctagaga accatcagat gtttccaggg tgccccaagg acctgaaatg accctgtgcc
 841 ttatttgaac taaccaatca gttcgcttct cgcttctgtt cgcgcgcttc tgctccccga
 901 gctctatata agcagagctc gtttagtgaa ccgtcagatc gcctggagac gccatccacg
 961 ctgttttgac ttccatagaa ggatctcgag gccaccatgg tgagcaaggg cgaggagctg
1021 ttcaccgggg tggtgcccat cctggtcgag ctggacggcg acgtaaacgg ccacaagttc
1081 agcgtgtccg gcgagggcga gggcgatgcc acctacggca agctgaccct gaagttcatc
1141 tgcaccaccg gcaagctgcc cgtgccctgg cccaccctcg tgaccaccct gacctacggc
```

-continued

```
1201 gtgcagtgct tcagccgcta ccccgaccac atgaagcagc acgacttctt caagtccgcc
1261 atgcccgaag gctacgtcca ggagcgcacc atcttcttca aggacgacgg caactacaag
1321 acccgcgccg aggtgaagtt cgagggcgac accctggtga accgcatcga gctgaagggc
1381 atcgacttca aggaggacgg caacatcctg gggcacaagc tggagtacaa ctacaacagc
1441 cacaacgtct atatcatggc cgacaagcag aagaacggca tcaaggtgaa cttcaagatc
1501 cgccacaaca tcgaggacgg cagcgtgcag ctcgccgacc actaccagca gaacaccccc
1561 atcggcgacg gccccgtgct gctgcccgac aaccactacc tgagcaccca gtccgccctg
1621 agcaaagacc ccaacgagaa gcgcgatcac atggtcctgc tggagttcgt gaccgccgcc
1681 gggatcactc tcggcatgga cgagctgtac aagtaaacta gtgtcgactg ctttatttgt
1741 gaaatttgtg atgctattgc tttatttgta accattataa gctgcaataa acaagttaac
1801 aacaacaatt gcattcattt tatgtttcag gttcaggggg aggtgtggga ggttttttaa
1861 aacgtacatc actcgctccc ccattccatc ctccaccact ccaagcccct ctgcaagaag
1921 cagccccgac caaagcctca agagctccag ccctcacaga agccctggga atacggtgtc
1981 ccctgtgggc cccggctctc aagagcaccg ggactcctac gcttacttga acgcgtccta
2041 cggcacggaa ggtttgggct cctacccctgg ctacgcaccc ctgccccacc tcccgccagc
2101 tttcatcccc tcgtacaacg ctcactaccc caagttcctc ttgcccccct acggcatgaa
2161 ttgtaatggc ctgagcgctg tgagcagcat gaatggcatc aacaactttg cctcttccc
2221 gaggctgtgc cctgtctaca gcaatctcct cggtgggggc actagtccac tccctctctg
2281 cgcgctcgct cgctcactga ggccgggcga ccaaaggtcg cccgacgccc gggctttgcc
2341 cgggcggcct cagtgagcga gcgagcgcgc agagagggac agatccgggc ccgcatgcgt
2401 cgacaattca ctggccgtcg ttttacaacg tcgtgactgg gaaaaccctg gcgttaccca
2461 acttaatcgc cttgcagcac atcccccttt cgccagctgg cgtaatagcg aagaggcccg
2521 caccgatcgc ccttcccaac agttgcgcag cctgaatggc gaatgcgcc tgatgcggta
2581 ttttctcctt acgcatctgt gcggtatttc acaccgcata tggtgcactc tcagtacaat
2641 ctgctctgat gccgcatagt taagccagcc ccgacacccg ccaacacccg ctgacgcgcc
2701 ctgacgggct tgtctgctcc cggcatccgc ttacagacaa gctgtgaccg tctccgggag
2761 ctgcatgtgt cagaggtttt caccgtcatc accgaaacgc gcgagacgaa agggcctcgt
2821 gatacgccta tttttatagg ttaatgtcat gataataatg gtttcttaga cgtcaggtgg
2881 cacttttcgg ggaaatgtgc gcggaacccc tatttgttta ttttttctaaa tacattcaaa
2941 tatgtatccg ctcatgagac aataaccctg ataaatgctt caataatatt gaaaaaggaa
3001 gagtatgagt attcaacatt tccgtgtcgc ccttattccc ttttttgcgg cattttgcct
3061 tcctgttttt gctcacccag aaacgctggt gaaagtaaaa gatgctgaag atcagttggg
3121 tgcacgagtg ggttacatcg aactggatct caacagcggt aagatccttg agagttttcg
3181 ccccgaagaa cgttttccaa tgatgagcac ttttaaagtt ctgctatgtg gcgcggtatt
3241 atcccgtatt gacgccgggc aagagcaact cggtcgccgc atacactatt ctcagaatga
3301 cttggttgag tactcaccag tcacagaaaa gcatcttacg gatggcatga cagtaagaga
3361 attatgcagt gctgccataa ccatgagtga taacactgcg ccaacttac ttctgacaac
3421 gatcggagga ccgaaggagc taaccgcttt tttgcacaac atgggggatc atgtaactcg
3481 ccttgatcgt tgggaaccgg agctgaatga agccatacca aacgacgagc gtgacaccac
3541 gatgcctgta gcaatggcaa caacgttgcg caaactatta actggcgaac tacttactct
3601 agcttcccgg caacaattaa tagactggat ggaggcggat aaagttgcag gaccacttct
```

-continued

```
3661 gcgctcggcc cttccggctg gctggtttat tgctgataaa tctggagccg gtgagcgtgg 3721 gtctcgcggt atcattgcag cactggggcc agatggtaag ccctcccgta tcgtagttat 3781 ctacacgacg gggagtcagg caactatgga tgaacgaaat agacagatcg ctgagatagg 3841 tgcctcactg attaagcatt ggtaactgtc agaccaagtt tactcatata tactttagat 3901 tgatttaaaa cttcattttt aatttaaaag gatctaggtg aagatccttt ttgataatct 3961 catgaccaaa atcccttaac gtgagttttc gttccactga gcgtcagacc ccgtagaaaa 4021 gatcaaagga tcttcttgag atcctttttt tctgcgcgta atctgctgct tgcaaacaaa 4081 aaaaccaccg ctaccagcgg tggtttgttt gccggatcaa gagctaccaa ctcttttttcc 4141 gaaggtaact ggcttcagca gagcgcagat accaaatact gttcttctag tgtagccgta 4201 gttaggccac cacttcaaga actctgtagc accgcctaca tacctcgctc tgctaatcct 4261 gttaccagtg gctgctgcca gtggcgataa gtcgtgtctt accgggttgg actcaagacg 4321 atagttaccg gataaggcgc agcggtcggg ctgaacgggg ggttcgtgca cacagcccag 4381 cttggagcga acgacctaca ccgaactgag atacctacag cgtgagctat gagaaagcgc 4441 cacgcttccc gaagggagaa aggcggacag gtatccggta agcggcaggg tcggaacagg 4501 agagcgcacg agggagcttc caggggggaaa cgcctggtat ctttatagtc ctgtcgggtt 4561 tcgccacctc tgacttgagc gtcgattttt gtgatgctcg tcaggggggc ggagcctatg 4621 gaaaaacgcc agcaacgcgg cctttttacg gttcctggcc ttttgctggc cttttgctca 4681 catgttcttt cctgcgttat cccctgattc tgtggataac cgtattaccg cctttgagtg 4741 agctgatacc gctcgccgca gccgaacgac cgagcgcagc gagtcagtga gcgaggaagc 4801 ggaagagcgc ccaatacgca aaccgcctct ccccgcgcgt tggccgattc attaatgcag 4861 ctggcacgac aggtttcccg actggaaagc gggcagtgag cgcaacgcaa ttaatgtgag 4921 ttagctcact cattaggcac cccaggcttt acactttatg cttccggctc gtatgttgtg 4981 tggaattgtg agcggataac aatttcacac aggaaacagc tatgaccatg attacgccaa 5041 gctctcgaga tctaga 1348_pAAV.Blimp.0.4 kb.MND.GFP.pA
                                                      (SEQ ID NO: 53)
LOCUS       (#1348)\pAAV.Bli 6006 bp DNA     circular UNA 10-MAR.-2017
DEFINITION  GFP in AAV, via MD expression cassette, ie, CMV, globin intron,
GFP, globin polyA. This plasmid sequence was corrected on
Oct. 3, 2002, with correction record #201. AAV non-vector error,
probably present in all AAV constructs. Merely deletes 3 bp prior
to left ITR sequence. Replacement of CAGCAGCTGC GCGCTCGCTC GCTCA
with CAGCTGCGCG CTCGCTCGCT CA.
ACCESSION   urn.local . . . e-6i3n6r4
VERSION     urn.local . . . e-6i3n6r4
KEYWORDS    .
SOURCE
ORGANISM
ORIGIN
    1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac acgcgtgcca 181 gctgttactc aggtttttctc aagaaggagg agcaactttg gcagttttgc ttcagttctc 241 tctagccctc tgtgtaatcg cccctttttc tttatttcag cacaaacaca gagcagtcta 301 aagcaaccga gcactgagaa aaatgaactc tgcccaaaga atgtcccaaa gagagagtac 361 agcgtgaaag aaatcctaaa attggactcc aaccccctcca aaggaaagga cctctaccgt 421 tctaacattt caccccctcac atcagaaaag gacctcgatg actttagaag acgtgggagc 481 cccgaaaatgc ccttctaccc tcgggtcgtt taccccatcc gggcccctct gccagaagac
```

-continued

```
 541 tttttgaaag cttccctggc ctacgggatc gagagagaac agagaaacag gagaatatgg 601 gccaaacagg atatctgtgg taagcagttc ctgccccggc tcagggccaa gaacagttgg 661 aacagcagaa tatgggccaa acaggatatc tgtggtaagc agttcctgcc ccggctcagg 721 gccaagaaca gatggtcccc agatgcggtc ccgccctcag cagtttctag agaaccatca 781 gatgtttcca gggtgcccca aggacctgaa atgaccctgt gccttatttg aactaaccaa 841 tcagttcgct tctcgcttct gttcgcgcgc ttctgctccc cgagctctat ataagcagag 901 ctcgtttagt gaaccgtcag atcgcctgga gacgccatcc acgctgtttt gacttccata 961 gaaggatctc gaggccacca tggtgagcaa gggcgaggag ctgttcaccg gggtggtgcc 1021 catcctggtc gagctggacg gcgacgtaaa cggccacaag ttcagcgtgt ccggcgaggg 1081 cgagggcgat gccacctacg gcaagctgac cctgaagttc atctgcacca ccggcaagct 1141 gcccgtgccc tggcccaccc tcgtgaccac cctgacctac ggcgtgcagt gcttcagccg 1201 ctacccccgac cacatgaagc agcacgactt cttcaagtcc gccatgcccg aaggctacgt 1261 ccaggagcgc accatcttct tcaaggacga cggcaactac aagacccgcg ccgaggtgaa 1321 gttcgagggc gacaccctgg tgaaccgcat cgagctgaag ggcatcgact tcaaggagga 1381 cggcaacatc ctggggcaca agctggagta caactacaac agccacaacg tctatatcat 1441 ggccgacaag cagaagaacg gcatcaaggt gaacttcaag atccgccaca acatcgagga 1501 cggcagcgtg cagctcgccg accactacca gcagaacacc cccatcggcg acggccccgt 1561 gctgctgccc gacaaccact acctgagcac ccagtccgcc ctgagcaaag accccaacga 1621 gaagcgcgat cacatggtcc tgctggagtt cgtgaccgcc gccgggatca ctctcggcat 1681 ggacgagctg tacaagtaaa ctagtgtcga ctgctttatt tgtgaaattt gtgatgctat 1741 tgctttattt gtaaccatta taagctgcaa taaacaagtt aacaacaaca attgcattca 1801 ttttatgttt caggttcagg gggaggtgtg ggaggttttt taaaacgtac atcactcgct 1861 ccccattcc atcctccacc actccaagcc cctctgcaag aagcagcccc gaccaaagcc 1921 tcaagagctc cagccctcac agcagccctg gaatacggt gtccctgtg ggccccggct 1981 ctcaagagca ccgggactcc tacgcttact tgaacgcgtc ctacggcacg gaaggtttgg 2041 gctcctaccc tggctacgca cccctgcccc acctcccgcc agctttcatc ccctcgtaca 2101 acgctcacta ccccaagttc ctcttgcccc cctacggcat gaattgtaat ggcctgagcg 2161 ctgtgagcag catgaatggc atcaacaact ttggcctctt cccgaggctg tgccctgtct 2221 acagcaatct cctcggtggg ggcatctaga gtagataagt agcatggcgg gttaatcatt 2281 aactacaagg aaccctagt gatggagttg gccactccct ctctgcgcgc tcgctcgctc 2341 actgaggccg ggcgaccaaa ggtcgcccga cgcccgggct tgcccgggc ggcctcagtg 2401 agcgagcgag cgcgccagct ggcgtaatag cgaagaggcc cgcaccgatc gcccttccca 2461 acagttcgc agcctgaatg gcgaatggcg attccgttgc aatggctggc ggtaatattg 2521 ttctggatat taccagcaag gccgatagtt tgagttcttc tactcaggca agtgatgtta 2581 ttactaatca agaagtatt gcgacaacgg ttaatttgcg tgatggacag actcttttac 2641 tcggtggcct cactgattat aaaaacactt ctcaggattc tggcgtaccg ttcctgtcta 2701 aaatcccttt aatcggcctc ctgtttagct cccgctctga ttctaacgag gaaagcacgt 2761 tatacgtgct cgtcaaagca accatagtac gcgccctgta gcggcgcatt aagcgcggcg 2821 ggtgtggtgg ttacgcgcag cgtgaccgct acacttgcca gcgccctagc gcccgctcct 2881 ttcgctttct tcccttcctt tctcgccacg ttcgccggct ttccccgtca agctctaaat
```

```
2941 cgggggctcc ctttagggtt ccgatttagt gctttacggc acctcgaccc caaaaaactt 3001 gattagggtg atggttcacg tagtgggcca tcgccctgat agacggtttt tcgcccttgt 3061 acgttggagt ccacgttctt taatagtgga ctcttgttcc aaactggaac aacactcaac 3121 cctatctcgg tctattcttt tgatttataa gggattttgc cgatttcggc ctattggtta 3181 aaaaatgagc tgatttaaca aaaatttaac gcgaatttta acaaaatatt aacgtttaca 3241 atttaaatat ttgcttatac aatcttcctg tttttgggc ttttctgatt atcaaccggg 3301 gtacatatga ttgacatgct agttttacga ttaccgttca tcgattctct tgtttgctcc 3361 agactctcag gcaatgacct gatagccttt gtagagacct ctcaaaaata gctaccctct 3421 ccggcatgaa tttatcagct agaacggttg aatatcatat tgatggtgat ttgactgtct 3481 ccggcctttc tcacccgttt gaatctttac ctacacatta ctcaggcatt gcatttaaaa 3541 tatatgaggg ttctaaaaat ttttatcctt gcgttgaaat aaaggcttct cccgcaaaag 3601 tattacaggg tcataatgtt tttggtacaa ccgatttagc tttatgctct gaggctttat 3661 tgcttaattt tgctaattct ttgccttgcc tgtatgattt attggatgtt ggaatcgcct 3721 gatgcggtat tttctcctta cgcatctgtg cggtatttca caccgcatat ggtgcactct 3781 cagtacaatc tgctctgatg ccgcatagtt aagccagccc cgacacccgc caacacccgc 3841 tgacgcgccc tgacgggctt gtctgctccc ggcatccgct tacagacaag ctgtgaccgt 3901 ctccggggagc tgcatgtgtc agaggttttc accgtcatca ccgaaacgcg cgagacgaaa 3961 gggcctcgtg atacgcctat ttttataggt taatgtcatg ataataatgg tttcttagac 4021 gtcaggtggc acttttcggg gaaatgtgcg cggaacccct atttgtttat ttttctaaat 4081 acattcaaat atgtatccgc tcatgagaca ataaccctga taaatgcttc aataatattg 4141 aaaaaggaag agtatgagta ttcaacattt ccgtgtcgcc cttattccct tttttgcggc 4201 attttgcctt cctgtttttg ctcacccaga aacgctggtg aaagtaaaag atgctgaaga 4261 tcagttgggt gcacgagtgg gttacatcga actggatctc aacagcggta agatccttga 4321 gagttttcgc cccgaagaac gttttccaat gatgagcact tttaaagttc tgctatgtgg 4381 cgcggtatta tcccgtattg acgccgggca agagcaactc ggtcgccgca tacactattc 4441 tcagaatgac ttggttgagt actcaccagt cacagaaaag catcttacgg atggcatgac 4501 agtaagagaa ttatgcagtg ctgccataac catgagtgat aacactgcgg ccaacttact 4561 tctgacaacg atcggaggac cgaaggagct aaccgctttt ttgcacaaca tgggggatca 4621 tgtaactcgc cttgatcgtt gggaaccgga gctgaatgaa gccataccaa acgacgagcg 4681 tgacaccacg atgcctgtag caatggcaac aacgttgcgc aaactattaa ctggcgaact 4741 acttactcta gcttcccggc aacaattaat agactggatg gaggcggata agttgcagg 4801 accacttctg cgctcggccc ttccggctgg ctggtttatt gctgataaat ctggagccgg 4861 tgagcgtggg tctcgcggta tcattgcagc actggggcca gatggtaagc cctcccgtat 4921 cgtagttatc tacacgacgg ggagtcaggc aactatggat gaacgaaata gacagatcgc 4981 tgagataggt gcctcactga ttaagcattg gtaactgtca gaccaagttt actcatatat 5041 actttagatt gatttaaaac ttcatttta atttaaaagg atctaggtga agatcctttt 5101 tgataatctc atgaccaaaa tcccttaacg tgagttttcg ttccactgag cgtcagaccc 5161 cgtagaaaag atcaaaggat cttcttgaga tcctttttt ctgcgcgtaa tctgctgctt 5221 gcaaacaaaa aaaccaccgc taccagcggt ggtttgtttg ccggatcaag agctaccaac 5281 tcttttccg aaggtaactg gcttcagcag agcgcagata ccaaatactg tccttctagt 5341 gtagccgtag ttaggccacc acttcaagaa ctctgtagca ccgcctacat acctcgctct
```

-continued

```
5401 gctaatcctg ttaccagtgg ctgctgccag tggcgataag tcgtgtctta ccggggttgga 5461 ctcaagacga tagttaccgg ataaggcgca gcggtcgggc tgaacggggg gttcgtgcac 5521 acagcccagc ttggagcgaa cgacctacac cgaactgaga tacctacagc gtgagctatg 5581 agaaagcgcc acgcttcccg aagggagaaa ggcggacagg tatccggtaa gcggcagggt 5641 cggaacagga gagcgcacga gggagcttcc agggggaaac gcctggtatc tttatagtcc 5701 tgtcgggttt cgccacctct gacttgagcg tcgatttttg tgatgctcgt caggggggcg 5761 gagcctatgg aaaaacgcca gcaacgcggc cttttacgg ttcctggcct tttgctggcc 5821 ttttgctcac atgttctttc ctgcgttatc ccctgattct gtggataacc gtattaccgc 5881 ctttgagtga gctgataccg ctcgccgcag ccgaacgacc gagcgcagcg agtcagtgag 5941 cgaggaagcg gaagagcgcc caatacgcaa accgcctctc cccgcgcgtt ggccgattca 6001 ttaatg
//
```

1361_pAAV.Blimp1.1.0 kb.MND.GFP.pA (SEQ ID NO: 54)

LOCUS       (#1361)\pAAV.Bli    7206 bp    DNA     circular UNA 10-MAR.-2017
DEFINITION  GFP in AAV, via MD expression cassette, ie, CMV, globin intron,
            GFP, globin polyA. This plasmid sequence was corrected on
            Oct. 3, 2002, with correction record #201. AAV non-vector error,
            probably present in all AAV constructs. Merely deletes 3 bp prior
            to left ITR sequence. Replacement of CAGCAGCTGC GCGCTCGCTC GCTCA
            with CAGCTGCGCG CTCGCTCGCT CA.
ACCESSION   urn.local . . . g-6q4aps1
ORIGIN

```
   1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac acgcgtggta 181 aaccatgaac atcagaaaga cttttattaa cctatgacag ggtccccacc ccagtatttt 241 tccactccat taaatggaa gttttttttt ttttttttctt ttttgagaca gagttttgct 301 cttgttgccc agtctggagt gcaatggcac aatctcggct caccacaacc tccacctccc 361 agattcaagc gattcttctg cctcagcctc ccaagtagct gggattacag gtgtgcgcca 421 ccacgcccag ctaattttgt attttagta gagatggggt ttctccatgt tggtcaggct 481 ggtctcgaac ttccgacctc aggtgatccg cccacctcgg cctcccaaag tgctgggatt 541 acaggcaaga gccactgcat ccagcttagg ctatcttact ccagcctaaa cagcaatttt 601 ctatcataag gtctgtacta atgaaaacag aatcacccaa ggctgctgtt tgttctgtct 661 gtgctgccat tgtccgcatt tgctgagga ggaaacggaa ctgcactttt gagtgagtgg 721 cccagagcct tctagaatga gagtgcgttg gaagccagat atgtggcgat tgtgtcgcca 781 gctgttactc aggttttctc aagaaggagg agcaactttg gcagttttgc ttcagttctc 841 tctagccctc tgtgtaatcg ccccttttc tttatttcag cacaaacaca gagcagtcta 901 aagcaaccga gcactgagaa aaatgaactc tgcccaaaga atgtcccaaa gagagagtac 961 agcgtgaaag aaatcctaaa attggactcc aacccctcca aaggaaagga cctctaccgt 1021 tctaacattt cacccctcac atcagaaaag gacctcgatg actttagaag acgtgggagc 1081 cccgaaatgc ccttctaccc tcgggtcgtt taccccatcc gggcccctct gccagaagac 1141 ttttttgaaag cttccctggc ctacgggatc gagagagaac agagaaacag gagaatatgg 1201 gccaaacagg atatctgtgg taagcagttc ctgcccggc tcagggccaa gaacagttgg 1261 aacagcagaa tatgggccaa acaggatatc tgtggtaagc agttcctgcc ccggctcagg 1321 gccaagaaca gatggtcccc agatgcggtc ccgccctcag cagtttctag agaaccatca
```

```
1381 gatgtttcca gggtgcccca aggacctgaa atgaccctgt gccttatttg aactaaccaa 1441 tcagttcgct tctcgcttct gttcgcgcgc ttctgctccc cgagctctat ataagcagag 1501 ctcgtttagt gaaccgtcag atcgcctgga gacgccatcc acgctgtttt gacttccata 1561 gaaggatctc gaggccacca tggtgagcaa gggcgaggag ctgttcaccg gggtggtgcc 1621 catcctggtc gagctggacg gcgacgtaaa cggccacaag ttcagcgtgt ccggcgaggg 1681 cgagggcgat gccacctacg gcaagctgac cctgaagttc atctgcacca ccggcaagct 1741 gcccgtgccc tggcccaccc tcgtgaccac cctgacctac ggcgtgcagt gcttcagccg 1801 ctacccccgac cacatgaagc agcacgactt cttcaagtcc gccatgcccg aaggctacgt 1861 ccaggagcgc accatcttct tcaaggacga cggcaactac aagacccgcg ccgaggtgaa 1921 gttcgagggc gacaccctgg tgaaccgcat cgagctgaag ggcatcgact tcaaggagga 1981 cggcaacatc ctggggcaca agctggagta caactacaac agccacaacg tctatatcat 2041 ggccgacaag cagaagaacg gcatcaaggt gaacttcaag atccgccaca acatcgagga 2101 cggcagcgtg cagctcgccg accactacca gcagaacacc cccatcggcg acggccccgt 2161 gctgctgccc gacaaccact acctgagcac ccagtccgcc ctgagcaaag accccaacga 2221 gaagcgcgat cacatggtcc tgctggagtt cgtgaccgcc gccgggatca ctctcggcat 2281 ggacgagctg tacaagtaaa ctagtgtcga ctgctttatt tgtgaaattt gtgatgctat 2341 tgctttattt gtaaccatta taagctgcaa taaacaagtt aacaacaaca attgcattca 2401 ttttatgttt caggttcagg gggaggtgtg ggaggttttt taaaacgtac atcactcgct 2461 cccccattcc atcctccacc actccaagcc cctctgcaag aagcagcccc gaccaaagcc 2521 tcaagagctc cagccctcac agcagccctg ggaatacggt gtccctgtg ggccccggct 2581 ctcaagagca ccgggactcc tacgcttact gaacgcgtc ctacggcacg gaaggtttgg 2641 gctcctaccc tggctacgca cccctgcccc acctcccgcc agctttcatc ccctcgtaca 2701 acgctcacta ccccaagttc ctcttgcccc cctacggcat gaattgtaat ggcctgagcg 2761 ctgtgagcag catgaatggc atcaacaact ttggcctctt cccgaggctg tgccctgtct 2821 acagcaatct cctcggtggg ggcagcctgc cccacccat gctcaacccc acttctctcc 2881 cgagctcgct gccctcagat ggagcccgga ggttgctcca gccggagcat cccagggagg 2941 tgcttgtccc ggcgcccac agtgccttct cctttaccgg ggccgccgcc agcatgaagg 3001 acaaggcctg tagccccaca agcgggtctc ccacggcggg aacagccgcc acggcagaac 3061 atgtggtgca gcccaaagct acctcagcag cgatggcagc cccagcagc gacgaagcca 3121 tgaatctcat taaaaacaaa agaaacatga ccggctacaa gacccttccc tacccgctga 3181 agaagcagaa cggcaagatc aagtacgaat gcaacgtttg cgccaagact tcggccagc 3241 tctccaatct gaaggtaggc cttgagagag agcagtccaa ggggctgtga gtgcatgctt 3301 gtgtttgtat ttagcttgct ttccatgggg tatcgattgc atttgcagta gtatgagccc 3361 ccggttgggg atagtgggta tggattccgc ctggcttttg ccacttctag ctctttgact 3421 ttggacaagt gacttccctt ctcctctaga gtagataagt agcatggcgg gttaatcatt 3481 aactacaagg aaccccctagt gatggagttg gccactccct ctctgcgcgc tcgctcgctc 3541 actgaggccg gcgaccaaa ggtcgcccga cgcccgggct tgcccgggc ggcctcagtg 3601 agcgagcgag cgcgccagct ggcgtaatag cgaagaggcc cgcaccgatc gcccttccca 3661 acagttgcgc agcctgaatg gcgaatggcg attccgttgc aatggctggc ggtaatattg 3721 ttctggatat taccagcaag gccgatagtt tgagttcttc tactcaggca agtgatgtta 3781 ttactaatca aagaagtatt gcgacaacgg ttaatttgcg tgatggacag actcttttac
```

-continued

```
3841 tcggtggcct cactgattat aaaaacactt ctcaggattc tggcgtaccg ttcctgtcta
3901 aaatccettt aatcggcctc ctgtttagct cccgctctga ttctaacgag gaaagcacgt
3961 tatacgtgct cgtcaaagca accatagtac gcgccctgta gcggcgcatt aagcgcggcg
4021 ggtgtggtgg ttacgcgcag cgtgaccgct acacttgcca gcgccctagc gcccgctcct
4081 ttcgctttct tcccttcctt tctcgccacg ttcgccggct ttccccgtca agctctaaat
4141 cgggggctcc ctttagggtt ccgatttagt gctttacggc acctcgaccc caaaaaactt
4201 gattagggtg atggttcacg tagtgggcca tcgccctgat agacggtttt tcgccctttg
4261 acgttggagt ccacgttctt taatagtgga ctcttgttcc aaactggaac aacactcaac
4321 cctatctcgg tctattcttt tgatttataa gggattttgc cgatttcggc ctattggtta
4381 aaaaatgagc tgatttaaca aaaatttaac gcgaatttta acaaaatatt aacgtttaca
4441 atttaaatat ttgcttatac aatcttcctg tttttgggc ttttctgatt atcaaccggg
4501 gtacatatga ttgacatgct agttttacga ttaccgttca tcgattctct tgtttgctcc
4561 agactctcag gcaatgacct gatagccttt gtagagacct ctcaaaaata gctaccctct
4621 ccggcatgaa tttatcagct agaacggttg aatatcatat tgatggtgat ttgactgtct
4681 ccggcctttc tcacccgttt gaatctttac ctacacatta ctcaggcatt gcatttaaaa
4741 tatatgaggg ttctaaaaat ttttatcctt gcgttgaaat aaaggcttct cccgcaaaag
4801 tattacaggg tcataatgtt tttggtacaa ccgatttagc tttatgctct gaggctttat
4861 tgcttaattt tgctaattct ttgccttgcc tgtatgattt attggatgtt ggaatcgcct
4921 gatgcggtat tttctcctta cgcatctgtg cggtatttca caccgcatat ggtgcactct
4981 cagtacaatc tgctctgatg ccgcatagtt aagccagccc cgacacccgc caacacccgc
5041 tgacgcgccc tgacgggctt gtctgctccc ggcatccgct tacagacaag ctgtgaccgt
5101 ctccggagc tgcatgtgtc agaggttttc accgtcatca ccgaaacgcg cgagacgaaa
5161 gggcctcgtg atacgcctat ttttataggt taatgtcatg ataataatgg tttcttagac
5221 gtcaggtggc acttttcggg gaaatgtgcg cggaacccct atttgtttat ttttctaaat
5281 acattcaaat atgtatccgc tcatgagaca ataaccctga taaatgcttc aataatattg
5341 aaaaaggaag agtatgagta ttcaacattt ccgtgtcgcc cttattccct ttttgcggc
5401 attttgcctt cctgttttg ctcacccaga aacgctggtg aaagtaaaag atgctgaaga
5461 tcagttgggt gcacgagtgg gttacatcga actggatctc aacagcggta agatccttga
5521 gagttttcgc cccgaagaac gttttccaat gatgagcact tttaaagttc tgctatgtgg
5581 cgcggtatta tcccgtattg acgccgggca agagcaactc ggtcgccgca tacactattc
5641 tcagaatgac ttggttgagt actcaccagt cacagaaaag catcttacgg atggcatgac
5701 agtaagagaa ttatgcagtg ctgccataac catgagtgat aacactgcgg ccaacttact
5761 tctgacaacg atcggaggac cgaaggagct aaccgctttt ttgcacaaca tgggggatca
5821 tgtaactcgc cttgatcgtt gggaaccgga gctgaatgaa gccataccaa acgacgagcg
5881 tgacaccacg atgcctgtag caatggcaac aacgttgcgc aaactattaa ctggcgaact
5941 acttactcta gcttcccggc aacaattaat agactggatg gaggcggata agttgcagg
6001 accacttctg cgctcggccc ttccggctgg ctggtttatt gctgataaat ctggagccgg
6061 tgagcgtggg tctcgcggta tcattgcagc actggggcca gatggtaagc cctcccgtat
6121 cgtagttatc tacacgacgg ggagtcaggc aactatggat gaacgaaata gacagatcgc
6181 tgagataggt gcctcactga ttaagcattg gtaactgtca gaccaagttt actcatatat
```

```
6241 actttagatt gatttaaaac ttcattttta atttaaaagg atctaggtga agatcctttt 6301 tgataatctc atgaccaaaa tcccttaacg tgagttttcg ttccactgag cgtcagaccc 6361 cgtagaaaag atcaaaggat cttcttgaga tccttttttt ctgcgcgtaa tctgctgctt 6421 gcaaacaaaa aaaccaccgc taccagcggt ggtttgtttg ccggatcaag agctaccaac 6481 tcttttttccg aaggtaactg gcttcagcag agcgcagata ccaaatactg tccttctagt 6541 gtagccgtag ttaggccacc acttcaagaa ctctgtagca ccgcctacat acctcgctct 6601 gctaatcctg ttaccagtgg ctgctgccag tggcgataag tcgtgtctta ccgggttgga 6661 ctcaagacga tagttaccgg ataaggcgca gcggtcgggc tgaacggggg gttcgtgcac 6721 acagcccagc ttggagcgaa cgacctacac cgaactgaga tacctacagc gtgagctatg 6781 agaaagcgcc acgcttcccg aagggagaaa ggcggacagg tatccggtaa gcggcagggt 6841 cggaacagga gagcgcacga gggagcttcc agggggaaac gcctggtatc tttatagtcc 6901 tgtcgggttt cgccacctct gacttgagcg tcgatttttg tgatgctcgt caggggggcg 6961 gagcctatgg aaaaacgcca gcaacgcggc ctttttacgg ttcctggcct tttgctggcc 7021 ttttgctcac atgttctttc ctgcgttatc ccctgattct gtggataacc gtattaccgc 7081 ctttgagtga gctgataccg ctcgccgcag ccgaacgacc gagcgcagcg agtcagtgag 7141 cgaggaagcg gaagagcgcc caatacgcaa accgcctctc cccgcgcgtt ggccgattca 7201 ttaatg
//
```

1366_CCR5.MND.BAFF_CRISPR.HR
(SEQ ID NO: 55)
LOCUS #1366\CCR5.MND.B 6707 bp DNA circular SYN 10-MAR.-2017
ORIGIN

```
    1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttgacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag attttatttg gtgagatggt gctttcatga attcccccaa cagagccaag 541 ctctccatct agtggacagg gaagctagca gcaaaccttc ccttcactac aaaacttcat 601 tgcttggcca aaaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacagggtg gaacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct ctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtccccag atgcggtccc gccctcagca gtttctagag
```

-continued

```
1261 aaccatcaga tgtttccagg gtgccccaag gacctgaaat gaccctgtgc cttatttgaa 1321 ctaaccaatc agttcgcttc tcgcttctgt tcgcgcgctt ctgctcccg agctctatat 1381 aagcagagct cgtttagtga accgtcagat cgcctggaga cgccatccac gctgttttga 1441 cttccataga aggatctcga ggccaccatg taccggatgc agctgctgag ctgcatcgca 1501 ctgagcctgg cactggtgac caacagcgca gtgcagggac cagaggagac cgtgacccag 1561 gactgcctgc agctgatcgc agacagcgag accccccacca tccagaaggg cagctacacc 1621 ttcgtgccct ggctgctgag cttcaagcgg ggcagcgccc tggaggagaa ggagaacaag 1681 attctggtga aggagaccgg ctacttcttc atctacggcc aggtgctgta caccgataag 1741 acctacgcca tgggccacct gatccagcgg aagaaggtgc acgtgttcgg cgacgagctg 1801 agcctggtga ccctgttccg gtgcatccag aacatgcccg agaccctgcc caacaacagc 1861 tgctacagcg caggaatcgc aaagctggag gagggcgacg agctgcagct ggcaatcccc 1921 cgggagaacg cacagatcag cctggacggc gacgtgacct tcttcggcgc cctgaagctc 1981 ctgtgagtcg actgctttat tgtgaaattt tgtgatgcta ttgctttatt tgtaaccatt 2041 ataagctgca ataaacaagt taacaacaac aattgcattc attttatgtt tcaggttcag 2101 ggggaggtgt gggaggtttt ttaaactcta ttttataggc ttcttctctg gaatcttctt 2161 catcatcctc ctgacaatcg ataggtacct ggctgtcgtc catgctgtgt ttgctttaaa 2221 agccaggacg tcacctttg gggtggtgac aagtgtgatc acttgggtgg tggctgtgtt 2281 tgcgtctctc ccaggaatca tctttaccag atctcaaaaa gaaggtcttc attacacctg 2341 cagctctcat tttccataca gtcagtatca attctgaag aatttccaga cattaaagat 2401 agtcatcttg gggctggtcc tgccgctgct tgtcatggtc atctgctact cgggaatcct 2461 aaaaactctg cttcggtgtc gaaatgagaa gaagaggcac agggctgtga ggcttatctt 2521 caccatcatg attgtttatt ttctcttctg ggctccctac aacattgtcc ttctcctgaa 2581 caccttccag gaattctttg gcctgaataa ttgcagtagc tctaacaggt tggaccaagc 2641 tatgcaggtg acagagactc ttgggatgac gcactgctgc atcaacccca tcatctatgc 2701 ctttgtcggg gagaagttca gaaactacct cttagtcttc ttccaaaagc acattgccaa 2761 acgcttctgc aaatgctgtt ctatttccca gcaagaggct cccgagcgag caagctcagt 2821 ttacacccga tccactgggg agcaggaaat atctgtgggc ttgtgacacg gactcaagtg 2881 ggctggtgac ccagtcagag ttgtgcacat ggcttagttt tcatacacac cgcggtctag 2941 agcatggcta cgtagataag tagcatggcg ggttaatcat taactacaag gaacccctag 3001 tgatggagtt ggccactccc tctctgcgcg ctcgctcgct cactgaggcc gggcgaccaa 3061 aggtcgcccg acgcccgggc tttgcccggg cggcctcagt gagcgagcga gcgcgccagc 3121 tggcgtaata gcgaagaggc ccgcaccgat cgcccttccc aacagttgcg cagcctgaat 3181 ggcgaatggc gattccgttg caatggctgg cggtaatatt gttctggata ttaccagcaa 3241 ggccgatagt ttgagttctt ctactcaggc aagtgatgtt attactaatc aaagaagtat 3301 tgcgacaacg gttaatttgc gtgatggaca gactctttta ctcggtggcc tcactgatta 3361 taaaaacact tctcaggatt ctggcgtacc gttcctgtct aaaatcccct taatcggcct 3421 cctgtttagc tcccgctctg attctaacga ggaaagcacg ttatacgtgc tcgtcaaagc 3481 aaccatagta cgcgccctgt agcggcgcat taagcgcggc gggtgtggtg gttacgcgca 3541 gcgtgaccgc tacacttgcc agcgccctag cgcccgctcc tttcgctttc ttcccttcct 3601 ttctcgccac gttcgccggc tttccccgtc aagctctaaa tcggggctc cctttagggt 3661 tccgatttag tgctttacgg cacctcgacc ccaaaaaact tgattagggt gatggttcac
```

-continued

```
3721 gtagtgggcc atcgccctga tagacggttt ttcgcccttt gacgttggag tccacgttct
3781 ttaatagtgg actcttgttc caaactggaa caacactcaa ccctatctcg gtctattctt
3841 ttgatttata agggattttg ccgatttcgg cctattggtt aaaaaatgag ctgatttaac
3901 aaaaatttaa cgcgaatttt aacaaaatat taacgtttac aatttaaata tttgcttata
3961 caatcttcct gttttggggg cttttctgat tatcaaccgg ggtacatatg attgacatgc
4021 tagttttacg attaccgttc atcgattctc ttgtttgctc cagactctca ggcaatgacc
4081 tgatagcctt tgtagagacc tctcaaaaat agctaccctc tccggcatga atttatcagc
4141 tagaacggtt gaatatcata ttgatggtga tttgactgtc tccggccttt ctcacccgtt
4201 tgaatcttta cctacacatt actcaggcat tgcatttaaa atatatgagg gttctaaaaa
4261 tttttatcct tgcgttgaaa taaaggcttc tcccgcaaaa gtattacagg gtcataatgt
4321 ttttggtaca accgatttag ctttatgctc tgaggcttta ttgcttaatt ttgctaattc
4381 tttgccttgc ctgtatgatt tattggatgt tggaatcgcc tgatgcggta ttttctcctt
4441 acgcatctgt gcggtatttc acaccgcata tggtgcactc tcagtacaat ctgctctgat
4501 gccgcatagt taagccagcc ccgacacccg ccaacacccg ctgacgcgcc ctgacgggct
4561 tgtctgctcc cggcatccgc ttacagacaa gctgtgaccg tctccgggag ctgcatgtgt
4621 cagaggtttt caccgtcatc accgaaacgc gcgagacgaa agggcctcgt gatacgccta
4681 tttttatagg ttaatgtcat gataataatg gtttcttaga cgtcaggtgg cacttttcgg
4741 ggaaatgtgc gcggaacccc tatttgttta ttttctaaa tacattcaaa tatgtatccg
4801 ctcatgagac aataaccctg ataaatgctt caataatatt gaaaaaggaa gagtatgagt
4861 attcaacatt tccgtgtcgc ccttattccc ttttttgcgg cattttgcct tcctgttttt
4921 gctcacccag aaacgctggt gaaagtaaaa gatgctgaag atcagttggg tgcacgagtg
4981 ggttacatcg aactggatct caacagcggt aagatccttg agagttttcg ccccgaagaa
5041 cgttttccaa tgatgagcac ttttaaagtt ctgctatgtg gcgcggtatt atcccgtatt
5101 gacgccgggc aagagcaact cggtcgccgc atacactatt ctcagaatga cttggttgag
5161 tactcaccag tcacagaaaa gcatcttacg gatggcatga cagtaagaga attatgcagt
5221 gctgccataa ccatgagtga taacactgcg gccaacttac ttctgacaac gatcggagga
5281 ccgaaggagc taaccgcttt tttgcacaac atgggggatc atgtaactcg ccttgatcgt
5341 tgggaaccgg agctgaatga agccatacca aacgacgagc gtgacaccac gatgcctgta
5401 gcaatggcaa caacgttgcg caaactatta actggcgaac tacttactct agcttcccgg
5461 caacaattaa tagactggat ggaggcggat aaagttgcag gaccacttct gcgctcggcc
5521 cttccggctg ctggtttat tgctgataaa tctggagccg gtgagcgtgg gtctcgcggt
5581 atcattgcag cactggggcc agatggtaag ccctcccgta tcgtagttat ctacacgacg
5641 gggagtcagc aactatgga tgaacgaaat agacagatcg ctgagatagg tgcctcactg
5701 attaagcatt ggtaactgtc agaccaagtt tactcatata tactttagat tgatttaaaa
5761 cttcattttt aatttaaaag gatctaggtg aagatccttt ttgataatct catgaccaaa
5821 atcccttaac gtgagttttc gttccactga gcgtcagacc ccgtagaaaa gatcaaagga
5881 tcttcttgag atcctttttt tctgcgcgta atctgctgct tgcaaacaaa aaaaccaccg
5941 ctaccagcgg tggtttgttt gccggatcaa gagctaccaa ctctttttcc gaaggtaact
6001 ggcttcagca gagcgcagat accaaatact gtccttctag tgtagccgta gttaggccac
6061 cacttcaaga actctgtagc accgcctaca tacctcgctc tgctaatcct gttaccagtg
```

-continued

```
6121 gctgctgcca gtggcgataa gtcgtgtctt accgggttgg actcaagacg atagttaccg
6181 gataaggcgc agcggtcggg ctgaacgggg ggttcgtgca cacagcccag cttggagcga
6241 acgacctaca ccgaactgag atacctacag cgtgagctat gagaaagcgc cacgcttccc
6301 gaagggagaa aggcggacag gtatccggta agcggcaggg tcggaacagg agagcgcacg
6361 agggagcttc caggggggaaa cgcctggtat ctttatagtc ctgtcgggtt tcgccacctc
6421 tgacttgagc gtcgattttt gtgatgctcg tcagggggc ggagcctatg gaaaaacgcc
6481 agcaacgcgg cctttttacg gttcctggcc ttttgctggc cttttgctca catgttcttt
6541 cctgcgttat cccctgattc tgtggataac cgtattaccg cctttgagtg agctgatacc
6601 gctcgccgca gccgaacgac cgagcgcagc gagtcagtga gcgaggaagc ggaagagcgc
6661 ccaatacgca aaccgcctct ccccgcgcgt tggccgattc attaatg
//
```

1367_CCR5.MND.BAFF.2A.GFP
(SEQ ID NO: 56)
LOCUS #1367\CCR5.MND.B 7494 bp DNA circular SYN 10-MAR.-2017
ORIGIN

```
   1 cagctgcgcg ctcgctcgct cactgaggcc gcccgggcaa agcccgggcg tcgggcgacc
  61 tttggtcgcc cggcctcagt gagcgagcga gcgcgcagag agggagtggc caactccatc
 121 actaggggtt ccttgtagtt aatgattaac ccgccatgct acttatctac gtagccatgc
 181 tctagcggcc tcggcctctg cataaataaa aaaaattagt cagccatgag cttggacgcg
 241 tttggtgtgg tggcgcctgt agtccccagc cacttggagg ggtgaggtga gaggattgct
 301 tgagcccggg atggtccagg ctgcagtgag ccatgatcgt gccactgcac tccagcctgg
 361 gcgacagagt gagaccctgt ctcacaacaa caacaacaac aacaaaaagg ctgagctgca
 421 ccatgcttga cccagttct taaaattgtt gtcaaagctt cattcactcc atggtgctat
 481 agagcacaag attttattg gtgagatggt gctttcatga attcccccaa cagagccaag
 541 ctctccatct agtggacagg gaagctagca gcaaaccttc ccttcactac aaaacttcat
 601 tgcttggcca aaagagagt taattcaatg tagacatcta tgtaggcaat taaaaaccta
 661 ttgatgtata aaacagtttg cattcatgga gggcaactaa atacattcta ggactttata
 721 aaagatcact ttttatttat gcacagggtg gaacaagatg gattatcaag tgtcaagtcc
 781 aatctatgac atcaattatt atacatcgga gccctgccaa aaaatcaatg tgaagcaaat
 841 cgcagcccgc ctcctgcctc cgctctactc actggtgttc atctttggtt ttgtgggcaa
 901 catgctggtc atcctcatcc tgataaactg caaaaggctg aagagcatga ctgacatcta
 961 cctgctcaac ctggccatct ctgacctgtt tttccttctt actgtcccct ctgggctcta
1021 ctatgctgcc gcccagtggg actttggaaa tacaatgtgt caacgaacag agaaacagga
1081 gaatatgggc caaacaggat atctgtggta agcagttcct gccccggctc agggccaaga
1141 acagttggaa cagcagaata tgggccaaac aggatatctg tggtaagcag ttcctgcccc
1201 ggctcagggc caagaacaga tggtcccag atgcggtccc gccctcagca gtttctagag
1261 aaccatcaga tgtttccagg gtgccccaag gacctgaaat gaccctgtgc cttatttgaa
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga ggccaccatg taccggatgc agctgctgag ctgcatcgca
1501 ctgagcctgg cactggtgac caacagcgca gtgcagggac cagaggagac cgtgacccag
1561 gactgcctgc agctgatcgc agacagcgag acccccacca tccagaaggg cagctacacc
1621 ttcgtgccct ggctgctgag cttcaagcgg ggcagcgccc tggaggagaa ggagaacaag
```

-continued

```
1681 attctggtga aggagaccgg ctacttcttc atctacggcc aggtgctgta caccgataag
1741 acctacgcca tgggccacct gatccagcgg aagaaggtgc acgtgttcgg cgacgagctg
1801 agcctggtga ccctgttccg gtgcatccag aacatgcccg agaccctgcc caacaacagc
1861 tgctacagcg caggaatcgc aaagctggag gagggcgacg agctgcagct ggcaatcccc
1921 cgggagaacg cacagatcag cctggacggc gacgtgacct tcttcggcgc cctgaagctc
1981 ctgggatccg gtgagggcag aggaagtctt ctaacatgcg gtgacgtgga ggagaatccg
2041 ggccccatgg tgagcaaggg cgaggagctg ttcaccgggg tggtgcccat cctggtcgag
2101 ctggacggcg acgtaaacgg ccacaagttc agcgtgtccg gcgagggcga gggcgatgcc
2161 acctacggca agctgaccct gaagttcatc tgcaccaccg gcaagctgcc cgtgccctgg
2221 cccaccctcg tgaccaccct gacctacggc gtgcagtgct tcagccgcta ccccgaccac
2281 atgaagcagc acgacttctt caagtccgcc atgcccgaag gctacgtcca ggagcgcacc
2341 atcttcttca aggacgacgg caactacaag acccgcgccg aggtgaagtt cgagggcgac
2401 accctggtga accgcatcga gctgaagggc atcgacttca aggaggacgg caacatcctg
2461 gggcacaagc tggagtacaa ctacaacagc cacaacgtct atatcatggc cgacaagcag
2521 aagaacggca tcaaggtgaa cttcaagatc cgccacaaca tcgaggacgg cagcgtgcag
2581 ctcgccgacc actaccagca gaacacccc atcggcgacg ccccgtgct gctgcccgac
2641 aaccactacc tgagcaccca gtccgccctg agcaaagacc ccaacgagaa gcgcgatcac
2701 atggtcctgc tggagttcgt gaccgccgcc gggatcactc tcggcatgga cgagctgtac
2761 aagtgaatct agagtcgact gctttatttg tgaaatttgt gatgctattg ctttatttgt
2821 aaccattata agctgcaata aacaagttaa caacaacaat tgcattcatt ttatgtttca
2881 ggttcagggg gaggtgtggg aggttttta aactctattt ataggcttc ttctctggaa
2941 tcttcttcat catcctcctg acaatcgata ggtacctggc tgtcgtccat gctgtgtttg
3001 ctttaaaagc caggacggtc acctttgggg tggtgacaag tgtgatcact tgggtggtgg
3061 ctgtgtttgc gtctctccca ggaatcatct ttaccagatc tcaaaaagaa ggtcttcatt
3121 acacctgcag ctctcatttt ccatacagtc agtatcaatt ctggaagaat ttccagacat
3181 taaagatagt catcttgggg ctggtcctgc cgctgcttgt catggtcatc tgctactcgg
3241 gaatcctaaa aactctgctt cggtgtcgaa atgagaagaa gaggcacagg gctgtgaggc
3301 ttatcttcac catcatgatt gtttatttc tcttctgggc tccctacaac attgtccttc
3361 tcctgaacac cttccaggaa ttctttggcc tgaataattg cagtagctct aacaggttgg
3421 accaagctat gcaggtgaca gagactcttg ggatgacgca ctgctgcatc aaccccatca
3481 tctatgcctt tgtcggggag aagttcagaa actacctctt agtcttcttc caaaagcaca
3541 ttgccaaacg cttctgcaaa tgctgttcta ttttccagca agaggctccc gagcgagcaa
3601 gctcagttta caccgatcc actggggagc aggaaatatc tgtgggcttg tgacacggac
3661 tcaagtgggc tggtgaccca gtcagagttg tgcacatggc ttagttttca tacacaccgc
3721 ggtctagagc atggctacgt agataagtag catggcgggt taatcattaa ctacaaggaa
3781 cccctagtga tggagttggc cactccctct ctgcgcgctc gctcgctcac tgaggccggg
3841 cgaccaaagg tcgcccgacg ccccgggcttt gcccgggcgg cctcagtgag cgagcgagcg
3901 cgccagctgg cgtaatagcg aagaggcccg caccgatcgc ccttcccaac agttgcgcag
3961 cctgaatggc gaatggcgat tccgttgcaa tggctggcgg taatattgtt ctggatatta
4021 ccagcaaggc cgatagtttg agttcttcta ctcaggcaag tgatgttatt actaatcaaa
4081 gaagtattgc gacaacggtt aatttgcgtg atggacagac tcttttactc ggtggcctca
```

-continued

```
4141 ctgattataa aaacacttct caggattctg gcgtaccgtt cctgtctaaa atccctttaa
4201 tcggcctcct gtttagctcc cgctctgatt ctaacgagga aagcacgtta tacgtgctcg
4261 tcaaagcaac catagtacgc gccctgtagc ggcgcattaa gcgcggcggg tgtggtggtt
4321 acgcgcagcg tgaccgctac acttgccagc gccctagcgc ccgctccttt cgctttcttc
4381 ccttcctttc tcgccacgtt cgccggcttt ccccgtcaag ctctaaatcg ggggctccct
4441 ttagggttcc gatttagtgc tttacggcac ctcgacccca aaaaacttga ttagggtgat
4501 ggttcacgta gtgggccatc gccctgatag acggttttc gccctttgac gttggagtcc
4561 acgttcttta atagtggact cttgttccaa actggaacaa cactcaaccc tatctcggtc
4621 tattcttttg atttataagg gattttgccg atttcggcct attggttaaa aaatgagctg
4681 atttaacaaa aatttaacgc gaattttaac aaaatattaa cgtttacaat ttaaatattt
4741 gcttatacaa tcttcctgtt tttggggctt ttctgattat caaccggggt acatatgatt
4801 gacatgctag ttttacgatt accgttcatc gattctcttg tttgctccag actctcaggc
4861 aatgacctga tagcctttgt agagacctct caaaaatagc taccctctcc ggcatgaatt
4921 tatcagctag aacggttgaa tatcatattg atggtgattt gactgtctcc ggcctttctc
4981 acccgtttga atctttacct acacattact caggcattgc atttaaaata tatgagggtt
5041 ctaaaaattt ttatccttgc gttgaaataa aggcttctcc cgcaaaagta ttacagggtc
5101 ataatgtttt tggtacaacc gatttagctt tatgctctga ggctttattg cttaattttg
5161 ctaattcttt gccttgcctg tatgattat tggatgttgg aatcgcctga tgcggtattt
5221 tctccttacg catctgtgcg gtatttcaca ccgcatatgg tgcactctca gtacaatctg
5281 ctctgatgcc gcatagttaa gccagccccg acacccgcca acaccgctg acgcgccctg
5341 acgggcttgt ctgctcccgg catccgctta cagacaagct gtgaccgtct ccgggagctg
5401 catgtgtcag aggttttcac cgtcatcacc gaaacgcgcg agacgaaagg gcctcgtgat
5461 acgcctattt ttataggtta atgtcatgat aataatggtt tcttagacgt caggtggcac
5521 ttttcgggga atgtgcgcg gaaccctat ttgtttattt ttctaaatac attcaaatat
5581 gtatccgctc atgagacaat aaccctgata aatgcttcaa taatattgaa aaaggaagag
5641 tatgagtatt caacatttcc gtgtcgccct tattcccttt tttgcggcat tttgccttcc
5701 tgttttgct cacccagaaa cgctggtgaa agtaaaagat gctgaagatc agttgggtgc
5761 acgagtgggt tacatcgaac tggatctcaa cagcggtaag atccttgaga gttttcgccc
5821 cgaagaacgt tttccaatga tgagcacttt taaagttctg ctatgtggcg cggtattatc
5881 ccgtattgac gccgggcaag agcaactcgg tcgccgcata cactattctc agaatgactt
5941 ggttgagtac tcaccagtca cagaaaagca tcttacggat ggcatgacag taagagaatt
6001 atgcagtgct gccataacca tgagtgataa cactgcggcc aacttacttc tgacaacgat
6061 cggaggaccg aaggagctaa ccgcttttt gcacaacatg gggatcatg taactcgcct
6121 tgatcgttgg gaaccggagc tgaatgaagc cataccaaac gacgagcgtg acaccacgat
6181 gcctgtagca atggcaacaa cgttgcgcaa actattaact ggcgaactac ttactctagc
6241 ttcccggcaa caattaatag actggatgga ggcggataaa gttgcaggac cacttctgcg
6301 ctcggccctt ccggctggct ggtttattgc tgataaatct ggagccggtg agcgtgggtc
6361 tcgcggtatc attgcagcac tggggccaga tggtaagccc tcccgtatcg tagttatcta
6421 cacgacgggg agtcaggcaa ctatggatga acgaaataga cagatcgctg agataggtgc
6481 ctcactgatt aagcattggt aactgtcaga ccaagtttac tcatatatac tttagattga
```

-continued

```
6541 tttaaaactt cattttttaat ttaaaaggat ctaggtgaag atccttttg ataatctcat 6601 gaccaaaatc ccttaacgtg agttttcgtt ccactgagcg tcagacccg tagaaaagat 6661 caaaggatct tcttgagatc ctttttttct gcgcgtaatc tgctgcttgc aaacaaaaaa 6721 accaccgcta ccagcggtgg tttgtttgcc ggatcaagag ctaccaactc tttttccgaa 6781 ggtaactggc ttcagcagag cgcagatacc aaatactgtc cttctagtgt agccgtagtt 6841 aggccaccac ttcaagaact ctgtagcacc gcctacatac ctcgctctgc taatcctgtt 6901 accagtggct gctgccagtg gcgataagtc gtgtcttacc gggttggact caagacgata 6961 gttaccggat aaggcgcagc ggtcgggctg aacggggggt tcgtgcacac agcccagctt 7021 ggagcgaacg acctacaccg aactgagata cctacagcgt gagctatgag aaagcgccac 7081 gcttcccgaa gggagaaagg cggacaggta tccggtaagc ggcagggtcg gaacaggaga 7141 gcgcacgagg gagcttccag ggggaaacgc ctggtatctt tatagtcctg tcgggtttcg 7201 ccacctctga cttgagcgtc gatttttgtg atgctcgtca ggggggcgga gcctatggaa 7261 aaacgccagc aacgcggcct ttttacggtt cctggccttt tgctggcctt ttgctcacat 7321 gttctttcct gcgttatccc ctgattctgt ggataaccgt attaccgcct ttgagtgagc 7381 tgataccgct cgccgcagcc gaacgaccga gcgcagcgag tcagtgagcg aggaagcgga 7441 agagcgccca atacgcaaac cgcctctccc cgcgcgttgg ccgattcatt aatg
//

1378_CCR5.MND.mCherry.2A.coFIXpadua.WPRE.pa
                                                                    (SEQ ID NO: 57)
LOCUS #1378 8330 bp DNA circular UNA 09-AUG.-2017
DEFINITION Gibson Assembly of mCherry T2A - coFIXpadua into 1367 XhoI + SalI
(6.2 kb).
ORIGIN
    1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt cctgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag atttatttg gtgagatggt gctttcatga attcccccaa cagagccaag 541 ctctccatct agtggacagg gaagctagca gcaaaccttc ccttcactac aaaacttcat 601 tgcttggcca aaagagagt taattcaatg tagacatcta tgtaggcaat taaaaaccta 661 ttgatgtata aaacagtttg cattcatgga gggcaactaa atacattcta ggactttata 721 aaagatcact tttatttat gcacagggtg aacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct tctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtccccag atgcggtccc gccctcagca gtttctagag
```

-continued

```
1261 aaccatcaga tgtttccagg gtgccccaag gacctgaaat gaccctgtgc cttatttgaa
1321 ctaaccaatc agttcgcttc tcgcttctgt tcgcgcgctt ctgctccccg agctctatat
1381 aagcagagct cgtttagtga accgtcagat cgcctggaga cgccatccac gctgttttga
1441 cttccataga aggatctcga ggccaccatg gtgagcaagg gcgaggagga taacatggcc
1501 atcatcaagg agttcatgcg cttcaaggtg cacatggagg gctccgtgaa cggccacgag
1561 ttcgagatcg agggcgaggg cgagggccgc ccctacgagg gcacccagac cgccaagctg
1621 aaggtgacca agggtggccc cctgcccttc gcctgggaca tcctgtcccc tcagttcatg
1681 tacggctcca aggcctacgt gaagcacccc gccgacatcc ccgactactt gaagctgtcc
1741 ttcccccgagg gcttcaagtg ggagcgcgtg atgaacttcg aggacggcgg cgtggtgacc
1801 gtgacccagg actcctctct gcaggacggc gagttcatct acaaggtgaa gctgcgcggc
1861 accaacttcc cctccgacgg ccccgtaatg cagaagaaga ccatgggctg ggaggcctcc
1921 tccgagcgga tgtaccccga ggacggcgcc ctgaagggcg agatcaagca gaggctgaag
1981 ctgaaggacg gcggccacta cgacgctgag gtcaagacca cctacaaggc caagaagccc
2041 gtgcagctgc ccggcgccta caacgtcaac atcaagttgg acatcacctc ccacaacgag
2101 gactacacca tcgtggaaca gtacgaacgc gccgagggcc gccactccac cggcggcatg
2161 gacgagctgt acaagggatc cggtgagggc agaggaagtc ttctaacatg cggtgacgtg
2221 gaggagaatc cgggccccat gatcatggcc gagagccctg gcctgatcac catctgcctg
2281 ctgggctacc tgctgagcgc cgagtgcacc gtgttcctgg accacgagaa cgccaacaag
2341 atcctgaacc ggcccaagag atacaacagc ggcaagctgg aggagttcgt gcagggcaac
2401 ctggagaggg agtgcatgga ggagaagtgc agcttcgagg aggccaggga agtgttcgag
2461 aacaccgagc ggaccaccga gttctggaag cagtacgtgg acggcgacca gtgcgagagc
2521 aacccttgcc tgaacggcgg cagctgcaag gacgacatca cagctacga gtgctggtgc
2581 cctttcggct tcgagggcaa gaactgcgag ctggacgtga cctgcaacat caagaacggc
2641 cgctgcgagc agttctgcaa gaacagcgcc gacaacaaag tggtgtgtag ctgcaccgag
2701 ggctacgagc tggccgagaa ccagaagagc tgcgagcccg ccgtgccctt cccctgcggc
2761 agagtgagcg tgtcccagac cagcaagctg accagagccg agaccgtgtt ccccgacgtg
2821 gactacgtga atagcaccga ggccgagacc atcctggaca acatcaccca gagcacccag
2881 tccttcaacg acttcaccag agttgtgggc ggcgaggacg ccaagcccgg ccagttcccc
2941 tggcaggtgg tgctgaacgg caaagtggat gccttctgcg gcggcagcat cgtgaacgag
3001 aagtggatcg tgacagccgc ccactgcgtg agaccggcg tgaagatcac cgtggtggcc
3061 ggcgaacaca tatcgagga gaccgagcac accgagcaga gcggaacgt catccggatt
3121 atccccacc acaactacaa cgccgccatc aacaagtaca accacgacat cgccctgctg
3181 gagctggacg agcctctggt gctgaatagc tacgtgaccc ccatctgcat cgccgacaag
3241 gagtacacca acatcttcct gaagttcggc agcggctacg tgtccggctg ggcagagtg
3301 ttccacaagg gcagaagcgc cctggtgctg cagtacctga gagtgcccct ggtggacaga
3361 gccacctgcc tgttgagcac caagttcacc atctacaaca catgttctg cgccggcttc
3421 cacgagggcg gcagagacag ctgccagggc gacagcggcg accccacgt gaccgaagtg
3481 gagggcacca gcttcctgac cggcatcatc agctggggcg aggagtgcgc catgaagggc
3541 aagtacggca tctacaccaa agtgagccgg tacgtgaact ggatcaagga gaaaccaag
3601 ctgacctgag tcgactgctt tatttgtgaa atttgtgatg ctattgcttt atttgtaacc
```

```
3661 attataagct gcaataaaca agttaacaac aacaattgca ttcattttat gtttcaggtt
3721 caggggagg tgtgggaggt tttttaaact ctattttata ggcttcttct ctggaatctt
3781 cttcatcatc ctcctgacaa tcgataggta cctggctgtc gtccatgctg tgtttgcttt
3841 aaaagccagg acggtcacct tggggtggt gacaagtgtg atcacttggg tggtggctgt
3901 gtttgcgtct ctcccaggaa tcatctttac cagatctcaa aaagaaggtc ttcattacac
3961 ctgcagctct cattttccat acagtcagta tcaattctgg aagaatttcc agacattaaa
4021 gatagtcatc ttggggctgg tcctgccgct gcttgtcatg gtcatctgct actcgggaat
4081 cctaaaaact ctgcttcggt gtcgaaatga aagaagagg cacagggctg tgaggcttat
4141 cttcaccatc atgattgttt attttctctt ctgggctccc tacaacattg tccttctcct
4201 gaacaccttc caggaattct ttggcctgaa taattgcagt agctctaaca ggttggacca
4261 agctatgcag gtgacagaga ctcttgggat gacgcactgc tgcatcaacc ccatcatcta
4321 tgcctttgtc ggggagaagt tcagaaacta cctcttagtc ttcttccaaa agcacattgc
4381 caaacgcttc tgcaaatgct gttctatttt ccagcaagag gctcccgagc gagcaagctc
4441 agtttacacc cgatccactg gggagcagga aatatctgtg ggcttgtgac acggactcaa
4501 gtgggctggt gacccagtca gagttgtgca catggcttag ttttcataca caccgcggtc
4561 tagagcatgg ctacgtagat aagtagcatg gcgggttaat cattaactac aaggaacccc
4621 tagtgatgga gttggccact ccctctctgc gcgctcgctc gctcactgag gccgggcgac
4681 caaaggtcgc ccgacgcccg ggctttgccc gggcggcctc agtgagcgag cgagcgcgcc
4741 agctggcgta atagcgaaga ggcccgcacc gatcgccctt cccaacagtt gcgcagcctg
4801 aatggcgaat ggcgattccg ttgcaatggc tggcggtaat attgttctgg atattaccag
4861 caaggccgat agtttgagtt cttctactca ggcaagtgat gttattacta atcaaagaag
4921 tattgcgaca acggttaatt tgcgtgatgg acagactctt ttactcggtg gcctcactga
4981 ttataaaaac acttctcagg attctggcgt accgttcctg tctaaaatcc ctttaatcgg
5041 cctcctgttt agctcccgct ctgattctaa cgaggaaagc acgttatacg tgctcgtcaa
5101 agcaaccata gtacgcgccc tgtagcggcg cattaagcgc ggcgggtgtg gtggttacgc
5161 gcagcgtgac cgctacactt gccagcgccc tagcgcccgc tcctttcgct ttcttccctt
5221 cctttctcgc cacgttcgcc ggctttcccc gtcaagctct aaatcggggg ctccctttag
5281 ggttccgatt tagtgcttta cggcacctcg accccaaaaa acttgattag ggtgatggtt
5341 cacgtagtgg gccatcgccc tgatagacgg ttttttcgcc cttgacgttg gagtccacgt
5401 tctttaatag tggactcttg ttccaaactg gaacaacact caaccctatc tcggtctatt
5461 cttttgattt ataagggatt ttgccgattt cggcctattg gttaaaaaat gagctgattt
5521 aacaaaaatt taacgcgaat tttaacaaaa tattaacgtt tacaatttaa atatttgctt
5581 atacaatctt cctgttttg gggcttttct gattatcaac cggggtacat atgattgaca
5641 tgctagtttt acgattaccg ttcatcgatt ctcttgtttg ctccagactc tcaggcaatg
5701 acctgatagc ctttgtagag acctctcaaa aatagctacc ctctccggca tgaatttatc
5761 agctagaacg gttgaatatc atattgatgg tgatttgact gtctccggcc tttctcaccc
5821 gtttgaatct ttacctacac attactcagg cattgcattt aaaatatatg agggttctaa
5881 aaatttttat ccttgcgttg aaataaaggc ttctcccgca aaagtattac agggtcataa
5941 tgttttttggt acaaccgatt tagctttatg ctctgaggct ttattgctta attttgctaa
6001 ttctttgcct tgcctgtatg atttattgga tgttggaatc gcctgatgcg gtattttctc
6061 cttacgcatc tgtgcggtat ttcacaccgc atatggtgca ctctcagtac aatctgctct
```

-continued

```
6121 gatgccgcat agttaagcca gccccgacac ccgccaacac ccgctgacgc gccctgacgg 6181 gcttgtctgc tcccggcatc cgcttacaga caagctgtga ccgtctccgg gagctgcatg 6241 tgtcagaggt tttcaccgtc atcaccgaaa cgcgcgagac gaaagggcct cgtgatacgc 6301 ctattttat aggttaatgt catgataata atggtttctt agacgtcagg tggcactttt 6361 cggggaaatg tgcgcggaac ccctatttgt ttattttct aaatacattc aaatatgtat 6421 ccgctcatga acaataacc ctgataaatg cttcaataat attgaaaaag gaagagtatg 6481 agtattcaac atttccgtgt cgcccttatt ccctttttg cggcattttg ccttcctgtt 6541 tttgctcacc cagaaacgct ggtgaaagta aaagatgctg aagatcagtt gggtgcacga 6601 gtgggttaca tcgaactgga tctcaacagc ggtaagatcc ttgagagttt tcgccccgaa 6661 gaacgttttc caatgatgag cacttttaaa gttctgctat gtggcgcggt attatcccgt 6721 attgacgccg ggcaagagca actcggtcgc cgcatacact attctcagaa tgacttggtt 6781 gagtactcac cagtcacaga aaagcatctt acggatggca tgacagtaag agaattatgc 6841 agtgctgcca taaccatgag tgataacact gcggccaact tacttctgac aacgatcgga 6901 ggaccgaagg agctaaccgc ttttttgcac aacatggggg atcatgtaac tcgccttgat 6961 cgttgggaac cggagctgaa tgaagccata ccaaacgacg agcgtgacac cacgatgcct 7021 gtagcaatgg caacaacgtt gcgcaaacta ttaactggcg aactacttac tctagcttcc 7081 cggcaacaat taatagactg gatggaggcg gataaagttg caggaccact tctgcgctcg 7141 gcccttccgg ctggctggtt tattgctgat aaatctggag ccggtgagcg tgggtctcgc 7201 ggtatcattg cagcactggg gccagatggt aagccctccc gtatcgtagt tatctacacg 7261 acggggagtc aggcaactat ggatgaacga atagacaga tcgctgagat aggtgcctca 7321 ctgattaagc attggtaact gtcagaccaa gtttactcat atatacttta gattgattta 7381 aaacttcatt tttaatttaa aaggatctag gtgaagatcc ttttttgataa tctcatgacc 7441 aaaatccctt aacgtgagtt ttcgttccac tgagcgtcag accccgtaga aaagatcaaa 7501 ggatcttctt gagatccttt tttctgcgc gtaatctgct gcttgcaaac aaaaaaacca 7561 ccgctaccag cggtggtttg tttgccggat caagagctac caactctttt tccgaaggta 7621 actggcttca gcagagcgca gataccaaat actgtccttc tagtgtagcc gtagttaggc 7681 caccacttca agaactctgt agcaccgcct acatacctcg ctctgctaat cctgttacca 7741 gtggctgctg ccagtggcga taagtcgtgt cttaccgggt tggactcaag acgatagtta 7801 ccggataagg cgcagcggtc gggctgaacg gggggttcgt gcacacagcc cagcttggag 7861 cgaacgacct acaccgaact gagatacta cagcgtgagc tatgagaaag cgccacgctt 7921 cccgaaggga gaaaggcgga caggtatccg gtaagcggca gggtcggaac aggagagcgc 7981 acgagggagc ttccaggggg aaacgcctgg tatctttata gtcctgtcgg gtttcgccac 8041 ctctgacttg agcgtcgatt tttgtgatgc tcgtcagggg ggcggagcct atggaaaaac 8101 gccagcaacg cggccttttt acggttcctg gccttttgct ggccttttgc tcacatgttc 8161 tttcctgcgt tatcccctga ttctgtggat aaccgtatta ccgcctttga gtgagctgat
```

-continued

```
8221 accgctcgcc gcagccgaac gaccgagcgc agcgagtcag tgagcgagga agcggaagag 8281 cgcccaatac gcaaaccgcc tctccccgcg cgttggccga ttcattaatg
//
```

1376_CCR5.MND.FiX.coFIXpadua.WPRE.pA (SEQ ID NO: 58)

LOCUS (#1376)\CCR5.MND 7806 bp DNA circular SYN 09-AUG.-2017
ORIGIN

```
   1 cagctgcgcg ctcgctcgct cactgaggcc gcccgggcaa agcccgggcg tcgggcgacc 61 tttggtcgcc cggcctcagt gagcgagcga gcgcgcagag agggagtggc caactccatc 121 actaggggtt ccttgtagtt aatgattaac ccgccatgct acttatctac gtagccatgc 181 tctagcggcc tcggcctctg cataaataaa aaaaattagt cagccatgag cttggacgcg 241 tttggtgtgg tggcgcctgt agtccccagc cacttggagg ggtgaggtga gaggattgct 301 tgagcccggg atggtccagg ctgcagtgag ccatgatcgt gccactgcac tccagcctgg 361 gcgacagagt gagaccctgt ctcacaacaa caacaacaac aacaaaaagg ctgagctgca 421 ccatgcttga cccagtttct taaaattgtt gtcaaagctt cattcactcc atggtgctat 481 agagcacaag attttatttg gtgagatggt gctttcatga attcccccaa cagagccaag 541 ctctccatct agtggacagg gaagctagca gcaaaccttc ccttcactac aaaacttcat 601 tgcttggcca aaaagagagt taattcaatg tagacatcta tgtaggcaat taaaaaccta 661 ttgatgtata aaacagtttg cattcatgga gggcaactaa atacattcta ggactttata 721 aaagatcact ttttatttat gcacagggtg aacaagatg gattatcaag tgtcaagtcc 781 aatctatgac atcaattatt atacatcgga gccctgccaa aaaatcaatg tgaagcaaat 841 cgcagcccgc ctcctgcctc cgctctactc actggtgttc atctttggtt ttgtgggcaa 901 catgctggtc atcctcatcc tgataaactg caaaaggctg aagagcatga ctgacatcta 961 cctgctcaac ctggccatct ctgacctgtt tttccttctt actgtcccct tctgggctca 1021 ctatgctgcc gcccagtggg actttggaaa tacaatgtgt caacgaacag agaaacagga 1081 gaatatgggc caaacaggat atctgtggta agcagttcct gccccggctc agggccaaga 1141 acagttggaa cagcagaata tgggccaaac aggatatctg tggtaagcag ttcctgcccc 1201 ggctcagggc caagaacaga tggtccccag atgcggtccc gccctcagca gtttctagag 1261 aaccatcaga tgtttccagg gtgccccaag gacctgaaat gaccctgtgc cttatttgaa 1321 ctaaccaatc agttcgcttc tcgcttctgt tcgcgcgctt ctgctccccg agctctatat 1381 aagcagagct cgtttagtga accgtcagat cgcctggaga cgccatccac gctgttttga 1441 cttccataga aggatctcga gatgatcatg gccgagagcc ctggcctgat caccatctgc 1501 ctgctgggct acctgctgag cgccgagtgc accgtgttcc tggaccacga gaacgccaac 1561 aagatcctga accggcccaa gagatacaac agcggcaagc tggaggagtt cgtgcagggc 1621 aacctggaga gggagtgcat ggaggagaag tgcagcttcg aggaggccag ggaagtgttc 1681 gagaacaccg agcggaccac cgagttctgg aagcagtacg tggacggcga ccagtgcgag 1741 agcaacccct tgcctgaacgg cggcagctgc aaggacgaca tcaacagcta cgagtgctgg 1801 tgcccttcg gcttcgaggg caagaactgc gagctggacg tgacctgcaa catcaagaac 1861 ggccgctgcg agcagttctg caagaacagc gccgacaaca agtggtgtg tagctgcacc 1921 gagggctaca gactggccga gaaccagaag agctgcgagc ccgccgtgcc cttcccctgc 1981 ggcagagtga gcgtgtccca gaccagcaag ctgaccagag ccgagaccgt gttccccgac 2041 gtggactacg tgaatagcac cgaggccgag accatcctgg acaacatcac ccagagcacc 2101 cagtccttca acgacttcac cagagttgtg ggcggcgagg acgccaagcc cggccagttc
```

-continued

```
2161 ccctggcagg tggtgctgaa cggcaaagtg gatgccttct gcggcggcag catcgtgaac
2221 gagaagtgga tcgtgacagc cgcccactgc gtggagaccg gcgtgaagat caccgtggtg
2281 gccggcgaac acaatatcga ggagaccgag cacaccgagc agaagcggaa cgtcatccgg
2341 attatccccc accacaacta caacgccgcc atcaacaagt acaaccacga catcgccctg
2401 ctggagctgg acgagcctct ggtgctgaat agctacgtga cccccatctg catcgccgac
2461 aaggagtaca ccaacatctt cctgaagttc ggcagcggct acgtgtccgg ctggggcaga
2521 gtgttccaca agggcagaag cgccctggtg ctgcagtacc tgagagtgcc cctggtggac
2581 agagccacct gcctgttgag caccaagttc accatctaca caacatgtt ctgcgccggc
2641 ttccacgagg gcggcagaga cagctgccag ggcgacagcg gcggacccca cgtgaccgaa
2701 gtggagggca ccagcttcct gaccggcatc atcagctggg gcgaggagtg cgccatgaag
2761 ggcaagtacg gcatctacac caaagtgagc cggtacgtga actggatcaa ggagaaaacc
2821 aagctgacct gagtcgacga taatcaacct ctggattaca aaatttgtga agattgact
2881 ggtattctta actatgttgc tcctttacg ctatgtggat acgctgcttt aatgcctttg
2941 tatcatgcta ttgcttcccg tatggctttc attttctcct ccttgtataa atcctggtta
3001 gttcttgcca cggcggaact catcgccgcc tgccttgccc gctgctggac aggggctcgg
3061 ctgttgggca ctgacaattc cgtgggtcga ctgctttatt tgtgaaattt gtgatgctat
3121 tgctttattt gtaaccatta taagctgcaa taaacaagtt aacaacaaca attgcattca
3181 ttttatgttt caggttcagg gggaggtgtg ggaggttttt taaactctat tttataggct
3241 tcttctctgg aatcttcttc atcatcctcc tgacaatcga taggtacctg gctgtcgtcc
3301 atgctgtgtt tgctttaaaa gccaggacgg tcacctttgg ggtggtgaca agtgtgatca
3361 cttgggtggt ggctgtgttt gcgtctctcc caggaatcat ctttaccaga tctcaaaaag
3421 aaggtcttca ttacacctgc agctctcatt ttccatacag tcagtatcaa ttctggaaga
3481 atttccagac attaaagata gtcatcttgg ggctggtcct gccgctgctt gtcatggtca
3541 tctgctactc gggaatccta aaaactctgc ttcggtgtcg aaatgagaag aagaggcaca
3601 gggctgtgag cttatcttc accatcatga ttgttattt tctcttctgg gctccctaca
3661 acattgtcct tctcctgaac accttccagg aattctttgg cctgaataat tgcagtagct
3721 ctaacaggtt ggaccaagct atgcaggtga cagagactct tgggatgacg cactgctgca
3781 tcaaccccat catctatgcc tttgtcgggg agaagttcag aaactacctc ttagtcttct
3841 tccaaaagca cattgccaaa cgcttctgca atgctgttc tattttccag caagaggctc
3901 ccgagcgagc aagctcagtt tacacccgat ccactgggga gcaggaaata tctgtgggct
3961 tgtgacacga actcaagtgg gctggtgacc cagtcagagt tgtgcacatg gcttagttt
4021 catacacacc gcggtctaga gcatggctac gtagataagt agcatggcgg gttaatcatt
4081 aactacaagg aaccctagt gatggagttg gccactccct ctctgcgcgc tcgctcgctc
4141 actgaggccg gcgaccaaa ggtcgcccga cgcccgggct tgcccgggc ggcctcagtg
4201 agcgagcgag cgcgccagct ggcgtaatag cgaagaggcc cgcaccgatc gcccttccca
4261 acagttgcgc agcctgaatg gcgaatggcg attccgttgc aatggctggc ggtaatattg
4321 ttctggatat taccagcaag gccgatagtt tgagttcttc tactcaggca agtgatgtta
4381 ttactaatca agaagtatt gcgacaacgg ttaatttgcg tgatggacag actctttac
4441 tcggtgccct cactgattat aaaaacactt ctcaggattc tggcgtaccg ttcctgtcta
4501 aaatcccttt aatcggcctc ctgtttagct cccgctctga ttctaacgag gaaagcacgt
```

```
4561 tatacgtgct cgtcaaagca accatagtac gcgccctgta gcggcgcatt aagcgcggcg
4621 ggtgtggtgg ttacgcgcag cgtgaccgct acacttgcca gcgccctagc gcccgctcct
4681 ttcgctttct tccttcctt tctcgccacg ttcgccggct ttccccgtca gctctaaat
4741 cgggggctcc ctttagggtt ccgatttagt gctttacggc acctcgaccc caaaaaactt
4801 gattagggtg atggttcacg tagtgggcca tcgccctgat agacggtttt tcgcccttg
4861 acgttggagt ccacgttctt taatagtgga ctcttgttcc aaactggaac aacactcaac
4921 cctatctcgg tctattcttt tgatttataa gggattttgc cgatttcggc ctattggtta
4981 aaaaatgagc tgatttaaca aaaatttaac gcgaatttta acaaaatatt aacgtttaca
5041 atttaaatat ttgcttatac aatcttcctg tttttgggc ttttctgatt atcaaccggg
5101 gtacatatga ttgacatgct agttttacga ttaccgttca tcgattctct tgtttgctcc
5161 agactctcag gcaatgacct gatagccttt gtagagacct ctcaaaaata gctaccctct
5221 ccggcatgaa tttatcagct agaacggttg aatatcatat tgatggtgat ttgactgtct
5281 ccggcctttc tcacccgttt gaatctttac ctacacatta ctcaggcatt gcatttaaaa
5341 tatatgaggg ttctaaaaat ttttatcctt gcgttgaaat aaaggcttct cccgcaaaag
5401 tattacaggg tcataatgtt tttggtacaa ccgatttagc tttatgctct gaggctttat
5461 tgcttaattt tgctaattct ttgccttgcc tgtatgattt attggatgtt ggaatcgcct
5521 gatgcggtat tttctcctta cgcatctgtg cggtatttca caccgcatat ggtgcactct
5581 cagtacaatc tgctctgatg ccgcatagtt aagccagccc cgacacccgc caacacccgc
5641 tgacgcgccc tgacgggctt gtctgctccc ggcatccgct tacagacaag ctgtgaccgt
5701 ctccgggagc tgcatgtgtc agaggttttc accgtcatca ccgaaacgcg cgagacgaaa
5761 gggcctcgtg atacgcctat ttttataggt taatgtcatg ataataatgg tttcttagac
5821 gtcaggtggc acttttcggg gaaatgtgcg cggaacccct atttgtttat ttttctaaat
5881 acattcaaat atgtatccgc tcatgagaca ataaccctga taaatgcttc aataatattg
5941 aaaaaggaag agtatgagta ttcaacattt ccgtgtcgcc cttattccct ttttgcggc
6001 attttgcctt cctgttttg ctcacccaga aacgctggtg aaagtaaaag atgctgaaga
6061 tcagttgggt gcacgagtgg gttacatcga actggatctc aacagcggta agatccttga
6121 gagttttcgc cccgaagaac gttttccaat gatgagcact tttaaagttc tgctatgtgg
6181 cgcggtatta tcccgtattg acgccgggca agagcaactc ggtcgccgca tacactattc
6241 tcagaatgac ttggttgagt actcaccagt cacagaaaag catcttacgg atggcatgac
6301 agtaagagaa ttatgcagtg ctgccataac catgagtgat aacactgcgg ccaacttact
6361 tctgacaacg atcggaggac cgaaggagct aaccgctttt ttgcacaaca tgggggatca
6421 tgtaactcgc cttgatcgtt gggaaccgga gctgaatgaa gccataccaa acgacgagcg
6481 tgacaccacg atgcctgtag caatggcaac aacgttgcgc aaactattaa ctggcgaact
6541 acttactcta gcttcccggc aacaattaat agactggatg gaggcggata agttgcagg
6601 accacttctg cgctcggccc ttccggctgg ctggtttatt gctgataaat ctggagccgg
6661 tgagcgtggg tctcgcggta tcattgcagc actggggcca gatggtaagc cctcccgtat
6721 cgtagttatc tacacgacgg ggagtcaggc aactatggat gaacgaaata gacagatcgc
6781 tgagataggt gcctcactga ttaagcattg gtaactgtca gaccaagttt actcatatat
6841 actttagatt gatttaaaac ttcattttta atttaaaagg atctaggtga agatcctttt
6901 tgataatctc atgaccaaaa tcccttaacg tgagttttcg ttccactgag cgtcagaccc
6961 cgtagaaaag atcaaaggat cttcttgaga tcctttttt ctgcgcgtaa tctgctgctt
```

```
-continued 7021 gcaaacaaaa aaaccaccgc taccagcggt ggtttgtttg ccggatcaag agctaccaac 7081 tcttttccg aaggtaactg gcttcagcag agcgcagata ccaaatactg tccttctagt 7141 gtagccgtag ttaggccacc acttcaagaa ctctgtagca ccgcctacat acctcgctct 7201 gctaatcctg ttaccagtgg ctgctgccag tggcgataag tcgtgtctta ccgggttgga 7261 ctcaagacga tagttaccgg ataaggcgca gcggtcgggc tgaacggggg gttcgtgcac 7321 acagcccagc ttggagcgaa cgacctacac cgaactgaga tacctacagc gtgagctatg 7381 agaaagcgcc acgcttcccg aagggagaaa ggcggacagg tatccggtaa gcggcagggt 7441 cggaacagga gagcgcacga gggagcttcc aggggaaac gcctggtatc tttatagtcc 7501 tgtcgggttt cgccacctct gacttgagcg tcgattttg tgatgctcgt caggggggcg 7561 gagcctatgg aaaaacgcca gcaacgcggc cttttacgg ttcctggcct tttgctggcc 7621 ttttgctcac atgttcttc ctgcgttatc ccctgattct gtggataacc gtattaccgc 7681 ctttgagtga gctgataccg ctcgccgcag ccgaacgacc gagcgcagcg agtcagtgag 7741 cgaggaagcg gaagagcgcc caatacgcaa accgcctctc cccgcgcgtt ggccgattca 7801 ttaatg
```

Compositions, Methods of Making Cells, and Cells that Secrete a Macromolecule for Promoting Tolerance of a Protein or Peptide, Survival of a B Cell or Engraftment of a Cell, Such as a B Cell.

In another aspect a method of making plasma cells or plasma cell precursors that expresses a second macromolecule, such as protein, or peptide is provided, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof. In some alternatives, second macromolecule is for inducing tolerance of a protein or peptide for therapeutic treatment or for inducing engraftment. In some alternatives, the second macromolecule is a protein. The protein may be BAFF, APRIL, IFN-alpha, IL-10 or IL-6. In some alternatives the protein is a viral vector capsid protein. In some alternatives, the viral vector capsid protein comprises at least one the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3). As described herein, B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof. In some alternatives, the method further comprises purifying the plasma cells or plasma cell precursors against CD138. In some alternatives, purifying comprises selecting the plasma cells by an anti-CD138 antibody for targeted removal of the plasma cells. In some alternatives, the purifying comprises using anti-CD138 beads for plasma cell selection.

In another aspect, a method of making a long lived plasma cell is provided, wherein the method comprises: isolating B cells; activating the B cells; a first round of genome editing of the B cells for macromolecule expression, such as a protein, protein mimetic or a peptide in the absence of viral integration; expanding the B cells; and differentiating the B cells. In some alternatives, the macromolecule is a protein, protein mimetic or peptide. In some alternatives, macromolecule is for inducing tolerance of a protein or peptide for therapeutic treatment or for inducing engraftment. In some alternatives, the macromolecule is a protein. The protein may be BAFF, APRIL, IFN-alpha, IL-10 or IL-6. In some alternatives the protein is a viral vector capsid protein. In some alternatives, the viral vector capsid protein comprises one or more of following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3). In some alternatives, the method further comprises purifying the plasma cells or plasma cell precursors against CD138. In some alternatives, purifying comprises selecting the plasma cells by an anti-CD138 antibody for targeted removal of the plasma cells. In some alternatives, the purifying comprises using anti-CD138 beads for plasma cell selection.

In another aspect, a plasma cell that expresses a macromolecule, such as a heterologous protein, protein mimetic or a peptide is provided. In some alternatives, the cell is a B cell. In some alternatives, the macromolecule is for inducing tolerance or for inducing engraftment. In some alternatives, the macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1

(VP1, VP2 and VP3), AAV8 (VP1, VP2 and VP3), AAV1 (VP1, VP2 and VP3) and/or AAV9 (VP1, VP2 and VP3). In some alternatives, the plasma cell expresses CD20.

In some alternatives a plasma cell is provided, wherein the plasma cell expresses a molecule, such as a macromolecule, protein, or peptide. The plasma cell or plasma cell precursors are manufactured by any one of the alternatives herein is provided. The method can comprise the steps: (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a CAS nuclease. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cell. In some alternatives, the method to prevent somatic hypermutation of an antibody locus in the B cell comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding of the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or any other length defined by a range that is set forth by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element and/or a synthetic engineered protein. In some alternatives, the protein is IFN-alpha, IL-6, Factor VIII, Factor IX, SERPING1 or SERPINA1. In some alternatives, the enzyme is ADAMTS13, LIPA, GLA, or ALPL. In some alternatives, the protein is a receptor antagonist that is used for the treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, a therapeutic antibody or binding portion thereof is used e.g., an antibody or binding portion thereof that is specific for a protein or other molecule expressed in an autoimmune disorder, autoinflammatory disorder, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion thereof. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies. In some alternatives, the protein is an engineered protein, wherein the engineered protein is protective in viral, fungal, parasitic and/or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or binding portion thereof, wherein the antibody or binding portion thereof is specific for an antigen that is expressed in a viral, fungal, parasitic or bacterial infection. In some alternatives, the B cells comprise B cell precursors such as hematopoietic stem cells (HSCs), multipotent progenitor (MPP) cells, lymphoid progenitor (CLP) cells, naïve B cells, GC B cell, plasmablast, early pro-B cells, late pro-B cells, large pre-B cells, small pre-B cells, immature B cells, T1 B cells, T2 B cells, marginal zone B cells, mature B cells and memory B cells. In some alternatives, the molecule is a macromolecule, protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein comprises a cofactor for enhanced enzymatic activity. In some alternatives the method of making the a long lived plasma cell comprises the steps: isolating B cells; activating the B cells; a first round of genome editing of the B cells for molecule expression, such as a protein, protein mimetic or a peptide in the absence of viral integration; expanding the B cells; and differentiating the B cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the B cells from the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion of any of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNABs). In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from a group selected from macromolecules, proteins, protein mimetics and peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the isolating is performed by negative selection isolation of hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the method further comprises purifying the plasma cells or plasma cell precursors against CD138. In some alternatives, purifying comprises selecting the plasma cells by an anti-CD138 antibody for targeted removal of the plasma cells. In some alternatives, the purifying comprises using anti-CD138 beads for plasma cell selection.

In another aspect, a composition comprising the plasma cell manufactured by any one of the alternatives provided herein or comprising the cell of any one of the alternatives provide herein, is provided. The plasma cell or plasma cell precursors are manufactured by any one of the alternatives herein is provided. The method can comprise the steps: (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the method further comprises purifying the plasma cells or plasma cell precursors against CD138. In some alternatives, purifying comprises selecting the plasma cells by an anti-CD138 antibody for targeted removal of the plasma cells. In some alternatives, the purifying comprises using anti-CD138 beads for plasma cell selection. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cells. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a CAS nuclease. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding of the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or any other length defined by a range that is set forth by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 μg/ml of CpG oligodeoxynucleotide 2006, 50 ng/ml of IL2, 50 ng/ml of IL10 and 10 ng/ml of IL15 for two days. In some alternatives, the cells were washed with IX PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element and/or a synthetic engineered protein. In some alternatives, the protein is IFN-alpha, IL-6, Factor VIII, Factor IX, SERPING1 or SERPINA1. In some alternatives, the enzyme is ADAMTS13, LIPA, GLA, or ALPL. In some alternatives, the protein is a receptor antagonist that is used for the treatment or amelioration of periodic fever or autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, a therapeutic antibody or binding portion thereof is used e.g., an antibody or binding portion thereof that is specific for a protein or other molecule expressed in an autoimmune disorder, autoinflammatory disorder, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion thereof. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies. In some alternatives, the protein is an engineered protein, wherein the engineered protein is protective in viral, fungal, parasitic and/or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or binding portion thereof, wherein the antibody or binding portion thereof is specific for an antigen that is expressed in a viral, fungal, parasitic or bacterial infection. In some alternatives, the B cells comprise B cell precursors such as hematopoietic stem cells (HSCs), multipotent progenitor (MPP) cells, lymphoid progenitor (CLP) cells, naïve B cells, GC B cell, plasmablast, early pro-B cells, late pro-B cells, large pre-B cells, small pre-B cells, immature B cells, T1 B cells, T2 B cells, marginal zone B cells, mature B cells and memory B cells. In some alternatives, the molecule is a macromolecule, protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein comprises a cofactor for enhanced enzymatic activity. In some alternatives the method of making the a long lived plasma cell comprises the steps: isolating B cells; activating the B cells; a first round of genome editing of the B cells for molecule expression, such as a protein, protein mimetic or a peptide in the absence of viral integration; expanding the B cells; and differentiating the B cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the B cells from the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL-1 monoclonal antibody, anti-TNF antibody, anti-IL-33 antibody or anti-C5 antibody or a binding portion of any of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNABs). In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from a group selected from macromolecules, proteins, protein mimetics and peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the isolating is performed by negative selection isolation of hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives herein, the method further comprises purifying the plasma cells or plasma cell precursors by positive selection against CD138. In some alternatives herein, purifying comprises selecting the plasma cells by an anti-CD138 antibody for targeted removal of the plasma cells. In some alternatives herein, the purifying comprises using anti-CD138 beads for plasma cell selection. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof. In some alternatives, the B cell expresses a macromolecule is for inducing tolerance or for inducing engraftment. In some alternatives, the macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3).

In another aspect, a method of expressing a molecule, such as a macromolecule in a subject in need is provided, wherein the method comprises: providing or administrating a plasma cell manufactured by any one of the alternative methods provided herein, the plasma cell that expresses molecule of any one of any one of the alternative plasma cells provided herein, or the composition of any one of the alternatives described herein, into the subject in need and administering a second B cell or second plasma cell, wherein the second B cell or second plasma cell expresses a second macromolecule, wherein the second macromolecule promotes inducing tolerance of a protein or peptide for therapy or induces engraftment. In some alternatives, the second plasma cell is derived from a B cell. In some alternatives, the second plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof. In some alternatives, the second B cell expresses a second macromolecule for inducing tolerance of a protein or peptide for therapy or induces or promotes engraftment. In some alternatives, the second macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3).

In another aspect, a method of treating, ameliorating or inhibiting a disease, such as a cancer, in a subject in need is provided, the method comprises administering a plasma cell manufactured by any one of the alternative methods herein or the plasma cell that expresses a molecule, such as a macromolecule manufactured by any one of the alternative methods herein, or the composition of any one of the alternative compositions herein into the subject in need and administering a second B cell or second plasma cell, wherein the second B cell or second plasma cell expresses a second macromolecule, wherein the second macromolecule promotes inducing tolerance of a protein or peptide for therapy or induces engraftment. In some alternatives, the second plasma cell is derived from a B cell. In some alternatives, the second plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof. In some alternatives, the second B cell expresses a second macromolecule for inducing tolerance of a protein or peptide for therapy or induces or promotes engraftment. In some alternatives, the second macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3). In some alternatives, the method comprises monitoring of the subject following plasma cell transplantation. In some alternatives, the subject is determined to no longer need treatment or therapy and the method further comprises administering Rituxan® or an anti-CD20 antibody or binding portion thereof for targeted removal of the plasma cells.

In another aspect, a method of expressing a molecule, such as a macromolecule in a subject in need is provided, wherein the method comprises: (a) isolating a first population of B cells; (b) developing the first population of B cells; (c) performing a first round of genome editing of the first population of B cells for protein expression in absence of viral integration; (d) expanding the first population of B cells; differentiating the first population of B cells, optionally, after step (c) or (d), thereby producing plasma cells that express a protein; (e) administering the first population of B cells into the subject in need and (f) administering a second population of B cells into the subject in need, wherein the second population of B cells expresses a second macromolecule for inducing tolerance of a protein or peptide for therapy or induces or promotes engraftment. In some alternatives, the second macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3). In some alternatives, the method further comprises purifying the plasma cells or plasma cell precursors by positive selection against CD138. In some alternatives, purifying comprises selecting the plasma cells by an anti-CD138 antibody for targeted removal of the plasma cells. In some alternatives, the purifying comprises using anti-CD138 beads for plasma cell selection.

In another aspect, a method of ameliorating a disease in a subject in need is provided, the method comprising: administering a plasma cell manufactured by any one of the alternatives herein or the plasma cell that expresses a molecule, such as a macromolecule manufactured by any one of the alternatives herein, or the composition of the alternatives herein into the subject in need and administering a second B cell or second plasma cell, wherein the second B cell or second plasma cell expresses a second macromolecule, wherein the second macromolecule promotes inducing tolerance of a protein or peptide for therapy or induces engraftment. In some alternatives, the second plasma cell is derived from a B cell. In some alternatives, the second plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells and/or any mixtures or combinations thereof. In some alternatives, the second B cell expresses a second macromolecule for inducing tolerance of a protein or peptide for therapy or induces or promotes engraftment. In some alternatives, the second macromolecule is a protein. The protein may be BAFF, APRIL, IFN-alpha, IL-10 or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3). In some alternatives, the administering is performed by adoptive transfer. In some alternatives, the subject has received a stem cell administration or solid organ transplantation. In some alternatives, the subject suffers from influenza, parainfluenza, rhinovirus, respiratory syncytial virus, HIV, or other pathogenic bacteria, virus, fungus or parasite. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives a second B cell expressing a second macromolecule is provided, wherein the second B cell provides the second macromolecule for inducing tolerance or for inducing engraftment. In some alternatives, the second macromolecule is a protein. The protein may be BAFF, APRIL, IFN-alpha, IL-10, IFN-alpha or IL-6. In some alternatives the protein is a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3).

In some alternatives, a method of inducing tolerance of a peptide useful for therapeutic application, secreted by a B cell in a subject in need in vivo and/or increasing engraftment of the B cell in a subject in need is provided, the method comprises A) isolating a first population of B cells; B) performing a first round of genome editing of the first population of B cells for protein or peptide expression in absence of viral integration, wherein the performing is under conditions of rapid B cell expansion; C) expanding the first population of B cells; D) differentiating the first population of B cells, optionally, after step (c) or (d), thereby producing an activated first population of B cells or naïve activated first population of B cells that express the molecule; E) providing or administering the first population of B cells that expresses the peptide into a subject in need; and F) administering a second population of B cells that expresses a macromolecule for tolerance, survival of a B cell or engraftment. In some alternatives, the therapeutic application is treatment of cancer. In some alternatives, the therapeutic application is immunotherapeutic application. In some alternatives, the cancer is a solid tumor. In some alternatives, the peptide is an anti-PD1 antibody or a PDL-1 ligand. In some alternatives, the second B cell expresses BAFF, APRIL, IFN-alpha, IL-10 or IL-6. In some alternatives, the second B cell expresses a second peptide that is expressed and presented as a MHC class II molecule on a surface of the B cells.

In some alternatives, a method of inducing tolerance of a peptide for immunotherapeutic application, secreted by a B cell in a subject in need in vivo and/or increasing engraftment or survival of the B cell in a subject in need, the method comprising: A) isolating a first population of B cells; B) performing a first round of genome editing of the first population of B cells for protein or peptide expression in absence of viral integration, wherein the performing is under conditions of rapid B cell expansion; C) expanding the first population of B cells; D) differentiating the first population of B cells, optionally, after step (c) or (d), thereby producing an activated first population of B cell or naïve activated first population of B cells that express the protein or peptide; E) providing or administering the first population of B cells that expresses the protein or peptide into a subject in need F) providing or administering a second population of B cells that expresses a macromolecule, wherein the second population of B cells allows tolerance of the protein or peptide and/or promotes engraftment and/or survival. In some alternatives, the first population of B cells and the second population of B cells are co-administered. In some alternatives, the macromolecule comprises BAFF, APRIL, IFN-alpha, IL-10 or IL-6. In some alternatives, the protein comprises an enzyme, neutralizing antibody or a binding portion thereof, cytokine, cytokine receptor, complement protein, inhibitory protein, anti-fibrotic molecule, therapeutic antibody or a binding portion thereof, anti-thrombotic molecule, glucose response element or monoclonal antibody or a binding portion thereof. In some alternatives, the protein is SERPING1 or SERPINA1. In some alternatives, the protein is a receptor antagonist for the treatment or inhibition of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the protein comprises therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof.

In some alternatives, a composition comprising the plasma cell manufactured by any one of the alternatives herein and a second B cell, wherein the second B cell secretes a macromolecule for inducing tolerance of a peptide for immunotherapeutic application or for inducing engraftment of the plasma cell manufactured by any one of the alternatives herein is provided. In some alternatives, the macromolecule expressed by the second B cell comprises IFN-alpha, BAFF, APRIL, IL-10 or IL-6. In some alternatives, the second B cell expresses a viral vector capsid protein. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) and/or AAV9 (VP1, VP2 and VP3).

TABLE 4

Additional guide sequences that are used for some of the alternatives herein.

| Sense/ Antisense | Broad rank | Guide Sequence - RNA | Guide sequence - mod & linker |
|---|---|---|---|
| antisense | | GGACTCCCCAGAAAAGCAAA (SEQ ID NO: 63) | mG*mG*mA*rCrUrCrCrCrArGrArArArArGrCrArArArGrUrUrUrArGrArGr CrUrArU*mG*mC*mU (SEQ ID NO: 88) |
| sense | | AAGAACCATTTGCTTTTCTG (SEQ ID NO: 64) | mA*mA*mG*rArArCrCrArUrUrUrGrCrUrUrUrUrCrUrGrGrUrUrUrArGrArGr CrUrArU*mG*mC*mU (SEQ ID NO: 89) |
| sense | | TTTGCTTTTCTGGGGAGTCC (SEQ ID NO: 65) | mU*mU*mU*rGrCrUrUrUrCrUrGrGrGrGrArGrUrCrCrGrUrUrUrArGrArGr CrUrArU*mG*mC*mU (SEQ ID NO: 90) |
| sense | | ATTAAGGCTGTTCATGTGAA (SEQ ID NO: 66) | mA*mU*mU*rArArGrGrCrUrGrUrUrCrArUrGrUrGrArArGrUrUrUrArGrArGr CrUrArU*mG*mC*mU (SEQ ID NO: 91) |
| antisense | | CCGGCGCGGCAGGCGCATGG (SEQ ID NO: 67) | mC*mC*mG*rGrCrGrCrGrGrCrArGrGrCrGrCrArUrGrGrGrUrUrUrArGrArGr CrUrArU*mG*mC*mU (SEQ ID NO: 92) |
| antisense | | AGCCCCAGCGCGGCCCGGCG (SEQ ID NO: 68) | mA*mG*mC*rCrCrCrArGrCrGrCrGrGrCrCrCrGrGrCrGrGrUrUrUrArGrArGr CrUrArU*mG*mC*mU (SEQ ID NO: 93) |
| sense | | TGCCGCGCCGGGCCGCGCTG (SEQ ID NO: 69) | mU*mG*mC*rCrGrCrGrCrCrGrGrGrCrCrGrCrGrCrUrGrGrUrUrUrArGrArGr CrUrArU*mG*mC*mU (SEQ ID NO: 94) |
| antisense | | AAGCGGCAGGAGCCCCAGCG (SEQ ID NO: 70) | mA*mA*mG*rCrGrGrCrArGrGrArGrCrCrCrCrArGrCrGrGrUrUrUrArGrArGr CrUrArU*mG*mC*mU (SEQ ID NO: 95) |
| sense | 1 | AGGTAGACAATTGCAGCCTG (SEQ ID NO: 71) | mA*mG*mG*rUrArGrArCrArArUrUrGrCrArGrCrCrUrGrGrUrUrUrArGrArGr CrUrArU*mG*mC*mU (SEQ ID NO: 96) |
| sense | 12 | TCCCTACAGACAGAGCCACA (SEQ ID NO: 72) | mU*mC*mC*rCrUrArCrArGrArCrArGrArGrCrCrArCrArGrUrUrUrArGrArGr CrUrArU*mG*mC*mU (SEQ ID NO: 97) |
| sense | 3 | AGATGTTGTCCTGACACTTG (SEQ ID NO: 73) | mA*mG*mA*rUrGrUrUrGrUrCrCrUrGrArCrArCrUrUrGrGrUrUrUrArGrArGr CrUrArU*mG*mC*mU (SEQ ID NO: 98) |
| sense | 16 | GCCTTCACCATGAAGTCCAG (SEQ ID NO: 74) | mG*mC*mC*rUrUrCrArCrCrArUrGrArArGrUrCrCrArGrGrUrUrUrArGrArGr CrUrArU*mG*mC*mU (SEQ ID NO: 99) |
| sense | 33 | TTCAACTGCTCATCAGATGG (SEQ ID NO: 75) | mU*mU*mC*rArArCrUrGrCrUrCrArUrCrArGrArUrGrGrGrUrUrUrArGrArGr CrUrArU*mG*mC*mU (SEQ ID NO: 100) |
| antisense | 4 | GGCCAAAGTACAGTGGAAGG (SEQ ID NO: 76) | mG*mG*mC*rCrArArArGrUrArCrArGrUrGrGrArArGrGrGrUrUrUrArGrArGr CrUrArU*mG*mC*mU (SEQ ID NO: 100 |
| sense | 4 | CACGCTGCTCGTATCCGACG (SEQ ID NO: 77) | mC*mA*mC*rGrCrUrGrCrUrCrGrUrArUrCrCrGrArCrGrGrUrUrUrArGrArGr CrUrArU*mG*mC*mU (SEQ ID NO: 102) |
| antisense | 5 | CCTTCCAAGGACGTCATGCA (SEQ ID NO: 78) | mC*mC*mU*rUrCrCrArArGrGrArCrGrUrCrArUrGrCrArGrUrUrUrArGrArGr CrUrArU*mG*mC*mU (SEQ ID NO: 103) |
| antisense | 4 | CAGCCTTAATAAAAACCGCC (SEQ ID NO: 79) | mC*mA*mG*rCrCrUrUrArArUrArArArArArCrCrGrCrCrGrUrUrUrArGrArGr CrUrArU*mG*mC*mU (SEQ ID NO: 104) |
| sense | 12 | TTCTTCCGAAGATCCTAATG (SEQ ID NO: 80) | mU*mU*mC*rUrUrCrCrGrArArGrArUrCrCrUrArArUrGrGrUrUrUrArGrArGr CrUrArU*mG*mC*mU (SEQ ID NO: 105) |
| antisense | 32 | GTCAGGATAGCAGGCATCTG (SEQ ID NO: 81) | mG*mU*mC*rArGrGrArUrArGrCrArGrGrCrArUrCrUrGrGrUrUrUrArGrArGr CrUrArU*mG*mC*mU (SEQ ID NO: 100 |
| antisense | 3 | TACTGGCTCCACTTCTCGAG (SEQ ID NO: 82) | mU*mA*mC*rUrGrGrCrUrCrCrArCrUrUrCrUrCrGrArGrGrUrUrUrArGrArGr CrUrArU*mG*mC*mU (SEQ ID NO: 107) |
| sense | 20 | GATATTGATATACTTCCTAG (SEQ ID NO: 83) | mG*mA*mU*rArUrUrGrArUrArUrArCrUrUrCrCrUrArGrGrUrUrUrArGrArGr CrUrArU*mG*mC*mU (SEQ ID NO: 108) |
| antisense | 2 | ACCCAAAGGGGTCTCAAAGG (SEQ ID NO: 84) | mA*mC*mC*rCrArArArGrGrGrGrUrCrUrCrArArArGrGrGrUrUrUrArGrArGr CrUrArU*mG*mC*mU (SEQ ID NO: 109) |
| antisense | 10 | CAGCGTCTTAGCACCCAAAG (SEQ ID NO: 85) | mC*mA*mG*rCrGrUrCrUrUrArGrCrArCrCrCrArArArGrGrUrUrUrArGrArGr CrUrArU*mG*mC*mU (SEQ ID NO: 110) |

TABLE 4-continued

Additional guide sequences that are used for some of the alternatives herein.

| Sense/<br>Antisense | Broad<br>rank | Guide Sequence - RNA | Guide sequence - mod & linker |
|---|---|---|---|
| sense | 3 | CGAATGCAATCAGATGCTAG<br>(SEQ ID NO: 86) | mC*mG*mA*rArUrGrCrArArUrCrArGrArUrGrCrUrArGrGrUrUrUrArGrArGr<br>CrUrArU*mG*mC*mU (SEQ ID NO: 111) |
| antisense | 4 | ACCGAGACAGTCGGGACCGT<br>(SEQ ID NO: 87) | mA*mC*mC*rGrArGrArCrArGrUrCrGrGrGrArCrCrGrUrGrUrUrUrArGrArGr<br>CrUrArU*mG*mC*mU (SEQ ID NO: 112) |

As shown the modifications are: m - 2'O methyl-modified bases, r - standard RNA bases* - phosphorothioate bond In some alternatives, a method of making plasma cells or plasma cell precursors that express a molecule is provided, wherein the method comprises: (a) isolating B cells, (b) developing the B cells, (c) performing a first round of genome editing of the B cells for protein expression in absence of viral integration, (d) expanding the B cells and (e) differentiating the B cells, optionally, after step (c) or (d), thereby producing plasma cells or plasma cell precursors that express the molecule. In some alternatives, the molecule is a protein, protein mimetic or peptide. In some alternatives, the molecule is Factor VIII, Factor IX, SERPING1, SERPINA1, complement inhibitory protein, Factor H, Factor I, a C1 inhibitor, an anti-fibrotic molecule, SCGB1A1, a therapeutic antibody or a binding portion thereof, an anti-IL-1 monoclonal antibody, an anti-TNF antibody, an anti-IL-33 antibody, an anti-C5 antibody, an anti-thrombotic molecule, APLN, an anti-PCSK9 inhibitory antibody or binding portion thereof, a neutralizing HIV-1 antibody (bNAbs) or binding portion thereof, IFN-alpha, BAFF, APRIL, IL-10, IL-6, ADAMTS13, LIPA, GLA or ALPL. In some alternatives, the developing of the B cells is performed after the B cells are arrested at a specific phase of development or activating the B cells such that the B cells are permissive for recombination without further B cell differentiation, wherein the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration, and wherein performing the first round of genome editing of the B cells for protein expression is performed by introduction of a single stranded nucleic acid. In some alternatives, the first round of genome editing is performed by an RNA and protein based transfection and, wherein the first round of genome editing comprises delivering a nuclease, wherein the nuclease targets at least one genetic loci in the B cell and, wherein the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the first round of genome editing comprises transducing the B cell with a recombinant adeno-associated virus vector to serve as a donor template for homologous recombination into a candidate genetic loci. In some alternatives, the method further comprises preventing somatic hypermutation of an antibody locus in the B cell. In some alternatives, the method further comprises selectively increasing a proportion of gene edited B cells and, wherein the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, step (a) further comprises removing IgM positive cells. In some alternatives, the method further comprises introducing a nucleic acid, wherein the nucleic acid encodes at least one cell surface protein. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 or IL-15, wherein the plasmablast differentiation step is performed in the presence any combination of IL-2, IL-6, IL-10 or IL-15 or wherein the plasma cell differentiation step is performed in the presence any combination of IL-6, IL-15, APRIL or IFNα. In some alternatives, the plasma cells are long lived plasma cells. In some alternatives, the method further comprises purifying the plasma cells by positive selection against CD138.

In some alternatives, a composition comprising a plasma cell, which expresses a molecule, wherein said molecule is a heterologous protein, protein mimetic or a peptide is provided. In some alternatives, the molecule comprises an enzyme, neutralizing antibody or binding portion thereof, cytokine, cytokine receptor, complement protein, inhibitory protein, anti-fibrotic molecule, therapeutic antibody or binding portion thereof, anti-thrombotic molecule, glucose response element, or a monoclonal antibody or binding portion thereof. In some alternatives, the composition further comprises a second B cell, wherein the second B cell secretes a molecule that induces tolerance of a peptide or that induces engraftment of the plasma cell.

In some alternatives, a method of expressing a molecule in a subject is provided wherein the method comprises administering the composition of anyone of the alternatives to the subject. In some alternatives, the composition comprises a plasma cell, which expresses a molecule, wherein said molecule is a heterologous protein, protein mimetic or a peptide is provided. In some alternatives of the composition, the molecule comprises an enzyme, neutralizing antibody or binding portion thereof, cytokine, cytokine receptor, complement protein, inhibitory protein, anti-fibrotic molecule, therapeutic antibody or binding portion thereof, anti-thrombotic molecule, glucose response element, or a monoclonal antibody or binding portion thereof. In some alternatives, the composition further comprises a second B cell, wherein the second B cell secretes a molecule that induces tolerance of a peptide or that induces engraftment of the plasma cell. In some alternatives, the subject has received a stem cell administration or a solid organ transplantation or is a subject identified or selected as one to receive a stem cell administration or a solid organ transplantation or, wherein the subject has an enzyme deficiency, pulmonary fibrosis, an autoimmune disorder, immune dysregulation, cancer, diabetes, HIV or hypercholesterolemia.

More Alternatives

In some alternatives, a method of making plasma cells or plasma cell precursors that expresses a molecule, such as a macromolecule, protein, or peptide is provided, wherein the method comprises (a) isolating B cells; (b) developing the B cells; (c) performing a first round of genome editing of the B cells for expression of a molecule in absence of viral integration; (d) expanding the B cells; and (e) differentiating the B cells, optionally, after step (c) or (d), thereby producing plasma cells or plasma cell precursors that express the molecule. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the protein comprises an enzyme, monoclonal antibody or a binding portion thereof, neutralizing antibodies or a binding portions thereof, therapeutic antibodies or binding portions thereof, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs), or a binding portion thereof. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed by a virus, fungus, parasite or bacteria. In some alternatives, the protein comprises an antibody or a binding portion thereof, wherein the antibody or a binding portion thereof is specific for an antigen that is expressed on a viral, fungal, parasitic or bacterial infection. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are patient derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a CAS nuclease. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cell with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cell. In some alternatives, the method to prevent somatic hypermutation of an antibody locus in the B cell comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cell short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding of the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or any other length defined by a range that is set forth by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL-2, 50 ng/ml of IL-10 and 10 ng/ml of IL-15 for two days. In some alternatives, the cells were washed with 1×PBS and seeded in medium with IL-6 (50 ng/ml), IL-15 (10 ng/ml) and human interferon-α 2B (100 U/ml, Sigma-Aldrich®) for three days to stimulate plasma cell differentiation. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element and/or a synthetic engineered protein. In some alternatives, the protein is IFN-alpha, IL-6, Factor VIII, Factor IX, SERPING1 or SERPINA1. In some alternatives, the enzyme is ADAMTS13, LIPA, GLA, or ALPL. In some alternatives, the protein is a receptor antagonist that is used for the treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, a therapeutic antibody or binding portion thereof is used e.g., an antibody or binding portion thereof that is specific for a protein or other molecule expressed in an autoimmune disorder, autoinflammatory disorder, immune dysregulation and/or cancer. In some alternatives, the antibody or binding portion thereof is an anti-IL1 monoclonal antibody, anti-TNF antibody, anti-IL33 antibody or anti-C5 antibody or a binding portion thereof. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies. In some alternatives, the protein is an engineered protein, wherein the engineered protein is protective in viral, fungal, parasitic and/or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or binding portion thereof, wherein the antibody or binding portion thereof is specific for an antigen that is expressed in a viral, fungal, parasitic or bacterial infection. In some alternatives, the B cells comprise B cell precursors such as hematopoietic stem cells (HSCs), multipotent progenitor (MPP) cells, lymphoid progenitor (CLP) cells, naïve B cells, GC B cell, plasmablast, early pro-B cells, late pro-B cells, large pre-B cells, small pre-B cells, immature B cells, T1 B cells, T2 B cells, marginal zone B cells, mature B cells and/or memory B cells. In some alternatives, the molecule is a macromolecule, protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein comprises a cofactor for enhanced enzymatic activity. In some alternatives, the method further comprises purifying the plasma cells or plasma cell precursors after step e) by positive selection against CD138. In some alternatives, purifying comprises selecting the plasma cells by an anti-CD138 antibody for targeted removal of the plasma cells. In some alternatives, the purifying comprises using anti-CD138 beads for plasma cell selection.

In some alternatives, a method of making a long lived plasma cell is provided, wherein the method comprises: isolating B cells; activating the B cells; a first round of genome editing of the B cells for molecule expression, such as a protein, protein mimetic or a peptide in the absence of viral integration; expanding the B cells; and differentiating the B cells, thereby producing the long lived plasma cell. In some alternatives, the method further comprises selecting the long lived plasma cell by CD138 selection of the plasma cells. In some alternatives, the macromolecule is a protein, protein mimetic or peptide. In some alternatives, the protein, protein mimetic, or peptide comprises natural amino acids and/or unnatural amino acids. In some alternatives, the macromolecule comprises a carbohydrate or lipid moiety. In some alternatives, the macromolecule comprises a cofactor. In some alternatives, the protein comprises a hydrophobic group for membrane localization. In some alternatives, the protein is acylated. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for the treatment or inhibition of periodic fever or autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL-1 monoclonal antibody, anti-TNF antibody, anti-IL-33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the B cells from the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cell with a recombinant adeno-associated virus vector for homologous recombination into a candidate genetic loci. In some alternatives, the method further comprises applying methods to prevent somatic hypermutation of an antibody locus and other target loci in the B cell. In some alternatives, the method to prevent somatic hypermutation of an antibody locus in the B cell comprises disruption of an AID gene. In some alternatives, the method further comprises introducing production enhancers into the B cell or disruption of candidate loci within the B cell to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL1 monoclonal antibody, anti-TNF antibody, anti-IL33 antibody or anti-C5 antibody or a binding portion of any of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNABs). In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from a group selected from macromolecules, proteins, protein mimetics and peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the isolating is performed by negative selection isolation of hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the method further comprises purifying long lived plasma cells are purified by positive selection against CD138. In some alternatives, purifying comprises selecting the plasma cells by an anti-CD138 antibody for targeted removal of the plasma cells. In some alternatives, the purifying comprises using anti-CD138 beads for plasma cell selection.

In some alternatives, a plasma cell that expresses a molecule, such as a heterologous protein, protein mimetic or a peptide is provided. In some alternatives, the cell is a B cell. In some alternatives, the heterologous protein comprises an enzyme, neutralizing antibody, cytokine, cytokine receptor, complement protein, inhibitory protein, anti-fibrotic molecule, therapeutic antibody, anti-thrombotic molecule, glucose response element and/or monoclonal antibody or binding portion thereof. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and cancer. In some alternatives, the antibody or binding portion thereof is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNABs). In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adeno-virus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-A antibodies. In some alternatives, the protein is an engineered protein, wherein the engineered protein is protective in viral, fungal, parasitic or bacterial infection. In some alternatives, the engineered protein comprises an antibody or binding portion thereof, wherein the antibody or binding portion thereof is specific for an antigen that is expressed on a virus, fungus, parasite or bacteria. In some alternatives, the protein comprises an antibody or a binding portion thereof, wherein the antibody or a binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cells. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, antifibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from a group of macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the plasma cell further comprises at least one cell surface protein. In some alternatives, the at least one cell surface protein is CD20.

In some alternatives, a composition comprising the plasma cell manufactured by any one of the alternatives provided herein or comprising the cell of any one of the alternatives herein, is provided. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, antifibrotic molecule, therapeutic antibody, anti-thrombotic molecule, glucose response element or a monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an antifibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-A antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the first round of genome editing comprises transfecting single stranded DNA oligonucleotides for homologous recombination into a candidate genetic loci. In some alternatives, the Cas nuclease comprises Cas1, Cas2, Cas3, Cas4, Cas5, Cas6, Cas7, Cas8 or Cas9. In some alternatives, the first round of genome editing comprises transducing the B cell with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity.

In some alternatives, a method of expressing a molecule, such as a macromolecule in a subject in need is provided, wherein the method comprises: providing or administrating a plasma cell manufactured by any one of the alternative methods provided herein, the plasma cell that expresses a molecule of any one of any one of the alternative plasma cells provided herein, or the composition of any one of the alternatives described herein, into the subject in need. In some alternatives, the method further comprises purifying the plasma cells of step d), wherein the purifying is performed after the expanding step. In some alternatives, the purifying comprises positive selecting of cells against CD138. In some alternatives, the selecting the plasma cells is performed by an anti-CD138 antibody for targeted removal of the plasma cells. In some alternatives, the purifying comprises using anti-CD138 beads for plasma cell selection. In some alternatives, the molecule is a macromolecule, such as a protein, protein mimetic or a peptide. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein is an enzyme. In some alternatives, the enzyme comprises a cofactor for enhanced enzymatic activity. In some alternatives, the composition comprises the plasma cell manufactured by any one of the alternatives provided herein or comprises the cell of any one of the alternatives provide herein. In some alternatives, the cell is a B cell. In some alternatives, the B cells comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or monoclonal antibody. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, the protein is the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is an early pro-B cell, late pro-B cell, large pre-B cell, small pre-B cell, immature B cell, T1 B cell, T2 B cell, marginal zone B cell, mature B cell, naïve B cell, plasmablast (short lived) cell, GC B cell, memory B cell, plasmablast cell and/or long lived plasma cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or portion thereof, wherein the antibody or portion thereof is specific for an antigen that is expressed on a virus, fungus, parasite or bacteria. In some alternatives, the protein comprises an antibody or binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cells. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives of the method of expressing a molecule, such as a macromolecule in a subject in need, the administrating is performed by adoptive transfer. In some alternatives of the method of expressing a molecule, such as a macromolecule in a subject in need, the subject has received a stem cell administration or solid organ transplantation. In some alternatives of the method of expressing protein in a subject in need, the subject suffers from influenza, parainfluenza, rhinovirus, respiratory syncytial virus, HIV, or other pathogenic bacteria, virus, fungus or parasite infection. In some alternatives of the method of expressing protein in a subject in need, the subject suffers from an enzyme deficiency. In some alternatives of the method of expressing a molecule, such as a macromolecule in a subject in need, the subject suffers from pulmonary fibrosis. In some alternatives of the method of expressing a molecule, such as a macromolecule in a subject in need, the subject suffers from an autoimmune disorder, immune dysregulation or cancer. In some alternatives, the subject suffers from HIV. In some alternatives of the method of expressing a molecule, such as a macromolecule in a subject in need, the subject suffers from diabetes. In some alternatives of the method of expressing a molecule, such as a macromolecule in a subject in need, the subject suffers from hypercholesterolemia. In some alternatives of the method of expressing a molecule, such as a macromolecule in a subject in need, the subject is also receiving CAR T-cell therapy. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method comprises monitoring of the subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a composition comprising the plasma cell manufactured by any one of the alternatives herein and a second B cell, wherein the second B cell secretes a macromolecule for inducing tolerance of a peptide for immunotherapeutic application or for inducing engraftment of the plasma cell manufactured by any one of anyone of the alternatives herein is provided. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or a monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the first round of genome editing comprises transfecting single stranded DNA oligonucleotides for homologous recombination into a candidate genetic loci. In some alternatives, the Cas nuclease comprises Cas1, Cas2, Cas3, Cas4, Cas5, Cas6, Cas7, Cas8 or Cas9. In some alternatives, the first round of genome editing comprises transducing the B cell with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method further comprises purifying the plasma cells or plasma cell precursors by positive selection against CD138. In some alternatives, purifying comprises selecting the plasma cells by an anti-CD138 antibody for targeted removal of the plasma cells. In some alternatives, the purifying comprises using anti-CD138 beads for plasma cell selection.

In some alternatives, a method of treating, ameliorating or inhibiting a disease, such as a cancer, in a subject in need, is provided, the method comprises administering a plasma cell manufactured by any one of the alternative methods herein or the plasma cell that expresses a molecule, such as a macromolecule manufactured by any one of the alternative methods herein, or the composition of any one of the alternative compositions herein into the subject in need. In some alternatives, the composition comprises the plasma cell manufactured by any one of the alternatives provided herein or comprises the cell of any one of the alternatives provided herein. In some alternatives, the cell is a B cell. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or a monoclonal antibody. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the Cas nuclease comprises Cas1, Cas2, Cas3, Cas4, Cas5, Cas6, Cas7, Cas8 or Cas9. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof that is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cell to enable selectable expansion of the B cells in vitro or in vivo. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence of any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, auto-inflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives of the method of treating, inhibiting or ameliorating a disease, such as cancer, in a subject in need, the administering is performed by adoptive transfer. In some alternatives of the method of treating, inhibiting, or ameliorating a disease, such as cancer, in a subject in need, the subject has received a stem cell administration or solid organ transplantation. In some alternatives of the method of ameliorating, treating, or inhibiting a disease in a subject in need, the subject suffers from influenza, parainfluenza, rhinovirus, respiratory syncytial virus, HIV, or other pathogenic bacteria, virus, fungus or parasite infection. In some alternatives of the method of ameliorating, treating, or inhibiting a disease in a subject in need, the subject suffers from an enzyme deficiency. In some alternatives of the method of ameliorating, treating, or inhibiting a disease in a subject in need, the subject suffers from pulmonary fibrosis. In some alternatives of the method of ameliorating, treating, or inhibiting a disease in a subject in need, the subject suffers from an autoimmune disorder, immune dysregulation and/or cancer. In some alternatives of the method of ameliorating, treating, or inhibiting a disease in a subject in need, the subject suffers from diabetes. In some alternatives of the method of ameliorating, treating, or inhibiting a disease in a subject in need, the subject suffers from hypercholesterolemia. In some alternatives of the method of ameliorating, treating, or inhibiting a disease in a subject in need, the subject is receiving therapy. In some alternatives of the method of ameliorating, treating, or inhibiting a disease in a subject in need, the subject is selected to receive cancer therapy, diabetes therapy, HIV treatment, or viral therapy. In some alternatives of the method of ameliorating, treating, or inhibiting a disease in a subject in need, the subject is also receiving CAR T-cell therapy. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of expressing a molecule, such as a macromolecule in a subject of need is provided, wherein the method comprises: (a) isolating B cells; (b) developing the B cells; (c) performing a first round of genome editing of the B cells for molecule expression in absence of viral integration; (d) expanding the B cells; differentiating the B cells, optionally, after step (c) or (d), thereby producing plasma cells that express a protein; and (e) administering the B cells into the subject in need. In some alternatives, the developing of the B cells is performed after the B cells are arrested at a specific phase of development and/or activating the B cells such that the B cells are permissive for recombination without further B cell differentiation. In some alternatives, the method further comprises purifying the plasma cells of step d), wherein the purifying is performed after the expanding step. In some alternatives, the purifying comprises positive selecting of cells against CD138. In some alternatives, the selecting the plasma cells is performed by an anti-CD138 antibody for targeted removal of the plasma cells. In some alternatives, the purifying comprises using anti-CD138 beads for plasma cell selection. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein is an enzyme. In some alternatives, the enzyme comprises a cofactor for enhanced enzymatic activity. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, wherein step (a) performing a second round of genome editing on the B cells to excise a region, further comprises removing IgM positive cells. In some alternatives, the method further comprises, activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP1 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence any combination of IL-2, IL-6, IL-10 and/or IL-15. In some alternatives, the plasma cell differentiation step is performed in the presence any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the administering is performed by adoptive transfer. In some alternatives, the subject has received a stem cell by administration or solid organ transplantation. In some alternatives, the subject suffers from influenza, parainfluenza, rhinovirus, respiratory syncytial virus, HIV, or other pathogenic bacteria, virus, fungus or parasite infection. In some alternatives, the subject suffers from an enzyme deficiency. In some alternatives, the subject suffers from pulmonary fibrosis. In some alternatives, the subject suffers from an autoimmune disorder, immune dysregulation and/or cancer. In some alternatives, the subject suffers from diabetes. In some alternatives, the subject suffers from hypercholesterolemia. In some alternatives, the subject is receiving a conventional therapy for the disease, malady or condition. In some alternatives, the subject is selected to receive cancer therapy, diabetes therapy, HIV treatment, or viral therapy. In some alternatives, the subject is also receiving CAR T-cell therapy. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of ameliorating a disease in a subject in need is provided, the method comprising: administering a plasma cell manufactured by any one of the alternatives herein or the plasma cell that expresses a molecule, such as a macromolecule manufactured by any one of the alternatives herein, or the composition of the alternatives herein into the subject in need. In some alternatives, the administering is performed by adoptive transfer. In some alternatives, the subject has received a stem cell administration or solid organ transplantation. In some alternatives, the subject suffers from influenza, parainfluenza, rhinovirus, respiratory syncytial virus, HIV, or other pathogenic bacteria, virus, fungus or parasite infection. In some alternatives, the composition comprises the plasma cell manufactured by any one of the alternatives provided herein or comprises the cell of any one of the alternatives provided herein. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or a monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells.

In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the first round of genome editing comprises transfecting single stranded DNA oligonucleotides for homologous recombination into a candidate genetic loci. In some alternatives, the Cas nuclease comprises Cas1, Cas2, Cas3, Cas4, Cas5, Cas6, Cas7, Cas8 or Cas9. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence of any combination of MCD40L, CpG, IL-2, IL-10 and/or IL-15. In some alternatives, cells are activated with 100 ng/ml of recombinant human MEGACD40L®), 1 μg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of enhancing immune tolerance to protein therapeutics in a subject in need is provided, the method comprising: administering a plasma cell manufactured by any one of the alternatives herein or the plasma cell that a macromolecule manufactured by any one of the alternatives herein, or the composition of the alternatives herein into the subject in need. In some alternatives, the macromolecule is a protein for inducing tolerance of a protein or peptide for therapy or induces or promotes engraftment and/or survival. In some alternatives, the macromolecule is a protein. The protein may be BAFF, APRIL, IFN-alpha, IL-10 and/or IL-6. In some alternatives the protein is a viral vector capsid protein. In some alternatives, the method further comprises purifying the plasma cells of step D), wherein the purifying is performed after the differentiating step. In some alternatives, the purifying comprises positive selecting of cells against CD138. In some alternatives, the selecting the plasma cells is performed by an anti-CD138 antibody for targeted removal of the plasma cells. In some alternatives, the purifying comprises using anti-CD138 beads for plasma cell selection. In some alternatives, the viral vector capsid protein comprises one or more of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) or AAV9 (VP1, VP2 and VP3). In some alternatives, the composition comprises the plasma cell manufactured by any one of the alternatives provided herein or comprises the cell of any one of the alternatives provided herein. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or a monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cells. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cells. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the first round of genome editing comprises transfecting single stranded DNA oligonucleotides for homologous recombination into a candidate genetic loci. In some alternatives, the Cas nuclease comprises Cas1, Cas2, Cas3, Cas4, Cas5, Cas6, Cas7, Cas8 or Cas9. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, antifibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of enhancing immune tolerance to a protein therapeutic in a subject in need is provided. The method comprises administering a B cell manufactured by any one of the alternatives provided herein or the B cell that expresses a molecule, such as a macromolecule manufactured by any one of the alternatives provided herein, or the composition of any one of the alternatives provided herein into the subject in need. In some alternatives, the subject suffers from Hemophilia A, Hemophilia B, Hereditary TPP, lysosomal acid deficiency, hereditary angioedema, alpha1 anti-trypsin deficiency, Fabry disease or hypophosphatasia. B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixture or combination thereof. In some alternatives, the composition comprises the plasma cell manufactured by any one of the alternatives provided herein or comprises the cell of any one of the alternatives provided herein. In some alternatives, the plasma cell is derived from a B cell. In some alternatives, the plasma cell expresses a molecule, such as a heterologous protein, protein mimetic or a peptide. In some alternatives, the cell is a B cell precursor. In some alternatives, the B cell precursor comprises hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the protein comprises an enzyme, neutralizing antibody, cytokine, cytokine receptor, complement protein, inhibitory protein, anti-fibrotic molecule, therapeutic antibody, anti-thrombotic molecule, glucose response element or a monoclonal antibody. In some alternatives, the protein is Factor VIII, Factor IX, SERPING1 or SERPINA1. In some alternatives, the enzyme is ADAMTS13, LIPA, GLA, or ALPL. In some alternatives, the enzyme is ADAMTS13, LIPA, GLA, or ALPL. In some alternatives, the protein is a receptor antagonist for treatment or amelioration of periodic fever or autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody. In some alternatives, the protein comprises broadly neutralizing HIV-1 antibodies (bNAbs) or a binding portion thereof. In some alternatives, the protein comprises a prodrug or a proenzyme. In some alternatives, the plasma cell is a long lived plasma cell. In some alternatives, the plasma cell is manufactured by any one of the alternative methods provided herein. In some alternatives, the plasma cell is manufactured by a method of making plasma cells or plasma cell precursors that express a molecule, such as a macromolecule, wherein the method comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells that express a protein. In some alternatives, the developing of the B cells is performed after the B cells are arrested at a specific phase of development and/or activating the B cells such that the B cells are permissive for recombination without further B cell differentiation. In some alternatives, the macromolecule is a protein, protein mimetic or a peptide. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a Cas nuclease. In some alternatives, the nuclease or synthetic guide RNAs targeting clustered regularly interspersed short palindromic repeat DNA (CRISPR) coupled to a Cas nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, the therapeutic antibody or a binding portion thereof is specific for a protein or other molecule expressed in autoimmune disorders, auto-inflammatory disorders, immune dysregulation and/or cancer. In some alternatives, the antibody is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the protein is an engineered protein, wherein the engineered protein is protective in viral, fungal, parasitic or bacterial infection. In some alternatives, the engineered protein comprises an antibody or a binding portion thereof, wherein the antibody or a binding portion thereof is specific for an antigen that is expressed on a virus, fungus, parasite or bacteria. In some alternatives, the protein comprises an antibody or a binding portion thereof, wherein the antibody or binding portion thereof is specific for an antigen that is expressed in a viral, fungal, parasitic or bacterial infection. In some alternatives, the plasma cell is manufactured by a method of making a long lived plasma cell, wherein the method comprises: isolating B cells; activating the B cells; a first round of genome editing of the B cells for protein expression in the absence of viral integration; expanding the B cells; and differentiating the B cells. In some alternatives, the B cells are subject derived or are allogeneic peripheral blood mononuclear cells. In some alternatives, the B cells are blood-derived human B cells. In some alternatives, the first round of genome editing is performed by an RNA or protein based transfection. In some alternatives, the first round of genome editing comprises delivering a nuclease, wherein the nuclease targets at least one genetic locus in the B cell. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives, the first round of genome editing comprises transfecting single stranded DNA oligonucleotides for homologous recombination into a candidate genetic loci. In some alternatives, the Cas nuclease comprises Cas1, Cas2, Cas3, Cas4, Cas5, Cas6, Cas7, Cas8 or Cas9. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever/autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angiodema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody is an anti-IL1 monoclonal antibody, anti-TNF antibody, anti-IL33 antibody or anti-C5 antibody. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cells, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of inducing tolerance of a macromolecule secreted by a B cell in a subject in need in vivo is provided, the method comprising: A) isolating B cells; B) performing a first round of genome editing of the B cells for protein expression in absence of viral integration, wherein the performing is under conditions of rapid B cell expansion; C) expanding the B cells; D) differentiating the B cells, optionally, after step (c) or (d), thereby producing activated B cells or naïve activated B cells that express the molecule; and E) providing or administering the B cells that expresses the macromolecule into a subject in need. In some alternatives, the macromolecule, is a protein, protein mimetic or peptide. In some alternatives, the macromolecule comprises natural amino acids and/or unnatural amino acids. In some alternatives, the protein is an enzyme. In some alternatives, the method further comprises activating the B cells prior to gene editing, where inactivating is performed using at least one stimulant. In some alternatives, the at least one stimulant is a CD40 ligand, CpG, IL2, IL10 and/or Il15. In some alternatives, cells are activated with 100 ng/ml of recombinant human MEGACD40L®), 1 µg/ml of CpG oligodeoxynucleotide 2006, 50 ng/ml of IL2, 50 ng/ml of IL10 and 10 ng/ml of IL15 for two days. In some alternatives, the CD40 ligand is artificially oligermized. In some alternatives, the CD40 ligand is oligermized with two linked CD40L trimers. In some alternatives, the cells are cultured for at least 13 days with the at least one stimulant. In some alternatives, the cells are a naïve B cell phenotype, activated B cell or activated edited B cell after differentiation. In some alternatives, the cells are CD27-CD138-CD38low/−CD19highIgM+ IgD+ after differentiation. In some alternatives, the providing or administering is performed by adoptive transfer. In some alternatives, the subject has received a stem cell administration or solid organ transplantation. In some alternatives, the subject suffers from influenza, parainfluenza, rhinovirus, respiratory syncytial virus, HIV, or other pathogenic bacteria, virus, fungus or a parasite infection. In some alternatives, the subject suffers from an enzyme deficiency. In some alternatives, the subject suffers from pulmonary fibrosis. In some alternatives, the subject suffers from an autoimmune disorder, immune dysregulation or cancer. In some alternatives, the subject suffers from diabetes. In some alternatives, the subject suffers from hypercholesterolemia. In some alternatives, the subject is also receiving CAR T-cell therapy. In some alternatives, the subject suffers from HIV. In some alternatives, the subject suffers from Hemophilia A, Hemophilia B, Hereditary TPP, lysosomal acid deficiency, hereditary angioedema, alpha1 anti-trypsin deficiency, Fabry disease or hypophosphatasia. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the first round of genome editing is performed by an RNA and protein based transfection. In some alternatives, the first round of genome editing comprises delivering a nuclease, wherein the nuclease targets at least one genetic loci in the B cell. In some alternatives, the first round of genome editing comprises delivering a nuclease, wherein the nuclease targets at least one genetic loci in the B cells and co-delivering the nuclease with a single stranded nucleic acid donor template. In some alternatives, the nuclease is a synthetic guide RNA targeting clustered regularly interspersed short palindromic repeat DNA (CRISPR) coupled to a Cas nuclease. B cells can include B cell precursors, stem cells, early pro-B cells, late pro-B cells, large pre-B cells, small pre-B cells, immature B cells, T1 B cells, T2 B cells, marginal zone B cells, naïve B cells, mature B cells, activated B cells derived from any starting B cell population, plasmablasts (short-lived) cells, GC B cells, memory B cells, and/or long- or short-lived plasma cells and/or any mixtures or combinations thereof. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of inducing tolerance of a peptide useful for immunotherapeutic application, secreted by a B cell in a subject in need in vivo and/or increasing engraftment of the B cell in a subject in need, the method comprising: A) isolating a first population of B cells; B) performing a first round of genome editing of the first population of B cells for protein or peptide expression in absence of viral integration, wherein the performing is under conditions of rapid B cell expansion; C) expanding the first population of B cells; D) differentiating the first population of B cells, optionally, after step (c) or (d), thereby producing an activated first population of B cells or a naïve first population of activated B cells that express the molecule; E) providing or administering the first population of B cells that expresses the peptide into a subject in need; and F) administering a second population of B cells that expresses a macromolecule, such as BAFF, APRIL, IFN-alpha, IL-10 or IL-6. In some alternatives, the immunotherapeutic application is treatment or amelioration of cancer. In some alternatives, the cancer comprises a solid tumor. In some alternatives, the peptide is an anti-PD1 antibody or a PDL-1 ligand. In some alternatives, the second population of B cells express BAFF, APRIL, IFN-alpha, IL-10 or IL-6. In some alternatives, the second population of B cells express a second peptide that is expressed and presented as a MHC class II molecule on a surface of the B cells. B cells can include B cell precursors, stem cells, early pro-B cells, late pro-B cells, large pre-B cells, small pre-B cells, immature B cells, Tb B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a method of inducing tolerance of a peptide for immunotherapeutic application, secreted by a B cell in a subject in need in vivo and/or increasing engraftment or survival of the B cells in a subject in need, the method comprising: A) isolating a first population of B cells; B) performing a first round of genome editing of the first population of B cells for protein or peptide expression in absence of viral integration, wherein the performing is under conditions of rapid B cell expansion; C) expanding the first population of B cells; D) differentiating the first population of B cells, optionally, after step (c) or (d), thereby producing activated B cells or naïve activated B cells that express the protein or peptide; E) providing or administering the first population of B cells that express the protein or peptide into a subject in need F) providing or administering a second population of B cells that express a macromolecule, wherein the second population of B cells allows tolerance of the protein or peptide and/or promotes engraftment. In some alternatives, the first population of B cells and the second population of B cells are co-administered. In some alternatives, the macromolecule comprises BAFF, APRIL, IL-10, IFN-alpha or IL-6. In some alternatives, the protein comprises an enzyme, neutralizing antibody or a binding portion thereof, cytokine, cytokine receptor, complement protein, inhibitory protein, anti-fibrotic molecule, therapeutic antibody or a binding portion thereof, anti-thrombotic molecule, glucose response element or monoclonal antibody or a binding portion thereof. In some alternatives the protein is a viral vector capsid protein. In some alternatives, the viral vector capsid protein comprises one or more of one of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) or AAV9 (VP1, VP2 and VP3). In some alternatives, the protein is a receptor antagonist for the treatment or inhibition of periodic fever/autoinflammatory syndromes, complement inhibitory proteins (including Factor H, Factor I) for the treatment or inhibition of atypical hemalytic uremic syndrome/membranoproliferative glomerulonephritis or a C1 inhibitor for hereditary angioedema.

In some alternatives, the protein is an anti-fibrotic molecule, wherein the anti-fibrotic molecule is SCGB1A1. In some alternatives, the protein comprises therapeutic antibodies or a binding portion thereof are specific for a protein expressed in autoimmune disorders, autoinflammatory disorders, immune dysregulation and/or cancer. In some alternatives, the antibody or a binding portion thereof is an anti-IL1 monoclonal antibody, anti-TNF antibody, anti-IL33 antibody or anti-C5 antibody or a binding portion of any one or more of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNAbs) or a binding portion thereof. B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof. In some alternatives, the method comprises monitoring of subject following plasma cell transplantation. In some alternatives, the subject is determined to no longer need treatment or therapy and the method further comprises administering Rituxan® or an anti-CD20 antibody or binding portion thereof for targeted removal of the plasma cells.

In some alternatives, a composition is provided, wherein the composition comprises a first population of B cells manufactured by any one of the alternatives herein and a second population of B cells, wherein the second population of B cells secretes a macromolecule for inducing tolerance of a peptide for immunotherapeutic application or for inducing engraftment of the plasma cell manufactured by any one of the alternatives herein. In some alternatives, the macromolecule expressed by the second population of B cells comprises BAFF, IFN-alpha, APRIL, IL-10 or IL-6. In some alternatives the macromolecule is a viral vector capsid protein. In some alternatives, the viral vector capsid protein comprises one or more of one of the following serotypes: AAV1 (VP1, VP2 and VP3), AAV2 (VP1, VP2 and VP3), AAV4 (VP1, VP2 and VP3), AAV5 (VP1, VP2 and VP3), AAV6 (VP1, VP2 and VP3), AAV1 (VP1, VP2 and VP3), AAV8 (VP1, VP2 and VP3), AAV1 (VP1, VP2 and VP3) or AAV9 (VP1, VP2 and VP3). B cells can include B cell precursors, stem cells, early pro-B cells, late pro-B cells, large pre-B cells, small pre-B cells, immature B cells, T1 B cells, T2 B cells, marginal zone B cells, mature B cells, naïve B cells, activated B cells derived from any starting B cell population, plasmablasts (short-lived) cells, GC B cells, memory B cells, and/or long- or short-lived plasma cells and/or any mixtures or combinations thereof. In some alternatives, the method of making plasma cells or plasma cell precursors that expresses a molecule, such as a macromolecule, protein, or peptide comprises (a) isolating B cells; (b) developing the B cells; (c) performing a first round of genome editing of the B cells for protein expression in absence of viral integration; (d) expanding the B cells; and (e) differentiating the B cells, optionally, after step (c) or (d), thereby producing plasma cells or plasma cell precursors that express the molecule. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the developing of the B cells is performed after the B cells are arrested at a specific phase of development and/or activating the B cells such that the B cells are permissive for recombination without further B cell differentiation. In some alternatives, the B cell is arrested as an early pro-B cell, a late pro-B cell, a large pre-B cell, a small pre-B cell, an immature B cell, a T1 B cell, a T2 B cell, a marginal-zone B cell, a mature B cell or a memory B cell. In some alternatives, performing the first round of genome editing of the B cells for protein expression is performed in the absence of viral integration. In some alternatives, performing the first round of genome editing of the B cells for protein expression is performed by introduction of a single stranded nucleic acid. In some alternatives, the B cells are subject derived or are allogeneic peripheral blood mononuclear cells. In some alternatives, the B cells are blood-derived human B cells. In some alternatives, the first round of genome editing is performed by an RNA and protein based transfection. In some alternatives, the first round of genome editing comprises delivering a nuclease, wherein the nuclease targets at least one genetic loci in the B cells. In some alternatives, the at least one genetic loci comprises JCHAIN, IGKC, IGMC, PON3, PRG2, FKBP11, SDC1, SLPI, DERL3, EDEM1, LY6C2, CRELD2, REXO2, PDIA4, PRDM1, CARD11, CCR5 or SDF2L1. In some alternatives, the nuclease is a zinc finger nuclease, transcription activator-like effector nuclease (TALEN), homing endonuclease (HEs), combined TALEN-HE protein (megaTALs) or synthetic guide RNAs targeting clustered regularly interspersed short palindromic repeat DNA (CRISPR) coupled to a CAS nuclease. In some alternatives, the nuclease or synthetic guide RNAs targeting clustered regularly interspersed short palindromic repeat DNA (CRISPR) coupled to a CAS nuclease are delivered via translatable RNA or recombinant protein. In some alternatives, the Cas nuclease comprises Cas1, Cas2, Cas3, Cas4, Cas5, Cas6, Cas7, Cas8 or Cas9. In some alternatives, the first round of genome editing comprises transfecting with single stranded DNA oligonucleotides for homologous recombination into a candidate genetic loci. In some alternatives, the single stranded DNA oligonucleotides are unmodified. In some alternatives, the single stranded DNA oligonucleotides are modified with 5' or 3' phosphorothioate linkages as repair templates. In some alternatives, the first round of genome editing comprises transducing the B cells with a recombinant adeno-associated virus vector to serve as a donor template for homologous recombination into a candidate genetic loci. In some alternatives, the recombinant adeno-associated virus vector is single-stranded, double stranded or self-complementary. In some alternatives, the method further comprises applying methods to prevent somatic hypermutation of an antibody locus in the B cells. In some alternatives, the method to prevent somatic hypermutation of an antibody locus in the B cells comprises disruption of an AID gene. In some alternatives, the method further comprises selectively increasing a proportion of gene edited B cells. In some alternatives, the increasing the proportion of gene edited B cells comprises the steps of: (a) performing a second round of genome editing on the B cells to excise a region; (b) performing a third round of genome editing on the B cells, wherein the third round of genome editing results in expression of drug activatable growth enhancers; (c) RNA transfecting into the B cells short lived drug activatable growth enhancers; and (d) inserting genetic modifications that artificially induce non-transformative expansion of gene edited B cells. In some alternatives, the first round of genome editing further comprises techniques for homology-directed repair. In some alternatives, the second round of genome editing results in the excision of the IgM constant region. In some alternatives, the second round of genome editing results in the B cells mimicking a class-switch to IgG1 positive cells. In some alternatives, step (a) of the step increasing the proportion of gene edited B cells further comprises removing IgM positive cells. In some alternatives, the method further comprises activating the IgG1 positive cells and expanding the IgG1 positive cells, wherein the expanding is performed by exogenous antigens that specifically bind the inserted surface-expressed IgG1. In some alternatives, the IgM positive cells are removed by negative selection. In some alternatives, the expanding of the IgG1 positive cells is performed by exogenous antigens that specifically bind the inserted surface-expressed IgG1. In some alternatives, the drug activatable growth enhancers expressed after the third round of genome editing are rapamycin-inducible FKBP11 dimers. In some alternatives, the activatable growth enhancers that are RNA transfected into the B cells of step (c) are rapamycin-inducible FKBP11 dimers. In some alternatives, the inserting genetic modifications that artificially induce triggerable, non-transformative expansion of edited cells results in disruption of a HPRT locus and negative selection of non-edited cells. In some alternatives, the negative selecting of non-edited cells is performed by 6-thioguanine. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the B-cells for homologous recombination of the single stranded DNA oligonucleotides or recombinant adeno-associated virus into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or any other length defined by a range that is set forth by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by isolation of naïve or memory B cells. In some alternatives, the isolating is performed from isolation from healthy donor PBMCs or cell apheresis collections. In some alternatives, the differentiating step is performed in a three-step culture system comprising an activation and proliferation step, a plasmablast differentiation step, and a plasma cell differentiation step. In some alternatives, the activation and proliferation step is performed in the presence of any combination of MCD40L (CD40 trimer), CpG, IL-2, IL-10 and/or IL-15. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element and/or a synthetic engineered protein. In some alternatives, the protein is IFN-alpha, IL-6, Factor VIII, Factor IX, SERPING1 or SERPINA1. In some alternatives, the enzyme is ADAMTS13, LIPA, GLA, or ALPL. In some alternatives, the protein is a receptor antagonist that is used for the treatment or amelioration of periodic fever/autoinflammatory syndromes or complement inhibitory proteins. In some alternatives, the compliment inhibitory protein is Factor H, Factor I or a C1 inhibitor. In some alternatives, the protein is an anti-fibrotic molecule, wherein the anti-fibrotic molecule is SCGB1A1. In some alternatives, a therapeutic antibody or binding portion thereof is used e.g., an antibody or binding portion thereof that is specific for a protein or other molecule expressed in an autoimmune disorder, autoinflammatory disorder, immune dysregulation and/or cancer. In some alternatives, the antibody or binding portion thereof is an anti-IL1 monoclonal antibody, anti-TNF antibody, anti-IL33 antibody or anti-C5 antibody or a binding portion thereof. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies. In some alternatives, the protein is an engineered protein, wherein the engineered protein is protective in viral, fungal, parasitic and/or bacterial infection. In some alternatives, the engineered protein comprises an antibody or a binding portion thereof, wherein the antibody or binding portion thereof is specific for an antigen that is expressed on a virus, fungus, parasite or bacteria. In some alternatives, the protein comprises an antibody or binding portion thereof, wherein the antibody or binding portion thereof is specific for an antigen that is expressed in a viral, fungal, parasitic or bacterial infection. In some alternatives, the B cells comprise B cell precursors such as hematopoietic stem cells (HSCs), multipotent progenitor (MPP) cells, lymphoid progenitor (CLP) cells, naïve B cells, GC B cell, plasmablast, early pro-B cells, late pro-B cells, large pre-B cells, small pre-B cells, immature B cells, T1 B cells, T2 B cells, marginal zone B cells, mature B cells and memory B cells. In some alternatives, the molecule is a macromolecule, protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein comprises a cofactor for enhanced enzymatic activity. In some alternatives, the method of making a long lived plasma cell comprises isolating B cells; activating the B cells; a first round of genome editing of the B cells for molecule expression, such as a protein, protein mimetic or a peptide in the absence of viral integration; expanding the B cells; and differentiating the B cells. In some alternatives, the molecule is a macromolecule, such as a protein, protein mimetic or peptide. In some alternatives, the macromolecule is a prodrug. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acylated. In some alternatives, the protein is an enzyme. In some alternatives, the enzyme comprises a cofactor for enhanced enzymatic activity. In some alternatives, the B cells in step (a) comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the B cells are subject derived or are allogeneic peripheral blood mononuclear cells. In some alternatives, the B cells are blood-derived human B cells. In some alternatives, the B cells from the isolating step comprise B cell precursors such as hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the first round of genome editing is performed by an RNA or protein based transfection. In some alternatives, the first round of genome editing comprises delivering a nuclease, wherein the nuclease targets at least one genetic locus in the B cells. In some alternatives, the nuclease is a zinc finger nuclease, transcription activator-like effector nuclease (TALEN), homing endonuclease (HEs), combined TALEN-HE protein (megaTALs) or clustered regularly interspersed short palindromic repeat DNA (CRISPR) coupled to a Cas nuclease. In some alternatives the Cas nuclease comprises Cas1, Cas2, Cas3, Cas4, Cas5, Cas6, Cas7, Cas8 or Cas9. In some alternatives, the first round of genome editing comprises transfecting single stranded DNA oligonucleotides for homologous recombination into a candidate genetic loci. In some alternatives, the first round of genome editing comprises transducing the B cells with a recombinant adeno-associated virus vector for homologous recombination into a candidate genetic loci. In some alternatives, the method further comprises applying methods to prevent somatic hypermutation of an antibody locus and other target loci in the B cells. In some alternatives, the method to prevent somatic hypermutation of an antibody locus in the B cells comprises disruption of an AID gene. In some alternatives, the method further comprises introducing production enhancers into the B cells or disruption of candidate loci within the B cells to enable selectable expansion of the B cells in vitro or in vivo. In some alternatives, the method further comprises introducing a nucleic acid, wherein the nucleic acid encodes at least one cell surface protein. In some alternatives, the at least one cell surface protein is CD20. In some alternatives, the first round of genome editing further comprises cycling the cells for homologous recombination of the single stranded DNA oligonucleotides or the recombinant adeno-associated virus vector into the candidate genetic loci. In some alternatives, the single stranded DNA oligonucleotides or recombinant adeno-associated virus comprises a length of 0.2 kb, 0.5 kb, 1 kb, 2 kb, 3 kb, 4 kb or 5 kb or a length within a range defined by any two of the aforementioned values. In some alternatives, the isolating is performed by isolation of early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells. In some alternatives, the isolating is performed by negative selection isolation of naïve or memory B cells. In some alternatives, the naïve or memory B cells are from healthy donor PBMCs or cells collected by apheresis. In some alternatives, the differentiating step is performed in a three-step culture system comprising an activation and proliferation step, a plasmablast differentiation step and a plasma cell differentiation step. In some alternatives, the activation and proliferation step is performed in the presence any combination of MCD40L, CpG, IL-2, IL-10 and/or IL-15. In some alternatives, the plasmablast differentiation step is performed in the presence of any combination of IL-2, IL-6, IL-10 and/or IL-15. In some alternatives, the plasma cell differentiation step is performed in the presence of any combination of IL-6, IL-15, APRIL and/or IFNα. In some alternatives, the single stranded DNA oligonucleotides or the recombinant adenovirus comprises a sequence encoding the protein. In some alternatives, the protein comprises an enzyme, monoclonal antibody, neutralizing antibodies, therapeutic antibodies, cytokine, cytokine receptor, complement protein, inhibitory protein, anti-fibrotic molecule, anti-thrombotic molecule, coagulation factor, glucose response element or a synthetic engineered protein. In some alternatives, the protein is IFN-alpha, Factor VIII, Factor IX, SERPING1 or SERPINA1. In some alternatives, the enzyme is ADAMTS13, LIPA, GLA, or ALPL. In some alternatives, the protein is a receptor antagonist for treatment or amelioration of periodic fever or autoinflammatory syndromes, complement inhibitory proteins (including Factor H, Factor I) for treatment or amelioration of atypical hemalytic uremic syndrome/membranoproliferative glomerulonephritis or a C1 inhibitor for hereditary angioedema. In some alternatives, the protein is an anti-fibrotic molecule, wherein the anti-fibrotic molecule is SCGB1A1. In some alternatives, the therapeutic antibodies or binding portions thereof are specific for a protein expressed in autoimmune disorders, autoinflammatory disorders, immune dysregulation and/or cancer. In some alternatives, the antibody or binding portion thereof is an anti-IL1 monoclonal antibody, anti-TNF antibody, anti-IL33 antibody or anti-C5 antibody or a binding portion of any of these antibodies. In some alternatives, the protein is an anti-thrombotic molecule, wherein the anti-thrombotic molecule is APLN. In some alternatives, the protein comprises an anti-PCSK9 inhibitory antibody or a binding portion thereof. In some alternatives, the protein comprises broadly neutralizing HIV-1 antibodies (bNABs). In some alternatives, the protein comprises a prodrug or a proenzyme. In some alternatives, the B cells comprise B cell precursors such as hematopoietic stem cells (HSCs), multipotent progenitor (MPP) cells, lymphoid progenitor (CLP) cells, naïve B cells, GC B cell, plasmablasts, early pro-B cells, late pro-B cells, large pre-B cells, small pre-B cells, immature B cells, T1 B cells, T2 B cells, marginal zone B cells, mature B cells and/or memory B cells. In some alternatives, the molecule is selected from macromolecules, proteins, protein mimetics and/or peptides. In some alternatives, the macromolecule, protein, protein mimetic, or peptide comprises natural amino acids and/or unnatural amino acids. In some alternatives, the molecule comprises a carbohydrate or lipid moiety. In some alternatives, the molecule comprises a cofactor. In some alternatives, the protein comprises a hydrophobic group for membrane localization. In some alternatives, the protein is acetylated. In some alternatives, the protein comprises a cofactor for enhanced enzymatic activity. In some alternatives, the isolating is performed by negative selection isolation of hematopoietic stem cells, early pro-B cells, late pro-B cells, large pre-B cells, small pre-B cells, immature B cells, T1 B cells, T2 B cells, marginal zone B cells, mature B cells, naïve B cells, plasmablast (short lived) cells, GC B cells, memory B cells, plasmablast cells and/or long lived plasma cells.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an alternative of the first through fifteenth aspects is applicable to all aspects and embodiments identified herein. Moreover, any of the features of an alternative of the first through fifteenth aspects is independently combinable, partly or wholly with other embodiments described herein in any way, e.g., one, two, or three or more alternative may be combinable in whole or in part. Further, any of the features of an alternative of the first through fifteenth aspects may be made optional to other aspects or alternatives.

REFERENCES

1. Radbruch, A, Muehlinghaus, G, Luger, E O, Inamine, A, Smith, KG, Dorner, T, et al. (2006). Competence and competition: the challenge of becoming a long-lived plasma cell. *Nature reviews Immunology* 6: 741-750.
2. Slifka, MK, Antia, R, Whitmire, J K, and Ahmed, R (1998). Humoral immunity due to long-lived plasma cells. *Immunity* 8: 363-372.
3. Kim, E K, Seo, HS, Chae, MJ, Jeon, IS, Song, BY, Park, Y J, et al. (2014). Enhanced antitumor immunotherapeutic effect of B-cell-based vaccine transduced with modified adenoviral vector containing type 35 fiber structures. *Gene therapy* 21: 106-114.
4. Hellebrand, E, Mautner, J, Reisbach, G, Nimmerjahn, F, Hallek, M, Mocikat, R, et al. (2006). Epstein-Barr virus vector-mediated gene transfer into human B cells: potential for antitumor vaccination. *Gene therapy* 13: 150-162.
5. Frecha, C, Costa, C, Levy, C, Negre, D, Russell, S J, Maisner, A, et al. (2009). Efficient and stable transduction of resting B lymphocytes and primary chronic lymphocyte leukemia cells using measles virus gp displaying lentiviral vectors. *Blood* 114: 3173-3180.
6. Serafini, M, Naldini, L, and Introna, M (2004). Molecular evidence of inefficient transduction of proliferating human B lymphocytes by VSV-pseudotyped HIV-1-derived lentivectors. *Virology* 325: 413-424.
7. Levy, C, Fusil, F, Amirache, F, Costa, C, Girard-Gagnepain, A, Negre, D, et al. (2016). Baboon envelope pseudotyped lentiviral vectors efficiently transduce human B cells and allow active factor IX B cell secretion in vivo in NOD/SCIDgammac−/− mice. Journal of thrombosis and haemostasis: *JTH* 14: 2478-2492.
8. Levy, C, Amirache, F, Costa, C, Frecha, C, Muller, CP, Kweder, H, et al. (2012). Lentiviral vectors displaying modified measles virus gp overcome pre-existing immunity in in vivo-like transduction of human T and B cells. *Molecular therapy: the journal of the American Society of Gene Therapy* 20: 1699-1712.

9. Mock, U, Thiele, R, Uhde, A, Fehse, B, and Horn, S (2012). Efficient lentiviral transduction and transgene expression in primary human B cells. *Human gene therapy methods* 23: 408-415.
10. Hale, M, Mesojednik, T, Romano Ibarra, GS, Sahni, J, Bernard, A, Sommer, K, et al. (2017). Engineering HIV-Resistant, Anti-HIV Chimeric Antigen Receptor T Cells. *Molecular therapy: the journal of the American Society of Gene Therapy* 25: 570-579.
11. Dever, DP, Bak, RO, Reinisch, A, Camarena, J, Washington, G, Nicolas, C E, et al. (2016). CRISPR/Cas9 beta-globin gene targeting in human haematopoietic stem cells. *Nature* 539: 384-389.
12. Sather, BD, Romano Ibarra, GS, Sommer, K, Curinga, G, Hale, M, Khan, I F, et al. (2015). Efficient modification of CCR5 in primary human hematopoietic cells using a megaTAL nuclease and AAV donor template. *Science translational medicine* 7: 307ra156.
13. Mali, P, Yang, L, Esvelt, KM, Aach, J, Guell, M, DiCarlo, J E, et al. (2013). RNA-guided human genome engineering via Cas9. *Science* 339: 823-826.
14. Cong, L, Ran, FA, Cox, D, Lin, S, Barretto, R, Habib, N, et al. (2013). Multiplex genome engineering using CRISPR/Cas systems. *Science* 339: 819-823.
15. Chu, VT, Graf, R, Wirtz, T, Weber, T, Favret, J, Li, X, et al. (2016). Efficient CRISPR-mediated mutagenesis in primary immune cells using CrispRGold and a C57BL/6 Cas9 transgenic mouse line. *Proceedings of the National Academy of Sciences of the United States of America* 113: 12514-12519.
16. Pogson, M, Parola, C, Kelton, W J, Heuberger, P, and Reddy, ST (2016). Immunogenomic engineering of a plug-and-(dis)play hybridoma platform. *Nature communications* 7: 12535.
17. Cheong, TC, Compagno, M, and Chiarle, R (2016). Editing of mouse and human immunoglobulin genes by CRISPR-Cas9 system. *Nature communications* 7: 10934.
18. Gwiazda, KS, Grier, AE, Sahni, J, Burleigh, SM, Martin, U, Yang, J G, et al. (2016). High Efficiency CRISPR/Cas9-mediated Gene Editing in Primary Human T-cells Using Mutant Adenoviral E4orf6/Elb55k "Helper" Proteins. *Molecular therapy: the journal of the American Society of Gene Therapy* 24: 1570-1580.
19. Lin, S, Staahl, BT, Alla, R K, and Doudna, JA (2014). Enhanced homology-directed human genome engineering by controlled timing of CRISPR/Cas9 delivery. *eLife* 3: e04766.
20. Heyer, WD, Ehmsen, K T, and Liu, J (2010). Regulation of homologous recombination in eukaryotes. *Annual review of genetics* 44: 113-139.
21. Jiang, W, Lederman, MM, Harding, CV, Rodriguez, B, Mohner, R J, and Sieg, SF (2007). TLR9 stimulation drives naïve B cells to proliferate and to attain enhanced antigen presenting function. *European journal of immunology* 37: 2205-2213.
22. Armitage, RJ, Macduff, BM, Eisenman, J, Paxton, R, and Grabstein, K H (1995). IL-15 has stimulatory activity for the induction of B cell proliferation and differentiation. *Journal of immunology* 154: 483-490.
23. Armitage, RJ, Macduff, BM, Spriggs, M K, and Fanslow, WC (1993). Human B cell proliferation and Ig secretion induced by recombinant CD40 ligand are modulated by soluble cytokines. *Journal of immunology* 150: 3671-3680.
24. Rottman, J B, Ganley, K P, Williams, K, Wu, L, Mackay, C R, and Ringler, DJ (1997). Cellular localization of the chemokine receptor CCR5. Correlation to cellular targets of HIV-1 infection. *The American journal of pathology* 151: 1341-1351.
25. Ran, FA, Hsu, PD, Wright, J, Agarwala, V, Scott, D A, and Zhang, F (2013). Genome engineering using the CRISPR-Cas9 system. *Nature protocols* 8: 2281-2308.
26. Richardson, CD, Ray, G J, DeWitt, MA, Curie, G L, and Corn, JE (2016). Enhancing homology-directed genome editing by catalytically active and inactive CRISPR-Cas9 using asymmetric donor DNA. *Nature biotechnology* 34: 339-344.
27. Jourdan, M, Caraux, A, De Vos, J, Fiol, G, Larroque, M, Cognot, C, et al. (2009). An in vitro model of differentiation of memory B cells into plasmablasts and plasma cells including detailed phenotypic and molecular characterization. *Blood* 114: 5173-5181.
28. Ochiai, K, Maienschein-Cline, M, Simonetti, G, Chen, J, Rosenthal, R, Brink, R, et al. (2013). Transcriptional regulation of germinal center B and plasma cell fates by dynamical control of IRF4. *Immunity* 38: 918-929.
29. Shaffer, A L, Lin, K I, Kuo, TC, Yu, X, Hurt, E M, Rosenwald, A, et al. (2002). Blimp-1 orchestrates plasma cell differentiation by extinguishing the mature B cell gene expression program. *Immunity* 17: 51-62.
30. Muto, A, Ochiai, K, Kimura, Y, Itoh-Nakadai, A, Calame, KL, Ikebe, D, et al. (2010). Bach2 represses plasma cell gene regulatory network in B cells to promote antibody class switch. *The EMBO journal* 29: 4048-4061.
31. Nera, K P, Kohonen, P, Narvi, E, Peippo, A, Mustonen, L, Terho, P, et al. (2006). Loss of Pax5 promotes plasma cell differentiation. *Immunity* 24: 283-293.
32. Muto, A, Tashiro, S, Nakajima, O, Hoshino, H, Takahashi, S, Sakoda, E, et al. (2004). The transcriptional programme of antibody class switching involves the repressor Bach2. *Nature* 429: 566-571.
33. Kozmik, Z, Wang, S, Dorfler, P, Adams, B, and Busslinger, M (1992). The promoter of the CD19 gene is a target for the B-cell-specific transcription factor BSAP. *Molecular and cellular biology* 12: 2662-2672.
34. Khan, IF, Hirata, R K, and Russell, DW (2011). AAV-mediated gene targeting methods for human cells. *Nature protocols* 6: 482-501.
35. Hirata, R, Chamberlain, J, Dong, R, and Russell, DW (2002). Targeted transgene insertion into human chromosomes by adeno-associated virus vectors. *Nature biotechnology* 20: 735-738.
36. Russell, D W, and Hirata, R K (1998). Human gene targeting by viral vectors. *Nature genetics* 18: 325-330.
37. Challita, P M, Skelton, D, el-Khoueiry, A, Yu, X J, Weinberg, K, and Kohn, DB (1995). Multiple modifications in cis elements of the long terminal repeat of retroviral vectors lead to increased expression and decreased DNA methylation in embryonic carcinoma cells. *Journal of virology* 69: 748-755.
38. Liu, R, Paxton, WA, Choe, S, Ceradini, D, Martin, SR, Horuk, R, et al. (1996). Homozygous defect in HIV-1 coreceptor accounts for resistance of some multiply-exposed individuals to HIV-1 infection. *Cell* 86: 367-377.
39. Simioni, P, Tormene, D, Tognin, G, Gavasso, S, Bulato, C, Iacobelli, N P, et al. (2009). X-linked thrombophilia with a mutant factor IX (factor IX Padua). *The New England journal of medicine* 361: 1671-1675.
40. Mackay, F, and Browning, J L (2002). BAFF: a fundamental survival factor for B cells. *Nature reviews Immunology* 2: 465-475.
41. Nathwani, AC, Reiss, UM, Tuddenham, EG, Rosales, C, Chowdary, P, McIntosh, J, et al. (2014). Long-term safety and efficacy of factor IX gene therapy in hemophilia B. *The New England journal of medicine* 371: 1994-2004.
42. Nathwani, AC, Tuddenham, EG, Rangarajan, S, Rosales, C, McIntosh, J, Linch, D C, et al. (2011). Adenovirus-associated virus vector-mediated gene transfer in hemophilia B. *The New England journal of medicine* 365: 2357-2365.
43. Calcedo, R, Morizono, H, Wang, L, McCarter, R, He, J, Jones, D, et al. (2011). Adeno-associated virus antibody profiles in newborns, children, and adolescents. *Clinical and vaccine immunology: CVI* 18: 1586-1588.
44. Li, C, Narkbunnam, N, Samulski, RJ, Asokan, A, Hu, G, Jacobson, L J, et al. (2012). Neutralizing antibodies against adeno-associated virus examined prospectively in pediatric patients with hemophilia. *Gene therapy* 19: 288-294.
45. Boutin, S, Monteilhet, V, Veron, P, Leborgne, C, Benveniste, O, Montus, M F, et al. (2010). Prevalence of serum IgG and neutralizing factors against adeno-associated virus (AAV) types 1, 2, 5, 6, 8, and 9 in the healthy population: implications for gene therapy using AAV vectors. *Human gene therapy* 21: 704-712.
46. Skupsky, J, Zhang, AH, Su, Y, and Scott, DW (2010). B-cell-delivered gene therapy induces functional T regulatory cells and leads to a loss of antigen-specific effector cells. *Molecular therapy: the journal of the American Society of Gene Therapy* 18: 1527-1535.
47. Lei, T C, and Scott, DW (2005). Induction of tolerance to factor VIII inhibitors by gene therapy with immunodominant A2 and C2 domains presented by B cells as Ig fusion proteins. *Blood* 105: 4865-4870.
48. Melo, ME, Qian, J, El-Amine, M, Agarwal, R K, Soukhareva, N, Kang, Y, et al. (2002). Gene transfer of Ig-fusion proteins into B cells prevents and treats autoimmune diseases. *Journal of immunology* 168: 4788-4795.
49. Yu, H, Borsotti, C, Schickel, J N, Zhu, S, Strowig, T, Eynon, E E, et al. (2017). A novel humanized mouse model with significant improvement of class-switched, antigen-specific antibody production. *Blood* 129: 959-969.
50. Villaudy, J, Schotte, R, Legrand, N, and Spits, H (2014). Critical assessment of human antibody generation in humanized mouse models. *Journal of immunological methods* 410: 18-27.
51. Lang, J, Kelly, M, Freed, BM, McCarter, MD, Kedl, R M, Torres, R M, et al. (2013). Studies of lymphocyte reconstitution in a humanized mouse model reveal a requirement of T cells for human B cell maturation. *Journal of immunology* 190: 2090-2101.
52. Cheng, Q, Mumtaz, IM, Khodadadi, L, Radbruch, A, Hoyer, B F, and Hiepe, F (2013). Autoantibodies from long-lived 'memory' plasma cells of NZB/W mice drive immune complex nephritis. *Annals of the rheumatic diseases* 72: 2011-2017.
53. Aurnhammer, C, Haase, M, Muether, N, Hausl, M, Rauschhuber, C, Huber, I, et al. (2012). Universal real-time PCR for the detection and quantification of adeno-associated virus serotype 2-derived inverted terminal repeat sequences. *Human gene therapy methods* 23: 18-28.

What is claimed is:

1. A method of making a population of plasma cells or plasma cell precursors edited to express a polypeptide, the method comprising:
  (a) isolating primary B cells;
  (b) activating the primary B cells in a culture medium for a period of time, so that a population of activated B cells is obtained, wherein the period of time is 7 days and the culture medium comprises (i) oligomerized CD40 ligand comprising two linked CD40L trimers, and (ii) CpG oligodeoxynucleotide, IL-2, IL10 and IL15;
  (c) during the period of time, editing the cells by contacting them with:
    (i) a ribonucleoprotein (RNP) complex comprising a Cas protein complexed with a guide RNA directed to a target site in a target locus, and (ii) a nucleic acid including a sequence that encodes the polypeptide and is flanked by homologous sequences to a target site in the target locus, so that the encoding sequence integrates at the target locus, and an edited cell population is obtained that comprises cells which express the polypeptide; and (d) expanding and differentiating the edited B cell population, thereby producing an edited plasma cell population or plasma cell precursor population characterized in that cells of the population express the polypeptide, wherein the differentiating comprises (i) contacting the edited B cell population with IL-2, IL-6, IL-10 and IL-15 for an initial 3 days to produce the edited plasma cell precursor population, and (ii) contacting the edited plasma cell precursor population with IL-6, IL-15 and IFNα for a further 3 days to produce the edited plasma cell population.

2. The method of claim 1, wherein the polypeptide is selected from Factor VIII, Factor IX, serpin family G member 1 (SERPING1), serpin family A member 1 (SERPINA1), Factor H, Factor I, secretoglobin family 1A member 1 (SCGB1A1), apelin (APLN), interferon alpha (IFNα), B-cell activating factor (BAFF), a proliferation-inducing ligand (APRIL), interleukin-10 (IL-10), interleukin-6 (IL-6), a disintegrin and metallopeptidase with thrombospondin type 1 motif 13 (ADAMTS13), lipase A lysosomal acid lipase (LIPA), α-galactosidase A (GLA), or alkaline phosphatase biomineralization associated (ALPL).

3. The method of claim 1, wherein the primary B cells comprise early pro-B cells, late pro-B cells, large pre-B cells, small pre-B cells, immature B cells, T1 B cells, T2 B cells, marginal zone B cells, mature B cells, naïve B cells, or memory B cells.

4. The method of claim 1, further comprising introducing a nucleic acid encoding at least one cell surface protein into the B cells.

5. The method of claim 1, wherein the edited plasma cell population comprises long lived plasma cells.

6. The method of claim 1 further comprising purifying CD138+ cells from the edited plasma cell population or plasma cell precursor population.

7. A method of expressing a polypeptide in a subject comprising:
performing the method of claim 1 to prepare a composition comprising the edited plasma cells or plasma cell precursors that express the polypeptide; and
administering the composition to the subject.

8. The method of claim 1, wherein an activation-induced cytidine deaminase gene is inactivated in the activated B cells.

9. The method of claim 4, wherein the at least one cell surface protein comprises CD20.

10. The method of claim 1, wherein the target locus is selected from the group consisting of joining chain of multimeric IgA and IgM (JCHAIN), immunoglobulin kappa light chain constant region (IGKC), immunoglobulin M heavy chain constant region (IGMC), paraoxonase 3 (PON3), proteoglycan 2 (PRG2), FK506-binding protein 11 (FKBP11), syndecan 1 (SDC1), secretory leukocyte protease inhibitor (SLPI), derlin-3 (DERL3), endoplasmic reticulum degradation-enhancing alpha-mannosidase-like protein 1 (EDEM1), lymphocyte antigen 6 complex, locus C2 (LY6C2), cysteine-rich protein with epidermal growth factor-like domains 2 (CRELD2), RNA exonuclease 2 (REXO2), protein disulfide isomerase family A member 4 (PDIA4), pattern recognition domain-containing protein 1 (PRDM1), caspase recruitment domain-containing protein 11 (CARD11), chemokine CC motif receptor 5 (CCR5), and stromal cell-derived factor 2-like 1 (SDF2L1).

11. The method of claim 1, wherein the nucleic acid comprises a recombinant adeno-associated virus (AAV) vector comprising a donor repair template for repair of DNA cleavage induced by the RNP complex.

12. The method of claim 4, wherein the AAV vector is of serotype AAV1, AAV2, AAV2.5, AAV5, AAV6, AAV8, AAV9 or AAVD-J.

13. The method of claim 1, wherein the Cas protein is a Cas9 nuclease.

14. The method of claim 1, further comprising:
(e) administering into a subject the edited plasma cell population or plasma cell precursor population.

15. The method of claim 14, further comprising:
(f) measuring serum levels from the subject for the polypeptide 10 or 21 days post-administration.

* * * * *

UNITED STATES PATENT AND TRADEMARK OFFICE
CERTIFICATE OF CORRECTION

PATENT NO. : 11,939,594 B2
APPLICATION NO. : 15/921353
DATED : March 26, 2024
INVENTOR(S) : David J. Rawlings et al.

It is certified that error appears in the above-identified patent and that said Letters Patent is hereby corrected as shown below:

On the Title Page

Page 2, Column 2 item (56) (Other Publications), Line 2, delete "OncoImmunology," and insert -- Oncoimmunology, --.

Page 2, Column 2 item (56) (Other Publications), Line 18, delete "intounstimulated" and insert -- into unstimulated --.

Page 2, Column 2 item (56) (Other Publications), Line 44, delete "ofretroviral" and insert -- of retroviral --.

Page 3, Column 2 item (56) (Other Publications), Line 63, delete "lymphocytesand" and insert -- lymphocytes and --.

In the Drawings

Sheet 8 of 72 (FIG. 8), Line 3, delete "Call" and insert -- Cell --.

Sheet 39 of 72 (FIG. 34), Line 2, delete "Call" and insert -- Cell --.

In the Specification

Column 3, Line 12 (approx.), delete "Syncitial" and insert -- Syncytial --.

Column 3, Line 59, delete "Syncitial" and insert -- Syncytial --.

Column 8, Line 6 (approx.), delete "FIG." and insert -- FIGS. --.

Column 8, Line 41, delete "FIG." and insert -- FIGS. --.

Signed and Sealed this
Third Day of September, 2024

Katherine Kelly Vidal
*Director of the United States Patent and Trademark Office*

CERTIFICATE OF CORRECTION (continued)
U.S. Pat. No. 11,939,594 B2

Column 8, Line 43, delete "(FIG." and insert -- (FIGS. --.

Column 8, Line 58, delete "FIG." and insert -- FIGS. --.

Column 9, Line 3, delete "FIG." and insert -- FIGS. --.

Column 9, Line 33, delete "FIG." and insert -- FIGS. --.

Column 9, Line 45, delete "FIG." and insert -- FIGS. --.

Column 10, Line 21, delete "FIG." and insert -- FIGS. --.

Column 10, Line 45, delete "FIG." and insert -- FIGS. --.

Column 10, Line 62, delete "FIG." and insert -- FIGS. --.

Column 13, Line 36-37 (approx.), delete "palmityolation," and insert -- palmitoylation, --.

Column 13, Line 37-38 (approx.), delete "farnesyltion, gerangylgeranylation," and insert -- farnesylation, geranylgeranylation, --.

Column 13, Line 41 (approx.), delete "lipolyation," and insert -- lipoylation, --.

Column 13, Line 42, delete "phophopantetheinylation," and insert -- phosphopantetheinylation, --.

Column 13, Line 62, delete "Syncitial" and insert -- Syncytial --.

Column 16, Line 16, delete "(PBNC)" and insert -- (PBMC) --.

Column 17, Line 49-50, delete "homolougous" and insert -- homologous --.

Column 18, Line 24, delete "homolougous" and insert -- homologous --.

Column 18, Line 25, delete "homolougous" and insert -- homologous --.

Column 18, Line 28, delete "homolougous" and insert -- homologous --.

Column 18, Line 34, delete "homolougous" and insert -- homologous --.

Column 18, Line 46, delete "homolougous" and insert -- homologous --.

Column 20, Line 23, delete "homolougous" and insert -- homologous --.

Column 21, Line 54, delete "Syncitial" and insert -- Syncytial --.

CERTIFICATE OF CORRECTION (continued)
U.S. Pat. No. 11,939,594 B2

Column 24, Line 45 (approx.), delete "s a" and insert -- is a --.

Column 24, Line 55, delete "Miltenyl" and insert -- Miltenyi --.

Column 26, Line 11, delete "homolougous" and insert -- homologous --.

Column 26, Line 40, delete "hemagglutin" and insert -- hemagglutinin --.

Column 27, Line 21, delete "homolougous" and insert -- homologous --.

Column 28, Line 58, delete "homolougous" and insert -- homologous --.

Column 32, Line 57, delete "E4orf6/Elb55k" and insert -- E4orf6/E1b55k --.

Column 33, Line 39-40, delete "homolougous" and insert -- homologous --.

Column 34, Line 8-9, delete "homolougous" and insert -- homologous --.

Column 35, Line 3, delete "cells/mi." and insert -- cells/ml. --.

Column 42, Line 40, delete "(FIG." and insert -- (FIGS. --.

Column 143, Line 61, delete "30.5 µmol" and insert -- 30.5 pmol --.

Column 143, Line 66, delete "cells/mi." and insert -- cells/ml. --.

Column 146, Line 39, delete "impart" and insert -- impact --.

Column 146, Line 48, delete "IL2/IL6/I115." and insert -- IL2/IL6/IL15. --.

Column 147, Line 8 (approx.), delete "cells cells," and insert -- cells, --.

Column 147, Line 10 (approx.), delete "R O" and insert -- RO --.

Column 147, Line 18 (approx.), delete "tero-" and insert -- retro- --.

Column 151, Line 59, delete "FIG." and insert -- FIGS. --.

Column 152, Line 4, delete "FIG." and insert -- FIGS. --.

Column 153, Line 4, delete "FIG." and insert -- FIGS. --.

Column 153, Line 23, delete "(FIG." and insert -- (FIGS. --.

Column 153, Line 48, delete "CD38high" and insert -- $CD38^{high}$ --.

CERTIFICATE OF CORRECTION (continued)
U.S. Pat. No. 11,939,594 B2

Column 156, Line 26 (approx.), delete "PAX5g" and insert -- PAXg --.

Column 156, Line 27 (approx.), delete "βACH2g" and insert -- BACH2g --.

Column 156, Line 61, delete "a" and insert -- α --.

Column 159-160, Line 13 (approx.), delete "G" and insert -- T --.

Column 159-160, Line 14 (approx.), delete "G" and insert -- C --.

Column 159, Line 24, delete "T7E" and insert -- T7E1 --.

Column 159, Line 49, delete "(FIG." and insert -- (FIGS. --.

Column 160, Line 43, delete "copies/l" and insert -- copies/µl --.

Column 164, Line 5, delete "FIG." and insert -- FIGS. --.

Column 164, Line 17, delete "FIG." and insert -- FIGS. --.

Column 165, Line 18, delete "FIG." and insert -- FIGS. --.

Column 165, Line 38, delete "(FIG." and insert -- (FIGS. --.

Column 165, Line 52, delete "CD38high" and insert -- CD38$^{high}$ --.

Column 166, Line 50, delete "(FIG." and insert -- (FIGS. --.

Column 168, Line 55, delete "CD19'" and insert -- CD19$^{+}$ --.

Column 170, Line 65, delete "CARD1l," and insert -- CARD11, --.

Column 173, Line 9, delete "homolougous" and insert -- homologous --.

Column 174, Line 33, delete "Syncitial" and insert -- Syncytial --.

Column 176, Line 54, delete "angiodema." and insert -- angioedema. --.

Column 177, Line 5 (approx.), delete "homolougous" and insert -- homologous --.

Column 177, Line 23, delete "Syncitial" and insert -- Syncytial --.

Column 178, Line 55, delete "angiodema." and insert -- angioedema. --.

Column 179, Line 60, delete "CARD1l," and insert -- CARD11, --.

CERTIFICATE OF CORRECTION (continued)
U.S. Pat. No. 11,939,594 B2

Column 182, Line 5, delete "homolougous" and insert -- homologous --.

Column 183, Line 30, delete "differentiation" and insert -- differentiation. --.

Column 183, Line 52, delete "angiodema." and insert -- angioedema. --.

Column 184, Line 3, delete "homolougous" and insert -- homologous --.

Column 184, Line 25, delete "angiodema." and insert -- angioedema. --.

Column 184, Line 59, delete "Syncitial" and insert -- Syncytial --.

Column 186, Line 43, delete "CARD1l," and insert -- CARD11, --.

Column 188, Line 17, delete "differentiation" and insert -- differentiation. --.

Column 188, Line 65-66, delete "homolougous" and insert -- homologous --.

Column 190, Line 19, delete "IX" and insert -- 1× --.

Column 190, Line 22, delete "differentiation" and insert -- differentiation. --.

Column 190, Line 44, delete "angiodema." and insert -- angioedema. --.

Column 190, Line 63, delete "homolougous" and insert -- homologous --.

Column 191, Line 14, delete "Syncitial" and insert -- Syncytial --.

Column 192, Line 15, delete "angiodema." and insert -- angioedema. --.

Column 192, Line 35, delete "homolougous" and insert -- homologous --.

Column 196, Line 26, delete "homolougous" and insert -- homologous --.

Column 198, Line 5, delete "angiodema." and insert -- angioedema. --.

Column 198, Line 23, delete "homolougous" and insert -- homologous --.

Column 198, Line 54, delete "angiodema." and insert -- angioedema. --.

Column 199, Line 7, delete "homolougous" and insert -- homologous --.

Column 199, Line 55, delete "Syncitial" and insert -- Syncytial --.

Column 204, Line 16-17, delete "homolougous" and insert -- homologous --.

Column 205, Line 36, delete "IX" and insert -- 1× --.

Column 205, Line 60, delete "angiodema." and insert -- angioedema. --.

Column 206, Line 11, delete "homolougous" and insert -- homologous --.

Column 206, Line 43, delete "angiodema." and insert -- angioedema. --.

Column 206, Line 63, delete "homolougous" and insert -- homologous --.

Column 207, Line 50, delete "Syncitial" and insert -- Syncytial --.

Column 210, Line 63, delete "1 g/ml" and insert -- 1 µg/ml --.

Column 212, Line 14-15, delete "homolougous" and insert -- homologous --.

Column 264, Line 30, delete "the a" and insert -- a --.

Column 266, Line 14, delete "angiodema." and insert -- angioedema. --.

Column 267, Line 59, delete "CARD1l," and insert -- CARD11, --.

Column 269, Line 26, delete "IX" and insert -- 1× --.

Column 270, Line 26, delete "the a" and insert -- a --.

Column 272, Line 10, delete "angiodema." and insert -- angioedema. --.

Column 282, Line 36, delete "CARD1l," and insert -- CARD11, --.

Column 285, Line 41, delete "angiodema." and insert -- angioedema. --.

Column 287, Line 28, delete "angiodema." and insert -- angioedema. --.

Column 288, Line 25, delete "angiodema." and insert -- angioedema. --.

Column 291, Line 4, delete "HIV-A" and insert -- HIV-1 --.

Column 292, Line 36, delete "angiodema." and insert -- angioedema. --.

Column 293, Line 32, delete "angiodema." and insert -- angioedema. --.

Column 294, Line 16, delete "CARD1l," and insert -- CARD11, --.

Column 296, Line 10, delete "HIV-A" and insert -- HIV-1 --.

CERTIFICATE OF CORRECTION (continued)
U.S. Pat. No. 11,939,594 B2

Column 297, Line 44, delete "angiodema." and insert -- angioedema. --.

Column 298, Line 65, delete "angiodema." and insert -- angioedema. --.

Column 303, Line 9, delete "angiodema." and insert -- angioedema. --.

Column 304, Line 40, delete "angiodema." and insert -- angioedema. --.

Column 305, Line 24, delete "CARD1l," and insert -- CARD11, --.

Column 308, Line 52, delete "angiodema." and insert -- angioedema. --.

Column 309, Line 49, delete "angiodema." and insert -- angioedema. --.

Column 310, Line 34, delete "CARD1l," and insert -- CARD11, --.

Column 313, Line 62, delete "angiodema." and insert -- angioedema. --.

Column 315, Line 54, delete "CARD1l," and insert -- CARD11, --.

Column 316, Line 49, delete "FKBP1" and insert -- FKBP11 --.

Column 318, Line 56, delete "angiodema." and insert -- angioedema. --.

Column 323, Line 1, delete "angiodema." and insert -- angioedema. --.

Column 324, Line 28, delete "angiodema." and insert -- angioedema. --.

Column 326, Line 38, delete "1L2," and insert -- IL2, --.

Column 328, Line 40, delete "angiodema." and insert -- angioedema. --.

Column 329, Line 58, delete "angiodema." and insert -- angioedema. --.

Column 333, Line 27, delete "I kb," and insert -- 1 kb, --.

Column 334, Line 3, delete "angiodema." and insert -- angioedema. --.

Column 334, Line 60, delete "I15." and insert -- IL15. --.

Column 336, Line 16, delete "Tb" and insert -- T1 --.

Column 342, Line 47, delete "angiodema." and insert -- angioedema. --.

Column 345, Line 42, delete "E4orf6/Elb55k" and insert -- E4orf6/E1b55k --.

In the Claims

Column 488, Line 31 (approx.), Claim 12, delete "claim 4," and insert -- claim 11, --.

```
                       SEQUENCE LISTING

<160> NUMBER OF SEQ ID NOS: 112

<210> SEQ ID NO 1
<211> LENGTH: 16
<212> TYPE: RNA
<213> ORGANISM: Artificial Sequence
<220> FEATURE:
<223> OTHER INFORMATION: tracrRNA recognition sequence

<400> SEQUENCE: 1
guuuuagagc uaugcu                                                     16

<210> SEQ ID NO 2
<211> LENGTH: 20
<212> TYPE: RNA
<213> ORGANISM: Artificial Sequence
<220> FEATURE:
<223> OTHER INFORMATION: PAX5

<400> SEQUENCE: 2
ugugaaugga cggccacucc                                                 20

<210> SEQ ID NO 3
<211> LENGTH: 20
<212> TYPE: RNA
<213> ORGANISM: Artificial Sequence
<220> FEATURE:
<223> OTHER INFORMATION: PAX5

<400> SEQUENCE: 3
uguaguccgc cagaggauag                                                 20

<210> SEQ ID NO 4
```

```
<211> LENGTH: 20
<212> TYPE: RNA
<213> ORGANISM: Artificial Sequence
<220> FEATURE:
<223> OTHER INFORMATION: IRF8

<400> SEQUENCE: 4
auugacagua gcauguaucc                                              20

<210> SEQ ID NO 5
<211> LENGTH: 20
<212> TYPE: RNA
<213> ORGANISM: Artificial Sequence
<220> FEATURE:
<223> OTHER INFORMATION: IRF8

<400> SEQUENCE: 5
cggaaauguc caguugggac                                              20

<210> SEQ ID NO 6
<211> LENGTH: 20
<212> TYPE: RNA
<213> ORGANISM: Artificial Sequence
<220> FEATURE:
<223> OTHER INFORMATION: BACH2

<400> SEQUENCE: 6
guuccugcgc augcacaacc                                              20

<210> SEQ ID NO 7
<211> LENGTH: 20
<212> TYPE: RNA
<213> ORGANISM: Artificial Sequence
<220> FEATURE:
<223> OTHER INFORMATION: BACH2

<400> SEQUENCE: 7
cugugacgug acuuugaucg                                              20

<210> SEQ ID NO 8
<211> LENGTH: 20
<212> TYPE: RNA
<213> ORGANISM: Artificial Sequence
<220> FEATURE:
<223> OTHER INFORMATION: CCR5

<400> SEQUENCE: 8
caauguguca acucuugaca                                              20

<210> SEQ ID NO 9
<211> LENGTH: 20
<212> TYPE: RNA
<213> ORGANISM: Artificial Sequence
<220> FEATURE:
<223> OTHER INFORMATION: CCR5

<400> SEQUENCE: 9
gcuguguuug cgucucuccc                                              20

<210> SEQ ID NO 10
<211> LENGTH: 20
<212> TYPE: RNA
<213> ORGANISM: Artificial Sequence
<220> FEATURE:
<223> OTHER INFORMATION: CARD11

<400> SEQUENCE: 10
```

```
caaugaccuu acacugacgc                                               20

<210> SEQ ID NO 11
<211> LENGTH: 20
<212> TYPE: RNA
<213> ORGANISM: Artificial Sequence
<220> FEATURE:
<223> OTHER INFORMATION: PRDM1

<400> SEQUENCE: 11
ugauggcggu acuucgguuc                                               20

<210> SEQ ID NO 12
<211> LENGTH: 20
<212> TYPE: RNA
<213> ORGANISM: Artificial Sequence
<220> FEATURE:
<223> OTHER INFORMATION: PRDM1

<400> SEQUENCE: 12
aggaugcgga uaugacucug                                               20

<210> SEQ ID NO 13
<211> LENGTH: 20
<212> TYPE: RNA
<213> ORGANISM: Artificial Sequence
<220> FEATURE:
<223> OTHER INFORMATION: PRDM1

<400> SEQUENCE: 13
ggggagcgag ugauguacgu                                               20

<210> SEQ ID NO 14
<211> LENGTH: 4875
<212> TYPE: DNA
<213> ORGANISM: Artificial Sequence
<220> FEATURE:
<223> OTHER INFORMATION: 1079_pscAAV-MND.GFP

<400> SEQUENCE: 14
aagcttcccg gggggatctg ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctggagggg tggagtcgtg     180
acctagggaa cagagaaaca ggagaatatg ggccaaacag gatatctgtg gtaagcagtt     240
cctgccccgg ctcagggcca agaacagttg gaacagcaga atatgggcca aacaggatat     300
ctgtggtaag cagttcctgc cccggctcag ggccaagaac agatggtccc cagatgcggt     360
cccgccctca gcagtttcta gagaaccatc agatgtttcc agggtgcccc aaggacctga     420
aatgaccctg tgccttattt gaactaacca atcagttcgc ttctcgcttc tgttcgcgcg     480
cttctgctcc ccgagctcta tataagcaga gctcgtttag tgaaccgtca gatcgcctgg     540
agacgccatc cacgctgttt tgacttccat agaaggatcc tcgaggccac catggtgagc     600
aagggcgagg agctgttcac cggggtggtg cccatcctgg tcgagctgga cggcgacgta     660
aacggccaca agttcagcgt gtccggcgag ggcgagggcg atgccaccta cggcaagctg     720
accctgaagt tcatctgcac caccggcaag ctgcccgtgc cctggcccac cctcgtgacc     780
accctgacct acggcgtgca gtgcttcagc cgctaccccg accacatgaa gcagcacgac     840
ttcttcaagt ccgccatgcc cgaaggctac gtccaggagc gcaccatctt cttcaaggac     900
```

| | |
|---|---|
| gacggcaact acaagacccg cgccgaggtg aagttcgagg gcgacaccct ggtgaaccgc | 960 |
| atcgagctga agggcatcga cttcaaggag gacggcaaca tcctgggggca caagctggag | 1020 |
| tacaactaca acagccacaa cgtctatatc atggccgaca agcagaagaa cggcatcaag | 1080 |
| gtgaacttca agatccgcca caacatcgag gacggcagcg tgcagctcgc cgaccactac | 1140 |
| cagcagaaca cccccatcgg cgacggcccc gtgctgctgc ccgacaacca ctacctgagc | 1200 |
| acccagtccg ccctgagcaa agaccccaac gagaagcgcg atcacatggt cctgctggag | 1260 |
| ttcgtgaccg ccgccgggat cactctcggc atggacgagc tgtacaagta agcggccgca | 1320 |
| attcacccca ccagtgcagg ctgcctatca gaaagtggtg gctggtgtgg ctaatgccct | 1380 |
| ggcccacaag tatcactaag ctcgctttct tgctgtccaa tttctattaa aggttccttt | 1440 |
| gttccctaag tccaactact aaactggggg atattatgaa gggccttgag catctggatt | 1500 |
| ctgcctaata aaaaacattt attttcattg caatgatgta tttaaattat ttctgaatat | 1560 |
| tttactaaaa agggaatgtg ggaggtcagt gcatttaaaa cataaagaaa tgaagagcta | 1620 |
| gttcaaacct tgggaaaata cactatatct taaactccat gaaagaaggt gaggctgcaa | 1680 |
| acagctaatg cacattggca acagcccctg atgcctatgc cttattcatc cctcagaaaa | 1740 |
| ggattcaagt agaggcttga tttggaggtt aaagttttgc tatgctgtat tttacattac | 1800 |
| ttattgtttt agctgtcctc atgaatgtct tttcactacc catttgctta tcctgcatct | 1860 |
| ctcagccttg actccactca gttctcttgc ttagagatac caccttttccc ctgaagtgtt | 1920 |
| ccttccatgt tttacggcga gatggtttct cctcgcctgg ccactcagcc ttagttgtct | 1980 |
| ctgttgtctt atagaggtct acttgaagaa ggaaaaacag ggggcatggt ttgactgtcc | 2040 |
| tgtgagccct tcttccctgc ctcccccact cacagtgaca ctagtccact ccctctctgc | 2100 |
| gcgctcgctc gctcactgag gccgggcgac caaaggtcgc ccgacgcccg gctttgcccc | 2160 |
| gggcggcctc agtgagcgag cgagcgcgca gagagggaca gatccgggcc cgcatgcgtc | 2220 |
| gacaattcac tggccgtcgt tttacaacgt cgtgactggg aaaaccctgg cgttacccaa | 2280 |
| cttaatcgcc ttgcagcaca tccccctttc gccagctggc gtaatagcga agaggcccgc | 2340 |
| accgatcgcc cttcccaaca gttgcgcagc ctgaatggcg aatggcgcct gatgcggtat | 2400 |
| tttctcctta cgcatctgtg cggtatttca caccgcatat ggtgcactct cagtacaatc | 2460 |
| tgctctgatg ccgcatagtt aagccagccc cgacacccgc caacacccgc tgacgcgccc | 2520 |
| tgacgggctt gtctgctccc ggcatccgct tacagacaag ctgtgaccgt ctccgggagc | 2580 |
| tgcatgtgtc agaggttttc accgtcatca ccgaaacgcg cgagacgaaa gggcctcgtg | 2640 |
| atacgcctat ttttataggt taatgtcatg ataataatgg tttcttagac gtcaggtggc | 2700 |
| acttttcggg gaaatgtgcg cggaacccct atttgtttat ttttctaaat acattcaaat | 2760 |
| atgtatccgc tcatgagaca ataaccctga taaatgcttc aataatattg aaaaaggaag | 2820 |
| agtatgagta ttcaacattt ccgtgtcgcc cttattccct ttttttgcggc attttgcctt | 2880 |
| cctgtttttg ctcacccaga aacgctggtg aaagtaaaag atgctgaaga tcagttgggt | 2940 |
| gcacgagtgg gttacatcga actggatctc aacagcggta agatccttga gttttcgc | 3000 |
| cccgaagaac gttttccaat gatgagcact tttaaagttc tgctatgtgg cgcggtatta | 3060 |
| tcccgtattg acgccgggca agagcaactc ggtcgccgca tacactattc tcagaatgac | 3120 |
| ttggttgagt actcaccagt cacagaaaag catcttacgg atggcatgac agtaagagaa | 3180 |
| ttatgcagtg ctgccataac catgagtgat aacactgcgg ccaacttact tctgacaacg | 3240 |
| atcggaggac cgaaggagct aaccgctttt ttgcacaaca tgggggatca tgtaactcgc | 3300 |

```
cttgatcgtt gggaaccgga gctgaatgaa gccataccaa acgacgagcg tgacaccacg    3360
atgcctgtag caatggcaac aacgttgcgc aaactattaa ctggcgaact acttactcta    3420
gcttcccggc aacaattaat agactggatg gaggcggata agttgcagg accacttctg    3480 cgctcggccc ttccggctgg ctggtttatt gctgataaat ctggagccgg tgagcgtggg    3540
tctcgcggta tcattgcagc actggggcca gatggtaagc cctcccgtat cgtagttatc    3600
tacacgacgg ggagtcaggc aactatggat gaacgaaata gacagatcgc tgagataggt    3660
gcctcactga ttaagcattg gtaactgtca gaccaagttt actcatatat actttagatt    3720
gatttaaaac ttcattttta atttaaaagg atctaggtga agatccttt tgataatctc    3780 atgaccaaaa tcccttaacg tgagttttcg ttccactgag cgtcagaccc cgtagaaaag    3840
atcaaaggat cttcttgaga tcctttttt ctgcgcgtaa tctgctgctt gcaaacaaaa    3900
aaaccaccgc taccagcggt ggtttgtttg ccggatcaag agctaccaac tcttttccg    3960 aaggtaactg gcttcagcag agcgcagata ccaaatactg ttcttctagt gtagccgtag    4020
ttaggccacc acttcaagaa ctctgtagca ccgcctacat acctcgctct gctaatcctg    4080
ttaccagtgg ctgctgccag tggcgataag tcgtgtctta ccgggttgga ctcaagacga    4140
tagttaccgg ataaggcgca gcggtcgggc tgaacgggg gttcgtgcac acagcccagc    4200
ttggagcgaa cgacctacac cgaactgaga tacctacagc gtgagctatg agaaagcgcc    4260
acgcttcccg aagggagaaa ggcggacagg tatccggtaa gcggcagggt cggaacagga    4320
gagcgcacga gggagcttcc agggggaaac gcctggtatc tttatagtcc tgtcgggttt    4380
cgccacctct gacttgagcg tcgatttttg tgatgctcgt cagggggggcg gagcctatgg    4440 aaaaacgcca gcaacgcggc cttttacgg ttcctggcct tttgctggcc ttttgctcac    4500
atgttctttc ctgcgttatc ccctgattct gtggataacc gtattaccgc ctttgagtga    4560
gctgataccg ctcgccgcag ccgaacgacc gagcgcagcg agtcagtgag cgaggaagcg    4620
gaagagcgcc caatacgcaa accgcctctc cccgcgcgtt ggccgattca ttaatgcagc    4680
tggcacgaca ggtttcccga ctggaaagcg ggcagtgagc gcaacgcaat taatgtgagt    4740
tagctcactc attaggcacc ccaggcttta cactttatgc ttccggctcg tatgttgtgt    4800
ggaattgtga gcggataaca atttcacaca ggaaacagct atgaccatga ttacgccaag    4860
ctctcgagat ctaga                                                    4875

<210> SEQ ID NO 15
<211> LENGTH: 5056
<212> TYPE: DNA
<213> ORGANISM: Artificial Sequence
<220> FEATURE:
<223> OTHER INFORMATION: 1347_pscAAV.Blimp.0.4kb.MND.GFP

<400> SEQUENCE: 15
aagcttcccg gggggatctg gccactccc tctctgcgcg ctcgctcgct cactgaggcc      60
gggcgaccaa aggtcgcccg acgcccgggc tttgcccggg cggcctcagt gagcgagcga    120
gcgcgcagag agggagtggc caactccatc actaggggtt cctggagggg tggagtcgtg    180
acctaggacg cgtgccagct gttactcagg ttttctcaag aaggaggagc aactttggca    240
gttttgcttc agttctctct agccctctgt gtaatcgccc cttttctttt atttcagcac    300
aaacacagag cagtctaaag caaccgagca ctgagaaaaa tgaactctgc ccaaagaatg    360
tcccaaagag agagtacagc gtgaaagaaa tcctaaaatt ggactccaac ccctccaaag    420
```

| | | | | |
|---|---|---|---|---|
| gaaaggacct | ctaccgttct | aacatttcac | ccctcacatc | agaaaaggac ctcgatgact | 480 |
| ttagaagacg | tgggagcccc | gaaatgccct | tctaccctcg | ggtcgtttac cccatccggg | 540 |
| cccctctgcc | agaagacttt | ttgaaagctt | ccctggccta | cgggatcgag agagaacaga | 600 |
| gaaacaggag | aatatgggcc | aaacaggata | tctgtggtaa | gcagttcctg ccccggctca | 660 |
| ggccaagaa | cagttggaac | agcagaatat | gggccaaaca | ggatatctgt ggtaagcagt | 720 |
| tcctgccccg | gctcagggcc | aagaacagat | ggtcccaga | tgcggtcccg ccctcagcag | 780 |
| tttctagaga | accatcagat | gtttccaggg | tgccccaagg | acctgaaatg accctgtgcc | 840 |
| ttatttgaac | taaccaatca | gttcgcttct | cgcttctgtt | cgcgcgcttc tgctccccga | 900 |
| gctctatata | agcagagctc | gtttagtgaa | ccgtcagatc | gcctggagac gccatccacg | 960 |
| ctgttttgac | ttccatagaa | ggatctcgag | gccaccatgg | tgagcaaggg cgaggagctg | 1020 |
| ttcaccgggg | tggtgcccat | cctggtcgag | ctggacggcg | acgtaaacgg ccacaagttc | 1080 |
| agcgtgtccg | gcgagggcga | gggcgatgcc | acctacggca | agctgaccct gaagttcatc | 1140 |
| tgcaccaccg | gcaagctgcc | cgtgccctgg | cccaccctcg | tgaccaccct gacctacggc | 1200 |
| gtgcagtgct | tcagccgcta | ccccgaccac | atgaagcagc | acgacttctt caagtccgcc | 1260 |
| atgcccgaag | gctacgtcca | ggagcgcacc | atcttcttca | aggacgacgg caactacaag | 1320 |
| acccgcgccg | aggtgaagtt | cgagggcgac | accctggtga | accgcatcga gctgaagggc | 1380 |
| atcgacttca | aggaggacgg | caacatcctg | gggcacaagc | tggagtacaa ctacaacagc | 1440 |
| cacaacgtct | atatcatggc | cgacaagcag | aagaacggca | tcaaggtgaa cttcaagatc | 1500 |
| cgccacaaca | tcgaggacgg | cagcgtgcag | ctcgccgacc | actaccagca gaacaccccc | 1560 |
| atcggcgacg | gccccgtgct | gctgcccgac | aaccactacc | tgagcaccca gtccgccctg | 1620 |
| agcaaagacc | ccaacgagaa | gcgcgatcac | atggtcctgc | tggagttcgt gaccgccgcc | 1680 |
| gggatcactc | tcggcatgga | cgagctgtac | aagtaaaacta | gtgtcgactg ctttatttgt | 1740 |
| gaaatttgtg | atgctattgc | tttatttgta | accattataa | gctgcaataa acaagttaac | 1800 |
| aacaacaatt | gcattcattt | tatgtttcag | gttcaggggg | aggtgtggga ggttttttaa | 1860 |
| aacgtacatc | actcgctccc | ccattccatc | ctccaccact | ccaagcccct ctgcaagaag | 1920 |
| cagccccgac | caaagcctca | agagctccag | ccctcacagc | agccctggga atacggtgtc | 1980 |
| ccctgtgggc | cccggctctc | aagagcaccg | ggactcctac | gcttacttga acgcgtccta | 2040 |
| cggcacggaa | ggtttgggct | cctaccctgg | ctacgcaccc | ctgccccacc tcccgccagc | 2100 |
| tttcatcccc | tcgtacaacg | ctcactaccc | caagttcctc | ttgccccccct acggcatgaa | 2160 |
| ttgtaatggc | ctgagcgctg | tgagcagcat | gaatggcatc | aacaactttg gcctcttccc | 2220 |
| gaggctgtgc | cctgtctaca | gcaatctcct | cggtgggggc | actagtccac tccctctctg | 2280 |
| cgcgctcgct | cgctcactga | ggccgggcga | ccaaaggtcg | cccgacgccc gggctttgcc | 2340 |
| cgggcggcct | cagtgagcga | gcgagcgcgc | agagagggac | agatccgggc cgcatgcgt | 2400 |
| cgacaattca | ctggccgtcg | ttttacaacg | tcgtgactgg | gaaaaccctg gcgttaccca | 2460 |
| acttaatcgc | cttgcagcac | atccccctttt | cgccagctgg | cgtaatagcg aagaggcccg | 2520 |
| caccgatcgc | ccttcccaac | agttgcgcag | cctgaatggc | gaatggcgcc tgatgcggta | 2580 |
| ttttctcctt | acgcatctgt | gcggtatttc | acaccgcata | tggtgcactc tcagtacaat | 2640 |
| ctgctctgat | gccgcatagt | taagccagcc | ccgacacccg | ccaacacccg ctgacgcgcc | 2700 |
| ctgacgggct | tgtctgctcc | cggcatccgc | ttacagacaa | gctgtgaccg tctccggag | 2760 |
| ctgcatgtgt | cagaggtttt | caccgtcatc | accgaaacgc | gcgagacgaa agggcctcgt | 2820 |

```
gatacgccta ttttatagg ttaatgtcat gataataatg gtttcttaga cgtcaggtgg    2880
cacttttcgg ggaaatgtgc gcggaacccc tatttgttta ttttctaaa tacattcaaa     2940 tatgtatccg ctcatgagac aataaccctg ataaatgctt caataatatt gaaaaaggaa    3000
gagtatgagt attcaacatt tccgtgtcgc ccttattccc ttttttgcgg cattttgcct    3060
tcctgttttt gctcacccag aaacgctggt gaaagtaaaa gatgctgaag atcagttggg    3120
tgcacgagtg ggttacatcg aactggatct caacagcggt aagatccttg agagttttcg    3180
ccccgaagaa cgttttccaa tgatgagcac ttttaaagtt ctgctatgtg gcgcggtatt    3240
atcccgtatt gacgccgggc aagagcaact cggtcgccgc atacactatt ctcagaatga    3300
cttggttgag tactcaccag tcacagaaaa gcatcttacg gatggcatga cagtaagaga    3360
attatgcagt gctgccataa ccatgagtga taacactgcg gccaacttac ttctgacaac    3420
gatcggagga ccgaaggagc taaccgcttt tttgcacaac atgggggatc atgtaactcg    3480
ccttgatcgt tgggaaccgg agctgaatga agccatacca aacgacgagc gtgacaccac    3540
gatgcctgta gcaatggcaa caacgttgcg caaactatta actggcgaac tacttactct    3600
agcttcccgg caacaattaa tagactggat ggaggcggat aaagttgcag gaccacttct    3660
gcgctcggcc cttccggctg gctggtttat tgctgataaa tctggagccg gtgagcgtgg    3720
gtctcgcggt atcattgcag cactggggcc agatggtaag ccctcccgta tcgtagttat    3780
ctacacgacg gggagtcagg caactatgga tgaacgaaat agacagatcg ctgagatagg    3840
tgcctcactg attaagcatt ggtaactgtc agaccaagtt tactcatata ctttagat     3900 tgatttaaaa cttcatttt aatttaaaag gatctaggtg aagatccttt ttgataatct    3960
catgaccaaa atcccttaac gtgagttttc gttccactga gcgtcagacc ccgtagaaaa    4020
gatcaaagga tcttcttgag atcctttttt tctgcgcgta atctgctgct tgcaaacaaa    4080
aaaaccaccg ctaccagcgg tggtttgttt gccggatcaa gagctaccaa ctcttttcc    4140 gaaggtaact ggcttcagca gagcgcagat accaaatact gttcttctag tgtagccgta    4200
gttaggccac cacttcaaga actctgtagc accgcctaca tacctcgctc tgctaatcct    4260
gttaccagtg gctgctgcca gtggcgataa gtcgtgtctt accgggttgg actcaagacg    4320
atagttaccg gataaggcgc agcggtcggg ctgaacgggg ggttcgtgca cacagcccag    4380
cttggagcga acgacctaca ccgaactgag atacctacag cgtgagctat gagaaagcgc    4440
cacgcttccc gaagggagaa aggcggacag gtatccggta agcggcaggg tcggaacagg    4500
agagcgcacg agggagcttc caggggaaa cgcctggtat ctttatagtc ctgtcgggtt    4560
tcgccacctc tgacttgagc gtcgattttt gtgatgctcg tcaggggggc ggagcctatg    4620
gaaaaacgcc agcaacgcgg cctttttacg gttcctggcc ttttgctggc cttttgctca    4680
catgttcttt cctgcgttat cccctgattc tgtggataac cgtattaccg cctttgagtg    4740
agctgatacc gctcgccgca gccgaacgac cgagcgcagc gagtcagtga gcgaggaagc    4800
ggaagagcgc ccaatacgca aaccgcctct ccccgcgcgt tggccgattc attaatgcag    4860
ctggcacgac aggtttcccg actggaaagc gggcagtgag cgcaacgcaa ttaatgtgag    4920
ttagctcact cattaggcac cccaggcttt acactttatg cttccggctc gtatgttgtg    4980
tggaattgtg agcggataac aatttcacac aggaaacagc tatgaccatg attacgccaa    5040
gctctcgaga tctaga                                                    5056
```

<210> SEQ ID NO 16

<211> LENGTH: 6006
<212> TYPE: DNA
<213> ORGANISM: Artificial Sequence
<220> FEATURE:
<223> OTHER INFORMATION: 1348_pAAV.Blimp.0.4kb.MND.GFP.pA

<400> SEQUENCE: 16

| | | | | | |
|---|---|---|---|---|---|
| cagctgcgcg | ctcgctcgct | cactgaggcc | gcccgggcaa | agcccgggcg | tcgggcgacc | 60 |
| tttggtcgcc | cggcctcagt | gagcgagcga | gcgcgcagag | agggagtggc | caactccatc | 120 |
| actagggtt | ccttgtagtt | aatgattaac | ccgccatgct | acttatctac | acgcgtgcca | 180 |
| gctgttactc | aggttttctc | aagaaggagg | agcaactttg | gcagttttgc | ttcagttctc | 240 |
| tctagccctc | tgtgtaatcg | ccccttttc | tttatttcag | cacaaacaca | gagcagtcta | 300 |
| aagcaaccga | gcactgagaa | aaatgaactc | tgcccaaaga | atgtcccaaa | gagagagtac | 360 |
| agcgtgaaag | aaatcctaaa | attggactcc | aaccccctcca | aaggaaagga | cctctaccgt | 420 |
| tctaacattt | caccccctcac | atcagaaaag | gacctcgatg | actttagaag | acgtgggagc | 480 |
| cccgaaatgc | ccttctaccc | tcgggtcgtt | taccccatcc | gggcccctct | gccagaagac | 540 |
| ttttgaaag | cttccctggc | ctacgggatc | gagagagaac | agagaaacag | gagaatatgg | 600 |
| gccaaacagg | atatctgtgg | taagcagttc | ctgccccggc | tcagggccaa | gaacagttgg | 660 |
| aacagcagaa | tatgggccaa | acaggatatc | tgtggtaagc | agttcctgcc | ccggctcagg | 720 |
| gccaagaaca | gatggtcccc | agatgcggtc | ccgccctcag | cagttctag | agaaccatca | 780 |
| gatgtttcca | gggtgcccca | aggacctgaa | atgaccctgt | gccttatttg | aactaaccaa | 840 |
| tcagttcgct | tctcgcttct | gttcgcgcgc | ttctgctccc | cgagctctat | ataagcagag | 900 |
| ctcgtttagt | gaaccgtcag | atcgcctgga | gacgccatcc | acgctgtttt | gacttccata | 960 |
| gaaggatctc | gaggccacca | tggtgagcaa | gggcgaggag | ctgttcaccg | gggtggtgcc | 1020 |
| catcctggtc | gagctggacg | gcgacgtaaa | cggccacaag | ttcagcgtgt | ccggcgaggg | 1080 |
| cgagggcgat | gccacctacg | gcaagctgac | cctgaagttc | atctgcacca | ccggcaagct | 1140 |
| gcccgtgccc | tggcccaccc | tcgtgaccac | cctgacctac | ggcgtgcagt | gcttcagccg | 1200 |
| ctaccccgac | cacatgaagc | agcacgactt | cttcaagtcc | gccatgcccg | aaggctacgt | 1260 |
| ccaggagcgc | accatcttct | tcaaggacga | cggcaactac | aagacccgcg | ccgaggtgaa | 1320 |
| gttcgagggc | gacaccctgg | tgaaccgcat | cgagctgaag | ggcatcgact | tcaaggagga | 1380 |
| cggcaacatc | ctggggcaca | agctggagta | caactacaac | agccacaacg | tctatatcat | 1440 |
| ggccgacaag | cagaagaacg | gcatcaaggt | gaacttcaag | atccgccaca | acatcgagga | 1500 |
| cggcagcgtg | cagctcgccg | accactacca | gcagaacacc | cccatcggcg | acggccccgt | 1560 |
| gctgctgccc | gacaaccact | acctgagcac | ccagtccgcc | ctgagcaaag | accccaacga | 1620 |
| gaagcgcgat | cacatggtcc | tgctggagtt | cgtgaccgcc | gccgggatca | ctctcggcat | 1680 |
| ggacgagctg | tacaagtaaa | ctagtgtcga | ctgctttatt | tgtgaaattt | gtgatgctat | 1740 |
| tgctttattt | gtaaccatta | taagctgcaa | taaacaagt | aacaacaaca | attgcattca | 1800 |
| ttttatgttt | caggttcagg | gggaggtgtg | ggaggttttt | taaaacgtac | atcactcgct | 1860 |
| cccccattcc | atcctccacc | actccaagcc | cctctgcaag | aagcagcccc | gaccaaagcc | 1920 |
| tcaagagctc | cagccctcac | agcagccctg | ggaatacggt | gtccctgtg | ggccccggct | 1980 |
| ctcaagagca | ccgggactcc | tacgcttact | tgaacgcgtc | ctacggcacg | gaaggtttgg | 2040 |
| gctcctaccc | tggctacgca | ccctgcccc | acctcccgcc | agctttcatc | ccctcgtaca | 2100 |
| acgctcacta | ccccaagttc | ctcttgcccc | cctacggcat | gaattgtaat | ggcctgagcg | 2160 |

```
ctgtgagcag catgaatggc atcaacaact ttggcctctt cccgaggctg tgccctgtct   2220
acagcaatct cctcggtggg ggcatctaga gtagataagt agcatggcgg gttaatcatt   2280
aactacaagg aaccccagt  gatggagttg gccactccct ctctgcgcgc tcgctcgctc   2340
actgaggccg ggcgaccaaa ggtcgcccga cgcccgggct tgcccgggc  ggcctcagtg   2400 agcgagcgag cgcgccagct ggcgtaatag cgaagaggcc cgcaccgatc gcccttccca   2460
acagttgcgc agcctgaatg gcgaatggcg attccgttgc aatggctggc ggtaatattg   2520
ttctggatat taccagcaag gccgatagtt tgagttcttc tactcaggca agtgatgtta   2580
ttactaatca aagaagtatt gcgacaacgg ttaatttgcg tgatggacag actcttttac   2640
tcggtggcct cactgattat aaaaacactt ctcaggattc tggcgtaccg ttcctgtcta   2700
aaatcccttt aatcggcctc ctgtttagct cccgctctga ttctaacgag gaaagcacgt   2760
tatacgtgct cgtcaaagca accatagtac gcgccctgta gcggcgcatt aagcgcggcg   2820
ggtgtggtgg ttacgcgcag cgtgaccgct acacttgcca gcgccctagc gcccgctcct   2880
ttcgctttct tcccttcctt tctcgccacg ttcgccggct ttccccgtca gctctaaat   2940 cgggggctcc ctttagggtt ccgatttagt gctttacggc acctcgaccc caaaaaactt   3000
gattagggtg atggttcacg tagtgggcca tcgccctgat agacggtttt tcgccctttg   3060
acgttggagt ccacgttctt taatagtgga ctcttgttcc aaactggaac aacactcaac   3120
cctatctcgg tctattcttt tgatttataa gggattttgc cgatttcggc ctattggtta   3180
aaaaatgagc tgatttaaca aaaatttaac gcgaatttta acaaaatatt aacgtttaca   3240
atttaaatat ttgcttatac aatcttcctg tttttggggc ttttctgatt atcaaccggg   3300
gtacatatga ttgacatgct agttttacga ttaccgttca tcgattctct tgtttgctcc   3360
agactctcag gcaatgacct gatagccttt gtagagacct ctcaaaaata gctaccctct   3420
ccggcatgaa tttatcagct agaacggttg aatatcatat tgatggtgat ttgactgtct   3480
ccggcctttc tcacccgttt gaatctttac ctacacatta ctcaggcatt gcatttaaaa   3540
tatatgaggg ttctaaaaat ttttatcctt gcgttgaaat aaaggcttct cccgcaaaag   3600
tattacaggg tcataatgtt tttggtacaa ccgatttagc tttatgctct gaggctttat   3660
tgcttaattt tgctaattct ttgccttgcc tgtatgattt attggatgtt ggaatcgcct   3720
gatgcggtat tttctcctta cgcatctgtg cggtatttca caccgcatat ggtgcactct   3780
cagtacaatc tgctctgatg ccgcatagtt aagccagccc cgacacccgc caacacccgc   3840
tgacgcgccc tgacgggctt gtctgctccc ggcatccgct tacagacaag ctgtgaccgt   3900
ctccgggagc tgcatgtgtc agaggttttc accgtcatca ccgaaacgcg cgagacgaaa   3960
gggcctcgtg atacgcctat ttttataggt taatgtcatg ataataatgg tttcttagac   4020
gtcaggtggc acttttcggg gaaatgtgcg cggaacccct atttgtttat ttttctaaat   4080
acattcaaat atgtatccgc tcatgagaca ataaccctga taaatgcttc aataatattg   4140
aaaaaggaag agtatgagta ttcaacattt ccgtgtcgcc cttattccct ttttgcggc   4200 attttgcctt cctgtttttg ctcacccaga aacgctggtg aaagtaaaag atgctgaaga   4260
tcagttgggt gcacgagtgg gttacatcga actggatctc aacagcggta agatccttga   4320
gagttttcgc cccgaagaac gttttccaat gatgagcact tttaaagttc tgctatgtgg   4380
cgcggtatta tcccgtattg acgccgggca agagcaactc ggtcgccgca tacactattc   4440
tcagaatgac ttggttgagt actcaccagt cacagaaaag catcttacgg atggcatgac   4500
```

```
agtaagagaa ttatgcagtg ctgccataac catgagtgat aacactgcgg ccaacttact    4560
tctgacaacg atcggaggac cgaaggagct aaccgctttt ttgcacaaca tgggggatca    4620
tgtaactcgc cttgatcgtt gggaaccgga gctgaatgaa gccataccaa cgacgagcg    4680 tgacaccacg atgcctgtag caatggcaac aacgttgcgc aaactattaa ctggcgaact    4740
acttactcta gcttcccggc aacaattaat agactggatg gaggcggata agttgcagg    4800 accacttctg cgctcggccc ttccggctgg ctggtttatt gctgataaat ctggagccgg    4860
tgagcgtggg tctcgcggta tcattgcagc actggggcca gatggtaagc cctcccgtat    4920
cgtagttatc tacacgacgg ggagtcaggc aactatggat gaacgaaata gacagatcgc    4980
tgagataggt gcctcactga ttaagcattg gtaactgtca gaccaagttt actcatatat    5040
actttagatt gatttaaaac ttcatttttta atttaaaagg atctaggtga agatcctttt    5100
tgataatctc atgaccaaaa tcccttaacg tgagttttcg ttccactgag cgtcagaccc    5160
cgtagaaaag atcaaaggat cttcttgaga tcctttttttt ctgcgcgtaa tctgctgctt    5220
gcaaacaaaa aaaccaccgc taccagcggt ggtttgtttg ccggatcaag agctaccaac    5280 tcttttttccg aaggtaactg gcttcagcag agcgcagata ccaaatactg tccttctagt    5340
gtagccgtag ttaggccacc acttcaagaa ctctgtagca ccgcctacat acctcgctct    5400
gctaatcctg ttaccagtgg ctgctgccag tggcgataag tcgtgtctta ccgggttgga    5460
ctcaagacga tagttaccgg ataaggcgca gcggtcgggc tgaacggggg gttcgtgcac    5520
acagcccagc ttggagcgaa cgacctacac cgaactgaga tacctacagc gtgagctatg    5580
agaaagcgcc acgcttcccg aagggagaaa ggcggacagg tatccggtaa gcggcagggt    5640
cggaacagga gagcgcacga gggagcttcc agggggaaac gcctggtatc tttatagtcc    5700
tgtcgggttt cgccacctct gacttgagcg tcgatttttg tgatgctcgt caggggggcg    5760
gagcctatgg aaaaacgcca gcaacgcggc cttttttacgg ttcctggcct tttgctggcc    5820
ttttgctcac atgttctttc ctgcgttatc ccctgattct gtggataacc gtattaccgc    5880
ctttgagtga gctgataccg ctcgccgcag ccgaacgacc gagcgcagcg agtcagtgag    5940
cgaggaagcg gaagagcgcc caatacgcaa accgcctctc ccgcgcgtt ggccgattca    6000 ttaatg                                                                6006
```

<210> SEQ ID NO 17
<211> LENGTH: 7206
<212> TYPE: DNA
<213> ORGANISM: Artificial Sequence
<220> FEATURE:
<223> OTHER INFORMATION: 1361_pAAV.Blimp1.1.0kb.MND.GFP.pA

<400> SEQUENCE: 17

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac acgcgtggta    180
aaccatgaac atcagaaaga ctttttattaa cctatgacag ggtccccacc ccagtatttt    240
tccactccat taaatggaa gttttttttt ttttttctt ttttgagaca gagttttgct    300
cttgttgccc agtctggagt gcaatggcac aatctcggct caccacaacc tccacctccc    360
agattcaagc gattcttctg cctcagcctc ccaagtagct gggattacag gtgtgcgcca    420
ccacgcccag ctaattttgt atttttagta gagatggggt ttctccatgt tggtcaggct    480
ggtctcgaac ttccgacctc aggtgatccg cccacctcgg cctcccaaag tgctgggatt    540
```

```
acaggcaaga gccactgcat ccagcttagg ctatcttact ccagcctaaa cagcaatttt    600
ctatcataag gtctgtacta atgaaaacag aatcacccaa ggctgctgtt tgttctgtct    660
gtgctgccat tgtccgcatt ttgctgagga ggaaacggaa ctgcacttttt gagtgagtgg   720
cccagagcct tctagaatga gagtgcgttg gaagccagat atgtggcgat tgtgtcgcca    780
gctgttactc aggttttctc aagaaggagg agcaactttg gcagttttgc ttcagttctc    840
tctagccctc tgtgtaatcg cccctttttc tttatttcag cacaaacaca gagcagtcta    900
aagcaaccga gcactgagaa aaatgaactc tgcccaaaga atgtcccaaa gagagagtac    960
agcgtgaaag aaatcctaaa attggactcc aaccccctcca aaggaaagga cctctaccgt   1020
tctaacattt caccctcac atcagaaaag acctcgatg actttagaag acgtgggagc      1080
cccgaaatgc ccttctaccc tcgggtcgtt taccccatcc gggcccctct gccagaagac    1140
ttttgaaag cttccctggc ctacgggatc gagagagaac agagaaacag gagaatatgg     1200
gccaaacagg atatctgtgg taagcagttc ctgccccggc tcagggccaa gaacagttgg    1260
aacagcagaa tatgggccaa acaggatatc tgtggtaagc agttcctgcc ccggctcagg    1320
gccaagaaca gatggtcccc agatgcggtc ccgccctcag cagtttctag agaaccatca    1380
gatgtttcca gggtgcccca aggacctgaa atgaccctgt gccttatttg aactaaccaa    1440
tcagttcgct tctcgcttct gttcgcgcgc ttctgctccc cgagctctat ataagcagag    1500
ctcgtttagt gaaccgtcag atcgcctgga gacgccatcc acgctgtttt gacttccata    1560
gaaggatctc gaggccacca tggtgagcaa gggcgaggag ctgttcaccg gggtggtgcc    1620
catcctggtc gagctggacg gcgacgtaaa cggccacaag ttcagcgtgt ccggcgaggg    1680
cgagggcgat gccacctacg gcaagctgac cctgaagttc atctgcacca ccggcaagct    1740
gcccgtgccc tggcccaccc tcgtgaccac cctgacctac ggcgtgcagt gcttcagccg    1800
ctacccgac cacatgaagc agcacgactt cttcaagtcc gccatgcccg aaggctacgt     1860
ccaggagcgc accatcttct tcaaggacga cggcaactac aagacccgcg ccgaggtgaa    1920
gttcgagggc gacacccrgg tgaaccgcat cgagctgaag ggcatcgact tcaaggagga    1980
cggcaacatc ctggggcaca agctggagta caactacaac agccacaacg tctatatcat    2040
ggccgacaag cagaagaacg gcatcaaggt gaacttcaag atccgccaca acatcgagga    2100
cggcagcgtg cagctcgccg accactacca gcagaacacc cccatcggcg acggccccgt    2160
gctgctgccc gacaaccact acctgagcac ccagtccgcc ctgagcaaag accccaacga    2220
gaagcgcgat cacatggtcc tgctggagtt cgtgaccgcc gccgggatca ctctcggcat    2280
ggacgagctg tacaagtaaa ctagtgtcga ctgctttatt tgtgaaattt gtgatgctat    2340
tgctttattt gtaaccatta taagctgcaa taaacaagtt aacaacaaca attgcattca    2400
ttttatgttt caggttcagg gggaggtgtg ggaggttttt taaaacgtac atcactcgct    2460
cccccattcc atcctccacc actccaagcc cctctgcaag aagcagcccc gaccaaagcc    2520
tcaagagctc cagccctcac agcagccctg gaatacggt gtccctgtg ggccccggct      2580
ctcaagagca ccgggactcc tacgcttact tgaacgcgtc ctacggcacg gaaggtttgg    2640
gctcctaccc tggctacgca ccctgccccc acctcccgcc agctttcatc ccctcgtaca    2700
acgctcacta ccccaagttc ctcttgcccc ctacggcat gaattgtaat ggcctgagcg     2760
ctgtgagcag catgaatggc atcaacaact ttggcctctt cccgaggctg tgccctgtct    2820
acagcaatct cctcggtggg ggcagcctgc cccacccccat gctcaacccc acttctctcc   2880
```

```
cgagctcgct gccctcagat ggagcccgga ggttgctcca gccggagcat cccagggagg   2940
tgcttgtccc ggcgcccccac agtgccttct cctttaccgg ggccgccgcc agcatgaagg   3000
acaaggcctg tagccccaca agcgggtctc ccacggcggg aacagccgcc acggcagaac   3060
atgtggtgca gcccaaagct acctcagcag cgatggcagc cccagcagc gacgaagcca   3120
tgaatctcat taaaaacaaa agaaacatga ccggctacaa gacccttccc tacccgctga   3180
agaagcagaa cggcaagatc aagtacgaat gcaacgtttg cgccaagact tccggccagc   3240
tctccaatct gaaggtaggc cttgagagag agcagtccaa ggggctgtga gtgcatgctt   3300
gtgtttgtat ttagcttgct ttccatgggg tatcgattgc atttgcagta gtatgagccc   3360
ccggttgggg atagtgggta tggattccgc ctggcttttg ccacttctag ctctttgact   3420
ttggacaagt gacttccctt ctcctctaga gtagataagt agcatggcgg ttaatcatt    3480
aactacaagg aaccccctagt gatggagttg gccactccct ctctgcgcgc tcgctcgctc   3540
actgaggccg ggcgaccaaa ggtcgcccga cgcccgggct tgcccgggc ggcctcagtg    3600
agcgagcgag cgcgccagct ggcgtaatag cgaagaggcc cgcaccgatc gcccttccca   3660
acagttgcgc agcctgaatg gcgaatggcg attccgttgc aatgctggc ggtaatattg     3720
ttctggatat taccagcaag gccgatagtt tgagttcttc tactcaggca agtgatgtta   3780
ttactaatca agaagtatt gcgacaacgg ttaatttgcg tgatggacag actcttttac     3840
tcggtggcct cactgattat aaaaacactt ctcaggattc tggcgtaccg ttcctgtcta   3900
aaatccctt aatcggcctc ctgtttagct cccgctctga ttctaacgag gaaagcacgt    3960
tatacgtgct cgtcaaagca accatagtac gcgccctgta gcggcgcatt aagcgcggcg   4020
ggtgtggtgg ttacgcgcag cgtgaccgct acacttgcca gcgccctagc gcccgctcct   4080
ttcgctttct tcccttcctt tctcgccacg ttcgccggct ttccccgtca agctctaaat   4140
cgggggctcc ctttagggtt ccgatttagt gctttacggc acctcgaccc caaaaaactt   4200
gattagggtg atggttcacg tagtgggcca tcgccctgat agacggtttt tcgccctttg   4260
acgttggagt ccacgttctt taatagtgga ctcttgttcc aaactggaac aacactcaac   4320
cctatctcgg tctattcttt tgatttataa gggattttgc cgatttcggc ctattggtta   4380
aaaaatgagc tgatttaaca aaaatttaac gcgaatttta acaaaatatt aacgtttaca   4440
atttaaatat ttgcttatac aatcttcctg ttttggggc ttttctgatt atcaaccggg    4500
gtacatatga ttgacatgct agttttacga ttaccgttca tcgattctct tgtttgctcc   4560
agactctcag gcaatgacct gatagccttt gtagagacct ctcaaaaata gctaccctct   4620
ccggcatgaa tttatcagct agaacggttg aatatcatat tgatggtgat ttgactgtct   4680
ccggcctttc tcacccgttt gaatctttac ctacacatta ctcaggcatt gcatttaaaa   4740
tatatgaggg ttctaaaaat ttttatcctt gcgttgaaat aaaggcttct cccgcaaaag   4800
tattacaggg tcataatgtt tttggtacaa ccgatttagc tttatgctct gaggctttat   4860
tgcttaattt tgctaattct ttgccttgcc tgtatgattt attggatgtt ggaatcgcct   4920
gatgcggtat tttctcctta cgcatctgtg cggtatttca caccgcatat ggtgcactct   4980
cagtacaatc tgctctgatg ccgcatagtt aagccagccc cgacacccgc caacacccgc   5040
tgacgcgccc tgacgggctt gtctgctccc ggcatccgct tacagacaag ctgtgaccgt   5100
ctccgggagc tgcatgtgtc agaggttttc accgtcatca ccgaaacgcg cgagacgaaa   5160
gggcctcgtg atacgcctat ttttataggt taatgtcatg ataataatgg tttcttagac   5220
gtcaggtggc acttttcggg gaaatgtgcg cggaacccct atttgtttat ttttctaaat   5280
```

```
acattcaaat atgtatccgc tcatgagaca ataaccctga taaatgcttc aataatattg    5340
aaaaaggaag agtatgagta ttcaacattt ccgtgtcgcc cttattccct tttttgcggc    5400
attttgcctt cctgttttg ctcacccaga acgctggtg aaagtaaaag atgctgaaga    5460
tcagttgggt gcacgagtgg gttacatcga actggatctc aacagcggta agatccttga    5520
gagttttcgc cccgaagaac gttttccaat gatgagcact tttaaagttc tgctatgtgg    5580
cgcggtatta tcccgtattg acgccgggca agagcaactc ggtcgccgca tacactattc    5640
tcagaatgac ttggttgagt actcaccagt cacagaaaag catcttacgg atggcatgac    5700
agtaagagaa ttatgcagtg ctgccataac catgagtgat aacactgcgg ccaacttact    5760
tctgacaacg atcggaggac cgaaggagct aaccgctttt ttgcacaaca tgggggatca    5820
tgtaactcgc cttgatcgtt gggaaccgga gctgaatgaa gccataccaa acgacgagcg    5880
tgacaccacg atgcctgtag caatggcaac aacgttgcgc aaactattaa ctggcgaact    5940
acttactcta gcttcccggc aacaattaat agactggatg gaggcggata agttgcagg    6000 accacttctg cgctcggccc ttccggctgg ctggtttatt gctgataaat ctggagccgg    6060
tgagcgtggg tctcgcggta tcattgcagc actggggcca gatggtaagc cctcccgtat    6120
cgtagttatc tacacgacgg ggagtcaggc aactatggat gaacgaaata gacagatcgc    6180
tgagataggt gcctcactga ttaagcattg gtaactgtca gaccaagttt actcatatat    6240
actttagatt gatttaaaac ttcatttta atttaaaagg atctaggtga agatcctttt    6300
tgataatctc atgaccaaaa tcccttaacg tgagttttcg ttccactgag cgtcagaccc    6360
cgtagaaaag atcaaaggat cttcttgaga tcctttttt ctgcgcgtaa tctgctgctt    6420
gcaaacaaaa aaaccaccgc taccagcggt ggtttgtttg ccggatcaag agctaccaac    6480 tcttttccg aaggtaactg gcttcagcag agcgcagata ccaaatactg tccttctagt    6540
gtagccgtag ttaggccacc acttcaagaa ctctgtagca ccgcctacat acctcgctct    6600
gctaatcctg ttaccagtgg ctgctgccag tggcgataag tcgtgtctta ccgggttgga    6660
ctcaagacga tagttaccgg ataaggcgca gcggtcgggc tgaacggggg gttcgtgcac    6720
acagcccagc ttggagcgaa cgacctacac cgaactgaga tacctacagc gtgagctatg    6780
agaaagcgcc acgcttcccg aagggagaaa ggcggacagg tatccggtaa gcggcagggt    6840
cggaacagga gagcgcacga gggagcttcc agggggaaac gcctggtatc tttatagtcc    6900
tgtcgggttt cgccacctct gacttgagcg tcatttttg tgatgctcgt caggggggcg    6960
gagcctatgg aaaaacgcca gcaacgcggc cttttacgg ttcctggcct tttgctggcc    7020
ttttgctcac atgttctttc ctgcgttatc ccctgattct gtggataacc gtattaccgc    7080
ctttgagtga gctgataccg ctcgccgcag ccgaacgacc gagcgcagcg agtcagtgag    7140
cgaggaagcg gaagagcgcc caatacgcaa accgcctctc cccgcgcgtt ggccgattca    7200
ttaatg                                                              7206
```

<210> SEQ ID NO 18
<211> LENGTH: 6707
<212> TYPE: DNA
<213> ORGANISM: Artificial Sequence
<220> FEATURE:
<223> OTHER INFORMATION: 1366_CCR5.MND.BAFF_CRISPR.HR

<400> SEQUENCE: 18

```
cagctgcgcg ctcgctcgct cactgaggcc gcccgggcaa agcccgggcg tcgggcgacc    60
```

| | |
|---|---|
| tttggtcgcc cggcctcagt gagcgagcga gcgcgcagag agggagtggc caactccatc | 120 |
| actaggggtt ccttgtagtt aatgattaac ccgccatgct acttatctac gtagccatgc | 180 |
| tctagcggcc tcggcctctg cataaataaa aaaaattagt cagccatgag cttggacgcg | 240 |
| tttggtgtgg tggcgcctgt agtcccagc cacttggagg ggtgaggtga gaggattgct | 300 |
| tgagcccggg atggtccagg ctgcagtgag ccatgatcgt gccactgcac tccagcctgg | 360 |
| gcgacagagt gagaccctgt ctcacaacaa caacaacaac aacaaaaagg ctgagctgca | 420 |
| ccatgcttga cccagtttct taaaattgtt gtcaaagctt cattcactcc atggtgctat | 480 |
| agagcacaag attttatttg gtgagatggt gctttcatga attcccccaa cagagccaag | 540 |
| ctctccatct agtggacagg gaagctagca gcaaaccttc ccttcactac aaaacttcat | 600 |
| tgcttggcca aaaagagagt taattcaatg tagacatcta tgtaggcaat taaaaaccta | 660 |
| ttgatgtata aaacagtttg cattcatgga gggcaactaa atacattcta ggactttata | 720 |
| aaagatcact ttttatttat gcacagggtg gaacaagatg gattatcaag tgtcaagtcc | 780 |
| aatctatgac atcaattatt atacatcgga gccctgccaa aaaatcaatg tgaagcaaat | 840 |
| cgcagcccgc ctcctgcctc cgctctactc actggtgttc atctttggtt ttgtgggcaa | 900 |
| catgctggtc atcctcatcc tgataaactg caaaaggctg aagagcatga ctgacatcta | 960 |
| cctgctcaac ctggccatct ctgacctgtt tttccttctt actgtcccct ctgggctca | 1020 |
| ctatgctgcc gcccagtggg actttggaaa tacaatgtgt caacgaacag agaaacagga | 1080 |
| gaatatgggc caaacaggat atctgtggta agcagttcct gccccggctc agggccaaga | 1140 |
| acagttggaa cagcagaata tgggccaaac aggatatctg tggtaagcag ttcctgcccc | 1200 |
| ggctcagggc caagaacaga tggtccccag atgcggtccc gccctcagca gtttctagag | 1260 |
| aaccatcaga tgtttccagg gtgccccaag gacctgaaat gaccctgtgc cttatttgaa | 1320 |
| ctaaccaatc agttcgcttc tcgcttctgt tcgcgcgctt ctgctccccg agctctatat | 1380 |
| aagcagagct cgtttagtga accgtcagat cgcctggaga cgccatccac gctgttttga | 1440 |
| cttccataga aggatctcga ggccaccatg taccggatgc agctgctgag ctgcatcgca | 1500 |
| ctgagcctgg cactggtgac caacagcgca gtgcagggac cagaggagac cgtgacccag | 1560 |
| gactgcctgc agctgatcgc agacagcgag acccccacca tccagaaggg cagctacacc | 1620 |
| ttcgtgccct ggctgctgag cttcaagcgg ggcagcgccc tggaggagaa ggagaacaag | 1680 |
| attctggtga aggagaccgg ctacttcttc atctacggcc aggtgctgta caccgataag | 1740 |
| acctacgcca tgggccacct gatccagcgg aagaaggtgc acgtgttcgg cgacgagctg | 1800 |
| agcctggtga ccctgttccg gtgcatccag aacatgcccg agaccctgcc caacaacagc | 1860 |
| tgctacagcg caggaatcgc aaagctggag gagggcgacg agctgcagct ggcaatcccc | 1920 |
| cgggagaacg cacagatcag cctggacggc gacgtgacct tcttcggcgc cctgaagctc | 1980 |
| ctgtgagtcg actgctttat ttgtgaaatt tgtgatgcta ttgctttatt tgtaaccatt | 2040 |
| ataagctgca ataaacaagt taacaacaac aattgcattc attttatgtt tcaggttcag | 2100 |
| ggggaggtgt gggaggtttt ttaaactcta ttttataggc ttcttctctg gaatcttctt | 2160 |
| catcatcctc ctgacaatcg ataggtacct ggctgtcgtc catgctgtgt ttgctttaaa | 2220 |
| agccaggacg gtcacctttg gggtggtgac aagtgtgatc acttgggtgg tggctgtgtt | 2280 |
| tgcgtctctc ccaggaatca tctttaccag atctcaaaaa gaaggtcttc attacacctg | 2340 |
| cagctctcat tttccataca gtcagtatca attctggaag aatttccaga cattaaagat | 2400 |
| agtcatcttg gggctggtcc tgccgctgct tgtcatggtc atctgctact cgggaatcct | 2460 |

```
aaaaactctg cttcggtgtc gaaatgagaa gaagaggcac agggctgtga ggcttatctt    2520
caccatcatg attgtttatt ttctcttctg ggctccctac aacattgtcc ttctcctgaa    2580
caccttccag gaattctttg gcctgaataa ttgcagtagc tctaacaggt tggaccaagc    2640
tatgcaggtg acagagactc ttgggatgac gcactgctgc atcaaccgcc tcatctatgc    2700
ctttgtcggg gagaagttca gaaactacct cttagtcttc ttccaaaagc acattgccaa    2760
acgcttctgc aaatgctgtt ctattttcca gcaagaggct cccgagcgag caagctcagt    2820
ttacacccga tccactgggg agcaggaaat atctgtgggc ttgtgacacg gactcaagtg    2880
ggctggtgac ccagtcagag ttgtgcacat ggcttagttt tcatacacac cgcggtctag    2940
agcatggcta cgtagataag tagcatggcg ggttaatcat taactacaag gaaccccctag    3000 tgatggagtt ggccactccc tctctgcgcg ctcgctcgct cactgaggcc gggcgaccaa    3060
aggtcgcccg acgcccgggc tttgcccggg cggcctcagt gagcgagcga gcgcgccagc    3120
tggcgtaata gcgaagaggc ccgcaccgat cgcccttccc aacagttgcg cagcctgaat    3180
ggcgaatggc gattccgttg caatggctgg cggtaatatt gttctggata ttaccagcaa    3240
ggccgatagt ttgagttctt ctactcaggc aagtgatgtt attactaatc aaagaagtat    3300
tgcgacaacg gttaatttgc gtgatggaca gactctttta ctcggtggcc tcactgatta    3360
taaaaacact tctcaggatt ctggcgtacc gttcctgtct aaaatccctt taatcggcct    3420
cctgtttagc tcccgctctg attctaacga ggaaagcacg ttatacgtgc tcgtcaaagc    3480
aaccatagta cgcgccctgt agcggcgcat taagcgcggc gggtgtggtg gttacgcgca    3540
gcgtgaccgc tacacttgcc agcgccctag cgcccgctcc tttcgctttc ttcccttcct    3600
ttctcgccac gttcgccggc tttccccgtc aagctctaaa tcgggggctc cctttagggt    3660
tccgatttag tgctttacgg cacctcgacc ccaaaaaact tgattagggt gatggttcac    3720
gtagtgggcc atcgccctga tagacggttt ttcgcccttt gacgttggag tccacgttct    3780
ttaatagtgg actcttgttc caaactggaa caacactcaa ccctatctcg gtctattctt    3840
ttgatttata agggattttg ccgatttcgg cctattggtt aaaaaatgag ctgatttaac    3900
aaaaatttaa cgcgaatttt aacaaaatat taacgtttac aatttaaata tttgcttata    3960
caatcttcct gtttttgggg cttttctgat tatcaaccgg ggtacatatg attgacatgc    4020
tagttttacg attaccgttc atcgattctc ttgtttgctc cagactctca ggcaatgacc    4080
tgatagcctt tgtagagacc tctcaaaaat agctaccctc tccggcatga atttatcagc    4140
tagaacggtt gaatatcata ttgatggtga tttgactgtc tccggccttt ctcacccgtt    4200
tgaatcttta cctacacatt actcaggcat tgcatttaaa atatatgagg gttctaaaaa    4260
tttttatcct tgcgttgaaa taaaggcttc tcccgcaaaa gtattacagg tcataatgt    4320 ttttggtaca accgatttag ctttatgctc tgaggcttta ttgcttaatt ttgctaattc    4380
tttgccttgc ctgtatgatt tattggatgt tggaatcgcc tgatgcggta ttttctcctt    4440
acgcatctgt gcggtatttc acaccgcata tggtgcactc tcagtacaat ctgctctgat    4500
gccgcatagt taagccagcc ccgacacccg ccaacacccg ctgacgcgcc ctgacgggct    4560
tgtctgctcc cggcatccgc ttacagacaa gctgtgaccg tctccgggag ctgcatgtgt    4620
cagaggtttt caccgtcatc accgaaacgc gcgagacgaa agggcctcgt gatacgccta    4680
tttttatagg ttaatgtcat gataataatg gtttcttaga cgtcaggtgg cacttttcgg    4740
ggaaatgtgc gcggaacccc tatttgttta ttttcctaaa tacattcaaa tatgtatccg    4800
```

```
ctcatgagac aataaccctg ataaatgctt caataatatt gaaaaaggaa gagtatgagt    4860
attcaacatt tccgtgtcgc ccttattccc ttttttgcgg cattttgcct tcctgttttt    4920
gctcacccag aaacgctggt gaaagtaaaa gatgctgaag atcagttggg tgcacgagtg    4980
ggttacatcg aactggatct caacagcggt aagatccttg agagttttcg ccccgaagaa    5040
cgttttccaa tgatgagcac ttttaaagtt ctgctatgtg gcgcggtatt atcccgtatt    5100
gacgccgggc aagagcaact cggtcgccgc atacactatt ctcagaatga cttggttgag    5160
tactcaccag tcacagaaaa gcatcttacg gatggcatga cagtaagaga attatgcagt    5220
gctgccataa ccatgagtga taacactgcg gccaacttac ttctgacaac gatcggagga    5280
ccgaaggagc taaccgcttt tttgcacaac atggggatc atgtaactcg ccttgatcgt     5340
tgggaaccgg agctgaatga agccatacca aacgacgagc gtgacaccac gatgcctgta    5400
gcaatggcaa caacgttgcg caaactatta actggcgaac tacttactct agcttcccgg    5460
caacaattaa tagactggat ggaggcggat aaagttgcag gaccacttct gcgctcggcc    5520
cttccggctg gctggtttat tgctgataaa tctggagccg gtgagcgtgg gtctcgcggt    5580
atcattgcag cactggggcc agatggtaag ccctcccgta tcgtagttat ctacacgacg    5640
gggagtcagg caactatgga tgaacgaaat agacagatcg ctgagatagg tgcctcactg    5700
attaagcatt ggtaactgtc agaccaagtt tactcatata cttttagat tgatttaaaa     5760
cttcattttt aatttaaaag gatctaggtg aagatccttt tgataatct catgaccaaa     5820
atcccttaac gtgagttttc gttccactga gcgtcagacc ccgtagaaaa gatcaaagga    5880
tcttcttgag atcctttttt tctgcgcgta atctgctgct tgcaaacaaa aaaaccaccg    5940
ctaccagcgg tggtttgttt gccggatcaa gagctaccaa ctctttttcc gaaggtaact    6000
ggcttcagca gagcgcagat accaaatact gtccttctag tgtagccgta gttaggccac    6060
cacttcaaga actctgtagc accgcctaca tacctcgctc tgctaatcct gttaccagtg    6120
gctgctgcca gtggcgataa gtcgtgtctt accgggttgg actcaagacg atagttaccg    6180
gataaggcgc agcggtcggg ctgaacgggg ggttcgtgca cacagcccag cttggagcga    6240
acgacctaca ccgaactgag atacctacag cgtgagctat gagaaagcgc cacgcttccc    6300
gaagggagaa aggcggacag gtatccggta agcggcaggg tcggaacagg agagcgcacg    6360
agggagcttc caggggaaa cgcctggtat ctttatagtc ctgtcgggtt tcgccacctc     6420
tgacttgagc gtcgattttt gtgatgctcg tcagggggc ggagcctatg gaaaaacgcc     6480
agcaacgcgg ccttttacg gttcctggcc ttttgctggc cttttgctca catgttcttt     6540
cctgcgttat cccctgattc tgtggataac cgtattaccg cctttgagtg agctgatacc    6600
gctcgccgca gccgaacgac cgagcgcagc gagtcagtga gcgaggaagc ggaagagcgc    6660
ccaatacgca aaccgcctct ccccgcgcgt tggccgattc attaatg               6707
```

<210> SEQ ID NO 19
<211> LENGTH: 7494
<212> TYPE: DNA
<213> ORGANISM: Artificial Sequence
<220> FEATURE:
<223> OTHER INFORMATION: 1367_CCR5.MND.BAFF.2A.GFP

<400> SEQUENCE: 19

```
cagctgcgcg ctcgctcgct cactgaggcc gcccgggcaa agcccgggcg tcgggcgacc       60
tttggtcgcc cggcctcagt gagcgagcga gcgcgcagag agggagtggc caactccatc     120
actaggggtt ccttgtagtt aatgattaac ccgccatgct acttatctac gtagccatgc     180
```

```
tctagcggcc tcggcctctg cataaataaa aaaaattagt cagccatgag cttggacgcg    240
tttggtgtgg tggcgcctgt agtccccagc cacttggagg ggtgaggtga gaggattgct    300
tgagcccggg atggtccagg ctgcagtgag ccatgatcgt gccactgcac tccagcctgg    360
gcgacagagt gagaccctgt ctcacaacaa caacaacaac aacaaaaagg ctgagctgca    420
ccatgcttga cccagtttct taaaattgtt gtcaaagctt cattcactcc atggtgctat    480
agagcacaag attttatttg gtgagatggt gctttcatga attccccaa cagagccaag     540 ctctccatct agtggacagg gaagctagca gcaaaccttc ccttcactac aaaacttcat    600
tgcttggcca aaaagagagt taattcaatg tagacatcta tgtaggcaat taaaaaccta    660
ttgatgtata aaacagtttg cattcatgga gggcaactaa atacattcta ggactttata    720
aaagatcact ttttatttat gcacagggtg gaacaagatg gattatcaag tgtcaagtcc    780
aatctatgac atcaattatt atacatcgga gccctgccaa aaaatcaatg tgaagcaaat    840
cgcagcccgc ctcctgcctc cgctctactc actggtgttc atctttggtt ttgtgggcaa    900
catgctggtc atcctcatcc tgataaactg caaaaggctg aagagcatga ctgacatcta    960
cctgctcaac ctggccatct ctgacctgtt tttccttctt actgtcccct tctgggctca   1020
ctatgctgcc gcccagtggg actttggaaa tacaatgtgt caacgaacag agaaacagga   1080
gaatatgggc caaacaggat atctgtggta agcagttcct gccccggctc agggccaaga   1140
acagttggaa cagcagaata tgggccaaac aggatatctg tggtaagcag ttcctgcccc   1200
ggctcagggc caagaacaga tggtcccag atgcggtccc gccctcagca gtttctagag    1260
aaccatcaga tgtttccagg gtgccccaag gacctgaaat gaccctgtgc cttatttgaa   1320
ctaaccaatc agttcgcttc tcgcttctgt tcgcgcgctt ctgctcccg agctctatat    1380 aagcagagct cgtttagtga accgtcagat cgcctggaga cgccatccac gctgttttga   1440
cttccataga aggatctcga ggccaccatg taccggatgc agctgctgag ctgcatcgca   1500
ctgagcctgg cactggtgac caacagcgca gtgcagggac cagaggagac cgtgacccag   1560
gactgcctgc agctgatcgc agacagcgag acccccacca tccagaaggg cagctacacc   1620
ttcgtgccct ggctgctgag cttcaagcgg gcagcgccc tggaggagaa ggagaacaag    1680
attctggtga aggagaccgg ctacttcttc atctacggcc aggtgctgta caccgataag   1740
acctacgcca tgggccacct gatccagcgg aagaaggtgc acgtgttcgg cgacgagctg   1800
agcctggtga ccctgttccg gtgcatccag aacatgcccg agaccctgcc caacaacagc   1860
tgctacagcg caggaatcgc aaagctggag gagggcgacg agctgcagct ggcaatcccc   1920
cgggagaacg cacagatcag cctggacggc gacgtgacct tcttcggcgc cctgaagctc   1980
ctgggatccg gtgagggcag aggaagtctt ctaacatgcg gtgacgtgga ggagaatccg    2040
ggccccatgg tgagcaaggg cgaggagctg ttcaccgggg tggtgcccat cctggtcgag   2100
ctggacggcg acgtaaacgg ccacaagttc agcgtgtccg gcgagggcga gggcgatgcc    2160
acctacggca agctgaccct gaagttcatc tgcaccaccg gcaagctgcc cgtgccctgg    2220
cccaccctcg tgaccaccct gacctacggc gtgcagtgct tcagccgcta ccccgaccac   2280
atgaagcagc acgacttctt caagtccgcc atgcccgaag ctacgtcca ggagcgcacc    2340 atcttcttca aggacgacgg caactacaag acccgcgccg aggtgaagtt cgagggcgac   2400
accctggtga accgcatcga gctgaagggc atcgacttca aggaggacgg caacatcctg   2460
gggcacaagc tggagtacaa ctacaacagc cacaacgtct atatcatggc cgacaagcag   2520
```

```
aagaacggca tcaaggtgaa cttcaagatc cgccacaaca tcgaggacgg cagcgtgcag    2580
ctcgccgacc actaccagca gaacacccCc atcggcgacg gccccgtgct gctgcccgac    2640
aaccactacc tgagcaccca gtccgccctg agcaaagacc ccaacgagaa gcgcgatcac    2700
atggtcctgc tggagttcgt gaccgccgcc gggatcactc tcggcatgga cgagctgtac    2760
aagtgaatct agagtcgact gctttatttg tgaaatttgt gatgctattg ctttatttgt    2820
aaccattata agctgcaata aacaagttaa caacaacaat tgcattcatt ttatgtttca    2880
ggttcagggg gaggtgtggg aggttttttA aactctattt tataggcttc ttctctggaa    2940
tcttcttcat catcctcctg acaatcgata ggtacctggc tgtcgtccat gctgtgtttg    3000 cttttaaaagc caggacggtc acctttgggg tggtgacaag tgtgatcact tgggtggtgg    3060
ctgtgtttgc gtctctccca ggaatcatct ttaccagatc tcaaaaagaa ggtcttcatt    3120
acacctgcag ctctcatttt ccatacagtc agtatcaatt ctggaagaat ttccagacat    3180
taaagatagt catcttgggg ctggtcctgc cgctgcttgt catggtcatc tgctactcgg    3240
gaatcctaaa aactctgctt cggtgtcgaa atgagaagaa gaggcacagg gctgtgaggc    3300
ttatcttcac catcatgatt gtttattttc tcttctgggc tccctacaac attgtccttc    3360
tcctgaacac cttccaggaa ttctttggcc tgaataattg cagtagctct aacaggttgg    3420
accaagctat gcaggtgaca gagactcttg ggatgacgca ctgctgcatc aaccccatca    3480
tctatgcctt tgtcggggag aagttcagaa actacctctt agtcttcttc caaaagcaca    3540
ttgccaaacg cttctgcaaa tgctgttcta ttttccagca agaggctccc gagcgagcaa    3600
gctcagttta cacccgatcc actggggagc aggaaatatc tgtgggcttg tgacacggac    3660
tcaagtgggc tggtgacccca gtcagagttg tgcacatggc ttagttttca tacacaccgc    3720
ggtctagagc atggctacgt agataagtag catggcgggt taatcattaa ctacaaggaa    3780
cccctagtga tggagttggc cactccctct ctgcgcgctc gctcgctcac tgaggccggg    3840
cgaccaaagg tcgcccgacg cccgggcttt gcccgggcgg cctcagtgag cgagcgagcg    3900
cgccagctgg cgtaatagcg aagaggcccg caccgatcgc ccttcccaac agttgcgcag    3960
cctgaatggc gaatggcgat tccgttgcaa tggctggcgg taatattgtt ctggatatta    4020
ccagcaaggc cgatagtttg agttcttcta ctcaggcaag tgatgttatt actaatcaaa    4080
gaagtattgc gacaacggtt aatttgcgtg atggacagac tctttttactc ggtggcctca    4140 ctgattataa aaacacttct caggattctg gcgtaccgtt cctgtctaaa atccctttaa    4200
tcggcctcct gtttagctcc cgctctgatt ctaacgagga aagcacgtta tacgtgctcg    4260
tcaaagcaac catagtacgc gccctgtagc ggcgcattaa gcgcggcggg tgtggtggtt    4320
acgcgcagcg tgaccgctac acttgccagc gccctagcgc ccgctccttt cgctttcttc    4380
ccttcctttc tcgccacgtt cgccggcttt ccccgtcaag ctctaaatcg gggctccct    4440 ttagggttcc gatttagtgc tttacggcac ctcgacccca aaaaacttga ttagggtgat    4500
ggttcacgta gtgggccatc gccctgatag acggtttttc gccctttgac gttggagtcc    4560
acgttcttta atagtggact cttgttccaa actggaacaa cactcaaccc tatctcggtc    4620
tattcttttg atttataagg gattttgccg atttcggcct attggttaaa aaatgagctg    4680
atttaacaaa aatttaacgc gaattttaac aaaatattaa cgtttacaat ttaaatattt    4740
gcttatacaa tcttcctgtt tttggggctt ttctgattat caaccggggt acatatgatt    4800
gacatgctag ttttacgatt accgttcatc gattctcttg tttgctccag actctcaggc    4860
aatgacctga tagcctttgt agagacctct caaaaatagc taccctctcc ggcatgaatt    4920
```

```
tatcagctag aacggttgaa tatcatattg atggtgattt gactgtctcc ggcctttctc    4980
acccgtttga atctttacct acacattact caggcattgc atttaaaata tatgagggtt    5040
ctaaaaattt ttatccttgc gttgaaataa aggcttctcc cgcaaaagta ttacagggtc    5100
ataatgtttt tggtacaacc gattttagctt tatgctctga ggctttattg cttaattttg    5160
ctaattcttt gccttgcctg tatgattat tggatgttgg aatcgcctga tgcggtattt    5220
tctccttacg catctgtgcg gtatttcaca ccgcatatgg tgcactctca gtacaatctg    5280
ctctgatgcc gcatagttaa gccagccccg acacccgcca cacccgctg acgcgccctg    5340 acgggcttgt ctgctcccgg catccgctta cagacaagct gtgaccgtct ccgggagctg    5400
catgtgtcag aggttttcac cgtcatcacc gaaacgcgcg agacgaaagg gcctcgtgat    5460
acgcctattt ttataggtta atgtcatgat aataatggtt tcttagacgt caggtggcac    5520
ttttcgggga atgtgcgcg gaacccctat ttgtttattt ttctaaatac attcaaatat    5580
gtatccgctc atgagacaat aaccctgata aatgcttcaa taatattgaa aaaggaagag    5640
tatgagtatt caacatttcc gtgtcgccct tattccctt tttgcggcat tttgccttcc    5700
tgtttttgct cacccagaaa cgctggtgaa agtaaaagat gctgaagatc agttgggtgc    5760
acgagtgggt tacatcgaac tggatctcaa cagcggtaag atccttgaga gttttcgccc    5820
cgaagaacgt tttccaatga tgagcacttt taaagttctg ctatgtggcg cggtattatc    5880
ccgtattgac gccgggcaag agcaactcgg tcgccgcata cactattctc agaatgactt    5940
ggttgagtac tcaccagtca cagaaaagca tcttacggat ggcatgacag taagagaatt    6000
atgcagtgct gccataacca tgagtgataa cactgcggcc aacttacttc tgacaacgat    6060
cggaggaccg aaggagctaa ccgcttttt gcacaacatg gggatcatg taactcgcct    6120 tgatcgttgg gaaccggagc tgaatgaagc cataccaaac gacgagcgtg acaccacgat    6180
gcctgtagca atggcaacaa cgttgcgcaa actattaact ggcgaactac ttactctagc    6240
ttcccggcaa caattaatag actggatgga ggcggataaa gttgcaggac cacttctgcg    6300
ctcggccctt ccggctggct ggtttattgc tgataaatct ggagccggtg agcgtgggtc    6360
tcgcggtatc attgcagcac tggggccaga tggtaagccc tcccgtatcg tagttatcta    6420
cacgacgggg agtcaggcaa ctatggatga acgaaataga cagatcgctg agataggtgc    6480
ctcactgatt aagcattggt aactgtcaga ccaagtttac tcatatatac tttagattga    6540
tttaaaactt cattttttaat ttaaaaggat ctaggtgaag atcctttttg ataatctcat    6600
gaccaaaatc ccttaacgtg agttttcgtt ccactgagcg tcagacccc tagaaaagat    6660 caaaggatct tcttgagatc cttttttttct gcgcgtaatc tgctgcttgc aaacaaaaaa    6720
accaccgcta ccagcggtgg tttgtttgcc ggatcaagag ctaccaactc tttttccgaa    6780
ggtaactggc ttcagcagag cgcagatacc aaatactgtc cttctagtgt agccgtagtt    6840
aggccaccac ttcaagaact ctgtagcacc gcctacatac ctcgctctgc taatcctgtt    6900
accagtggct gctgccagtg gcgataagtc gtgtcttacc gggttggact caagacgata    6960
gttaccggat aaggcgcagc ggtcgggctg aacggggggt tcgtgcacac agcccagctt    7020
ggagcgaacg acctacaccg aactgagata cctacagcgt gagctatgag aaagcgccac    7080
gcttcccgaa gggagaaagg cggacaggta tccggtaagc ggcagggtcg gaacaggaga    7140
gcgcacgagg gagcttccag ggggaaacgc ctggtatctt tatagtcctg tcgggtttcg    7200
ccacctctga cttgagcgtc gatttttgtg atgctcgtca ggggggcgga gcctatggaa    7260
```

```
aaacgccagc aacgcggcct ttttacggtt cctggccttt tgctggcctt ttgctcacat    7320
gttctttcct gcgttatccc ctgattctgt ggataaccgt attaccgcct ttgagtgagc    7380
tgataccgct cgccgcagcc gaacgaccga gcgcagcgag tcagtgagcg aggaagcgga    7440
agagcgccca atacgcaaac cgcctctccc cgcgcgttgg ccgattcatt aatg          7494
```

```
<210> SEQ ID NO 20
<211> LENGTH: 20
<212> TYPE: RNA
<213> ORGANISM: Artificial Sequence
<220> FEATURE:
<223> OTHER INFORMATION: CCR5 target guide RNA

<400> SEQUENCE: 20
caauguguca acucuugaca                                                  20

<210> SEQ ID NO 21
<211> LENGTH: 20
<212> TYPE: DNA
<213> ORGANISM: Artificial Sequence
<220> FEATURE:
<223> OTHER INFORMATION: PRDM1 target guide RNA 1

<400> SEQUENCE: 21
aggatgcgga tatgactctg                                                  20

<210> SEQ ID NO 22
<211> LENGTH: 20
<212> TYPE: DNA
<213> ORGANISM: Artificial Sequence
<220> FEATURE:
<223> OTHER INFORMATION: PRDM1 target guide RNA 2

<400> SEQUENCE: 22
ggggagcgag tgatgtacgt                                                  20

<210> SEQ ID NO 23
<211> LENGTH: 20
<212> TYPE: DNA
<213> ORGANISM: Artificial Sequence
<220> FEATURE:
<223> OTHER INFORMATION: IRF4g target guide RNA

<400> SEQUENCE: 23
caagcaggac tacaaccgcg                                                  20

<210> SEQ ID NO 24
<211> LENGTH: 20
<212> TYPE: RNA
<213> ORGANISM: Artificial Sequence
<220> FEATURE:
<223> OTHER INFORMATION: PAX5g target guide RNA

<400> SEQUENCE: 24
ugugaaugga cggccacucc                                                  20

<210> SEQ ID NO 25
<211> LENGTH: 20
<212> TYPE: RNA
<213> ORGANISM: Artificial Sequence
<220> FEATURE:
<223> OTHER INFORMATION: BACH2 target guide RNA

<400> SEQUENCE: 25
guuccugcgc augcacaacc                                                  20
```

<210> SEQ ID NO 26
<211> LENGTH: 16
<212> TYPE: RNA
<213> ORGANISM: Artificial Sequence
<220> FEATURE:
<223> OTHER INFORMATION: tracrRNA binding sequence

<400> SEQUENCE: 26
guuuuagagc uaugcu                                                    16

<210> SEQ ID NO 27
<211> LENGTH: 20
<212> TYPE: DNA
<213> ORGANISM: Artificial Sequence
<220> FEATURE:
<223> OTHER INFORMATION: CCR5g forward primer T7E1

<400> SEQUENCE: 27
atgtgaagca aatcgcagcc                                                20

<210> SEQ ID NO 28
<211> LENGTH: 30
<212> TYPE: DNA
<213> ORGANISM: Artificial Sequence
<220> FEATURE:
<223> OTHER INFORMATION: PRDM1g-1 forward primer T7E1

<400> SEQUENCE: 28
tagcatttaa aaaccttgct tcttttcaag                                      30

<210> SEQ ID NO 29
<211> LENGTH: 21
<212> TYPE: DNA
<213> ORGANISM: Artificial Sequence
<220> FEATURE:
<223> OTHER INFORMATION: PRDM1g-2 forward primer T7E1

<400> SEQUENCE: 29
cagtctaaag caaccgagca c                                              21

<210> SEQ ID NO 30
<211> LENGTH: 20
<212> TYPE: DNA
<213> ORGANISM: Artificial Sequence
<220> FEATURE:
<223> OTHER INFORMATION: CCR5 reverse primer T7E1

<400> SEQUENCE: 30
tcccgagtag cagatgacca                                                20

<210> SEQ ID NO 31
<211> LENGTH: 26
<212> TYPE: DNA
<213> ORGANISM: Artificial Sequence
<220> FEATURE:
<223> OTHER INFORMATION: PRDM1g-1 reverse primer T7E1

<400> SEQUENCE: 31
tacagattct cagaggtttt cagaga                                         26

<210> SEQ ID NO 32
<211> LENGTH: 21
<212> TYPE: DNA
<213> ORGANISM: Artificial Sequence
<220> FEATURE:

<223> OTHER INFORMATION: PRDM1g-2 reverse primer T7E1

<400> SEQUENCE: 32
cttggggtag tgagcgttgt a                                    21

<210> SEQ ID NO 33
<211> LENGTH: 20
<212> TYPE: DNA
<213> ORGANISM: Artificial Sequence
<220> FEATURE:
<223> OTHER INFORMATION: CCR5g forward primer Illumina

<400> SEQUENCE: 33
ggcaacatgc tggtcatcct                                      20

<210> SEQ ID NO 34
<211> LENGTH: 20
<212> TYPE: DNA
<213> ORGANISM: Artificial Sequence
<220> FEATURE:
<223> OTHER INFORMATION: PRDM1g-1 forward primer Illumina

<400> SEQUENCE: 34
ctctcagaag gagccacagg                                      20

<210> SEQ ID NO 35
<211> LENGTH: 20
<212> TYPE: DNA
<213> ORGANISM: Artificial Sequence
<220> FEATURE:
<223> OTHER INFORMATION: PRDM1g-2 forward primer Illumina

<400> SEQUENCE: 35
cccctcacat cagaaaagga                                      20

<210> SEQ ID NO 36
<211> LENGTH: 19
<212> TYPE: DNA
<213> ORGANISM: Artificial Sequence
<220> FEATURE:
<223> OTHER INFORMATION: IRF4g forward primer Illumina

<400> SEQUENCE: 36
agatcgacag cggcaagta                                       19

<210> SEQ ID NO 37
<211> LENGTH: 20
<212> TYPE: DNA
<213> ORGANISM: Artificial Sequence
<220> FEATURE:
<223> OTHER INFORMATION: PAX5g forward primer Illumina

<400> SEQUENCE: 37
cacagcggtg cttctcctat                                      20

<210> SEQ ID NO 38
<211> LENGTH: 20
<212> TYPE: DNA
<213> ORGANISM: Artificial Sequence
<220> FEATURE:
<223> OTHER INFORMATION: BACH2g forward primer Illumina

<400> SEQUENCE: 38
tgagggattc gggacaatag                                      20

-continued

```
<210> SEQ ID NO 39
<211> LENGTH: 20
<212> TYPE: DNA
<213> ORGANISM: Artificial Sequence
<220> FEATURE:
<223> OTHER INFORMATION: CCR5g reverse primer Illumina

<400> SEQUENCE: 39
ggtgaccgtc ctggctttta                                                 20

<210> SEQ ID NO 40
<211> LENGTH: 21
<212> TYPE: DNA
<213> ORGANISM: Artificial Sequence
<220> FEATURE:
<223> OTHER INFORMATION: PRDM1g-1 reverse primer Illumina

<400> SEQUENCE: 40
ttggtggcat acttgaaaag c                                               21

<210> SEQ ID NO 41
<211> LENGTH: 20
<212> TYPE: DNA
<213> ORGANISM: Artificial Sequence
<220> FEATURE:
<223> OTHER INFORMATION: PRDM1g-2 reverse primer Illumina

<400> SEQUENCE: 41
ctggagctct tgaggctttg                                                 20

<210> SEQ ID NO 42
<211> LENGTH: 19
<212> TYPE: DNA
<213> ORGANISM: Artificial Sequence
<220> FEATURE:
<223> OTHER INFORMATION: IRF4g reverse primer Illumina

<400> SEQUENCE: 42
gaggcctcct ttcctcctc                                                  19

<210> SEQ ID NO 43
<211> LENGTH: 20
<212> TYPE: DNA
<213> ORGANISM: Artificial Sequence
<220> FEATURE:
<223> OTHER INFORMATION: PAX5g reverse primer Illumina

<400> SEQUENCE: 43
gcctcgagct actgccttta                                                 20

<210> SEQ ID NO 44
<211> LENGTH: 20
<212> TYPE: DNA
<213> ORGANISM: Artificial Sequence
<220> FEATURE:
<223> OTHER INFORMATION: BACH2g reverse primer Illumina

<400> SEQUENCE: 44
agttctcgca gtcctcgtgt                                                 20

<210> SEQ ID NO 45
<211> LENGTH: 23
<212> TYPE: DNA
<213> ORGANISM: Artificial Sequence
<220> FEATURE:
<223> OTHER INFORMATION: CCR5 forward primer In-out
```

```
<400> SEQUENCE: 45
ggtatgatgc ttagaacagt gat                                              23

<210> SEQ ID NO 46
<211> LENGTH: 20
<212> TYPE: DNA
<213> ORGANISM: Artificial Sequence
<220> FEATURE:
<223> OTHER INFORMATION: ActB forward primer In-out

<400> SEQUENCE: 46
actctgcagg ttctatttgc                                                  20

<210> SEQ ID NO 47
<211> LENGTH: 21
<212> TYPE: DNA
<213> ORGANISM: Artificial Sequence
<220> FEATURE:
<223> OTHER INFORMATION: CCR5 reverse primer In-out

<400> SEQUENCE: 47
ccatattctg ctgttccaac t                                                21

<210> SEQ ID NO 48
<211> LENGTH: 20
<212> TYPE: DNA
<213> ORGANISM: Artificial Sequence
<220> FEATURE:
<223> OTHER INFORMATION: ActB reverse primer In-out

<400> SEQUENCE: 48
aatgatctga ggagggaagg                                                  20

<210> SEQ ID NO 49
<211> LENGTH: 21
<212> TYPE: DNA
<213> ORGANISM: Artificial Sequence
<220> FEATURE:
<223> OTHER INFORMATION: CCR5 probe In-out

<400> SEQUENCE: 49
cctgggcaac atagtgtgat c                                                21

<210> SEQ ID NO 50
<211> LENGTH: 20
<212> TYPE: DNA
<213> ORGANISM: Artificial Sequence
<220> FEATURE:
<223> OTHER INFORMATION: ActB probe In-out

<400> SEQUENCE: 50
atcaaggtgg gtctctttcc                                                  20

<210> SEQ ID NO 51
<211> LENGTH: 4875
<212> TYPE: DNA
<213> ORGANISM: Artificial Sequence
<220> FEATURE:
<223> OTHER INFORMATION: 1079_pscAAV-MND.GFP

<400> SEQUENCE: 51
aagcttcccg gggggatctg ggccactccc tctctgcgcg ctcgctcgct cactgaggcc       60
gggcgaccaa agtcgcccg acgcccggc tttgcccggg cggcctcagt gagcgagcga       120
gcgcgcagag agggagtggc caactccatc actaggggtt cctggagggg tggagtcgtg      180
```

```
acctagggaa cagagaaaca ggagaatatg ggccaaacag gatatctgtg gtaagcagtt      240
cctgccccgg ctcagggcca agaacagttg gaacagcaga atatgggcca aacaggatat      300
ctgtggtaag cagttcctgc cccggctcag ggccaagaac agatggtccc cagatgcggt      360
cccgccctca gcagtttcta gagaaccatc agatgtttcc agggtgcccc aaggacctga      420
aatgaccctg tgccttattt gaactaacca atcagttcgc ttctcgcttc tgttcgcgcg      480
cttctgctcc ccgagctcta tataagcaga gctcgtttag tgaaccgtca gatcgcctgg      540
agacgccatc cacgctgttt tgacttccat agaaggatcc tcgaggccac catggtgagc      600
aagggcgagg agctgttcac cggggtggtg cccatcctgg tcgagctgga cggcgacgta      660
aacggccaca gttcagcgt gtccggcgag ggcgagggcg atgccaccta cggcaagctg      720
accctgaagt tcatctgcac caccggcaag ctgcccgtgc cctggcccac cctcgtgacc      780
accctgacct acggcgtgca gtgcttcagc cgctaccccg accacatgaa gcagcacgac      840
ttcttcaagt ccgccatgcc cgaaggctac gtccaggagc gcaccatctt cttcaaggac      900
gacggcaact acaagacccg cgccgaggtg aagttcgagg gcgacaccct ggtgaaccgc      960
atcgagctga agggcatcga cttcaaggag gacggcaaca tcctggggca caagctggag     1020
tacaactaca acagccacaa cgtctatatc atggccgaca agcagaagaa cggcatcaag     1080
gtgaacttca agatccgcca caacatcgag gacggcagcg tgcagctcgc cgaccactac     1140
cagcagaaca cccccatcgg cgacggcccc gtgctgctgc ccgacaacca ctacctgagc     1200
acccagtccg ccctgagcaa agaccccaac gagaagcgcg atcacatggt cctgctggag     1260
ttcgtgaccg ccgccgggat cactctcggc atggacgagc tgtacaagta agcggccgca     1320
attcacccca ccagtgcagg ctgcctatca gaaagtggtg gctggtgtgg ctaatgccct     1380
ggcccacaag tatcactaag ctcgctttct tgctgtccaa tttctattaa aggttccttt     1440
gttccctaag tccaactact aaactggggg atattatgaa gggccttgag catctggatt     1500
ctgcctaata aaaaacattt attttcattg caatgatgta tttaaattat ttctgaatat     1560
tttactaaaa agggaatgtg ggaggtcagt gcatttaaaa cataaagaaa tgaagagcta     1620
gttcaaacct tgggaaaata cactatatct taaactccat gaaagaaggt gaggctgcaa     1680
acagctaatg cacattggca acagcccctg atgcctatgc cttattcatc cctcagaaaa     1740
ggattcaagt agaggcttga tttggaggtt aaagttttgc tatgctgtat tttacattac     1800
ttattgtttt agctgtcctc atgaatgtct tttcactacc catttgctta tcctgcatct     1860
ctcagccttg actccactca gttctcttgc ttagagatac cacctttccc ctgaagtgtt     1920
ccttccatgt tttacggcga gatggttct cctcgcctgg ccactcagcc ttagttgtct     1980
ctgttgtctt atagaggtct acttgaagaa ggaaaaacag ggggcatggt ttgactgtcc     2040
tgtgagccct tcttccctgc ctcccccact cacagtgaca ctagtccact ccctctctgc     2100
gcgctcgctc gctcactgag gccgggcgac caaaggtcgc ccgacgcccg gctttgccc      2160 gggcggcctc agtgagcgag cgagcgcgca gagagggaca gatccgggcc cgcatgcgtc     2220
gacaattcac tggccgtcgt tttacaacgt cgtgactggg aaaaccctgg cgttacccaa     2280
cttaatcgcc ttgcagcaca tccccctttc gccagctggc gtaatagcga agaggcccgc     2340
accgatcgcc cttcccaaca gttgcgcagc ctgaatggcg aatggcgcct gatgcggtat     2400
tttctcctta cgcatctgtg cggtatttca caccgcatat ggtgcactct cagtacaatc     2460
tgctctgatg ccgcatagtt aagccagccc cgacacccgc caacacccgc tgacgcgccc     2520
```

```
tgacgggctt gtctgctccc ggcatccgct tacagacaag ctgtgaccgt ctccgggagc    2580
tgcatgtgtc agaggttttc accgtcatca ccgaaacgcg cgagacgaaa gggcctcgtg    2640
atacgcctat ttttataggt taatgtcatg ataataatgg tttcttagac gtcaggtggc    2700
acttttcggg gaaatgtgcg cggaacccct atttgtttat ttttctaaat acattcaaat    2760
atgtatccgc tcatgagaca ataaccctga taaatgcttc aataatattg aaaaaggaag    2820
agtatgagta ttcaacattt ccgtgtcgcc cttattccct tttttgcggc attttgcctt    2880
cctgtttttg ctcacccaga aacgctggtg aaagtaaaag atgctgaaga tcagttgggt    2940
gcacgagtgg gttacatcga actggatctc aacagcggta agatccttga gttttcgc      3000
cccgaagaac gttttccaat gatgagcact tttaaagttc tgctatgtgg cgcggtatta    3060
tcccgtattg acgccgggca agagcaactc ggtcgccgca tacactattc tcagaatgac    3120
ttggttgagt actcaccagt cacagaaaag catcttacgg atggcatgac agtaagagaa    3180
ttatgcagtg ctgccataac catgagtgat aacactgcgg ccaacttact tctgacaacg    3240
atcggaggac cgaaggagct aaccgctttt ttgcacaaca tgggggatca tgtaactcgc    3300
cttgatcgtt gggaaccgga gctgaatgaa gccataccaa acgacgagcg tgacaccacg    3360
atgcctgtag caatggcaac aacgttgcgc aaactattaa ctggcgaact acttactcta    3420
gcttcccggc aacaattaat agactggatg gaggcggata agttgcagg accacttctg     3480
cgctcggccc ttccggctgg ctggtttatt gctgataaat ctggagccgg tgagcgtggg    3540
tctcgcggta tcattgcagc actggggcca gatggtaagc cctcccgtat cgtagttatc    3600
tacacgacgg ggagtcaggc aactatggat gaacgaaata gacagatcgc tgagataggt    3660
gcctcactga ttaagcattg gtaactgtca gaccaagttt actcatatat actttagatt    3720
gatttaaaac ttcattttta atttaaaagg atctaggtga agatccttt tgataatctc     3780
atgaccaaaa tcccttaacg tgagttttcg ttccactgag cgtcagaccc cgtagaaaag    3840
atcaaaggat cttcttgaga tcctttttt ctgcgcgtaa tctgctgctt gcaaacaaaa     3900
aaaccaccgc taccagcggt ggtttgtttg ccggatcaag agctaccaac tctttttccg    3960
aaggtaactg gcttcagcag agcgcagata ccaaatactg ttcttctagt gtagccgtag    4020
ttaggccacc acttcaagaa ctctgtagca ccgcctacat acctcgctct gctaatcctg    4080
ttaccagtgg ctgctgccag tggcgataag tcgtgtctta ccgggttgga ctcaagacga    4140
tagttaccgg ataaggcgca gcggtcgggc tgaacggggg gttcgtgcac acagcccagc    4200
ttggagcgaa cgacctacac cgaactgaga tacctacagc gtgagctatg agaaagcgcc    4260
acgcttcccg aagggagaaa ggcggacagg tatccggtaa gcggcagggt cggaacagga    4320
gagcgcacga gggagcttcc agggggaaac gcctggtatc tttatagtcc tgtcgggttt    4380
cgccacctct gacttgagcg tcgatttttg tgatgctcgt cagggggggcg gagcctatgg    4440
aaaaacgcca gcaacgcggc ctttttacgg ttcctggcct tttgctggcc ttttgctcac    4500
atgttctttc ctgcgttatc ccctgattct gtggataacc gtattaccgc ctttgagtga    4560
gctgataccg ctcgccgcag ccgaacgacc gagcgcagcg agtcagtgag cgaggaagcg    4620
gaagagcgcc caatacgcaa accgcctctc ccgcgcgtt ggcgattca ttaatgcagc       4680
tggcacgaca ggtttcccga ctggaaagcg ggcagtgagc gcaacgcaat taatgtgagt    4740
tagctcactc attaggcacc ccaggcttta cactttatgc ttccggctcg tatgttgtgt    4800
ggaattgtga gcggataaca atttcacaca ggaaacagct atgaccatga ttacgccaag    4860
ctctcgagat ctaga                                                     4875
```

<210> SEQ ID NO 52
<211> LENGTH: 5056
<212> TYPE: DNA
<213> ORGANISM: Artificial Sequence
<220> FEATURE:
<223> OTHER INFORMATION: 1347_pscAAV.Blimp.0.4kb.MND.GFP

<400> SEQUENCE: 52

```
aagcttcccg gggggatctg gccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctggagggg tggagtcgtg     180
acctaggacg cgtgccagct gttactcagg ttttctcaag aaggaggagc aactttggca     240
gttttgcttc agttctctct agccctctgt gtaatcgccc ctttttcttt atttcagcac     300
aaacacagag cagtctaaag caaccgagca ctgagaaaaa tgaactctgc ccaaagaatg     360
tcccaaagag agagtacagc gtgaaagaaa tcctaaaatt ggactccaac ccctccaaag     420
gaaaggacct ctaccgttct aacatttcac ccctcacatc agaaaaggac ctcgatgact     480
ttagaagacg tgggagcccc gaaatgccct tctaccctcg ggtcgtttac cccatccggg     540
cccctctgcc agaagacttt ttgaaagctt ccctggccta cgggatcgag agagaacaga     600
gaaacaggag aatatgggcc aaacaggata tctgtggtaa gcagttcctg ccccggctca     660
gggccaagaa cagttggaac agcagaatat gggccaaaca ggatatctgt ggtaagcagt     720
tcctgccccg gctcagggcc aagaacagat ggtcccagat gcggtcccg ccctcagcag     780
tttctagaga accatcagat gtttccaggg tgccccaagg acctgaaatg accctgtgcc     840
ttatttgaac taaccaatca gttcgcttct cgcttctgtt cgcgcgcttc tgctccccga     900
gctctatata agcagagctc gtttagtgaa ccgtcagatc gcctggagac gccatccacg     960
ctgttttgac ttccatagaa ggatctcgag gccaccatgg tgagcaaggg cgaggagctg    1020
ttcaccgggg tggtgcccat cctggtcgag ctggacggcg acgtaaacgg ccacaagttc    1080
agcgtgtccg gcgagggcga gggcgatgcc acctacggca agctgaccct gaagttcatc    1140
tgcaccaccg gcaagctgcc cgtgccctgg cccaccctcg tgaccaccct gacctacggc    1200
gtgcagtgct tcagccgcta ccccgaccac atgaagcagc acgacttctt caagtccgcc    1260
atgcccgaag gctacgtcca ggagcgcacc atcttcttca aggacgacgg caactacaag    1320
acccgcgccg aggtgaagtt cgagggcgac accctggtga accgcatcga gctgaagggc    1380
atcgacttca aggaggacgg caacatcctg gggcacaagc tggagtacaa ctacaacagc    1440
cacaacgtct atatcatggc cgacaagcag aagaacggca tcaaggtgaa cttcaagatc    1500
cgccacaaca tcgaggacgg cagcgtgcag ctcgccgacc actaccagca gaacaccccc    1560
atcggcgacg gccccgtgct gctgcccgac aaccactacc tgagcaccca gtccgccctg    1620
agcaaagacc ccaacgagaa gcgcgatcac atggtcctgc tggagttcgt gaccgccgcc    1680
gggatcactc tcggcatgga cgagctgtac aagtaaacta gtgtcgactg ctttatttgt    1740
gaaatttgtg atgctattgc tttatttgta accattataa gctgcaataa acaagttaac    1800
aacaacaatt gcattcattt tatgtttcag gttcaggggg aggtgtggga ggttttttaa    1860
aacgtacatc actcgctccc ccattccatc ctccaccact ccaagcccct ctgcaagaag    1920
cagccccgac caaagcctca agagctccag ccctcacagc agccctggga atacggtgtc    1980
ccctgtgggc cccggctctc aagagcaccg ggactcctac gcttacttga acgcgtccta    2040
```

```
cggcacggaa ggtttgggct cctaccctgg ctacgcaccc ctgccccacc tcccgccagc   2100
tttcatcccc tcgtacaacg ctcactaccc caagttcctc ttgccccct acggcatgaa    2160 ttgtaatggc ctgagcgctg tgagcagcat gaatggcatc aacaactttg gcctcttccc   2220
gaggctgtgc cctgtctaca gcaatctcct cggtgggggc actagtccac tccctctctg   2280
cgcgctcgct cgctcactga ggccgggcga ccaaaggtcg cccgacgccc gggctttgcc   2340
cgggcggcct cagtgagcga gcgagcgcgc agagagggac agatccgggc cgcatgcgt    2400 cgacaattca ctggccgtcg ttttacaacg tcgtgactgg gaaaaccctg gcgttaccca   2460
acttaatcgc cttgcagcac atccccctt cgccagctgg cgtaatagcg aagaggcccg    2520
caccgatcgc ccttcccaac agttgcgcag cctgaatggc gaatggcgcc tgatgcggta   2580 tttctcctt acgcatctgt gcggtatttc acaccgcata tggtgcactc tcagtacaat    2640
ctgctctgat gccgcatagt taagccagcc ccgacacccg ccaacacccg ctgacgcgcc   2700
ctgacgggct tgtctgctcc cggcatccgc ttacagacaa gctgtgaccg tctccgggag   2760
ctgcatgtgt cagaggtttt caccgtcatc accgaaacgc gcgagacgaa agggcctcgt   2820
gatacgccta ttttataggg ttaatgtcat gataataatg gtttcttaga cgtcaggtgg   2880
cacttttcgg ggaaatgtgc gcggaacccc tatttgttta ttttctaaa tacattcaaa    2940 tatgtatccg ctcatgagac aataaccctg ataaatgctt caataatatt gaaaaggaa    3000 gagtatgagt attcaacatt tccgtgtcgc ccttattccc ttttttgcgg cattttgcct   3060
tcctgttttt gctcacccag aaacgctggt gaaagtaaaa gatgctgaag atcagttggg   3120
tgcacgagtg ggttacatcg aactggatct caacagcggt aagatccttg agagttttcg   3180
ccccgaagaa cgttttccaa tgatgagcac ttttaaagtt ctgctatgtg gcgcggtatt   3240
atcccgtatt gacgccgggc aagagcaact cggtcgccgc atacactatt ctcagaatga   3300
cttggttgag tactcaccag tcacagaaaa gcatcttacg gatggcatga cagtaagaga   3360
attatgcagt gctgccataa ccatgagtga taacactgcg ccaacttac ttctgacaac    3420 gatcggagga ccgaaggagc taaccgcttt tttgcacaac atggggatc atgtaactcg    3480 ccttgatcgt tgggaaccgg agctgaatga agccatacca aacgacgagc gtgacaccac   3540
gatgcctgta gcaatggcaa caacgttgcg caaactatta ctggcgaac tacttactct    3600 agcttcccgg caacaattaa tagactggat ggaggcggat aaagttgcag gaccacttct   3660
gcgctcggcc cttccggctg gctggtttat tgctgataaa tctggagccg gtgagcgtgg   3720
gtctcgcggt atcattgcag cactggggcc agatggtaag ccctcccgta tcgtagttat   3780
ctacacgacg gggagtcagg caactatgga tgaacgaaat agacagatcg ctgagatagg   3840
tgcctcactg attaagcatt ggtaactgtc agaccaagtt tactcatata ctttagat    3900 tgatttaaaa cttcatttt aatttaaaag gatctaggtg aagatccttt ttgataatct    3960
catgaccaaa atcccttaac gtgagttttc gttccactga gcgtcagacc ccgtagaaaa   4020
gatcaaagga tcttcttgag atcctttttt tctgcgcgta atctgctgct tgcaaacaaa   4080
aaaaccaccg ctaccagcgg tggtttgttt gccggatcaa gagctaccaa ctctttttcc   4140
gaaggtaact ggcttcagca gagcgcagat accaaatact gttcttctag tgtagccgta   4200
gttaggccac cacttcaaga actctgtagc accgcctaca tacctcgctc tgctaatcct   4260
gttaccagtg gctgctgcca gtggcgataa gtcgtgtctt accgggttgg actcaagacg   4320
atagttaccg gataaggcgc agcggtcggg ctgaacgggg ggttcgtgca cacagcccag   4380
cttggagcga acgacctaca ccgaactgag atacctacag cgtgagctat gagaaagcgc   4440
```

```
cacgcttccc gaagggagaa aggcggacag gtatccggta agcggcaggg tcggaacagg    4500
agagcgcacg agggagcttc caggggggaaa cgcctggtat ctttatagtc ctgtcgggtt    4560
tcgccacctc tgacttgagc gtcgattttt gtgatgctcg tcaggggggc ggagcctatg    4620
gaaaaacgcc agcaacgcgg cctttttacg gttcctggcc ttttgctggc cttttgctca    4680
catgttcttt cctgcgttat cccctgattc tgtggataac cgtattaccg cctttgagtg    4740
agctgatacc gctcgccgca gccgaacgac cgagcgcagc gagtcagtga gcgaggaagc    4800
ggaagagcgc ccaatacgca aaccgcctct ccccgcgcgt tggccgattc attaatgcag    4860
ctggcacgac aggtttcccg actggaaagc gggcagtgag cgcaacgcaa ttaatgtgag    4920
ttagctcact cattaggcac cccaggcttt acactttatg cttccggctc gtatgttgtg    4980
tggaattgtg agcggataac aatttcacac aggaaacagc tatgaccatg attacgccaa    5040
gctctcgaga tctaga                                                    5056

<210> SEQ ID NO 53
<211> LENGTH: 6006
<212> TYPE: DNA
<213> ORGANISM: Artificial Sequence
<220> FEATURE:
<223> OTHER INFORMATION: 1348_pAAV.Blimp.0.4kb.MND.GFP.pA

<400> SEQUENCE: 53
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac acgcgtgcca     180
gctgttactc aggttttctc aagaaggagg agcaactttg gcagttttgc ttcagttctc     240
tctagccctc tgtgtaatcg cccctttttc tttatttcag cacaaacaca gagcagtcta     300
aagcaaccga gcactgagaa aaatgaactc tgcccaaaga atgtcccaaa gagagagtac     360
agcgtgaaag aaatcctaaa attggactcc aacccctcca aaggaaagga cctctaccgt     420
tctaacattt caccccctcac atcagaaaag gacctcgatg actttagaag acgtgggagc     480
cccgaaatgc ccttctaccc tcgggtcgtt taccccatcc gggcccctct gccagaagac     540 ttttgaaag cttccctggc ctacgggatc gagagagaac agagaaacag gagaatatgg     600
gccaaacagg atatctgtgg taagcagttc ctgccccggc tcagggccaa gaacagttgg     660
aacagcagaa tatgggccaa acaggatatc tgtggtaagc agttcctgcc ccggctcagg     720
gccaagaaca gatggtcccc cagatgcggtc ccgccctcag cagtttctag agaaccatca     780
gatgtttcca gggtgcccca aggacctgaa atgaccctgt gccttatttg aactaaccaa     840
tcagttcgct tctcgcttct gttcgcgcgc ttctgctccc cgagctctat ataagcagag     900
ctcgtttagt gaaccgtcag atcgcctgga gacgccatcc acgctgtttt gacttccata     960
gaaggatctc gaggccacca tggtgagcaa gggcgaggag ctgttcaccg gggtggtgcc    1020
catcctggtc gagctggacg gcgacgtaaa cggccacaag ttcagcgtgt ccggcgaggg    1080
cgagggcgat gccacctacg gcaagctgac cctgaagttc atctgcacca ccggcaagct    1140
gcccgtgccc tggcccaccc tcgtgaccac cctgacctac ggcgtgcagt gcttcagccg    1200
ctaccccgac cacatgaagc agcacgactt cttcaagtcc gccatgcccg aaggctacgt    1260
ccaggagcgc accatcttct tcaaggacga cggcaactac aagacccgcg ccgaggtgaa    1320
gttcgagggc gacaccctgg tgaaccgcat cgagctgaag ggcatcgact tcaaggagga    1380
```

```
cggcaacatc ctggggcaca agctggagta caactacaac agccacaacg tctatatcat    1440
ggccgacaag cagaagaacg gcatcaaggt gaacttcaag atccgccaca acatcgagga    1500
cggcagcgtg cagctcgccg accactacca gcagaacacc cccatcggcg acggccccgt    1560
gctgctgccc gacaaccact acctgagcac ccagtccgcc ctgagcaaag accccaacga    1620
gaagcgcgat cacatggtcc tgctggagtt cgtgaccgcc gccgggatca ctctcggcat    1680
ggacgagctg tacaagtaaa ctagtgtcga ctgctttatt tgtgaaattt gtgatgctat    1740
tgctttattt gtaaccatta agctgcaa taaacaagtt aacaacaaca attgcattca     1800
ttttatgttt caggttcagg gggaggtgtg ggaggttttt taaaacgtac atcactcgct    1860
cccccattcc atcctccacc actccaagcc cctctgcaag aagcagcccc gaccaaagcc    1920
tcaagagctc cagccctcac agcagccctg ggaatacggt gtccctgtg ggccccggct     1980
ctcaagagca ccgggactcc tacgcttact tgaacgcgtc ctacggcacg aaggtttgg     2040
gctcctaccc tggctacgca ccctgcccc acctcccgcc agctttcatc ccctcgtaca     2100
acgctcacta ccccaagttc ctcttgcccc cctacggcat gaattgtaat ggcctgagcg    2160
ctgtgagcag catgaatggc atcaacaact ttggcctctt cccgaggctg tgccctgtct    2220
acagcaatct cctcggtggg ggcatctaga gtagataagt agcatggcgg gttaatcatt    2280
aactacaagg aaccctagt gatggagttg gccactccct ctctgcgcgc tcgctcgctc     2340
actgaggccg ggcgaccaaa ggtcgcccga cgcccgggct tgcccgggc ggcctcagtg     2400
agcgagcgag cgcgccagct ggcgtaatag cgaagaggcc cgcaccgatc gcccttccca    2460
acagttgcgc agcctgaatg gcgaatggcg attccgttgc aatggctggc ggtaatattg    2520
ttctggatat taccagcaag gccgatagtt tgagttcttc tactcaggca agtgatgtta    2580
ttactaatca aagaagtatt gcgacaacg ttaatttgcg tgatggacag actcttttac      2640
tcggtggcct cactgattat aaaaacactt ctcaggattc tggcgtaccg ttcctgtcta    2700
aaatcccttt aatcggcctc ctgtttagct cccgctctga ttctaacgag gaaagcacgt    2760
tatacgtgct cgtcaaagca accatagtac gcgccctgta gcggcgcatt aagcgcggcg    2820
ggtgtggtgg ttacgcgcag cgtgaccgct acacttgcca gcgccctagc gcccgctcct    2880
ttcgctttct tcccttcctt tctcgccacg ttcgccggct ttccccgtca agctctaaat    2940
cggggggctcc ctttagggtt ccgatttagt gctttacggc acctcgaccc caaaaaactt   3000
gattagggtg atggttcacg tagtgggcca tcgccctgat agacggtttt tcgccctttg    3060
acgttggagt ccacgttctt taatagtgga ctcttgttcc aaactggaac aacactcaac    3120
cctatctcgg tctattcttt tgatttataa gggattttgc cgatttcggc ctattggtta    3180
aaaaatgagc tgatttaaca aaaatttaac gcgaatttta acaaaatatt aacgtttaca    3240
atttaaatat ttgcttatac aatcttcctg ttttggggc ttttctgatt atcaaccggg     3300
gtacatatga ttgacatgct agttttacga ttaccgttca tcgattctct tgtttgctcc    3360
agactctcag gcaatgacct gatagccttt gtagagacct ctcaaaaata gctaccctct    3420
ccggcatgaa tttatcagct agaacggttg aatatcatat tgatggtgat ttgactgtct    3480
ccggcctttc tcaccgtttt gaatctttac ctacacatta tcaggcatt gcatttaaaa     3540
tatatgaggg ttctaaaaat ttttatcctt gcgttgaaat aaaggcttct cccgcaaaag    3600
tattacaggg tcataatgtt tttggtacaa ccgatttagc tttatgctct gaggctttat    3660
tgcttaattt tgctaattct ttgccttgcc tgtatgattt attggatgtt ggaatcgcct    3720
gatgcggtat tttctcctta cgcatctgtg cggtatttca caccgcatat ggtgcactct    3780
```

```
cagtacaatc tgctctgatg ccgcatagtt aagccagccc cgacacccgc caacacccgc    3840
tgacgcgccc tgacgggctt gtctgctccc ggcatccgct tacagacaag ctgtgaccgt    3900
ctccgggagc tgcatgtgtc agaggttttc accgtcatca ccgaaacgcg cgagacgaaa    3960
gggcctcgtg atacgcctat ttttataggt taatgtcatg ataataatgg tttcttagac    4020
gtcaggtggc acttttcggg gaaatgtgcg cggaacccct atttgtttat ttttctaaat    4080
acattcaaat atgtatccgc tcatgagaca ataaccctga taaatgcttc aataatattg    4140
aaaaaggaag agtatgagta ttcaacattt ccgtgtcgcc cttattccct ttttgcggc    4200 attttgcctt cctgtttttg ctcacccaga acgctggtg aaagtaaaag atgctgaaga    4260
tcagttgggt gcacgagtgg gttacatcga actggatctc aacagcggta agatccttga    4320
gagttttcgc cccgaagaac gttttccaat gatgagcact tttaaagttc tgctatgtgg    4380
cgcggtatta tcccgtattg acgccgggca agagcaactc ggtcgccgca tacactattc    4440
tcagaatgac ttggttgagt actcaccagt cacagaaaag catcttacgg atggcatgac    4500
agtaagagaa ttatgcagtg ctgccataac catgagtgat aacactgcgg ccaacttact    4560
tctgacaacg atcggaggac cgaaggagct aaccgctttt ttgcacaaca tgggggatca    4620
tgtaactcgc cttgatcgtt gggaaccgga gctgaatgaa gccataccaa acgacgagcg    4680
tgacaccacg atgcctgtag caatggcaac aacgttgcgc aaactattaa ctggcgaact    4740
acttactcta gcttcccggc aacaattaat agactggatg gaggcggata agttgcagg    4800 accacttctg cgctcggccc ttccggctgg ctggtttatt gctgataaat ctggagccgg    4860
tgagcgtggg tctcgcggta tcattgcagc actggggcca gatggtaagc cctcccgtat    4920
cgtagttatc tacacgacgg ggagtcaggc aactatggat gaacgaaata cagatcgc    4980 tgagataggt gcctcactga ttaagcattg gtaactgtca gaccaagttt actcatatat    5040
actttagatt gatttaaaac ttcatttta atttaaaagg atctaggtga agatccttt    5100 tgataatctc atgaccaaaa tcccttaacg tgagttttcg ttccactgag cgtcagaccc    5160
cgtagaaaag atcaaaggat cttcttgaga tcctttttt ctgcgcgtaa tctgctgctt    5220
gcaaacaaaa aaaccaccgc taccagcggt ggtttgtttg ccggatcaag agctaccaac    5280 tcttttccg aagtaactg gcttcagcag agcgcagata ccaaatactg tccttctagt    5340
gtagccgtag ttaggccacc acttcaagaa ctctgtagca ccgcctacat acctcgctct    5400
gctaatcctg ttaccagtgg ctgctgccag tggcgataag tcgtgtctta ccgggttgga    5460
ctcaagacga tagttaccgg ataaggcgca gcggtcgggc tgaacggggg gttcgtgcac    5520
acagcccagc ttggagcgaa cgacctacac cgaactgaga tacctacagc gtgagctatg    5580
agaaagcgcc acgcttcccg aagggagaaa ggcggacagg tatccggtaa gcggcagggt    5640
cggaacagga gagcgcacga gggagcttcc agggggaaac gcctggtatc tttatagtcc    5700
tgtcgggttt cgccacctct gacttgagcg tcgatttttg tgatgctcgt caggggggcg    5760
gagcctatgg aaaaacgcca gcaacgcggc ctttttacgg ttcctggcct tttgctggcc    5820
ttttgctcac atgttctttc ctgcgttatc ccctgattct gtggataacc gtattaccgc    5880
ctttgagtga gctgataccg ctcgccgcag ccgaacgacc gagcgcagcg agtcagtgag    5940
cgaggaagcg gaagagcgcc caatacgcaa accgcctctc ccgcgcgtt ggccgattca    6000 ttaatg                                                              6006
```

<210> SEQ ID NO 54

<211> LENGTH: 7206
<212> TYPE: DNA
<213> ORGANISM: Artificial Sequence
<220> FEATURE:
<223> OTHER INFORMATION: 1361_pAAV.Blimp1.1.0kb.MND.GFP.pA

<400> SEQUENCE: 54

| | | | | | |
|---|---|---|---|---|---|
| cagctgcgcg | ctcgctcgct | cactgaggcc | gcccgggcaa | agcccgggcg | tcgggcgacc | 60 |
| tttggtcgcc | cggcctcagt | gagcgagcga | gcgcgcagag | agggagtggc | caactccatc | 120 |
| actagggggtt | ccttgtagtt | aatgattaac | ccgccatgct | acttatctac | acgcgtggta | 180 |
| aaccatgaac | atcagaaaga | cttttattaa | cctatgacag | ggtccccacc | ccagtatttt | 240 |
| tccactccat | taaaatggaa | gttttttttt | ttttttttctt | ttttgagaca | gagttttgct | 300 |
| cttgttgccc | agtctggagt | gcaatggcac | aatctcggct | caccacaacc | tccacctccc | 360 |
| agattcaagc | gattcttctg | cctcagcctc | ccaagtagct | gggattacag | gtgtgcgcca | 420 |
| ccacgcccag | ctaattttgt | atttttagta | gagatggggt | ttctccatgt | tggtcaggct | 480 |
| ggtctcgaac | ttccgacctc | aggtgatccg | cccacctcgg | cctcccaaag | tgctgggatt | 540 |
| acaggcaaga | gccactgcat | ccagcttagg | ctatcttact | ccagcctaaa | cagcaatttt | 600 |
| ctatcataag | gtctgtacta | atgaaaacag | aatcacccaa | ggctgctgtt | tgttctgtct | 660 |
| gtgctgccat | tgtccgcatt | tgctgagga | ggaaacggaa | ctgcactttt | gagtgagtgg | 720 |
| cccagagcct | tctagaatga | gagtgcgttg | gaagccagat | atgtggcgat | tgtgtcgcca | 780 |
| gctgttactc | aggttttctc | aagaaggagg | agcaactttg | gcagttttgc | ttcagttctc | 840 |
| tctagccctc | tgtgtaatcg | cccctttttc | tttatttcag | cacaaacaca | gagcagtcta | 900 |
| aagcaaccga | gcactgagaa | aaatgaactc | tgcccaaaga | atgtcccaaa | gagagagtac | 960 |
| agcgtgaaag | aaatcctaaa | attggactcc | aaccccctcca | aaggaaagga | cctctaccgt | 1020 |
| tctaacattt | caccccctcac | atcagaaaag | gacctcgatg | actttagaag | acgtgggagc | 1080 |
| cccgaaatgc | ccttctaccc | tcgggtcgtt | taccccatcc | gggcccctct | gccagaagac | 1140 |
| tttttgaaag | cttccctggc | ctacgggatc | gagagagaac | agagaaacag | gagaatatgg | 1200 |
| gccaaacagg | atatctgtgg | taagcagttc | ctgccccggc | tcagggccaa | gaacagttgg | 1260 |
| aacagcagaa | tatgggccaa | acaggatatc | tgtggtaagc | agttcctgcc | ccggctcagg | 1320 |
| gccaagaaca | gatggtcccc | agatgcggtc | ccgccctcag | cagtttctag | agaaccatca | 1380 |
| gatgtttcca | gggtgcccca | aggacctgaa | atgaccctgt | gccttatttg | aactaaccaa | 1440 |
| tcagttcgct | tctcgcttct | gttcgcgcgc | ttctgctccc | cgagctctat | ataagcagag | 1500 |
| ctcgtttagt | gaaccgtcag | atcgcctgga | gacgccatcc | acgctgtttt | gacttccata | 1560 |
| gaaggatctc | gaggccacca | tggtgagcaa | gggcgaggag | ctgttcaccg | gggtggtgcc | 1620 |
| catcctggtc | gagctggacg | gcgacgtaaa | cggccacaag | ttcagcgtgt | ccggcgaggg | 1680 |
| cgagggcgat | gccacctacg | gcaagctgac | cctgaagttc | atctgcacca | ccggcaagct | 1740 |
| gcccgtgccc | tggcccaccc | tcgtgaccac | cctgacctac | ggcgtgcagt | gcttcagccg | 1800 |
| ctaccccgac | cacatgaagc | agcacgactt | cttcaagtcc | gccatgcccg | aaggctacgt | 1860 |
| ccaggagcgc | accatcttct | tcaaggacga | cggcaactac | aagacccgcg | ccgaggtgaa | 1920 |
| gttcgagggc | gacaccctgg | tgaaccgcat | cgagctgaag | ggcatcgact | tcaaggagga | 1980 |
| cggcaacatc | ctggggcaca | agctggagta | caactacaac | agccacaacg | tctatatcat | 2040 |
| ggccgacaag | cagaagaacg | gcatcaaggt | gaacttcaag | atccgccaca | acatcgagga | 2100 |
| cggcagcgtg | cagctcgccg | accactacca | gcagaacacc | cccatcggcg | acggccccgt | 2160 |

-continued

```
gctgctgccc gacaaccact acctgagcac ccagtccgcc ctgagcaaag accccaacga    2220
gaagcgcgat cacatggtcc tgctggagtt cgtgaccgcc gccgggatca ctctcggcat    2280
ggacgagctg tacaagtaaa ctagtgtcga ctgctttatt tgtgaaattt gtgatgctat    2340
tgctttattt gtaaccatta taagctgcaa taaacaagtt aacaacaaca attgcattca    2400
ttttatgttt caggttcagg ggaggtgtg ggaggttttt taaaacgtac atcactcgct    2460
cccccattcc atcctccacc actccaagcc cctctgcaag aagcagcccc gaccaaagcc    2520
tcaagagctc cagccctcac agcagccctg ggaatacggt gtccctgtgg ggccccggct    2580
ctcaagagca ccgggactcc tacgcttact gaacgcgtc ctacggcacg aaggtttgg     2640 gctcctaccc tggctacgca ccctgcccc acctcccgcc agctttcatc ccctcgtaca    2700
acgctcacta ccccaagttc ctcttgcccc cctacggcat gaattgtaat ggcctgagcg    2760
ctgtgagcag catgaatggc atcaacaact ttggcctctt cccgaggctg tgcctgtct    2820 acagcaatct cctcggtggg ggcagcctgc cccaccccat gctcaacccc acttctctcc    2880
cgagctcgct gccctcagat ggagcccgga ggttgctcca gccggagcat cccagggagg    2940
tgcttgtccc ggcgccccac agtgccttct cctttaccgg ggccgccgcc agcatgaagg    3000
acaaggcctg tagccccaca agcgggtctc ccacggcggg aacagccgcc acggcagaac    3060
atgtggtgca gcccaaagct acctcagcag cgatggcagc cccagcagc gacgaagcca    3120 tgaatctcat taaaaacaaa agaaacatga ccggctacaa gacccttccc tacccgctga    3180
agaagcagaa cggcaagatc aagtacgaat gcaacgtttg cgccaagact ttcggccagc    3240
tctccaatct gaaggtaggc cttgagagag agcagtccaa ggggctgtga gtgcatgctt    3300
gtgtttgtat ttagcttgct ttccatgggg tatcgattgc atttgcagta gtatgagccc    3360
ccggttgggg atagtgggta tggattccgc ctggcttttg ccacttctag ctctttgact    3420
ttggacaagt gacttccctt ctcctctaga gtagataagt agcatggcgg gttaatcatt    3480
aactacaagg aaccctagt gatggagttg gccactccct ctctgcgcgc tcgctcgctc    3540
actgaggccg ggcgaccaaa ggtcgcccga cgcccgggct tgcccgggc ggcctcagtg    3600 agcgagcgag cgcgccagct ggcgtaatag cgaagaggcc cgcaccgatc gcccttccca    3660
acagttgcgc agcctgaatg gcgaatggcg attccgttgc aatggctggc ggtaatattg    3720
ttctggatat taccagcaag gccgatagtt tgagttcttc tactcaggca agtgatgtta    3780
ttactaatca agaagtatt gcgacaacgg ttaatttgcg tgatggacag actcttttac     3840
tcggtggcct cactgattat aaaaacactt ctcaggattc tggcgtaccg ttcctgtcta    3900
aaatcccttt aatcggcctc ctgtttagct cccgctctga ttctaacgag gaaagcacgt    3960
tatacgtgct cgtcaaagca accatagtac gcgccctgta gcggcgcatt aagcgcggcg    4020
ggtgtggtgg ttacgcgcag cgtgaccgct acacttgcca gcgccctagc gcccgctcct    4080
ttcgctttct tcccttcctt tctcgccacg ttcgccggct ttccccgtca agctctaaat    4140 cggggggctcc ctttagggtt ccgatttagt gctttacggc acctcgaccc caaaaaactt    4200
gattagggtg atggttcacg tagtgggcca tcgccctgat agacggtttt tcgccctttg    4260
acgttggagt ccacgttctt taatagtgga ctcttgttcc aaactggaac aacactcaac    4320
cctatctcgg tctattcttt tgatttataa gggattttgc cgatttcggc ctattggtta    4380
aaaaatgagc tgatttaaca aaaatttaac gcgaatttta acaaaatatt aacgtttaca    4440
atttaaatat ttgcttatac aatcttcctg ttttgggc ttttctgatt atcaaccggg      4500
```

```
gtacatatga ttgacatgct agttttacga ttaccgttca tcgattctct tgtttgctcc   4560
agactctcag gcaatgacct gatagccttt gtagagacct ctcaaaaata gctaccctct   4620
ccggcatgaa tttatcagct agaacggttg aatatcatat tgatggtgat ttgactgtct   4680
ccggcctttc tcacccgttt gaatctttac ctacacatta ctcaggcatt gcatttaaaa   4740
tatatgaggg ttctaaaaat ttttatcctt gcgttgaaat aaaggcttct cccgcaaaag   4800
tattacaggg tcataatgtt tttggtacaa ccgatttagc tttatgctct gaggctttat   4860
tgcttaattt tgctaattct ttgccttgcc tgtatgattt attggatgtt ggaatcgcct   4920
gatgcggtat tttctcctta cgcatctgtg cggtatttca caccgcatat ggtgcactct   4980
cagtacaatc tgctctgatg ccgcatagtt aagccagccc cgacacccgc caacacccgc   5040
tgacgcgccc tgacgggctt gtctgctccc ggcatccgct tacagacaag ctgtgaccgt   5100
ctccgggagc tgcatgtgtc agaggttttc accgtcatca ccgaaacgcg cgagacgaaa   5160
gggcctcgtg atacgcctat ttttataggt taatgtcatg ataataatgg tttcttagac   5220
gtcaggtggc acttttcggg gaaatgtgcg cggaaccccT atttgtttat ttttctaaat   5280
acattcaaat atgtatccgc tcatgagaca ataaccctga taaatgcttc aataatattg   5340
aaaaaggaag agtatgagta ttcaacattt ccgtgtcgcc cttattccct ttttTgcggc   5400
attttgcctt cctgtttttg ctcacccaga aacgctggtg aaagtaaaag atgctgaaga   5460
tcagttgggt gcacgagtgg gttacatcga actggatctc aacagcggta agatccttga   5520
gagttttcgc cccgaagaac gttttccaat gatgagcact tttaaagttc tgctatgtgg   5580
cgcggtatta tcccgtattg acgccgggca agagcaactc ggtcgccgca tacactattc   5640
tcagaatgac ttggttgagt actcaccagt cacagaaaag catcttacgg atggcatgac   5700
agtaagagaa ttatgcagtg ctgccataac catgagtgat aacactgcgg ccaacttact   5760
tctgacaacg atcggaggac cgaaggagct aaccgctttt ttgcacaaca tgggggatca   5820
tgtaactcgc cttgatcgtt gggaaccgga gctgaatgaa gccataccaa acgacgagcg   5880
tgacaccacg atgcctgtag caatggcaac aacgttgcgc aaactattaa ctggcgaact   5940
acttactcta gcttcccggc aacaattaat agactggatg gaggcggata agttgcagg   6000 accacttctg cgctcggccc ttccggctgg ctggtttatt gctgataaat ctggagccgg   6060
tgagcgtggg tctcgcggta tcattgcagc actggggcca gatggtaagc cctcccgtat   6120
cgtagttatc tacacgacgg ggagtcaggc aactatggat gaacgaaata gacagatcgc   6180
tgagataggt gcctcactga ttaagcattg gtaactgtca gaccaagttt actcatatat   6240
actttagatt gatttaaaac ttcattttta atttaaaagg atctaggtga agatcctttt   6300
tgataatctc atgaccaaaa tcccttaacg tgagttttcg ttccactgag cgtcagaccc   6360
cgtagaaaag atcaaaggat cttcttgaga tcctttttt ctgcgcgtaa tctgctgctt   6420
gcaaacaaaa aaaccaccgc taccagcggt ggtttgtttg ccggatcaag agctaccaac   6480 tcttttccg aaggtaactg gcttcagcag agcgcagata ccaaatactg tccttctagt   6540
gtagccgtag ttaggccacc acttcaagaa ctctgtagca ccgcctacat acctcgctct   6600
gctaatcctg ttaccagtgg ctgctgccag tggcgataag tcgtgtctta ccgggttgga   6660
ctcaagacga tagttaccgg ataaggcgca gcggtcgggc tgaacggggg gttcgtgcac   6720
acagcccagc ttggagcgaa cgacctacac cgaactgaga tacctacagc gtgagctatg   6780
agaaagcgcc acgcttcccg aagggagaaa ggcggacagg tatccggtaa gcggcagggt   6840
cggaacagga gagcgcacga gggagcttcc agggggaaac gcctggtatc tttatagtcc   6900
```

-continued

```
tgtcgggttt cgccacctct gacttgagcg tcgattttttg tgatgctcgt caggggggcg    6960
gagcctatgg aaaaacgcca gcaacgcggc cttttttacgg ttcctggcct tttgctggcc    7020
ttttgctcac atgttctttc ctgcgttatc ccctgattct gtggataacc gtattaccgc    7080 cttttgagtga gctgataccg ctcgccgcag ccgaacgacc gagcgcagcg agtcagtgag    7140
cgaggaagcg gaagagcgcc caatacgcaa accgcctctc cccgcgcgtt ggccgattca    7200
ttaatg                                                               7206
```

<210> SEQ ID NO 55
<211> LENGTH: 6707
<212> TYPE: DNA
<213> ORGANISM: Artificial Sequence
<220> FEATURE:
<223> OTHER INFORMATION: 1366_CCR5.MND.BAFF_CRISPR.HR

<400> SEQUENCE: 55

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggcctctg cataaataaa aaaaattagt cagccatgag cttggacgcg    240
tttggtgtgg tggcgcctgt agtccccagc cacttggagg ggtgaggtga gaggattgct    300
tgagcccggg atggtccagg ctgcagtgag ccatgatcgt gccactgcac tccagcctgg    360
gcgacagagt gagaccctgt ctcacaacaa caacaacaac aacaaaaagg ctgagctgca    420
ccatgcttga cccagtttct taaaattgtt gtcaaagctt cattcactcc atggtgctat    480
agagcacaag attttatttg gtgagatggt gctttcatga attcccccaa cagagccaag    540
ctctccatct agtggacagg gaagctagca gcaaaccttc ccttcactac aaaacttcat    600
tgcttggcca aaaagagagt taattcaatg tagacatcta tgtaggcaat taaaaaccta    660
ttgatgtata aaacagtttg cattcatgga gggcaactaa atacattcta ggactttata    720
aaagatcact ttttattttat gcacagggtg gaacaagatg gattatcaag tgtcaagtcc    780
aatctatgac atcaattatt atacatcgga gccctgccaa aaaatcaatg tgaagcaaat    840
cgcagcccgc ctcctgcctc cgctctactc actggtgttc atctttggtt ttgtgggcaa    900
catgctggtc atcctcatcc tgataaactg caaaaggctg aagagcatga ctgacatcta    960
cctgctcaac ctggccatct ctgacctgtt tttccttctt actgtcccct tctgggctca   1020
ctatgctgcc gcccagtggg actttggaaa tacaatgtgt caacgaacag agaaacagga   1080
gaatatgggc caaacaggat atctgtggta agcagttcct gccccggctc agggccaaga   1140
acagttggaa cagcagaata tgggccaaac aggatatctg tggtaagcag ttcctgcccc   1200
ggctcagggc caagaacaga tggtccccag atgcggtccc gccctcagca gtttctagag   1260
aaccatcaga tgtttccagg gtgccccaag gacctgaaat gaccctgtgc cttatttgaa   1320
ctaaccaatc agttcgcttc tcgcttctgt tcgcgcgctt ctgctccccg agctctatat   1380
aagcagagct cgtttagtga accgtcagat cgcctggaga cgccatccac gctgttttga   1440
cttccataga aggatctcga ggccaccatg taccggatgc agctgctgag ctgcatcgca   1500
ctgagcctgg cactggtgac aacagcgca gtgcaggac cagaggagac cgtgacccag   1560
gactgcctgc agctgatcgc agacagcgag acccccacca tccagaaggg cagctacacc   1620
ttcgtgccct ggctgctgag cttcaagcgg ggcagcgccc tggaggagaa ggagaacaag   1680
```

```
attctggtga aggagaccgg ctacttcttc atctacggcc aggtgctgta caccgataag    1740
acctacgcca tgggccacct gatccagcgg aagaaggtgc acgtgttcgg cgacgagctg    1800
agcctggtga ccctgttccg gtgcatccag aacatgcccg agaccctgcc caacaacagc    1860
tgctacagcg caggaatcgc aaagctggag gagggcgacg agctgcagct ggcaatcccc    1920
cgggagaacg cacagatcag cctggacggc gacgtgacct tcttcggcgc cctgaagctc    1980
ctgtgagtcg actgctttat tgtgaaattt tgtgatgcta ttgctttatt tgtaaccatt    2040
ataagctgca ataaacaagt taacaacaac aattgcattc attttatgtt tcaggttcag    2100
ggggaggtgt gggaggtttt ttaaactcta ttttataggc ttcttctctg aatcttctt    2160
catcatcctc ctgacaatcg ataggtacct ggctgtcgtc catgctgtgt tgctttaaa    2220
agccaggacg gtcacctttg gggtggtgac aagtgtgatc acttgggtgg tggctgtgtt    2280
tgcgtctctc ccaggaatca tctttaccag atctcaaaaa gaaggtcttc attacacctg    2340
cagctctcat tttccataca gtcagtatca attctggaag aatttccaga cattaaagat    2400
agtcatcttg gggctggtcc tgccgctgct tgtcatggtc atctgctact cgggaatcct    2460
aaaaactctg cttcggtgtc gaaatgagaa gaagaggcac agggctgtga ggcttatctt    2520
caccatcatg attgtttatt ttctcttctg ggctccctac aacattgtcc ttctcctgaa    2580
cacttccag gaattctttg gcctgaataa ttgcagtagc tctaacaggt tggaccaagc    2640
tatgcaggtg acagagactc ttgggatgac gcactgctgc atcaaccca tcatctatgc    2700
ctttgtcggg gagaagttca gaaactacct cttagtcttc ttccaaaagc acattgccaa    2760
acgcttctgc aaatgctgtt ctattttcca gcaagaggct cccgagcgag caagctcagt    2820
ttacacccga tccactgggg agcaggaaat atctgtgggc ttgtgacacg gactcaagtg    2880
ggctggtgac ccagtcagag ttgtgcacat ggcttagttt tcatacacac cgcggtctag    2940
agcatggcta cgtagataag tagcatggcg ggttaatcat taactacaag gaaccctag    3000
tgatggagtt ggccactccc tctctgcgcg ctcgctcgct cactgaggcc gggcgaccaa    3060
aggtcgcccg acgcccgggc tttgcccggg cggcctcagt gagcgagcga gcgcgccagc    3120
tggcgtaata gcgaagaggc ccgcaccgat cgcccttccc aacagttgcg cagcctgaat    3180
ggcgaatggc gattccgttg caatggctgg cggtaatatt gttctggata ttaccagcaa    3240
ggccgatagt ttgagttctt ctactcaggc aagtgatgtt attactaatc aaagaagtat    3300
tgcgacaacg gttaatttgc gtgatggaca gactctttta ctcggtggcc tcactgatta    3360
taaaaacact tctcaggatt ctggcgtacc gttcctgtct aaaatccctt taatcggcct    3420
cctgtttagc tcccgctctg attctaacga ggaaagcacg ttatacgtgc tcgtcaaagc    3480
aaccatagta cgcgccctgt agcggcgcat taagcgcggc gggtgtggtg ttacgcgca    3540
gcgtgaccgc tacacttgcc agcgccctag cgcccgctcc tttcgctttc ttcccttcct    3600
ttctcgccac gttcgccggc tttccccgtc aagctctaaa tcggggggctc ctttagggt    3660
tccgatttag tgctttacgg cacctcgacc ccaaaaaact tgattagggt gatggttcac    3720
gtagtgggcc atcgccctga tagacggttt ttcgcccttt gacgttggag tccacgttct    3780
ttaatagtgg actcttgttc caaactggaa caacactcaa ccctatctcg gtctattctt    3840
ttgatttata agggattttg ccgatttcgg cctattggtt aaaaaatgag ctgatttaac    3900
aaaaatttaa cgcgaatttt aacaaaatat taacgtttac aatttaaata tttgcttata    3960
caatcttcct gttttggggg cttttctgat tatcaaccgg ggtacatatg attgacatgc    4020
tagttttacg attaccgttc atcgattctc ttgtttgctc cagactctca ggcaatgacc    4080
```

```
tgatagcctt tgtagagacc tctcaaaaat agctaccctc tccggcatga atttatcagc   4140
tagaacggtt gaatatcata ttgatggtga tttgactgtc tccggccttt ctcacccgtt   4200
tgaatcttta cctacacatt actcaggcat tgcatttaaa atatatgagg gttctaaaaa   4260
tttttatcct tgcgttgaaa taaaggcttc tcccgcaaaa gtattacagg gtcataatgt   4320
ttttggtaca accgatttag ctttatgctc tgaggcttta ttgcttaatt ttgctaattc   4380
tttgccttgc ctgtatgatt tattggatgt tggaatcgcc tgatgcggta ttttctcctt   4440
acgcatctgt gcggtatttc acaccgcata tggtgcactc tcagtacaat ctgctctgat   4500
gccgcatagt taagccagcc ccgacacccg ccaacacccg ctgacgcgcc ctgacgggct   4560
tgtctgctcc cggcatccgc ttacagacaa gctgtgaccg tctccgggag ctgcatgtgt   4620
cagaggtttt caccgtcatc accgaaacgc gcgagacgaa agggcctcgt gatacgccta   4680
tttttatagg ttaatgtcat gataataatg gtttcttaga cgtcaggtgg cacttttcgg   4740
ggaaatgtgc gcggaacccc tatttgttta ttttctaaa tacattcaaa tatgtatccg   4800
ctcatgagac aataaccctg ataaatgctt caataatatt gaaaaaggaa gagtatgagt   4860
attcaacatt tccgtgtcgc ccttattccc ttttttgcgg cattttgcct tcctgttttt   4920
gctcacccag aaacgctggt gaaagtaaaa gatgctgaag atcagttggg tgcacgagtg   4980
ggttacatcg aactggatct caacagcggt aagatccttg agagttttcg ccccgaagaa   5040
cgttttccaa tgatgagcac ttttaaagtt ctgctatgtg gcgcggtatt atcccgtatt   5100
gacgccgggc aagagcaact cggtcgccgc atacactatt ctcagaatga cttggttgag   5160
tactcaccag tcacagaaaa gcatcttacg gatggcatga cagtaagaga attatgcagt   5220
gctgccataa ccatgagtga taacactgcg gccaacttac ttctgacaac gatcggagga   5280
ccgaaggagc taaccgcttt tttgcacaac atggggatc atgtaactcg ccttgatcgt   5340
tgggaaccgg agctgaatga agccatacca aacgacgagc gtgacaccac gatgcctgta   5400
gcaatggcaa caacgttgcg caaactatta actggcgaac tacttactct agcttcccgg   5460
caacaattaa tagactggat ggaggcggat aaagttgcag gaccacttct gcgctcggcc   5520
cttccggctg gctggtttat tgctgataaa tctggagccg gtgagcgtgg gtctcgcggt   5580
atcattgcag cactggggcc agatggtaag ccctcccgta tcgtagttat ctacacgacg   5640
gggagtcagg caactatgga tgaacgaaat agacagatcg ctgagatagg tgcctcactg   5700
attaagcatt ggtaactgtc agaccaagtt tactcatata ctttagat tgatttaaaa   5760 cttcattttt aatttaaaag gatctaggtg aagatccttt ttgataatct catgaccaaa   5820
atcccttaac gtgagttttc gttccactga gcgtcagacc ccgtagaaaa gatcaaagga   5880
tcttcttgag atccttttt tctgcgcgta atctgctgct tgcaaacaaa aaaaccaccg   5940
ctaccagcgg tggtttgttt gccggatcaa gagctaccaa ctcttttcc gaaggtaact   6000 ggcttcagca gagcgcagat accaaatact gtccttctag tgtagccgta gttaggccac   6060
cacttcaaga actctgtagc accgcctaca tacctcgctc tgctaatcct gttaccagtg   6120
gctgctgcca gtggcgataa gtcgtgtctt accgggttgg actcaagacg atagttaccg   6180
gataaggcgc agcggtcggg ctgaacgggg gttcgtgca cacagcccag cttggagcga   6240
acgacctaca ccgaactgag atacctacag cgtgagctat gagaaagcgc cacgcttccc   6300
gaagggagaa aggcggacag gtatccggta agcggcaggg tcggaacagg agagcgcacg   6360
agggagcttc caggggggaaa cgcctggtat ctttatagtc ctgtcgggtt tcgccacctc   6420
```

```
tgacttgagc gtcgattttt gtgatgctcg tcagggggc ggagcctatg gaaaaacgcc      6480
agcaacgcgg cctttttacg gttcctggcc ttttgctggc cttttgctca catgttcttt      6540
cctgcgttat ccctgattc tgtggataac cgtattaccg cctttgagtg agctgatacc      6600
gctcgccgca gccgaacgac cgagcgcagc gagtcagtga gcgaggaagc ggaagagcgc      6660
ccaatacgca aaccgcctct ccccgcgcgt tggccgattc attaatg                    6707

<210> SEQ ID NO 56
<211> LENGTH: 7494
<212> TYPE: DNA
<213> ORGANISM: Artificial Sequence
<220> FEATURE:
<223> OTHER INFORMATION: 1367_CCR5.MND.BAFF.2A.GFP

<400> SEQUENCE: 56
cagctgcgcg ctcgctcgct cactgaggcc gcccgggcaa agcccgggcg tcgggcgacc        60
tttggtcgcc cggcctcagt gagcgagcga gcgcgcagag agggagtggc caactccatc       120
actaggggtt ccttgtagtt aatgattaac ccgccatgct acttatctac gtagccatgc       180
tctagcggcc tcggcctctg cataaataaa aaaaattagt cagccatgag cttggacgcg       240
tttggtgtgg tggcgcctgt agtccccagc cacttggagg ggtgaggtga gaggattgct       300
tgagcccggg atggtccagg ctgcagtgag ccatgatcgt gccactgcac tccagcctgg       360
gcgacagagt gagaccctgt ctcacaacaa caacaacaac aacaaaaagg ctgagctgca       420
ccatgcttga cccagtttct taaaattgtt gtcaaagctt cattcactcc atggtgctat       480
agagcacaag attttatttg gtgagatggt gctttcatga attcccccaa cagagccaag       540
ctctccatct agtggacagg gaagctagca gcaaaccttc ccttcactac aaaacttcat       600
tgcttggcca aaagagagt taattcaatg tagacatcta tgtaggcaat taaaaaccta       660
ttgatgtata aaacagtttg cattcatgga gggcaactaa atacattcta ggactttata       720
aaagatcact ttttatttat gcacaggtg gaacaagatg gattatcaag tgtcaagtcc       780
aatctatgac atcaattatt atacatcgga gccctgccaa aaaatcaatg tgaagcaaat       840
cgcagcccgc ctcctgcctc cgctctactc actggtgttc atctttggtt ttgtgggcaa       900
catgctggtc atcctcatcc tgataaactg caaaaggctg aagagcatga ctgacatcta       960
cctgctcaac ctggccatct ctgacctgtt tttccttctt actgtcccct ctgggctca      1020 ctatgctgcc gcccagtggg actttggaaa tacaatgtgt caacgaacag agaaacagga      1080
gaatatgggc caaacaggat atctgtggta agcagttcct gccccggctc agggccaaga      1140
acagttggaa cagcagaata tgggccaaac aggatatctg tggtaagcag ttcctgcccc      1200
ggctcagggc caagaacaga tggtcccag atgcggtccc gccctcagca gtttctagag      1260
aaccatcaga tgtttccagg gtgccccaag gacctgaaat gaccctgtgc cttatttgaa      1320
ctaaccaatc agttcgcttc tcgcttctgt tcgcgcgctt ctgctccccg agctctatat      1380
aagcagagct cgtttagtga accgtcagat cgcctggaga cgccatccac gctgttttga      1440
cttccataga aggatctcga ggccaccatg taccggatgc agctgctgag ctgcatcgca      1500
ctgagcctgg cactggtgac caacagcgca gtgcagggac cagaggagac cgtgacccag      1560
gactgcctgc agctgatcgc agacagcgag acccccacca tccagaaggg cagctacacc      1620
ttcgtgccct ggctgctgag cttcaagcgg ggcagcgccc tggaggagaa ggagaacaag      1680
attctggtga aggagaccgg ctacttcttc atctacggcc aggtgctgta caccgataag      1740
acctacgcca tgggccacct gatccagcgg aagaaggtgc acgtgttcgg cgacgagctg      1800
```

```
agcctggtga ccctgttccg gtgcatccag aacatgcccg agaccctgcc caacaacagc    1860
tgctacagcg caggaatcgc aaagctggag gagggcgacg agctgcagct ggcaatcccc    1920
cgggagaacg cacagatcag cctggacggc gacgtgacct tcttcggcgc cctgaagctc    1980
ctgggatccg gtgagggcag aggaagtctt ctaacatgcg gtgacgtgga ggagaatccg    2040
ggccccatgg tgagcaaggg cgaggagctg ttcaccgggg tggtgcccat cctggtcgag    2100
ctggacggcg acgtaaacgg ccacaagttc agcgtgtccg gcgagggcga gggcgatgcc    2160
acctacggca agctgaccct gaagttcatc tgcaccaccg gcaagctgcc cgtgccctgg    2220
cccaccctcg tgaccaccct gacctacggc gtgcagtgct tcagccgcta ccccgaccac    2280
atgaagcagc acgacttctt caagtccgcc atgcccgaag ctacgtcca ggagcgcacc    2340 atcttcttca aggacgacgg caactacaag acccgcgccg aggtgaagtt cgagggcgac    2400
accctggtga accgcatcga gctgaagggc atcgacttca aggaggacgg caacatcctg    2460
gggcacaagc tggagtacaa ctacaacagc cacaacgtct atatcatggc cgacaagcag    2520
aagaacggca tcaaggtgaa cttcaagatc cgccacaaca tcgaggacgg cagcgtgcag    2580
ctcgccgacc actaccagca gaacaccccc atcggcgacg gccccgtgct gctgcccgac    2640
aaccactacc tgagcaccca gtccgccctg agcaaagacc ccaacgagaa gcgcgatcac    2700
atggtcctgc tggagttcgt gaccgccgcc gggatcactc tcggcatgga cgagctgtac    2760
aagtgaatct agagtcgact gctttatttg tgaaatttgt gatgctattg ctttatttgt    2820
aaccattata agctgcaata acaagttaa caacaacaat tgcattcatt ttatgtttca    2880
ggttcagggg gaggtgtggg aggttttta aactctattt tataggcttc ttctctggaa    2940
tcttcttcat catcctcctg acaatcgata ggtacctggc tgtcgtccat gctgtgtttg    3000 cttaaaagc caggacggtc acctttgggg tggtgacaag tgtgatcact tgggtggtgg    3060
ctgtgtttgc gtctctccca ggaatcatct ttaccagatc tcaaaaagaa ggtcttcatt    3120
acacctgcag ctctcatttt ccatacagtc agtatcaatt ctggaagaat ttccagacat    3180
taaagatagt catcttgggg ctggtcctgc cgctgcttgt catggtcatc tgctactcgg    3240
gaatcctaaa aactctgctt cggtgtcgaa atgagaagaa gaggcacagg gctgtgaggc    3300
ttatcttcac catcatgatt gtttattttc tcttctgggc tccctacaac attgtccttc    3360
tcctgaacac cttccaggaa ttctttggcc tgaataattg cagtagctct aacaggttgg    3420
accaagctat gcaggtgaca gagactcttg ggatgacgca ctgctgcatc aaccccatca    3480
tctatgcctt tgtcggggag aagttcagaa actacctctt agtcttcttc caaaagcaca    3540
ttgccaaacg cttctgcaaa tgctgttcta ttttccagca agaggctccc gagcgagcaa    3600
gctcagttta cacccgatcc actggggagc aggaaatatc tgtgggcttg tgacacggac    3660
tcaagtgggc tggtgaccca gtcagagttg tgcacatggc ttagttttca tacacaccgc    3720
ggtctagagc atggctacgt agataagtag catggcgggt taatcattaa ctacaaggaa    3780
cccctagtga tggagttggc cactccctct ctgcgcgctc gctcgctcac tgaggccggg    3840
cgaccaaagg tcgcccgacg cccgggcttt gcccggcgg cctcagtgag cgagcgagcg    3900
cgccagctgg cgtaatagcg aagaggcccg caccgatcgc ccttcccaac agttgcgcag    3960
cctgaatggc gaatggcgat tccgttgcaa tggctggcgg taatattgtt ctggatatta    4020
ccagcaaggc cgatagtttg agttcttcta ctcaggcaag tgatgttatt actaatcaaa    4080
gaagtattgc gacaacggtt aatttgcgtg atggacagac tcttttactc ggtggcctca    4140
```

```
ctgattataa aaacacttct caggattctg gcgtaccgtt cctgtctaaa atcccttaa    4200 tcggcctcct gtttagctcc cgctctgatt ctaacgagga aagcacgtta tacgtgctcg    4260
tcaaagcaac catagtacgc gccctgtagc ggcgcattaa gcgcggcggg tgtggtggtt    4320
acgcgcagcg tgaccgctac acttgccagc gccctagcgc ccgctccttt cgctttcttc    4380
ccttcctttc tcgccacgtt cgccggcttt ccccgtcaag ctctaaatcg ggggctccct    4440
ttagggttcc gatttagtgc tttacggcac ctcgacccca aaaaacttga ttagggtgat    4500
ggttcacgta gtgggccatc gccctgatag acggttttc gcccttttgac gttggagtcc    4560 acgttcttta atagtggact cttgttccaa actggaacaa cactcaaccc tatctcggtc    4620
tattcttttg atttataagg gattttgccg atttcggcct attggttaaa aaatgagctg    4680
atttaacaaa aatttaacgc gaattttaac aaaatattaa cgtttacaat ttaaatattt    4740
gcttatacaa tcttcctgtt tttggggctt ttctgattat caaccggggt acatatgatt    4800
gacatgctag ttttacgatt accgttcatc gattctcttg tttgctccag actctcaggc    4860
aatgacctga tagcctttgt agagacctct caaaaatagc taccctctcc ggcatgaatt    4920
tatcagctag aacggttgaa tatcatattg atggtgattt gactgtctcc ggcctttctc    4980
acccgtttga atctttacct acacattact caggcattgc atttaaaata tatgagggtt    5040
ctaaaaattt ttatccttgc gttgaaataa aggcttctcc cgcaaaagta ttacagggtc    5100
ataatgtttt tggtacaacc gatttagctt tatgctctga ggctttattg cttaattttg    5160
ctaattcttt gccttgcctg tatgatttat tggatgttgg aatcgcctga tgcggtattt    5220
tctccttacg catctgtgcg gtatttcaca ccgcatatgg tgcactctca gtacaatctg    5280
ctctgatgcc gcatagttaa gccagccccg acacccgcca cacccgctg acgcgccctg    5340 acgggcttgt ctgctcccgg catccgctta cagacaagct gtgaccgtct ccgggagctg    5400
catgtgtcag aggttttcac cgtcatcacc gaaacgcgcg agacgaaagg gcctcgtgat    5460
acgcctattt ttataggtta atgtcatgat aataatggtt tcttagacgt caggtggcac    5520
ttttcgggga atgtgcgcg gaaccccctat ttgtttattt ttctaaatac attcaaatat    5580
gtatccgctc atgagacaat aaccctgata aatgcttcaa taatattgaa aaaggaagag    5640
tatgagtatt caacatttcc gtgtcgccct tattccctt tttgcggcat tttgccttcc    5700 tgttttgct cacccagaaa cgctggtgaa agtaaaagat gctgaagatc agttgggtgc    5760
acgagtgggt tacatcgaac tggatctcaa cagcggtaag atccttgaga gttttcgccc    5820
cgaagaacgt tttccaatga tgagcacttt taaagttctg ctatgtggcg cggtattatc    5880
ccgtattgac gccgggcaag agcaactcgg tcgccgcata cactattctc agaatgactt    5940
ggttgagtac tcaccagtca cagaaaagca tcttacggat ggcatgacag taagagaatt    6000
atgcagtgct gccataacca tgagtgataa cactgcggcc aacttacttc tgacaacgat    6060
cggaggaccg aaggagctaa ccgcttttt gcacaacatg ggggatcatg taactcgcct    6120
tgatcgttgg gaaccggagc tgaatgaagc cataccaaac gacgagcgtg acaccacgat    6180
gcctgtagca atggcaacaa cgttgcgcaa actattaact ggcgaactac ttactctagc    6240
ttcccggcaa caattaatag actggatgga ggcggataaa gttgcaggac cacttctgcg    6300
ctcggccctt ccggctggct ggtttattgc tgataaatct ggagccggtg agcgtgggtc    6360
tcgcggtatc attgcagcac tggggccaga tggtaagccc tcccgtatcg tagttatcta    6420
cacgacgggg agtcaggcaa ctatggatga acgaaataga cagatcgctg agataggtgc    6480
ctcactgatt aagcattggt aactgtcaga ccaagtttac tcatatatac tttagattga    6540
```

| | | | |
|---|---|---|---|
| tttaaaactt | cattttaat | ttaaaaggat | ctaggtgaag atcctttttg ataatctcat | 6600 |
| gaccaaaatc | ccttaacgtg | agttttcgtt | ccactgagcg tcagacccg tagaaaagat | 6660 |
| caaaggatct | tcttgagatc | ctttttttct | gcgcgtaatc tgctgcttgc aaacaaaaaa | 6720 |
| accaccgcta | ccagcggtgg | tttgtttgcc | ggatcaagag ctaccaactc tttttccgaa | 6780 |
| ggtaactggc | ttcagcagag | cgcagatacc | aaatactgtc cttctagtgt agccgtagtt | 6840 |
| aggccaccac | ttcaagaact | ctgtagcacc | gcctacatac ctcgctctgc taatcctgtt | 6900 |
| accagtggct | gctgccagtg | gcgataagtc | gtgtcttacc gggttggact caagacgata | 6960 |
| gttaccggat | aaggcgcagc | ggtcgggctg | aacggggggt tcgtgcacac agcccagctt | 7020 |
| ggagcgaacg | acctacaccg | aactgagata | cctacagcgt gagctatgag aaagcgccac | 7080 |
| gcttcccgaa | gggagaaagg | cggacaggta | tccggtaagc ggcagggtcg gaacaggaga | 7140 |
| gcgcacgagg | gagcttccag | ggggaaacgc | ctggtatctt tatagtcctg tcgggtttcg | 7200 |
| ccacctctga | cttgagcgtc | gatttttgtg | atgctcgtca gggggcgga gcctatggaa | 7260 |
| aaacgccagc | aacgcggcct | ttttacggtt | cctggccttt tgctggcctt ttgctcacat | 7320 |
| gttctttcct | gcgttatccc | ctgattctgt | ggataaccgt attaccgcct ttgagtgagc | 7380 |
| tgataccgct | cgccgcagcc | gaacgaccga | gcgcagcgag tcagtgagcg aggaagcgga | 7440 |
| agagcgccca | atacgcaaac | cgcctctccc | cgcgcgttgg ccgattcatt aatg | 7494 |

<210> SEQ ID NO 57
<211> LENGTH: 8330
<212> TYPE: DNA
<213> ORGANISM: Artificial Sequence
<220> FEATURE:
<223> OTHER INFORMATION: 1378_CCR5.MND.mCherry.2A.coFIXpadua.WPRE.pa

<400> SEQUENCE: 57

| | | | |
|---|---|---|---|
| cagctgcgcg | ctcgctcgct | cactgaggcc | gcccgggcaa agcccgggcg tcgggcgacc | 60 |
| tttggtcgcc | cggcctcagt | gagcgagcga | gcgcgcagag agggagtggc caactccatc | 120 |
| actaggggtt | ccttgtagtt | aatgattaac | ccgccatgct acttatctac gtagccatgc | 180 |
| tctagcggcc | tcggcctctg | cataaataaa | aaaaattagt cagccatgag cttggacgcg | 240 |
| tttggtgtgg | tggcgcctgt | agtccccagc | cacttggagg ggtgaggtga gaggattgct | 300 |
| tgagcccggg | atggtccagg | ctgcagtgag | ccatgatcgt gccactgcac tccagcctgg | 360 |
| gcgacagagt | gagaccctgt | ctcacaacaa | caacaacaac aacaaaaagg ctgagctgca | 420 |
| ccatgcttga | cccagtttct | taaaattgtt | gtcaaagctt cattcactcc atggtgctat | 480 |
| agagcacaag | attttatttg | gtgagatggt | gctttcatga attcccccaa cagagccaag | 540 |
| ctctccatct | agtggacagg | gaagctagca | gcaaaccttc ccttcactac aaaacttcat | 600 |
| tgcttggcca | aaaagagagt | taattcaatg | tagacatcta tgtaggcaat taaaaaccta | 660 |
| ttgatgtata | aaacagtttg | cattcatgga | gggcaactaa atacattcta ggactttata | 720 |
| aaagatcact | ttttatttat | gcacagggtg | gaacaagatg gattatcaag tgtcaagtcc | 780 |
| aatctatgac | atcaattatt | atacatcgga | gccctgccaa aaaatcaatg tgaagcaaat | 840 |
| cgcagcccgc | ctcctgcctc | cgctctactc | actggtgttc atctttggtt ttgtgggcaa | 900 |
| catgctggtc | atcctcatcc | tgataaactg | caaaaggctg aagagcatga ctgacatcta | 960 |
| cctgctcaac | ctggccatct | ctgacctgtt | ttccttctt actgtcccct tctgggctca | 1020 |
| ctatgctgcc | gcccagtggg | actttggaaa | tacaatgtgt caacgaacag agaaacagga | 1080 |

```
gaatatgggc caaacaggat atctgtggta agcagttcct gccccggctc agggccaaga    1140
acagttggaa cagcagaata tgggccaaac aggatatctg tggtaagcag ttcctgcccc    1200
ggctcagggc caagaacaga tggtccccag atgcggtccc gccctcagca gtttctagag    1260
aaccatcaga tgtttccagg gtgcccaaag gacctgaaat gaccctgtgc cttatttgaa    1320
ctaaccaatc agttcgcttc tcgcttctgt tcgcgcgctt ctgctccccg agctctatat    1380
aagcagagct cgtttagtga accgtcagat cgcctggaga cgccatccac gctgttttga    1440
cttccataga aggatctcga ggccaccatg gtgagcaagg gcgaggagga taacatggcc    1500
atcatcaagg agttcatgcg cttcaaggtg cacatggagg ctccgtgaa cggccacgag    1560 ttcgagatcg agggcgaggg cgagggccgc ccctacgagg gcacccagac cgccaagctg    1620
aaggtgacca gggtggcccc cctgcccttc gctgggaca tcctgtcccc tcagttcatg    1680
tacggctcca aggcctacgt gaagcacccc gccgacatcc ccgactactt gaagctgtcc    1740
ttccccgagg gcttcaagtg ggagcgcgtg atgaacttcg aggacggcgg cgtggtgacc    1800
gtgacccagg actcctctct gcaggacggc gagttcatct acaaggtgaa gctgcgcggc    1860
accaacttcc cctccgacgg ccccgtaatg cagaagaaga ccatgggctg ggaggcctcc    1920
tccgagcgga tgtaccccga ggacggcgcc ctgaagggcg agatcaagca gaggctgaag    1980
ctgaaggacg gcggccacta cgacgctgag gtcaagacca cctacaaggc caagaagccc    2040
gtgcagctgc ccggcgccta caacgtcaac atcaagttgg acatcacctc ccacaacgag    2100
gactacacca tcgtggaaca gtacgaacgc gccgagggcc gccactccac cggcggcatg    2160
gacgagctgt acaagggatc cggtgagggc agaggaagtc ttctaacatg cggtgacgtg    2220
gaggagaatc cgggccccat gatcatggcc gagagccctg gcctgatcac catctgcctg    2280
ctgggctacc tgctgagcgc cgagtgcacc gtgttcctgg accacgagaa cgccaacaag    2340
atcctgaacc ggcccaagag atacaacagc ggcaagctgg aggagttcgt gcagggcaac    2400
ctggagaggg agtgcatgga ggagaagtgc agcttcgagg aggccaggga agtgttcgag    2460
aacaccgagc ggaccaccga gttctggaag cagtacgtgg acggcgacca gtgcgagagc    2520
aacccttgcc tgaacggcgg cagctgcaag gacgacatca cagctacga gtgctggtgc    2580 cctttcggct tcgagggcaa gaactgcgag ctggacgtga cctgcaacat caagaacggc    2640
cgctgcgagc agttctgcaa gaacagcgcc gacaacaaag tggtgtgtag ctgcaccgag    2700
ggctacagac tggccgagaa ccagaagagc tgcgagcccg ccgtgccctt ccctgcggc    2760 agagtgagcg tgtcccagac cagcaagctg accagagccg agaccgtgtt ccccgacgtg    2820
gactacgtga atagcaccga ggccgagacc atcctggaca acatcaccca gagcacccag    2880
tccttcaacg acttcaccag agttgtgggc ggcgaggacg ccaagcccgg ccagttcccc    2940
tggcaggtgg tgctgaacgg caaagtggat gccttctgcg gcggcagcat cgtgaacgag    3000
aagtggatcg tgacagccgc ccactgcgtg gagaccggcg tgaagatcac cgtggtggcc    3060
ggcgaacaca atatcgagga gaccgagcac accgagcaga agcggaacgt catccggatt    3120
atcccccacc acaactacaa cgccgccatc aacaagtaca accacgacat cgccctgctg    3180
gagctggacg agcctctggt gctgaatagc tacgtgaccc ccatctgcat cgccgacaag    3240
gagtacacca acatcttcct gaagttcggc agcggctacg tgtccggctg gggcagagtg    3300
ttccacaagg gcagaagcgc cctggtgctg cagtacctga gagtgccct ggtggacaga    3360 gccacctgcc tgttgagcac caagttcacc atctacaaca catgttctg cgccggcttc    3420 cacgagggcg gcagagacag ctgccagggc gacagcggcg accccacgt gaccgaagtg    3480
```

```
gagggcacca gcttcctgac cggcatcatc agctggggcg aggagtgcgc catgaagggc   3540
aagtacggca tctacaccaa agtgagccgg tacgtgaact ggatcaagga gaaaaccaag   3600
ctgacctgag tcgactgctt tatttgtgaa atttgtgatg ctattgcttt atttgtaacc   3660
attataagct gcaataaaca agttaacaac aacaattgca ttcattttat gtttcaggtt   3720
caggggagg tgtgggaggt ttttaaact ctattttata ggcttcttct ctggaatctt    3780
cttcatcatc ctcctgacaa tcgataggta cctggctgtc gtccatgctg tgtttgcttt   3840
aaaagccagg acggtcacct ttggggtggt gacaagtgtg atcacttggg tggtggctgt   3900
gtttgcgtct ctcccaggaa tcatctttac cagatctcaa aaagaaggtc ttcattacac   3960
ctgcagctct cattttccat acagtcagta tcaattctgg aagaatttcc agacattaaa   4020
gatagtcatc ttggggctgg tcctgccgct gcttgtcatg gtcatctgct actcgggaat   4080
cctaaaaact ctgcttcggt gtcgaaatga aagaagagg cacagggctg tgaggcttat    4140
cttcaccatc atgattgttt attttctctt ctgggctccc tacaacattg tccttctcct   4200
gaacaccttc caggaattct ttggcctgaa taattgcagt agctctaaca ggttggacca   4260
agctatgcag gtgacagaga ctcttgggat gacgcactgc tgcatcaacc ccatcatcta   4320
tgcctttgtc ggggagaagt tcagaaacta cctcttagtc ttcttccaaa agcacattgc   4380
caaacgcttc tgcaaatgct gttctatttt ccagcaagag gctcccgagc gagcaagctc   4440
agtttacacc cgatccactg gggagcagga aatatctgtg ggcttgtgac acggactcaa   4500
gtgggctggt gacccagtca gagttgtgca catggcttag ttttcataca caccgcggtc   4560
tagagcatgg ctacgtagat aagtagcatg gcgggttaat cattaactac aaggaacccc   4620
tagtgatgga gttggccact ccctctctgc gcgctcgctc gctcactgag gccgggcgac   4680
caaaggtcgc ccgacgcccg ggctttgccc gggcggcctc agtgagcgag cgagcgcgcc   4740
agctggcgta atagcgaaga ggcccgcacc gatcgccctt cccaacagtt gcgcagcctg   4800
aatggcgaat ggcgattccg ttgcaatggc tggcggtaat attgttctgg atattaccag   4860
caaggccgat agtttgagtt cttctactca ggcaagtgat gttattacta atcaaagaag   4920
tattgcgaca acgttaatt tgcgtgatgg acagactctt ttactcggtg gcctcactga    4980
ttataaaaac acttctcagg attctggcgt accgttcctg tctaaaatcc ctttaatcgg   5040
cctcctgttt agctcccgct ctgattctaa cgaggaaagc acgttatacg tgctcgtcaa   5100
agcaaccata gtacgcgccc tgtagcggcg cattaagcgc ggcgggtgtg gtggttacgc   5160
gcagcgtgac cgctacactt gccagcgccc tagcgcccgc tcctttcgct ttcttccctt   5220
cctttctcgc cacgttcgcc ggctttcccc gtcaagctct aaatcggggg ctccctttag   5280
ggttccgatt tagtgcttta cggcacctcg accccaaaaa acttgattag ggtgatggtt   5340
cacgtagtgg gccatcgccc tgatagacgg ttttttcgccc tttgacgttg gagtccacgt   5400
tctttaatag tggactcttg ttccaaactg gaacaacact caaccctatc tcggtctatt   5460
cttttgattt ataagggatt ttgccgattt cggcctattg gttaaaaaat gagctgattt   5520
aacaaaaatt taacgcgaat tttaacaaaa tattaacgtt tacaatttaa atatttgctt   5580
atacaatctt cctgttttg gggcttttct gattatcaac cggggtacat atgattgaca   5640
tgctagtttt acgattaccg ttcatcgatt ctcttgtttg ctccagactc tcaggcaatg   5700
acctgatagc ctttgtagag acctctcaaa aatagctacc ctctccggca tgaatttatc   5760
agctagaacg gttgaatatc atattgatgg tgatttgact gtctccggcc tttctcaccc   5820
```

```
gtttgaatct ttacctacac attactcagg cattgcattt aaaatatatg agggttctaa    5880
aaatttttat ccttgcgttg aaataaaggc ttctcccgca aaagtattac agggtcataa    5940
tgttttttggt acaaccgatt tagctttatg ctctgaggct ttattgctta attttgctaa   6000
ttctttgcct tgcctgtatg atttattgga tgttggaatc gcctgatgcg gtattttctc    6060
cttacgcatc tgtgcggtat ttcacaccgc atatggtgca ctctcagtac aatctgctct    6120
gatgccgcat agttaagcca gccccgacac ccgccaacac ccgctgacgc gccctgacgg    6180
gcttgtctgc tcccggcatc cgcttacaga caagctgtga ccgtctccgg gagctgcatg    6240
tgtcagaggt tttcaccgtc atcaccgaaa cgcgcgagac gaaagggcct cgtgatacgc    6300
ctatttttat aggttaatgt catgataata atggtttctt agacgtcagg tggcacttt     6360
cggggaaatg tgcgcggaac ccctatttgt ttatttttct aaatacattc aaatatgtat    6420
ccgctcatga gacaataacc ctgataaatg cttcaataat attgaaaaag gaagagtatg    6480
agtattcaac atttccgtgt cgcccttatt ccctttttttg cggcatttttg ccttcctgtt   6540
tttgctcacc cagaaacgct ggtgaaagta aaagatgctg aagatcagtt gggtgcacga    6600
gtgggttaca tcgaactgga tctcaacagc ggtaagatcc ttgagagttt tcgccccgaa    6660
gaacgttttc caatgatgag cacttttaaa gttctgctat gtggcgcggt attatcccgt    6720
attgacgccg ggcaagagca actcggtcgc cgcatacact attctcagaa tgacttggtt    6780
gagtactcac cagtcacaga aaagcatctt acggatggca tgacagtaag agaattatgc    6840
agtgctgcca taaccatgag tgataacact gcggccaact tacttctgac aacgatcgga    6900
ggaccgaagg agctaaccgc ttttttgcac aacatggggg atcatgtaac tcgccttgat    6960
cgttgggaac cggagctgaa tgaagccata ccaaacgacg agcgtgacac cacgatgcct    7020
gtagcaatgg caacaacgtt gcgcaaacta ttaactggcg aactacttac tctagcttcc    7080
cggcaacaat taatagactg gatggaggcg gataaagttg caggaccact tctgcgctcg    7140
gcccttccgg ctggctggtt tattgctgat aaatctggag ccggtgagcg tgggtctcgc    7200
ggtatcattg cagcactggg gccagatggt aagccctccc gtatcgtagt tatctacacg    7260
acggggagtc aggcaactat ggatgaacga aatagacaga tcgctgagat aggtgcctca    7320
ctgattaagc attggtaact gtcagaccaa gtttactcat atatacttta gattgattta    7380
aaacttcatt tttaatttaa aaggatctag gtgaagatcc tttttgataa tctcatgacc    7440
aaaatccctt aacgtgagtt ttcgttccac tgagcgtcag accccgtaga aaagatcaaa    7500
ggatcttctt gagatccttt ttttctgcgc gtaatctgct gcttgcaaac aaaaaaacca    7560
ccgctaccag cggtggtttg tttgccggat caagagctac caactctttt tccgaaggta    7620
actggcttca gcagagcgca gataccaaat actgtccttc tagtgtagcc gtagttaggc    7680
caccacttca agaactctgt agcaccgcct acatacctcg ctctgctaat cctgttacca    7740
gtggctgctg ccagtggcga taagtcgtgt cttaccgggt tggactcaag acgatagtta    7800
ccggataagg cgcagcggtc gggctgaacg gggggttcgt gcacacagcc cagcttggag    7860
cgaacgacct acaccgaact gagatacccta gcgtgagc tatgagaaag cgccacgctt    7920
cccgaaggga gaaaggcgga caggtatccg gtaagcggca gggtcggaac aggagagcgc    7980
acgagggagc ttccaggggg aaacgcctgg tatctttata gtcctgtcgg gtttcgccac    8040
ctctgacttg agcgtcgatt tttgtgatgc tcgtcagggg ggcggagcct atggaaaaac    8100
gccagcaacg cggccttttt acggttcctg gccttttgct ggccttttgc tcacatgttc    8160
tttcctgcgt tatcccctga ttctgtggat aaccgtatta ccgcctttga gtgagctgat    8220
```

```
accgctcgcc gcagccgaac gaccgagcgc agcgagtcag tgagcgagga agcggaagag     8280
cgcccaatac gcaaaccgcc tctccccgcg cgttggccga ttcattaatg                8330
```

<210> SEQ ID NO 58
<211> LENGTH: 7806
<212> TYPE: DNA
<213> ORGANISM: Artificial Sequence
<220> FEATURE:
<223> OTHER INFORMATION: 1376_CCR5.MND.FiX.coFIXpadua.WPRE.pA

<400> SEQUENCE: 58

```
cagctgcgcg ctcgctcgct cactgaggcc gcccgggcaa agcccgggcg tcgggcgacc       60
tttggtcgcc cggcctcagt gagcgagcga gcgcgcagag agggagtggc caactccatc      120
actaggggtt ccttgtagtt aatgattaac ccgccatgct acttatctac gtagccatgc      180
tctagcggcc tcggcctctg cataaataaa aaaaattagt cagccatgag cttggacgcg      240
tttggtgtgg tggcgcctgt agtccccagc cacttggagg ggtgaggtga gaggattgct      300
tgagcccggg atggtccagg ctgcagtgag ccatgatcgt gccactgcac tccagcctgg      360
gcgacagagt gagaccctgt ctcacaacaa caacaacaac aacaaaaagg ctgagctgca      420
ccatgcttga cccagtttct taaaattgtt gtcaaagctt cattcactcc atggtgctat      480
agagcacaag attttatttg gtgagatggt gctttcatga attcccccaa cagagccaag      540
ctctccatct agtggacagg gaagctagca gcaaaccttc ccttcactac aaaacttcat      600
tgcttggcca aaagagagt taattcaatg tagacatcta tgtaggcaat taaaaaccta      660
ttgatgtata aaacagtttg cattcatgga gggcaactaa atacattcta ggactttata      720
aaagatcact ttttatttat gcacagggtg gaacaagatg gattatcaag tgtcaagtcc      780
aatctatgac atcaattatt atacatcgga gccctgccaa aaaatcaatg tgaagcaaat      840
cgcagcccgc ctcctgcctc cgctctactc actggtgttc atctttggtt ttgtgggcaa      900
catgctggtc atcctcatcc tgataaactg caaaaggctg aagagcatga ctgacatcta      960
cctgctcaac ctggccatct ctgacctgtt tttccttctt actgtcccct ctgggctca     1020 ctatgctgcc gcccagtggg actttggaaa tacaatgtgt caacgaacag agaaacagga     1080
gaatatgggc caaacaggat atctgtggta agcagttcct gccccggctc agggccaaga     1140
acagttggaa cagcagaata tgggccaaac aggatatctg tggtaagcag ttcctgcccc     1200
ggctcagggc caagaacaga tggtccccag atgcggtccc gccctcagca gtttctagag     1260
aaccatcaga tgtttccagg gtgccccaag gacctgaaat gaccctgtgc cttatttgaa     1320
ctaaccaatc agttcgcttc tcgcttctgt tcgcgcgctt ctgctccccg agctctatat     1380
aagcagagct cgtttagtga accgtcagat cgcctggaga cgccatccac gctgttttga     1440
cttccataga aggatctcga gatgatcatg gccgagagcc ctggcctgat caccatctgc     1500
ctgctgggct acctgctgag cgccgagtgc accgtgttcc tggaccacga aacgccaac      1560 aagatcctga accggcccaa gagatacaac agcggcaagc tggaggagtt cgtgcagggc     1620
aacctggaga gggagtgcat ggaggagaag tgcagcttcg aggaggccag ggaagtgttc     1680
gagaacaccg agcggaccac cgagttctgg aagcagtacg tggacggcga ccagtgcgag     1740
agcaacccct tgcctgaacgg cggcagctgc aaggacgaca tcaacagcta cgagtgctgg     1800 tgcccttttcg gcttcgaggg caagaactgc gagctggacg tgacctgcaa catcaagaac     1860
ggccgctgcg agcagttctg caagaacagc gccgacaaca aagtggtgtg tagctgcacc     1920
```

-continued

```
gagggctaca gactggccga gaaccagaag agctgcgagc ccgccgtgcc cttcccctgc    1980
ggcagagtga gcgtgtccca gaccagcaag ctgaccagag ccgagaccgt gttccccgac    2040
gtggactacg tgaatagcac cgaggccgag accatcctgg acaacatcac ccagagcacc    2100
cagtccttca acgacttcac cagagttgtg ggcggcgagg acgccaagcc cggccagttc    2160
ccctggcagg tggtgctgaa cggcaaagtg gatgccttct gcggcggcag catcgtgaac    2220
gagaagtgga tcgtgacagc cgcccactgc gtggagaccg gcgtgaagat caccgtggtg    2280
gccggcgaac acaatatcga ggagaccgag cacaccgagc agaagcggaa cgtcatccgg    2340
attatccccc accacaacta caacgccgcc atcaacaagt acaaccacga catcgccctg    2400
ctggagctgg acgagcctct ggtgctgaat agctacgtga cccccatctg catcgccgac    2460
aaggagtaca ccaacatctt cctgaagttc ggcagcggct acgtgtccgg ctggggcaga    2520
gtgttccaca agggcagaag cgccctggtg ctgcagtacc tgagagtgcc cctggtggac    2580
agagccacct gcctgttgag caccaagttc accatctaca acaacatgtt ctgcgccggc    2640
ttccacgagg gcggcagaga cagctgccag ggcgacagcg gcggaccccca cgtgaccgaa    2700 gtggagggca ccagcttcct gaccggcatc atcagctggg gcgaggagtg cgccatgaag    2760
ggcaagtacg gcatctacac caaagtgagc cggtacgtga actggatcaa ggagaaaacc    2820
aagctgacct gagtcgacga taatcaacct ctggattaca aaatttgtga agattgact    2880 ggtattctta actatgttgc tccttttacg ctatgtggat acgctgcttt aatgcctttg    2940
tatcatgcta ttgcttcccg tatggctttc attttctcct ccttgtataa atcctggtta    3000
gttcttgcca cggcggaact catcgccgcc tgccttgccc gctgctggac aggggctcgg    3060
ctgttgggca ctgacaattc cgtgggtcga ctgctttatt tgtgaaattt gtgatgctat    3120
tgctttattt gtaaccatta taagctgcaa taaacaagtt aacaacaaca attgcattca    3180
ttttatgttt caggttcagg gggaggtgtg ggaggttttt taaactctat tttataggct    3240
tcttctctgg aatcttcttc atcatcctcc tgacaatcga taggtacctg gctgtcgtcc    3300
atgctgtgtt tgctttaaaa gccaggacgg tcacctttgg ggtggtgaca agtgtgatca    3360
cttgggtggt ggctgtgttt gcgtctctcc caggaatcat cttaccaga tctcaaaaag    3420 aaggtcttca ttacacctgc agctctcatt ttccatacag tcagtatcaa ttctggaaga    3480
atttccagac attaaagata gtcatcttgg ggctggtcct gccgctgctt gtcatggtca    3540
tctgctactc gggaatccta aaaactctgc ttcggtgtcg aaatgagaag aagaggcaca    3600
gggctgtgag gcttatcttc accatcatga ttgtttattt tctcttctgg gctccctaca    3660
acattgtcct tctcctgaac accttccagg aattctttgg cctgaataat tgcagtagct    3720
ctaacaggtt ggaccaagct atgcaggtga cagagactct tgggatgacg cactgctgca    3780
tcaaccccat catctatgcc tttgtcgggg agaagttcag aaactacctc ttagtcttct    3840
tccaaaagca cattgccaaa cgcttctgca aatgctgttc tattttccag caagaggctc    3900
ccgagcgagc aagctcagtt tacacccgat ccactgggga gcaggaaata tctgtgggct    3960
tgtgacacgg actcaagtgg gctggtgacc cagtcagagt tgtgcacatg cttagttttt    4020
catacacacc gcggtctaga gcatggctac gtagataagt agcatggcgg gttaatcatt    4080
aactacaagg aaccctagt gatggagttg gccactccct ctctgcgcgc tcgctcgctc    4140
actgaggccg ggcgaccaaa ggtcgcccga cgcccgggct tgcccgggc ggcctcagtg    4200 agcgagcgag cgcgccagct ggcgtaatag cgaagaggcc cgcaccgatc gcccttccca    4260
acagttgcgc agcctgaatg gcgaatggcg attccgttgc aatggctggc ggtaatattg    4320
```

```
ttctggatat taccagcaag gccgatagtt tgagttcttc tactcaggca agtgatgtta    4380
ttactaatca aagaagtatt gcgacaacgg ttaatttgcg tgatggacag actcttttac    4440
tcggtggcct cactgattat aaaaacactt ctcaggattc tggcgtaccg ttcctgtcta    4500
aaatcccttt aatcggcctc ctgtttagct cccgctctga ttctaacgag gaaagcacgt    4560
tatacgtgct cgtcaaagca accatagtac gcgccctgta gcggcgcatt aagcgcggcg    4620
ggtgtggtgg ttacgcgcag cgtgaccgct acacttgcca gcgccctagc gcccgctcct    4680
ttcgctttct tcccttcctt tctcgccacg ttcgccggct ttccccgtca gctctaaat     4740 cgggggctcc ctttagggtt ccgatttagt gctttacggc acctcgaccc caaaaaactt    4800
gattagggtg atggttcacg tagtgggcca tcgccctgat agacggtttt tcgccctttg    4860
acgttggagt ccacgttctt taatagtgga ctcttgttcc aaactggaac aacactcaac    4920
cctatctcgg tctattcttt tgatttataa gggattttgc cgatttcggc ctattggtta    4980
aaaaatgagc tgatttaaca aaaatttaac gcgaattttta acaaaatatt aacgtttaca    5040
atttaaatat ttgcttatac aatcttcctg tttttgggc ttttctgatt atcaaccggg    5100
gtacatatga ttgacatgct agttttacga ttaccgttca tcgattctct tgtttgctcc    5160
agactctcag gcaatgacct gatagccttt gtagagacct ctcaaaaata gctaccctct    5220
ccggcatgaa tttatcagct agaacggttg aatatcatat tgatggtgat ttgactgtct    5280
ccggcctttc tcacccgttt gaatctttac ctacacatta ctcaggcatt gcatttaaaa    5340
tatatgaggg ttctaaaaat ttttatcctt gcgttgaaat aaaggcttct cccgcaaaag    5400
tattacaggg tcataatgtt tttggtacaa ccgatttagc tttatgctct gaggctttat    5460 tgcttaatttt tgctaattct ttgccttgcc tgtatgattt attggatgtt ggaatcgcct    5520
gatgcggtat tttctcctta cgcatctgtg cggtatttca caccgcatat ggtgcactct    5580
cagtacaatc tgctctgatg ccgcatagtt aagccagccc cgacacccgc caacacccgc    5640
tgacgcgccc tgacgggctt gtctgctccc ggcatccgct tacagacaag ctgtgaccgt    5700
ctccgggagc tgcatgtgtc agaggttttc accgtcatca ccgaaacgcg cgagacgaaa    5760
gggcctcgtg atacgcctat ttttataggt taatgtcatg ataataatgg tttcttagac    5820
gtcaggtggc acttttcggg gaaatgtgcg cggaacccct atttgtttat ttttctaaat    5880
acattcaaat atgtatccgc tcatgagaca ataaccctga taaatgcttc aataatattg    5940
aaaaaggaag agtatgagta ttcaacattt ccgtgtcgcc cttattccct ttttttgcggc    6000 attttgcctt cctgttttttg ctcacccaga acgctggtg aaagtaaaag atgctgaaga    6060
tcagttgggt gcacgagtgg gttacatcga actggatctc aacagcggta agatccttga    6120
gagttttcgc cccgaagaac gttttccaat gatgagcact tttaaagttc tgctatgtgg    6180
cgcggtatta tcccgtattg acgccgggca agagcaactc ggtcgccgca tacactattc    6240
tcagaatgac ttggttgagt actcaccagt cacagaaaag catcttacgg atggcatgac    6300
agtaagagaa ttatgcagtg ctgccataac catgagtgat aacactgcgg ccaacttact    6360
tctgacaacg atcggaggac cgaaggagct aaccgctttt ttgcacaaca tgggggatca    6420
tgtaactcgc cttgatcgtt gggaaccgga gctgaatgaa gccataccaa acgacgagcg    6480
tgacaccacg atgcctgtag caatggcaac aacgttgcgc aaactattaa ctggcgaact    6540
acttactcta gcttcccggc aacaattaat agactggatg gaggcggata agttgcagg    6600 accacttctg cgctcggccc ttccggctgg ctggtttatt gctgataaat ctggagccgg    6660
```

```
tgagcgtggg tctcgcggta tcattgcagc actggggcca gatggtaagc cctcccgtat    6720
cgtagttatc tacacgacgg ggagtcaggc aactatggat gaacgaaata gacagatcgc    6780
tgagataggt gcctcactga ttaagcattg gtaactgtca gaccaagttt actcatatat    6840
actttagatt gatttaaaac ttcattttta atttaaaagg atctaggtga agatcctttt    6900
tgataatctc atgaccaaaa tcccttaacg tgagttttcg ttccactgag cgtcagaccc    6960
cgtagaaaag atcaaaggat cttcttgaga tcctttttt ctgcgcgtaa tctgctgctt    7020
gcaaacaaaa aaaccaccgc taccagcggt ggtttgtttg ccggatcaag agctaccaac    7080
tcttttccg aaggtaactg gcttcagcag agcgcagata ccaaatactg tccttctagt     7140
gtagccgtag ttaggccacc acttcaagaa ctctgtagca ccgcctacat acctcgctct    7200
gctaatcctg ttaccagtgg ctgctgccag tggcgataag tcgtgtctta ccgggttgga    7260
ctcaagacga tagttaccgg ataaggcgca gcggtcgggc tgaacggggg gttcgtgcac    7320
acagcccagc ttggagcgaa cgacctacac cgaactgaga tacctacagc gtgagctatg    7380
agaaagcgcc acgcttcccg aagggagaaa ggcggacagg tatccggtaa gcggcagggt    7440
cggaacagga gagcgcacga gggagcttcc agggggaaac gcctggtatc tttatagtcc    7500
tgtcgggttt cgccacctct gacttgagcg tcgatttttg tgatgctcgt caggggggcg    7560
gagcctatgg aaaaacgcca gcaacgcggc ctttttacgg ttcctggcct tttgctggcc    7620
ttttgctcac atgttctttc ctgcgttatc ccctgattct gtggataacc gtattaccgc    7680
ctttgagtga gctgataccg ctcgccgcag ccgaacgacc gagcgcagcg agtcagtgag    7740
cgaggaagcg gaagagcgcc caatacgcaa accgcctctc cccgcgcgtt ggccgattca    7800
ttaatg                                                               7806
```

<210> SEQ ID NO 59
<211> LENGTH: 6968
<212> TYPE: DNA
<213> ORGANISM: Artificial Sequence
<220> FEATURE:
<223> OTHER INFORMATION: pAAV_CCR5.MND.II2ss.ADP.mAPRIL

<400> SEQUENCE: 59

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggctctg cataaataaa aaaaattagt cagccatgag cttggacgcg     240
tttggtgtgg tggcgcctgt agtccccagc cacttggagg ggtgaggtga gaggattgct    300
tgagcccggg atggtccagg ctgcagtgag ccatgatcgt gccactgcac tccagcctgg    360
gcgacagagt gagaccctgt ctcacaacaa caacaacaac aacaaaaagg ctgagctgca    420
ccatgcttga cccagtttct taaaattgtt gtcaaagctt cattcactcc atggtgctat    480
agagcacaag atttatttg gtgagatggt gctttcatga attcccccaa cagagccaag    540
ctctccatct agtggacagg gaagctagca gcaaaccttc ccttcactac aaaacttcat    600
tgcttggcca aaagagagt taattcaatg tagacatcta tgtaggcaat taaaaaccta    660
ttgatgtata aaacagtttg cattcatgga gggcaactaa atacattcta ggactttata    720
aaagatcact ttttatttat gcacagggtg gaacaagatg gattatcaag tgtcaagtcc    780
aatctatgac atcaattatt atacatcgga gccctgccaa aaaatcaatg tgaagcaaat    840
cgcagcccgc ctcctgcctc cgctctactc actggtgttc atctttggtt ttgtgggcaa    900
```

```
catgctggtc atcctcatcc tgataaactg caaaaggctg aagagcatga ctgacatcta   960
cctgctcaac ctggccatct ctgacctgtt tttccttctt actgtcccct tctgggctca  1020
ctatgctgcc gcccagtggg actttggaaa tacaatgtgt caacgaacag agaaacagga  1080
gaatatgggc caaacaggat atctgtggta agcagttcct gccccggctc agggccaaga  1140
acagttggaa cagcagaata tgggccaaac aggatatctg tggtaagcag ttcctgcccc  1200
ggctcagggc caagaacaga tggtcccag atgcggtccc gccctcagca gtttctagag  1260
aaccatcaga tgtttccagg gtgccccaag acctgaaat gaccctgtgc cttatttgaa  1320
ctaaccaatc agttcgcttc tcgcttctgt tcgcgcgctt ctgctcccg agctctatat  1380
aagcagagct cgtttagtga accgtcagat cgcctggaga cgccatccac gctgttttga  1440
cttccataga aggatctcga gatgtatcgg atgcagctct tgagctgtat cgctctgtca  1500
ctggcacttg ttaccaactc agaggatgac gttaccacca cggaagaact tgcgcccgct  1560
ttggtaccgc ctccgaaagg aacctgtgcc ggttggatgg ctggaatacc aggacatccc  1620
ggacacaatg gaacgccagg acgggatgga cgcgacggca cgcccggaga aaaaggggag  1680
aaaggggatg caggcttgct cgggccaaag ggcgaaaccg gcgacgttgg aatgacaggc  1740
gctgaaggac ctcggggttt tccgggaacc ccgggccgca agggcgaacc tggcgaggcc  1800
gccgcagtat tgacacagaa acagaaaaag caacattccg tccttcatct ggtccccatc  1860
aacgcaacct ccaaggatga tagtgatgtg accgaggtaa tgtggcaacc cgcgcttagg  1920
cgaggaagag gtctgcaggc gcagggatac ggggtgcgaa tccaagatgc tggggtgtac  1980
ctgctgtact cacaggtttt gtttcaggac gtaacattta cgatggggca ggtcgtgtcc  2040
cgagaaggac aagggagaca ggaaacactc ttccggtgta ttagaagtat gccttcacat  2100
cctgatcgcg cttacaactc ttgttattcc gctggcgtct ttcacttgca tcagggcgac  2160
atccttttcag tgataattcc gagagcgcgg gctaagttga atcttagccc ccacggcaca  2220
tttctcggat tcgtgaagct ttgatgagtc gactgcttta tttgtgaaat ttgtgatgct  2280
attgctttat ttgtaaccat tataagctgc aataaacaag ttaacaacaa caattgcatt  2340
cattttatgt ttcaggttca gggggaggtg tgggaggttt tttaaactct attttatagg  2400
cttcttctct ggaatcttct tcatcatcct cctgacaatc gataggtacc tggctgtcgt  2460
ccatgctgtg tttgctttaa aagccaggac ggtcaccttt ggggtggtga caagtgtgat  2520
cacttgggtg gtggctgtgt ttgcgtctct cccaggaatc atctttacca gatctcaaaa  2580
agaaggtctt cattcacacct gcagctctca ttttccatac agtcagtatc aattctggaa  2640
gaatttccag acattaaaga tagtcatctt ggggctggtc ctgccgctgc ttgtcatggt  2700
catctgctac tcgggaatcc taaaaactct gcttcggtgt cgaaatgaga agaagaggca  2760
cagggctgtg aggcttatct tcaccatcat gattgtttat tttctcttct gggctcccta  2820
caacattgtc cttctcctga acaccttcca ggaattcttt ggcctgaata attgcagtag  2880
ctctaacagg ttggaccaag ctatgcaggt gacagagact cttgggatga cgcactgctg  2940
catcaacccc atcatctatg cctttgtcgg ggagaagttc agaaactacc tcttagtctt  3000
cttccaaaag cacattgcca aacgcttctg caaatgctgt tctatttcc agcaagaggc  3060
tcccgagcga gcaagctcag tttacacccg atccactggg gagcaggaaa tatctgtggg  3120
cttgtgacac ggactcaagt gggctggtga cccagtcaga gttgtgcaca tggcttagtt  3180
ttcatacaca ccgcggtcta gagcatggct acgtagataa gtagcatggc gggttaatca  3240
```

-continued

```
ttaactacaa ggaacccta gtgatggagt tggccactcc ctctctgcgc gctcgctcgc    3300
tcactgaggc cgggcgacca aaggtcgccc gacgcccggg cttttgcccgg gcggcctcag   3360 tgagcgagcg agcgcgccag ctggcgtaat agcgaagagg cccgcaccga tcgcccttcc   3420
caacagttgc gcagcctgaa tggcgaatgg cgattccgtt gcaatggctg gcggtaatat   3480
tgttctggat attaccagca aggccgatag tttgagttct tctactcagg caagtgatgt   3540
tattactaat caaagaagta ttgcgacaac ggttaatttg cgtgatggac agactctttt   3600
actcggtggc ctcactgatt ataaaaacac ttctcaggat tctggcgtac cgttcctgtc   3660
taaaatccct ttaatcggcc tcctgtttag ctcccgctct gattctaacg aggaaagcac   3720
gttatacgtg ctcgtcaaag caaccatagt acgcgccctg tagcggcgca ttaagcgcgg   3780
cgggtgtggt ggttacgcgc agcgtgaccg ctacacttgc cagcgcccta gcgcccgctc   3840
ctttcgcttt cttcccttcc tttctcgcca cgttcgccgg ctttccccgt caagctctaa   3900
atcgggggct ccctttaggg ttccgattta gtgctttacg gcacctcgac cccaaaaaac   3960
ttgattaggg tgatggttca cgtagtgggc catcgccctg atagacggtt tttcgccctt   4020
tgacgttgga gtccacgttc tttaatagtg gactcttgtt ccaaactgga acaacactca   4080
accctatctc ggtctattct tttgatttat aagggatttt gccgatttcg gcctattggt   4140
taaaaaatga gctgatttaa caaaaattta acgcgaattt taacaaaata ttaacgttta   4200
caatttaaat atttgcttat acaatcttcc tgttttggg gcttttctga ttatcaaccg   4260
gggtacatat gattgacatg ctagttttac gattaccgtt catcgattct cttgtttgct   4320
ccagactctc aggcaatgac ctgatagcct ttgtagagac ctctcaaaaa tagctaccct   4380
ctccggcatg aatttatcag ctagaacggt tgaatatcat attgatggtg atttgactgt   4440
ctccggcctt tctcacccgt ttgaatcttt acctacacat tactcaggca ttgcatttaa   4500
aatatatgag ggttctaaaa atttttatcc ttgcgttgaa ataaaggctt ctcccgcaaa   4560
agtattacag ggtcataatg tttttggtac aaccgattta gctttatgct ctgaggcttt   4620
attgcttaat tttgctaatt ctttgccttg cctgtatgat ttattggatg ttggaatcgc   4680
ctgatgcggt attttctcct tacgcatctg tgcggtattt cacaccgcat atggtgcact   4740
ctcagtacaa tctgctctga tgccgcatag ttaagccagc cccgacaccc gccaacaccc   4800
gctgacgcgc cctgacgggc ttgtctgctc ccggcatccg cttacagaca gctgtgacc   4860 gtctccggga gctgcatgtg tcagaggttt tcaccgtcat caccgaaacg cgcgagacga   4920
aagggcctcg tgatacgcct atttttatag gttaatgtca tgataataat ggtttcttag   4980
acgtcaggtg gcacttttcg gggaaatgtg cgcggaaccc ctatttgttt attttttctaa   5040 atacattcaa atatgtatcc gctcatgaga caataaccct gataaatgct tcaataatat   5100
tgaaaaagga agagtatgag tattcaacat ttccgtgtcg cccttattcc cttttttgcg   5160
gcattttgcc ttcctgtttt tgctcaccca gaaacgctgg tgaaagtaaa agatgctgaa   5220
gatcagttgg gtgcacgagt gggttacatc gaactggatc tcaacagcgg taagatcctt   5280
gagagttttc gccccgaaga acgttttcca atgatgagca cttttaaagt tctgctatgt   5340
ggcgcggtat tatcccgtat tgacgccggg caagagcaac tcggtcgccg catacactat   5400
tctcagaatg acttggttga gtactcacca gtcacagaaa agcatcttac ggatggcatg   5460
acagtaagag aattatgcag tgctgccata accatgagtg ataacactgc ggccaactta   5520
cttctgacaa cgatcggagg accgaaggag ctaaccgctt ttttgcacaa catggggat   5580 catgtaactc gccttgatcg ttgggaaccg gagctgaatg aagccatacc aaacgacgag   5640
```

```
cgtgacacca cgatgcctgt agcaatggca acaacgttgc gcaaactatt aactggcgaa   5700
ctacttactc tagcttcccg gcaacaatta atagactgga tggaggcgga taaagttgca   5760
ggaccacttc tgcgctcggc ccttccggct ggctggttta ttgctgataa atctggagcc   5820
ggtgagcgtg ggtctcgcgg tatcattgca gcactgggc cagatggtaa gccctcccgt    5880
atcgtagtta tctacacgac ggggagtcag gcaactatgg atgaacgaaa tagacagatc   5940
gctgagatag gtgcctcact gattaagcat tggtaactgt cagaccaagt ttactcatat   6000
atactttaga ttgattttaaa acttcatttt taatttaaaa ggatctaggt gaagatcctt   6060
tttgataatc tcatgaccaa aatcccttaa cgtgagtttt cgttccactg agcgtcagac   6120
cccgtagaaa agatcaaagg atcttcttga gatccttttt ttctgcgcgt aatctgctgc   6180
ttgcaaacaa aaaaaccacc gctaccagcg gtggtttgtt tgccggatca agagctacca   6240 actcttttc cgaaggtaac tggcttcagc agagcgcaga taccaaatac tgtccttcta    6300
gtgtagccgt agttaggcca ccacttcaag aactctgtag caccgcctac atacctcgct   6360
ctgctaatcc tgttaccagt ggctgctgcc agtggcgata agtcgtgtct taccgggttg   6420
gactcaagac gatagttacc ggataaggcg cagcggtcgg gctgaacggg gggttcgtgc   6480
acacagccca gcttggagcg aacgacctac accgaactga gatacctaca gcgtgagcta   6540
tgagaaagcg ccacgcttcc cgaagggaga aaggcggaca ggtatccggt aagcggcagg   6600
gtcggaacag gagagcgcac gagggagctt ccaggggaa acgcctggta tctttatagt    6660
cctgtcgggt ttcgccacct ctgacttgag cgtcgatttt tgtgatgctc gtcagggggg   6720
cggagcctat ggaaaaacgc cagcaacgcg gcctttttac ggttcctggc cttttgctgg   6780
ccttttgctc acatgttctt tcctgcgtta tcccctgatt ctgtggataa ccgtattacc   6840
gcctttgagt gagctgatac cgctcgccgc agccgaacga ccgagcgcag cgagtcagtg   6900
agcgaggaag cggaagagcg cccaatacgc aaaccgcctc tccccgcgcg ttggccgatt   6960
cattaatg                                                            6968

<210> SEQ ID NO 60
<211> LENGTH: 7620
<212> TYPE: DNA
<213> ORGANISM: Artificial Sequence
<220> FEATURE:
<223> OTHER INFORMATION: pAAV CCR5.MND.IL6.Frun.T2A.GFP

<400> SEQUENCE: 60
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggcctctg cataaataaa aaaaattagt cagccatgag cttggacgcg    240
tttggtgtgg tggcgcctgt agtccccagc cacttggagg ggtgaggtga gaggattgct    300
tgagcccggg atggtccagg ctgcagtgag ccatgatcgt gccactgcac tccagcctgg    360
gcgacagagt gagaccctgt ctcacaacaa caacaacaac aacaaaaagg ctgagctgca    420
ccatgcttga cccagtttct taaaattgtt gtcaaagctt cattcactcc atggtgctat    480
agagcacaag attttatttg gtgagatggt gctttcatga attccccaa cagagccaag     540 ctctccatct agtggacagg gaagctagca gcaaaccttc ccttcactac aaaacttcat    600
tgcttggcca aaagagagt taattcaatg tagacatcta tgtaggcaat taaaaaccta    660
```

```
ttgatgtata aaacagtttg cattcatgga gggcaactaa atacattcta ggactttata      720
aaagatcact ttttatttat gcacagggtg aacaagatg gattatcaag tgtcaagtcc       780
aatctatgac atcaattatt atacatcgga gccctgccaa aaaatcaatg tgaagcaaat      840
cgcagcccgc ctcctgcctc cgctctactc actggtgttc atctttggtt ttgtgggcaa      900
catgctggtc atcctcatcc tgataaactg caaaaggctg aagagcatga ctgacatcta      960
cctgctcaac ctggccatct ctgacctgtt tttccttctt actgtcccct ctgggctca     1020 ctatgctgcc gcccagtggg actttggaaa tacaatgtgt caacgaacag agaaacagga     1080
gaatatgggc caaacaggat atctgtggta agcagttcct gccccggctc agggccaaga     1140
acagttggaa cagcagaata tgggccaaac aggatatctg tggtaagcag ttcctgcccc     1200
ggctcagggc caagaacaga tggtcccag atgcggtccc gccctcagca gtttctagag      1260
aaccatcaga tgtttccagg gtgccccaag gacctgaaat gaccctgtgc cttatttgaa     1320
ctaaccaatc agttcgcttc tcgcttctgt tcgcgcgctt ctgctccccg agctctatat     1380
aagcagagct cgtttagtga accgtcagat cgcctgagaa cgccatccac gctgttttga     1440
cttccataga aggatctcga gatgaacagt ttttctactt ctgccttcgg acccgtcgcc     1500
tttagcctgg gcctgctgct ggtgctgcct gccgcattcc ccgctcctgt gcccctggaa     1560
gaagactcca aggatgtcgc cgctcctcac agacagccac tgactagctc cgagaggatc     1620
gacaaacaga tccgctacat tctggatggc attagcgccc tgcgcaagga aacctgcaac     1680
aaatccaata tgtgtgagtc tagtaaggaa gcactggccg agaacaatct gaacctgccc     1740
aagatggctg agaagacgg ctgcttccag tctgggttta atgaggaaac ctgtctggtg      1800
aaaatcatta cagggctgct ggagttcgaa gtctacctgg aatatctgca gaaccgattt     1860
gagtcaagcg aggaacaggc tcgggcagtg cagatgagca caaaggtcct gatccagttc     1920
ctgcagaaga agccaaaaa tctggacgct attaccacac cagatcccac taccaacgct     1980
tctctgctga ccaagctgca ggcacagaat cagtggctgc aggatatgac aactcacctg     2040
atcctgagga gtttcaaaga atttctgcag tcctctctgc gggcactgag acagatgcgc     2100
gctaagcgag gatccggtga gggcagagga agtcttctaa catgcggtga cgtggaggag     2160
aatccgggcc ccatggtgag caagggcgag gagctgttca ccggggtggt gcccatcctg     2220
gtcgagctgg acggcgacgt aaacggccac aagttcagcg tgtccggcga gggcgagggc     2280
gatgccacct acggcaagct gaccctgaag ttcatctgca ccaccggcaa gctgcccgtg     2340
ccctggccca ccctcgtgac caccctgacc tacggcgtgc agtgcttcag ccgctacccc     2400
gaccacatga agcagcacga cttcttcaag tccgccatgc ccgaaggcta cgtccaggag     2460
cgcaccatct tcttcaagga cgacggcaac tacaagaccc gcgccgaggt gaagttcgag     2520
ggcgacaccc tggtgaaccg catcgagctg aagggcatcg acttcaagga ggacggcaac     2580
atcctggggc acaagctgga gtacaactac aacagccaca acgtctatat catggccgac     2640
aagcagaaga acggcatcaa ggtgaacttc aagatccgcc acaacatcga ggacggcagc     2700
gtgcagctcg ccgaccacta ccagcagaac ccccatcg cgacggccc cgtgctgctg        2760 cccgacaacc actacctgag cacccagtcc gccctgagca agacccaa cgagaagcgc       2820 gatcacatgg tcctgctgga gttcgtgacc gccgccggga tcactctcgg catggacgag     2880
ctgtacaagt gaatctagag tcgactgctt tatttgtgaa atttgtgatg ctattgcttt     2940
atttgtaacc attataagct gcaataaaca agttaacaac aacaattgca ttcattttat     3000
gtttcaggtt cagggggagg tgtgggaggt ttttaaact ctatttata ggcttcttct       3060
```

```
ctggaatctt cttcatcatc ctcctgacaa tcgataggta cctggctgtc gtccatgctg    3120
tgtttgcttt aaaagccagg acggtcacct ttggggtggt gacaagtgtg atcacttggg    3180
tggtggctgt gtttgcgtct ctcccaggaa tcatctttac cagatctcaa aaagaaggtc    3240
ttcattacac ctgcagctct cattttccat acagtcagta tcaattctgg aagaatttcc    3300
agacattaaa gatagtcatc ttggggctgg tcctgccgct gcttgtcatg gtcatctgct    3360
actcgggaat cctaaaaact ctgcttcggt gtcgaaatga aagaagagg cacagggctg     3420 tgaggcttat cttccaccatc atgattgttt attttctctt ctgggctccc tacaacattg    3480
tccttctcct gaacaccttc caggaattct ttggcctgaa taattgcagt agctctaaca    3540
ggttggacca agctatgcag gtgacagaga ctcttgggat gacgcactgc tgcatcaacc    3600
ccatcatcta tgcctttgtc ggggagaagt tcagaaacta cctcttagtc ttcttccaaa    3660
agcacattgc caaacgcttc tgcaaatgct gttctatttt ccagcaagag gctcccgagc    3720
gagcaagctc agtttacacc cgatccactg gggagcagga atatctgtg ggcttgtgac      3780 acggactcaa gtgggctggt gacccagtca gagttgtgca catggcttag ttttcataca    3840
caccgcggtc tagagcatgg ctacgtagat aagtagcatg gcgggttaat cattaactac    3900
aaggaacccc tagtgatgga gttggccact ccctctctgc gcgctcgctc gctcactgag    3960
gccgggcgac caaggtcgc ccgacgcccg ggctttgccc gggcggcctc agtgagcgag       4020
cgagcgcgcc agctggcgta atagcgaaga ggcccgcacc gatcgccctt cccaacagtt    4080
gcgcagcctg aatggcgaat ggcgattccg ttgcaatggc tggcggtaat attgttctgg    4140
atattaccag caaggccgat agtttgagtt cttctactca ggcaagtgat gttattacta    4200
atcaaagaag tattgcgaca acggttaatt tgcgtgatgg acagactctt ttactcggtg    4260
gcctcactga ttataaaaac acttctcagg attctggcgt accgttcctg tctaaaatcc    4320
ctttaatcgg cctcctgttt agctcccgct ctgattctaa cgaggaaagc acgttatacg    4380
tgctcgtcaa agcaaccata gtacgcgccc tgtagcggcg cattaagcgc ggcgggtgtg    4440
gtggttacgc gcagcgtgac cgctacactt gccagcgccc tagcgcccgc tcctttcgct    4500
ttcttccctt cctttctcgc cacgttcgcc ggctttcccc gtcaagctct aaatcggggg    4560
ctccctttag ggttccgatt tagtgcttta cggcacctcg accccaaaaa acttgattag    4620
ggtgatggtt cacgtagtgg gccatcgccc tgatagacgg ttttcgccc tttgacgttg      4680 gagtccacgt tctttaatag tggactcttg ttccaaactg gaacaacact caaccctatc    4740
tcggtctatt cttttgattt ataagggatt ttgccgattt cggcctattg gttaaaaaat    4800
gagctgattt aacaaaaatt taacgcgaat tttaacaaaa tattaacgtt tacaatttaa    4860
atatttgctt atacaatctt cctgttttg gggcttttct gattatcaac cggggtacat     4920
atgattgaca tgctagtttt acgattaccg ttcatcgatt ctcttgtttg ctccagactc    4980
tcaggcaatg acctgatagc ctttgtagag acctctcaaa aatagctacc ctctccggca    5040
tgaatttatc agctagaacg gttgaatatc atattgatgg tgatttgact gtctccggcc    5100
tttctcaccc gtttgaatct ttacctacac attactcagg cattgcattt aaaatatatg    5160
agggttctaa aaatttttat ccttgcgttg aaataaaggc ttctcccgca aaagtattac    5220
agggtcataa tgtttttggt acaaccgatt tagctttatg ctctgaggct ttattgctta    5280
attttgctaa ttctttgcct tgcctgtatg atttattgga tgttggaatc gcctgatgcg    5340
gtattttctc cttacgcatc tgtgcggtat ttcacaccgc atatggtgca ctctcagtac    5400
```

-continued

```
aatctgctct gatgccgcat agttaagcca gccccgacac ccgccaacac ccgctgacgc   5460
gccctgacgg gcttgtctgc tcccggcatc cgcttacaga caagctgtga ccgtctccgg   5520
gagctgcatg tgtcagaggt tttcaccgtc atcaccgaaa cgcgcgagac gaaagggcct   5580
cgtgatacgc ctatttttat aggttaatgt catgataata atggtttctt agacgtcagg   5640
tggcactttt cggggaaatg tgcgcggaac ccctatttgt ttatttttct aaatacattc   5700
aaatatgtat ccgctcatga acaataacc ctgataaatg cttcaataat attgaaaaag   5760
gaagagtatg agtattcaac atttccgtgt cgcccttatt cccttttttg cggcattttg   5820
ccttcctgtt tttgctcacc cagaaacgct ggtgaaagta aaagatgctg aagatcagtt   5880
gggtgcacga gtgggttaca tcgaactgga tctcaacagc ggtaagatcc ttgagagttt   5940
tcgccccgaa gaacgttttc caatgatgag cacttttaaa gttctgctat gtggcgcggt   6000
attatcccgt attgacgccg ggcaagagca actcggtcgc cgcatacact attctcagaa   6060
tgacttggtt gagtactcac cagtcacaga aaagcatctt acggatggca tgacagtaag   6120
agaattatgc agtgctgcca taaccatgag tgataacact gcggccaact tacttctgac   6180
aacgatcgga ggaccgaagg agctaaccgc ttttttgcac aacatggggg atcatgtaac   6240
tcgccttgat cgttgggaac cggagctgaa tgaagccata ccaaacgacg agcgtgacac   6300
cacgatgcct gtagcaatgg caacaacgtt gcgcaaacta ttaactggcg aactacttac   6360
tctagcttcc cggcaacaat taatagactg gatggaggcg gataaagttg caggaccact   6420
tctgcgctcg gcccttccgg ctggctggtt tattgctgat aaatctggag ccggtgagcg   6480
tgggtctcgc ggtatcattg cagcactggg gccagatggt aagccctccc gtatcgtagt   6540
tatctacacg acggggagtc aggcaactat ggatgaacga atagacaga tcgctgagat   6600 aggtgcctca ctgattaagc attggtaact gtcagaccaa gtttactcat atatacttta   6660
gattgattta aaacttcatt tttaatttaa aaggatctag gtgaagatcc ttttttgataa   6720 tctcatgacc aaaatccctt aacgtgagtt ttcgttccac tgagcgtcag accccgtaga   6780
aaagatcaaa ggatcttctt gagatccttt ttttctgcgc gtaatctgct gcttgcaaac   6840
aaaaaaacca ccgctaccag cggtggtttg tttgccggat caagagctac caactctttt   6900
tccgaaggta actggcttca gcagagcgca gataccaaat actgtccttc tagtgtagcc   6960
gtagttaggc caccacttca agaactctgt agcaccgcct acatacctcg ctctgctaat   7020
cctgttacca gtggctgctg ccagtggcga taagtcgtgt cttaccgggt tggactcaag   7080
acgatagtta ccggataagg cgcagcggtc gggctgaacg gggggttcgt gcacacagcc   7140
cagcttggag cgaacgacct acaccgaact gagatacta cagcgtgagc tatgagaaag   7200
cgccacgctt cccgaaggga gaaaggcgga caggtatccg gtaagcggca gggtcggaac   7260
aggagagcgc acgagggagc ttccagggg aaacgcctgg tatctttata gtcctgtcgg   7320
gtttcgccac ctctgacttg agcgtcgatt tttgtgatgc tcgtcagggg gcggagcct   7380 atggaaaaac gccagcaacg cggcctttt acggttcctg ccttttgct ggccttttgc   7440 tcacatgttc tttcctgcgt tatcccctga ttctgtggat aaccgtatta ccgccttga   7500 gtgagctgat accgctcgcc gcagccgaac gaccgagcgc agcgagtcag tgagcgagga   7560
agcggaagag cgcccaatac gcaaaccgcc tctccccgcg cgttggccga ttcattaatg   7620
```

<210> SEQ ID NO 61
<211> LENGTH: 7764
<212> TYPE: DNA
<213> ORGANISM: Artificial Sequence
<220> FEATURE:
<223> OTHER INFORMATION: pAAV.CCR5.MND.II2ss-ADP.mAPRIL.Furin.T2A.GFP

<400> SEQUENCE: 61

| | |
|---|---|
| cagctgcgcg ctcgctcgct cactgaggcc gcccgggcaa agcccgggcg tcgggcgacc | 60 |
| tttggtcgcc cggcctcagt gagcgagcga gcgcgcagag agggagtggc caactccatc | 120 |
| actaggggtt ccttgtagtt aatgattaac ccgccatgct acttatctac gtagccatgc | 180 |
| tctagcggcc tcggcctctg cataaataaa aaaaattagt cagccatgag cttgacgcg | 240 |
| tttggtgtgg tggcgcctgt agtccccagc cacttggagg ggtgaggtga gaggattgct | 300 |
| tgagcccggg atggtccagg ctgcagtgag ccatgatcgt gccactgcac tccagcctgg | 360 |
| gcgacagagt gagaccctgt ctcacaacaa caacaacaac aacaaaaagg ctgagctgca | 420 |
| ccatgcttga cccagtttct taaaattgtt gtcaaagctt cattcactcc atggtgctat | 480 |
| agagcacaag attttatttg gtgagatggt gctttcatga attcccccaa cagagccaag | 540 |
| ctctccatct agtggacagg gaagctagca gcaaaccttc ccttcactac aaaacttcat | 600 |
| tgcttggcca aaagagagt taattcaatg tagacatcta tgtaggcaat taaaaaccta | 660 |
| ttgatgtata aaacagtttg cattcatgga gggcaactaa atacattcta ggactttata | 720 |
| aaagatcact ttttatttat gcacagggtg gaacaagatg gattatcaag tgtcaagtcc | 780 |
| aatctatgac atcaattatt atacatcgga gccctgccaa aaaatcaatg tgaagcaaat | 840 |
| cgcagcccgc ctcctgcctc cgctctactc actggtgttc atctttggtt ttgtgggcaa | 900 |
| catgctggtc atcctcatcc tgataaactg caaaaggctg aagagcatga ctgacatcta | 960 |
| cctgctcaac ctggccatct ctgacctgtt tttccttctt actgtcccct tctgggctca | 1020 |
| ctatgctgcc gcccagtggg actttggaaa tacaatgtgt caacgaacag agaaacagga | 1080 |
| gaatatgggc caaacaggat atctgtggta agcagttcct gccccggctc agggccaaga | 1140 |
| acagttggaa cagcagaata tgggccaaac aggatatctg tggtaagcag ttcctgcccc | 1200 |
| ggctcagggc caagaacaga tggtccccag atgcggtccc gccctcagca gtttctagag | 1260 |
| aaccatcaga tgtttccagg gtgccccaag gacctgaaat gaccctgtgc cttatttgaa | 1320 |
| ctaaccaatc agttcgcttc tcgcttctgt tcgcgcgctt ctgctccccg agctctatat | 1380 |
| aagcagagct cgtttagtga accgtcagat cgcctggaga cgccatccac gctgttttga | 1440 |
| cttccataga aggatctcga gatgtatcgg atgcagctct tgagctgtat cgctctgtca | 1500 |
| ctggcacttg ttaccaactc agaggatgac gttaccacca cggaagaact tgcgcccgct | 1560 |
| ttggtaccgc ctccgaaagg aacctgtgcc ggttggatgg ctggaatacc aggacatccc | 1620 |
| ggacacaatg gaacgccagg acgggatgga cgcgacggca cgcccggaga aaaaggggag | 1680 |
| aaaggggatg caggcttgct cgggccaaag gcgaaaccg cgacgttgg aatgacaggc | 1740 |
| gctgaaggac ctcggggttt tccgggaacc ccgggccgca agggcgaacc tggcgaggcc | 1800 |
| gccgcagtat tgcacacagaa acagaaaaag caacattccg tccttcatct ggtccccatc | 1860 |
| aacgcaacct ccaaggatga tagtgatgtg accgaggtaa tgtggcaacc cgcgcttagg | 1920 |
| cgaggaagag gtctgcaggc gcagggatac ggggtgcgaa tccaagatgc tggggtgtac | 1980 |
| ctgctgtact cacaggtttt gtttcaggac gtaacattta cgatgggca ggtcgtgtcc | 2040 |
| cgagaaggac aagggagaca ggaaacactc ttccggtgta ttagaagtat gccttcacat | 2100 |
| cctgatcgcg cttacaactc ttgttattcc gctggcgtct ttcacttgca tcagggcgac | 2160 |
| atcctttcag tgataattcc gagagcgcgg gctaagttga atcttagccc ccacggcaca | 2220 |

```
tttctcggat tcgtgaagct tcgcgctaag cgaggatccg gtgagggcag aggaagtctt    2280
ctaacatgcg gtgacgtgga ggagaatccg ggccccatgg tgagcaaggg cgaggagctg    2340
ttcaccgggg tggtgcccat cctggtcgag ctggacggcg acgtaaacgg ccacaagttc    2400
agcgtgtccg gcgagggcga gggcgatgcc acctacggca agctgaccct gaagttcatc    2460
tgcaccaccg gcaagctgcc cgtgccctgg cccaccctcg tgaccaccct gacctacggc    2520
gtgcagtgct tcagccgcta ccccgaccac atgaagcagc acgacttctt caagtccgcc    2580
atgcccgaag ctacgtcca ggagcgcacc atcttcttca aggacgacgg caactacaag    2640
acccgcgccg aggtgaagtt cgagggcgac accctggtga accgcatcga gctgaagggc    2700
atcgacttca aggaggacgg caacatcctg gggcacaagc tggagtacaa ctacaacagc    2760
cacaacgtct atatcatggc cgacaagcag aagaacggca tcaaggtgaa cttcaagatc    2820
cgccacaaca tcgaggacgg cagcgtgcag ctcgccgacc actaccagca gaacaccccc    2880
atcggcgacg gccccgtgct gctgcccgac aaccactacc tgagcaccca gtccgccctg    2940
agcaaagacc ccaacgagaa gcgcgatcac atggtcctgc tggagttcgt gaccgccgcc    3000
gggatcactc tcggcatgga cgagctgtac aagtgaatct agagtcgact gctttatttg    3060
tgaaatttgt gatgctattg ctttatttgt aaccattata agctgcaata acaagttaa     3120 caacaacaat tgcattcatt ttatgtttca ggttcagggg gaggtgtggg aggttttta     3180 aactctattt tataggcttc ttctctggaa tcttcttcat catcctcctg acaatcgata    3240
ggtacctggc tgtcgtccat gctgtgtttg ctttaaaagc caggacggtc acctttgggg    3300
tggtgacaag tgtgatcact tgggtggtgg ctgtgtttgc gtctctccca ggaatcatct    3360
ttaccagatc tcaaaaagaa ggtcttcatt acacctgcag ctctcatttt ccatacagtc    3420
agtatcaatt ctggaagaat ttccagacat taaagatagt catcttgggg ctggtcctgc    3480
cgctgcttgt catggtcatc tgctactcgg gaatcctaaa aactctgctt cggtgtcgaa    3540
atgagaagaa gaggcacagg gctgtgaggc ttatcttcac catcatgatt gtttattttc    3600
tcttctgggc tccctacaac attgtccttc cctgaacac cttccaggaa ttctttggcc      3660
tgaataattg cagtagctct aacaggttgg accaagctat gcaggtgaca gagactcttg    3720
ggatgacgca ctgctgcatc aaccccatca tctatgcctt tgtcggggag aagttcagaa    3780
actacctctt agtcttcttc caaaagcaca ttgccaaacg cttctgcaaa tgctgttcta    3840
ttttccagca agaggctccc gagcgagcaa gctcagttta cacccgatcc actggggagc    3900
aggaaatatc tgtgggcttg tgacacggac tcaagtgggc tggtgaccca gtcagagttg    3960
tgcacatggc ttagttttca tacacaccgc ggtctagagc atggctacgt agataagtag    4020
catggcgggt taatcattaa ctacaaggaa cccctagtga tggagttggc cactccctct    4080
ctgcgcgctc gctcgctcac tgaggccggg cgaccaaagg tcgcccgacg cccgggcttt    4140
gcccgggcgg cctcagtgag cgagcagcgc gccagctgg cgtaatagcg aagaggcccg    4200
caccgatcgc ccttcccaac agttgcgcag cctgaatggc gaatggcgat tccgttgcaa    4260
tggctggcgg taatattgtt ctggatatta ccagcaaggc cgatagtttg agttcttcta    4320
ctcaggcaag tgatgttatt actaatcaaa gaagtattgc gacaacggtt aatttgcgtg    4380
atggacagac tcttttactc ggtggcctca ctgattataa aaacacttct caggattctg    4440
gcgtaccgtt cctgtctaaa atcccttta tcggcctcct gtttagctcc cgctctgatt    4500
ctaacgagga aagcacgtta tacgtgctcg tcaaagcaac catagtacgc gccctgtagc    4560
ggcgcattaa gcgcggcggg tgtggtggtt acgcgcagcg tgaccgctac acttgccagc    4620
```

```
gccctagcgc ccgctccttt cgctttcttc ccttcctttc tcgccacgtt cgccggcttt    4680
ccccgtcaag ctctaaatcg ggggctccct ttagggttcc gatttagtgc tttacggcac    4740
ctcgacccca aaaacttga ttagggtgat ggttcacgta gtgggccatc gccctgatag    4800
acggtttttc gcccttgac gttggagtcc acgttcttta atagtggact cttgttccaa    4860
actggaacaa cactcaaccc tatctcggtc tattcttttg atttataagg gattttgccg    4920
atttcggcct attggttaaa aaatgagctg atttaacaaa aatttaacgc gaattttaac    4980
aaaatattaa cgtttacaat ttaaatattt gcttatacaa tcttcctgtt tttggggctt    5040
ttctgattat caaccggggt acatatgatt gacatgctag ttttacgatt accgttcatc    5100
gattctcttg tttgctccag actctcaggc aatgacctga tagcctttgt agagacctct    5160
caaaaatagc taccctctcc ggcatgaatt tatcagctag aacggttgaa tatcatattg    5220
atggtgattt gactgtctcc ggcctttctc acccgtttga atctttacct acacattact    5280
caggcattgc atttaaaata tatgaggggtt ctaaaaattt ttatccttgc gttgaaataa    5340
aggcttctcc cgcaaaagta ttacagggtc ataatgtttt tggtacaacc gatttagctt    5400
tatgctctga ggctttattg cttaattttg ctaattcttt gccttgcctg tatgatttat    5460
tggatgttgg aatcgcctga tgcggtattt tctccttacg catctgtgcg gtatttcaca    5520
ccgcatatgg tgcactctca gtacaatctg ctctgatgcc gcatagttaa gccagccccg    5580
acacccgcca cacccgctg acgcgccctg acgggcttgt ctgctcccgg catccgctta    5640
cagacaagct gtgaccgtct ccgggagctg catgtgtcag aggttttcac cgtcatcacc    5700
gaaacgcgcg agacgaaagg gcctcgtgat acgcctattt ttataggtta atgtcatgat    5760
aataatggtt tcttagacgt caggtggcac ttttcgggga atgtgcgcg gaacccctat    5820
ttgtttattt ttctaaatac attcaaatat gtatccgctc atgagacaat aaccctgata    5880
aatgcttcaa taatattgaa aaaggaagag tatgagtatt caacatttcc gtgtcgccct    5940
tattcccttt tttgcggcat tttgccttcc tgtttttgct cacccagaaa cgctggtgaa    6000
agtaaaagat gctgaagatc agttgggtgc acgagtgggt tacatcgaac tggatctcaa    6060
cagcggtaag atccttgaga gttttcgccc cgaagaacgt tttccaatga tgagcacttt    6120
taaagttctg ctatgtggcg cggtattatc ccgtattgac gccgggcaag agcaactcgg    6180
tcgccgcata cactattctc agaatgactt ggttgagtac tcaccagtca cagaaaagca    6240
tcttacggat ggcatgacag taagagaatt atgcagtgct gccataacca tgagtgataa    6300
cactgcggcc aacttacttc tgacaacgat cggaggaccg aaggagctaa ccgcttttttt    6360
gcacaacatg ggggatcatg taactcgcct tgatcgttgg gaaccggagc tgaatgaagc    6420
cataccaaac gacgagcgtg acaccacgat gcctgtagca atggcaacaa cgttgcgcaa    6480
actattaact ggcgaactac ttactctagc ttcccggcaa caattaatag actggatgga    6540
ggcggataaa gttgcaggac cacttctgcg ctcggccctt ccggctggct ggtttattgc    6600
tgataaatct ggagccggtg agcgtgggtc tcgcggtatc attgcagcac tggggccaga    6660
tggtaagccc tcccgtatcg tagttatcta cacgacgggg agtcaggcaa ctatggatga    6720
acgaaataga cagatcgctg agataggtgc ctcactgatt aagcattggt aactgtcaga    6780
ccaagtttac tcatatatac tttagattga tttaaaactt catttttaat ttaaaaggat    6840
ctaggtgaag atccttttttg ataatctcat gaccaaaatc ccttaacgtg agttttcgtt    6900
ccactgagcg tcagaccccg tagaaaagat caaaggatct tcttgagatc cttttttttct    6960
```

```
gcgcgtaatc tgctgcttgc aaacaaaaaa accaccgcta ccagcggtgg tttgtttgcc    7020
ggatcaagag ctaccaactc ttttttccgaa ggtaactggc ttcagcagag cgcagatacc    7080
aaatactgtc cttctagtgt agccgtagtt aggccaccac ttcaagaact ctgtagcacc    7140
gcctacatac ctcgctctgc taatcctgtt accagtggct gctgccagtg gcgataagtc    7200
gtgtcttacc gggttggact caagacgata gttaccggat aaggcgcagc ggtcgggctg    7260
aacggggggt tcgtgcacac agcccagctt ggagcgaacg acctacaccg aactgagata    7320
cctacagcgt gagctatgag aaagcgccac gcttcccgaa gggagaaagg cggacaggta    7380
tccggtaagc ggcagggtcg aacaggaga gcgcacgagg gagcttccag ggggaaacgc    7440
ctggtatctt tatagtcctg tcgggtttcg ccacctctga cttgagcgtc gatttttgtg    7500
atgctcgtca ggggggcgga gcctatggaa aaacgccagc aacgcggcct ttttacggtt    7560
cctggccttt tgctggcctt tgctcacat gttctttcct gcgttatccc ctgattctgt    7620
ggataaccgt attaccgcct ttgagtgagc tgataccgct cgccgcagcc gaacgaccga    7680
gcgcagcgag tcagtgagcg aggaagcgga agagcgccca atacgcaaac cgcctctccc    7740
cgcgcgttgg ccgattcatt aatg                                            7764

<210> SEQ ID NO 62
<211> LENGTH: 6821
<212> TYPE: DNA
<213> ORGANISM: Artificial Sequence
<220> FEATURE:
<223> OTHER INFORMATION: pAAV CCR5 MND IL6

<400> SEQUENCE: 62
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac cgccatgct acttatctac gtagccatgc    180
tctagcggcc tcggcctctg cataaataaa aaaaattagt cagccatgag cttggacgcg    240
tttggtgtgg tggcgcctgt agtccccagc cacttggagg ggtgaggtga gaggattgct    300
tgagcccggg atggtccagg ctgcagtgag ccatgatcgt gccactgcac tccagcctgg    360
gcgacagagt gagaccctgt ctcacaacaa caacaacaac aacaaaaagg ctgagctgca    420
ccatgcttga cccagtttct taaaattgtt gtcaaagctt cattcactcc atggtgctat    480
agagcacaag attttatttg gtgagatggt gctttcatga attcccccaa cagagccaag    540
ctctccatct agtggacagg gaagctagca gcaaaccttc ccttcactac aaaacttcat    600
tgcttggcca aaaagagagt taattcaatg tagacatcta tgtaggcaat taaaaaccta    660
ttgatgtata aaacagtttg cattcatgga gggcaactaa atacattcta ggactttata    720
aaagatcact tttatttat gcacagggtg gaacaagatg gattatcaag tgtcaagtcc    780
aatctatgac atcaattatt atacatcgga gccctgccaa aaaatcaatg tgaagcaaat    840
cgcagcccgc ctcctgcctc cgctctactc actggtgttc atctttggtt ttgtgggcaa    900
catgctggtc atcctcatcc tgataaactg caaaaggctg aagagcatga ctgacatcta    960
cctgctcaac ctggccatct ctgacctgtt tttccttctt actgtcccct ctgggctca    1020 ctatgctgcc gcccagtggg actttggaaa tacaatgtgt caacgaacag agaaacagga    1080
gaatatgggg caaacaggat atctgtggta agcagttcct gccccggctc agggccaaga    1140
acagttggaa cagcagaata tgggccaaac aggatatctg tggtaagcag ttcctgcccc    1200
ggctcagggc caagaacaga tggtccccag atgcggtccc gccctcagca gtttctagag    1260
```

```
aaccatcaga tgtttccagg gtgccccaag gacctgaaat gaccctgtgc cttatttgaa    1320
ctaaccaatc agttcgcttc tcgcttctgt tcgcgcgctt ctgctccccg agctctatat    1380
aagcagagct cgtttagtga accgtcagat cgcctggaga cgccatccac gctgttttga    1440
cttccataga aggatctcga gatgaacagt ttttctactt ctgccttcgg acccgtcgcc    1500
tttagcctgg gcctgctgct ggtgctgcct gccgcattcc ccgctcctgt gcccctgga     1560 gaagactcca aggatgtcgc cgctcctcac agacagccac tgactagctc cgagaggatc    1620
gacaaacaga tccgctacat tctggatggc attagcgccc tgcgcaagga aacctgcaac    1680
aaatccaata tgtgtgagtc tagtaaggaa gcactggccg agaacaatct gaacctgccc    1740
aagatggctg agaaagacgg ctgcttccag tctgggttta atgaggaaac ctgtctggtg    1800
aaaatcatta cagggctgct ggagttcgaa gtctacctgg aatatctgca gaaccgattt    1860
gagtcaagcg aggaacaggc tcgggcagtg cagatgagca caaaggtcct gatccagttc    1920
ctgcagaaga aagccaaaaa tctggacgct attaccacac agatcccac taccaacgct     1980 tctctgctga ccaagctgca ggcacagaat cagtggctgc aggatatgac aactcacctg    2040
atcctgagga gtttcaaaga atttctgcag tcctctctgc gggcactgag acagatgtga    2100
gtcgactgct ttatttgtga aatttgtgat gctattgctt tatttgtaac cattataagc    2160
tgcaataaac aagttaacaa caacaattgc attcatttta tgtttcaggt tcaggggag    2220 gtgtgggagg ttttttaaac tctatttat aggcttcttc tctggaatct tcttcatcat     2280
cctcctgaca atcgataggt acctggctgt cgtccatgct gtgtttgctt taaaagccag    2340
gacggtcacc tttggggtgg tgacaagtgt gatcacttgg gtggtggctg tgtttgcgtc    2400
tctcccagga atcatcttta ccagatctca aaaagaaggt cttcattaca cctgcagctc    2460
tcattttcca tacagtcagt atcaattctg gaagaatttc cagacattaa agatagtcat    2520 cttgggctg gtcctgccgc tgcttgtcat ggtcatctgc tactcgggaa tcctaaaaac     2580
tctgcttcgg tgtcgaaatg agaagaagag gcacagggct gtgaggctta tcttcaccat    2640
catgattgtt tattttctct tctgggctcc ctacaacatt gtccttctcc tgaacacctt    2700
ccaggaattc tttggcctga ataattgcag tagctctaac aggttggacc aagctatgca    2760
ggtgacagag actcttggga tgacgcactg ctgcatcaac cccatcatct atgcctttgt    2820
cggggagaag ttcagaaact acctcttagt cttcttccaa aagcacattg ccaaacgctt    2880
ctgcaaatgc tgttctattt tccagcaaga ggctcccgag cgagcaagct cagtttacac    2940
ccgatccact ggggagcagg aaatatctgt gggcttgtga cacggactca agtgggctgg    3000
tgacccagtc agagttgtgc acatggctta gttttcatac acccgcggt ctagagcatg      3060 gctacgtaga taagtagcat ggcgggttaa tcattaacta caaggaaccc ctagtgatgg    3120
agttggccac tcctctctg cgcgctcgct cgctcactga ggccgggcga ccaaaggtcg      3180
cccgacgccc gggctttgcc cggcggcct cagtgagcga gcgagcgcgc agctggcgt       3240 aatagcgaag aggcccgcac cgatcgccct tcccaacagt tgcgcagcct gaatggcgaa    3300
tggcgattcc gttgcaatgg ctggcggtaa tattgttctg gatattacca gcaaggccga    3360
tagtttgagt tcttctactc aggcaagtga tgttattact aatcaaagaa gtattgcgac    3420
aacggttaat ttgcgtgatg gacagactct tttactcggt ggcctcactg attataaaaa    3480
cacttctcag gattctggcg taccgttcct gtctaaaatc cctttaatcg gcctcctgtt    3540
tagctcccgc tctgattcta acgaggaaag cacgttatac gtgctcgtca aagcaaccat    3600
```

-continued

```
agtacgcgcc ctgtagcggc gcattaagcg cggcgggtgt ggtggttacg cgcagcgtga    3660
ccgctacact tgccagcgcc ctagcgcccg ctcctttcgc tttcttccct tcctttctcg    3720
ccacgttcgc cggctttccc cgtcaagctc taaatcgggg gctcccttta gggttccgat    3780
ttagtgcttt acggcacctc gacccgaaaa aacttgatta gggtgatggt tcacgtagtg    3840
ggccatcgcc ctgatagacg gttttttcgcc ctttgacgtt ggagtccacg ttctttaata    3900
gtggactctt gttccaaact ggaacaacac tcaaccctat ctcggtctat tcttttgatt    3960
tataagggat tttgccgatt tcggcctatt ggttaaaaaa tgagctgatt taacaaaaat    4020
ttaacgcgaa ttttaacaaa atattaacgt ttacaattta atatttgct tatacaatct    4080 tcctgttttt ggggcttttc tgattatcaa ccggggtaca tatgattgac atgctagttt    4140
tacgattacc gttcatcgat tctcttgttt gctccagact ctcaggcaat gacctgatag    4200
cctttgtaga gacctctcaa aaatagctac cctctccggc atgaatttat cagctagaac    4260
ggttgaatat catattgatg gtgatttgac tgtctccggc cttctcacc cgtttgaatc     4320 tttacctaca cattactcag gcattgcatt taaaatatat gagggttcta aaaattttta    4380
tccttgcgtt gaataaaagg cttctcccgc aaaagtatta cagggtcata atgtttttgg    4440
tacaaccgat ttagctttat gctctgaggc tttattgctt aattttgcta attctttgcc    4500
ttgcctgtat gatttattgg atgttggaat cgcctgatgc ggtattttct ccttacgcat    4560
ctgtgcggta tttcacaccg catatggtgc actctcagta caatctgctc tgatgccgca    4620
tagttaagcc agccccgaca cccgccaaca cccgctgacg cgccctgacg ggcttgtctg    4680
ctcccggcat ccgcttacag acaagctgtg accgtctccg ggagctgcat gtgtcagagg    4740
ttttcaccgt catcaccgaa acgcgcgaga cgaaagggcc tcgtgatacg cctatttta    4800 taggttaatg tcatgataat aatggtttct tagacgtcag gtggcacttt tcggggaaat    4860
gtgcgcggaa cccctatttg tttatttttc taaatacatt caaatatgta tccgctcatg    4920
agacaataac cctgataaat gcttcaataa tattgaaaaa ggaagagtat gagtattcaa    4980
catttccgtg tcgcccttat tcccttttt gcggcatttt gccttcctgt ttttgctcac    5040
ccagaaacgc tggtgaaagt aaaagatgct gaagatcagt tgggtgcacg agtgggttac    5100
atcgaactgg atctcaacag cggtaagatc cttgagagtt ttcgccccga agaacgtttt    5160
ccaatgatga gcacttttaa agttctgcta tgtggcgcgg tattatcccg tattgacgcc    5220
gggcaagagc aactcggtcg ccgcatacac tattctcaga atgacttggt tgagtactca    5280
ccagtcacag aaaagcatct tacgatggc atgacagtaa gagaattatg cagtgctgcc    5340
ataaccatga gtgataacac tgcggccaac ttacttctga caacgatcgg aggaccgaag    5400
gagctaaccg cttttttgca caacatgggg gatcatgtaa ctcgccttga tcgttgggaa    5460
ccggagctga atgaagccat accaaacgac gagcgtgaca ccacgatgcc tgtagcaatg    5520
gcaacaacgt tgcgcaaact attaactggc gaactactta ctctagcttc ccggcaacaa    5580
ttaatagact ggatggaggc ggataaagtt gcaggaccac ttctgcgctc ggcccttccg    5640
gctggctggt ttattgctga taaatctgga gccggtgagc gtgggtctcg cggtatcatt    5700
gcagcactgg ggccagatgg taagccctcc cgtatcgtag ttatctacac gacggggagt    5760
caggcaacta tggatgaacg aaatagacag atcgctgaga taggtgcctc actgattaag    5820
cattggtaac tgtcagacca agtttactca tatatacttt agattgattt aaaacttcat    5880
ttttaattta aaaggatcta ggtgaagatc ctttttgata atctcatgac caaaatccct    5940
taacgtgagt tttcgttcca ctgagcgtca gaccccgtag aaaagatcaa aggatcttct    6000
```

-continued

```
tgagatcctt ttttctgcg cgtaatctgc tgcttgcaaa caaaaaaacc accgctacca      6060
gcggtggttt gtttgccgga tcaagagcta ccaactcttt ttccgaaggt aactggcttc      6120
agcagagcgc agataccaaa tactgtcctt ctagtgtagc cgtagttagg ccaccacttc      6180
aagaactctg tagcaccgcc tacatacctc gctctgctaa tcctgttacc agtggctgct      6240
gccagtggcg ataagtcgtg tcttaccggg ttggactcaa gacgatagtt accggataag      6300
gcgcagcggt cgggctgaac ggggggttcg tgcacacagc ccagcttgga gcgaacgacc      6360
tacaccgaac tgagatacct acagcgtgag ctatgagaaa gcgccacgct tcccgaaggg      6420
agaaaggcgg acaggtatcc ggtaagcggc agggtcggaa caggagagcg cacgaggag      6480 cttccagggg gaaacgcctg gtatctttat agtcctgtcg ggtttcgcca cctctgactt      6540
gagcgtcgat ttttgtgatg ctcgtcaggg gggcggagcc tatggaaaaa cgccagcaac      6600 gcggccttt tacggttcct ggccttttgc tggccttttg ctcacatgtt ctttcctgcg      6660
ttatcccctg attctgtgga taaccgtatt accgcctttg agtgagctga taccgctcgc      6720
cgcagccgaa cgaccgagcg cagcgagtca gtgagcgagg aagcggaaga gcgcccaata      6780
cgcaaaccgc ctctccccgc gcgttggccg attcattaat g                         6821
```

<210> SEQ ID NO 63
<211> LENGTH: 20
<212> TYPE: DNA
<213> ORGANISM: Artificial Sequence
<220> FEATURE:
<223> OTHER INFORMATION: antisense gRNA

<400> SEQUENCE: 63
ggactcccca gaaaagcaaa                                                  20

<210> SEQ ID NO 64
<211> LENGTH: 20
<212> TYPE: DNA
<213> ORGANISM: Artificial Sequence
<220> FEATURE:
<223> OTHER INFORMATION: sense gRNA

<400> SEQUENCE: 64
aagaaccatt tgcttttctg                                                  20

<210> SEQ ID NO 65
<211> LENGTH: 20
<212> TYPE: DNA
<213> ORGANISM: Artificial Sequence
<220> FEATURE:
<223> OTHER INFORMATION: sense gRNA

<400> SEQUENCE: 65
tttgcttttc tggggagtcc                                                  20

<210> SEQ ID NO 66
<211> LENGTH: 20
<212> TYPE: DNA
<213> ORGANISM: Artificial Sequence
<220> FEATURE:
<223> OTHER INFORMATION: sense gRNA

<400> SEQUENCE: 66
attaaggctg ttcatgtgaa                                                  20

<210> SEQ ID NO 67

```
<211> LENGTH: 20
<212> TYPE: DNA
<213> ORGANISM: Artificial Sequence
<220> FEATURE:
<223> OTHER INFORMATION: antisense gRNA

<400> SEQUENCE: 67
ccggcgcggc aggcgcatgg                                               20

<210> SEQ ID NO 68
<211> LENGTH: 20
<212> TYPE: DNA
<213> ORGANISM: Artificial Sequence
<220> FEATURE:
<223> OTHER INFORMATION: antisense gRNA

<400> SEQUENCE: 68
agccccagcg cggcccggcg                                               20

<210> SEQ ID NO 69
<211> LENGTH: 20
<212> TYPE: DNA
<213> ORGANISM: Artificial Sequence
<220> FEATURE:
<223> OTHER INFORMATION: sense gRNA

<400> SEQUENCE: 69
tgccgcgccg ggccgcgctg                                               20

<210> SEQ ID NO 70
<211> LENGTH: 20
<212> TYPE: DNA
<213> ORGANISM: Artificial Sequence
<220> FEATURE:
<223> OTHER INFORMATION: antisense gRNA

<400> SEQUENCE: 70
aagcggcagg agccccagcg                                               20

<210> SEQ ID NO 71
<211> LENGTH: 20
<212> TYPE: DNA
<213> ORGANISM: Artificial Sequence
<220> FEATURE:
<223> OTHER INFORMATION: sense gRNA

<400> SEQUENCE: 71
aggtagacaa ttgcagcctg                                               20

<210> SEQ ID NO 72
<211> LENGTH: 20
<212> TYPE: DNA
<213> ORGANISM: Artificial Sequence
<220> FEATURE:
<223> OTHER INFORMATION: sense gRNA

<400> SEQUENCE: 72
tccctacaga cagagccaca                                               20

<210> SEQ ID NO 73
<211> LENGTH: 20
<212> TYPE: DNA
<213> ORGANISM: Artificial Sequence
<220> FEATURE:
<223> OTHER INFORMATION: sense gRNA

<400> SEQUENCE: 73
```
agatgttgtc ctgacacttg                                         20

<210> SEQ ID NO 74
<211> LENGTH: 20
<212> TYPE: DNA
<213> ORGANISM: Artificial Sequence
<220> FEATURE:
<223> OTHER INFORMATION: sense gRNA

<400> SEQUENCE: 74
gccttcacca tgaagtccag                                         20

<210> SEQ ID NO 75
<211> LENGTH: 20
<212> TYPE: DNA
<213> ORGANISM: Artificial Sequence
<220> FEATURE:
<223> OTHER INFORMATION: sense gRNA

<400> SEQUENCE: 75
ttcaactgct catcagatgg                                         20

<210> SEQ ID NO 76
<211> LENGTH: 20
<212> TYPE: DNA
<213> ORGANISM: Artificial Sequence
<220> FEATURE:
<223> OTHER INFORMATION: antisense gRNA

<400> SEQUENCE: 76
ggccaaagta cagtggaagg                                         20

<210> SEQ ID NO 77
<211> LENGTH: 20
<212> TYPE: DNA
<213> ORGANISM: Artificial Sequence
<220> FEATURE:
<223> OTHER INFORMATION: sense gRNA

<400> SEQUENCE: 77
cacgctgctc gtatccgacg                                         20

<210> SEQ ID NO 78
<211> LENGTH: 20
<212> TYPE: DNA
<213> ORGANISM: Artificial Sequence
<220> FEATURE:
<223> OTHER INFORMATION: antisense gRNA

<400> SEQUENCE: 78
ccttccaagg acgtcatgca                                         20

<210> SEQ ID NO 79
<211> LENGTH: 20
<212> TYPE: DNA
<213> ORGANISM: Artificial Sequence
<220> FEATURE:
<223> OTHER INFORMATION: antisense gRNA

<400> SEQUENCE: 79
cagccttaat aaaaaccgcc                                         20

<210> SEQ ID NO 80
<211> LENGTH: 20
<212> TYPE: DNA

```
<213> ORGANISM: Artificial Sequence
<220> FEATURE:
<223> OTHER INFORMATION: sense gRNA

<400> SEQUENCE: 80
ttcttccgaa gatcctaatg                                            20

<210> SEQ ID NO 81
<211> LENGTH: 20
<212> TYPE: DNA
<213> ORGANISM: Artificial Sequence
<220> FEATURE:
<223> OTHER INFORMATION: antisense gRNA

<400> SEQUENCE: 81
gtcaggatag caggcatctg                                            20

<210> SEQ ID NO 82
<211> LENGTH: 20
<212> TYPE: DNA
<213> ORGANISM: Artificial Sequence
<220> FEATURE:
<223> OTHER INFORMATION: antisense gRNA

<400> SEQUENCE: 82
tactggctcc acttctcgag                                            20

<210> SEQ ID NO 83
<211> LENGTH: 20
<212> TYPE: DNA
<213> ORGANISM: Artificial Sequence
<220> FEATURE:
<223> OTHER INFORMATION: sense gRNA

<400> SEQUENCE: 83
gatattgata tacttcctag                                            20

<210> SEQ ID NO 84
<211> LENGTH: 20
<212> TYPE: DNA
<213> ORGANISM: Artificial Sequence
<220> FEATURE:
<223> OTHER INFORMATION: antisense gRNA

<400> SEQUENCE: 84
acccaaaggg gtctcaaagg                                            20

<210> SEQ ID NO 85
<211> LENGTH: 20
<212> TYPE: DNA
<213> ORGANISM: Artificial Sequence
<220> FEATURE:
<223> OTHER INFORMATION: antisense gRNA

<400> SEQUENCE: 85
cagcgtctta gcacccaaag                                            20

<210> SEQ ID NO 86
<211> LENGTH: 20
<212> TYPE: DNA
<213> ORGANISM: Artificial Sequence
<220> FEATURE:
<223> OTHER INFORMATION: sense gRNA

<400> SEQUENCE: 86
cgaatgcaat cagatgctag                                            20
```

```
<210> SEQ ID NO 87
<211> LENGTH: 20
<212> TYPE: DNA
<213> ORGANISM: Artificial Sequence
<220> FEATURE:
<223> OTHER INFORMATION: antisense gRNA

<400> SEQUENCE: 87
accgagacag tcgggaccgt                                               20

<210> SEQ ID NO 88
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 88
ggacucccca gaaaagcaaa guuuuagagc uaugcu                             36

<210> SEQ ID NO 89
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 89
aagaaccauu ugcuuuucug guuuuagagc uaugcu                             36

<210> SEQ ID NO 90
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 90
uuugcuuuuc ugggagucc guuuuagagc uaugcu                              36

<210> SEQ ID NO 91
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
```

<222> LOCATION: (34)..(36)

<400> SEQUENCE: 91
auuaaggcug uucaugugaa guuuuagagc uaugcu        36

<210> SEQ ID NO 92
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 92
ccggcgcggc aggcgcaugg guuuuagagc uaugcu        36

<210> SEQ ID NO 93
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 93
agccccagcg cggcccggcg guuuuagagc uaugcu        36

<210> SEQ ID NO 94
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 94
ugccgcgccg ggccgcgcug guuuuagagc uaugcu        36

<210> SEQ ID NO 95
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 95
aagcggcagg agccccagcg guuuuagagc uaugcu        36

```
<210> SEQ ID NO 96
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 96
agguagacaa uugcagccug guuuuagagc uaugcu                                    36

<210> SEQ ID NO 97
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 97
ucccuacaga cagagccaca guuuuagagc uaugcu                                    36

<210> SEQ ID NO 98
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 98
agauguuguc cugacacuug guuuuagagc uaugcu                                    36

<210> SEQ ID NO 99
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 99
gccuucacca ugaaguccag guuuuagagc uaugcu                                    36

<210> SEQ ID NO 100
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
```

```
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 100
uucaacugcu caucagaugg guuuuagagc uaugcu                              36

<210> SEQ ID NO 101
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 101
ggccaaagua caguggaagg guuuuagagc uaugcu                              36

<210> SEQ ID NO 102
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 102
cacgcugcuc guauccgacg guuuuagagc uaugcu                              36

<210> SEQ ID NO 103
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 103
ccuuccaagg acgucaugca guuuuagagc uaugcu                              36

<210> SEQ ID NO 104
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 104
```
cagccuuaau aaaaaccgcc guuuuagagc uaugcu        36

<210> SEQ ID NO 105
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 105
uucuuccgaa gauccuaaug guuuuagagc uaugcu        36

<210> SEQ ID NO 106
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 106
gucaggauag caggcaucug guuuuagagc uaugcu        36

<210> SEQ ID NO 107
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 107
uacuggcucc acuucucgag guuuuagagc uaugcu        36

<210> SEQ ID NO 108
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 108
gauauugaua uacuuccuag guuuuagagc uaugcu        36

<210> SEQ ID NO 109
<211> LENGTH: 36
<212> TYPE: RNA

```
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 109
acccaaaggg gucucaaagg guuuuagagc uaugcu                               36

<210> SEQ ID NO 110
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 110
cagcgucuua gcacccaaag guuuuagagc uaugcu                               36

<210> SEQ ID NO 111
<211> LENGTH: 36
<212> TYPE: RNA
<213> ORGANISM: Artificial Sequence
<220> FEATURE:
<223> OTHER INFORMATION: sense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 111
cgaaugcaau cagaugcuag guuuuagagc uaugcu                               36

<210> SEQ ID NO 112
<211> LENGTH: 36
<212> TYPE: RNA
<213> ORGANISM: Artificial Sequence
<220> FEATURE:
<223> OTHER INFORMATION: antisense gRNA - mod and linker
<220> FEATURE:
<221> NAME/KEY: m-2'O-methyl-modified-base-phosphorothioate-bond
<222> LOCATION: (1)..(3)
<220> FEATURE:
<221> NAME/KEY: m-2'O-methyl-modified-base-phosphorothioate-bond
<222> LOCATION: (34)..(36)

<400> SEQUENCE: 112
accgagacag ucgggaccgu guuuuagagc uaugcu                               36
```